US012661480B2

(12) United States Patent
Poltorak

(10) Patent No.: US 12,661,480 B2
(45) Date of Patent: Jun. 23, 2026

(54) SYSTEM AND METHOD FOR INDUCING SLEEP BY TRANSPLANTING MENTAL STATES

(71) Applicant: Neuroenhancement Lab, LLC, Suffern, NY (US)

(72) Inventor: Alexander Poltorak, Monsey, NY (US)

(73) Assignee: NeuroLight, Inc., Pomona, NY (US)

( * ) Notice: Subject to any disclaimer, the term of this patent is extended or adjusted under 35 U.S.C. 154(b) by 794 days.

(21) Appl. No.: 17/844,714

(22) Filed: Jun. 20, 2022

(65) Prior Publication Data

US 2022/0387748 A1     Dec. 8, 2022

Related U.S. Application Data

(63) Continuation of application No. 16/388,845, filed on Apr. 18, 2019, now Pat. No. 11,364,361.

(Continued)

(51) Int. Cl.
| | |
|---|---|
| *A61M 21/02* | (2006.01) |
| *A61B 5/00* | (2006.01) |
| *A61B 5/245* | (2021.01) |
| *A61B 5/291* | (2021.01) |
| *A61B 5/316* | (2021.01) |

(Continued)

(52) U.S. Cl.
CPC ............. *A61M 21/02* (2013.01); *A61B 5/245* (2021.01); *A61B 5/378* (2021.01); *A61B 5/38* (2021.01); *A61B 5/7253* (2013.01); *A61N 1/36025* (2013.01); *A61B 5/291* (2021.01); *A61B 5/316* (2021.01); *A61B 5/4812* (2013.01); *A61M 2021/0027* (2013.01); *A61M 2021/0044* (2013.01)

(58) Field of Classification Search
CPC .......... A61M 21/02; A61M 2021/0027; A61M 2021/0044; A61M 2021/0072; A61M 2021/0016; A61M 2021/0055; A61M 2230/08; A61M 2205/50; A61M 2230/10; A61M 2021/0022; A61B 5/38; A61B 5/245; A61B 5/378; A61B 5/7253; A61B 5/291; A61B 5/316; A61B 5/4812; A61B 5/369; A61B 5/389; A61B 5/486; A61B 5/055; A61N 1/36025; A61N 1/0456; A61N 2/006; A61N 1/36031
USPC ..................................................... 600/26–28
See application file for complete search history.

(56) References Cited

U.S. PATENT DOCUMENTS

| | | | |
|---|---|---|---|
| 2,858,388 | A | 10/1958 | Eastman |
| 3,951,134 | A | 4/1976 | Malech |

(Continued)

FOREIGN PATENT DOCUMENTS

| | | |
|---|---|---|
| EP | 1304073 A2 | 4/2003 |
| EP | 1304073 A3 | 9/2003 |

(Continued)

*Primary Examiner* — Sunita Reddy
(74) *Attorney, Agent, or Firm* — Hoffberg & Associates; Steven Hoffberg

(57) ABSTRACT

A system for replicating a mental state of a first subject in a second subject comprising: a memory storing a captured mental state of the first subject represented by brain activity patterns; and a stimulator for producing a stimulus dependent on the captured mental state adapted to replicate the mental state of the first subject in the second subject by inducing the brain activity patterns in the second subject.

20 Claims, 10 Drawing Sheets

Related U.S. Application Data

(60) Provisional application No. 62/660,839, filed on Apr. 20, 2018.

(51) Int. Cl.

| | |
|---|---|
| *A61B 5/378* | (2021.01) |
| *A61B 5/38* | (2021.01) |
| *A61M 21/00* | (2006.01) |
| *A61N 1/36* | (2006.01) |

(56) References Cited

U.S. PATENT DOCUMENTS

| | | | |
|---|---|---|---|
| 4,030,126 | A | 6/1977 | Puhak |
| 4,172,014 | A | 10/1979 | Sequeira, Jr. et al. |
| 4,296,756 | A | 10/1981 | Dunning et al. |
| 4,367,527 | A | 1/1983 | Desjacques |
| 4,407,299 | A | 10/1983 | Culver |
| 4,408,616 | A | 10/1983 | Duffy et al. |
| 4,421,122 | A | 12/1983 | Duffy |
| 4,437,064 | A | 3/1984 | Overton, Jr. et al. |
| 4,493,327 | A | 1/1985 | Bergelson et al. |
| 4,550,736 | A | 11/1985 | Broughton et al. |
| 4,557,270 | A | 12/1985 | John |
| 4,562,540 | A | 12/1985 | Devaney |
| 4,579,125 | A | 4/1986 | Strobl et al. |
| 4,583,190 | A | 4/1986 | Salb |
| 4,585,011 | A | 4/1986 | Broughton et al. |
| 4,591,787 | A | 5/1986 | Hoenig |
| 4,594,662 | A | 6/1986 | Devaney |
| 4,610,259 | A | 9/1986 | Cohen et al. |
| 4,613,817 | A | 9/1986 | Hoenig |
| 4,649,482 | A | 3/1987 | Raviv et al. |
| 4,689,559 | A | 8/1987 | Hastings et al. |
| 4,693,000 | A | 9/1987 | Hoenig |
| 4,700,135 | A | 10/1987 | Hoenig |
| 4,705,049 | A | 11/1987 | John |
| 4,733,180 | A | 3/1988 | Hoenig et al. |
| 4,736,307 | A | 4/1988 | Salb |
| 4,736,751 | A | 4/1988 | Gevins et al. |
| 4,744,029 | A | 5/1988 | Raviv et al. |
| 4,749,946 | A | 6/1988 | Hoenig |
| 4,753,246 | A | 6/1988 | Freeman |
| 4,761,611 | A | 8/1988 | Hoenig |
| 4,776,345 | A | 10/1988 | Cohen et al. |
| 4,792,145 | A | 12/1988 | Eisenberg et al. |
| 4,794,533 | A | 12/1988 | Cohen |
| 4,801,882 | A | 1/1989 | Daalmans |
| 4,846,190 | A | 7/1989 | John |
| 4,862,359 | A | 8/1989 | Trivedi et al. |
| 4,883,067 | A | 11/1989 | Knispel et al. |
| 4,907,597 | A | 3/1990 | Chamoun |
| 4,913,152 | A | 4/1990 | Ko et al. |
| 4,924,875 | A | 5/1990 | Chamoun |
| 4,937,525 | A | 6/1990 | Daalmans |
| 4,940,058 | A | 7/1990 | Taff et al. |
| 4,947,480 | A | 8/1990 | Lewis |
| 4,949,725 | A | 8/1990 | Raviv et al. |
| 4,951,674 | A | 8/1990 | Zanakis et al. |
| 4,974,602 | A | 12/1990 | Abraham-Fuchs et al. |
| 4,977,505 | A | 12/1990 | Pelizzari et al. |
| 4,982,157 | A | 1/1991 | Seifert |
| 4,983,912 | A | 1/1991 | Roehrlein et al. |
| 4,996,479 | A | 2/1991 | Hoenig |
| 5,008,622 | A | 4/1991 | Overton, Jr. et al. |
| 5,010,891 | A | 4/1991 | Chamoun |
| 5,012,190 | A | 4/1991 | Dossel |
| 5,020,538 | A | 6/1991 | Morgan et al. |
| 5,020,540 | A | 6/1991 | Chamoun |
| 5,027,817 | A | 7/1991 | John |
| 5,029,082 | A | 7/1991 | Shen et al. |
| 5,059,814 | A | 10/1991 | Mead et al. |
| 5,061,680 | A | 10/1991 | Paulson et al. |
| 5,069,218 | A | 12/1991 | Ikeda |
| 5,070,399 | A | 12/1991 | Martel |
| 5,083,571 | A | 1/1992 | Prichep |
| 5,088,497 | A | 2/1992 | Ikeda |
| 5,092,341 | A | 3/1992 | Kelen |
| 5,092,835 | A | 3/1992 | Schurig et al. |
| 5,095,270 | A | 3/1992 | Ludeke |
| 5,105,354 | A | 4/1992 | Nishimura |
| 5,109,862 | A | 5/1992 | Kelen et al. |
| 5,118,606 | A | 6/1992 | Lynch et al. |
| 5,126,315 | A | 6/1992 | Nishino et al. |
| RE34,015 | E | 8/1992 | Duffy |
| 5,136,687 | A | 8/1992 | Edelman et al. |
| 5,158,932 | A | 10/1992 | Hinshaw et al. |
| 5,159,703 | A | 10/1992 | Lowery |
| 5,159,928 | A | 11/1992 | Keppel |
| 5,166,614 | A | 11/1992 | Yokosawa et al. |
| 5,187,327 | A | 2/1993 | Ohta et al. |
| 5,198,977 | A | 3/1993 | Salb |
| 5,213,338 | A | 5/1993 | Brotz |
| 5,215,086 | A | 6/1993 | Terry, Jr. et al. |
| 5,218,530 | A | 6/1993 | Jastrzebski et al. |
| 5,224,203 | A | 6/1993 | Skeirik |
| 5,230,344 | A | 7/1993 | Ozdamar et al. |
| 5,230,346 | A | 7/1993 | Leuchter et al. |
| 5,231,988 | A | 8/1993 | Wernicke et al. |
| 5,233,517 | A | 8/1993 | Jindra |
| 5,241,967 | A | 9/1993 | Yasushi et al. |
| 5,243,281 | A | 9/1993 | Ahonen et al. |
| 5,243,517 | A | 9/1993 | Schmidt et al. |
| 5,263,488 | A | 11/1993 | Van Veen et al. |
| 5,265,611 | A | 11/1993 | Hoenig et al. |
| 5,269,315 | A | 12/1993 | Leuchter et al. |
| 5,269,325 | A | 12/1993 | Robinson et al. |
| 5,273,038 | A | 12/1993 | Beavin |
| 5,280,791 | A | 1/1994 | Lavie |
| 5,282,474 | A | 2/1994 | Valdes Sosa et al. |
| 5,283,523 | A | 2/1994 | Uhl et al. |
| 5,287,859 | A | 2/1994 | John |
| 5,291,888 | A | 3/1994 | Tucker |
| 5,293,187 | A | 3/1994 | Knapp et al. |
| 5,299,569 | A | 4/1994 | Wernicke et al. |
| 5,303,705 | A | 4/1994 | Nenov |
| 5,306,228 | A | 4/1994 | Rubins |
| 5,307,807 | A | 5/1994 | Valdes Sosa et al. |
| 5,309,095 | A | 5/1994 | Ahonen et al. |
| 5,309,917 | A | 5/1994 | Wang et al. |
| 5,309,923 | A | 5/1994 | Leuchter et al. |
| 5,311,129 | A | 5/1994 | Ludwig et al. |
| 5,320,109 | A | 6/1994 | Chamoun et al. |
| 5,323,777 | A | 6/1994 | Ahonen et al. |
| 5,325,862 | A | 7/1994 | Lewis et al. |
| 5,326,745 | A | 7/1994 | Nishino et al. |
| 5,331,970 | A | 7/1994 | Gevins et al. |
| 5,335,657 | A | 8/1994 | Terry, Jr. et al. |
| 5,339,811 | A | 8/1994 | Ohta et al. |
| 5,339,826 | A | 8/1994 | Schmidt et al. |
| 5,343,871 | A | 9/1994 | Bittman et al. |
| 5,356,368 | A * | 10/1994 | Monroe .............. A61M 21/00 600/545 |
| 5,359,363 | A | 10/1994 | Kuban et al. |
| 5,377,100 | A | 12/1994 | Pope et al. |
| 5,384,588 | A | 1/1995 | Martin et al. |
| 5,406,956 | A | 4/1995 | Farwell |
| 5,406,957 | A | 4/1995 | Tansey |
| 5,409,445 | A | 4/1995 | Rubins |
| 5,417,211 | A | 5/1995 | Abraham-Fuchs et al. |
| 5,418,512 | A | 5/1995 | Ohta et al. |
| 5,422,689 | A | 6/1995 | Knapp et al. |
| 5,442,289 | A | 8/1995 | DiIorio et al. |
| 5,443,073 | A | 8/1995 | Wang et al. |
| 5,447,154 | A | 9/1995 | Cinquin et al. |
| 5,447,166 | A | 9/1995 | Gevins |
| 5,458,117 | A | 10/1995 | Chamoun et al. |
| 5,458,142 | A | 10/1995 | Farmer et al. |
| 5,459,536 | A | 10/1995 | Shalon et al. |
| 5,461,699 | A | 10/1995 | Arbabi et al. |
| 5,469,057 | A | 11/1995 | Robinson |
| 5,474,082 | A | 12/1995 | Junker |
| 5,476,438 | A | 12/1995 | Edrich et al. |
| 5,491,492 | A | 2/1996 | Knapp et al. |

(56)  References Cited

U.S. PATENT DOCUMENTS

| | | | |
|---|---|---|---|
| 5,496,798 A | 3/1996 | Sakai et al. |
| 5,503,149 A | 4/1996 | Beavin |
| 5,513,649 A | 5/1996 | Gevins et al. |
| 5,515,301 A | 5/1996 | Corby, Jr. et al. |
| 5,522,863 A | 6/1996 | Spano et al. |
| 5,546,943 A | 8/1996 | Gould |
| 5,552,375 A | 9/1996 | Nishino et al. |
| 5,555,889 A | 9/1996 | Karagueuzian et al. |
| 5,568,816 A | 10/1996 | Gevins et al. |
| 5,571,150 A | 11/1996 | Wernicke et al. |
| 5,579,241 A | 11/1996 | Corby, Jr. et al. |
| 5,594,849 A | 1/1997 | Kuc et al. |
| 5,600,243 A | 2/1997 | Colclough |
| 5,601,081 A | 2/1997 | Tomita et al. |
| 5,611,350 A | 3/1997 | John |
| 5,617,856 A | 4/1997 | Tamura et al. |
| 5,619,995 A | 4/1997 | Lobodzinski |
| 5,622,168 A | 4/1997 | Keusch et al. |
| 5,626,145 A | 5/1997 | Clapp et al. |
| 5,632,272 A | 5/1997 | Diab et al. |
| 5,640,493 A | 6/1997 | Skeirik |
| 5,643,325 A | 7/1997 | Karagueuzian et al. |
| 5,649,061 A | 7/1997 | Smyth |
| 5,650,726 A | 7/1997 | Gasnier et al. |
| 5,656,937 A | 8/1997 | Cantor |
| 5,662,109 A | 9/1997 | Hutson |
| 5,671,740 A | 9/1997 | Tomita et al. |
| 5,678,561 A | 10/1997 | Karagueuzian et al. |
| 5,682,889 A | 11/1997 | Tomita et al. |
| 5,685,313 A | 11/1997 | Mayevsky |
| 5,692,517 A | 12/1997 | Junker |
| 5,694,939 A | 12/1997 | Cowings |
| 5,699,808 A | 12/1997 | John |
| 5,701,909 A | 12/1997 | Amir et al. |
| 5,706,402 A | 1/1998 | Bell |
| 5,706,811 A | 1/1998 | Takeda et al. |
| 5,711,305 A | 1/1998 | Swanson et al. |
| 5,715,821 A | 2/1998 | Faupel |
| 5,719,561 A | 2/1998 | Gonzales |
| 5,720,619 A | 2/1998 | Fisslinger |
| 5,722,418 A | 3/1998 | Bro |
| 5,724,987 A | 3/1998 | Gevins et al. |
| 5,729,046 A | 3/1998 | Nishino et al. |
| 5,730,146 A | 3/1998 | Itil et al. |
| 5,736,543 A | 4/1998 | Rogers et al. |
| 5,737,485 A | 4/1998 | Flanagan et al. |
| 5,740,812 A | 4/1998 | Cowan |
| 5,742,748 A | 4/1998 | Sever, Jr. |
| 5,743,854 A | 4/1998 | Dobson et al. |
| 5,743,860 A | 4/1998 | Hively et al. |
| 5,747,492 A | 5/1998 | Lynch et al. |
| 5,752,514 A | 5/1998 | Okamura et al. |
| 5,752,521 A | 5/1998 | Dardik |
| 5,752,911 A | 5/1998 | Canedo et al. |
| 5,755,227 A | 5/1998 | Tomita et al. |
| 5,755,739 A | 5/1998 | Sun et al. |
| 5,761,332 A | 6/1998 | Wischmann et al. |
| 5,762,611 A | 6/1998 | Lewis et al. |
| 5,767,043 A | 6/1998 | Cantor et al. |
| 5,771,261 A | 6/1998 | Anbar |
| 5,771,893 A | 6/1998 | Kassai et al. |
| 5,771,894 A | 6/1998 | Richards et al. |
| 5,771,897 A | 6/1998 | Zufrin |
| 5,791,342 A | 8/1998 | Woodard |
| 5,794,623 A | 8/1998 | Forbes |
| 5,795,304 A | 8/1998 | Sun et al. |
| 5,797,840 A | 8/1998 | Akselrod et al. |
| 5,797,853 A | 8/1998 | Musha et al. |
| 5,810,737 A | 9/1998 | Dardik |
| 5,813,993 A | 9/1998 | Kaplan et al. |
| 5,815,413 A | 9/1998 | Hively et al. |
| 5,816,247 A | 10/1998 | Maynard |
| 5,825,830 A | 10/1998 | Kopf |
| 5,827,195 A | 10/1998 | Lander |
| 5,840,040 A | 11/1998 | Altschuler et al. |
| 5,842,986 A | 12/1998 | Avrin et al. |
| 5,845,639 A | 12/1998 | Hochman et al. |
| 5,846,189 A | 12/1998 | Pincus |
| 5,846,208 A | 12/1998 | Pichlmayr et al. |
| 5,853,005 A | 12/1998 | Scanlon |
| 5,857,978 A | 1/1999 | Hively et al. |
| 5,859,533 A | 1/1999 | Gasnier et al. |
| 5,871,517 A | 2/1999 | Abrams et al. |
| 5,877,801 A | 3/1999 | Martin et al. |
| 5,884,626 A | 3/1999 | Kuroda et al. |
| 5,885,976 A | 3/1999 | Sandyk |
| 5,891,131 A | 4/1999 | Rajan et al. |
| 5,899,867 A | 5/1999 | Collura |
| 5,911,581 A | 6/1999 | Reynolds et al. |
| 5,916,171 A | 6/1999 | Mayevsky |
| 5,921,245 A | 7/1999 | O'Donnell, Jr. |
| 5,928,272 A | 7/1999 | Adkins et al. |
| 5,938,598 A | 8/1999 | Takeda et al. |
| 5,938,688 A | 8/1999 | Schiff |
| 5,954,662 A | 9/1999 | Swanson et al. |
| 5,970,499 A | 10/1999 | Smith et al. |
| 5,971,923 A | 10/1999 | Finger |
| 5,983,129 A | 11/1999 | Cowan et al. |
| 5,995,868 A | 11/1999 | Dorfmeister et al. |
| 5,999,856 A | 12/1999 | Kennedy |
| 6,002,254 A | 12/1999 | Kassai et al. |
| 6,002,952 A | 12/1999 | Diab et al. |
| 6,011,990 A | 1/2000 | Schultz et al. |
| 6,011,991 A | 1/2000 | Mardirossian |
| 6,016,444 A | 1/2000 | John |
| 6,021,345 A | 2/2000 | Karagueuzian et al. |
| 6,023,161 A | 2/2000 | Dantsker et al. |
| 6,026,173 A | 2/2000 | Svenson et al. |
| 6,032,072 A | 2/2000 | Greenwald et al. |
| 6,042,548 A | 3/2000 | Giuffre |
| 6,044,292 A | 3/2000 | Heyrend et al. |
| 6,050,940 A | 4/2000 | Braun et al. |
| 6,050,962 A | 4/2000 | Kramer et al. |
| 6,052,619 A | 4/2000 | John |
| 6,053,739 A | 4/2000 | Stewart et al. |
| 6,057,846 A | 5/2000 | Sever, Jr. |
| 6,066,084 A | 5/2000 | Edrich et al. |
| 6,067,462 A | 5/2000 | Diab et al. |
| 6,067,467 A | 5/2000 | John |
| 6,069,369 A | 5/2000 | Nishino et al. |
| 6,070,098 A | 5/2000 | Moore-Ede et al. |
| 6,071,246 A | 6/2000 | Sturzebecher et al. |
| 6,080,164 A | 6/2000 | Oshio et al. |
| 6,081,735 A | 6/2000 | Diab et al. |
| 6,088,611 A | 7/2000 | Lauterbur et al. |
| 6,092,058 A | 7/2000 | Smyth |
| 6,097,980 A | 8/2000 | Monastra et al. |
| 6,097,981 A | 8/2000 | Freer |
| 6,099,319 A | 8/2000 | Zaltman et al. |
| 6,104,956 A | 8/2000 | Naritoku et al. |
| 6,115,631 A | 9/2000 | Heyrend et al. |
| 6,117,075 A | 9/2000 | Barnea |
| 6,129,681 A | 10/2000 | Kuroda et al. |
| 6,132,724 A | 10/2000 | Blum |
| 6,144,872 A | 11/2000 | Graetz |
| 6,149,586 A | 11/2000 | Elkind |
| 6,154,026 A | 11/2000 | Dantsker et al. |
| 6,155,966 A | 12/2000 | Parker |
| 6,155,993 A | 12/2000 | Scott |
| 6,157,850 A | 12/2000 | Diab et al. |
| 6,157,857 A | 12/2000 | Dimpfel |
| 6,161,031 A | 12/2000 | Hochman et al. |
| 6,167,298 A | 12/2000 | Levin |
| 6,167,311 A | 12/2000 | Rezai |
| 6,171,239 B1 | 1/2001 | Humphrey |
| 6,171,258 B1 | 1/2001 | Karakasoglu et al. |
| 6,182,013 B1 | 1/2001 | Malinverno et al. |
| 6,188,924 B1 | 2/2001 | Swanson et al. |
| 6,195,576 B1 | 2/2001 | John |
| 6,196,972 B1 | 3/2001 | Moehring |
| 6,205,359 B1 | 3/2001 | Boveja |
| 6,208,902 B1 | 3/2001 | Boveja |
| 6,224,549 B1 | 5/2001 | Drongelen |
| 6,226,418 B1 | 5/2001 | Miller et al. |

(56) References Cited

U.S. PATENT DOCUMENTS

| 6,230,037 | B1 | 5/2001 | Tsukada et al. |
| 6,236,872 | B1 | 5/2001 | Diab et al. |
| 6,239,145 | B1 | 5/2001 | Utsumi et al. |
| 6,240,308 | B1 | 5/2001 | Hardy et al. |
| 6,241,686 | B1 | 6/2001 | Balkin et al. |
| 6,248,126 | B1 | 6/2001 | Lesser et al. |
| 6,259,399 | B1 | 7/2001 | Krasner |
| 6,263,189 | B1 | 7/2001 | Reagor |
| 6,266,453 | B1 | 7/2001 | Hibbard et al. |
| 6,269,270 | B1 | 7/2001 | Boveja |
| 6,272,370 | B1 | 8/2001 | Gillies et al. |
| 6,280,393 | B1 | 8/2001 | Granger et al. |
| 6,287,328 | B1 | 9/2001 | Snyder et al. |
| 6,290,638 | B1 | 9/2001 | Canedo et al. |
| 6,292,688 | B1 | 9/2001 | Patton |
| 6,293,904 | B1 | 9/2001 | Blazey et al. |
| 6,294,917 | B1 | 9/2001 | Nichols |
| 6,298,259 | B1 | 10/2001 | Kucharczyk et al. |
| 6,305,943 | B1 | 10/2001 | Pougatchev et al. |
| 6,306,077 | B1 | 10/2001 | Prabhu et al. |
| 6,309,342 | B1 | 10/2001 | Blazey et al. |
| 6,309,361 | B1 | 10/2001 | Thornton |
| 6,315,736 | B1 | 11/2001 | Tsutsumi et al. |
| 6,317,627 | B1 | 11/2001 | Ennen et al. |
| 6,319,205 | B1 | 11/2001 | Goor et al. |
| 6,322,515 | B1 | 11/2001 | Goor et al. |
| 6,325,475 | B1 | 12/2001 | Hayes et al. |
| 6,325,761 | B1 | 12/2001 | Jay |
| 6,331,164 | B1 | 12/2001 | Shaw et al. |
| 6,332,087 | B1 | 12/2001 | Svenson et al. |
| 6,338,713 | B1 | 1/2002 | Chamoun et al. |
| 6,339,725 | B1 | 1/2002 | Naritoku et al. |
| 6,341,236 | B1 | 1/2002 | Osorio et al. |
| 6,343,229 | B1 | 1/2002 | Siebler et al. |
| 6,346,036 | B1 | 2/2002 | Halley |
| 6,346,067 | B1 | 2/2002 | Walters |
| 6,346,075 | B1 | 2/2002 | Arai et al. |
| 6,346,985 | B1 | 2/2002 | Hall |
| 6,347,465 | B1 | 2/2002 | Jensen |
| 6,347,504 | B1 | 2/2002 | Willibald |
| 6,354,087 | B1 | 3/2002 | Nakahara et al. |
| 6,354,299 | B1 | 3/2002 | Fischell et al. |
| 6,356,079 | B1 | 3/2002 | Mizoguchi et al. |
| 6,356,781 | B1 | 3/2002 | Lee et al. |
| 6,356,788 | B2 | 3/2002 | Boveja |
| 6,358,201 | B1 | 3/2002 | Childre et al. |
| 6,364,845 | B1 | 4/2002 | Duffy et al. |
| 6,366,813 | B1 | 4/2002 | DiLorenzo |
| 6,366,814 | B1 | 4/2002 | Boveja et al. |
| 6,370,414 | B1 | 4/2002 | Robinson |
| 6,370,423 | B1 | 4/2002 | Guerrero et al. |
| 6,374,131 | B1 | 4/2002 | Tomita et al. |
| 6,375,614 | B1 | 4/2002 | Braun et al. |
| 6,377,833 | B1 | 4/2002 | Albert |
| 6,385,479 | B1 | 5/2002 | Sibbitt et al. |
| 6,385,486 | B1 | 5/2002 | John et al. |
| 6,390,979 | B1 | 5/2002 | Njemanze |
| 6,393,363 | B1 | 5/2002 | Wilt et al. |
| 6,394,963 | B1 | 5/2002 | Blazey et al. |
| 6,402,520 | B1 | 6/2002 | Freer |
| 6,402,689 | B1 | 6/2002 | Scarantino et al. |
| 6,408,107 | B1 | 6/2002 | Miller et al. |
| 6,418,344 | B1 | 7/2002 | Rezai et al. |
| 6,419,629 | B1 | 7/2002 | Balkin et al. |
| 6,427,086 | B1 | 7/2002 | Fischell et al. |
| 6,428,490 | B1 | 8/2002 | Kramer et al. |
| 6,430,443 | B1 | 8/2002 | Karell |
| 6,435,878 | B1 | 8/2002 | Reynolds et al. |
| 6,442,421 | B1 | 8/2002 | Le Van Quyen et al. |
| 6,442,948 | B1 | 9/2002 | Takeda |
| 6,466,816 | B2 | 10/2002 | Granger et al. |
| 6,470,220 | B1 | 10/2002 | Kraus, Jr. et al. |
| 6,475,163 | B1 | 11/2002 | Smits et al. |
| 6,482,165 | B1 | 11/2002 | Patton et al. |
| 6,487,441 | B1 | 11/2002 | Swanson et al. |
| 6,488,617 | B1 | 12/2002 | Katz |
| 6,490,472 | B1 | 12/2002 | Li et al. |
| 6,493,577 | B1 | 12/2002 | Williams |
| 6,496,724 | B1 | 12/2002 | Levendowski et al. |
| 6,497,658 | B2 | 12/2002 | Roizen et al. |
| 6,497,699 | B1 | 12/2002 | Ludvig et al. |
| 6,503,085 | B1 | 1/2003 | Elkind |
| 6,507,754 | B2 | 1/2003 | Le Van Quyen et al. |
| 6,510,340 | B1 | 1/2003 | Jordan |
| 6,511,424 | B1 | 1/2003 | Moore-Ede et al. |
| 6,516,246 | B2 | 2/2003 | Derakhshan |
| 6,520,905 | B1 | 2/2003 | Surve et al. |
| 6,520,921 | B1 | 2/2003 | Patton et al. |
| 6,522,906 | B1 | 2/2003 | Salisbury, Jr. et al. |
| 6,524,249 | B2 | 2/2003 | Moehring et al. |
| 6,526,297 | B1 | 2/2003 | Merilainen |
| 6,526,415 | B2 | 2/2003 | Smith et al. |
| 6,527,715 | B2 | 3/2003 | Balkin et al. |
| 6,527,730 | B2 | 3/2003 | Blazey et al. |
| 6,529,759 | B1 | 3/2003 | Tucker et al. |
| 6,529,773 | B1 | 3/2003 | Dewan |
| 6,530,884 | B2 | 3/2003 | Balkin et al. |
| 6,534,986 | B2 | 3/2003 | Nichols |
| 6,538,436 | B1 | 3/2003 | Simola et al. |
| 6,539,245 | B2 | 3/2003 | Tsukada et al. |
| 6,539,263 | B1 | 3/2003 | Schiff et al. |
| 6,544,170 | B1 | 4/2003 | Kajihara et al. |
| 6,546,378 | B1 | 4/2003 | Cook |
| 6,547,736 | B1 | 4/2003 | Moehring et al. |
| 6,547,746 | B1 | 4/2003 | Marino |
| 6,549,804 | B1 | 4/2003 | Osorio et al. |
| 6,551,243 | B2 | 4/2003 | Bocionek et al. |
| 6,553,252 | B2 | 4/2003 | Balkin et al. |
| 6,556,695 | B1 | 4/2003 | Packer et al. |
| 6,556,861 | B1 | 4/2003 | Prichep |
| 6,556,868 | B2 | 4/2003 | Naritoku et al. |
| 6,557,558 | B1 | 5/2003 | Tajima et al. |
| 6,560,486 | B1 | 5/2003 | Osorio et al. |
| 6,565,518 | B2 | 5/2003 | Blazey et al. |
| 6,574,573 | B1 | 6/2003 | Asano |
| 6,587,727 | B2 | 7/2003 | Osorio et al. |
| 6,587,729 | B2 | 7/2003 | O'Loughlin et al. |
| 6,591,132 | B2 | 7/2003 | Gotman et al. |
| 6,591,137 | B1 | 7/2003 | Fischell et al. |
| 6,594,524 | B2 | 7/2003 | Esteller et al. |
| 6,597,954 | B1 | 7/2003 | Pless et al. |
| 6,602,202 | B2 | 8/2003 | John et al. |
| 6,603,502 | B2 | 8/2003 | Martin et al. |
| 6,609,030 | B1 | 8/2003 | Rezai et al. |
| 6,611,698 | B1 | 8/2003 | Yamashita et al. |
| 6,615,158 | B2 | 9/2003 | Wenzel et al. |
| 6,616,611 | B1 | 9/2003 | Moehring |
| 6,622,036 | B1 | 9/2003 | Suffin |
| 6,622,047 | B2 | 9/2003 | Barrett et al. |
| 6,625,485 | B2 | 9/2003 | Levendowski et al. |
| 6,626,676 | B2 | 9/2003 | Freer |
| 6,633,686 | B1 | 10/2003 | Bakircioglu et al. |
| 6,644,976 | B2 | 11/2003 | Kullok et al. |
| 6,648,822 | B2 | 11/2003 | Hamamoto et al. |
| 6,648,880 | B2 | 11/2003 | Chauvet et al. |
| 6,650,917 | B2 | 11/2003 | Diab et al. |
| 6,652,458 | B2 | 11/2003 | Blazey et al. |
| 6,652,470 | B2 | 11/2003 | Patton et al. |
| 6,654,632 | B2 | 11/2003 | Lange et al. |
| 6,654,729 | B1 | 11/2003 | Hickman et al. |
| 6,656,137 | B1 | 12/2003 | Tyldsley et al. |
| 6,658,287 | B1 | 12/2003 | Litt et al. |
| 6,663,571 | B1 | 12/2003 | Njemanze |
| 6,665,552 | B2 | 12/2003 | Yokosawa et al. |
| 6,665,553 | B2 | 12/2003 | Kandori et al. |
| 6,665,562 | B2 | 12/2003 | Gluckman et al. |
| 6,671,555 | B2 | 12/2003 | Gielen et al. |
| 6,671,556 | B2 | 12/2003 | Osorio et al. |
| 6,678,548 | B1 | 1/2004 | Echauz et al. |
| 6,684,098 | B2 | 1/2004 | Oshio et al. |
| 6,684,105 | B2 | 1/2004 | Cohen et al. |
| 6,687,525 | B2 | 2/2004 | Llinas et al. |
| 6,695,761 | B2 | 2/2004 | Oschman et al. |
| 6,697,660 | B1 | 2/2004 | Robinson |

(56)  References Cited

U.S. PATENT DOCUMENTS

| | | | |
|---|---|---|---|
| RE38,476 | E | 3/2004 | Diab et al. |
| 6,699,194 | B1 | 3/2004 | Diab et al. |
| 6,701,173 | B2 | 3/2004 | Nowinski et al. |
| 6,703,838 | B2 | 3/2004 | Conti |
| 6,708,051 | B1 | 3/2004 | Durousseau |
| 6,708,064 | B2 | 3/2004 | Rezai |
| 6,708,184 | B2 | 3/2004 | Smith et al. |
| 6,709,399 | B1 | 3/2004 | Shen et al. |
| 6,725,080 | B2 | 4/2004 | Melkent et al. |
| 6,726,624 | B2 | 4/2004 | Keirsbilck et al. |
| 6,728,424 | B1 | 4/2004 | Zhu et al. |
| 6,728,564 | B2 | 4/2004 | Lahteenmaki |
| 6,731,975 | B1 | 5/2004 | Viertio-Oja et al. |
| 6,735,460 | B2 | 5/2004 | Tsukada et al. |
| 6,735,467 | B2 | 5/2004 | Wilson |
| 6,735,475 | B1 | 5/2004 | Whitehurst et al. |
| 6,740,032 | B2 | 5/2004 | Balkin et al. |
| 6,743,167 | B2 | 6/2004 | Balkin et al. |
| 6,743,182 | B2 | 6/2004 | Miller et al. |
| 6,745,060 | B2 | 6/2004 | Diab et al. |
| 6,745,156 | B2 | 6/2004 | Cook |
| 6,746,409 | B2 | 6/2004 | Keirsbilck et al. |
| 6,751,499 | B2 | 6/2004 | Lange et al. |
| 6,758,813 | B2 | 7/2004 | Meadows |
| 6,768,920 | B2 | 7/2004 | Lange et al. |
| 6,773,400 | B2 | 8/2004 | Njemanze |
| 6,774,929 | B1 | 8/2004 | Kopp |
| 6,775,405 | B1 | 8/2004 | Zhu |
| 6,782,292 | B2 | 8/2004 | Whitehurst |
| 6,785,409 | B1 | 8/2004 | Suri |
| 6,788,975 | B1 | 9/2004 | Whitehurst et al. |
| 6,791,331 | B2 | 9/2004 | Conti |
| 6,795,724 | B2 | 9/2004 | Hogan |
| 6,798,898 | B1 | 9/2004 | Fedorovskaya et al. |
| 6,801,648 | B2 | 10/2004 | Cheng |
| 6,801,803 | B2 | 10/2004 | Viertio-Oja |
| 6,804,558 | B2 | 10/2004 | Haller et al. |
| 6,804,661 | B2 | 10/2004 | Cook |
| 6,815,949 | B2 | 11/2004 | Kandori et al. |
| 6,816,744 | B2 | 11/2004 | Garfield et al. |
| 6,819,956 | B2 | 11/2004 | DiLorenzo |
| 6,826,426 | B2 | 11/2004 | Lange et al. |
| 6,843,774 | B2 | 1/2005 | Foust et al. |
| 6,853,186 | B2 | 2/2005 | Li |
| 6,856,830 | B2 | 2/2005 | He |
| 6,863,127 | B2 | 3/2005 | Clark et al. |
| 6,865,494 | B2 | 3/2005 | Duensing et al. |
| 6,873,872 | B2 | 3/2005 | Gluckman et al. |
| 6,875,174 | B2 | 4/2005 | Braun et al. |
| 6,876,196 | B1 | 4/2005 | Taulu et al. |
| 6,879,859 | B1 | 4/2005 | Boveja |
| 6,882,881 | B1 | 4/2005 | Lesser et al. |
| 6,885,192 | B2 | 4/2005 | Clarke et al. |
| 6,885,886 | B2 | 4/2005 | Bauch et al. |
| 6,886,964 | B2 | 5/2005 | Gardiner et al. |
| 6,893,407 | B1 | 5/2005 | Brooks et al. |
| 6,896,655 | B2 | 5/2005 | Patton et al. |
| RE38,749 | E | 6/2005 | Dardik |
| 6,907,280 | B2 | 6/2005 | Becerra et al. |
| 6,915,241 | B2 | 7/2005 | Kohlmorgen et al. |
| 6,920,357 | B2 | 7/2005 | Osorio et al. |
| 6,926,921 | B2 | 8/2005 | Stasiak et al. |
| 6,928,354 | B2 | 8/2005 | Ryu et al. |
| 6,931,274 | B2 | 8/2005 | Williams |
| 6,931,275 | B2 | 8/2005 | Collura |
| 6,936,012 | B2 | 8/2005 | Wells |
| 6,947,790 | B2 | 9/2005 | Gevins et al. |
| 6,950,697 | B2 | 9/2005 | Jordan |
| 6,950,698 | B2 | 9/2005 | Sarkela et al. |
| 6,959,215 | B2 | 10/2005 | Gliner et al. |
| 6,961,618 | B2 | 11/2005 | Osorio et al. |
| 6,963,770 | B2 | 11/2005 | Scarantino et al. |
| 6,963,771 | B2 | 11/2005 | Scarantino et al. |
| 6,978,179 | B1 | 12/2005 | Flagg et al. |
| 6,980,863 | B2 | 12/2005 | van Venrooij et al. |
| 6,981,947 | B2 | 1/2006 | Melker |
| 6,983,184 | B2 | 1/2006 | Price |
| 6,983,264 | B2 | 1/2006 | Shimizu |
| 6,985,769 | B2 | 1/2006 | Jordan |
| 6,988,056 | B2 | 1/2006 | Cook |
| 6,990,377 | B2 | 1/2006 | Gliner et al. |
| 6,993,380 | B1 | 1/2006 | Modarres |
| 6,996,261 | B2 | 2/2006 | deCharms |
| 6,996,549 | B2 | 2/2006 | Zhang et al. |
| 7,003,352 | B1 | 2/2006 | Whitehurst |
| 7,006,872 | B2 | 2/2006 | Gielen et al. |
| 7,010,340 | B2 | 3/2006 | Scarantino et al. |
| 7,010,351 | B2 | 3/2006 | Firlik et al. |
| 7,011,410 | B2 | 3/2006 | Bolger et al. |
| 7,011,814 | B2 | 3/2006 | Suddarth et al. |
| 7,014,613 | B2 | 3/2006 | John et al. |
| 7,016,722 | B2 | 3/2006 | Prichep |
| 7,022,083 | B2 | 4/2006 | Tanaka et al. |
| 7,023,206 | B2 | 4/2006 | Viehland et al. |
| 7,024,247 | B2 | 4/2006 | Gliner et al. |
| 7,030,617 | B2 | 4/2006 | Conti |
| 7,035,686 | B2 | 4/2006 | Hogan |
| 7,037,260 | B2 | 5/2006 | Keirsbilck et al. |
| 7,038,450 | B2 | 5/2006 | Romalis et al. |
| 7,039,266 | B1 | 5/2006 | Doty |
| 7,039,547 | B2 | 5/2006 | Wilson |
| 7,043,293 | B1 | 5/2006 | Baura |
| 7,053,610 | B2 | 5/2006 | Clarke et al. |
| 7,054,454 | B2 | 5/2006 | Causevic et al. |
| 7,062,391 | B2 | 6/2006 | Wilson |
| 7,063,535 | B2 | 6/2006 | Stamm et al. |
| 7,070,571 | B2 | 7/2006 | Kramer et al. |
| 7,079,977 | B2 | 7/2006 | Osorio et al. |
| 7,089,927 | B2 | 8/2006 | John et al. |
| 7,092,748 | B2 | 8/2006 | Valdes Sosa et al. |
| 7,099,714 | B2 | 8/2006 | Houben |
| 7,104,947 | B2 | 9/2006 | Riehl |
| 7,104,963 | B2 | 9/2006 | Melker et al. |
| 7,105,824 | B2 | 9/2006 | Stoddart et al. |
| 7,107,090 | B2 | 9/2006 | Salisbury, Jr. et al. |
| 7,116,102 | B2 | 10/2006 | Clarke et al. |
| 7,117,026 | B2 | 10/2006 | Shao et al. |
| 7,119,553 | B2 | 10/2006 | Yang et al. |
| 7,120,486 | B2 | 10/2006 | Leuthardt et al. |
| 7,123,955 | B1 | 10/2006 | Gao et al. |
| 7,127,100 | B2 | 10/2006 | Wenzel et al. |
| 7,128,713 | B2 | 10/2006 | Moehring et al. |
| 7,130,673 | B2 | 10/2006 | Tolvanen-Laakso et al. |
| 7,130,675 | B2 | 10/2006 | Ewing et al. |
| 7,130,691 | B2 | 10/2006 | Falci |
| 7,145,333 | B2 | 12/2006 | Romalis et al. |
| 7,146,211 | B2 | 12/2006 | Frei et al. |
| 7,146,217 | B2 | 12/2006 | Firlik et al. |
| 7,146,218 | B2 | 12/2006 | Esteller et al. |
| 7,149,572 | B2 | 12/2006 | Frei et al. |
| 7,149,773 | B2 | 12/2006 | Haller et al. |
| 7,150,710 | B2 | 12/2006 | Haber et al. |
| 7,150,715 | B2 | 12/2006 | Collura et al. |
| 7,150,717 | B2 | 12/2006 | Katura et al. |
| 7,150,718 | B2 | 12/2006 | Okada et al. |
| 7,151,961 | B1 | 12/2006 | Whitehurst et al. |
| 7,155,279 | B2 | 12/2006 | Whitehurst et al. |
| 7,163,512 | B1 | 1/2007 | Childre et al. |
| 7,164,941 | B2 | 1/2007 | Misczynski et al. |
| 7,167,751 | B1 | 1/2007 | Whitehurst et al. |
| 7,170,294 | B2 | 1/2007 | Kasevich |
| 7,171,252 | B1 | 1/2007 | Scarantino et al. |
| 7,171,339 | B2 | 1/2007 | Repucci et al. |
| 7,174,206 | B2 | 2/2007 | Frei et al. |
| 7,176,680 | B1 | 2/2007 | Veryaskin |
| 7,177,675 | B2 | 2/2007 | Suffin et al. |
| 7,177,678 | B2 | 2/2007 | Osorio et al. |
| 7,181,505 | B2 | 2/2007 | Haller et al. |
| 7,183,381 | B2 | 2/2007 | Varadhachary et al. |
| 7,184,837 | B2 | 2/2007 | Goetz |
| 7,186,209 | B2 | 3/2007 | Jacobson et al. |
| 7,187,169 | B2 | 3/2007 | Clarke et al. |
| 7,190,826 | B2 | 3/2007 | Russell et al. |
| 7,190,995 | B2 | 3/2007 | Chervin et al. |

(56) References Cited

U.S. PATENT DOCUMENTS

| | | | |
|---|---|---|---|
| 7,193,413 B2 | 3/2007 | Kandori et al. |
| 7,196,514 B2 | 3/2007 | Li |
| 7,197,352 B2 | 3/2007 | Gott et al. |
| 7,199,708 B2 | 4/2007 | Terauchi et al. |
| 7,203,548 B2 | 4/2007 | Whitehurst et al. |
| 7,207,948 B2 | 4/2007 | Coyle |
| 7,209,787 B2 | 4/2007 | DiLorenzo |
| 7,209,788 B2 | 4/2007 | Nicolelis et al. |
| 7,212,851 B2 | 5/2007 | Donoghue et al. |
| 7,215,986 B2 | 5/2007 | Diab et al. |
| 7,215,994 B2 | 5/2007 | Huiku |
| 7,218,104 B2 | 5/2007 | Clarke et al. |
| 7,221,981 B2 | 5/2007 | Gliner |
| 7,222,964 B2 | 5/2007 | Gotze et al. |
| 7,224,282 B2 | 5/2007 | Terauchi et al. |
| 7,225,013 B2 | 5/2007 | Geva et al. |
| 7,228,167 B2 | 6/2007 | Kara et al. |
| 7,228,169 B2 | 6/2007 | Viertio-Oja et al. |
| 7,228,171 B2 | 6/2007 | Lesser et al. |
| 7,228,178 B2 | 6/2007 | Carroll et al. |
| 7,231,245 B2 | 6/2007 | Greenwald et al. |
| 7,231,254 B2 | 6/2007 | DiLorenzo |
| 7,236,830 B2 | 6/2007 | Gliner |
| 7,236,831 B2 | 6/2007 | Firlik et al. |
| 7,239,731 B1 | 7/2007 | Semenov et al. |
| 7,239,926 B2 | 7/2007 | Goetz |
| 7,242,983 B2 | 7/2007 | Frei et al. |
| 7,242,984 B2 | 7/2007 | DiLorenzo |
| 7,252,090 B2 | 8/2007 | Goetz |
| 7,254,433 B2 | 8/2007 | Diab et al. |
| 7,254,439 B2 | 8/2007 | Misczynski et al. |
| 7,254,500 B2 | 8/2007 | Makeig et al. |
| 7,257,439 B2 | 8/2007 | Llinas |
| 7,258,659 B2 | 8/2007 | Anninou et al. |
| 7,260,430 B2 | 8/2007 | Wu et al. |
| 7,267,644 B2 | 9/2007 | Thomas et al. |
| 7,267,652 B2 | 9/2007 | Coyle et al. |
| 7,269,455 B2 | 9/2007 | Pineda |
| 7,269,456 B2 | 9/2007 | Collura |
| 7,269,516 B2 | 9/2007 | Brunner et al. |
| 7,276,916 B2 | 10/2007 | Hammer |
| 7,277,758 B2 | 10/2007 | DiLorenzo |
| 7,278,966 B2 | 10/2007 | Hjelt et al. |
| 7,280,861 B2 | 10/2007 | Thomas et al. |
| 7,280,867 B2 | 10/2007 | Frei et al. |
| 7,280,870 B2 | 10/2007 | Nurmikko et al. |
| 7,282,030 B2 | 10/2007 | Frei et al. |
| 7,283,861 B2 | 10/2007 | Bystritsky |
| 7,286,871 B2 | 10/2007 | Cohen |
| 7,288,066 B2 | 10/2007 | Drew |
| 7,292,890 B2 | 11/2007 | Whitehurst et al. |
| 7,295,019 B2 | 11/2007 | Yang et al. |
| 7,297,110 B2 | 11/2007 | Goyal et al. |
| 7,299,088 B1 | 11/2007 | Thakor et al. |
| 7,299,096 B2 | 11/2007 | Balzer et al. |
| 7,302,298 B2 | 11/2007 | Lowry et al. |
| 7,305,268 B2 | 12/2007 | Gliner et al. |
| 7,309,315 B2 | 12/2007 | Kullok et al. |
| 7,313,442 B2 | 12/2007 | Velasco et al. |
| 7,318,343 B2 | 1/2008 | Coenen |
| 7,321,837 B2 | 1/2008 | Osorio et al. |
| 7,324,845 B2 | 1/2008 | Mietus et al. |
| 7,324,851 B1 | 1/2008 | DiLorenzo |
| 7,328,053 B1 | 2/2008 | Diab et al. |
| 7,330,032 B2 | 2/2008 | Donnangelo |
| 7,333,619 B2 | 2/2008 | Causevic et al. |
| 7,333,851 B2 | 2/2008 | Echauz et al. |
| 7,334,892 B2 | 2/2008 | Goodall et al. |
| 7,338,171 B2 | 3/2008 | Hsieh et al. |
| 7,338,455 B2 | 3/2008 | White et al. |
| 7,340,125 B1 | 3/2008 | Doty |
| 7,340,289 B2 | 3/2008 | Kandori et al. |
| 7,343,198 B2 | 3/2008 | Behbehani et al. |
| 7,346,382 B2 | 3/2008 | McIntyre et al. |
| 7,346,395 B2 | 3/2008 | Lozano et al. |
| 7,353,064 B2 | 4/2008 | Gliner et al. |
| 7,353,065 B2 | 4/2008 | Morrell |
| 7,355,597 B2 | 4/2008 | Laidlaw et al. |
| 7,359,837 B2 | 4/2008 | Drew |
| 7,363,164 B2 | 4/2008 | Little et al. |
| 7,366,571 B2 | 4/2008 | Armstrong |
| 7,367,807 B1 | 5/2008 | Pennebaker |
| 7,367,949 B2 | 5/2008 | Korhonen et al. |
| 7,369,896 B2 | 5/2008 | Gesotti |
| 7,371,365 B2 | 5/2008 | Poduslo et al. |
| 7,373,198 B2 | 5/2008 | Bibian et al. |
| 7,376,453 B1 | 5/2008 | Diab et al. |
| 7,376,459 B2 | 5/2008 | Rosenfeld |
| 7,378,056 B2 | 5/2008 | Black |
| 7,381,185 B2 | 6/2008 | Zhirnov et al. |
| 7,383,070 B2 | 6/2008 | Diab et al. |
| 7,383,237 B2 | 6/2008 | Zhang et al. |
| 7,386,347 B2 | 6/2008 | Chung et al. |
| 7,389,144 B1 | 6/2008 | Osorio et al. |
| 7,392,079 B2 | 6/2008 | Donoghue et al. |
| 7,394,246 B2 | 7/2008 | Chieh et al. |
| 7,395,292 B2 | 7/2008 | Johnson |
| 7,396,333 B2 | 7/2008 | Stahmann et al. |
| 7,399,282 B2 | 7/2008 | John et al. |
| 7,400,984 B2 | 7/2008 | Kandori et al. |
| 7,403,809 B2 | 7/2008 | Tsukada et al. |
| 7,403,814 B2 | 7/2008 | Cox et al. |
| 7,403,815 B2 | 7/2008 | Katz et al. |
| 7,403,820 B2 | 7/2008 | DiLorenzo |
| 7,407,485 B2 | 8/2008 | Huiku |
| 7,409,321 B2 | 8/2008 | Repucci et al. |
| 7,418,290 B2 | 8/2008 | Devlin et al. |
| 7,420,033 B2 | 9/2008 | Varadhachary et al. |
| 7,422,555 B2 | 9/2008 | Zabara |
| 7,429,247 B2 | 9/2008 | Okada et al. |
| 7,437,196 B2 | 10/2008 | Wyler et al. |
| 7,440,789 B2 | 10/2008 | Hannula et al. |
| 7,440,806 B1 | 10/2008 | Whitehurst et al. |
| 7,444,184 B2 | 10/2008 | Boveja et al. |
| 7,450,986 B2 | 11/2008 | Nguyen et al. |
| 7,453,263 B2 | 11/2008 | Kim et al. |
| 7,454,240 B2 | 11/2008 | Diab et al. |
| 7,454,243 B2 | 11/2008 | Silberstein |
| 7,454,245 B2 | 11/2008 | Armstrong et al. |
| 7,454,387 B2 | 11/2008 | Abercrombie et al. |
| 7,457,653 B2 | 11/2008 | Fujimaki |
| 7,457,665 B1 | 11/2008 | Osorio et al. |
| 7,461,045 B1 | 12/2008 | Chaovalitwongse et al. |
| 7,462,151 B2 | 12/2008 | Childre et al. |
| 7,462,155 B2 | 12/2008 | England |
| 7,463,024 B2 | 12/2008 | Simola et al. |
| 7,463,142 B2 | 12/2008 | Lindsay |
| 7,463,927 B1 | 12/2008 | Chaouat |
| 7,466,132 B2 | 12/2008 | Clarke et al. |
| 7,468,040 B2 | 12/2008 | Hartley et al. |
| 7,468,350 B2 | 12/2008 | Gong et al. |
| 7,469,697 B2 | 12/2008 | Lee et al. |
| 7,471,971 B2 | 12/2008 | Diab et al. |
| 7,471,978 B2 | 12/2008 | John et al. |
| 7,478,108 B2 | 1/2009 | Townsend et al. |
| 7,482,298 B2 | 1/2009 | Nepela |
| 7,483,747 B2 | 1/2009 | Gliner et al. |
| 7,486,986 B1 | 2/2009 | Osorio et al. |
| 7,488,294 B2 | 2/2009 | Torch |
| 7,489,958 B2 | 2/2009 | Diab et al. |
| 7,489,964 B2 | 2/2009 | Suffin et al. |
| 7,490,085 B2 | 2/2009 | Walker et al. |
| 7,491,173 B2 | 2/2009 | Heim |
| 7,493,171 B1 | 2/2009 | Whitehurst et al. |
| 7,493,172 B2 | 2/2009 | Whitehurst et al. |
| 7,496,393 B2 | 2/2009 | Diab et al. |
| 7,497,828 B2 | 3/2009 | Wilk et al. |
| 7,499,741 B2 | 3/2009 | Diab et al. |
| 7,499,745 B2 | 3/2009 | Littrup et al. |
| 7,499,752 B2 | 3/2009 | Maschino et al. |
| 7,499,894 B2 | 3/2009 | Marom et al. |
| 7,502,720 B2 | 3/2009 | Taulu |
| 7,509,154 B2 | 3/2009 | Diab et al. |
| 7,509,161 B2 | 3/2009 | Viertio-Oja |

(56) References Cited

U.S. PATENT DOCUMENTS

| | | | |
|---|---|---|---|
| 7,509,163 B1 | 3/2009 | Luo et al. |
| 7,510,531 B2 | 3/2009 | Lee et al. |
| 7,510,699 B2 | 3/2009 | Black et al. |
| 7,515,054 B2 | 4/2009 | Torch |
| 7,530,955 B2 | 5/2009 | Diab et al. |
| 7,537,568 B2 | 5/2009 | Moehring |
| 7,539,528 B2 | 5/2009 | Xiong et al. |
| 7,539,532 B2 | 5/2009 | Tran |
| 7,539,533 B2 | 5/2009 | Tran |
| 7,539,543 B2 | 5/2009 | Schiff et al. |
| 7,547,284 B2 | 6/2009 | Brainard, II |
| 7,553,810 B2 | 6/2009 | Gong et al. |
| 7,558,622 B2 | 7/2009 | Tran |
| 7,559,903 B2 | 7/2009 | Moussavi et al. |
| 7,561,918 B2 | 7/2009 | Armstrong et al. |
| 7,565,193 B2 | 7/2009 | Laken |
| 7,565,199 B2 | 7/2009 | Sheffield et al. |
| 7,565,200 B2 | 7/2009 | Wyler et al. |
| 7,565,809 B2 | 7/2009 | Takeda |
| 7,567,693 B2 | 7/2009 | deCharms |
| 7,570,054 B1 | 8/2009 | Lin |
| 7,570,991 B2 | 8/2009 | Milgramm et al. |
| 7,572,225 B2 | 8/2009 | Stahmann et al. |
| 7,573,264 B2 | 8/2009 | Xu et al. |
| 7,573,268 B2 | 8/2009 | Volegov et al. |
| 7,574,007 B2 | 8/2009 | Shaw et al. |
| 7,574,254 B2 | 8/2009 | Milgramm et al. |
| 7,577,472 B2 | 8/2009 | Li et al. |
| 7,577,481 B2 | 8/2009 | Firlik et al. |
| 7,580,798 B2 | 8/2009 | Brunner et al. |
| 7,582,062 B2 | 9/2009 | Magill et al. |
| 7,583,857 B2 | 9/2009 | Xu et al. |
| 7,593,767 B1 | 9/2009 | Modarres |
| 7,594,122 B2 | 9/2009 | Milgramm et al. |
| 7,594,889 B2 | 9/2009 | St. Ores et al. |
| 7,596,535 B2 | 9/2009 | de Voir et al. |
| 7,597,665 B2 | 10/2009 | Wilk et al. |
| 7,603,168 B2 | 10/2009 | Bibian et al. |
| 7,603,174 B2 | 10/2009 | De Ridder |
| 7,604,603 B2 | 10/2009 | Sackner et al. |
| 7,606,405 B2 | 10/2009 | Sawyer et al. |
| 7,608,579 B2 | 10/2009 | Gong et al. |
| 7,610,083 B2 | 10/2009 | Drew et al. |
| 7,610,094 B2 | 10/2009 | Stahmann et al. |
| 7,610,096 B2 | 10/2009 | McDonald, III |
| 7,610,100 B2 | 10/2009 | Jaax et al. |
| 7,613,502 B2 | 11/2009 | Yamamoto et al. |
| 7,613,519 B2 | 11/2009 | De Ridder |
| 7,613,520 B2 | 11/2009 | De Ridder |
| 7,617,002 B2 | 11/2009 | Goetz |
| 7,618,381 B2 | 11/2009 | Krebs et al. |
| 7,620,455 B2 | 11/2009 | Maschino |
| 7,620,456 B2 | 11/2009 | Gliner et al. |
| 7,623,912 B2 | 11/2009 | Akselrod et al. |
| 7,623,927 B2 | 11/2009 | Rezai |
| 7,623,928 B2 | 11/2009 | DiLorenzo |
| 7,624,293 B2 | 11/2009 | Osorio et al. |
| 7,625,340 B2 | 12/2009 | Sarkela |
| 7,627,370 B2 | 12/2009 | Marks |
| 7,629,889 B2 | 12/2009 | Sachanandani et al. |
| 7,630,757 B2 | 12/2009 | Dorfmeister et al. |
| 7,634,317 B2 | 12/2009 | Ben-David et al. |
| 7,640,055 B2 | 12/2009 | Geva et al. |
| 7,643,655 B2 | 1/2010 | Liang et al. |
| 7,643,881 B2 | 1/2010 | Armstrong |
| 7,647,097 B2 | 1/2010 | Flaherty et al. |
| 7,647,098 B2 | 1/2010 | Prichep |
| 7,648,498 B2 | 1/2010 | Hempel |
| 7,649,351 B2 | 1/2010 | Kajola et al. |
| 7,653,433 B2 | 1/2010 | Lozano et al. |
| 7,654,948 B2 | 2/2010 | Kaplan et al. |
| 7,657,316 B2 | 2/2010 | Jaax et al. |
| 7,668,579 B2 | 2/2010 | Lynn |
| 7,668,591 B2 | 2/2010 | Lee et al. |
| 7,670,838 B2 | 3/2010 | Deisseroth et al. |
| 7,672,707 B2 | 3/2010 | Takeda |
| 7,672,717 B1 | 3/2010 | Zikov et al. |
| 7,672,730 B2 | 3/2010 | Firlik et al. |
| 7,676,263 B2 | 3/2010 | Harris et al. |
| 7,678,047 B2 | 3/2010 | Shiomi et al. |
| 7,678,061 B2 | 3/2010 | Lee et al. |
| 7,678,767 B2 | 3/2010 | Gong et al. |
| 7,680,526 B2 | 3/2010 | McIntyre et al. |
| 7,680,540 B2 | 3/2010 | Jensen et al. |
| 7,684,856 B2 | 3/2010 | Virtanen et al. |
| 7,684,858 B2 | 3/2010 | He et al. |
| 7,684,866 B2 | 3/2010 | Fowler et al. |
| 7,684,867 B2 | 3/2010 | Jaax et al. |
| 7,697,979 B2 | 4/2010 | Martinerie et al. |
| 7,702,387 B2 | 4/2010 | Stevenson et al. |
| 7,702,502 B2 | 4/2010 | Ricci et al. |
| 7,706,871 B2 | 4/2010 | Devlin et al. |
| 7,706,992 B2 | 4/2010 | Ricci et al. |
| 7,711,417 B2 | 5/2010 | John et al. |
| 7,711,432 B2 | 5/2010 | Thimineur et al. |
| 7,714,936 B1 | 5/2010 | Martin et al. |
| 7,715,894 B2 | 5/2010 | Dunseath et al. |
| 7,715,910 B2 | 5/2010 | Hargrove et al. |
| 7,715,919 B2 | 5/2010 | Osorio et al. |
| 7,720,519 B2 | 5/2010 | Ruohonen |
| 7,720,530 B2 | 5/2010 | Causevic |
| 7,725,174 B2 | 5/2010 | Kern et al. |
| 7,725,192 B2 | 5/2010 | Eskandar et al. |
| 7,727,161 B2 | 6/2010 | Coyle et al. |
| 7,729,740 B2 | 6/2010 | Kraus, Jr. et al. |
| 7,729,753 B2 | 6/2010 | Kremliovsky et al. |
| 7,729,755 B2 | 6/2010 | Laken |
| 7,729,773 B2 | 6/2010 | Sloan |
| 7,733,224 B2 | 6/2010 | Tran |
| 7,733,973 B2 | 6/2010 | Moriya et al. |
| 7,734,334 B2 | 6/2010 | Mietus et al. |
| 7,734,340 B2 | 6/2010 | De Ridder |
| 7,734,355 B2 | 6/2010 | Cohen et al. |
| 7,736,382 B2 | 6/2010 | Webb et al. |
| 7,737,687 B2 | 6/2010 | Na et al. |
| 7,738,683 B2 | 6/2010 | Cahill et al. |
| 7,740,592 B2 | 6/2010 | Graham et al. |
| 7,742,820 B2 | 6/2010 | Wyler et al. |
| 7,746,979 B2 | 6/2010 | Dilmanian et al. |
| 7,747,318 B2 | 6/2010 | John et al. |
| 7,747,325 B2 | 6/2010 | Dilorenzo |
| 7,747,326 B2 | 6/2010 | Velasco et al. |
| 7,747,551 B2 | 6/2010 | Snyder |
| 7,749,155 B1 | 7/2010 | Anderson et al. |
| 7,751,877 B2 | 7/2010 | Flaherty et al. |
| 7,751,878 B1 | 7/2010 | Merkle et al. |
| 7,753,836 B2 | 7/2010 | Peterchev |
| 7,754,190 B2 | 7/2010 | Suffin |
| 7,756,564 B2 | 7/2010 | Matsui et al. |
| 7,756,568 B2 | 7/2010 | Scarantino et al. |
| 7,756,584 B2 | 7/2010 | Sheffield et al. |
| 7,757,690 B2 | 7/2010 | Stahmann et al. |
| 7,758,503 B2 | 7/2010 | Lynn et al. |
| 7,763,588 B2 | 7/2010 | van Praag et al. |
| 7,764,987 B2 | 7/2010 | Dorr et al. |
| 7,765,088 B2 | 7/2010 | Drew |
| 7,766,827 B2 | 8/2010 | Balkin et al. |
| 7,769,424 B2 | 8/2010 | Sato |
| 7,769,431 B2 | 8/2010 | Scarantino et al. |
| 7,769,461 B2 | 8/2010 | Whitehurst et al. |
| 7,769,464 B2 | 8/2010 | Gerber et al. |
| 7,771,341 B2 | 8/2010 | Rogers |
| 7,771,364 B2 | 8/2010 | Arbel et al. |
| 7,774,052 B2 | 8/2010 | Burton et al. |
| 7,774,064 B2 | 8/2010 | Meyer et al. |
| 7,775,993 B2 | 8/2010 | Heruth et al. |
| 7,778,490 B2 | 8/2010 | Quist |
| 7,778,692 B2 | 8/2010 | Scarantino et al. |
| 7,778,693 B2 | 8/2010 | Barbour et al. |
| 7,783,362 B2 | 8/2010 | Whitehurst et al. |
| 7,787,937 B2 | 8/2010 | Scarantino et al. |
| 7,787,946 B2 | 8/2010 | Stahmann et al. |
| 7,792,575 B2 | 9/2010 | Fujimaki et al. |
| 7,794,403 B2 | 9/2010 | Schaafsma |

(56)                    References Cited

U.S. PATENT DOCUMENTS

| | | | |
|---|---|---|---|
| 7,794,406 | B2 | 9/2010 | Reisfeld et al. |
| 7,797,040 | B2 | 9/2010 | Pesaran et al. |
| 7,800,493 | B2 | 9/2010 | Terauchi et al. |
| 7,801,591 | B1 | 9/2010 | Shusterman |
| 7,801,592 | B2 | 9/2010 | Shan et al. |
| 7,801,593 | B2 | 9/2010 | Behbehani et al. |
| 7,801,601 | B2 | 9/2010 | Maschino et al. |
| 7,801,686 | B2 | 9/2010 | Hyde et al. |
| 7,803,118 | B2 | 9/2010 | Reisfeld et al. |
| 7,803,119 | B2 | 9/2010 | Reisfeld |
| 7,804,441 | B1 | 9/2010 | DeChiaro, Jr. |
| 7,805,203 | B2 | 9/2010 | Ben-David et al. |
| 7,809,433 | B2 | 10/2010 | Keenan |
| 7,809,434 | B2 | 10/2010 | Kofol et al. |
| 7,811,279 | B2 | 10/2010 | John |
| 7,819,794 | B2 | 10/2010 | Becker |
| 7,819,812 | B2 | 10/2010 | John et al. |
| 7,822,481 | B2 | 10/2010 | Gerber et al. |
| D627,476 | S | 11/2010 | Gaw et al. |
| 7,829,562 | B2 | 11/2010 | Shamloo et al. |
| 7,831,302 | B2 | 11/2010 | Thomas |
| 7,831,305 | B2 | 11/2010 | Gliner |
| 7,834,627 | B2 | 11/2010 | Sakai et al. |
| 7,835,787 | B2 | 11/2010 | Sajda et al. |
| 7,840,039 | B2 | 11/2010 | Fuchs |
| 7,840,248 | B2 | 11/2010 | Fuchs et al. |
| 7,840,250 | B2 | 11/2010 | Tucker |
| 7,840,257 | B2 | 11/2010 | Chance |
| 7,840,280 | B2 | 11/2010 | Parnis et al. |
| 7,841,986 | B2 | 11/2010 | He et al. |
| 7,844,324 | B2 | 11/2010 | Sarkela et al. |
| 7,848,803 | B1 | 12/2010 | Jaax et al. |
| 7,852,087 | B2 | 12/2010 | Wilt et al. |
| 7,853,321 | B2 | 12/2010 | Jaax et al. |
| 7,853,322 | B2 | 12/2010 | Bourget et al. |
| 7,853,323 | B2 | 12/2010 | Goetz |
| 7,853,329 | B2 | 12/2010 | DiLorenzo |
| 7,856,264 | B2 | 12/2010 | Firlik et al. |
| 7,860,548 | B2 | 12/2010 | McIntyre et al. |
| 7,860,552 | B2 | 12/2010 | Borsook et al. |
| 7,860,561 | B1 | 12/2010 | Modarres |
| 7,860,570 | B2 | 12/2010 | Whitehurst et al. |
| 7,863,272 | B2 | 1/2011 | Oksenberg et al. |
| 7,865,234 | B1 | 1/2011 | Modarres |
| 7,865,235 | B2 | 1/2011 | Le et al. |
| 7,865,244 | B2 | 1/2011 | Giftakis et al. |
| 7,869,867 | B2 | 1/2011 | Armstrong et al. |
| 7,869,884 | B2 | 1/2011 | Scott et al. |
| 7,869,885 | B2 | 1/2011 | Begnaud et al. |
| 7,872,235 | B2 | 1/2011 | Rousso et al. |
| 7,873,411 | B2 | 1/2011 | Eda et al. |
| 7,876,938 | B2 | 1/2011 | Huang et al. |
| 7,878,965 | B2 | 2/2011 | Haber et al. |
| 7,879,043 | B2 | 2/2011 | Meneghini et al. |
| 7,881,760 | B2 | 2/2011 | Matsui et al. |
| 7,881,770 | B2 | 2/2011 | Melkent et al. |
| 7,881,780 | B2 | 2/2011 | Flaherty |
| 7,882,135 | B2 | 2/2011 | Brunner et al. |
| 7,884,101 | B2 | 2/2011 | Teegarden et al. |
| 7,887,493 | B2 | 2/2011 | Stahmann et al. |
| 7,890,155 | B2 | 2/2011 | Burns et al. |
| 7,890,176 | B2 | 2/2011 | Jaax et al. |
| 7,890,185 | B2 | 2/2011 | Cohen et al. |
| 7,891,814 | B2 | 2/2011 | Harada et al. |
| 7,892,764 | B2 | 2/2011 | Xiong et al. |
| 7,894,890 | B2 | 2/2011 | Sun et al. |
| 7,894,903 | B2 | 2/2011 | John |
| 7,895,033 | B2 | 2/2011 | Joublin et al. |
| 7,896,807 | B2 | 3/2011 | Clancy et al. |
| 7,899,524 | B2 | 3/2011 | Kozel |
| 7,899,525 | B2 | 3/2011 | John et al. |
| 7,899,539 | B2 | 3/2011 | Whitehurst et al. |
| 7,899,545 | B2 | 3/2011 | John |
| 7,901,211 | B2 | 3/2011 | Pennebaker |
| 7,904,134 | B2 | 3/2011 | McIntyre et al. |
| 7,904,139 | B2 | 3/2011 | Chance |
| 7,904,144 | B2 | 3/2011 | Causevic et al. |
| 7,904,151 | B2 | 3/2011 | Ben-David et al. |
| 7,904,175 | B2 | 3/2011 | Scott et al. |
| 7,904,507 | B2 | 3/2011 | Jung et al. |
| 7,907,994 | B2 | 3/2011 | Stolarski et al. |
| 7,907,998 | B2 | 3/2011 | Arad |
| 7,908,008 | B2 | 3/2011 | Ben-David et al. |
| 7,908,009 | B2 | 3/2011 | Wyler et al. |
| 7,909,771 | B2 | 3/2011 | Meyer et al. |
| 7,912,530 | B2 | 3/2011 | Seki et al. |
| 7,917,199 | B2 | 3/2011 | Drew et al. |
| 7,917,206 | B2 | 3/2011 | Frei et al. |
| 7,917,221 | B2 | 3/2011 | Tass |
| 7,917,225 | B2 | 3/2011 | Wyler et al. |
| 7,918,779 | B2 | 4/2011 | Haber et al. |
| 7,920,914 | B2 | 4/2011 | Shieh et al. |
| 7,920,915 | B2 | 4/2011 | Mann et al. |
| 7,920,916 | B2 | 4/2011 | Johnson et al. |
| 7,925,353 | B1 | 4/2011 | Whitehurst et al. |
| 7,929,693 | B2 | 4/2011 | Terauchi et al. |
| 7,930,035 | B2 | 4/2011 | DiLorenzo |
| 7,932,225 | B2 | 4/2011 | Gong et al. |
| 7,933,645 | B2 | 4/2011 | Strychacz et al. |
| 7,933,646 | B2 | 4/2011 | Frei et al. |
| 7,933,727 | B2 | 4/2011 | Taulu et al. |
| 7,937,138 | B2 | 5/2011 | Liley |
| 7,937,152 | B1 | 5/2011 | Lozano |
| 7,937,222 | B2 | 5/2011 | Donadille et al. |
| 7,938,782 | B2 | 5/2011 | Stahmann et al. |
| 7,938,785 | B2 | 5/2011 | Aguilar et al. |
| 7,941,209 | B2 | 5/2011 | Hughes et al. |
| 7,942,824 | B1 | 5/2011 | Kayyali et al. |
| 7,944,551 | B2 | 5/2011 | Addison et al. |
| 7,945,304 | B2 | 5/2011 | Feinberg |
| 7,945,316 | B2 | 5/2011 | Giftakis et al. |
| 7,945,330 | B2 | 5/2011 | Gliner et al. |
| 7,957,796 | B2 | 6/2011 | Maschino |
| 7,957,797 | B2 | 6/2011 | Bourget et al. |
| 7,957,806 | B2 | 6/2011 | Stevenson et al. |
| 7,957,809 | B2 | 6/2011 | Bourget et al. |
| 7,961,922 | B2 | 6/2011 | Spence et al. |
| 7,962,204 | B2 | 6/2011 | Suffin et al. |
| 7,962,214 | B2 | 6/2011 | Byerman et al. |
| 7,962,219 | B2 | 6/2011 | Jaax et al. |
| 7,962,220 | B2 | 6/2011 | Kolafa et al. |
| 7,970,734 | B2 | 6/2011 | Townsend et al. |
| 7,972,278 | B2 | 7/2011 | Graham et al. |
| 7,974,688 | B2 | 7/2011 | Armstrong et al. |
| 7,974,693 | B2 | 7/2011 | Ben-David et al. |
| 7,974,696 | B1 | 7/2011 | DiLorenzo |
| 7,974,697 | B2 | 7/2011 | Maschino et al. |
| 7,974,701 | B2 | 7/2011 | Armstrong |
| 7,974,787 | B2 | 7/2011 | Hyde et al. |
| 7,976,465 | B2 | 7/2011 | Frei et al. |
| 7,983,740 | B2 | 7/2011 | Culver et al. |
| 7,983,741 | B2 | 7/2011 | Chance |
| 7,983,757 | B2 | 7/2011 | Miyazawa et al. |
| 7,983,762 | B2 | 7/2011 | Gliner et al. |
| 7,986,991 | B2 | 7/2011 | Prichep |
| 7,988,613 | B2 | 8/2011 | Becker |
| 7,988,969 | B2 | 8/2011 | Poduslo et al. |
| 7,991,461 | B2 | 8/2011 | Flaherty et al. |
| 7,991,477 | B2 | 8/2011 | McDonald, III |
| 7,993,279 | B2 | 8/2011 | Hartley et al. |
| 7,996,075 | B2 | 8/2011 | Korzinov et al. |
| 7,996,079 | B2 | 8/2011 | Armstrong |
| 8,000,767 | B2 | 8/2011 | Eden et al. |
| 8,000,773 | B2 | 8/2011 | Rousso et al. |
| 8,000,788 | B2 | 8/2011 | Giftakis et al. |
| 8,000,793 | B2 | 8/2011 | Libbus |
| 8,000,794 | B2 | 8/2011 | Lozano |
| 8,000,795 | B2 | 8/2011 | Lozano |
| 8,001,179 | B2 | 8/2011 | Jung et al. |
| 8,002,553 | B2 | 8/2011 | Hatlestad et al. |
| 8,005,534 | B2 | 8/2011 | Greenwald et al. |
| 8,005,624 | B1 | 8/2011 | Starr |
| 8,005,894 | B2 | 8/2011 | Jung et al. |
| 8,010,178 | B2 | 8/2011 | Seki et al. |

(56) References Cited

U.S. PATENT DOCUMENTS

| | | | |
|---|---|---|---|
| 8,010,347 B2 | 8/2011 | Ricci et al. |
| 8,012,107 B2 | 9/2011 | Einav et al. |
| 8,014,847 B2 | 9/2011 | Shastri et al. |
| 8,014,870 B2 | 9/2011 | Seidman |
| 8,016,597 B2 | 9/2011 | Becker et al. |
| 8,019,400 B2 | 9/2011 | Diab et al. |
| 8,019,410 B1 | 9/2011 | Bharmi et al. |
| 8,024,029 B2 | 9/2011 | Drew et al. |
| 8,024,032 B1 | 9/2011 | Osorio et al. |
| 8,025,404 B2 | 9/2011 | Bolger et al. |
| 8,027,730 B2 | 9/2011 | John |
| 8,029,553 B2 | 10/2011 | Nemenov |
| 8,031,076 B2 | 10/2011 | Sachanandani et al. |
| 8,032,209 B2 | 10/2011 | He et al. |
| 8,032,229 B2 | 10/2011 | Gerber et al. |
| 8,032,486 B2 | 10/2011 | Townsend et al. |
| 8,033,996 B2 | 10/2011 | Behar |
| 8,036,434 B2 | 10/2011 | Hewett et al. |
| 8,036,728 B2 | 10/2011 | Diab et al. |
| 8,036,736 B2 | 10/2011 | Snyder et al. |
| 8,036,745 B2 | 10/2011 | Ben-David et al. |
| 8,041,136 B2 | 10/2011 | Causevic |
| 8,041,418 B2 | 10/2011 | Giftakis et al. |
| 8,041,419 B2 | 10/2011 | Giftakis et al. |
| 8,046,041 B2 | 10/2011 | Diab et al. |
| 8,046,042 B2 | 10/2011 | Diab et al. |
| 8,046,076 B2 | 10/2011 | Whitehurst et al. |
| 8,050,768 B2 | 11/2011 | Firlik et al. |
| 8,055,348 B2 | 11/2011 | Heruth et al. |
| 8,055,591 B2 | 11/2011 | Jung et al. |
| 8,059,879 B2 | 11/2011 | Tsukimoto |
| 8,060,181 B2 | 11/2011 | Rodriguez Ponce et al. |
| 8,060,194 B2 | 11/2011 | Flaherty |
| 8,064,994 B2 | 11/2011 | Pardo et al. |
| 8,065,011 B2 | 11/2011 | Echauz et al. |
| 8,065,012 B2 | 11/2011 | Firlik et al. |
| 8,065,017 B2 | 11/2011 | Cornejo Cruz et al. |
| 8,065,240 B2 | 11/2011 | Jung et al. |
| 8,065,360 B2 | 11/2011 | Jung et al. |
| 8,066,637 B2 | 11/2011 | Childre et al. |
| 8,066,647 B2 | 11/2011 | Armitstead |
| 8,068,904 B2 | 11/2011 | Sun et al. |
| 8,068,911 B2 | 11/2011 | Giftakis et al. |
| 8,069,125 B2 | 11/2011 | Jung et al. |
| 8,073,534 B2 | 12/2011 | Low |
| 8,073,546 B2 | 12/2011 | Sheffield et al. |
| 8,073,631 B2 | 12/2011 | Wilber et al. |
| 8,075,499 B2 | 12/2011 | Nathan et al. |
| 8,079,953 B2 | 12/2011 | Braun et al. |
| 8,082,031 B2 | 12/2011 | Ochs |
| 8,082,033 B2 | 12/2011 | Rezai et al. |
| 8,082,215 B2 | 12/2011 | Jung et al. |
| 8,083,786 B2 | 12/2011 | Gafni et al. |
| 8,086,294 B2 | 12/2011 | Echauz et al. |
| 8,086,296 B2 | 12/2011 | Bystritsky |
| 8,086,563 B2 | 12/2011 | Jung et al. |
| 8,088,057 B2 | 1/2012 | Honeycutt et al. |
| 8,089,283 B2 | 1/2012 | Kaplan et al. |
| 8,090,164 B2 | 1/2012 | Bullitt et al. |
| 8,092,549 B2 | 1/2012 | Hillis et al. |
| 8,095,209 B2 | 1/2012 | Flaherty |
| 8,095,210 B2 | 1/2012 | Burdick et al. |
| 8,097,926 B2 | 1/2012 | De Graff et al. |
| 8,099,299 B2 | 1/2012 | Sirohey et al. |
| 8,103,333 B2 | 1/2012 | Tran |
| 8,108,033 B2 | 1/2012 | Drew et al. |
| 8,108,036 B2 | 1/2012 | Tran |
| 8,108,038 B2 | 1/2012 | Giftakis et al. |
| 8,108,039 B2 | 1/2012 | Saliga et al. |
| 8,108,042 B1 | 1/2012 | Johnson et al. |
| 8,112,148 B2 | 2/2012 | Giftakis et al. |
| 8,112,153 B2 | 2/2012 | Giftakis et al. |
| 8,114,021 B2 | 2/2012 | Robertson et al. |
| 8,116,874 B2 | 2/2012 | Tass |
| 8,116,877 B2 | 2/2012 | Lozano |
| 8,116,883 B2 | 2/2012 | Williams et al. |
| 8,121,361 B2 | 2/2012 | Ernst et al. |
| 8,121,673 B2 | 2/2012 | Tran |
| 8,121,694 B2 | 2/2012 | Molnar et al. |
| 8,121,695 B2 | 2/2012 | Gliner et al. |
| 8,126,228 B2 | 2/2012 | Fueyo et al. |
| 8,126,243 B2 | 2/2012 | Hamada et al. |
| 8,126,528 B2 | 2/2012 | Diab et al. |
| 8,126,542 B2 | 2/2012 | Grey |
| 8,126,567 B2 | 2/2012 | Gerber et al. |
| 8,126,568 B2 | 2/2012 | Gliner |
| 8,128,572 B2 | 3/2012 | Diab et al. |
| 8,131,354 B2 | 3/2012 | Arad |
| 8,131,526 B2 | 3/2012 | Neville |
| 8,133,172 B2 | 3/2012 | Shachar et al. |
| 8,135,472 B2 | 3/2012 | Fowler et al. |
| 8,135,957 B2 | 3/2012 | Dinges et al. |
| 8,137,269 B2 | 3/2012 | Sheikhzadeh-Nadjar et al. |
| 8,137,270 B2 | 3/2012 | Keenan et al. |
| 8,140,152 B2 | 3/2012 | John et al. |
| 8,145,295 B2 | 3/2012 | Boyden et al. |
| 8,145,310 B2 | 3/2012 | Dong et al. |
| 8,148,417 B2 | 4/2012 | Teegarden et al. |
| 8,148,418 B2 | 4/2012 | Teegarden et al. |
| 8,150,508 B2 | 4/2012 | Craig |
| 8,150,523 B2 | 4/2012 | Schiff et al. |
| 8,150,524 B2 | 4/2012 | Maschino et al. |
| 8,150,796 B2 | 4/2012 | Jung et al. |
| 8,152,732 B2 | 4/2012 | Lynn et al. |
| 8,155,726 B2 | 4/2012 | Seki et al. |
| 8,155,736 B2 | 4/2012 | Sullivan et al. |
| 8,160,273 B2 | 4/2012 | Visser et al. |
| 8,160,317 B2 | 4/2012 | Amunts et al. |
| 8,160,680 B2 | 4/2012 | Boyden et al. |
| 8,160,689 B2 | 4/2012 | Jadidi |
| 8,160,696 B2 | 4/2012 | Bendett et al. |
| 8,165,687 B2 | 4/2012 | Cornejo Cruz et al. |
| 8,167,784 B1 | 5/2012 | Honeycutt et al. |
| 8,167,826 B2 | 5/2012 | Oohashi et al. |
| 8,170,315 B2 | 5/2012 | Mistretta et al. |
| 8,170,347 B2 | 5/2012 | Ancelin |
| 8,172,759 B2 | 5/2012 | Bukhman |
| 8,172,766 B1 | 5/2012 | Kayyali et al. |
| 8,174,430 B1 | 5/2012 | DeChiaro, Jr. |
| 8,175,359 B2 | 5/2012 | O'Halloran et al. |
| 8,175,360 B2 | 5/2012 | Razifar et al. |
| 8,175,686 B2 | 5/2012 | Utsugi et al. |
| 8,175,696 B2 | 5/2012 | Liley et al. |
| 8,175,700 B2 | 5/2012 | Johnson et al. |
| 8,177,724 B2 | 5/2012 | Derchak et al. |
| 8,177,726 B2 | 5/2012 | John |
| 8,177,727 B2 | 5/2012 | Kwak |
| 8,180,125 B2 | 5/2012 | Avinash et al. |
| 8,180,148 B2 | 5/2012 | Cover et al. |
| 8,180,420 B2 | 5/2012 | Diab et al. |
| 8,180,436 B2 | 5/2012 | Boyden et al. |
| 8,180,601 B2 | 5/2012 | Butson et al. |
| 8,185,186 B2 | 5/2012 | Ross et al. |
| 8,185,207 B2 | 5/2012 | Molnar et al. |
| 8,185,382 B2 | 5/2012 | Joublin et al. |
| 8,187,181 B2 | 5/2012 | Osorio et al. |
| 8,187,201 B2 | 5/2012 | Lynn |
| 8,188,749 B2 | 5/2012 | Wilt et al. |
| 8,190,227 B2 | 5/2012 | Diab et al. |
| 8,190,248 B2 | 5/2012 | Besio et al. |
| 8,190,249 B1 | 5/2012 | Gharieb et al. |
| 8,190,251 B2 | 5/2012 | Molnar et al. |
| 8,190,264 B2 | 5/2012 | Lozano et al. |
| 8,195,295 B2 | 6/2012 | Stevenson et al. |
| 8,195,298 B2 | 6/2012 | Lozano |
| 8,195,300 B2 | 6/2012 | Gliner et al. |
| 8,195,593 B2 | 6/2012 | Jung et al. |
| 8,197,395 B2 | 6/2012 | Jassemidis et al. |
| 8,197,437 B2 | 6/2012 | Kalafut et al. |
| 8,199,982 B2 | 6/2012 | Fueyo et al. |
| 8,199,985 B2 | 6/2012 | Jakobsson et al. |
| 8,200,319 B2 | 6/2012 | Pu et al. |
| 8,200,340 B2 | 6/2012 | Skelton et al. |
| 8,204,583 B2 | 6/2012 | Sackellares et al. |

(56) References Cited

U.S. PATENT DOCUMENTS

| | | |
|---|---|---|
| 8,204,603 B2 | 6/2012 | Maschino |
| 8,209,009 B2 | 6/2012 | Giftakis et al. |
| 8,209,018 B2 | 6/2012 | Osorio et al. |
| 8,209,019 B2 | 6/2012 | Giftakis et al. |
| 8,209,224 B2 | 6/2012 | Pradeep et al. |
| 8,211,035 B2 | 7/2012 | Melker et al. |
| 8,212,556 B1 | 7/2012 | Schwindt et al. |
| 8,213,670 B2 | 7/2012 | Lai |
| 8,214,007 B2 | 7/2012 | Baker et al. |
| 8,214,035 B2 | 7/2012 | Giftakis et al. |
| 8,219,188 B2 | 7/2012 | Craig |
| 8,221,330 B2 | 7/2012 | Sarkela et al. |
| 8,222,378 B2 | 7/2012 | Masure |
| 8,223,023 B2 | 7/2012 | Sachanandani et al. |
| 8,224,431 B2 | 7/2012 | Drew |
| 8,224,433 B2 | 7/2012 | Suffin et al. |
| 8,224,444 B2 | 7/2012 | Ben-David et al. |
| 8,224,451 B2 | 7/2012 | Jaax et al. |
| 8,229,540 B2 | 7/2012 | Sami et al. |
| 8,229,559 B2 | 7/2012 | Westendorp et al. |
| 8,233,682 B2 | 7/2012 | Fessler et al. |
| 8,233,689 B2 | 7/2012 | Razifar et al. |
| 8,233,965 B2 | 7/2012 | Bjornerud et al. |
| 8,233,990 B2 | 7/2012 | Goetz |
| 8,235,907 B2 | 8/2012 | Wilk et al. |
| 8,236,005 B2 | 8/2012 | Meneghini et al. |
| 8,236,038 B2 | 8/2012 | Nofzinger |
| 8,239,014 B2 | 8/2012 | Ochs |
| 8,239,028 B2 | 8/2012 | Scott |
| 8,239,029 B2 | 8/2012 | De Ridder |
| 8,239,030 B1 | 8/2012 | Hagedorn et al. |
| 8,241,213 B2 | 8/2012 | Lynn et al. |
| 8,244,340 B2 | 8/2012 | Wu et al. |
| 8,244,341 B2 | 8/2012 | Hinrikus et al. |
| 8,244,347 B2 | 8/2012 | Lozano |
| 8,244,475 B2 | 8/2012 | Aguilar et al. |
| 8,244,552 B2 | 8/2012 | Firminger et al. |
| 8,244,553 B2 | 8/2012 | Firminger et al. |
| 8,248,069 B2 | 8/2012 | Buracas |
| 8,249,316 B2 | 8/2012 | Hu et al. |
| 8,249,698 B2 | 8/2012 | Mugler et al. |
| 8,249,718 B2 | 8/2012 | Skelton et al. |
| 8,249,815 B2 | 8/2012 | Taylor |
| 8,260,426 B2 | 9/2012 | Armstrong et al. |
| 8,262,714 B2 | 9/2012 | Hulvershorn et al. |
| 8,263,574 B2 | 9/2012 | Schaller et al. |
| 8,267,851 B1 | 9/2012 | Kroll |
| 8,270,814 B2 | 9/2012 | Pradeep et al. |
| 8,271,077 B1 | 9/2012 | Rotenberg |
| 8,280,502 B2 | 10/2012 | Hargrove et al. |
| 8,280,503 B2 | 10/2012 | Linderman |
| 8,280,505 B2 | 10/2012 | Craig |
| 8,280,514 B2 | 10/2012 | Lozano et al. |
| 8,280,517 B2 | 10/2012 | Skelton et al. |
| 8,285,351 B2 | 10/2012 | Johnson et al. |
| 8,285,368 B2 | 10/2012 | Chen et al. |
| 8,290,575 B2 | 10/2012 | Tarassenko et al. |
| 8,290,596 B2 | 10/2012 | Wei et al. |
| 8,295,914 B2 | 10/2012 | Kalafut et al. |
| 8,295,934 B2 | 10/2012 | Leyde |
| 8,295,935 B2 | 10/2012 | Okun et al. |
| 8,296,108 B2 | 10/2012 | Tanaka |
| 8,298,078 B2 | 10/2012 | Sutton et al. |
| 8,298,140 B2 | 10/2012 | Beck-Nielsen et al. |
| 8,301,222 B2 | 10/2012 | Rongen et al. |
| 8,301,232 B2 | 10/2012 | Albert et al. |
| 8,301,233 B2 | 10/2012 | Zhang et al. |
| 8,301,257 B2 | 10/2012 | Hsu et al. |
| 8,303,636 B2 | 11/2012 | Schiffer |
| 8,304,246 B2 | 11/2012 | Cook et al. |
| 8,305,078 B2 | 11/2012 | Savukov et al. |
| 8,306,607 B1 | 11/2012 | Levi et al. |
| 8,306,610 B2 | 11/2012 | Mirow |
| 8,306,627 B2 | 11/2012 | Armstrong |
| 8,308,646 B2 | 11/2012 | Belohlavek et al. |
| 8,308,661 B2 | 11/2012 | Miesel et al. |
| 8,311,622 B2 | 11/2012 | Snyder et al. |
| 8,311,747 B2 | 11/2012 | Taylor |
| 8,311,748 B2 | 11/2012 | Taylor et al. |
| 8,311,750 B2 | 11/2012 | Taylor |
| 8,313,441 B2 | 11/2012 | Dalton |
| 8,314,707 B2 | 11/2012 | Kobetski et al. |
| 8,315,703 B2 | 11/2012 | Lozano |
| 8,315,704 B2 | 11/2012 | Jaax et al. |
| 8,315,710 B2 | 11/2012 | Skelton et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,315,962 B1 | 11/2012 | Horne |
| 8,315,970 B2 | 11/2012 | Zalay et al. |
| 8,320,649 B2 | 11/2012 | Shahaf et al. |
| 8,321,150 B2 | 11/2012 | Taylor |
| 8,323,188 B2 | 12/2012 | Tran |
| 8,323,189 B2 | 12/2012 | Tran et al. |
| 8,323,204 B2 | 12/2012 | Stahmann et al. |
| 8,326,418 B2 | 12/2012 | Sommer et al. |
| 8,326,420 B2 | 12/2012 | Skelton et al. |
| 8,326,433 B2 | 12/2012 | Blum et al. |
| 8,328,718 B2 | 12/2012 | Tran |
| 8,332,017 B2 | 12/2012 | Tarassenko et al. |
| 8,332,024 B2 | 12/2012 | Rapoport et al. |
| 8,332,038 B2 | 12/2012 | Heruth et al. |
| 8,332,041 B2 | 12/2012 | Skelton et al. |
| 8,332,191 B2 | 12/2012 | Rosthal et al. |
| 8,334,690 B2 | 12/2012 | Kitching et al. |
| 8,335,561 B1 | 12/2012 | Modarres |
| 8,335,664 B2 | 12/2012 | Eberle |
| 8,335,715 B2 | 12/2012 | Pradeep et al. |
| 8,335,716 B2 | 12/2012 | Pradeep et al. |
| 8,337,404 B2 | 12/2012 | Osorio |
| 8,340,752 B2 | 12/2012 | Cox et al. |
| 8,340,753 B2 | 12/2012 | Hardt |
| 8,340,771 B2 | 12/2012 | Thimineur et al. |
| 8,343,026 B2 | 1/2013 | Gardiner et al. |
| 8,343,027 B1 | 1/2013 | DiMino et al. |
| 8,343,066 B1 | 1/2013 | Eagleman et al. |
| 8,346,331 B2 | 1/2013 | Bunce et al. |
| 8,346,342 B2 | 1/2013 | Kalafut |
| 8,346,349 B2 | 1/2013 | Guttag et al. |
| 8,346,354 B2 | 1/2013 | Hyde et al. |
| 8,346,365 B2 | 1/2013 | Lozano |
| 8,350,804 B1 | 1/2013 | Moll |
| 8,352,023 B2 | 1/2013 | John et al. |
| 8,352,031 B2 | 1/2013 | Rousso et al. |
| 8,353,837 B2 | 1/2013 | John et al. |
| 8,354,438 B2 | 1/2013 | Chez |
| 8,354,881 B2 | 1/2013 | Denison |
| 8,355,768 B2 | 1/2013 | Masmanidis et al. |
| 8,356,004 B2 | 1/2013 | Jung et al. |
| 8,356,594 B2 | 1/2013 | Ujhazy et al. |
| 8,358,818 B2 | 1/2013 | Miga et al. |
| 8,359,080 B2 | 1/2013 | Diab et al. |
| 8,362,780 B2 | 1/2013 | Rosthal et al. |
| 8,364,226 B2 | 1/2013 | Diab et al. |
| 8,364,254 B2 | 1/2013 | Jacquin et al. |
| 8,364,255 B2 | 1/2013 | Isenhart et al. |
| 8,364,271 B2 | 1/2013 | De Ridder |
| 8,364,272 B2 | 1/2013 | Goetz |
| 8,369,940 B2 | 2/2013 | Sun et al. |
| 8,374,411 B2 | 2/2013 | Ernst et al. |
| 8,374,412 B2 | 2/2013 | Kimura |
| 8,374,690 B2 | 2/2013 | Ma |
| 8,374,696 B2 | 2/2013 | Sanchez et al. |
| 8,374,701 B2 | 2/2013 | Hyde et al. |
| 8,374,703 B2 | 2/2013 | Imran |
| 8,376,965 B2 | 2/2013 | Schuette et al. |
| 8,379,947 B2 | 2/2013 | Garg et al. |
| 8,379,952 B2 | 2/2013 | McIntyre et al. |
| 8,380,289 B2 | 2/2013 | Zellers et al. |
| 8,380,290 B2 | 2/2013 | Scarantino et al. |
| 8,380,296 B2 | 2/2013 | Lee et al. |
| 8,380,314 B2 | 2/2013 | Panken et al. |
| 8,380,316 B2 | 2/2013 | Hagedorn et al. |
| 8,380,658 B2 | 2/2013 | Jung et al. |

(56)                References Cited

U.S. PATENT DOCUMENTS

| | | | |
|---|---|---|---|
| 8,382,667 | B2 | 2/2013 | Osorio |
| 8,386,188 | B2 | 2/2013 | Taylor et al. |
| 8,386,244 | B2 | 2/2013 | Ricci et al. |
| 8,386,312 | B2 | 2/2013 | Pradeep et al. |
| 8,386,313 | B2 | 2/2013 | Pradeep et al. |
| RE44,097 | E | 3/2013 | Wilber et al. |
| 8,388,529 | B2 | 3/2013 | Fueyo et al. |
| 8,388,530 | B2 | 3/2013 | Shusterman |
| 8,388,555 | B2 | 3/2013 | Panken et al. |
| 8,391,942 | B2 | 3/2013 | Benni |
| 8,391,956 | B2 | 3/2013 | Zellers et al. |
| 8,391,966 | B2 | 3/2013 | Luo et al. |
| 8,392,250 | B2 | 3/2013 | Pradeep et al. |
| 8,392,251 | B2 | 3/2013 | Pradeep et al. |
| 8,392,253 | B2 | 3/2013 | Pradeep et al. |
| 8,392,254 | B2 | 3/2013 | Pradeep et al. |
| 8,392,255 | B2 | 3/2013 | Pradeep et al. |
| 8,396,542 | B2 | 3/2013 | Johnson et al. |
| 8,396,545 | B2 | 3/2013 | Berridge et al. |
| 8,396,546 | B2 | 3/2013 | Hirata et al. |
| 8,396,557 | B2 | 3/2013 | DiLorenzo |
| 8,396,565 | B2 | 3/2013 | Singhal et al. |
| 8,396,744 | B2 | 3/2013 | Pradeep et al. |
| 8,398,692 | B2 | 3/2013 | Deisseroth et al. |
| 8,401,624 | B2 | 3/2013 | Govari |
| 8,401,626 | B2 | 3/2013 | Mietus et al. |
| 8,401,634 | B2 | 3/2013 | Whitehurst et al. |
| 8,401,654 | B1 | 3/2013 | Foster et al. |
| 8,401,655 | B2 | 3/2013 | De Ridder |
| 8,401,666 | B2 | 3/2013 | Skelton et al. |
| 8,403,848 | B2 | 3/2013 | Mietus et al. |
| 8,406,838 | B2 | 3/2013 | Kato |
| 8,406,841 | B2 | 3/2013 | Lin et al. |
| 8,406,848 | B2 | 3/2013 | Wu et al. |
| 8,406,862 | B2 | 3/2013 | Hopenfeld |
| 8,406,890 | B2 | 3/2013 | Goetz |
| 8,412,334 | B2 | 4/2013 | Whitehurst et al. |
| 8,412,335 | B2 | 4/2013 | Gliner et al. |
| 8,412,337 | B2 | 4/2013 | Lozano |
| 8,412,338 | B2 | 4/2013 | Faltys |
| 8,412,655 | B2 | 4/2013 | Colman et al. |
| 8,415,123 | B2 | 4/2013 | Pilla et al. |
| 8,417,344 | B2 | 4/2013 | Colborn et al. |
| 8,423,118 | B2 | 4/2013 | Wenzel et al. |
| 8,423,125 | B2 | 4/2013 | Rousso et al. |
| 8,423,144 | B2 | 4/2013 | Tass et al. |
| 8,423,155 | B1 | 4/2013 | Jaax et al. |
| 8,423,297 | B2 | 4/2013 | Wilber |
| 8,425,415 | B2 | 4/2013 | Tran |
| 8,425,583 | B2 | 4/2013 | Nofzinger |
| 8,428,696 | B2 | 4/2013 | Foo |
| 8,428,703 | B2 | 4/2013 | Hopenfeld |
| 8,428,704 | B2 | 4/2013 | Johnson et al. |
| 8,428,726 | B2 | 4/2013 | Ignagni et al. |
| 8,429,225 | B2 | 4/2013 | Jung et al. |
| 8,430,805 | B2 | 4/2013 | Burnett et al. |
| 8,430,816 | B2 | 4/2013 | Avinash et al. |
| 8,431,537 | B2 | 4/2013 | Gong et al. |
| 8,433,388 | B2 | 4/2013 | Blunt et al. |
| 8,433,410 | B2 | 4/2013 | Stevenson et al. |
| 8,433,414 | B2 | 4/2013 | Gliner et al. |
| 8,433,418 | B2 | 4/2013 | DeRidder |
| 8,435,166 | B2 | 5/2013 | Burnett et al. |
| 8,437,843 | B1 | 5/2013 | Kayyali et al. |
| 8,437,844 | B2 | 5/2013 | Syed Momen et al. |
| 8,437,861 | B2 | 5/2013 | Skelton et al. |
| 8,439,845 | B2 | 5/2013 | Folkerts et al. |
| 8,442,626 | B2 | 5/2013 | Zavoronkovs et al. |
| 8,444,571 | B2 | 5/2013 | Folkerts et al. |
| 8,445,021 | B2 | 5/2013 | Akhtari et al. |
| 8,445,851 | B2 | 5/2013 | Rousso et al. |
| 8,447,392 | B2 | 5/2013 | Llinas |
| 8,447,407 | B2 | 5/2013 | Talathi et al. |
| 8,447,411 | B2 | 5/2013 | Skelton et al. |
| 8,449,471 | B2 | 5/2013 | Tran |
| 8,452,387 | B2 | 5/2013 | Osorio et al. |
| 8,452,544 | B2 | 5/2013 | Hymel |
| 8,454,555 | B2 | 6/2013 | Struijk et al. |
| 8,456,164 | B2 | 6/2013 | Subbarao |
| 8,456,166 | B2 | 6/2013 | DePavia et al. |
| 8,456,309 | B2 | 6/2013 | Sachanandani et al. |
| 8,457,730 | B2 | 6/2013 | Makinen |
| 8,457,746 | B2 | 6/2013 | Libbus |
| 8,457,747 | B2 | 6/2013 | Terry, Jr. |
| 8,461,988 | B2 | 6/2013 | Tran |
| 8,463,006 | B2 | 6/2013 | Prokoski |
| 8,463,007 | B2 | 6/2013 | Steinberg et al. |
| 8,463,349 | B2 | 6/2013 | Diab et al. |
| 8,463,370 | B2 | 6/2013 | Korhonen et al. |
| 8,463,374 | B2 | 6/2013 | Hudson et al. |
| 8,463,378 | B2 | 6/2013 | Tass |
| 8,463,386 | B2 | 6/2013 | Tass |
| 8,463,387 | B2 | 6/2013 | De Ridder |
| 8,464,288 | B2 | 6/2013 | Pradeep et al. |
| 8,465,408 | B2 | 6/2013 | Phillips et al. |
| 8,467,877 | B2 | 6/2013 | Imran |
| 8,467,878 | B2 | 6/2013 | Lozano et al. |
| 8,473,024 | B2 | 6/2013 | Causevic et al. |
| 8,473,044 | B2 | 6/2013 | Lee et al. |
| 8,473,306 | B2 | 6/2013 | Seely |
| 8,473,345 | B2 | 6/2013 | Pradeep et al. |
| 8,475,354 | B2 | 7/2013 | Phillips et al. |
| 8,475,368 | B2 | 7/2013 | Tran et al. |
| 8,475,371 | B2 | 7/2013 | Derchak et al. |
| 8,475,387 | B2 | 7/2013 | Derchak et al. |
| 8,475,506 | B1 | 7/2013 | Bendett et al. |
| 8,478,389 | B1 | 7/2013 | Brockway et al. |
| 8,478,394 | B2 | 7/2013 | Prichep et al. |
| 8,478,402 | B2 | 7/2013 | Wahlstrand et al. |
| 8,478,417 | B2 | 7/2013 | Drew et al. |
| 8,478,428 | B2 | 7/2013 | Cowley |
| 8,480,554 | B2 | 7/2013 | Phillips et al. |
| 8,483,795 | B2 | 7/2013 | Okada |
| 8,483,815 | B2 | 7/2013 | Liley |
| 8,483,816 | B1 | 7/2013 | Payton et al. |
| 8,484,081 | B2 | 7/2013 | Pradeep et al. |
| 8,484,270 | B2 | 7/2013 | Kurtz et al. |
| 8,485,979 | B2 | 7/2013 | Giftakis et al. |
| 8,487,760 | B2 | 7/2013 | Kangas et al. |
| 8,489,185 | B2 | 7/2013 | Kilgard et al. |
| 8,492,336 | B2 | 7/2013 | Masure |
| 8,494,610 | B2 | 7/2013 | Pradeep et al. |
| 8,494,829 | B2 | 7/2013 | Teixeira |
| 8,494,857 | B2 | 7/2013 | Pakhomov |
| 8,494,905 | B2 | 7/2013 | Pradeep et al. |
| 8,496,594 | B2 | 7/2013 | Taylor et al. |
| 8,498,697 | B2 | 7/2013 | Yong et al. |
| 8,498,699 | B2 | 7/2013 | Wells et al. |
| 8,498,708 | B2 | 7/2013 | Bentwich |
| RE44,408 | E | 8/2013 | Lindsay |
| 8,500,282 | B2 | 8/2013 | Bolger et al. |
| 8,500,636 | B2 | 8/2013 | Tran |
| 8,504,150 | B2 | 8/2013 | Skelton |
| 8,506,469 | B2 | 8/2013 | Dietrich et al. |
| 8,509,879 | B2 | 8/2013 | Durkin et al. |
| 8,509,881 | B2 | 8/2013 | Thiagarajan et al. |
| 8,509,885 | B2 | 8/2013 | Snyder et al. |
| 8,509,904 | B2 | 8/2013 | Rickert et al. |
| 8,512,219 | B2 | 8/2013 | Ferren et al. |
| 8,512,221 | B2 | 8/2013 | Kaplan et al. |
| 8,512,240 | B1 | 8/2013 | Zuckerman-Stark et al. |
| 8,515,535 | B2 | 8/2013 | Hopper et al. |
| 8,515,538 | B1 | 8/2013 | Osorio et al. |
| 8,515,541 | B1 | 8/2013 | Jaax et al. |
| 8,515,549 | B2 | 8/2013 | Panken et al. |
| 8,515,550 | B2 | 8/2013 | Skelton et al. |
| 8,517,909 | B2 | 8/2013 | Honeycutt et al. |
| 8,517,912 | B2 | 8/2013 | Clare |
| 8,519,705 | B2 | 8/2013 | Savukov et al. |
| 8,519,853 | B2 | 8/2013 | Eskandarian et al. |
| 8,520,974 | B2 | 8/2013 | Fujita et al. |
| 8,521,284 | B2 | 8/2013 | Kim et al. |
| 8,523,779 | B2 | 9/2013 | Taylor et al. |
| 8,525,673 | B2 | 9/2013 | Tran |

(56) References Cited

U.S. PATENT DOCUMENTS

| | | | |
|---|---|---|---|
| 8,525,687 | B2 | 9/2013 | Tran |
| 8,527,029 | B2 | 9/2013 | Okada |
| 8,527,035 | B2 | 9/2013 | Diamond |
| 8,527,435 | B1 | 9/2013 | Han et al. |
| 8,529,463 | B2 | 9/2013 | Della Santina et al. |
| 8,531,291 | B2 | 9/2013 | Tran |
| 8,532,756 | B2 | 9/2013 | Schalk et al. |
| 8,532,757 | B2 | 9/2013 | Molnar et al. |
| 8,533,042 | B2 | 9/2013 | Pradeep et al. |
| 8,536,667 | B2 | 9/2013 | de Graff et al. |
| 8,538,108 | B2 | 9/2013 | Shekhar et al. |
| 8,538,512 | B1 | 9/2013 | Bibian et al. |
| 8,538,513 | B2 | 9/2013 | Molnar et al. |
| 8,538,514 | B2 | 9/2013 | Sun et al. |
| 8,538,523 | B2 | 9/2013 | Sommer et al. |
| 8,538,536 | B2 | 9/2013 | Rezai et al. |
| 8,538,543 | B2 | 9/2013 | McIntyre et al. |
| 8,538,700 | B2 | 9/2013 | Badri et al. |
| 8,538,705 | B2 | 9/2013 | Greenwald |
| 8,542,900 | B2 | 9/2013 | Tolkowsky et al. |
| 8,542,916 | B2 | 9/2013 | Tognoli et al. |
| 8,543,189 | B2 | 9/2013 | Paitel et al. |
| 8,543,199 | B2 | 9/2013 | Snyder et al. |
| 8,543,214 | B2 | 9/2013 | Osorio et al. |
| 8,543,219 | B2 | 9/2013 | Tass |
| 8,545,378 | B2 | 10/2013 | Peterchev |
| 8,545,416 | B1 | 10/2013 | Kayyali et al. |
| 8,545,420 | B2 | 10/2013 | Einav et al. |
| 8,545,436 | B2 | 10/2013 | Robertson et al. |
| 8,548,583 | B2 | 10/2013 | Rousso et al. |
| 8,548,594 | B2 | 10/2013 | Thimineur et al. |
| 8,548,604 | B2 | 10/2013 | Whitehurst et al. |
| 8,548,786 | B2 | 10/2013 | Plenz |
| 8,548,852 | B2 | 10/2013 | Pradeep et al. |
| 8,553,956 | B2 | 10/2013 | Wu et al. |
| 8,554,311 | B2 | 10/2013 | Warner et al. |
| 8,554,325 | B2 | 10/2013 | Molnar et al. |
| 8,559,645 | B2 | 10/2013 | Corona-Strauss et al. |
| 8,560,034 | B1 | 10/2013 | Diab et al. |
| 8,560,041 | B2 | 10/2013 | Flaherty et al. |
| 8,560,073 | B2 | 10/2013 | Osorio |
| 8,562,525 | B2 | 10/2013 | Nakashima et al. |
| 8,562,526 | B2 | 10/2013 | Heneghan et al. |
| 8,562,527 | B2 | 10/2013 | Braun et al. |
| 8,562,536 | B2 | 10/2013 | Osorio et al. |
| 8,562,540 | B2 | 10/2013 | Goodall et al. |
| 8,562,548 | B2 | 10/2013 | Shimada et al. |
| 8,562,660 | B2 | 10/2013 | Peyman |
| 8,562,951 | B2 | 10/2013 | Suffin et al. |
| 8,565,606 | B2 | 10/2013 | Kim et al. |
| 8,565,864 | B2 | 10/2013 | Drew et al. |
| 8,565,867 | B2 | 10/2013 | Armstrong et al. |
| 8,565,883 | B2 | 10/2013 | Lozano |
| 8,565,886 | B2 | 10/2013 | Nelson et al. |
| 8,568,231 | B2 | 10/2013 | Solanki et al. |
| 8,568,329 | B2 | 10/2013 | Lee et al. |
| 8,571,293 | B2 | 10/2013 | Ernst et al. |
| 8,571,629 | B2 | 10/2013 | Faro et al. |
| 8,571,642 | B2 | 10/2013 | Gill et al. |
| 8,571,643 | B2 | 10/2013 | Osorio et al. |
| 8,571,653 | B2 | 10/2013 | Ben-David et al. |
| 8,574,164 | B2 | 11/2013 | Mashiach |
| 8,574,279 | B2 | 11/2013 | Schiffer |
| 8,577,103 | B2 | 11/2013 | Vija et al. |
| 8,577,464 | B2 | 11/2013 | Mashiach |
| 8,577,465 | B2 | 11/2013 | Mashiach |
| 8,577,466 | B2 | 11/2013 | Mashiach |
| 8,577,467 | B2 | 11/2013 | Mashiach et al. |
| 8,577,468 | B2 | 11/2013 | Mashiach et al. |
| 8,577,472 | B2 | 11/2013 | Mashiach et al. |
| 8,577,478 | B2 | 11/2013 | Mashiach et al. |
| 8,579,786 | B2 | 11/2013 | Osorio et al. |
| 8,579,793 | B1 | 11/2013 | Honeycutt et al. |
| 8,579,795 | B2 | 11/2013 | Martel |
| 8,579,834 | B2 | 11/2013 | Davis et al. |
| 8,583,238 | B1 | 11/2013 | Heldman et al. |
| 8,583,252 | B2 | 11/2013 | Skelton et al. |
| 8,585,568 | B2 | 11/2013 | Phillips et al. |
| 8,586,019 | B2 | 11/2013 | Satchi-Fainaro et al. |
| 8,586,932 | B2 | 11/2013 | Rousso et al. |
| 8,587,304 | B2 | 11/2013 | Budker et al. |
| 8,588,486 | B2 | 11/2013 | Virtue et al. |
| 8,588,552 | B2 | 11/2013 | Garg et al. |
| 8,588,899 | B2 | 11/2013 | Schiff |
| 8,588,929 | B2 | 11/2013 | Skelton et al. |
| 8,588,933 | B2 | 11/2013 | Floyd et al. |
| 8,588,941 | B2 | 11/2013 | Mashiach |
| 8,589,316 | B2 | 11/2013 | Lujan et al. |
| 8,591,419 | B2 | 11/2013 | Tyler |
| 8,591,498 | B2 | 11/2013 | John |
| 8,593,141 | B1 | 11/2013 | Radparvar et al. |
| 8,593,154 | B2 | 11/2013 | Ross |
| 8,594,798 | B2 | 11/2013 | Osorio et al. |
| 8,594,800 | B2 | 11/2013 | Butson et al. |
| 8,594,950 | B2 | 11/2013 | Taylor |
| 8,597,171 | B2 | 12/2013 | Altman et al. |
| 8,597,193 | B2 | 12/2013 | Grunwald et al. |
| 8,600,493 | B2 | 12/2013 | Tanner et al. |
| 8,600,502 | B2 | 12/2013 | Lovett et al. |
| 8,600,513 | B2 | 12/2013 | Aur et al. |
| 8,600,521 | B2 | 12/2013 | Armstrong et al. |
| 8,600,696 | B2 | 12/2013 | Zafiris |
| 8,603,790 | B2 | 12/2013 | Deisseroth et al. |
| 8,606,349 | B2 | 12/2013 | Rousso et al. |
| 8,606,351 | B2 | 12/2013 | Wheeler |
| 8,606,356 | B2 | 12/2013 | Lee et al. |
| 8,606,360 | B2 | 12/2013 | Butson et al. |
| 8,606,361 | B2 | 12/2013 | Gliner et al. |
| 8,606,530 | B2 | 12/2013 | Taylor |
| 8,606,592 | B2 | 12/2013 | Hyde et al. |
| 8,612,005 | B2 | 12/2013 | Rezai et al. |
| 8,613,695 | B2 | 12/2013 | Von Ohlsen et al. |
| 8,613,905 | B2 | 12/2013 | El-Agnaf |
| 8,614,254 | B2 | 12/2013 | Llinas et al. |
| 8,614,873 | B1 | 12/2013 | Beran |
| 8,615,293 | B2 | 12/2013 | Jacobson et al. |
| 8,615,309 | B2 | 12/2013 | Craig |
| 8,615,479 | B2 | 12/2013 | Jung et al. |
| 8,615,664 | B2 | 12/2013 | Jung et al. |
| 8,618,799 | B1 | 12/2013 | Radparvar et al. |
| 8,620,206 | B2 | 12/2013 | Brown et al. |
| 8,620,419 | B2 | 12/2013 | Rotenberg et al. |
| 8,626,264 | B1 | 1/2014 | Beran |
| 8,626,301 | B2 | 1/2014 | Libbus |
| 8,628,328 | B2 | 1/2014 | Palacios |
| 8,628,480 | B2 | 1/2014 | Derchak |
| 8,630,699 | B2 | 1/2014 | Baker et al. |
| 8,630,705 | B2 | 1/2014 | Mann et al. |
| 8,630,812 | B2 | 1/2014 | Taylor |
| 8,632,465 | B1 | 1/2014 | Brockway |
| 8,632,750 | B2 | 1/2014 | Suffin et al. |
| 8,634,616 | B2 | 1/2014 | Den Harder et al. |
| 8,634,922 | B1 | 1/2014 | Osorio et al. |
| 8,635,105 | B2 | 1/2014 | Pradeep et al. |
| 8,636,640 | B2 | 1/2014 | Chang |
| 8,638,950 | B2 | 1/2014 | Anderson et al. |
| 8,641,632 | B2 | 2/2014 | Quintin et al. |
| 8,641,646 | B2 | 2/2014 | Colborn |
| 8,644,754 | B2 | 2/2014 | Brown |
| 8,644,910 | B2 | 2/2014 | Rousso et al. |
| 8,644,914 | B2 | 2/2014 | Hunt |
| 8,644,921 | B2 | 2/2014 | Wilson |
| 8,644,945 | B2 | 2/2014 | Skelton et al. |
| 8,644,946 | B2 | 2/2014 | Butson et al. |
| 8,644,954 | B2 | 2/2014 | Jaax et al. |
| 8,644,957 | B2 | 2/2014 | Mashiach |
| 8,647,278 | B2 | 2/2014 | Ji et al. |
| 8,648,017 | B2 | 2/2014 | Umansky et al. |
| 8,649,845 | B2 | 2/2014 | McIntyre et al. |
| 8,649,866 | B2 | 2/2014 | Brooke |
| 8,649,871 | B2 | 2/2014 | Frei et al. |
| 8,652,038 | B2 | 2/2014 | Tran et al. |
| 8,652,187 | B2 | 2/2014 | Wells et al. |
| 8,652,189 | B2 | 2/2014 | Gafni et al. |

(56)  References Cited

U.S. PATENT DOCUMENTS

| | | | |
|---|---|---|---|
| 8,655,428 B2 | 2/2014 | Pradeep et al. |
| 8,655,437 B2 | 2/2014 | Pradeep et al. |
| 8,655,817 B2 | 2/2014 | Hasey et al. |
| 8,657,732 B2 | 2/2014 | Vasishta |
| 8,657,756 B2 | 2/2014 | Stahmann et al. |
| 8,658,149 B2 | 2/2014 | Satchi-Fainaro et al. |
| 8,660,642 B2 | 2/2014 | Ferren et al. |
| 8,660,649 B2 | 2/2014 | Ruffini et al. |
| 8,660,666 B2 | 2/2014 | Craig |
| 8,660,799 B2 | 2/2014 | Watson et al. |
| 8,664,258 B2 | 3/2014 | Teegarden et al. |
| 8,666,099 B2 | 3/2014 | Nielsen et al. |
| 8,666,467 B2 | 3/2014 | Lynn et al. |
| 8,666,478 B2 | 3/2014 | Violette et al. |
| 8,666,501 B2 | 3/2014 | Kilgard et al. |
| 8,668,496 B2 | 3/2014 | Nolen |
| 8,670,603 B2 | 3/2014 | Tolkowsky et al. |
| 8,672,852 B2 | 3/2014 | Gavish |
| 8,675,936 B2 | 3/2014 | Vija et al. |
| 8,675,945 B2 | 3/2014 | Barnhorst et al. |
| 8,675,983 B2 | 3/2014 | Yahil |
| 8,676,324 B2 | 3/2014 | Simon et al. |
| 8,676,325 B2 | 3/2014 | Lindenthaler et al. |
| 8,676,330 B2 | 3/2014 | Simon et al. |
| 8,679,009 B2 | 3/2014 | Osorio |
| 8,680,119 B2 | 3/2014 | Teegarden et al. |
| 8,680,991 B2 | 3/2014 | Tran |
| 8,682,422 B2 | 3/2014 | Hopenfeld |
| 8,682,441 B2 | 3/2014 | De Ridder |
| 8,682,449 B2 | 3/2014 | Simon |
| 8,682,687 B2 | 3/2014 | Hyde et al. |
| 8,684,742 B2 | 4/2014 | Siefert |
| 8,684,900 B2 | 4/2014 | Tran |
| 8,684,921 B2 | 4/2014 | Osorio |
| 8,684,922 B2 | 4/2014 | Tran |
| 8,684,926 B2 | 4/2014 | Arndt |
| 8,688,209 B2 | 4/2014 | Verbitskiy |
| 8,690,748 B1 | 4/2014 | Fu |
| 8,693,756 B2 | 4/2014 | Tolkowsky et al. |
| 8,693,765 B2 | 4/2014 | Mercier et al. |
| 8,694,087 B2 | 4/2014 | Schiff |
| 8,694,089 B2 | 4/2014 | Arad |
| 8,694,092 B2 | 4/2014 | Ferren et al. |
| 8,694,107 B2 | 4/2014 | Falci |
| 8,694,118 B2 | 4/2014 | Armstrong |
| 8,694,157 B2 | 4/2014 | Wenderow et al. |
| 8,696,722 B2 | 4/2014 | Deisseroth et al. |
| 8,696,724 B2 | 4/2014 | Rogers |
| 8,698,639 B2 | 4/2014 | Fung et al. |
| 8,700,137 B2 | 4/2014 | Albert |
| 8,700,141 B2 | 4/2014 | Causevic |
| 8,700,142 B2 | 4/2014 | John et al. |
| 8,700,163 B2 | 4/2014 | Terry, Jr. et al. |
| 8,700,167 B2 | 4/2014 | Sabel |
| 8,700,174 B2 | 4/2014 | Skelton et al. |
| 8,700,183 B2 | 4/2014 | Mashiach |
| 8,703,114 B2 | 4/2014 | Satchi-Fainaro et al. |
| 8,706,183 B2 | 4/2014 | Cui et al. |
| 8,706,205 B2 | 4/2014 | Shahaf et al. |
| 8,706,206 B2 | 4/2014 | Kanai et al. |
| 8,706,207 B2 | 4/2014 | Flint |
| 8,706,237 B2 | 4/2014 | Giftakis et al. |
| 8,706,241 B2 | 4/2014 | Firlik et al. |
| 8,706,518 B2 | 4/2014 | Hyde et al. |
| 8,708,903 B2 | 4/2014 | Tran |
| 8,708,934 B2 | 4/2014 | Skelton et al. |
| 8,711,655 B2 | 4/2014 | Gzara et al. |
| 8,712,507 B2 | 4/2014 | Cazares et al. |
| 8,712,512 B2 | 4/2014 | Doidge et al. |
| 8,712,513 B1 | 4/2014 | Modarres |
| 8,712,547 B2 | 4/2014 | Whitehurst et al. |
| 8,716,447 B2 | 5/2014 | Deisseroth et al. |
| 8,717,430 B2 | 5/2014 | Simon et al. |
| 8,718,747 B2 | 5/2014 | Bjornerud et al. |
| 8,718,776 B2 | 5/2014 | Mashiach et al. |
| 8,718,777 B2 | 5/2014 | Lowry et al. |
| 8,718,779 B2 | 5/2014 | Whitehurst et al. |
| 8,721,695 B2 | 5/2014 | Tass et al. |
| 8,724,871 B1 | 5/2014 | Biagiotti et al. |
| 8,725,238 B2 | 5/2014 | Liu et al. |
| 8,725,243 B2 | 5/2014 | Dilorenzo et al. |
| 8,725,311 B1 | 5/2014 | Breed |
| 8,725,668 B2 | 5/2014 | Georgopoulos |
| 8,725,669 B1 | 5/2014 | Fu |
| 8,725,796 B2 | 5/2014 | Serena |
| 8,727,978 B2 | 5/2014 | Tran et al. |
| 8,728,001 B2 | 5/2014 | Lynn |
| 8,729,040 B2 | 5/2014 | Deisseroth et al. |
| 8,731,650 B2 | 5/2014 | Sajda et al. |
| 8,731,656 B2 | 5/2014 | Bourget et al. |
| 8,731,987 B2 | 5/2014 | Chen et al. |
| 8,733,290 B2 | 5/2014 | Gerashchenko |
| 8,734,356 B2 | 5/2014 | Taylor |
| 8,734,357 B2 | 5/2014 | Taylor |
| 8,734,498 B2 | 5/2014 | DiMauro et al. |
| 8,738,121 B2 | 5/2014 | Virag et al. |
| 8,738,126 B2 | 5/2014 | Craig |
| 8,738,136 B2 | 5/2014 | Frei et al. |
| 8,738,140 B2 | 5/2014 | De Ridder |
| 8,738,395 B2 | 5/2014 | Hyde et al. |
| 8,744,562 B2 | 6/2014 | Giftakis et al. |
| 8,744,563 B2 | 6/2014 | Yoshida |
| 8,747,313 B2 | 6/2014 | Tran et al. |
| 8,747,336 B2 | 6/2014 | Tran |
| 8,747,382 B2 | 6/2014 | D'Souza et al. |
| 8,750,971 B2 | 6/2014 | Tran |
| 8,750,974 B2 | 6/2014 | Baker et al. |
| 8,750,992 B2 | 6/2014 | Hopper et al. |
| 8,751,008 B2 | 6/2014 | Carlton et al. |
| 8,751,011 B2 | 6/2014 | Skelton et al. |
| 8,753,296 B2 | 6/2014 | Einav et al. |
| 8,754,238 B2 | 6/2014 | Teegarden et al. |
| 8,755,854 B2 | 6/2014 | Addison et al. |
| 8,755,856 B2 | 6/2014 | Diab et al. |
| 8,755,868 B2 | 6/2014 | Yazicioglu |
| 8,755,869 B2 | 6/2014 | Zhang et al. |
| 8,755,871 B2 | 6/2014 | Weng et al. |
| 8,755,877 B2 | 6/2014 | Zoica |
| 8,755,901 B2 | 6/2014 | Skelton et al. |
| 8,756,017 B2 | 6/2014 | Hu et al. |
| 8,758,274 B2 | 6/2014 | Sahasrabudhe et al. |
| 8,761,438 B2 | 6/2014 | Lee et al. |
| 8,761,866 B2 | 6/2014 | Chance |
| 8,761,868 B2 | 6/2014 | Giftakis et al. |
| 8,761,869 B2 | 6/2014 | Leuthardt et al. |
| 8,761,889 B2 | 6/2014 | Wingeier et al. |
| 8,762,065 B2 | 6/2014 | DiLorenzo |
| 8,762,202 B2 | 6/2014 | Pradeep et al. |
| 8,764,651 B2 | 7/2014 | Tran |
| 8,764,652 B2 | 7/2014 | Lee et al. |
| 8,764,653 B2 | 7/2014 | Kaminska et al. |
| 8,764,673 B2 | 7/2014 | McCraty et al. |
| 8,768,022 B2 | 7/2014 | Miga et al. |
| 8,768,427 B2 | 7/2014 | Sjaaheim et al. |
| 8,768,431 B2 | 7/2014 | Ross et al. |
| 8,768,446 B2 | 7/2014 | Drew et al. |
| 8,768,447 B2 | 7/2014 | Ermes et al. |
| 8,768,449 B2 | 7/2014 | Pesaran et al. |
| 8,768,471 B2 | 7/2014 | Colborn et al. |
| 8,768,477 B2 | 7/2014 | Spitzer et al. |
| 8,768,718 B2 | 7/2014 | Cazares et al. |
| 8,771,194 B2 | 7/2014 | John et al. |
| 8,774,923 B2 | 7/2014 | Rom |
| 8,775,340 B2 | 7/2014 | Waxman et al. |
| 8,781,193 B2 | 7/2014 | Steinberg et al. |
| 8,781,197 B2 | 7/2014 | Wang et al. |
| 8,781,557 B2 | 7/2014 | Dean et al. |
| 8,781,563 B2 | 7/2014 | Foo |
| 8,781,595 B2 | 7/2014 | Grevious et al. |
| 8,781,597 B2 | 7/2014 | DiLorenzo |
| 8,781,796 B2 | 7/2014 | Mott et al. |
| 8,784,109 B2 | 7/2014 | Gottfried |
| 8,784,322 B2 | 7/2014 | Kim et al. |
| 8,785,441 B2 | 7/2014 | Teegarden et al. |

(56) References Cited

U.S. PATENT DOCUMENTS

| | | | |
|---|---|---|---|
| 8,786,624 | B2 | 7/2014 | Echauz et al. |
| 8,787,637 | B2 | 7/2014 | Duchesnay et al. |
| 8,788,030 | B1 | 7/2014 | Payton et al. |
| 8,788,033 | B2 | 7/2014 | Rossi |
| 8,788,044 | B2 | 7/2014 | John |
| 8,788,055 | B2 | 7/2014 | Gerber et al. |
| 8,788,057 | B2 | 7/2014 | Stevenson et al. |
| 8,790,255 | B2 | 7/2014 | Behar |
| 8,790,272 | B2 | 7/2014 | Sackner et al. |
| 8,790,297 | B2 | 7/2014 | Bromander et al. |
| 8,792,972 | B2 | 7/2014 | Zaidel et al. |
| 8,792,974 | B2 | 7/2014 | Rothman |
| 8,792,991 | B2 | 7/2014 | Gerber et al. |
| 8,795,175 | B2 | 8/2014 | Funane et al. |
| 8,798,717 | B2 | 8/2014 | Roscher |
| 8,798,728 | B2 | 8/2014 | Drew et al. |
| 8,798,735 | B1 | 8/2014 | Bibian et al. |
| 8,798,736 | B2 | 8/2014 | Sullivan et al. |
| 8,798,773 | B2 | 8/2014 | Mashiach |
| 8,801,620 | B2 | 8/2014 | Melker et al. |
| 8,805,516 | B2 | 8/2014 | Bentwich |
| 8,805,518 | B2 | 8/2014 | King et al. |
| 8,812,126 | B2 | 8/2014 | Butson et al. |
| 8,812,237 | B2 | 8/2014 | Wilt et al. |
| 8,812,245 | B2 | 8/2014 | Taylor |
| 8,812,246 | B2 | 8/2014 | Taylor |
| 8,814,923 | B2 | 8/2014 | Nissila et al. |
| 8,815,582 | B2 | 8/2014 | Deisseroth et al. |
| 8,821,376 | B2 | 9/2014 | Tolkowsky |
| 8,821,408 | B2 | 9/2014 | Hu et al. |
| 8,821,559 | B2 | 9/2014 | DiMauro et al. |
| 8,825,149 | B2 | 9/2014 | Kraus et al. |
| 8,825,166 | B2 | 9/2014 | John |
| 8,825,167 | B2 | 9/2014 | Tass et al. |
| 8,825,428 | B2 | 9/2014 | Addison et al. |
| 8,827,912 | B2 | 9/2014 | Bukhman |
| 8,827,917 | B2 | 9/2014 | Watson et al. |
| 8,829,908 | B2 | 9/2014 | Roshtal et al. |
| 8,831,705 | B2 | 9/2014 | Dobak |
| 8,831,731 | B2 | 9/2014 | Blum et al. |
| 8,831,732 | B2 | 9/2014 | Frei et al. |
| 8,834,392 | B2 | 9/2014 | Panken et al. |
| 8,834,546 | B2 | 9/2014 | Deisseroth et al. |
| 8,838,201 | B2 | 9/2014 | Mori et al. |
| 8,838,225 | B2 | 9/2014 | Ahonen et al. |
| 8,838,226 | B2 | 9/2014 | Bibian et al. |
| 8,838,227 | B2 | 9/2014 | Causevic et al. |
| 8,838,247 | B2 | 9/2014 | Hagedorn et al. |
| 8,843,199 | B2 | 9/2014 | Kim et al. |
| 8,843,201 | B1 | 9/2014 | Heldman et al. |
| 8,843,210 | B2 | 9/2014 | Simon et al. |
| 8,845,545 | B2 | 9/2014 | Folkerts et al. |
| 8,849,390 | B2 | 9/2014 | Echauz et al. |
| 8,849,392 | B2 | 9/2014 | Lozano |
| 8,849,407 | B1 | 9/2014 | Danilov et al. |
| 8,849,409 | B2 | 9/2014 | Colborn et al. |
| 8,849,632 | B2 | 9/2014 | Sparks et al. |
| 8,849,681 | B2 | 9/2014 | Hargrove et al. |
| 8,852,073 | B2 | 10/2014 | Genereux et al. |
| 8,852,100 | B2 | 10/2014 | Osorio |
| 8,852,103 | B2 | 10/2014 | Rothberg et al. |
| 8,855,758 | B2 | 10/2014 | Rodriquez-Villegas et al. |
| 8,855,773 | B2 | 10/2014 | Kokones et al. |
| 8,855,775 | B2 | 10/2014 | Leyde |
| 8,858,440 | B2 | 10/2014 | Tyler |
| 8,858,449 | B2 | 10/2014 | Inan et al. |
| 8,861,819 | B2 | 10/2014 | Lee et al. |
| 8,862,196 | B2 | 10/2014 | Lynn |
| 8,862,210 | B2 | 10/2014 | Yazicioglu et al. |
| 8,862,236 | B2 | 10/2014 | Wolpaw et al. |
| 8,862,581 | B2 | 10/2014 | Zhang et al. |
| 8,864,310 | B2 | 10/2014 | Gross et al. |
| 8,864,806 | B2 | 10/2014 | Wells et al. |
| 8,868,148 | B2 | 10/2014 | Engelbrecht et al. |
| 8,868,163 | B2 | 10/2014 | Guttag et al. |
| 8,868,172 | B2 | 10/2014 | Leyde et al. |
| 8,868,173 | B2 | 10/2014 | Nelson et al. |
| 8,868,174 | B2 | 10/2014 | Sato et al. |
| 8,868,175 | B2 | 10/2014 | Arad |
| 8,868,177 | B2 | 10/2014 | Simon et al. |
| 8,868,189 | B2 | 10/2014 | Stevenson et al. |
| 8,868,201 | B2 | 10/2014 | Roberts et al. |
| 8,870,737 | B2 | 10/2014 | Phillips et al. |
| 8,871,797 | B2 | 10/2014 | Teegarden et al. |
| 8,872,640 | B2 | 10/2014 | Horseman |
| 8,874,205 | B2 | 10/2014 | Simon et al. |
| 8,874,218 | B2 | 10/2014 | Terry, Jr. |
| 8,874,227 | B2 | 10/2014 | Simon et al. |
| 8,874,439 | B2 | 10/2014 | Kim et al. |
| 8,880,207 | B2 | 11/2014 | Abeyratne et al. |
| 8,880,576 | B2 | 11/2014 | Ochs et al. |
| 8,886,299 | B2 | 11/2014 | Yazicioglu et al. |
| 8,886,302 | B2 | 11/2014 | Skelton et al. |
| 8,888,672 | B2 | 11/2014 | Phillips et al. |
| 8,888,673 | B2 | 11/2014 | Phillips et al. |
| 8,888,702 | B2 | 11/2014 | Osorio |
| 8,888,708 | B2 | 11/2014 | Diab et al. |
| 8,888,723 | B2 | 11/2014 | Einav |
| 8,892,207 | B2 | 11/2014 | Nelson et al. |
| 8,893,120 | B2 | 11/2014 | Pinsky et al. |
| 8,898,037 | B2 | 11/2014 | Watson et al. |
| 8,900,284 | B2 | 12/2014 | DiMauro et al. |
| 8,902,070 | B2 | 12/2014 | Kobetski et al. |
| 8,903,479 | B2 | 12/2014 | Zoicas |
| 8,903,483 | B2 | 12/2014 | Sun et al. |
| 8,903,486 | B2 | 12/2014 | Bourget et al. |
| 8,903,494 | B2 | 12/2014 | Goldwasser et al. |
| 8,906,360 | B2 | 12/2014 | Deisseroth et al. |
| 8,907,668 | B2 | 12/2014 | Okada |
| 8,909,345 | B1 | 12/2014 | Danilov et al. |
| 8,910,638 | B2 | 12/2014 | Boyden et al. |
| 8,913,810 | B2 | 12/2014 | Panin et al. |
| 8,914,100 | B2 | 12/2014 | Adachi et al. |
| 8,914,115 | B2 | 12/2014 | Giftakis et al. |
| 8,914,119 | B2 | 12/2014 | Wu et al. |
| 8,914,122 | B2 | 12/2014 | Simon et al. |
| 8,915,741 | B2 | 12/2014 | Hatlestad et al. |
| 8,915,871 | B2 | 12/2014 | Einav |
| 8,918,162 | B2 | 12/2014 | Prokoski |
| 8,918,176 | B2 | 12/2014 | Nelson et al. |
| 8,918,178 | B2 | 12/2014 | Simon et al. |
| 8,918,183 | B2 | 12/2014 | Carlton et al. |
| 8,921,320 | B2 | 12/2014 | Paul et al. |
| 8,922,376 | B2 | 12/2014 | Kangas et al. |
| 8,922,788 | B2 | 12/2014 | Addison et al. |
| 8,923,958 | B2 | 12/2014 | Gupta et al. |
| 8,924,235 | B2 | 12/2014 | Seely |
| RE45,336 | E | 1/2015 | Teegarden et al. |
| RE45,337 | E | 1/2015 | Teegarden et al. |
| 8,926,959 | | 1/2015 | Deisseroth et al. |
| 8,929,991 | B2 | 1/2015 | Fowler et al. |
| 8,929,999 | B2 | 1/2015 | Maschiach |
| 8,932,218 | B1 | 1/2015 | Thompson |
| 8,932,227 | B2 | 1/2015 | Lynn |
| 8,932,562 | B2 | 1/2015 | Deisseroth et al. |
| 8,933,696 | B2 | 1/2015 | Nishikawa |
| 8,934,685 | B2 | 1/2015 | Avinash et al. |
| 8,934,965 | B2 | 1/2015 | Rogers et al. |
| 8,934,967 | B2 | 1/2015 | Kilgard et al. |
| 8,934,979 | B2 | 1/2015 | Moffitt |
| 8,934,986 | B2 | 1/2015 | Goetz |
| 8,936,629 | B2 | 1/2015 | Boyden et al. |
| 8,936,630 | B2 | 1/2015 | Denison et al. |
| 8,938,102 | B2 | 1/2015 | Carroll |
| 8,938,289 | B2 | 1/2015 | Einav et al. |
| 8,938,290 | B2 | 1/2015 | Wingeier et al. |
| 8,938,301 | B2 | 1/2015 | Hagedorn |
| 8,939,903 | B2 | 1/2015 | Roberts et al. |
| 8,942,777 | B2 | 1/2015 | Diab et al. |
| 8,942,813 | B1 | 1/2015 | Hagedorn et al. |
| 8,942,817 | B2 | 1/2015 | Hyde et al. |
| 8,945,006 | B2 | 2/2015 | Osorio |
| 8,948,834 | B2 | 2/2015 | Diab et al. |
| 8,948,849 | B2 | 2/2015 | Diamond et al. |

(56) References Cited

U.S. PATENT DOCUMENTS

| | | | |
|---|---|---|---|
| 8,948,855 B2 | 2/2015 | Osorio et al. |
| 8,948,860 B2 | 2/2015 | Causevic |
| 8,951,189 B2 | 2/2015 | Osorio |
| 8,951,190 B2 | 2/2015 | Chmiel et al. |
| 8,951,192 B2 | 2/2015 | Osorio |
| 8,951,203 B2 | 2/2015 | Patangay et al. |
| 8,954,139 B2 | 2/2015 | Hopenfeld et al. |
| 8,954,146 B2 | 2/2015 | Hopper et al. |
| 8,954,293 B2 | 2/2015 | Klinkenbusch |
| 8,955,010 B2 | 2/2015 | Pradeep et al. |
| 8,955,974 B2 | 2/2015 | Gross et al. |
| 8,956,277 B2 | 2/2015 | Mishelevich |
| 8,956,363 B2 | 2/2015 | Schneider et al. |
| 8,958,868 B2 | 2/2015 | Ghovanloo et al. |
| 8,958,870 B2 | 2/2015 | Gerber et al. |
| 8,958,882 B1 | 2/2015 | Hagedorn |
| 8,961,187 B2 | 2/2015 | Boers et al. |
| 8,961,385 B2 | 2/2015 | Pilla et al. |
| 8,961,386 B2 | 2/2015 | Phillips et al. |
| 8,962,042 B2 | 2/2015 | Geng |
| 8,962,589 B2 | 2/2015 | Deisseroth et al. |
| 8,964,298 B2 | 2/2015 | Haddick et al. |
| 8,965,492 B2 | 2/2015 | Baker et al. |
| 8,965,513 B2 | 2/2015 | Wingeier et al. |
| 8,965,514 B2 | 2/2015 | Bikson et al. |
| 8,968,172 B2 | 3/2015 | Wang et al. |
| 8,968,176 B2 | 3/2015 | Altman et al. |
| 8,968,195 B2 | 3/2015 | Tran |
| 8,968,376 B2 | 3/2015 | Wells et al. |
| 8,971,936 B2 | 3/2015 | Derchak |
| 8,972,004 B2 | 3/2015 | Simon et al. |
| 8,972,013 B2 | 3/2015 | Maschino |
| 8,974,365 B2 | 3/2015 | Best |
| 8,977,024 B1 | 3/2015 | Rex et al. |
| 8,977,110 B2 | 3/2015 | Pradeep et al. |
| 8,977,362 B2 | 3/2015 | Saab |
| 8,980,891 B2 | 3/2015 | Stirn et al. |
| 8,983,155 B2 | 3/2015 | McIntyre et al. |
| 8,983,591 B2 | 3/2015 | Leininger et al. |
| 8,983,620 B2 | 3/2015 | Cinbis |
| 8,983,628 B2 | 3/2015 | Simon et al. |
| 8,983,629 B2 | 3/2015 | Simon et al. |
| 8,985,119 B1 | 3/2015 | Webb et al. |
| 8,986,207 B2 | 3/2015 | Li et al. |
| 8,989,835 B2 | 3/2015 | Badower et al. |
| 8,989,836 B2 | 3/2015 | Machon et al. |
| 8,989,863 B2 | 3/2015 | Osorio |
| 8,989,867 B2 | 3/2015 | Chow et al. |
| 8,989,868 B2 | 3/2015 | Mashiach et al. |
| 8,989,871 B2 | 3/2015 | Ollivier |
| 8,992,230 B2 | 3/2015 | Tuchschmid et al. |
| 8,993,623 B2 | 3/2015 | Goodenowe |
| 8,996,112 B2 | 3/2015 | Brooke |
| 8,996,120 B1 | 3/2015 | Calle et al. |
| 8,998,828 B2 | 4/2015 | Reichow et al. |
| 9,002,458 B2 | 4/2015 | Pal et al. |
| 9,002,471 B2 | 4/2015 | Stevenson et al. |
| 9,002,477 B2 | 4/2015 | Burnett |
| 9,004,687 B2 | 4/2015 | Stack |
| 9,005,102 B2 | 4/2015 | Burnett et al. |
| 9,005,126 B2 | 4/2015 | Beach et al. |
| 9,005,649 B2 | 4/2015 | Ho et al. |
| 9,008,367 B2 | 4/2015 | Tolkowsky et al. |
| 9,008,754 B2 | 4/2015 | Steinberg et al. |
| 9,008,771 B2 | 4/2015 | Dong et al. |
| 9,008,780 B2 | 4/2015 | Nudo et al. |
| 9,008,970 B2 | 4/2015 | Donderici et al. |
| 9,011,329 B2 | 4/2015 | Ferren et al. |
| 9,014,216 B2 | 4/2015 | Lazar et al. |
| 9,014,453 B2 | 4/2015 | Steinberg et al. |
| 9,014,804 B2 | 4/2015 | Giftakis et al. |
| 9,014,811 B2 | 4/2015 | Pal et al. |
| 9,014,819 B2 | 4/2015 | Lee et al. |
| 9,014,823 B2 | 4/2015 | Simon et al. |
| 9,015,057 B2 | 4/2015 | Phillips et al. |
| 9,015,087 B2 | 4/2015 | Li et al. |
| 9,020,576 B2 | 4/2015 | Nagatani |
| 9,020,582 B2 | 4/2015 | Osorio et al. |
| 9,020,585 B2 | 4/2015 | John et al. |
| 9,020,586 B2 | 4/2015 | Yamada et al. |
| 9,020,598 B2 | 4/2015 | Simon et al. |
| 9,020,612 B1 | 4/2015 | Danilov et al. |
| 9,020,789 B2 | 4/2015 | Butson et al. |
| 9,022,930 B2 | 5/2015 | Sachanandani et al. |
| 9,022,936 B2 | 5/2015 | Rothberg et al. |
| 9,025,845 B2 | 5/2015 | Carroll |
| 9,026,194 B2 | 5/2015 | Okada |
| 9,026,202 B2 | 5/2015 | Albert |
| 9,026,217 B2 | 5/2015 | Kokones et al. |
| 9,026,218 B2 | 5/2015 | Lozano et al. |
| 9,026,372 B2 | 5/2015 | O'Donnell, Jr. et al. |
| 9,028,405 B2 | 5/2015 | Tran |
| 9,028,412 B2 | 5/2015 | Rothberg et al. |
| 9,031,644 B2 | 5/2015 | Johnson et al. |
| 9,031,653 B2 | 5/2015 | Mashiach |
| 9,031,655 B2 | 5/2015 | Osorio et al. |
| 9,031,658 B2 | 5/2015 | Chiao et al. |
| 9,033,884 B2 | 5/2015 | Rothberg et al. |
| 9,034,055 B2 | 5/2015 | Vinjamuri et al. |
| 9,034,911 B2 | 5/2015 | Selvey et al. |
| 9,034,923 B2 | 5/2015 | Goodenowe |
| 9,035,657 B2 | 5/2015 | Zhang et al. |
| 9,036,844 B1 | 5/2015 | Suhami et al. |
| 9,037,224 B1 | 5/2015 | Fu |
| 9,037,225 B1 | 5/2015 | Saliga et al. |
| 9,037,254 B2 | 5/2015 | John |
| 9,037,256 B2 | 5/2015 | Bokil |
| 9,037,530 B2 | 5/2015 | Tan et al. |
| 9,042,074 B1 | 5/2015 | Beran |
| 9,042,201 B2 | 5/2015 | Tyler et al. |
| 9,042,952 B2 | 5/2015 | Lynn et al. |
| 9,042,958 B2 | 5/2015 | Karmarkar et al. |
| 9,042,988 B2 | 5/2015 | DiLorenzo |
| 9,043,001 B2 | 5/2015 | Simon et al. |
| 9,044,188 B2 | 6/2015 | DiLorenzo et al. |
| 9,044,612 B2 | 6/2015 | Mashiach et al. |
| 9,050,469 B1 | 6/2015 | Osorio et al. |
| 9,050,470 B2 | 6/2015 | Carlton et al. |
| 9,050,471 B2 | 6/2015 | Skelton et al. |
| 9,053,516 B2 | 6/2015 | Stempora |
| 9,053,534 B2 | 6/2015 | Ross et al. |
| 9,055,871 B2 | 6/2015 | Inan et al. |
| 9,055,974 B2 | 6/2015 | Goetz |
| 9,056,195 B2 | 6/2015 | Sabesan |
| 9,058,473 B2 | 6/2015 | Navratil et al. |
| 9,060,671 B2 | 6/2015 | Badower et al. |
| 9,060,683 B2 | 6/2015 | Tran |
| 9,060,695 B2 | 6/2015 | Peters |
| 9,060,722 B2 | 6/2015 | Teixeira |
| 9,060,746 B2 | 6/2015 | Weng et al. |
| 9,061,132 B1 | 6/2015 | Zweber et al. |
| 9,061,133 B2 | 6/2015 | Wurster et al. |
| 9,061,151 B2 | 6/2015 | Mashiach et al. |
| 9,061,153 B1 | 6/2015 | Lebovitz et al. |
| 9,063,183 B2 | 6/2015 | Toda et al. |
| 9,063,643 B2 | 6/2015 | Sparks et al. |
| 9,064,036 B2 | 6/2015 | Hyde et al. |
| 9,067,052 B2 | 6/2015 | Moses et al. |
| 9,067,054 B2 | 6/2015 | Simon et al. |
| 9,067,070 B2 | 6/2015 | Connor |
| 9,069,031 B2 | 6/2015 | Guedes et al. |
| 9,069,097 B2 | 6/2015 | Zhang et al. |
| 9,070,492 B2 | 6/2015 | Yarmush et al. |
| 9,072,449 B2 | 7/2015 | Semenov |
| 9,072,482 B2 | 7/2015 | Sarkela et al. |
| 9,072,832 B2 | 7/2015 | Frei et al. |
| 9,072,870 B2 | 7/2015 | Wu et al. |
| 9,072,905 B2 | 7/2015 | Kokones et al. |
| 9,074,976 B2 | 7/2015 | Adolphi et al. |
| 9,076,212 B2 | 7/2015 | Ernst et al. |
| 9,078,564 B2 | 7/2015 | Taylor |
| 9,078,577 B2 | 7/2015 | He et al. |
| 9,078,584 B2 | 7/2015 | Jorge et al. |
| 9,079,039 B2 | 7/2015 | Carlson et al. |

(56)         References Cited

U.S. PATENT DOCUMENTS

| | | | |
|---|---|---|---|
| 9,079,940 | B2 | 7/2015 | Deisseroth et al. |
| 9,081,488 | B2 | 7/2015 | Soederstroem |
| 9,081,882 | B2 | 7/2015 | Taylor |
| 9,081,890 | B2 | 7/2015 | An et al. |
| 9,082,169 | B2 | 7/2015 | Thomson et al. |
| 9,084,584 | B2 | 7/2015 | Weiland et al. |
| 9,084,885 | B2 | 7/2015 | Deisseroth et al. |
| 9,084,896 | B2 | 7/2015 | Kokones et al. |
| 9,084,900 | B2 | 7/2015 | Hershey et al. |
| 9,087,147 | B1 | 7/2015 | Fonte |
| 9,089,310 | B2 | 7/2015 | Isenhart et al. |
| 9,089,400 | B2 | 7/2015 | Nofzinger |
| 9,089,683 | B2 | 7/2015 | Mishelevich |
| 9,089,707 | B2 | 7/2015 | Kilgard et al. |
| 9,089,713 | B2 | 7/2015 | John |
| 9,089,719 | B2 | 7/2015 | Simon et al. |
| 9,091,785 | B2 | 7/2015 | Donderici et al. |
| 9,092,556 | B2 | 7/2015 | Amble et al. |
| 9,092,895 | B2 | 7/2015 | Ross et al. |
| 9,095,266 | B1 | 8/2015 | Fu |
| 9,095,268 | B2 | 8/2015 | Kurtz et al. |
| 9,095,295 | B2 | 8/2015 | Eagleman et al. |
| 9,095,303 | B2 | 8/2015 | Osorio |
| 9,095,314 | B2 | 8/2015 | Osorio et al. |
| 9,095,618 | B2 | 8/2015 | Satchi-Fainaro et al. |
| 9,095,713 | B2 | 8/2015 | Foster et al. |
| 9,100,758 | B2 | 8/2015 | Adachi et al. |
| 9,101,263 | B2 | 8/2015 | Jung et al. |
| 9,101,276 | B2 | 8/2015 | Georgopoulos |
| 9,101,279 | B2 | 8/2015 | Ritchey et al. |
| 9,101,690 | B2 | 8/2015 | Deisseroth et al. |
| 9,101,759 | B2 | 8/2015 | Delp et al. |
| 9,101,766 | B2 | 8/2015 | Nekhendzy |
| 9,102,717 | B2 | 8/2015 | Huang et al. |
| 9,107,586 | B2 | 8/2015 | Tran |
| 9,107,595 | B1 | 8/2015 | Smyth |
| 9,108,041 | B2 | 8/2015 | Craig |
| 9,113,777 | B2 | 8/2015 | Mittal |
| 9,113,801 | B2 | 8/2015 | DiLorenzo |
| 9,113,803 | B2 | 8/2015 | Zhang |
| 9,113,830 | B2 | 8/2015 | Galen et al. |
| 9,116,201 | B2 | 8/2015 | Shah et al. |
| 9,116,835 | B1 | 8/2015 | Smyth |
| 9,118,775 | B2 | 8/2015 | Lim et al. |
| 9,119,533 | B2 | 9/2015 | Ghaffari |
| 9,119,551 | B2 | 9/2015 | Qi et al. |
| 9,119,583 | B2 | 9/2015 | Tass |
| 9,119,597 | B2 | 9/2015 | Dripps et al. |
| 9,119,598 | B2 | 9/2015 | Engelbrecht et al. |
| 9,121,964 | B2 | 9/2015 | Lewis et al. |
| 9,125,574 | B2 | 9/2015 | Zia et al. |
| 9,125,581 | B2 | 9/2015 | Wu et al. |
| 9,125,788 | B2 | 9/2015 | Tee et al. |
| 9,126,050 | B2 | 9/2015 | Simon et al. |
| 9,131,864 | B2 | 9/2015 | Korenberg |
| 9,133,024 | B2 | 9/2015 | Phan et al. |
| 9,133,709 | B2 | 9/2015 | Huh et al. |
| 9,135,221 | B2 | 9/2015 | Shahaf et al. |
| 9,135,400 | B2 | 9/2015 | McIntyre et al. |
| 9,138,156 | B2 | 9/2015 | Wu et al. |
| 9,138,175 | B2 | 9/2015 | Ernst et al. |
| 9,138,183 | B2 | 9/2015 | McKenna et al. |
| 9,138,579 | B2 | 9/2015 | Wolpaw et al. |
| 9,138,580 | B2 | 9/2015 | Ignagni et al. |
| 9,142,145 | B2 | 9/2015 | Tuchschmid et al. |
| 9,142,185 | B2 | 9/2015 | Fateh |
| 9,144,392 | B2 | 9/2015 | Santosh et al. |
| RE45,766 | E | 10/2015 | Lindsay |
| 9,149,195 | B2 | 10/2015 | Hadley |
| 9,149,197 | B2 | 10/2015 | Taylor |
| 9,149,210 | B2 | 10/2015 | Sahasrabudhe et al. |
| 9,149,214 | B2 | 10/2015 | Adachi et al. |
| 9,149,226 | B2 | 10/2015 | Jadidi |
| 9,149,255 | B2 | 10/2015 | Rothberg et al. |
| 9,149,577 | B2 | 10/2015 | Robertson et al. |
| 9,149,599 | B2 | 10/2015 | Walter et al. |
| 9,149,719 | B2 | 10/2015 | Guan et al. |
| 9,152,757 | B2 | 10/2015 | Taylor |
| 9,155,373 | B2 | 10/2015 | Allen et al. |
| 9,155,484 | B2 | 10/2015 | Baker et al. |
| 9,155,487 | B2 | 10/2015 | Linderman et al. |
| 9,155,521 | B2 | 10/2015 | Rothberg et al. |
| 9,161,715 | B2 | 10/2015 | Jung et al. |
| 9,162,051 | B2 | 10/2015 | Morrell |
| 9,162,052 | B2 | 10/2015 | Morrell |
| 9,165,472 | B2 | 10/2015 | Hagedorn et al. |
| 9,167,970 | B2 | 10/2015 | Gratton et al. |
| 9,167,974 | B2 | 10/2015 | Taylor |
| 9,167,976 | B2 | 10/2015 | Wingeier et al. |
| 9,167,977 | B2 | 10/2015 | Wingeier et al. |
| 9,167,978 | B2 | 10/2015 | Wingeier et al. |
| 9,167,979 | B2 | 10/2015 | Skidmore et al. |
| 9,171,353 | B2 | 10/2015 | Vija et al. |
| 9,171,366 | B2 | 10/2015 | Declerck et al. |
| 9,173,582 | B2 | 11/2015 | Popovic et al. |
| 9,173,609 | B2 | 11/2015 | Nelson |
| 9,173,610 | B2 | 11/2015 | Navakatikyan |
| 9,174,045 | B2 | 11/2015 | Simon et al. |
| 9,174,055 | B2 | 11/2015 | Davis et al. |
| 9,174,066 | B2 | 11/2015 | Simon et al. |
| 9,175,095 | B2 | 11/2015 | Deisseroth et al. |
| 9,177,379 | B1 | 11/2015 | Biagiotti et al. |
| 9,177,416 | B2 | 11/2015 | Sharp |
| 9,179,850 | B2 | 11/2015 | Wingeier et al. |
| 9,179,854 | B2 | 11/2015 | Doidge et al. |
| 9,179,855 | B2 | 11/2015 | Burdea et al. |
| 9,179,858 | B2 | 11/2015 | Hasson et al. |
| 9,179,875 | B2 | 11/2015 | Hua |
| 9,179,876 | B2 | 11/2015 | Ochs et al. |
| 9,183,351 | B2 | 11/2015 | Shusterman |
| 9,186,060 | B2 | 11/2015 | De Graff et al. |
| 9,186,106 | B2 | 11/2015 | Osorio |
| 9,186,503 | B2 | 11/2015 | Lindenthaler et al. |
| 9,186,510 | B2 | 11/2015 | Gliner et al. |
| 9,187,745 | B2 | 11/2015 | Deisseroth et al. |
| 9,192,300 | B2 | 11/2015 | Jung et al. |
| 9,192,309 | B1 | 11/2015 | Hopenfeld et al. |
| 9,198,563 | B2 | 12/2015 | Ferren et al. |
| 9,198,612 | B2 | 12/2015 | Fueyo et al. |
| 9,198,621 | B2 | 12/2015 | Fernstrom et al. |
| 9,198,624 | B2 | 12/2015 | Funane et al. |
| 9,198,637 | B2 | 12/2015 | Rothberg et al. |
| 9,198,707 | B2 | 12/2015 | Mckay et al. |
| 9,198,733 | B2 | 12/2015 | Neal, II et al. |
| 9,204,796 | B2 | 12/2015 | Tran |
| 9,204,835 | B2 | 12/2015 | Parsey et al. |
| 9,204,838 | B2 | 12/2015 | Osorio |
| 9,204,998 | B2 | 12/2015 | Kilgard et al. |
| 9,208,430 | B2 | 12/2015 | Solari |
| 9,208,557 | B2 | 12/2015 | Pautot |
| 9,208,558 | B2 | 12/2015 | Dean et al. |
| 9,211,076 | B2 | 12/2015 | Kim |
| 9,211,077 | B2 | 12/2015 | Jung et al. |
| 9,211,212 | B2 | 12/2015 | Nofzinger et al. |
| 9,211,411 | B2 | 12/2015 | Wu et al. |
| 9,211,417 | B2 | 12/2015 | Heldman et al. |
| 9,213,074 | B2 | 12/2015 | van der Kouwe et al. |
| 9,213,076 | B2 | 12/2015 | Liu |
| 9,215,298 | B2 | 12/2015 | Schiff |
| 9,215,978 | B2 | 12/2015 | Knight et al. |
| 9,220,910 | B2 | 12/2015 | Colborn |
| 9,220,917 | B2 | 12/2015 | Boyden et al. |
| 9,221,755 | B2 | 12/2015 | Teegarden et al. |
| 9,226,672 | B2 | 1/2016 | Taylor |
| 9,227,056 | B1 | 1/2016 | Heldman et al. |
| 9,229,080 | B2 | 1/2016 | Lin |
| 9,230,065 | B2 | 1/2016 | Hasegawa et al. |
| 9,230,539 | B2 | 1/2016 | Pakhomov |
| 9,232,910 | B2 | 1/2016 | Alshaer et al. |
| 9,232,984 | B2 | 1/2016 | Guthart et al. |
| 9,233,244 | B2 | 1/2016 | Pal et al. |
| 9,233,245 | B2 | 1/2016 | Lamensdorf et al. |
| 9,233,246 | B2 | 1/2016 | Simon et al. |
| 9,233,258 | B2 | 1/2016 | Simon et al. |

(56) References Cited

U.S. PATENT DOCUMENTS

| | | | |
|---|---|---|---|
| 9,235,679 B2 | 1/2016 | Taylor |
| 9,235,685 B2 | 1/2016 | McIntyre et al. |
| 9,238,142 B2 | 1/2016 | Heldman et al. |
| 9,238,150 B2 | 1/2016 | Deisseroth et al. |
| 9,241,647 B2 | 1/2016 | Osorio et al. |
| 9,241,665 B2 | 1/2016 | deCharms |
| 9,242,067 B2 | 1/2016 | Shore et al. |
| 9,242,092 B2 | 1/2016 | Simon et al. |
| 9,247,890 B2 | 2/2016 | Turnbull et al. |
| 9,247,911 B2 | 2/2016 | Galloway et al. |
| 9,247,924 B2 | 2/2016 | Rothberg et al. |
| 9,248,003 B2 | 2/2016 | Wright et al. |
| 9,248,280 B2 | 2/2016 | Moffitt et al. |
| 9,248,286 B2 | 2/2016 | Simon et al. |
| 9,248,288 B2 | 2/2016 | Panken et al. |
| 9,248,290 B2 | 2/2016 | Mashiach |
| 9,248,291 B2 | 2/2016 | Mashiach |
| 9,248,296 B2 | 2/2016 | Carcieri et al. |
| 9,249,200 B2 | 2/2016 | Deisseroth et al. |
| 9,249,234 B2 | 2/2016 | Deisseroth et al. |
| 9,251,566 B1 | 2/2016 | Bajic |
| 9,254,097 B2 | 2/2016 | Espy et al. |
| 9,254,099 B2 | 2/2016 | Connor |
| 9,254,383 B2 | 2/2016 | Simon et al. |
| 9,254,387 B2 | 2/2016 | Blum et al. |
| 9,256,982 B2 | 2/2016 | Sharp et al. |
| 9,259,177 B2 | 2/2016 | Drew et al. |
| 9,259,482 B2 | 2/2016 | Satchi-Fainaro et al. |
| 9,259,591 B2 | 2/2016 | Brown et al. |
| 9,261,573 B1 | 2/2016 | Radparvar et al. |
| 9,265,458 B2 | 2/2016 | Stack |
| 9,265,660 B2 | 2/2016 | Kilgard et al. |
| 9,265,661 B2 | 2/2016 | Kilgard et al. |
| 9,265,662 B2 | 2/2016 | Kilgard et al. |
| 9,265,663 B2 | 2/2016 | Kilgard et al. |
| 9,265,931 B2 | 2/2016 | Morrell |
| 9,265,943 B2 | 2/2016 | Yun et al. |
| 9,265,946 B2 | 2/2016 | Morrell |
| 9,265,965 B2 | 2/2016 | Fox et al. |
| 9,265,974 B2 | 2/2016 | You et al. |
| 9,268,014 B2 | 2/2016 | Rothberg et al. |
| 9,268,015 B2 | 2/2016 | Rothberg et al. |
| 9,268,902 B2 | 2/2016 | Taylor et al. |
| 9,271,651 B2 | 3/2016 | Avinash et al. |
| 9,271,657 B2 | 3/2016 | Taylor |
| 9,271,660 B2 | 3/2016 | Luo et al. |
| 9,271,674 B2 | 3/2016 | Deisseroth et al. |
| 9,271,679 B2 | 3/2016 | Cho et al. |
| 9,272,091 B2 | 3/2016 | Skelton et al. |
| 9,272,139 B2 | 3/2016 | Hamilton et al. |
| 9,272,145 B2 | 3/2016 | Kilgard et al. |
| 9,272,153 B2 | 3/2016 | Blum et al. |
| 9,273,035 B2 | 3/2016 | Teegarden et al. |
| 9,275,191 B2 | 3/2016 | Dean et al. |
| 9,275,451 B2 | 3/2016 | Ben-Haim et al. |
| 9,277,871 B2 | 3/2016 | Keenan et al. |
| 9,277,873 B2 | 3/2016 | Sarma et al. |
| 9,278,159 B2 | 3/2016 | Deisseroth et al. |
| 9,278,231 B2 | 3/2016 | Vasishta |
| 9,280,784 B2 | 3/2016 | Barnett et al. |
| 9,282,927 B2 | 3/2016 | Hyde et al. |
| 9,282,930 B2 | 3/2016 | Machon et al. |
| 9,282,934 B2 | 3/2016 | Liley et al. |
| 9,283,279 B2 | 3/2016 | Satchi-Fainaro et al. |
| 9,283,394 B2 | 3/2016 | Whitehurst et al. |
| 9,284,353 B2 | 3/2016 | Deisseroth et al. |
| 9,285,249 B2 | 3/2016 | Schober et al. |
| 9,289,143 B2 | 3/2016 | Wingeier et al. |
| 9,289,595 B2 | 3/2016 | Floyd et al. |
| 9,289,599 B2 | 3/2016 | Craig |
| 9,289,603 B1 | 3/2016 | Giuffrida et al. |
| 9,289,609 B2 | 3/2016 | Moffitt |
| 9,292,471 B2 | 3/2016 | Fung et al. |
| 9,292,858 B2 | 3/2016 | Marci et al. |
| 9,292,920 B2 | 3/2016 | Dean et al. |
| 9,295,838 B2 | 3/2016 | Starr et al. |
| 9,296,382 B2 | 3/2016 | Fung et al. |
| 9,302,069 B2 | 4/2016 | Tass et al. |
| 9,302,093 B2 | 4/2016 | Mashiach |
| 9,302,103 B1 | 4/2016 | Nirenberg |
| 9,302,109 B2 | 4/2016 | Sabesan |
| 9,302,110 B2 | 4/2016 | Kokones et al. |
| 9,302,114 B2 | 4/2016 | Rossi |
| 9,302,116 B2 | 4/2016 | Vo-Dinh et al. |
| 9,305,376 B2 | 4/2016 | Lee et al. |
| 9,307,925 B2 | 4/2016 | Russell et al. |
| 9,307,944 B2 | 4/2016 | Colman et al. |
| 9,308,372 B2 | 4/2016 | Sparks et al. |
| 9,308,392 B2 | 4/2016 | Deisseroth et al. |
| 9,309,296 B2 | 4/2016 | Deisseroth et al. |
| 9,310,985 B2 | 4/2016 | Blum et al. |
| 9,311,335 B2 | 4/2016 | Simon |
| 9,314,190 B1 | 4/2016 | Giuffrida et al. |
| 9,314,613 B2 | 4/2016 | Mashiach |
| 9,314,633 B2 | 4/2016 | Osorio et al. |
| 9,314,635 B2 | 4/2016 | Libbus |
| 9,320,449 B2 | 4/2016 | Gu |
| 9,320,450 B2 | 4/2016 | Badower |
| 9,320,451 B2 | 4/2016 | Feldkamp et al. |
| 9,320,900 B2 | 4/2016 | DiLorenzo |
| 9,320,913 B2 | 4/2016 | Dimino et al. |
| 9,320,914 B2 | 4/2016 | Toselli et al. |
| 9,322,895 B2 | 4/2016 | Santosh et al. |
| 9,326,705 B2 | 5/2016 | Derchak |
| 9,326,720 B2 | 5/2016 | McLaughlin |
| 9,326,742 B2 | 5/2016 | Hirschman et al. |
| 9,327,069 B2 | 5/2016 | Foster et al. |
| 9,327,070 B2 | 5/2016 | Skelton et al. |
| 9,328,107 B2 | 5/2016 | Teegarden et al. |
| 9,329,758 B2 | 5/2016 | Guzak et al. |
| 9,330,206 B2 | 5/2016 | Dean et al. |
| 9,330,523 B2 | 5/2016 | Sutton et al. |
| 9,331,841 B2 | 5/2016 | Kim et al. |
| 9,332,939 B2 | 5/2016 | Osorio |
| 9,333,334 B2 | 5/2016 | Jeffery et al. |
| 9,333,347 B2 | 5/2016 | Simon et al. |
| 9,333,350 B2 | 5/2016 | Rise et al. |
| 9,336,302 B1 | 5/2016 | Swamy |
| 9,336,535 B2 | 5/2016 | Pradeep et al. |
| 9,336,611 B2 | 5/2016 | Bilgic et al. |
| 9,339,200 B2 | 5/2016 | Fonte |
| 9,339,227 B2 | 5/2016 | D'Arcy et al. |
| 9,339,641 B2 | 5/2016 | Rajguru et al. |
| 9,339,654 B2 | 5/2016 | Kilgard et al. |
| 9,340,589 B2 | 5/2016 | Deisseroth et al. |
| 9,345,412 B2 | 5/2016 | Horne |
| 9,345,609 B2 | 5/2016 | Hyde et al. |
| 9,345,886 B2 | 5/2016 | Kilgard et al. |
| 9,345,901 B2 | 5/2016 | Peterchev |
| 9,348,974 B2 | 5/2016 | Goetz |
| 9,349,178 B1 | 5/2016 | Itu et al. |
| 9,351,640 B2 | 5/2016 | Tran |
| 9,351,651 B2 | 5/2016 | Nagasaka |
| 9,352,145 B2 | 5/2016 | Whitehurst et al. |
| 9,352,152 B2 | 5/2016 | Lindenthaler et al. |
| 9,352,156 B2 | 5/2016 | Lane et al. |
| 9,357,240 B2 | 5/2016 | Pradeep et al. |
| 9,357,298 B2 | 5/2016 | Hiroe |
| 9,357,941 B2 | 6/2016 | Simon |
| 9,357,949 B2 | 6/2016 | Drew |
| 9,357,970 B2 | 6/2016 | Clark et al. |
| 9,358,361 B2 | 6/2016 | Hyde et al. |
| 9,358,381 B2 | 6/2016 | Simon et al. |
| 9,358,392 B2 | 6/2016 | Mashiach |
| 9,358,393 B1 | 6/2016 | Lozano |
| 9,358,398 B2 | 6/2016 | Moffitt et al. |
| 9,359,449 B2 | 6/2016 | Deisseroth et al. |
| 9,360,472 B2 | 6/2016 | Deisseroth et al. |
| 9,364,462 B2 | 6/2016 | Simpson, Jr. |
| 9,364,665 B2 | 6/2016 | Bokil et al. |
| 9,364,674 B2 | 6/2016 | Cook et al. |
| 9,364,679 B2 | 6/2016 | John |
| 9,365,628 B2 | 6/2016 | Deisseroth et al. |
| 9,367,131 B2 | 6/2016 | Klappert et al. |

(56) References Cited

U.S. PATENT DOCUMENTS

| | | |
|---|---|---|
| 9,367,738 B2 | 6/2016 | Harumatsu et al. |
| 9,368,018 B2 | 6/2016 | Kangas et al. |
| 9,368,265 B2 | 6/2016 | Park et al. |
| 9,370,309 B2 | 6/2016 | Ko et al. |
| 9,370,667 B2 | 6/2016 | Schmidt |
| 9,375,145 B2 | 6/2016 | Chin et al. |
| 9,375,151 B1 | 6/2016 | Hopenfeld et al. |
| 9,375,171 B2 | 6/2016 | Teixeira |
| 9,375,564 B2 | 6/2016 | Wingeier et al. |
| 9,375,571 B2 | 6/2016 | Errico et al. |
| 9,375,573 B2 | 6/2016 | Dilorenzo |
| 9,377,348 B2 | 6/2016 | Kataoka |
| 9,377,515 B2 | 6/2016 | Kim et al. |
| 9,380,976 B2 | 7/2016 | Stack |
| 9,381,346 B2 | 7/2016 | Lee et al. |
| 9,381,352 B2 | 7/2016 | Yun et al. |
| 9,383,208 B2 | 7/2016 | Mohanty |
| 9,387,320 B2 | 7/2016 | Wingeier et al. |
| 9,387,338 B2 | 7/2016 | Burnett |
| 9,390,233 B2 | 7/2016 | Fueyo et al. |
| 9,392,955 B2 | 7/2016 | Folkerts et al. |
| 9,393,406 B2 | 7/2016 | Ollivier |
| 9,393,418 B2 | 7/2016 | Giuffrida et al. |
| 9,394,347 B2 | 7/2016 | Deisseroth et al. |
| 9,395,425 B2 | 7/2016 | Diamond et al. |
| 9,396,533 B2 | 7/2016 | Skidmore |
| 9,396,669 B2 | 7/2016 | Karkanias et al. |
| 9,398,873 B2 | 7/2016 | Van Dooren et al. |
| 9,399,126 B2 | 7/2016 | Pal et al. |
| 9,399,133 B2 | 7/2016 | Besio |
| 9,399,134 B2 | 7/2016 | Simon et al. |
| 9,399,144 B2 | 7/2016 | Howard |
| 9,401,021 B1 | 7/2016 | Biagiotti et al. |
| 9,401,033 B2 | 7/2016 | Bajic |
| 9,402,558 B2 | 8/2016 | John et al. |
| 9,402,994 B2 | 8/2016 | Chow et al. |
| 9,403,000 B2 | 8/2016 | Lyons et al. |
| 9,403,001 B2 | 8/2016 | Simon et al. |
| 9,403,009 B2 | 8/2016 | Mashiach |
| 9,403,010 B2 | 8/2016 | Fried et al. |
| 9,403,038 B2 | 8/2016 | Tyler |
| 9,405,366 B2 | 8/2016 | Segal |
| 9,408,530 B2 | 8/2016 | Ferren et al. |
| 9,409,013 B2 | 8/2016 | Mashiach et al. |
| 9,409,022 B2 | 8/2016 | Jaax et al. |
| 9,409,028 B2 | 8/2016 | Whitehurst et al. |
| 9,410,885 B2 | 8/2016 | Schober et al. |
| 9,411,033 B2 | 8/2016 | He et al. |
| 9,411,935 B2 | 8/2016 | Moffitt et al. |
| 9,412,076 B2 | 8/2016 | Sapiro et al. |
| 9,412,233 B1 | 8/2016 | Bagherzadeh et al. |
| 9,414,029 B2 | 8/2016 | Miyazaki et al. |
| 9,414,749 B2 | 8/2016 | Semenov |
| 9,414,763 B2 | 8/2016 | Semenov |
| 9,414,764 B2 | 8/2016 | Semenov |
| 9,414,776 B2 | 8/2016 | Sillay et al. |
| 9,414,780 B2 | 8/2016 | Rhoads |
| 9,414,907 B2 | 8/2016 | Wortz et al. |
| 9,415,215 B2 | 8/2016 | Mashiach |
| 9,415,216 B2 | 8/2016 | Mashiach |
| 9,415,219 B2 | 8/2016 | Simon et al. |
| 9,415,222 B2 | 8/2016 | DiLorenzo |
| 9,415,233 B2 | 8/2016 | Pilla et al. |
| 9,418,368 B2 | 8/2016 | Jung et al. |
| 9,420,970 B2 | 8/2016 | Dagum |
| 9,421,258 B2 | 8/2016 | Deisseroth et al. |
| 9,421,372 B2 | 8/2016 | Mashiach et al. |
| 9,421,373 B2 | 8/2016 | DiLorenzo |
| 9,421,379 B2 | 8/2016 | Zhu |
| 9,424,761 B2 | 8/2016 | Tuchschmid et al. |
| 9,427,474 B2 | 8/2016 | Satchi-Fainaro et al. |
| 9,427,581 B2 | 8/2016 | Simon et al. |
| 9,427,585 B2 | 8/2016 | Gliner |
| 9,427,598 B2 | 8/2016 | Pilla et al. |
| 9,430,615 B2 | 8/2016 | Michaelis et al. |
| 9,432,777 B2 | 8/2016 | Lunner et al. |
| 9,433,797 B2 | 9/2016 | Pilla et al. |
| 9,434,692 B2 | 9/2016 | Xiong et al. |
| 9,436,989 B2 | 9/2016 | Uber, III |
| 9,438,650 B2 | 9/2016 | Serena |
| 9,439,150 B2 | 9/2016 | Carlson et al. |
| 9,440,063 B2 | 9/2016 | Ho et al. |
| 9,440,064 B2 | 9/2016 | Wingeier et al. |
| 9,440,070 B2 | 9/2016 | Goldwasser et al. |
| 9,440,084 B2 | 9/2016 | Davis et al. |
| 9,440,089 B2 | 9/2016 | Pilla et al. |
| 9,440,646 B2 | 9/2016 | Fung et al. |
| 9,442,088 B2 | 9/2016 | Feldkamp et al. |
| 9,442,525 B2 | 9/2016 | Choi et al. |
| 9,443,141 B2 | 9/2016 | Mirowski et al. |
| 9,444,998 B2 | 9/2016 | Kim et al. |
| 9,445,713 B2 | 9/2016 | Douglas et al. |
| 9,445,730 B2 | 9/2016 | Snyder et al. |
| 9,445,739 B1 | 9/2016 | Payton et al. |
| 9,445,763 B2 | 9/2016 | Davis et al. |
| 9,446,238 B2 | 9/2016 | Lozano |
| 9,448,289 B2 | 9/2016 | Wang et al. |
| 9,449,147 B2 | 9/2016 | Taylor |
| 9,451,303 B2 | 9/2016 | Kothuri et al. |
| 9,451,734 B2 | 9/2016 | Onuma et al. |
| 9,451,883 B2 | 9/2016 | Gallant et al. |
| 9,451,886 B2 | 9/2016 | Teixeira |
| 9,451,899 B2 | 9/2016 | Ritchey et al. |
| 9,452,287 B2 | 9/2016 | Rosenbluth et al. |
| 9,453,215 B2 | 9/2016 | Deisseroth et al. |
| 9,454,646 B2 | 9/2016 | Siefert |
| 9,458,208 B2 | 10/2016 | Deisseroth et al. |
| 9,459,597 B2 | 10/2016 | Kahn et al. |
| 9,460,400 B2 | 10/2016 | De Bruin et al. |
| 9,462,733 B2 | 10/2016 | Hokari |
| 9,462,956 B2 | 10/2016 | Pandia et al. |
| 9,462,975 B2 | 10/2016 | Sackner et al. |
| 9,462,977 B2 | 10/2016 | Horseman |
| 9,463,327 B2 | 10/2016 | Lempka et al. |
| 9,468,541 B2 | 10/2016 | Contreras-Vidal et al. |
| 9,468,761 B2 | 10/2016 | Frei et al. |
| 9,470,728 B2 | 10/2016 | George et al. |
| 9,471,978 B2 | 10/2016 | Chen et al. |
| 9,472,000 B2 | 10/2016 | Dempsey et al. |
| 9,474,481 B2 | 10/2016 | Dagum |
| 9,474,852 B2 | 10/2016 | Lozano et al. |
| 9,474,903 B2 | 10/2016 | Chen et al. |
| 9,475,502 B2 | 10/2016 | Fung et al. |
| RE46,189 E | 11/2016 | Prichep et al. |
| RE46,209 E | 11/2016 | Gong et al. |
| 9,480,402 B2 | 11/2016 | Leuthardt et al. |
| 9,480,425 B2 | 11/2016 | Culver et al. |
| 9,480,812 B1 | 11/2016 | Thompson |
| 9,480,841 B2 | 11/2016 | Hershey et al. |
| 9,480,845 B2 | 11/2016 | Harris et al. |
| 9,480,854 B2 | 11/2016 | Von Ohlsen et al. |
| 9,483,117 B2 | 11/2016 | Karkkainen et al. |
| 9,483,613 B2 | 11/2016 | Fueyo et al. |
| 9,486,168 B2 | 11/2016 | Bonmassar et al. |
| 9,486,381 B2 | 11/2016 | Juto et al. |
| 9,486,389 B2 | 11/2016 | Tass |
| 9,486,618 B2 | 11/2016 | Wingeier et al. |
| 9,486,632 B2 | 11/2016 | Saab |
| 9,489,854 B2 | 11/2016 | Haruta et al. |
| 9,492,084 B2 | 11/2016 | Behar et al. |
| 9,492,114 B2 | 11/2016 | Reiman |
| 9,492,120 B2 | 11/2016 | Horseman |
| 9,492,313 B2 | 11/2016 | Nofzinger |
| 9,492,656 B2 | 11/2016 | Chow et al. |
| 9,492,678 B2 | 11/2016 | Chow |
| 9,495,684 B2 | 11/2016 | Jung et al. |
| 9,497,017 B1 | 11/2016 | Kim et al. |
| 9,498,134 B1 | 11/2016 | Trobaugh et al. |
| 9,498,628 B2 | 11/2016 | Kaemmerer et al. |
| 9,498,634 B2 | 11/2016 | De Ridder |
| 9,500,722 B2 | 11/2016 | Takahashi |
| 9,501,829 B2 | 11/2016 | Carlton et al. |
| 9,504,390 B2 | 11/2016 | Osorio |
| 9,504,410 B2 | 11/2016 | Gal |

(56) References Cited

U.S. PATENT DOCUMENTS

| | | | |
|---|---|---|---|
| 9,504,420 | B2 | 11/2016 | Davis et al. |
| 9,504,788 | B2 | 11/2016 | Hyde et al. |
| 9,505,402 | B2 | 11/2016 | Fung et al. |
| 9,505,817 | B2 | 11/2016 | Deisseroth et al. |
| 9,510,790 | B2 | 12/2016 | Kang et al. |
| 9,513,398 | B2 | 12/2016 | Wilson et al. |
| 9,517,020 | B2 | 12/2016 | Shacham-Diamand et al. |
| 9,517,031 | B2 | 12/2016 | Jung |
| 9,517,222 | B2 | 12/2016 | Goodenowe |
| 9,519,981 | B2 | 12/2016 | Sudarsky et al. |
| 9,521,958 | B2 | 12/2016 | Nagasaka et al. |
| 9,522,085 | B2 | 12/2016 | Kilgard et al. |
| 9,522,278 | B1 | 12/2016 | Heldman et al. |
| 9,522,282 | B2 | 12/2016 | Chow et al. |
| 9,522,288 | B2 | 12/2016 | Deisseroth et al. |
| 9,526,419 | B2 | 12/2016 | Derchak et al. |
| 9,526,902 | B2 | 12/2016 | Blum et al. |
| 9,526,906 | B2 | 12/2016 | Mashiach |
| 9,526,913 | B2 | 12/2016 | Vo-Dinh et al. |
| 9,526,914 | B2 | 12/2016 | Vo-Dinh et al. |
| 9,533,113 | B2 | 1/2017 | Lain et al. |
| 9,533,144 | B2 | 1/2017 | Bahmer |
| 9,533,147 | B2 | 1/2017 | Osorio |
| 9,533,148 | B2 | 1/2017 | Carcieri |
| 9,533,150 | B2 | 1/2017 | Nudo et al. |
| 9,533,151 | B2 | 1/2017 | Craig |
| 9,534,044 | B2 | 1/2017 | El-Agnaf |
| 9,538,635 | B1 | 1/2017 | Beran |
| 9,538,948 | B2 | 1/2017 | Dagum |
| 9,538,951 | B2 | 1/2017 | Osorio |
| 9,539,118 | B2 | 1/2017 | Leuthardt et al. |
| 9,541,383 | B2 | 1/2017 | Abovitz et al. |
| 9,545,221 | B2 | 1/2017 | Adhikari et al. |
| 9,545,222 | B2 | 1/2017 | Derchak et al. |
| 9,545,225 | B2 | 1/2017 | Cavuoto et al. |
| 9,545,226 | B2 | 1/2017 | Osorio |
| 9,545,285 | B2 | 1/2017 | Ghaffari et al. |
| 9,545,510 | B2 | 1/2017 | Kokones et al. |
| 9,545,515 | B2 | 1/2017 | Wolpaw et al. |
| 9,549,691 | B2 | 1/2017 | Tran |
| 9,550,064 | B2 | 1/2017 | Mashiach |
| 9,556,149 | B2 | 1/2017 | Krishnan et al. |
| 9,556,487 | B2 | 1/2017 | Umansky et al. |
| 9,557,439 | B2 | 1/2017 | Wilson et al. |
| 9,558,558 | B2 | 1/2017 | Stehle et al. |
| 9,560,458 | B2 | 1/2017 | Lunner et al. |
| 9,560,967 | B2 | 2/2017 | Hyde et al. |
| 9,560,984 | B2 | 2/2017 | Pradeep et al. |
| 9,560,986 | B2 | 2/2017 | Varcoe |
| 9,561,380 | B2 | 2/2017 | Carcieri et al. |
| 9,562,988 | B2 | 2/2017 | Wilson et al. |
| 9,563,273 | B2 | 2/2017 | Mann |
| 9,563,740 | B2 | 2/2017 | Abdelghani et al. |
| 9,563,950 | B2 | 2/2017 | Raj |
| 9,566,426 | B2 | 2/2017 | Simon et al. |
| 9,567,327 | B2 | 2/2017 | Xiong et al. |
| 9,568,564 | B2 | 2/2017 | Ma et al. |
| 9,568,635 | B2 | 2/2017 | Suhami |
| 9,572,996 | B2 | 2/2017 | Tass et al. |
| 9,577,992 | B2 | 2/2017 | Zizi et al. |
| 9,578,425 | B2 | 2/2017 | Hakansson |
| 9,579,035 | B2 | 2/2017 | Sarkela |
| 9,579,048 | B2 | 2/2017 | Rayner et al. |
| 9,579,247 | B2 | 2/2017 | Juto et al. |
| 9,579,457 | B2 | 2/2017 | Osorio |
| 9,579,506 | B2 | 2/2017 | Osorio |
| 9,582,072 | B2 | 2/2017 | Connor |
| 9,582,152 | B2 | 2/2017 | Gulaka et al. |
| 9,582,925 | B2 | 2/2017 | Durand et al. |
| 9,584,928 | B2 | 2/2017 | Laudanski et al. |
| 9,585,581 | B1 | 3/2017 | Mullins et al. |
| 9,585,723 | B2 | 3/2017 | Taylor |
| 9,586,047 | B2 | 3/2017 | Osorio et al. |
| 9,586,053 | B2 | 3/2017 | Moffitt et al. |
| 9,588,203 | B2 | 3/2017 | Zhu et al. |
| 9,588,490 | B2 | 3/2017 | Tsang |
| 9,590,986 | B2 | 3/2017 | Zizi et al. |
| 9,592,003 | B2 | 3/2017 | Osorio et al. |
| 9,592,004 | B2 | 3/2017 | DiLorenzo et al. |
| 9,592,384 | B2 | 3/2017 | Tass |
| 9,592,387 | B2 | 3/2017 | Skelton et al. |
| 9,592,389 | B2 | 3/2017 | Moffitt |
| 9,592,409 | B2 | 3/2017 | Yoo et al. |
| 9,596,224 | B2 | 3/2017 | Woods et al. |
| 9,597,493 | B2 | 3/2017 | Wingeier et al. |
| 9,597,494 | B2 | 3/2017 | Wingeier et al. |
| 9,597,501 | B1 | 3/2017 | Danilov et al. |
| 9,597,504 | B1 | 3/2017 | Danilov et al. |
| 9,600,138 | B2 | 3/2017 | Thomas et al. |
| 9,600,778 | B2 | 3/2017 | Sapiro et al. |
| 9,604,056 | B2 | 3/2017 | Starr et al. |
| 9,604,067 | B2 | 3/2017 | Kothandaraman et al. |
| 9,604,073 | B2 | 3/2017 | Deisseroth et al. |
| 9,607,023 | B1 | 3/2017 | Swamy |
| 9,607,377 | B2 | 3/2017 | Lovberg et al. |
| 9,609,453 | B2 | 3/2017 | Jabri |
| 9,610,442 | B2 | 4/2017 | Yoo et al. |
| 9,610,456 | B2 | 4/2017 | Linke et al. |
| 9,610,459 | B2 | 4/2017 | Burnett et al. |
| 9,612,295 | B2 | 4/2017 | Toda et al. |
| 9,613,184 | B2 | 4/2017 | Giftakis et al. |
| 9,613,186 | B2 | 4/2017 | Fonte |
| 9,615,746 | B2 | 4/2017 | Horseman |
| 9,615,749 | B2 | 4/2017 | Clifton et al. |
| 9,615,789 | B2 | 4/2017 | Deisseroth et al. |
| 9,616,166 | B2 | 4/2017 | Kalafut et al. |
| 9,616,227 | B2 | 4/2017 | Lindenthaler et al. |
| 9,618,591 | B1 | 4/2017 | Radparvar et al. |
| 9,622,660 | B2 | 4/2017 | Le et al. |
| 9,622,672 | B2 | 4/2017 | Yoshida et al. |
| 9,622,675 | B2 | 4/2017 | Leyde et al. |
| 9,622,676 | B2 | 4/2017 | Masmanidis et al. |
| 9,622,700 | B2 | 4/2017 | Sahasrabudhe et al. |
| 9,622,702 | B2 | 4/2017 | Badower et al. |
| 9,622,703 | B2 | 4/2017 | Badower et al. |
| 9,623,240 | B2 | 4/2017 | Simon et al. |
| 9,623,241 | B2 | 4/2017 | Wagner et al. |
| 9,626,756 | B2 | 4/2017 | Dean et al. |
| 9,629,548 | B2 | 4/2017 | Sachanandani et al. |
| 9,629,568 | B2 | 4/2017 | Hagedorn et al. |
| 9,629,976 | B1 | 4/2017 | Acton |
| 9,630,004 | B2 | 4/2017 | Rajguru et al. |
| 9,630,008 | B2 | 4/2017 | McLaughlin et al. |
| 9,630,011 | B2 | 4/2017 | Lipani |
| 9,630,029 | B2 | 4/2017 | Wurster et al. |
| 9,636,019 | B2 | 5/2017 | Hendler et al. |
| 9,636,185 | B2 | 5/2017 | Quaid et al. |
| 9,640,167 | B2 | 5/2017 | DeFranks et al. |
| 9,641,665 | B2 | 5/2017 | Lee et al. |
| 9,642,552 | B2 | 5/2017 | Hua |
| 9,642,553 | B2 | 5/2017 | Hokari |
| 9,642,554 | B2 | 5/2017 | Simola et al. |
| 9,642,699 | B2 | 5/2017 | Wortz et al. |
| 9,643,015 | B2 | 5/2017 | Moffitt et al. |
| 9,643,017 | B2 | 5/2017 | Carcieri et al. |
| 9,643,019 | B2 | 5/2017 | Higgins et al. |
| 9,646,248 | B1 | 5/2017 | Benvenuto et al. |
| 9,649,030 | B2 | 5/2017 | Gross et al. |
| 9,649,036 | B2 | 5/2017 | Teixeira |
| 9,649,439 | B2 | 5/2017 | John |
| 9,649,493 | B2 | 5/2017 | Mashiach |
| 9,649,494 | B2 | 5/2017 | Gerber et al. |
| 9,649,501 | B2 | 5/2017 | Best |
| 9,651,368 | B2 | 5/2017 | Abovitz et al. |
| 9,651,706 | B2 | 5/2017 | Mandviwala et al. |
| 9,652,626 | B2 | 5/2017 | Son et al. |
| 9,652,871 | B2 | 5/2017 | Han et al. |
| 9,655,573 | B2 | 5/2017 | Majewski et al. |
| 9,655,669 | B2 | 5/2017 | Palti et al. |
| 9,656,069 | B1 | 5/2017 | Danilov et al. |
| 9,656,075 | B2 | 5/2017 | Osorio |
| 9,656,078 | B1 | 5/2017 | Danilov et al. |
| 9,656,096 | B2 | 5/2017 | Pilla |
| 9,659,186 | B2 | 5/2017 | Pinsky et al. |

(56) References Cited

U.S. PATENT DOCUMENTS

| | | | |
|---|---|---|---|
| 9,659,229 B2 | 5/2017 | Clifton et al. |
| 9,662,049 B2 | 5/2017 | Scarantino et al. |
| 9,662,069 B2 | 5/2017 | De Graff et al. |
| 9,662,083 B2 | 5/2017 | Sakaue |
| 9,662,490 B2 | 5/2017 | Tracey et al. |
| 9,662,492 B1 | 5/2017 | Tucker et al. |
| 9,662,502 B2 | 5/2017 | Giuffrida et al. |
| 9,664,856 B2 | 5/2017 | Nagasaka |
| 9,665,824 B2 | 5/2017 | Chang et al. |
| 9,665,987 B2 | 5/2017 | Fateh |
| 9,668,694 B2 | 6/2017 | Badower |
| 9,669,185 B2 | 6/2017 | Nofzinger |
| 9,669,239 B2 | 6/2017 | Carpentier |
| 9,672,302 B2 | 6/2017 | Dean et al. |
| 9,672,617 B2 | 6/2017 | Dean et al. |
| 9,674,621 B2 | 6/2017 | Bahmer |
| 9,675,254 B2 | 6/2017 | Semenov |
| 9,675,255 B2 | 6/2017 | Semenov |
| 9,675,292 B2 | 6/2017 | Fadem |
| 9,675,794 B2 | 6/2017 | Miller |
| 9,675,809 B2 | 6/2017 | Chow |
| 9,681,814 B2 | 6/2017 | Galloway et al. |
| 9,681,820 B2 | 6/2017 | Wagner |
| 9,682,232 B2 | 6/2017 | Shore et al. |
| 9,682,241 B2 | 6/2017 | Hyde et al. |
| 9,684,051 B2 | 6/2017 | Nieminen et al. |
| 9,684,335 B2 | 6/2017 | Kim et al. |
| 9,685,600 B2 | 6/2017 | Washington, II et al. |
| 9,687,187 B2 | 6/2017 | Dagum |
| 9,687,562 B2 | 6/2017 | Satchi-Fainaro et al. |
| 9,693,684 B2 | 7/2017 | Lopez et al. |
| 9,693,724 B2 | 7/2017 | Dagum |
| 9,693,725 B2 | 7/2017 | Soza |
| 9,693,734 B2 | 7/2017 | Horseman |
| 9,694,155 B2 | 7/2017 | Panova et al. |
| 9,694,178 B2 | 7/2017 | Ruffini et al. |
| 9,694,197 B2 | 7/2017 | Segal |
| 9,697,330 B2 | 7/2017 | Taylor |
| 9,697,336 B2 | 7/2017 | Hyde et al. |
| 9,700,256 B2 | 7/2017 | Osorio et al. |
| 9,700,716 B2 | 7/2017 | Faltys et al. |
| 9,700,723 B2 | 7/2017 | Sabesan |
| 9,704,205 B2 | 7/2017 | Akutagawa et al. |
| 9,706,910 B1 | 7/2017 | Blaha et al. |
| 9,706,925 B2 | 7/2017 | Taylor |
| 9,706,957 B2 | 7/2017 | Wu et al. |
| 9,706,963 B2 | 7/2017 | Gupta et al. |
| 9,707,372 B2 | 7/2017 | Smith |
| 9,707,390 B2 | 7/2017 | Ahmed |
| 9,707,391 B2 | 7/2017 | Ahmed |
| 9,707,396 B2 | 7/2017 | Su et al. |
| 9,710,788 B2 | 7/2017 | Horseman |
| 9,712,736 B2 | 7/2017 | Kearns et al. |
| 9,713,428 B2 | 7/2017 | Chon et al. |
| 9,713,433 B2 | 7/2017 | Gadot et al. |
| 9,713,444 B2 | 7/2017 | Severson |
| 9,713,712 B2 | 7/2017 | Wingeier et al. |
| 9,715,032 B2 | 7/2017 | Song et al. |
| 9,717,461 B2 | 8/2017 | Yu et al. |
| 9,717,904 B2 | 8/2017 | Simon et al. |
| 9,717,920 B1 | 8/2017 | Heldman et al. |
| 9,724,517 B2 | 8/2017 | Giftakis et al. |
| 9,729,252 B2 | 8/2017 | Tyler et al. |
| 9,732,039 B2 | 8/2017 | Xiong et al. |
| 9,734,589 B2 | 8/2017 | Yu et al. |
| 9,734,601 B2 | 8/2017 | Bresler et al. |
| 9,734,632 B2 | 8/2017 | Thomas et al. |
| 9,737,230 B2 | 8/2017 | Sarma et al. |
| 9,740,710 B2 | 8/2017 | Han et al. |
| 9,740,946 B2 | 8/2017 | Varkuti et al. |
| 9,741,114 B2 | 8/2017 | Varkuti |
| 9,743,197 B2 | 8/2017 | Petersen et al. |
| 9,743,835 B2 | 8/2017 | Taylor |
| 9,744,358 B2 | 8/2017 | Hehrmann et al. |
| 9,763,592 B2 | 9/2017 | Le et al. |
| 9,991,026 B2 | 6/2018 | Kanagawa |
| 2001/0003799 A1 | 6/2001 | Boveja |
| 2001/0009975 A1 | 7/2001 | Tsukada et al. |
| 2001/0014818 A1 | 8/2001 | Kennedy |
| 2001/0020127 A1 | 9/2001 | Oshio et al. |
| 2001/0021800 A1 | 9/2001 | Balkin et al. |
| 2001/0029391 A1 | 10/2001 | Gluckman et al. |
| 2001/0049480 A1 | 12/2001 | John et al. |
| 2001/0051774 A1 | 12/2001 | Littrup et al. |
| 2001/0051787 A1 | 12/2001 | Haller et al. |
| 2002/0000808 A1 | 1/2002 | Nichols |
| 2002/0005784 A1 | 1/2002 | Balkin et al. |
| 2002/0006875 A1 | 1/2002 | Mcfetridge |
| 2002/0013612 A1 | 1/2002 | Whitehurst |
| 2002/0013613 A1 | 1/2002 | Haller et al. |
| 2002/0016552 A1 | 2/2002 | Granger et al. |
| 2002/0017905 A1 | 2/2002 | Conti |
| 2002/0017994 A1 | 2/2002 | Balkin et al. |
| 2002/0024450 A1 | 2/2002 | Townsend et al. |
| 2002/0032375 A1 | 3/2002 | Bauch et al. |
| 2002/0033454 A1 | 3/2002 | Cheng et al. |
| 2002/0035317 A1 | 3/2002 | Cheng et al. |
| 2002/0035338 A1 | 3/2002 | Dear et al. |
| 2002/0037095 A1 | 3/2002 | Cheng |
| 2002/0042563 A1 | 4/2002 | Becerra et al. |
| 2002/0052539 A1 | 5/2002 | Haller et al. |
| 2002/0055675 A1 | 5/2002 | Llinas et al. |
| 2002/0058867 A1 | 5/2002 | Breiter et al. |
| 2002/0059159 A1 | 5/2002 | Cook |
| 2002/0072776 A1 | 6/2002 | Osorio et al. |
| 2002/0072782 A1 | 6/2002 | Osorio et al. |
| 2002/0077536 A1 | 6/2002 | Diab et al. |
| 2002/0082513 A1 | 6/2002 | Ennen et al. |
| 2002/0082665 A1 | 6/2002 | Haller et al. |
| 2002/0085174 A1 | 7/2002 | Bolger et al. |
| 2002/0087201 A1 | 7/2002 | Firlik et al. |
| 2002/0091319 A1 | 7/2002 | Moehring et al. |
| 2002/0091335 A1 | 7/2002 | John et al. |
| 2002/0091419 A1 | 7/2002 | Firlik et al. |
| 2002/0095099 A1 | 7/2002 | Quyen et al. |
| 2002/0097332 A1 | 7/2002 | Martin et al. |
| 2002/0099273 A1 | 7/2002 | Bocionek et al. |
| 2002/0099295 A1 | 7/2002 | Gil et al. |
| 2002/0099306 A1 | 7/2002 | Shaw et al. |
| 2002/0099412 A1 | 7/2002 | Fischell et al. |
| 2002/0099417 A1 | 7/2002 | Naritoku et al. |
| 2002/0099418 A1 | 7/2002 | Naritoku et al. |
| 2002/0103428 A1 | 8/2002 | deCharms |
| 2002/0103429 A1 | 8/2002 | deCharms |
| 2002/0103512 A1 | 8/2002 | Echauz et al. |
| 2002/0107454 A1 | 8/2002 | Collura et al. |
| 2002/0112732 A1 | 8/2002 | Blazey et al. |
| 2002/0117176 A1 | 8/2002 | Mantzaridis et al. |
| 2002/0128540 A1 | 9/2002 | Kim et al. |
| 2002/0128544 A1 | 9/2002 | Diab et al. |
| 2002/0128638 A1 | 9/2002 | Chauvet et al. |
| 2002/0138013 A1 | 9/2002 | Guerrero et al. |
| 2002/0151771 A1 | 10/2002 | Braun et al. |
| 2002/0151939 A1 | 10/2002 | Rezai |
| 2002/0158631 A1 | 10/2002 | Kandori et al. |
| 2002/0173714 A1 | 11/2002 | Tsukada et al. |
| 2002/0177882 A1 | 11/2002 | DiLorenzo |
| 2002/0182574 A1 | 12/2002 | Freer |
| 2002/0183607 A1 | 12/2002 | Bauch et al. |
| 2002/0183644 A1 | 12/2002 | Levendowski et al. |
| 2002/0188330 A1 | 12/2002 | Gielen et al. |
| 2002/0193670 A1 | 12/2002 | Garfield et al. |
| 2003/0001098 A1 | 1/2003 | Stoddart et al. |
| 2003/0004429 A1 | 1/2003 | Price |
| 2003/0009078 A1 | 1/2003 | Fedorovskaya et al. |
| 2003/0009096 A1 | 1/2003 | Lahteenmaki |
| 2003/0013981 A1 | 1/2003 | Gevins et al. |
| 2003/0018277 A1 | 1/2003 | He |
| 2003/0018278 A1 | 1/2003 | Jordan |
| 2003/0023183 A1 | 1/2003 | Williams |
| 2003/0023282 A1 | 1/2003 | Barrett et al. |
| 2003/0028081 A1 | 2/2003 | Blazey et al. |
| 2003/0028121 A1 | 2/2003 | Blazey et al. |
| 2003/0028348 A1 | 2/2003 | Wenzel et al. |

(56) References Cited

U.S. PATENT DOCUMENTS

| | | |
|---|---|---|
| 2003/0031357 A1 | 2/2003 | Wenzel et al. |
| 2003/0032870 A1 | 2/2003 | Farwell |
| 2003/0032888 A1 | 2/2003 | Dewan |
| 2003/0032889 A1 | 2/2003 | Wells |
| 2003/0035301 A1 | 2/2003 | Gardiner et al. |
| 2003/0036689 A1 | 2/2003 | Diab et al. |
| 2003/0040660 A1 | 2/2003 | Jackowski et al. |
| 2003/0045914 A1 | 3/2003 | Cohen et al. |
| 2003/0046018 A1 | 3/2003 | Kohlmorgen et al. |
| 2003/0055355 A1 | 3/2003 | Viertio-Oja |
| 2003/0068605 A1 | 4/2003 | Kullok et al. |
| 2003/0070685 A1 | 4/2003 | Patton et al. |
| 2003/0074032 A1 | 4/2003 | Gliner |
| 2003/0081818 A1 | 5/2003 | Fujimaki |
| 2003/0083596 A1 | 5/2003 | Kramer et al. |
| 2003/0083716 A1 | 5/2003 | Nicolelis et al. |
| 2003/0088274 A1 | 5/2003 | Gliner et al. |
| 2003/0093004 A1 | 5/2003 | Sosa et al. |
| 2003/0093005 A1 | 5/2003 | Tucker |
| 2003/0093129 A1 | 5/2003 | Nicolelis et al. |
| 2003/0097159 A1 | 5/2003 | Schiff et al. |
| 2003/0097161 A1 | 5/2003 | Firlik et al. |
| 2003/0100844 A1 | 5/2003 | Miller et al. |
| 2003/0105408 A1 | 6/2003 | Gotman et al. |
| 2003/0114886 A1 | 6/2003 | Gluckman et al. |
| 2003/0120140 A1 | 6/2003 | Bango |
| 2003/0120172 A1 | 6/2003 | Foust et al. |
| 2003/0125786 A1 | 7/2003 | Gliner et al. |
| 2003/0128801 A1 | 7/2003 | Eisenberg et al. |
| 2003/0130706 A1 | 7/2003 | Sheffield et al. |
| 2003/0130709 A1 | 7/2003 | D.C. et al. |
| 2003/0135128 A1 | 7/2003 | Suffin et al. |
| 2003/0139681 A1 | 7/2003 | Melker et al. |
| 2003/0144601 A1 | 7/2003 | Prichep |
| 2003/0149351 A1 | 8/2003 | Nowinski et al. |
| 2003/0149678 A1 | 8/2003 | Cook |
| 2003/0153818 A1 | 8/2003 | Bocionek et al. |
| 2003/0158466 A1 | 8/2003 | Lynn et al. |
| 2003/0158495 A1 | 8/2003 | Hogan |
| 2003/0158496 A1 | 8/2003 | Keirsbilck et al. |
| 2003/0158497 A1 | 8/2003 | Graham et al. |
| 2003/0158587 A1 | 8/2003 | Esteller et al. |
| 2003/0160622 A1 | 8/2003 | Duensing et al. |
| 2003/0163027 A1 | 8/2003 | Balkin et al. |
| 2003/0163028 A1 | 8/2003 | Balkin et al. |
| 2003/0167019 A1 | 9/2003 | Viertio-Oja et al. |
| 2003/0171658 A1 | 9/2003 | Keirsbilck et al. |
| 2003/0171685 A1 | 9/2003 | Lesser et al. |
| 2003/0171689 A1 | 9/2003 | Millan et al. |
| 2003/0176804 A1 | 9/2003 | Melker |
| 2003/0181791 A1 | 9/2003 | Thomas et al. |
| 2003/0181821 A1 | 9/2003 | Greenwald et al. |
| 2003/0181954 A1 | 9/2003 | Rezai |
| 2003/0181955 A1 | 9/2003 | Gielen et al. |
| 2003/0185408 A1 | 10/2003 | Causevic et al. |
| 2003/0187359 A1 | 10/2003 | Njemanze |
| 2003/0195429 A1 | 10/2003 | Wilson |
| 2003/0195574 A1 | 10/2003 | Osorio et al. |
| 2003/0199749 A1 | 10/2003 | Lowery, Jr. et al. |
| 2003/0204135 A1 | 10/2003 | Bystritsky |
| 2003/0216654 A1 | 11/2003 | Xu et al. |
| 2003/0225335 A1 | 12/2003 | Njemanze |
| 2003/0225340 A1 | 12/2003 | Collura |
| 2003/0229291 A1 | 12/2003 | Collura |
| 2003/0233039 A1 | 12/2003 | Shao et al. |
| 2003/0233250 A1 | 12/2003 | Joffe et al. |
| 2003/0234781 A1 | 12/2003 | Laidlaw et al. |
| 2003/0236458 A1 | 12/2003 | Hochman |
| 2003/0236557 A1 | 12/2003 | Whitehurst et al. |
| 2003/0236558 A1 | 12/2003 | Whitehurst et al. |
| 2004/0002635 A1 | 1/2004 | Hargrove et al. |
| 2004/0006265 A1 | 1/2004 | Alhussiny |
| 2004/0006376 A1 | 1/2004 | Falci |
| 2004/0010203 A1 | 1/2004 | Bibian et al. |
| 2004/0015204 A1 | 1/2004 | Whitehurst et al. |
| 2004/0015205 A1 | 1/2004 | Whitehurst et al. |
| 2004/0019257 A1 | 1/2004 | Meadows |
| 2004/0019370 A1 | 1/2004 | Gliner et al. |
| 2004/0024287 A1 | 2/2004 | Patton et al. |
| 2004/0030585 A1 | 2/2004 | Sariel |
| 2004/0034299 A1 | 2/2004 | Kandori et al. |
| 2004/0039268 A1 | 2/2004 | Barbour et al. |
| 2004/0049124 A1 | 3/2004 | Kullok et al. |
| 2004/0049484 A1 | 3/2004 | Kamba |
| 2004/0059203 A1 | 3/2004 | Guerrero et al. |
| 2004/0059241 A1 | 3/2004 | Suffin |
| 2004/0064020 A1 | 4/2004 | Diab et al. |
| 2004/0064066 A1 | 4/2004 | John et al. |
| 2004/0068164 A1 | 4/2004 | Diab et al. |
| 2004/0068172 A1 | 4/2004 | Nowinski et al. |
| 2004/0068199 A1 | 4/2004 | Echauz et al. |
| 2004/0072133 A1 | 4/2004 | Kullok et al. |
| 2004/0073098 A1 | 4/2004 | Geva et al. |
| 2004/0073129 A1 | 4/2004 | Caldwell et al. |
| 2004/0073273 A1 | 4/2004 | Gluckman et al. |
| 2004/0077960 A1 | 4/2004 | Tanaka et al. |
| 2004/0077967 A1 | 4/2004 | Jordan |
| 2004/0078056 A1 | 4/2004 | Zangen et al. |
| 2004/0079372 A1 | 4/2004 | John et al. |
| 2004/0082862 A1 | 4/2004 | Chance |
| 2004/0082876 A1 | 4/2004 | Viertio-Oja et al. |
| 2004/0088732 A1 | 5/2004 | Martin et al. |
| 2004/0092809 A1 | 5/2004 | DeCharms |
| 2004/0096395 A1 | 5/2004 | Xiong et al. |
| 2004/0097802 A1 | 5/2004 | Cohen |
| 2004/0101146 A1 | 5/2004 | Laitinen et al. |
| 2004/0116784 A1 | 6/2004 | Gavish |
| 2004/0116791 A1 | 6/2004 | Miyauchi |
| 2004/0116798 A1 | 6/2004 | Cancro et al. |
| 2004/0116825 A1 | 6/2004 | Sturzebecher |
| 2004/0117098 A1 | 6/2004 | Ryu et al. |
| 2004/0122787 A1 | 6/2004 | Avinash et al. |
| 2004/0122790 A1 | 6/2004 | Walker et al. |
| 2004/0127803 A1 | 7/2004 | Berkes et al. |
| 2004/0131998 A1 | 7/2004 | Marom et al. |
| 2004/0133118 A1 | 7/2004 | Llinas |
| 2004/0133119 A1 | 7/2004 | Osorio et al. |
| 2004/0133120 A1 | 7/2004 | Frei et al. |
| 2004/0133248 A1 | 7/2004 | Frei et al. |
| 2004/0133390 A1 | 7/2004 | Osorio et al. |
| 2004/0138516 A1 | 7/2004 | Osorio et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0138580 A1 | 7/2004 | Frei et al. |
| 2004/0138581 A1 | 7/2004 | Frei et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0140811 A1 | 7/2004 | Conti |
| 2004/0143170 A1 | 7/2004 | DuRousseau |
| 2004/0144925 A1 | 7/2004 | Stoddart et al. |
| 2004/0145370 A1 | 7/2004 | Conti |
| 2004/0151368 A1 | 8/2004 | Cruickshank et al. |
| 2004/0152958 A1 | 8/2004 | Frei et al. |
| 2004/0152995 A1 | 8/2004 | Cox et al. |
| 2004/0153129 A1 | 8/2004 | Pless et al. |
| 2004/0158119 A1 | 8/2004 | Osorio et al. |
| 2004/0158298 A1 | 8/2004 | Gliner et al. |
| 2004/0158300 A1 | 8/2004 | Gardiner |
| 2004/0166536 A1 | 8/2004 | Kerkman et al. |
| 2004/0167418 A1 | 8/2004 | Nguyen et al. |
| 2004/0172089 A1 | 9/2004 | Whitehurst et al. |
| 2004/0172091 A1 | 9/2004 | Rezai |
| 2004/0172094 A1 | 9/2004 | Cohen et al. |
| 2004/0181162 A1 | 9/2004 | Wilson |
| 2004/0184024 A1 | 9/2004 | Katura et al. |
| 2004/0186542 A1 | 9/2004 | van Venrooij et al. |
| 2004/0193037 A1 | 9/2004 | Tsukada et al. |
| 2004/0193068 A1 | 9/2004 | Burton et al. |
| 2004/0193220 A1 | 9/2004 | Whitehurst et al. |
| 2004/0195512 A1 | 10/2004 | Crosetto |
| 2004/0199482 A1 | 10/2004 | Wilson |
| 2004/0204636 A1 | 10/2004 | Diab et al. |

(56)　　　　References Cited

U.S. PATENT DOCUMENTS

| | | |
|---|---|---|
| 2004/0204637 A1 | 10/2004 | Diab et al. |
| 2004/0204656 A1 | 10/2004 | Tolvanen-Laakso et al. |
| 2004/0204659 A1 | 10/2004 | John et al. |
| 2004/0210127 A1 | 10/2004 | Kandori et al. |
| 2004/0210146 A1 | 10/2004 | Diab et al. |
| 2004/0210156 A1 | 10/2004 | Hogan |
| 2004/0215082 A1 | 10/2004 | Chance |
| 2004/0220494 A1 | 11/2004 | Sturzebecher |
| 2004/0220782 A1 | 11/2004 | Cook |
| 2004/0225179 A1 | 11/2004 | Kaplan et al. |
| 2004/0230105 A1 | 11/2004 | Geva et al. |
| 2004/0243017 A1 | 12/2004 | Causevic |
| 2004/0243182 A1 | 12/2004 | Cohen et al. |
| 2004/0254493 A1 | 12/2004 | Chervin et al. |
| 2004/0260169 A1 | 12/2004 | Sternnickel |
| 2004/0260356 A1 | 12/2004 | Kara et al. |
| 2004/0263162 A1 | 12/2004 | Kandori et al. |
| 2004/0267152 A1 | 12/2004 | Pineda |
| 2005/0004489 A1 | 1/2005 | Sarkela et al. |
| 2005/0007091 A1 | 1/2005 | Makeig et al. |
| 2005/0010091 A1 | 1/2005 | Woods et al. |
| 2005/0010116 A1 | 1/2005 | Korhonen et al. |
| 2005/0015205 A1 | 1/2005 | Repucci et al. |
| 2005/0018858 A1 | 1/2005 | John |
| 2005/0019734 A1 | 1/2005 | Peled |
| 2005/0020483 A1 | 1/2005 | Oksenberg et al. |
| 2005/0020918 A1 | 1/2005 | Wilk et al. |
| 2005/0021105 A1 | 1/2005 | Firlik et al. |
| 2005/0025704 A1 | 2/2005 | Keirsbilck et al. |
| 2005/0027284 A1 | 2/2005 | Lozano et al. |
| 2005/0032827 A1 | 2/2005 | Oksenberg et al. |
| 2005/0033122 A1 | 2/2005 | Balkin et al. |
| 2005/0033154 A1 | 2/2005 | deCharms |
| 2005/0033174 A1 | 2/2005 | Moehring et al. |
| 2005/0033379 A1 | 2/2005 | Lozano et al. |
| 2005/0038354 A1 | 2/2005 | Miller et al. |
| 2005/0043774 A1 | 2/2005 | Devlin et al. |
| 2005/0049651 A1 | 3/2005 | Whitehurst et al. |
| 2005/0059689 A1 | 3/2005 | Oksenberg et al. |
| 2005/0059874 A1 | 3/2005 | Fuchs et al. |
| 2005/0060001 A1 | 3/2005 | Singhal et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0065412 A1 | 3/2005 | Shiomi et al. |
| 2005/0065427 A1 | 3/2005 | Magill et al. |
| 2005/0075568 A1 | 4/2005 | Moehring |
| 2005/0079474 A1 | 4/2005 | Lowe |
| 2005/0079636 A1 | 4/2005 | White et al. |
| 2005/0080124 A1 | 4/2005 | Teegarden et al. |
| 2005/0080349 A1 | 4/2005 | Okada et al. |
| 2005/0080828 A1 | 4/2005 | Johnson |
| 2005/0085744 A1 | 4/2005 | Beverina et al. |
| 2005/0096311 A1 | 5/2005 | Suffin et al. |
| 2005/0096517 A1 | 5/2005 | Diab et al. |
| 2005/0106713 A1 | 5/2005 | Phan et al. |
| 2005/0107654 A1 | 5/2005 | Riehl |
| 2005/0113713 A1 | 5/2005 | Foust et al. |
| 2005/0118286 A1 | 6/2005 | Suffin et al. |
| 2005/0119547 A1 | 6/2005 | Shastri et al. |
| 2005/0119586 A1 | 6/2005 | Coyle et al. |
| 2005/0124848 A1 | 6/2005 | Holzner |
| 2005/0124851 A1 | 6/2005 | Patton et al. |
| 2005/0124863 A1 | 6/2005 | Cook |
| 2005/0131311 A1 | 6/2005 | Leuthardt et al. |
| 2005/0135102 A1 | 6/2005 | Gardiner et al. |
| 2005/0136002 A1 | 6/2005 | Fossheim et al. |
| 2005/0137494 A1 | 6/2005 | Viertio-Oja |
| 2005/0137645 A1 | 6/2005 | Voipio et al. |
| 2005/0144042 A1 | 6/2005 | Joffe et al. |
| 2005/0148828 A1 | 7/2005 | Lindsay |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0149123 A1 | 7/2005 | Lesser et al. |
| 2005/0149157 A1 | 7/2005 | Hunter et al. |
| 2005/0153268 A1 | 7/2005 | Junkin et al. |
| 2005/0154290 A1 | 7/2005 | Langleben |
| 2005/0154419 A1 | 7/2005 | Whitehurst et al. |
| 2005/0154425 A1 | 7/2005 | Boveja et al. |
| 2005/0154426 A1 | 7/2005 | Boveja et al. |
| 2005/0156602 A1 | 7/2005 | Conti |
| 2005/0159670 A1 | 7/2005 | Sneddon |
| 2005/0159671 A1 | 7/2005 | Sneddon |
| 2005/0165458 A1 | 7/2005 | Boveja et al. |
| 2005/0167588 A1 | 8/2005 | Donnangelo |
| 2005/0171410 A1 | 8/2005 | Hjelt et al. |
| 2005/0182287 A1 | 8/2005 | Becker |
| 2005/0182288 A1 | 8/2005 | Zabara |
| 2005/0182389 A1 | 8/2005 | LaPorte et al. |
| 2005/0182450 A1 | 8/2005 | Hunter et al. |
| 2005/0182453 A1 | 8/2005 | Whitehurst et al. |
| 2005/0182456 A1 | 8/2005 | Ziobro et al. |
| 2005/0182467 A1 | 8/2005 | Hunter et al. |
| 2005/0182468 A1 | 8/2005 | Hunter et al. |
| 2005/0182469 A1 | 8/2005 | Hunter et al. |
| 2005/0187600 A1 | 8/2005 | Hunter et al. |
| 2005/0192514 A1 | 9/2005 | Kearby et al. |
| 2005/0192644 A1 | 9/2005 | Boveja et al. |
| 2005/0192647 A1 | 9/2005 | Hunter et al. |
| 2005/0197590 A1 | 9/2005 | Osorio et al. |
| 2005/0197675 A1 | 9/2005 | David et al. |
| 2005/0197678 A1 | 9/2005 | Boveja et al. |
| 2005/0209512 A1 | 9/2005 | Heruth et al. |
| 2005/0209517 A1 | 9/2005 | Diab et al. |
| 2005/0209654 A1 | 9/2005 | Boveja et al. |
| 2005/0209664 A1 | 9/2005 | Hunter et al. |
| 2005/0209665 A1 | 9/2005 | Hunter et al. |
| 2005/0209666 A1 | 9/2005 | Hunter et al. |
| 2005/0215889 A1 | 9/2005 | Patterson |
| 2005/0216070 A1 | 9/2005 | Boveja et al. |
| 2005/0216071 A1 | 9/2005 | Devlin et al. |
| 2005/0222522 A1 | 10/2005 | Heruth et al. |
| 2005/0222639 A1 | 10/2005 | Seifritz et al. |
| 2005/0228451 A1 | 10/2005 | Jaax et al. |
| 2005/0228785 A1 | 10/2005 | Wolcott et al. |
| 2005/0240087 A1 | 10/2005 | Keenan et al. |
| 2005/0240229 A1 | 10/2005 | Whitehurst et al. |
| 2005/0240253 A1 | 10/2005 | Tyler et al. |
| 2005/0244045 A1 | 11/2005 | Eriksson |
| 2005/0245796 A1 | 11/2005 | Woods et al. |
| 2005/0251055 A1 | 11/2005 | Zhirnov et al. |
| 2005/0251220 A1 | 11/2005 | Barrett et al. |
| 2005/0256378 A1 | 11/2005 | Takai et al. |
| 2005/0256385 A1 | 11/2005 | Diab et al. |
| 2005/0256418 A1 | 11/2005 | Mietus et al. |
| 2005/0267011 A1 | 12/2005 | Deisseroth et al. |
| 2005/0267343 A1 | 12/2005 | Woods et al. |
| 2005/0267344 A1 | 12/2005 | Woods et al. |
| 2005/0267362 A1 | 12/2005 | Mietus et al. |
| 2005/0267542 A1 | 12/2005 | David et al. |
| 2005/0273017 A1 | 12/2005 | Gordon |
| 2005/0277813 A1 | 12/2005 | Katz et al. |
| 2005/0277912 A1 | 12/2005 | John |
| 2005/0283053 A1 | 12/2005 | deCharms |
| 2005/0283090 A1 | 12/2005 | Wells |
| 2006/0004298 A1 | 1/2006 | Kennedy et al. |
| 2006/0004422 A1 | 1/2006 | De Ridder |
| 2006/0009704 A1 | 1/2006 | Okada et al. |
| 2006/0009815 A1 | 1/2006 | Boveja et al. |
| 2006/0014753 A1 | 1/2006 | Shamloo et al. |
| 2006/0015034 A1 | 1/2006 | Martinerie et al. |
| 2006/0015153 A1 | 1/2006 | Gliner et al. |
| 2006/0018525 A1 | 1/2006 | Barbour |
| 2006/0020184 A1 | 1/2006 | Woods et al. |
| 2006/0036152 A1 | 2/2006 | Kozel |
| 2006/0036153 A1 | 2/2006 | Laken |
| 2006/0041201 A1 | 2/2006 | Behbehani et al. |
| 2006/0047187 A1 | 3/2006 | Goyal et al. |
| 2006/0047216 A1 | 3/2006 | Dorr et al. |
| 2006/0047324 A1 | 3/2006 | Tass |
| 2006/0047325 A1 | 3/2006 | Thimineur et al. |
| 2006/0051814 A1 | 3/2006 | Jackowski et al. |

(56)            References Cited

U.S. PATENT DOCUMENTS

| | | |
|---|---|---|
| 2006/0052386 A1 | 3/2006 | Wieloch et al. |
| 2006/0052657 A9 | 3/2006 | Zabara |
| 2006/0052706 A1 | 3/2006 | Hynynen et al. |
| 2006/0058590 A1 | 3/2006 | Shaw et al. |
| 2006/0058683 A1 | 3/2006 | Chance |
| 2006/0058856 A1 | 3/2006 | Morrell |
| 2006/0061544 A1 | 3/2006 | Min et al. |
| 2006/0064138 A1 | 3/2006 | Velasco et al. |
| 2006/0064139 A1 | 3/2006 | Chung et al. |
| 2006/0064140 A1 | 3/2006 | Whitehurst et al. |
| 2006/0069059 A1 | 3/2006 | Schaller et al. |
| 2006/0069415 A1 | 3/2006 | Cameron et al. |
| 2006/0074290 A1 | 4/2006 | Chen et al. |
| 2006/0074298 A1 | 4/2006 | Borsook et al. |
| 2006/0074334 A1 | 4/2006 | Coyle |
| 2006/0074822 A1 | 4/2006 | Eda et al. |
| 2006/0078183 A1 | 4/2006 | deCharms |
| 2006/0079936 A1 | 4/2006 | Boveja et al. |
| 2006/0082727 A1 | 4/2006 | Bolger et al. |
| 2006/0084858 A1 | 4/2006 | Marks |
| 2006/0084877 A1 | 4/2006 | Ujhazy et al. |
| 2006/0087746 A1 | 4/2006 | Lipow |
| 2006/0089541 A1 | 4/2006 | Braun et al. |
| 2006/0089549 A1 | 4/2006 | Diab et al. |
| 2006/0094968 A1 | 5/2006 | Drew |
| 2006/0094970 A1 | 5/2006 | Drew |
| 2006/0094971 A1 | 5/2006 | Drew |
| 2006/0094972 A1 | 5/2006 | Drew |
| 2006/0095091 A1 | 5/2006 | Drew |
| 2006/0095092 A1 | 5/2006 | Drew |
| 2006/0100526 A1 | 5/2006 | Yamamoto et al. |
| 2006/0100530 A1 | 5/2006 | Kliot et al. |
| 2006/0100671 A1 | 5/2006 | Ridder |
| 2006/0102171 A1 | 5/2006 | Gavish |
| 2006/0106274 A1 | 5/2006 | Thomas et al. |
| 2006/0106326 A1 | 5/2006 | Krebs et al. |
| 2006/0106430 A1 | 5/2006 | Fowler et al. |
| 2006/0106434 A1 | 5/2006 | Padgitt et al. |
| 2006/0111644 A1 | 5/2006 | Guttag et al. |
| 2006/0116556 A1 | 6/2006 | Duhamel |
| 2006/0122481 A1 | 6/2006 | Sievenpiper et al. |
| 2006/0129022 A1 | 6/2006 | Venza et al. |
| 2006/0129202 A1 | 6/2006 | Armstrong |
| 2006/0129277 A1 | 6/2006 | Wu et al. |
| 2006/0129324 A1 | 6/2006 | Rabinoff et al. |
| 2006/0135879 A1 | 6/2006 | Liley |
| 2006/0135880 A1 | 6/2006 | Sarkela |
| 2006/0136135 A1 | 6/2006 | Little et al. |
| 2006/0142802 A1 | 6/2006 | Armstrong |
| 2006/0149144 A1 | 7/2006 | Lynn et al. |
| 2006/0149160 A1 | 7/2006 | Kofol et al. |
| 2006/0149337 A1 | 7/2006 | John |
| 2006/0152227 A1 | 7/2006 | Hammer |
| 2006/0153396 A1 | 7/2006 | John |
| 2006/0155206 A1 | 7/2006 | Lynn |
| 2006/0155207 A1 | 7/2006 | Lynn et al. |
| 2006/0155348 A1 | 7/2006 | deCharms |
| 2006/0155495 A1 | 7/2006 | Osorio et al. |
| 2006/0161071 A1 | 7/2006 | Lynn et al. |
| 2006/0161075 A1 | 7/2006 | Kurtz |
| 2006/0161217 A1 | 7/2006 | Jaax et al. |
| 2006/0161218 A1 | 7/2006 | Danilov |
| 2006/0161384 A1 | 7/2006 | Osorio et al. |
| 2006/0167370 A1 | 7/2006 | Greenwald et al. |
| 2006/0167497 A1 | 7/2006 | Armstrong et al. |
| 2006/0167564 A1 | 7/2006 | Flaherty et al. |
| 2006/0167722 A1 | 7/2006 | Mrf Struys et al. |
| 2006/0170424 A1 | 8/2006 | Kasevich |
| 2006/0173259 A1 | 8/2006 | Flaherty et al. |
| 2006/0173364 A1 | 8/2006 | Clancy et al. |
| 2006/0173493 A1 | 8/2006 | Armstrong et al. |
| 2006/0173494 A1 | 8/2006 | Armstrong et al. |
| 2006/0173495 A1 | 8/2006 | Armstrong et al. |
| 2006/0173510 A1 | 8/2006 | Besio et al. |
| 2006/0176062 A1 | 8/2006 | Yang et al. |
| 2006/0178709 A1 | 8/2006 | Foster et al. |
| 2006/0184058 A1 | 8/2006 | Silberstein |
| 2006/0184059 A1 | 8/2006 | Jadidi |
| 2006/0188134 A1 | 8/2006 | Quist |
| 2006/0189866 A1 | 8/2006 | Thomas et al. |
| 2006/0189880 A1 | 8/2006 | Lynn et al. |
| 2006/0189882 A1 | 8/2006 | Thomas |
| 2006/0189899 A1 | 8/2006 | Flaherty et al. |
| 2006/0191543 A1 | 8/2006 | Becker et al. |
| 2006/0195039 A1 | 8/2006 | Drew et al. |
| 2006/0195154 A1 | 8/2006 | Jaax et al. |
| 2006/0195155 A1 | 8/2006 | Firlik et al. |
| 2006/0200013 A1 | 9/2006 | Smith et al. |
| 2006/0200016 A1 | 9/2006 | Diab et al. |
| 2006/0200034 A1 | 9/2006 | Ricci et al. |
| 2006/0200035 A1 | 9/2006 | Ricci et al. |
| 2006/0200206 A1 | 9/2006 | Firlik et al. |
| 2006/0204532 A1 | 9/2006 | John |
| 2006/0206033 A1 | 9/2006 | Guerrero et al. |
| 2006/0206108 A1 | 9/2006 | Hempel |
| 2006/0206155 A1 | 9/2006 | Ben-David et al. |
| 2006/0206165 A1 | 9/2006 | Jaax et al. |
| 2006/0206174 A1 | 9/2006 | Honeycutt et al. |
| 2006/0212090 A1 | 9/2006 | Lozano et al. |
| 2006/0212091 A1 | 9/2006 | Lozano et al. |
| 2006/0217609 A1 | 9/2006 | Diab et al. |
| 2006/0217781 A1 | 9/2006 | John |
| 2006/0217816 A1 | 9/2006 | Pesaran et al. |
| 2006/0224216 A1 | 10/2006 | Pless et al. |
| 2006/0224421 A1 | 10/2006 | St. Ores et al. |
| 2006/0225437 A1 | 10/2006 | Kazami |
| 2006/0229164 A1 | 10/2006 | Einav |
| 2006/0233390 A1 | 10/2006 | Causevic et al. |
| 2006/0235315 A1 | 10/2006 | Akselrod et al. |
| 2006/0235324 A1 | 10/2006 | Lynn |
| 2006/0235484 A1 | 10/2006 | Jaax et al. |
| 2006/0235489 A1 | 10/2006 | Drew et al. |
| 2006/0239482 A1 | 10/2006 | Hatoum |
| 2006/0241373 A1 | 10/2006 | Strychacz et al. |
| 2006/0241382 A1 | 10/2006 | Li et al. |
| 2006/0241562 A1 | 10/2006 | John et al. |
| 2006/0241718 A1 | 10/2006 | Tyler et al. |
| 2006/0247728 A1 | 11/2006 | Foster et al. |
| 2006/0251303 A1 | 11/2006 | He et al. |
| 2006/0252978 A1 | 11/2006 | Vesely et al. |
| 2006/0252979 A1 | 11/2006 | Vesely et al. |
| 2006/0258896 A1 | 11/2006 | Haber et al. |
| 2006/0258950 A1 | 11/2006 | Hargrove et al. |
| 2006/0259077 A1 | 11/2006 | Pardo et al. |
| 2006/0265022 A1 | 11/2006 | John et al. |
| 2006/0276695 A9 | 12/2006 | Lynn et al. |
| 2006/0281543 A1 | 12/2006 | Sutton et al. |
| 2006/0281980 A1 | 12/2006 | Randlov et al. |
| 2006/0282123 A1 | 12/2006 | Hunter et al. |
| 2006/0287691 A1 | 12/2006 | Drew |
| 2006/0293578 A1 | 12/2006 | Rennaker |
| 2006/0293721 A1 | 12/2006 | Tarver et al. |
| 2006/0293723 A1 | 12/2006 | Whitehurst et al. |
| 2007/0000372 A1 | 1/2007 | Rezai et al. |
| 2007/0005115 A1 | 1/2007 | Lozano et al. |
| 2007/0005391 A1 | 1/2007 | Repucci et al. |
| 2007/0007454 A1 | 1/2007 | Stoddart et al. |
| 2007/0008172 A1 | 1/2007 | Hewett et al. |
| 2007/0014454 A1 | 1/2007 | Sawyer et al. |
| 2007/0015985 A1 | 1/2007 | Tolvanen-Laakso et al. |
| 2007/0016095 A1 | 1/2007 | Low et al. |
| 2007/0016264 A1 | 1/2007 | Falci |
| 2007/0019846 A1 | 1/2007 | Bullitt et al. |
| 2007/0021673 A1 | 1/2007 | Arbel et al. |
| 2007/0021675 A1 | 1/2007 | Childre et al. |
| 2007/0021800 A1 | 1/2007 | Whitehurst et al. |
| 2007/0025608 A1 | 2/2007 | Armstrong |
| 2007/0027486 A1 | 2/2007 | Armstrong |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027501 A1 | 2/2007 | Jensen et al. |
| 2007/0031798 A1 | 2/2007 | Gottfried |
| 2007/0032733 A1 | 2/2007 | Burton |

(56)  References Cited

U.S. PATENT DOCUMENTS

| | | |
|---|---|---|
| 2007/0032737 A1 | 2/2007 | Causevic et al. |
| 2007/0032834 A1 | 2/2007 | Gliner et al. |
| 2007/0036355 A1 | 2/2007 | Terauchi et al. |
| 2007/0036402 A1 | 2/2007 | Cahill et al. |
| 2007/0038067 A1 | 2/2007 | Kandori et al. |
| 2007/0038264 A1 | 2/2007 | Jaax et al. |
| 2007/0038382 A1 | 2/2007 | Keenan |
| 2007/0043392 A1 | 2/2007 | Gliner et al. |
| 2007/0043401 A1 | 2/2007 | John |
| 2007/0049844 A1 | 3/2007 | Rosenfeld |
| 2007/0049988 A1 | 3/2007 | Carbunaru et al. |
| 2007/0050715 A1 | 3/2007 | Behar |
| 2007/0055145 A1 | 3/2007 | Zelnik et al. |
| 2007/0060830 A1 | 3/2007 | Le et al. |
| 2007/0060831 A1 | 3/2007 | Le et al. |
| 2007/0060954 A1 | 3/2007 | Cameron et al. |
| 2007/0060974 A1 | 3/2007 | Lozano |
| 2007/0060984 A1 | 3/2007 | Webb et al. |
| 2007/0066403 A1 | 3/2007 | Conkwright |
| 2007/0066914 A1 | 3/2007 | Le et al. |
| 2007/0066915 A1 | 3/2007 | Frei et al. |
| 2007/0066997 A1 | 3/2007 | He et al. |
| 2007/0067003 A1 | 3/2007 | Sanchez et al. |
| 2007/0067004 A1 | 3/2007 | Boveja et al. |
| 2007/0072857 A1 | 3/2007 | Teegarden et al. |
| 2007/0078134 A1 | 4/2007 | Teegarden et al. |
| 2007/0081712 A1 | 4/2007 | Huang et al. |
| 2007/0083128 A1 | 4/2007 | Cote et al. |
| 2007/0093721 A1 | 4/2007 | Lynn et al. |
| 2007/0093870 A1 | 4/2007 | Maschino |
| 2007/0100246 A1 | 5/2007 | Hyde |
| 2007/0100251 A1 | 5/2007 | Prichep |
| 2007/0100278 A1 | 5/2007 | Frei et al. |
| 2007/0100377 A1 | 5/2007 | Armstrong et al. |
| 2007/0100378 A1 | 5/2007 | Maschino |
| 2007/0100389 A1 | 5/2007 | Jaax et al. |
| 2007/0100392 A1 | 5/2007 | Maschino et al. |
| 2007/0100398 A1 | 5/2007 | Sloan |
| 2007/0100666 A1 | 5/2007 | Stivoric et al. |
| 2007/0112404 A1 | 5/2007 | Mann et al. |
| 2007/0118197 A1 | 5/2007 | Loeb |
| 2007/0127793 A1 | 6/2007 | Beckett et al. |
| 2007/0129647 A1 | 6/2007 | Lynn |
| 2007/0129769 A1 | 6/2007 | Bourget et al. |
| 2007/0129774 A1 | 6/2007 | Bourget et al. |
| 2007/0135724 A1 | 6/2007 | Ujhazy et al. |
| 2007/0135728 A1 | 6/2007 | Snyder et al. |
| 2007/0138886 A1 | 6/2007 | Krebs et al. |
| 2007/0142862 A1 | 6/2007 | Dilorenzo |
| 2007/0142873 A1 | 6/2007 | Esteller et al. |
| 2007/0142874 A1 | 6/2007 | John |
| 2007/0149860 A1 | 6/2007 | Lynn et al. |
| 2007/0150024 A1 | 6/2007 | Leyde et al. |
| 2007/0150025 A1 | 6/2007 | Dilorenzo et al. |
| 2007/0150026 A1 | 6/2007 | Bourget et al. |
| 2007/0150029 A1 | 6/2007 | Bourget et al. |
| 2007/0156180 A1 | 7/2007 | Jaax et al. |
| 2007/0156457 A1 | 7/2007 | Brown |
| 2007/0159185 A1 | 7/2007 | Yang et al. |
| 2007/0161919 A1 | 7/2007 | DiLorenzo |
| 2007/0162085 A1 | 7/2007 | DiLorenzo |
| 2007/0162086 A1 | 7/2007 | DiLorenzo |
| 2007/0165915 A1 | 7/2007 | Fuchs |
| 2007/0167694 A1 | 7/2007 | Causevic et al. |
| 2007/0167723 A1 | 7/2007 | Park et al. |
| 2007/0167853 A1 | 7/2007 | Melker et al. |
| 2007/0167858 A1 | 7/2007 | Virtanen et al. |
| 2007/0167991 A1 | 7/2007 | DiLorenzo |
| 2007/0173733 A1 | 7/2007 | Le et al. |
| 2007/0173902 A1 | 7/2007 | Maschino et al. |
| 2007/0179395 A1 | 8/2007 | Sotos et al. |
| 2007/0179396 A1 | 8/2007 | Le et al. |
| 2007/0179534 A1 | 8/2007 | Firlik et al. |
| 2007/0179558 A1 | 8/2007 | Gliner et al. |
| 2007/0179734 A1 | 8/2007 | Chmiel et al. |
| 2007/0184507 A1 | 8/2007 | Jackowski et al. |
| 2007/0191688 A1 | 8/2007 | Lynn |
| 2007/0191691 A1 | 8/2007 | Polanco |
| 2007/0191697 A1 | 8/2007 | Lynn et al. |
| 2007/0191704 A1 | 8/2007 | DeCharms |
| 2007/0191727 A1 | 8/2007 | Fadem |
| 2007/0197930 A1 | 8/2007 | Sarkela |
| 2007/0198063 A1 | 8/2007 | Hunter et al. |
| 2007/0203401 A1 | 8/2007 | Gordon et al. |
| 2007/0203448 A1 | 8/2007 | Melker et al. |
| 2007/0208212 A1 | 9/2007 | DiLorenzo |
| 2007/0208269 A1 | 9/2007 | Mumford et al. |
| 2007/0209669 A1 | 9/2007 | Derchak |
| 2007/0213785 A1 | 9/2007 | Osorio et al. |
| 2007/0213786 A1 | 9/2007 | Sackellares et al. |
| 2007/0225581 A1 | 9/2007 | Diab et al. |
| 2007/0225674 A1 | 9/2007 | Molnar et al. |
| 2007/0225774 A1 | 9/2007 | Eskandar et al. |
| 2007/0225932 A1 | 9/2007 | Halford |
| 2007/0233192 A1 | 10/2007 | Craig |
| 2007/0233193 A1 | 10/2007 | Craig |
| 2007/0238934 A1 | 10/2007 | Viswanathan |
| 2007/0239059 A1 | 10/2007 | McIver |
| 2007/0244387 A1 | 10/2007 | Rodriguez Ponce et al. |
| 2007/0244407 A1 | 10/2007 | Osorio |
| 2007/0249918 A1 | 10/2007 | Diab et al. |
| 2007/0249949 A1 | 10/2007 | Hadley |
| 2007/0249952 A1 | 10/2007 | Rubin et al. |
| 2007/0250119 A1 | 10/2007 | Tyler et al. |
| 2007/0250138 A1 | 10/2007 | Nofzinger |
| 2007/0255122 A1 | 11/2007 | Vol et al. |
| 2007/0255135 A1 | 11/2007 | Kalafut et al. |
| 2007/0255155 A1 | 11/2007 | Drew et al. |
| 2007/0255320 A1 | 11/2007 | Inman et al. |
| 2007/0255379 A1 | 11/2007 | Williams et al. |
| 2007/0255531 A1 | 11/2007 | Drew |
| 2007/0259323 A1 | 11/2007 | Brown et al. |
| 2007/0260151 A1 | 11/2007 | Clifford |
| 2007/0265508 A1 | 11/2007 | Sheikhzadeh-Nadjar et al. |
| 2007/0265533 A1 | 11/2007 | Tran |
| 2007/0273504 A1 | 11/2007 | Tran |
| 2007/0273611 A1 | 11/2007 | Torch |
| 2007/0276270 A1 | 11/2007 | Tran |
| 2007/0276278 A1 | 11/2007 | Coyle et al. |
| 2007/0276279 A1 | 11/2007 | Echauz et al. |
| 2007/0276441 A1 | 11/2007 | Goetz |
| 2007/0276609 A1 | 11/2007 | Greenwald |
| 2007/0280508 A1 | 12/2007 | Ernst et al. |
| 2007/0282228 A1 | 12/2007 | Einav et al. |
| 2007/0287896 A1 | 12/2007 | Derchak et al. |
| 2007/0291832 A1 | 12/2007 | Diab et al. |
| 2007/0293760 A1 | 12/2007 | Schaafsma |
| 2007/0299370 A1 | 12/2007 | Bystritsky |
| 2007/0299371 A1 | 12/2007 | Einav et al. |
| 2008/0001600 A1 | 1/2008 | deCharms |
| 2008/0001735 A1 | 1/2008 | Tran |
| 2008/0004514 A1 | 1/2008 | Diab et al. |
| 2008/0004550 A1 | 1/2008 | Einav et al. |
| 2008/0004904 A1 | 1/2008 | Tran |
| 2008/0009685 A1 | 1/2008 | Kim et al. |
| 2008/0009772 A1 | 1/2008 | Tyler et al. |
| 2008/0013747 A1 | 1/2008 | Tran |
| 2008/0015458 A1 | 1/2008 | Buarque de Macedo et al. |
| 2008/0015459 A1 | 1/2008 | Llinas |
| 2008/0021332 A1 | 1/2008 | Brainard |
| 2008/0021336 A1 | 1/2008 | Dobak |
| 2008/0021340 A1 | 1/2008 | Sarkela |
| 2008/0021341 A1 | 1/2008 | Harris et al. |
| 2008/0021342 A1 | 1/2008 | Echauz et al. |
| 2008/0021345 A1 | 1/2008 | Kern et al. |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033266 A1 | 2/2008 | Diab et al. |
| 2008/0033291 A1 | 2/2008 | Rousso et al. |
| 2008/0033297 A1 | 2/2008 | Sliwa |
| 2008/0033502 A1 | 2/2008 | Harris et al. |
| 2008/0033503 A1 | 2/2008 | Fowler et al. |
| 2008/0033508 A1 | 2/2008 | Frei et al. |

(56)        References Cited

U.S. PATENT DOCUMENTS

| | | |
|---|---|---|
| 2008/0033513 A1 | 2/2008 | Man et al. |
| 2008/0036752 A1 | 2/2008 | Diab et al. |
| 2008/0039677 A1 | 2/2008 | Adams |
| 2008/0039698 A1 | 2/2008 | Burton |
| 2008/0039737 A1 | 2/2008 | Breiter et al. |
| 2008/0039904 A1 | 2/2008 | Bulkes et al. |
| 2008/0042067 A1 | 2/2008 | Rousso et al. |
| 2008/0045775 A1 | 2/2008 | Lozano |
| 2008/0045823 A1 | 2/2008 | Diab et al. |
| 2008/0045844 A1 | 2/2008 | Arbel et al. |
| 2008/0046012 A1 | 2/2008 | Covalin et al. |
| 2008/0046035 A1 | 2/2008 | Fowler et al. |
| 2008/0049376 A1 | 2/2008 | Stevenson et al. |
| 2008/0051669 A1 | 2/2008 | Meyer et al. |
| 2008/0051858 A1 | 2/2008 | Haber et al. |
| 2008/0058664 A1 | 3/2008 | Mirro |
| 2008/0058668 A1 | 3/2008 | Seyed Momen et al. |
| 2008/0058773 A1 | 3/2008 | John |
| 2008/0064934 A1 | 3/2008 | Frei et al. |
| 2008/0065183 A1 | 3/2008 | Whitehurst et al. |
| 2008/0069446 A1 | 3/2008 | Ancelin |
| 2008/0071150 A1 | 3/2008 | Miesel et al. |
| 2008/0071326 A1 | 3/2008 | Heruth et al. |
| 2008/0074307 A1 | 3/2008 | Boric-Lubecke et al. |
| 2008/0077010 A1 | 3/2008 | Cohen-Solal et al. |
| 2008/0077015 A1 | 3/2008 | Boric-Lubecke et al. |
| 2008/0077191 A1 | 3/2008 | Morrell |
| 2008/0081963 A1 | 4/2008 | Naghavi et al. |
| 2008/0082018 A1 | 4/2008 | Sackner et al. |
| 2008/0086182 A1 | 4/2008 | Ben-David et al. |
| 2008/0091118 A1 | 4/2008 | Georgopoulos |
| 2008/0091240 A1 | 4/2008 | Ben-David et al. |
| 2008/0097197 A1 | 4/2008 | Kalafut et al. |
| 2008/0097235 A1 | 4/2008 | Ofek et al. |
| 2008/0097553 A1 | 4/2008 | John |
| 2008/0097785 A1 | 4/2008 | Ali |
| 2008/0103547 A1 | 5/2008 | Okun et al. |
| 2008/0103548 A1 | 5/2008 | Fowler et al. |
| 2008/0109050 A1 | 5/2008 | John |
| 2008/0119716 A1 | 5/2008 | Boric-Lubecke et al. |
| 2008/0119747 A1 | 5/2008 | Mietus et al. |
| 2008/0119763 A1 | 5/2008 | Wiener |
| 2008/0119900 A1 | 5/2008 | DiLorenzo |
| 2008/0123927 A1 | 5/2008 | Miga et al. |
| 2008/0125669 A1 | 5/2008 | Suffin et al. |
| 2008/0125829 A1 | 5/2008 | Velasco et al. |
| 2008/0125830 A1 | 5/2008 | Morrell |
| 2008/0125831 A1 | 5/2008 | Morrell |
| 2008/0128626 A1 | 6/2008 | Rousso et al. |
| 2008/0132383 A1 | 6/2008 | Einav et al. |
| 2008/0139953 A1 | 6/2008 | Baker et al. |
| 2008/0140141 A1 | 6/2008 | Ben-David et al. |
| 2008/0140149 A1 | 6/2008 | John et al. |
| 2008/0140403 A1 | 6/2008 | Hughes et al. |
| 2008/0147137 A1 | 6/2008 | Cohen et al. |
| 2008/0154111 A1 | 6/2008 | Wu et al. |
| 2008/0154126 A1 | 6/2008 | Culver et al. |
| 2008/0154148 A1 | 6/2008 | Chung et al. |
| 2008/0154331 A1 | 6/2008 | John et al. |
| 2008/0154332 A1 | 6/2008 | Rezai |
| 2008/0157980 A1 | 7/2008 | Sachanandani et al. |
| 2008/0161700 A1 | 7/2008 | Sachanandani et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161886 A1 | 7/2008 | Stevenson et al. |
| 2008/0161894 A1 | 7/2008 | Ben-David et al. |
| 2008/0162182 A1 | 7/2008 | Cazares et al. |
| 2008/0167535 A1 | 7/2008 | Stivoric et al. |
| 2008/0167540 A1 | 7/2008 | Korhonen et al. |
| 2008/0167569 A1 | 7/2008 | Ermes et al. |
| 2008/0167571 A1 | 7/2008 | Gevins |
| 2008/0177195 A1 | 7/2008 | Armitstead |
| 2008/0177196 A1 | 7/2008 | Burdick et al. |
| 2008/0177197 A1 | 7/2008 | Lee et al. |
| 2008/0183072 A1 | 7/2008 | Robertson et al. |
| 2008/0183097 A1 | 7/2008 | Leyde et al. |
| 2008/0188765 A1 | 8/2008 | Stolarski et al. |
| 2008/0194981 A1 | 8/2008 | Sarkela et al. |
| 2008/0195166 A1 | 8/2008 | Sun et al. |
| 2008/0200831 A1 | 8/2008 | Sturzebecher |
| 2008/0208072 A1 | 8/2008 | Fadem et al. |
| 2008/0208073 A1 | 8/2008 | Causevic |
| 2008/0208280 A1 | 8/2008 | Lindenthaler et al. |
| 2008/0208285 A1 | 8/2008 | Fowler et al. |
| 2008/0214902 A1 | 9/2008 | Lee et al. |
| 2008/0215112 A1 | 9/2008 | Firlik et al. |
| 2008/0219917 A1 | 9/2008 | Koruga |
| 2008/0221400 A1 | 9/2008 | Lee et al. |
| 2008/0221401 A1 | 9/2008 | Derchak et al. |
| 2008/0221441 A1 | 9/2008 | Bjornerud et al. |
| 2008/0221472 A1 | 9/2008 | Lee et al. |
| 2008/0221969 A1 | 9/2008 | Lee et al. |
| 2008/0228077 A1 | 9/2008 | Wilk et al. |
| 2008/0228100 A1 | 9/2008 | Navakatikyan |
| 2008/0228239 A1 | 9/2008 | Tyler et al. |
| 2008/0229408 A1 | 9/2008 | Dinges et al. |
| 2008/0230702 A1 | 9/2008 | Rousso et al. |
| 2008/0230705 A1 | 9/2008 | Rousso et al. |
| 2008/0234113 A1 | 9/2008 | Einav |
| 2008/0234601 A1 | 9/2008 | Wexelman |
| 2008/0235469 A1 | 9/2008 | Drew |
| 2008/0241804 A1 | 10/2008 | Pennebaker |
| 2008/0242521 A1 | 10/2008 | Einav |
| 2008/0242976 A1 | 10/2008 | Robertson et al. |
| 2008/0243005 A1 | 10/2008 | Jung et al. |
| 2008/0243014 A1 | 10/2008 | Moussavi et al. |
| 2008/0243017 A1 | 10/2008 | Moussavi et al. |
| 2008/0243021 A1 | 10/2008 | Causevic et al. |
| 2008/0247618 A1 | 10/2008 | Laine et al. |
| 2008/0249430 A1 | 10/2008 | John et al. |
| 2008/0249589 A1 | 10/2008 | Cornejo Cruz et al. |
| 2008/0255469 A1 | 10/2008 | Shieh et al. |
| 2008/0255816 A1 | 10/2008 | Neville |
| 2008/0255949 A1 | 10/2008 | Genco et al. |
| 2008/0257349 A1 | 10/2008 | Hedner et al. |
| 2008/0260212 A1 | 10/2008 | Moskal et al. |
| 2008/0262327 A1 | 10/2008 | Kato |
| 2008/0262367 A1 | 10/2008 | Mugler et al. |
| 2008/0262371 A1 | 10/2008 | Causevic |
| 2008/0269542 A1 | 10/2008 | Zabara |
| 2008/0269812 A1 | 10/2008 | Gerber et al. |
| 2008/0269833 A1 | 10/2008 | Scott et al. |
| 2008/0269834 A1 | 10/2008 | Byerman et al. |
| 2008/0269840 A1 | 10/2008 | Scott et al. |
| 2008/0269843 A1 | 10/2008 | Gerber et al. |
| 2008/0275327 A1 | 11/2008 | Faarbaek et al. |
| 2008/0275340 A1 | 11/2008 | Beach et al. |
| 2008/0275526 A1 | 11/2008 | Lozano |
| 2008/0279436 A1 | 11/2008 | Razifar et al. |
| 2008/0281238 A1 | 11/2008 | Oohashi et al. |
| 2008/0281381 A1 | 11/2008 | Gerber et al. |
| 2008/0281667 A1 | 11/2008 | Chen et al. |
| 2008/0286453 A1 | 11/2008 | Koruga |
| 2008/0287774 A1 | 11/2008 | Katz-Brull |
| 2008/0287821 A1 | 11/2008 | Jung et al. |
| 2008/0288018 A1 | 11/2008 | Rezai et al. |
| 2008/0294019 A1 | 11/2008 | Tran |
| 2008/0294063 A1 | 11/2008 | Bibian et al. |
| 2008/0298653 A1 | 12/2008 | Amunts et al. |
| 2008/0298659 A1 | 12/2008 | Spence et al. |
| 2008/0304691 A1 | 12/2008 | Lai |
| 2008/0304731 A1 | 12/2008 | Kimura |
| 2008/0306365 A1 | 12/2008 | Bunce et al. |
| 2008/0310697 A1 | 12/2008 | Razifar et al. |
| 2008/0311549 A1 | 12/2008 | Belitsiotis |
| 2008/0317317 A1 | 12/2008 | Shekhar et al. |
| 2008/0319326 A1 | 12/2008 | Behbehani et al. |
| 2008/0319505 A1 | 12/2008 | Boyden et al. |
| 2009/0005654 A1 | 1/2009 | Jung et al. |
| 2009/0005667 A1 | 1/2009 | Cui et al. |
| 2009/0005675 A1 | 1/2009 | Grunwald et al. |
| 2009/0006001 A1 | 1/2009 | Niculescu et al. |
| 2009/0009284 A1 | 1/2009 | Sako |

(56)          References Cited

U.S. PATENT DOCUMENTS

| | | |
|---|---|---|
| 2009/0012387 A1 | 1/2009 | Hanson et al. |
| 2009/0018407 A1 | 1/2009 | Jung et al. |
| 2009/0018419 A1 | 1/2009 | Torch |
| 2009/0018429 A1 | 1/2009 | Saliga et al. |
| 2009/0018431 A1 | 1/2009 | Feiweier et al. |
| 2009/0018432 A1 | 1/2009 | He et al. |
| 2009/0018462 A1 | 1/2009 | Bell |
| 2009/0022825 A1 | 1/2009 | Kerkman et al. |
| 2009/0024007 A1 | 1/2009 | Lee et al. |
| 2009/0024050 A1 | 1/2009 | Jung et al. |
| 2009/0030476 A1 | 1/2009 | Hargrove |
| 2009/0030930 A1 | 1/2009 | Pradeep et al. |
| 2009/0033333 A1 | 2/2009 | Gribova et al. |
| 2009/0036781 A1 | 2/2009 | Utsugi et al. |
| 2009/0036791 A1 | 2/2009 | Plenz |
| 2009/0036950 A1 | 2/2009 | Armstrong et al. |
| 2009/0039889 A1 | 2/2009 | Wilt et al. |
| 2009/0043221 A1 | 2/2009 | Kaplan et al. |
| 2009/0048507 A1 | 2/2009 | Feiweier et al. |
| 2009/0048530 A1 | 2/2009 | Sarkela et al. |
| 2009/0054788 A1 | 2/2009 | Hauger et al. |
| 2009/0054800 A1 | 2/2009 | Martinerie et al. |
| 2009/0054801 A1 | 2/2009 | Hinrikus et al. |
| 2009/0054946 A1 | 2/2009 | Sommer et al. |
| 2009/0054958 A1 | 2/2009 | Nofzinger |
| 2009/0058660 A1 | 3/2009 | Torch |
| 2009/0062660 A1 | 3/2009 | Chance |
| 2009/0062670 A1 | 3/2009 | Sterling et al. |
| 2009/0062676 A1 | 3/2009 | Kruglikov et al. |
| 2009/0062679 A1 | 3/2009 | Tan et al. |
| 2009/0062680 A1 | 3/2009 | Sandford |
| 2009/0062696 A1 | 3/2009 | Nathan et al. |
| 2009/0062698 A1 | 3/2009 | Einav et al. |
| 2009/0069707 A1 | 3/2009 | Sandford |
| 2009/0074279 A1 | 3/2009 | Razifar et al. |
| 2009/0076339 A1 | 3/2009 | Quintin et al. |
| 2009/0076399 A1 | 3/2009 | Arbel et al. |
| 2009/0076400 A1 | 3/2009 | Diab et al. |
| 2009/0076406 A1 | 3/2009 | Graham et al. |
| 2009/0076407 A1 | 3/2009 | John et al. |
| 2009/0076567 A1 | 3/2009 | Fowler et al. |
| 2009/0078875 A1 | 3/2009 | Rousso et al. |
| 2009/0082688 A1 | 3/2009 | Wagner |
| 2009/0082689 A1 | 3/2009 | Guttag et al. |
| 2009/0082690 A1 | 3/2009 | Phillips et al. |
| 2009/0082829 A1 | 3/2009 | Panken et al. |
| 2009/0083071 A1 | 3/2009 | Phillips et al. |
| 2009/0088658 A1 | 4/2009 | Luo et al. |
| 2009/0088680 A1 | 4/2009 | Aravanis et al. |
| 2009/0093403 A1 | 4/2009 | Zhang et al. |
| 2009/0093862 A1 | 4/2009 | Gliner et al. |
| 2009/0094305 A1 | 4/2009 | Johnson |
| 2009/0099474 A1 | 4/2009 | Pineda et al. |
| 2009/0099627 A1 | 4/2009 | Molnar et al. |
| 2009/0099783 A1 | 4/2009 | Reisberg |
| 2009/0105785 A1 | 4/2009 | Wei et al. |
| 2009/0112117 A1 | 4/2009 | Rewari |
| 2009/0112273 A1 | 4/2009 | Wingeier et al. |
| 2009/0112277 A1 | 4/2009 | Wingeier et al. |
| 2009/0112278 A1 | 4/2009 | Wingeier et al. |
| 2009/0112279 A1 | 4/2009 | Wingeier et al. |
| 2009/0112280 A1 | 4/2009 | Wingeier et al. |
| 2009/0112281 A1 | 4/2009 | Miyazawa et al. |
| 2009/0112523 A1 | 4/2009 | Townsend et al. |
| 2009/0118593 A1 | 5/2009 | Jung et al. |
| 2009/0118610 A1 | 5/2009 | Karmarkar et al. |
| 2009/0118622 A1 | 5/2009 | Durkin et al. |
| 2009/0118636 A1 | 5/2009 | Collura |
| 2009/0118780 A1 | 5/2009 | DiLorenzo |
| 2009/0118786 A1 | 5/2009 | Meadows et al. |
| 2009/0118787 A1 | 5/2009 | Moffitt et al. |
| 2009/0119154 A1 | 5/2009 | Jung et al. |
| 2009/0124869 A1 | 5/2009 | Hu et al. |
| 2009/0124921 A1 | 5/2009 | Milgramm et al. |
| 2009/0124922 A1 | 5/2009 | Milgramm et al. |
| 2009/0124923 A1 | 5/2009 | Sackellares et al. |
| 2009/0131995 A1 | 5/2009 | Sloan et al. |
| 2009/0132275 A1 | 5/2009 | Jung et al. |
| 2009/0137915 A1 | 5/2009 | Childre et al. |
| 2009/0137923 A1 | 5/2009 | Suffin et al. |
| 2009/0143654 A1 | 6/2009 | Funane et al. |
| 2009/0148019 A1 | 6/2009 | Hamada et al. |
| 2009/0149148 A1 | 6/2009 | Kurtz et al. |
| 2009/0149736 A1 | 6/2009 | Skidmore et al. |
| 2009/0156907 A1 | 6/2009 | Jung et al. |
| 2009/0156954 A1 | 6/2009 | Cox et al. |
| 2009/0156955 A1 | 6/2009 | Jung et al. |
| 2009/0156956 A1 | 6/2009 | Milgramm et al. |
| 2009/0157323 A1 | 6/2009 | Jung et al. |
| 2009/0157481 A1 | 6/2009 | Jung et al. |
| 2009/0157482 A1 | 6/2009 | Jung et al. |
| 2009/0157625 A1 | 6/2009 | Jung et al. |
| 2009/0157660 A1 | 6/2009 | Jung et al. |
| 2009/0157662 A1 | 6/2009 | Suffin et al. |
| 2009/0157751 A1 | 6/2009 | Jung et al. |
| 2009/0157813 A1 | 6/2009 | Jung et al. |
| 2009/0163777 A1 | 6/2009 | Jung et al. |
| 2009/0163980 A1 | 6/2009 | Stevenson |
| 2009/0163981 A1 | 6/2009 | Stevenson et al. |
| 2009/0163982 A1 | 6/2009 | deCharms |
| 2009/0164131 A1 | 6/2009 | Jung et al. |
| 2009/0164132 A1 | 6/2009 | Jung et al. |
| 2009/0164302 A1 | 6/2009 | Jung et al. |
| 2009/0164401 A1 | 6/2009 | Jung et al. |
| 2009/0164403 A1 | 6/2009 | Jung et al. |
| 2009/0164458 A1 | 6/2009 | Jung et al. |
| 2009/0164503 A1 | 6/2009 | Jung et al. |
| 2009/0164549 A1 | 6/2009 | Jung et al. |
| 2009/0171164 A1 | 7/2009 | Jung et al. |
| 2009/0171232 A1 | 7/2009 | Hu et al. |
| 2009/0171240 A1 | 7/2009 | Aguilar et al. |
| 2009/0171405 A1 | 7/2009 | Craig |
| 2009/0172540 A1 | 7/2009 | Jung et al. |
| 2009/0177050 A1 | 7/2009 | Griffiths et al. |
| 2009/0177090 A1 | 7/2009 | Grunwald et al. |
| 2009/0177108 A1 | 7/2009 | Shieh et al. |
| 2009/0177144 A1 | 7/2009 | Masmanidis et al. |
| 2009/0179642 A1 | 7/2009 | deCharms |
| 2009/0182211 A1 | 7/2009 | Diab et al. |
| 2009/0187230 A1 | 7/2009 | Dilorenzo |
| 2009/0191131 A1 | 7/2009 | Fossheim et al. |
| 2009/0192394 A1 | 7/2009 | Guttag et al. |
| 2009/0192556 A1 | 7/2009 | Wu et al. |
| 2009/0198144 A1 | 8/2009 | Phillips et al. |
| 2009/0198145 A1 | 8/2009 | Chow |
| 2009/0204015 A1 | 8/2009 | Phillips et al. |
| 2009/0209831 A1 | 8/2009 | Kucharczyk et al. |
| 2009/0209835 A1 | 8/2009 | Diab et al. |
| 2009/0209845 A1 | 8/2009 | Christen et al. |
| 2009/0210018 A1 | 8/2009 | Lozano |
| 2009/0216091 A1 | 8/2009 | Arndt |
| 2009/0216146 A1 | 8/2009 | Teicher et al. |
| 2009/0216288 A1 | 8/2009 | Schiff et al. |
| 2009/0220425 A1 | 9/2009 | Moxon et al. |
| 2009/0220429 A1 | 9/2009 | Johnsen et al. |
| 2009/0221904 A1 | 9/2009 | Shealy et al. |
| 2009/0221928 A1 | 9/2009 | Einav et al. |
| 2009/0221930 A1 | 9/2009 | Laken |
| 2009/0227876 A1 | 9/2009 | Tran |
| 2009/0227877 A1 | 9/2009 | Tran |
| 2009/0227882 A1 | 9/2009 | Foo |
| 2009/0227889 A2 | 9/2009 | John et al. |
| 2009/0234419 A1 | 9/2009 | Maschino et al. |
| 2009/0240119 A1 | 9/2009 | Schwaibold et al. |
| 2009/0243756 A1 | 10/2009 | Stevenson et al. |
| 2009/0246138 A1 | 10/2009 | Santosh et al. |
| 2009/0247893 A1 | 10/2009 | Lapinlampi et al. |
| 2009/0247894 A1 | 10/2009 | Causevic |
| 2009/0259277 A1 | 10/2009 | Cornejo Cruz et al. |
| 2009/0261832 A1 | 10/2009 | DePavia et al. |
| 2009/0264785 A1 | 10/2009 | Causevic et al. |
| 2009/0264789 A1 | 10/2009 | Molnar et al. |
| 2009/0264952 A1 | 10/2009 | Jassemidis et al. |
| 2009/0264954 A1 | 10/2009 | Rise et al. |

(56) References Cited

U.S. PATENT DOCUMENTS

| | | |
|---|---|---|
| 2009/0264955 A1 | 10/2009 | Giftakis et al. |
| 2009/0264956 A1 | 10/2009 | Rise et al. |
| 2009/0264957 A1 | 10/2009 | Giftakis et al. |
| 2009/0264958 A1 | 10/2009 | Hsu et al. |
| 2009/0264967 A1 | 10/2009 | Giftakis et al. |
| 2009/0267758 A1 | 10/2009 | Hyde et al. |
| 2009/0270687 A1 | 10/2009 | Hyde et al. |
| 2009/0270688 A1 | 10/2009 | Hyde et al. |
| 2009/0270692 A1 | 10/2009 | Hyde et al. |
| 2009/0270693 A1 | 10/2009 | Hyde et al. |
| 2009/0270694 A1 | 10/2009 | Hyde et al. |
| 2009/0270754 A1 | 10/2009 | Moridaira |
| 2009/0270758 A1 | 10/2009 | Eagleman et al. |
| 2009/0270786 A1 | 10/2009 | Hyde et al. |
| 2009/0270944 A1 | 10/2009 | Whitehurst et al. |
| 2009/0271011 A1 | 10/2009 | Hyde et al. |
| 2009/0271120 A1 | 10/2009 | Hyde et al. |
| 2009/0271122 A1 | 10/2009 | Hyde et al. |
| 2009/0271347 A1 | 10/2009 | Hyde et al. |
| 2009/0275853 A1 | 11/2009 | Sarkela |
| 2009/0276011 A1 | 11/2009 | Hyde et al. |
| 2009/0276012 A1 | 11/2009 | Hyde et al. |
| 2009/0280153 A1 | 11/2009 | Hunter et al. |
| 2009/0281400 A1 | 11/2009 | McCraty et al. |
| 2009/0281448 A1 | 11/2009 | Wright et al. |
| 2009/0281594 A1 | 11/2009 | King et al. |
| 2009/0287035 A1 | 11/2009 | Dietrich et al. |
| 2009/0287107 A1 | 11/2009 | Beck-Nielsen et al. |
| 2009/0287108 A1 | 11/2009 | Levy |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287274 A1 | 11/2009 | De Ridder |
| 2009/0287467 A1 | 11/2009 | Sparks et al. |
| 2009/0290767 A1 | 11/2009 | Jung et al. |
| 2009/0290772 A1 | 11/2009 | Avinash et al. |
| 2009/0292180 A1 | 11/2009 | Mirow |
| 2009/0292478 A1 | 11/2009 | Avinash et al. |
| 2009/0292551 A1 | 11/2009 | Sirohey et al. |
| 2009/0292713 A1 | 11/2009 | Jung et al. |
| 2009/0292724 A1 | 11/2009 | Jung et al. |
| 2009/0297000 A1 | 12/2009 | Shahaf et al. |
| 2009/0299126 A1 | 12/2009 | Fowler et al. |
| 2009/0299169 A1 | 12/2009 | deCharms |
| 2009/0299435 A1 | 12/2009 | Gliner et al. |
| 2009/0304582 A1 | 12/2009 | Rousso et al. |
| 2009/0306491 A1 | 12/2009 | Haggers |
| 2009/0306531 A1 | 12/2009 | Leuthardt et al. |
| 2009/0306532 A1 | 12/2009 | Tucker |
| 2009/0306534 A1 | 12/2009 | Pizzagalli |
| 2009/0306741 A1 | 12/2009 | Hogle et al. |
| 2009/0311655 A1 | 12/2009 | Karkanias et al. |
| 2009/0312595 A1 | 12/2009 | Leuthardt et al. |
| 2009/0312624 A1 | 12/2009 | Berridge et al. |
| 2009/0312646 A1 | 12/2009 | Binder et al. |
| 2009/0312663 A1 | 12/2009 | John et al. |
| 2009/0312664 A1 | 12/2009 | Rodriguez Villegas et al. |
| 2009/0312668 A1 | 12/2009 | Leuthardt et al. |
| 2009/0312808 A1 | 12/2009 | Tyler et al. |
| 2009/0312817 A1 | 12/2009 | Hogle et al. |
| 2009/0312998 A1 | 12/2009 | Berckmans et al. |
| 2009/0316925 A1 | 12/2009 | Eisenfeld et al. |
| 2009/0316968 A1 | 12/2009 | Fueyo et al. |
| 2009/0316969 A1 | 12/2009 | Fueyo et al. |
| 2009/0318773 A1 | 12/2009 | Jung et al. |
| 2009/0318779 A1 | 12/2009 | Tran |
| 2009/0318794 A1 | 12/2009 | DeCharms |
| 2009/0319000 A1 | 12/2009 | Firlik et al. |
| 2009/0319001 A1 | 12/2009 | Schiff |
| 2009/0319002 A1 | 12/2009 | Simon |
| 2009/0319004 A1 | 12/2009 | Sabel |
| 2009/0322331 A1 | 12/2009 | Buracas |
| 2009/0323049 A1 | 12/2009 | Addison et al. |
| 2009/0326353 A1 | 12/2009 | Watson et al. |
| 2009/0326604 A1 | 12/2009 | Tyler et al. |
| 2009/0326605 A1 | 12/2009 | Morrell |
| 2009/0327068 A1 | 12/2009 | Pradeep et al. |
| 2010/0003656 A1 | 1/2010 | Kilgard et al. |
| 2010/0004500 A1 | 1/2010 | Gliner et al. |
| 2010/0004705 A1 | 1/2010 | Kilgard et al. |
| 2010/0004717 A1 | 1/2010 | Kilgard et al. |
| 2010/0004762 A1 | 1/2010 | Leuthardt et al. |
| 2010/0004977 A1 | 1/2010 | Marci et al. |
| 2010/0010289 A1 | 1/2010 | Clare |
| 2010/0010316 A1 | 1/2010 | Fueyo et al. |
| 2010/0010363 A1 | 1/2010 | Fueyo et al. |
| 2010/0010364 A1 | 1/2010 | Verbitskiy |
| 2010/0010365 A1 | 1/2010 | Terao et al. |
| 2010/0010366 A1 | 1/2010 | Silberstein |
| 2010/0010383 A1 | 1/2010 | Skelton et al. |
| 2010/0010388 A1 | 1/2010 | Panken et al. |
| 2010/0010391 A1 | 1/2010 | Skelton et al. |
| 2010/0010392 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010584 A1 | 1/2010 | Skelton et al. |
| 2010/0010585 A1 | 1/2010 | Davis et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0010844 A1 | 1/2010 | Isaksen |
| 2010/0014730 A1 | 1/2010 | Hahn et al. |
| 2010/0014732 A1 | 1/2010 | Vija et al. |
| 2010/0015583 A1 | 1/2010 | Leuthardt et al. |
| 2010/0016783 A1 | 1/2010 | Bourke, Jr. et al. |
| 2010/0017001 A1 | 1/2010 | Leuthardt et al. |
| 2010/0021378 A1 | 1/2010 | Rousso et al. |
| 2010/0022820 A1 | 1/2010 | Leuthardt et al. |
| 2010/0023089 A1 | 1/2010 | DiLorenzo |
| 2010/0028841 A1 | 2/2010 | Eatough et al. |
| 2010/0030073 A1 | 2/2010 | Kalafut |
| 2010/0030089 A1 | 2/2010 | Hyde et al. |
| 2010/0030097 A1 | 2/2010 | Silberstein |
| 2010/0030287 A1 | 2/2010 | Jaax et al. |
| 2010/0036211 A1 | 2/2010 | La Rue et al. |
| 2010/0036233 A1 | 2/2010 | Zhu et al. |
| 2010/0036276 A1 | 2/2010 | Ochs |
| 2010/0036453 A1 | 2/2010 | Hulvershorn et al. |
| 2010/0041949 A1 | 2/2010 | Tolkowsky |
| 2010/0041958 A1 | 2/2010 | Leuthardt et al. |
| 2010/0041962 A1 | 2/2010 | Causevic et al. |
| 2010/0041964 A1 | 2/2010 | Hyde et al. |
| 2010/0042011 A1 | 2/2010 | Doidge et al. |
| 2010/0042578 A1 | 2/2010 | Leuthardt et al. |
| 2010/0043795 A1 | 2/2010 | Ujhazy et al. |
| 2010/0045467 A1 | 2/2010 | Sachanandani et al. |
| 2010/0049069 A1 | 2/2010 | Tarassenko et al. |
| 2010/0049075 A1 | 2/2010 | Bolger et al. |
| 2010/0049276 A1 | 2/2010 | Blum et al. |
| 2010/0049482 A1 | 2/2010 | He et al. |
| 2010/0056276 A1 | 3/2010 | Silberstein |
| 2010/0056854 A1 | 3/2010 | Chang |
| 2010/0056939 A1 | 3/2010 | Tarassenko et al. |
| 2010/0057159 A1 | 3/2010 | Lozano |
| 2010/0057160 A1 | 3/2010 | De Ridder |
| 2010/0057655 A1 | 3/2010 | Jacobson et al. |
| 2010/0063368 A1 | 3/2010 | Leuthardt et al. |
| 2010/0063563 A1 | 3/2010 | Craig |
| 2010/0068751 A1 | 3/2010 | Eberle |
| 2010/0069724 A1 | 3/2010 | Leuthardt et al. |
| 2010/0069739 A1 | 3/2010 | deCharms |
| 2010/0069762 A1 | 3/2010 | Mietus et al. |
| 2010/0069775 A1 | 3/2010 | Milgramm et al. |
| 2010/0069777 A1 | 3/2010 | Marks |
| 2010/0069780 A1 | 3/2010 | Schuette et al. |

(56)  References Cited

U.S. PATENT DOCUMENTS

| | | |
|---|---|---|
| 2010/0070001 A1 | 3/2010 | Goetz |
| 2010/0076249 A1 | 3/2010 | Leuthardt et al. |
| 2010/0076253 A1 | 3/2010 | Altman et al. |
| 2010/0076274 A1 | 3/2010 | Severson |
| 2010/0076333 A9 | 3/2010 | Burton et al. |
| 2010/0076334 A1 | 3/2010 | Rothblatt |
| 2010/0076338 A1 | 3/2010 | Kwak |
| 2010/0076525 A1 | 3/2010 | Skelton et al. |
| 2010/0079292 A1 | 4/2010 | Lynn et al. |
| 2010/0080432 A1 | 4/2010 | Lilja et al. |
| 2010/0081860 A1 | 4/2010 | Leuthardt et al. |
| 2010/0081861 A1 | 4/2010 | Leuthardt et al. |
| 2010/0082506 A1 | 4/2010 | Avinash et al. |
| 2010/0087719 A1 | 4/2010 | Benni |
| 2010/0087900 A1 | 4/2010 | Flint |
| 2010/0090835 A1 | 4/2010 | Liu et al. |
| 2010/0092934 A1 | 4/2010 | Silberstein |
| 2010/0094103 A1 | 4/2010 | Kaplan et al. |
| 2010/0094152 A1 | 4/2010 | Semmlow |
| 2010/0094154 A1 | 4/2010 | Schalk et al. |
| 2010/0094155 A1 | 4/2010 | Prichep |
| 2010/0098289 A1 | 4/2010 | Tognoli et al. |
| 2010/0099954 A1 | 4/2010 | Dickinson et al. |
| 2010/0099975 A1 | 4/2010 | Faro et al. |
| 2010/0100036 A1 | 4/2010 | Leuthardt et al. |
| 2010/0100164 A1 | 4/2010 | Johnson et al. |
| 2010/0106041 A1 | 4/2010 | Ghovanloo et al. |
| 2010/0106043 A1 | 4/2010 | Robinson et al. |
| 2010/0106044 A1 | 4/2010 | Linderman |
| 2010/0106217 A1 | 4/2010 | Colborn |
| 2010/0113959 A1 | 5/2010 | Pascual-Leone et al. |
| 2010/0114190 A1 | 5/2010 | Bendett et al. |
| 2010/0114192 A1 | 5/2010 | Jaax et al. |
| 2010/0114193 A1 | 5/2010 | Lozano et al. |
| 2010/0114237 A1 | 5/2010 | Giftakis et al. |
| 2010/0114272 A1 | 5/2010 | Haidarliu et al. |
| 2010/0114813 A1 | 5/2010 | Zalay et al. |
| 2010/0121415 A1 | 5/2010 | Skelton et al. |
| 2010/0125219 A1 | 5/2010 | Harris et al. |
| 2010/0125304 A1 | 5/2010 | Faltys |
| 2010/0125561 A1 | 5/2010 | Leuthardt et al. |
| 2010/0130811 A1 | 5/2010 | Leuthardt et al. |
| 2010/0130812 A1 | 5/2010 | Martel |
| 2010/0130869 A1 | 5/2010 | Hauger et al. |
| 2010/0130878 A1 | 5/2010 | Lasso et al. |
| 2010/0131030 A1 | 5/2010 | Firlik et al. |
| 2010/0131034 A1 | 5/2010 | Gliner et al. |
| 2010/0132448 A1 | 6/2010 | Donadille et al. |
| 2010/0134113 A1 | 6/2010 | DePavia et al. |
| 2010/0135556 A1 | 6/2010 | Razifar et al. |
| 2010/0137728 A1 | 6/2010 | Govari |
| 2010/0137937 A1 | 6/2010 | John et al. |
| 2010/0142774 A1 | 6/2010 | Ben-Haim et al. |
| 2010/0143256 A1 | 6/2010 | Suffin et al. |
| 2010/0145215 A1 | 6/2010 | Pradeep et al. |
| 2010/0145219 A1 | 6/2010 | Grey |
| 2010/0145427 A1 | 6/2010 | Gliner et al. |
| 2010/0145428 A1 | 6/2010 | Cameron et al. |
| 2010/0152621 A1 | 6/2010 | Janna et al. |
| 2010/0160737 A1 | 6/2010 | Shachar et al. |
| 2010/0163027 A1 | 7/2010 | Hyde et al. |
| 2010/0163028 A1 | 7/2010 | Hyde et al. |
| 2010/0163035 A1 | 7/2010 | Hyde et al. |
| 2010/0165593 A1 | 7/2010 | Townsend et al. |
| 2010/0168053 A1 | 7/2010 | Kurtz |
| 2010/0168525 A1 | 7/2010 | Hyde et al. |
| 2010/0168529 A1 | 7/2010 | Hyde et al. |
| 2010/0168602 A1 | 7/2010 | Hyde et al. |
| 2010/0172567 A1 | 7/2010 | Prokoski |
| 2010/0174161 A1 | 7/2010 | Lynn |
| 2010/0174533 A1 | 7/2010 | Pakhomov |
| 2010/0179415 A1 | 7/2010 | Wenzel et al. |
| 2010/0179447 A1 | 7/2010 | Hunt |
| 2010/0185113 A1 | 7/2010 | Peot et al. |
| 2010/0189318 A1 | 7/2010 | Chang et al. |
| 2010/0191095 A1 | 7/2010 | Felblinger et al. |
| 2010/0191124 A1 | 7/2010 | Prokoski |
| 2010/0191139 A1 | 7/2010 | Jacquin et al. |
| 2010/0191304 A1 | 7/2010 | Scott |
| 2010/0191305 A1 | 7/2010 | Imran et al. |
| 2010/0195770 A1 | 8/2010 | Ricci et al. |
| 2010/0197610 A1 | 8/2010 | Lian et al. |
| 2010/0197993 A1 | 8/2010 | Vasishta |
| 2010/0198090 A1 | 8/2010 | Hudson et al. |
| 2010/0198098 A1 | 8/2010 | Osorio et al. |
| 2010/0198101 A1 | 8/2010 | Song et al. |
| 2010/0198282 A1 | 8/2010 | Rogers |
| 2010/0198296 A1 | 8/2010 | Ignagni et al. |
| 2010/0198519 A1 | 8/2010 | Wilt et al. |
| 2010/0204604 A1 | 8/2010 | Liley et al. |
| 2010/0204614 A1 | 8/2010 | Lindquist et al. |
| 2010/0204748 A1 | 8/2010 | Lozano et al. |
| 2010/0204749 A1 | 8/2010 | Thimineur et al. |
| 2010/0204750 A1 | 8/2010 | Hargrove et al. |
| 2010/0217100 A1 | 8/2010 | LeBoeuf et al. |
| 2010/0217146 A1 | 8/2010 | Osvath |
| 2010/0217341 A1 | 8/2010 | John et al. |
| 2010/0217348 A1 | 8/2010 | DiLorenzo |
| 2010/0219820 A1 | 9/2010 | Skidmore et al. |
| 2010/0222640 A1 | 9/2010 | Anderson et al. |
| 2010/0222694 A1 | 9/2010 | Causevic |
| 2010/0222845 A1 | 9/2010 | Goetz |
| 2010/0224188 A1 | 9/2010 | John et al. |
| 2010/0231221 A1 | 9/2010 | Rosthal et al. |
| 2010/0231327 A1 | 9/2010 | Johnson et al. |
| 2010/0234705 A1 | 9/2010 | Lynn |
| 2010/0234752 A1 | 9/2010 | Sullivan et al. |
| 2010/0234753 A1 | 9/2010 | Ma |
| 2010/0238763 A1 | 9/2010 | Gzara et al. |
| 2010/0241020 A1 | 9/2010 | Zaidel et al. |
| 2010/0241195 A1 | 9/2010 | Meadows et al. |
| 2010/0241449 A1 | 9/2010 | Firminger et al. |
| 2010/0245093 A1 | 9/2010 | Kobetski et al. |
| 2010/0248275 A1 | 9/2010 | Jackowski et al. |
| 2010/0249573 A1 | 9/2010 | Marks |
| 2010/0249627 A1 | 9/2010 | Zhang et al. |
| 2010/0249635 A1 | 9/2010 | Van Der Reijden |
| 2010/0249638 A1 | 9/2010 | Liley |
| 2010/0256592 A1 | 10/2010 | Gerber et al. |
| 2010/0258126 A1 | 10/2010 | Ujhazy et al. |
| 2010/0260402 A1 | 10/2010 | Axelsson et al. |
| 2010/0261977 A1 | 10/2010 | Seely |
| 2010/0261993 A1 | 10/2010 | van der Kouwe et al. |
| 2010/0262377 A1 | 10/2010 | Jensen |
| 2010/0268055 A1 | 10/2010 | Jung et al. |
| 2010/0268057 A1 | 10/2010 | Firminger et al. |
| 2010/0268108 A1 | 10/2010 | Firminger et al. |
| 2010/0268288 A1 | 10/2010 | Hunter et al. |
| 2010/0274106 A1 | 10/2010 | Heruth et al. |
| 2010/0274141 A1 | 10/2010 | Patangay et al. |
| 2010/0274147 A1 | 10/2010 | Patangay et al. |
| 2010/0274303 A1 | 10/2010 | Bukhman |
| 2010/0274305 A1 | 10/2010 | Gliner et al. |
| 2010/0274308 A1 | 10/2010 | Scott |
| 2010/0274577 A1 | 10/2010 | Firminger et al. |
| 2010/0274578 A1 | 10/2010 | Firminger et al. |
| 2010/0280332 A1 | 11/2010 | Hyde et al. |
| 2010/0280334 A1 | 11/2010 | Carlson et al. |
| 2010/0280335 A1 | 11/2010 | Carlson et al. |
| 2010/0280372 A1 | 11/2010 | Poolman et al. |
| 2010/0280403 A1 | 11/2010 | Erdogmus et al. |
| 2010/0280500 A1 | 11/2010 | Skelton et al. |
| 2010/0280571 A1 | 11/2010 | Sloan |
| 2010/0280574 A1 | 11/2010 | Carlson et al. |
| 2010/0280579 A1 | 11/2010 | Denison et al. |
| 2010/0286549 A1 | 11/2010 | John et al. |
| 2010/0286747 A1 | 11/2010 | Sabesan et al. |
| 2010/0292602 A1 | 11/2010 | Worrell et al. |
| 2010/0292752 A1 | 11/2010 | Bardakjian et al. |
| 2010/0293002 A1 | 11/2010 | Firminger et al. |
| 2010/0293115 A1 | 11/2010 | Seyed Momen |
| 2010/0298624 A1 | 11/2010 | Becker |
| 2010/0298735 A1 | 11/2010 | Suffin |
| 2010/0303101 A1 | 12/2010 | Lazar et al. |

(56)  References Cited

U.S. PATENT DOCUMENTS

| | | |
|---|---|---|
| 2010/0305962 A1 | 12/2010 | Firminger et al. |
| 2010/0305963 A1 | 12/2010 | Firminger et al. |
| 2010/0312188 A1 | 12/2010 | Robertson et al. |
| 2010/0312579 A1 | 12/2010 | Firminger et al. |
| 2010/0318025 A1 | 12/2010 | John |
| 2010/0318160 A1 | 12/2010 | Stevenson et al. |
| 2010/0322488 A1 | 12/2010 | Virtue et al. |
| 2010/0322497 A1 | 12/2010 | Dempsey et al. |
| 2010/0324441 A1 | 12/2010 | Hargrove et al. |
| 2010/0331649 A1 | 12/2010 | Chou |
| 2010/0331715 A1 | 12/2010 | Addison et al. |
| 2010/0331976 A1 | 12/2010 | Pesaran et al. |
| 2011/0004115 A1 | 1/2011 | Shahaf et al. |
| 2011/0004270 A1 | 1/2011 | Sheffield et al. |
| 2011/0004283 A1 | 1/2011 | Stevenson et al. |
| 2011/0004412 A1 | 1/2011 | Shahaf et al. |
| 2011/0007129 A1 | 1/2011 | Martin et al. |
| 2011/0009715 A1 | 1/2011 | O' Reilly et al. |
| 2011/0009729 A1 | 1/2011 | Shin et al. |
| 2011/0009752 A1 | 1/2011 | Chen et al. |
| 2011/0009777 A1 | 1/2011 | Reichow et al. |
| 2011/0009920 A1 | 1/2011 | Whitehurst et al. |
| 2011/0009928 A1 | 1/2011 | Gerber et al. |
| 2011/0015209 A1 | 1/2011 | Shamloo et al. |
| 2011/0015469 A1 | 1/2011 | Walter et al. |
| 2011/0015501 A1 | 1/2011 | Lynn et al. |
| 2011/0015515 A1 | 1/2011 | deCharms |
| 2011/0015536 A1 | 1/2011 | Milgramm et al. |
| 2011/0015539 A1 | 1/2011 | deCharms |
| 2011/0021899 A1 | 1/2011 | Arps et al. |
| 2011/0021970 A1 | 1/2011 | Vo-Dinh et al. |
| 2011/0022981 A1 | 1/2011 | Mahajan et al. |
| 2011/0028798 A1 | 2/2011 | Hyde et al. |
| 2011/0028799 A1 | 2/2011 | Hyde et al. |
| 2011/0028802 A1 | 2/2011 | Addison et al. |
| 2011/0028825 A1 | 2/2011 | Douglas et al. |
| 2011/0028827 A1 | 2/2011 | Sitaram et al. |
| 2011/0028859 A1 | 2/2011 | Chian |
| 2011/0029038 A1 | 2/2011 | Hyde et al. |
| 2011/0029044 A1 | 2/2011 | Hyde et al. |
| 2011/0034812 A1 | 2/2011 | Patangay et al. |
| 2011/0034821 A1 | 2/2011 | Ekpar |
| 2011/0034822 A1 | 2/2011 | Phillips et al. |
| 2011/0034912 A1 | 2/2011 | de Graff et al. |
| 2011/0035231 A1 | 2/2011 | Firminger et al. |
| 2011/0038515 A1 | 2/2011 | Jacquin et al. |
| 2011/0038850 A1 | 2/2011 | Bagnol et al. |
| 2011/0040202 A1 | 2/2011 | Luo et al. |
| 2011/0040356 A1 | 2/2011 | Schiffer |
| 2011/0040546 A1 | 2/2011 | Gerber et al. |
| 2011/0040547 A1 | 2/2011 | Gerber et al. |
| 2011/0040713 A1 | 2/2011 | Colman et al. |
| 2011/0043759 A1 | 2/2011 | Bushinsky |
| 2011/0046451 A1 | 2/2011 | Horn et al. |
| 2011/0046473 A1 | 2/2011 | Pradeep et al. |
| 2011/0046491 A1 | 2/2011 | Diamond |
| 2011/0050232 A1 | 3/2011 | Wilt et al. |
| 2011/0054272 A1 | 3/2011 | Derchak |
| 2011/0054279 A1 | 3/2011 | Reisfeld et al. |
| 2011/0054345 A1 | 3/2011 | Nagatani |
| 2011/0054562 A1 | 3/2011 | Gliner |
| 2011/0054569 A1 | 3/2011 | Zitnik et al. |
| 2011/0060382 A1 | 3/2011 | Jaax et al. |
| 2011/0066005 A1 | 3/2011 | Rotenberg |
| 2011/0066041 A1 | 3/2011 | Pandia et al. |
| 2011/0066042 A1 | 3/2011 | Pandia et al. |
| 2011/0066053 A1 | 3/2011 | Yazicioglu |
| 2011/0074396 A1 | 3/2011 | Liao et al. |
| 2011/0077503 A1 | 3/2011 | Bonilha et al. |
| 2011/0077538 A1 | 3/2011 | Liu et al. |
| 2011/0077548 A1 | 3/2011 | Torch |
| 2011/0077721 A1 | 3/2011 | Whitehurst et al. |
| 2011/0082154 A1 | 4/2011 | Oksenberg et al. |
| 2011/0082360 A1 | 4/2011 | Fuchs et al. |
| 2011/0082381 A1 | 4/2011 | Uthman et al. |
| 2011/0082522 A1 | 4/2011 | Bourget et al. |
| 2011/0087125 A1 | 4/2011 | Causevic |
| 2011/0087127 A1 | 4/2011 | Sarkela et al. |
| 2011/0092800 A1 | 4/2011 | Yoo et al. |
| 2011/0092834 A1 | 4/2011 | Yazicioglu et al. |
| 2011/0092839 A1 | 4/2011 | Alshaer et al. |
| 2011/0092882 A1 | 4/2011 | Firlik et al. |
| 2011/0093033 A1 | 4/2011 | Nekhendzy |
| 2011/0098583 A1 | 4/2011 | Pandia et al. |
| 2011/0098778 A1 | 4/2011 | Thimineur et al. |
| 2011/0105859 A1 | 5/2011 | Popovic et al. |
| 2011/0105915 A1 | 5/2011 | Bauer et al. |
| 2011/0105938 A1 | 5/2011 | Hardt |
| 2011/0105998 A1 | 5/2011 | Zhang et al. |
| 2011/0106206 A1 | 5/2011 | Schiff |
| 2011/0106750 A1 | 5/2011 | Pradeep et al. |
| 2011/0110868 A1 | 5/2011 | Akhtari et al. |
| 2011/0112379 A1 | 5/2011 | Li et al. |
| 2011/0112381 A1 | 5/2011 | Sun et al. |
| 2011/0112394 A1 | 5/2011 | Mishelevich |
| 2011/0112426 A1 | 5/2011 | Causevic |
| 2011/0112427 A1 | 5/2011 | Phillips et al. |
| 2011/0112590 A1 | 5/2011 | Wu et al. |
| 2011/0115624 A1 | 5/2011 | Tran |
| 2011/0118536 A1 | 5/2011 | Phillips et al. |
| 2011/0118618 A1 | 5/2011 | John et al. |
| 2011/0118619 A1 | 5/2011 | Burton et al. |
| 2011/0119212 A1 | 5/2011 | De Bruin et al. |
| 2011/0125046 A1 | 5/2011 | Burton et al. |
| 2011/0125048 A1 | 5/2011 | Causevic et al. |
| 2011/0125077 A1 | 5/2011 | Denison et al. |
| 2011/0125078 A1 | 5/2011 | Denison et al. |
| 2011/0125203 A1 | 5/2011 | Simon et al. |
| 2011/0125238 A1 | 5/2011 | Nofzinger |
| 2011/0129129 A1 | 6/2011 | Avinash et al. |
| 2011/0130615 A1 | 6/2011 | Mishelevich |
| 2011/0130643 A1 | 6/2011 | Derchak et al. |
| 2011/0130675 A1 | 6/2011 | Bibian et al. |
| 2011/0137371 A1 | 6/2011 | Giftakis et al. |
| 2011/0137381 A1 | 6/2011 | Lee et al. |
| 2011/0144520 A1 | 6/2011 | Causevic et al. |
| 2011/0144521 A1 | 6/2011 | Molnar et al. |
| 2011/0150253 A1 | 6/2011 | Corona-Strauss et al. |
| 2011/0152284 A1 | 6/2011 | Wieloch et al. |
| 2011/0152710 A1 | 6/2011 | Kim et al. |
| 2011/0152729 A1 | 6/2011 | Oohashi et al. |
| 2011/0152967 A1 | 6/2011 | Simon et al. |
| 2011/0152988 A1 | 6/2011 | Whitehurst et al. |
| 2011/0160543 A1 | 6/2011 | Parsey et al. |
| 2011/0160607 A1 | 6/2011 | John et al. |
| 2011/0160608 A1 | 6/2011 | Hargrove |
| 2011/0160795 A1 | 6/2011 | Osorio |
| 2011/0160796 A1 | 6/2011 | Lane et al. |
| 2011/0161011 A1 | 6/2011 | Hasson et al. |
| 2011/0162645 A1 | 7/2011 | John et al. |
| 2011/0166430 A1 | 7/2011 | Harris et al. |
| 2011/0166471 A1 | 7/2011 | Drew et al. |
| 2011/0166546 A1 | 7/2011 | Jaax et al. |
| 2011/0172500 A1 | 7/2011 | Van Dooren et al. |
| 2011/0172509 A1 | 7/2011 | Chance |
| 2011/0172553 A1 | 7/2011 | John et al. |
| 2011/0172554 A1 | 7/2011 | Leyde et al. |
| 2011/0172562 A1 | 7/2011 | Sahasrabudhe et al. |
| 2011/0172564 A1 | 7/2011 | Drew |
| 2011/0172567 A1 | 7/2011 | Panken et al. |
| 2011/0172725 A1 | 7/2011 | Wells et al. |
| 2011/0172732 A1 | 7/2011 | Maschino |
| 2011/0172738 A1 | 7/2011 | Davis et al. |
| 2011/0172739 A1 | 7/2011 | Mann et al. |
| 2011/0172743 A1 | 7/2011 | Davis et al. |
| 2011/0172927 A1 | 7/2011 | Sahasrabudhe et al. |
| 2011/0178359 A1 | 7/2011 | Hirschman et al. |
| 2011/0178441 A1 | 7/2011 | Tyler |
| 2011/0178442 A1 | 7/2011 | Mishelevich |
| 2011/0178581 A1 | 7/2011 | Haber et al. |
| 2011/0181422 A1 | 7/2011 | Tran |
| 2011/0182501 A1 | 7/2011 | Mercier et al. |
| 2011/0184305 A1 | 7/2011 | Liley |
| 2011/0184487 A1 | 7/2011 | Alberts et al. |

(56) References Cited

U.S. PATENT DOCUMENTS

| | | |
|---|---|---|
| 2011/0184650 A1 | 7/2011 | Hymel |
| 2011/0190569 A1 | 8/2011 | Simon et al. |
| 2011/0190600 A1 | 8/2011 | McKenna et al. |
| 2011/0190846 A1 | 8/2011 | Ruffini et al. |
| 2011/0191275 A1 | 8/2011 | Lujan et al. |
| 2011/0191350 A1 | 8/2011 | Zhang et al. |
| 2011/0196693 A1 | 8/2011 | Hargrove et al. |
| 2011/0201944 A1 | 8/2011 | Higgins et al. |
| 2011/0207988 A1 | 8/2011 | Ruohonen et al. |
| 2011/0208012 A1 | 8/2011 | Gerber et al. |
| 2011/0208094 A1 | 8/2011 | Mishelevich |
| 2011/0208264 A1 | 8/2011 | Gliner et al. |
| 2011/0208539 A1 | 8/2011 | Lynn |
| 2011/0213200 A1 | 9/2011 | Mishelevich |
| 2011/0213222 A1 | 9/2011 | Leyde et al. |
| 2011/0217240 A1 | 9/2011 | Ferris |
| 2011/0218405 A1 | 9/2011 | Avinash et al. |
| 2011/0218453 A1 | 9/2011 | Hirata et al. |
| 2011/0218456 A1 | 9/2011 | Graham et al. |
| 2011/0218950 A1 | 9/2011 | Mirowski et al. |
| 2011/0224569 A1 | 9/2011 | Isenhart et al. |
| 2011/0224570 A1 | 9/2011 | Causevic |
| 2011/0224571 A1 | 9/2011 | Pascual-Leone et al. |
| 2011/0224602 A1 | 9/2011 | Struijk et al. |
| 2011/0224749 A1 | 9/2011 | Ben-David et al. |
| 2011/0229005 A1 | 9/2011 | Den Harder et al. |
| 2011/0230701 A1 | 9/2011 | Simon et al. |
| 2011/0230738 A1 | 9/2011 | Chance |
| 2011/0230755 A1 | 9/2011 | MacFarlane et al. |
| 2011/0230938 A1 | 9/2011 | Simon et al. |
| 2011/0238130 A1 | 9/2011 | Bourget et al. |
| 2011/0238136 A1 | 9/2011 | Bourget et al. |
| 2011/0245709 A1 | 10/2011 | Greenwald |
| 2011/0245734 A1 | 10/2011 | Wagner et al. |
| 2011/0251583 A1 | 10/2011 | Miyazawa et al. |
| 2011/0251985 A1 | 10/2011 | Waxman et al. |
| 2011/0256520 A1 | 10/2011 | Siefert |
| 2011/0257501 A1 | 10/2011 | Huys et al. |
| 2011/0257517 A1 | 10/2011 | Guttag et al. |
| 2011/0257519 A1 | 10/2011 | Bjørnerud et al. |
| 2011/0263962 A1 | 10/2011 | Marks |
| 2011/0263968 A1 | 10/2011 | Quattrocki-Knight et al. |
| 2011/0263995 A1 | 10/2011 | Chen |
| 2011/0264182 A1 | 10/2011 | Cowley |
| 2011/0270074 A1 | 11/2011 | deCharms |
| 2011/0270095 A1 | 11/2011 | Bukhman |
| 2011/0270096 A1 | 11/2011 | Osorio et al. |
| 2011/0270117 A1 | 11/2011 | Warwick et al. |
| 2011/0270346 A1 | 11/2011 | Frei et al. |
| 2011/0270347 A1 | 11/2011 | Frei et al. |
| 2011/0270348 A1 | 11/2011 | Goetz |
| 2011/0270579 A1 | 11/2011 | Watson et al. |
| 2011/0270914 A1 | 11/2011 | Jung et al. |
| 2011/0275927 A1 | 11/2011 | Wagner et al. |
| 2011/0276107 A1 | 11/2011 | Simon et al. |
| 2011/0276112 A1 | 11/2011 | Simon et al. |
| 2011/0282225 A1 | 11/2011 | Anderson et al. |
| 2011/0282230 A9 | 11/2011 | Liley |
| 2011/0282234 A1 | 11/2011 | Ochs |
| 2011/0288119 A1 | 11/2011 | Chesworth et al. |
| 2011/0288400 A1 | 11/2011 | Russell et al. |
| 2011/0288424 A1 | 11/2011 | Kanai et al. |
| 2011/0288431 A1 | 11/2011 | Alshaer et al. |
| 2011/0293193 A1 | 12/2011 | Garg et al. |
| 2011/0295142 A1 | 12/2011 | Chakravarthy et al. |
| 2011/0295143 A1 | 12/2011 | Leuthardt et al. |
| 2011/0295166 A1 | 12/2011 | Dalton |
| 2011/0295338 A1 | 12/2011 | Rickert et al. |
| 2011/0295344 A1 | 12/2011 | Wells et al. |
| 2011/0295345 A1 | 12/2011 | Wells et al. |
| 2011/0295346 A1 | 12/2011 | Wells et al. |
| 2011/0295347 A1 | 12/2011 | Wells et al. |
| 2011/0298706 A1 | 12/2011 | Mann |
| 2011/0301436 A1 | 12/2011 | Teixeira |
| 2011/0301439 A1 | 12/2011 | Albert et al. |
| 2011/0301441 A1 | 12/2011 | Bandic et al. |
| 2011/0301448 A1 | 12/2011 | deCharms |
| 2011/0301486 A1 | 12/2011 | Van Hek et al. |
| 2011/0301487 A1 | 12/2011 | Abeyratne et al. |
| 2011/0301488 A1 | 12/2011 | Schuette et al. |
| 2011/0301529 A1 | 12/2011 | Zhang et al. |
| 2011/0306845 A1 | 12/2011 | Osorio |
| 2011/0306846 A1 | 12/2011 | Osorio |
| 2011/0307029 A1 | 12/2011 | Hargrove |
| 2011/0307030 A1 | 12/2011 | John |
| 2011/0307079 A1 | 12/2011 | Oweiss et al. |
| 2011/0308789 A1 | 12/2011 | Zhang et al. |
| 2011/0311021 A1 | 12/2011 | Tsukagoshi |
| 2011/0311489 A1 | 12/2011 | Deisseroth et al. |
| 2011/0313268 A1 | 12/2011 | Kokones et al. |
| 2011/0313274 A1 | 12/2011 | Subbarao |
| 2011/0313308 A1 | 12/2011 | Zavoronkovs et al. |
| 2011/0313487 A1 | 12/2011 | Kokones et al. |
| 2011/0313760 A1 | 12/2011 | Ricci et al. |
| 2011/0319482 A1 | 12/2011 | Blower et al. |
| 2011/0319724 A1 | 12/2011 | Cox |
| 2011/0319726 A1 | 12/2011 | Sachanandani et al. |
| 2011/0319975 A1 | 12/2011 | Ho et al. |
| 2012/0003615 A1 | 1/2012 | Ochs |
| 2012/0004518 A1 | 1/2012 | D'Souza et al. |
| 2012/0004561 A1 | 1/2012 | John |
| 2012/0004564 A1 | 1/2012 | Daniel |
| 2012/0004579 A1 | 1/2012 | Luo et al. |
| 2012/0004749 A1 | 1/2012 | Abeyratne et al. |
| 2012/0010493 A1 | 1/2012 | Semenov |
| 2012/0010536 A1 | 1/2012 | Bolger et al. |
| 2012/0011927 A1 | 1/2012 | Badri et al. |
| 2012/0016218 A1 | 1/2012 | Lau et al. |
| 2012/0016252 A1 | 1/2012 | Melker et al. |
| 2012/0016336 A1 | 1/2012 | Whitehurst et al. |
| 2012/0016430 A1 | 1/2012 | Lozano |
| 2012/0016432 A1 | 1/2012 | Westendorp et al. |
| 2012/0016435 A1 | 1/2012 | Rom |
| 2012/0021394 A1 | 1/2012 | deCharms |
| 2012/0022336 A1 | 1/2012 | Teixeira |
| 2012/0022340 A1 | 1/2012 | Heruth et al. |
| 2012/0022343 A1 | 1/2012 | Shastri et al. |
| 2012/0022350 A1 | 1/2012 | Teixeira |
| 2012/0022351 A1 | 1/2012 | Starr |
| 2012/0022365 A1 | 1/2012 | Mansfield |
| 2012/0022384 A1 | 1/2012 | Teixeira |
| 2012/0022392 A1 | 1/2012 | Leuthardt et al. |
| 2012/0022611 A1 | 1/2012 | Firlik et al. |
| 2012/0022844 A1 | 1/2012 | Teixeira |
| 2012/0022884 A1 | 1/2012 | Chillemi |
| 2012/0029320 A1 | 2/2012 | Watson et al. |
| 2012/0029378 A1 | 2/2012 | Low |
| 2012/0029379 A1 | 2/2012 | Sivadas |
| 2012/0029591 A1 | 2/2012 | Simon et al. |
| 2012/0029601 A1 | 2/2012 | Simon et al. |
| 2012/0035428 A1 | 2/2012 | Roberts et al. |
| 2012/0035431 A1 | 2/2012 | Sun et al. |
| 2012/0035433 A1 | 2/2012 | Chance |
| 2012/0035698 A1 | 2/2012 | Johnson et al. |
| 2012/0035765 A1 | 2/2012 | Sato et al. |
| 2012/0036004 A1 | 2/2012 | Pradeep et al. |
| 2012/0041279 A1 | 2/2012 | Freeman et al. |
| 2012/0041318 A1 | 2/2012 | Taylor |
| 2012/0041319 A1 | 2/2012 | Taylor et al. |
| 2012/0041320 A1 | 2/2012 | Taylor |
| 2012/0041321 A1 | 2/2012 | Taylor et al. |
| 2012/0041322 A1 | 2/2012 | Taylor et al. |
| 2012/0041323 A1 | 2/2012 | Taylor et al. |
| 2012/0041324 A1 | 2/2012 | Taylor et al. |
| 2012/0041330 A1 | 2/2012 | Prichep et al. |
| 2012/0041498 A1 | 2/2012 | Gliner et al. |
| 2012/0041735 A1 | 2/2012 | Taylor |
| 2012/0041739 A1 | 2/2012 | Taylor |
| 2012/0046531 A1 | 2/2012 | Hua |
| 2012/0046535 A1 | 2/2012 | Lin et al. |
| 2012/0046711 A1 | 2/2012 | Osorio |
| 2012/0046715 A1 | 2/2012 | Moffitt et al. |
| 2012/0046971 A1 | 2/2012 | Walker et al. |
| 2012/0052469 A1 | 3/2012 | Sobel et al. |

(56) References Cited

U.S. PATENT DOCUMENTS

| | | |
|---|---|---|
| 2012/0052905 A1 | 3/2012 | Lim et al. |
| 2012/0053394 A1 | 3/2012 | Honeycutt |
| 2012/0053433 A1 | 3/2012 | Chamoun et al. |
| 2012/0053449 A1 | 3/2012 | Moses et al. |
| 2012/0053473 A1 | 3/2012 | Johnson et al. |
| 2012/0053476 A1 | 3/2012 | Hopenfeld |
| 2012/0053478 A1 | 3/2012 | Johnson et al. |
| 2012/0053479 A1 | 3/2012 | Hopenfeld |
| 2012/0053483 A1 | 3/2012 | Doidge et al. |
| 2012/0053491 A1 | 3/2012 | Nathan et al. |
| 2012/0053508 A1 | 3/2012 | Wu et al. |
| 2012/0053919 A1 | 3/2012 | Taylor |
| 2012/0053921 A1 | 3/2012 | Taylor |
| 2012/0059246 A1 | 3/2012 | Taylor |
| 2012/0059273 A1 | 3/2012 | Meggiolaro et al. |
| 2012/0059431 A1 | 3/2012 | Williams et al. |
| 2012/0060851 A1 | 3/2012 | Amberg |
| 2012/0065536 A1 | 3/2012 | Causevic et al. |
| 2012/0070044 A1 | 3/2012 | Avinash et al. |
| 2012/0071771 A1 | 3/2012 | Behar |
| 2012/0078115 A1 | 3/2012 | Lonky |
| 2012/0078323 A1 | 3/2012 | Osorio |
| 2012/0078327 A1 | 3/2012 | Sloan et al. |
| 2012/0080305 A1 | 4/2012 | Koruga |
| 2012/0083668 A1 | 4/2012 | Pradeep et al. |
| 2012/0083690 A1 | 4/2012 | Semenov |
| 2012/0083700 A1 | 4/2012 | Osorio |
| 2012/0083701 A1 | 4/2012 | Osorio |
| 2012/0083708 A1 | 4/2012 | Rajdev et al. |
| 2012/0088987 A1 | 4/2012 | Braun et al. |
| 2012/0088992 A1 | 4/2012 | Armitstead |
| 2012/0089004 A1 | 4/2012 | Hsu et al. |
| 2012/0089205 A1 | 4/2012 | Boyden et al. |
| 2012/0092156 A1 | 4/2012 | Tran |
| 2012/0092157 A1 | 4/2012 | Tran |
| 2012/0095352 A1 | 4/2012 | Tran |
| 2012/0095357 A1 | 4/2012 | Tran |
| 2012/0100514 A1 | 4/2012 | Desain et al. |
| 2012/0101326 A1 | 4/2012 | Simon et al. |
| 2012/0101387 A1 | 4/2012 | Ji et al. |
| 2012/0101401 A1 | 4/2012 | Faul et al. |
| 2012/0101402 A1 | 4/2012 | Nguyen |
| 2012/0101430 A1 | 4/2012 | Robertson et al. |
| 2012/0101544 A1 | 4/2012 | Hoberman et al. |
| 2012/0108909 A1 | 5/2012 | Slobounov et al. |
| 2012/0108918 A1 | 5/2012 | Jarvik et al. |
| 2012/0108995 A1 | 5/2012 | Pradeep et al. |
| 2012/0108997 A1 | 5/2012 | Guan et al. |
| 2012/0108998 A1 | 5/2012 | Molnar et al. |
| 2012/0108999 A1 | 5/2012 | Leininger et al. |
| 2012/0109020 A1 | 5/2012 | Wagner et al. |
| 2012/0116149 A1 | 5/2012 | Pilla et al. |
| 2012/0116179 A1 | 5/2012 | Drew et al. |
| 2012/0116235 A1 | 5/2012 | Trumble et al. |
| 2012/0116244 A1 | 5/2012 | Mcintyre et al. |
| 2012/0116475 A1 | 5/2012 | Nelson et al. |
| 2012/0116741 A1 | 5/2012 | Choi et al. |
| 2012/0123232 A1 | 5/2012 | Najarian et al. |
| 2012/0123290 A1 | 5/2012 | Kidmose et al. |
| 2012/0125337 A1 | 5/2012 | Asanoi |
| 2012/0128683 A1 | 5/2012 | Shantha |
| 2012/0130204 A1 | 5/2012 | Basta et al. |
| 2012/0130228 A1 | 5/2012 | Zellers et al. |
| 2012/0130229 A1 | 5/2012 | Zellers et al. |
| 2012/0130300 A1 | 5/2012 | Stavchansky et al. |
| 2012/0130641 A1 | 5/2012 | Morrison et al. |
| 2012/0136242 A1 | 5/2012 | Qi et al. |
| 2012/0136274 A1 | 5/2012 | Burdea et al. |
| 2012/0136605 A1 | 5/2012 | Addison et al. |
| 2012/0143038 A1 | 6/2012 | Georgopoulos |
| 2012/0143074 A1 | 6/2012 | Shin et al. |
| 2012/0143075 A1 | 6/2012 | Tansey |
| 2012/0143104 A1 | 6/2012 | Tee et al. |
| 2012/0143285 A1 | 6/2012 | Wang et al. |
| 2012/0145152 A1 | 6/2012 | Lain et al. |
| 2012/0149042 A1 | 6/2012 | Jackowski et al. |
| 2012/0149997 A1 | 6/2012 | Diab et al. |
| 2012/0150255 A1 | 6/2012 | Lindenthaler et al. |
| 2012/0150257 A1 | 6/2012 | Aur et al. |
| 2012/0150262 A1 | 6/2012 | Gliner et al. |
| 2012/0150516 A1 | 6/2012 | Taylor et al. |
| 2012/0150545 A1 | 6/2012 | Simon |
| 2012/0157804 A1 | 6/2012 | Rogers et al. |
| 2012/0157963 A1 | 6/2012 | Imran |
| 2012/0158092 A1 | 6/2012 | Thimineur et al. |
| 2012/0159656 A1 | 6/2012 | Gerber et al. |
| 2012/0162002 A1 | 6/2012 | Semenov |
| 2012/0163689 A1 | 6/2012 | Bottger et al. |
| 2012/0164613 A1 | 6/2012 | Jung et al. |
| 2012/0165624 A1 | 6/2012 | Diab et al. |
| 2012/0165631 A1 | 6/2012 | Diab et al. |
| 2012/0165696 A1 | 6/2012 | Arns |
| 2012/0165898 A1 | 6/2012 | Moffitt |
| 2012/0165899 A1 | 6/2012 | Gliner |
| 2012/0165904 A1 | 6/2012 | Lee et al. |
| 2012/0172682 A1 | 7/2012 | Linderman et al. |
| 2012/0172689 A1 | 7/2012 | Albert et al. |
| 2012/0172743 A1 | 7/2012 | Aguilar et al. |
| 2012/0177716 A1 | 7/2012 | Ho et al. |
| 2012/0179071 A1 | 7/2012 | Skelton |
| 2012/0179228 A1 | 7/2012 | DeCharms |
| 2012/0184801 A1 | 7/2012 | Simon et al. |
| 2012/0184826 A1 | 7/2012 | Keenan et al. |
| 2012/0185020 A1 | 7/2012 | Simon et al. |
| 2012/0191000 A1 | 7/2012 | Adachi et al. |
| 2012/0191158 A1 | 7/2012 | Craig |
| 2012/0191542 A1 | 7/2012 | Nurmi |
| 2012/0195860 A1 | 8/2012 | Walker et al. |
| 2012/0197092 A1 | 8/2012 | Luo et al. |
| 2012/0197153 A1 | 8/2012 | Kraus et al. |
| 2012/0197163 A1 | 8/2012 | Mishelevich |
| 2012/0197322 A1 | 8/2012 | Skelton et al. |
| 2012/0203079 A1 | 8/2012 | McLaughlin |
| 2012/0203087 A1 | 8/2012 | McKenna et al. |
| 2012/0203130 A1 | 8/2012 | Bernhard |
| 2012/0203131 A1 | 8/2012 | DiLorenzo |
| 2012/0203133 A1 | 8/2012 | Jadidi |
| 2012/0203725 A1 | 8/2012 | Stoica |
| 2012/0207362 A1 | 8/2012 | Fueyo et al. |
| 2012/0209126 A1 | 8/2012 | Amos et al. |
| 2012/0209136 A1 | 8/2012 | Ma |
| 2012/0209139 A1 | 8/2012 | John |
| 2012/0209346 A1 | 8/2012 | Bikson et al. |
| 2012/0212353 A1 | 8/2012 | Fung et al. |
| 2012/0215114 A1 | 8/2012 | Gratton et al. |
| 2012/0215448 A1 | 8/2012 | Hu et al. |
| 2012/0219195 A1 | 8/2012 | Wu et al. |
| 2012/0219507 A1 | 8/2012 | Santosh et al. |
| 2012/0220843 A1 | 8/2012 | Diab et al. |
| 2012/0220889 A1 | 8/2012 | Sullivan et al. |
| 2012/0221310 A1 | 8/2012 | Sarrafzadeh et al. |
| 2012/0226091 A1 | 9/2012 | Mishelevich |
| 2012/0226130 A1 | 9/2012 | De Graff et al. |
| 2012/0226185 A1 | 9/2012 | Chung et al. |
| 2012/0226334 A1 | 9/2012 | Gardiner et al. |
| 2012/0232327 A1 | 9/2012 | Lozano et al. |
| 2012/0232376 A1 | 9/2012 | Crevecoeur et al. |
| 2012/0232433 A1 | 9/2012 | Mishelevich |
| 2012/0238890 A1 | 9/2012 | Baker et al. |
| 2012/0242501 A1 | 9/2012 | Tran et al. |
| 2012/0245464 A1 | 9/2012 | Tran |
| 2012/0245474 A1 | 9/2012 | Ofek et al. |
| 2012/0245481 A1 | 9/2012 | Blanco et al. |
| 2012/0245493 A1 | 9/2012 | Mishelevich |
| 2012/0245655 A1 | 9/2012 | Spitzer et al. |
| 2012/0249274 A1 | 10/2012 | Toda et al. |
| 2012/0253101 A1 | 10/2012 | Wang et al. |
| 2012/0253141 A1 | 10/2012 | Addison et al. |
| 2012/0253168 A1 | 10/2012 | Hu et al. |
| 2012/0253219 A1 | 10/2012 | Suffin et al. |
| 2012/0253249 A1 | 10/2012 | Wilson |
| 2012/0253261 A1 | 10/2012 | Poletto et al. |
| 2012/0253421 A1 | 10/2012 | Gliner et al. |
| 2012/0253429 A1 | 10/2012 | Schiffer |

(56)     References Cited

U.S. PATENT DOCUMENTS

| | | |
|---|---|---|
| 2012/0253434 A1 | 10/2012 | Nissila et al. |
| 2012/0253442 A1 | 10/2012 | Gliner et al. |
| 2012/0259249 A1 | 10/2012 | Khuri-Yakub et al. |
| 2012/0262250 A1 | 10/2012 | Stevenson et al. |
| 2012/0262558 A1 | 10/2012 | Boger et al. |
| 2012/0263393 A1 | 10/2012 | Yahil |
| 2012/0265080 A1 | 10/2012 | Yu et al. |
| 2012/0265262 A1 | 10/2012 | Osorio |
| 2012/0265267 A1 | 10/2012 | Blum et al. |
| 2012/0265270 A1 | 10/2012 | Cornejo Cruz et al. |
| 2012/0265271 A1 | 10/2012 | Goetz |
| 2012/0268272 A1 | 10/2012 | Lee et al. |
| 2012/0269385 A1 | 10/2012 | Lee et al. |
| 2012/0271148 A1 | 10/2012 | Nelson |
| 2012/0271151 A1 | 10/2012 | LaVoilette et al. |
| 2012/0271183 A1 | 10/2012 | Sachanandani et al. |
| 2012/0271189 A1 | 10/2012 | Nelson et al. |
| 2012/0271190 A1 | 10/2012 | Mortensen et al. |
| 2012/0271374 A1 | 10/2012 | Nelson et al. |
| 2012/0271375 A1 | 10/2012 | Wu et al. |
| 2012/0271376 A1 | 10/2012 | Kokones et al. |
| 2012/0271377 A1 | 10/2012 | Hagedorn et al. |
| 2012/0271380 A1 | 10/2012 | Roberts et al. |
| 2012/0277545 A1 | 11/2012 | Teixeira |
| 2012/0277548 A1 | 11/2012 | Burton |
| 2012/0277816 A1 | 11/2012 | Zhang et al. |
| 2012/0277833 A1 | 11/2012 | Gerber et al. |
| 2012/0283502 A1 | 11/2012 | Mishelevich et al. |
| 2012/0283604 A1 | 11/2012 | Mishelevich |
| 2012/0288143 A1 | 11/2012 | Ernst et al. |
| 2012/0289854 A1 | 11/2012 | Yamada et al. |
| 2012/0289869 A1 | 11/2012 | Tyler |
| 2012/0290058 A1 | 11/2012 | Langevin et al. |
| 2012/0296182 A1 | 11/2012 | Hornero Sanchez et al. |
| 2012/0296241 A1 | 11/2012 | Mishelevich |
| 2012/0296253 A1 | 11/2012 | Mathews et al. |
| 2012/0296569 A1 | 11/2012 | Shahaf et al. |
| 2012/0302842 A1 | 11/2012 | Kurtz et al. |
| 2012/0302845 A1 | 11/2012 | Lynn et al. |
| 2012/0302856 A1 | 11/2012 | Chang et al. |
| 2012/0302867 A1 | 11/2012 | Ichimura |
| 2012/0302894 A1 | 11/2012 | Diab et al. |
| 2012/0302912 A1 | 11/2012 | Moffitt et al. |
| 2012/0303080 A1 | 11/2012 | Ben-David et al. |
| 2012/0303087 A1 | 11/2012 | Moffitt et al. |
| 2012/0310050 A1 | 12/2012 | Osorio |
| 2012/0310100 A1 | 12/2012 | Galen et al. |
| 2012/0310105 A1 | 12/2012 | Feingold et al. |
| 2012/0310106 A1 | 12/2012 | Cavuoto |
| 2012/0310107 A1 | 12/2012 | Doidge et al. |
| 2012/0310298 A1 | 12/2012 | Besio et al. |
| 2012/0316622 A1 | 12/2012 | Whitehurst et al. |
| 2012/0316630 A1 | 12/2012 | Firlik et al. |
| 2012/0316793 A1 | 12/2012 | Jung et al. |
| 2012/0321152 A1 | 12/2012 | Carroll |
| 2012/0321160 A1 | 12/2012 | Carroll |
| 2012/0321759 A1 | 12/2012 | Marinkovich et al. |
| 2012/0323108 A1 | 12/2012 | Carroll |
| 2012/0323132 A1 | 12/2012 | Warner et al. |
| 2012/0330109 A1 | 12/2012 | Tran |
| 2012/0330369 A1 | 12/2012 | Osorio et al. |
| 2013/0006124 A1 | 1/2013 | Eyal et al. |
| 2013/0006332 A1 | 1/2013 | Sommer et al. |
| 2013/0009783 A1 | 1/2013 | Tran |
| 2013/0011819 A1 | 1/2013 | Horseman |
| 2013/0012786 A1 | 1/2013 | Horseman |
| 2013/0012787 A1 | 1/2013 | Horseman |
| 2013/0012788 A1 | 1/2013 | Horseman |
| 2013/0012789 A1 | 1/2013 | Horseman |
| 2013/0012790 A1 | 1/2013 | Horseman |
| 2013/0012802 A1 | 1/2013 | Horseman |
| 2013/0012804 A1 | 1/2013 | deCharms |
| 2013/0012830 A1 | 1/2013 | Leininger et al. |
| 2013/0013327 A1 | 1/2013 | Horseman |
| 2013/0013339 A1 | 1/2013 | Goldman et al. |
| 2013/0013667 A1 | 1/2013 | Serena |
| 2013/0018435 A1 | 1/2013 | De Ridder |
| 2013/0018438 A1 | 1/2013 | Chow |
| 2013/0018439 A1 | 1/2013 | Chow et al. |
| 2013/0018440 A1 | 1/2013 | Chow et al. |
| 2013/0018592 A1 | 1/2013 | Mollicone et al. |
| 2013/0018596 A1 | 1/2013 | Bottger et al. |
| 2013/0019325 A1 | 1/2013 | Deisseroth et al. |
| 2013/0023783 A1 | 1/2013 | Snyder et al. |
| 2013/0028496 A1 | 1/2013 | Panin et al. |
| 2013/0030241 A1 | 1/2013 | Smith |
| 2013/0030257 A1 | 1/2013 | Nakata et al. |
| 2013/0031038 A1 | 1/2013 | Horne |
| 2013/0034837 A1 | 2/2013 | Clapp et al. |
| 2013/0035579 A1 | 2/2013 | Le et al. |
| 2013/0039498 A1 | 2/2013 | Adachi et al. |
| 2013/0041235 A1 | 2/2013 | Rogers et al. |
| 2013/0041281 A1 | 2/2013 | Park et al. |
| 2013/0046151 A1 | 2/2013 | Bsoul et al. |
| 2013/0046193 A1 | 2/2013 | Guttag et al. |
| 2013/0046358 A1 | 2/2013 | Leyde |
| 2013/0046715 A1 | 2/2013 | Castermans et al. |
| 2013/0053656 A1 | 2/2013 | Mollicone et al. |
| 2013/0054214 A1 | 2/2013 | Taylor |
| 2013/0054215 A1 | 2/2013 | Stubna et al. |
| 2013/0058548 A1 | 3/2013 | Garg et al. |
| 2013/0060110 A1 | 3/2013 | Lynn et al. |
| 2013/0060125 A1 | 3/2013 | Zeman et al. |
| 2013/0060158 A1 | 3/2013 | Perez-Velazquez et al. |
| 2013/0063434 A1 | 3/2013 | Miga et al. |
| 2013/0063550 A1 | 3/2013 | Ritchey et al. |
| 2013/0064438 A1 | 3/2013 | Taylor et al. |
| 2013/0066350 A1 | 3/2013 | Mishelevich |
| 2013/0066391 A1 | 3/2013 | Hulvershorn et al. |
| 2013/0066392 A1 | 3/2013 | Simon et al. |
| 2013/0066394 A1 | 3/2013 | Saab |
| 2013/0066395 A1 | 3/2013 | Simon et al. |
| 2013/0066618 A1 | 3/2013 | Taylor et al. |
| 2013/0069780 A1 | 3/2013 | Tran et al. |
| 2013/0070929 A1 | 3/2013 | Adachi et al. |
| 2013/0072292 A1 | 3/2013 | Sutton et al. |
| 2013/0072775 A1 | 3/2013 | Rogers et al. |
| 2013/0072780 A1 | 3/2013 | Espy et al. |
| 2013/0072807 A1 | 3/2013 | Tran |
| 2013/0072996 A1 | 3/2013 | Kilgard et al. |
| 2013/0073022 A1 | 3/2013 | Ollivier |
| 2013/0076885 A1 | 3/2013 | Kobetski et al. |
| 2013/0079606 A1 | 3/2013 | McGonigle et al. |
| 2013/0079621 A1 | 3/2013 | Shoham et al. |
| 2013/0079647 A1 | 3/2013 | McGonigle et al. |
| 2013/0079656 A1 | 3/2013 | Dripps et al. |
| 2013/0079657 A1 | 3/2013 | Ochs et al. |
| 2013/0080127 A1 | 3/2013 | Shahaf et al. |
| 2013/0080489 A1 | 3/2013 | Ochs et al. |
| 2013/0085678 A1 | 4/2013 | Jung et al. |
| 2013/0089503 A1 | 4/2013 | Deisseroth et al. |
| 2013/0090454 A1 | 4/2013 | Deisseroth et al. |
| 2013/0090706 A1 | 4/2013 | Nudo et al. |
| 2013/0091941 A1 | 4/2013 | Huh et al. |
| 2013/0095459 A1 | 4/2013 | Tran |
| 2013/0096391 A1 | 4/2013 | Osorio et al. |
| 2013/0096393 A1 | 4/2013 | Osorio et al. |
| 2013/0096394 A1 | 4/2013 | Gupta et al. |
| 2013/0096408 A1 | 4/2013 | He et al. |
| 2013/0096441 A1 | 4/2013 | Osorio |
| 2013/0096453 A1 | 4/2013 | Chung et al. |
| 2013/0096454 A1 | 4/2013 | Jang et al. |
| 2013/0096839 A1 | 4/2013 | Osorio et al. |
| 2013/0096840 A1 | 4/2013 | Osorio et al. |
| 2013/0102833 A1 | 4/2013 | John et al. |
| 2013/0102877 A1 | 4/2013 | Mori et al. |
| 2013/0102897 A1 | 4/2013 | Kalafut et al. |
| 2013/0102907 A1 | 4/2013 | Funane et al. |
| 2013/0102919 A1 | 4/2013 | Schiff |
| 2013/0104066 A1 | 4/2013 | Soederstroem |
| 2013/0109995 A1 | 5/2013 | Rothman et al. |
| 2013/0109996 A1 | 5/2013 | Turnbull et al. |
| 2013/0110616 A1 | 5/2013 | Bakalash et al. |
| 2013/0113816 A1 | 5/2013 | Sudarsky et al. |

(56) References Cited

U.S. PATENT DOCUMENTS

| | | |
|---|---|---|
| 2013/0116520 A1 | 5/2013 | Roham et al. |
| 2013/0116540 A1 | 5/2013 | Li et al. |
| 2013/0116561 A1 | 5/2013 | Rothberg et al. |
| 2013/0116578 A1 | 5/2013 | An et al. |
| 2013/0116588 A1 | 5/2013 | Yazicioglu et al. |
| 2013/0116748 A1 | 5/2013 | Bokil et al. |
| 2013/0118494 A1 | 5/2013 | Ujhazy et al. |
| 2013/0120246 A1 | 5/2013 | Schuette et al. |
| 2013/0121984 A1 | 5/2013 | Haslett et al. |
| 2013/0123568 A1 | 5/2013 | Hamilton et al. |
| 2013/0123584 A1 | 5/2013 | Sun et al. |
| 2013/0123607 A1 | 5/2013 | Leuthardt et al. |
| 2013/0123684 A1 | 5/2013 | Giuffrida et al. |
| 2013/0127708 A1 | 5/2013 | Jung et al. |
| 2013/0127980 A1 | 5/2013 | Haddick et al. |
| 2013/0130799 A1 | 5/2013 | Van Hulle et al. |
| 2013/0131438 A1 | 5/2013 | Brewer et al. |
| 2013/0131461 A1 | 5/2013 | Jorge et al. |
| 2013/0131537 A1 | 5/2013 | Tam |
| 2013/0131746 A1 | 5/2013 | Simon et al. |
| 2013/0131753 A1 | 5/2013 | Simon et al. |
| 2013/0131755 A1 | 5/2013 | Panken et al. |
| 2013/0132029 A1 | 5/2013 | Mollicone et al. |
| 2013/0137717 A1 | 5/2013 | Chesworth et al. |
| 2013/0137936 A1 | 5/2013 | Baker, Jr. et al. |
| 2013/0137938 A1 | 5/2013 | Peters |
| 2013/0138002 A1 | 5/2013 | Weng et al. |
| 2013/0138176 A1 | 5/2013 | Goetz |
| 2013/0138177 A1 | 5/2013 | DeRidder |
| 2013/0141103 A1 | 6/2013 | Roshtal et al. |
| 2013/0144106 A1 | 6/2013 | Phillips et al. |
| 2013/0144107 A1 | 6/2013 | Phillips et al. |
| 2013/0144108 A1 | 6/2013 | Phillips et al. |
| 2013/0144183 A1 | 6/2013 | John et al. |
| 2013/0144192 A1 | 6/2013 | Mischelevich et al. |
| 2013/0144353 A1 | 6/2013 | Lozano |
| 2013/0144537 A1 | 6/2013 | Schalk et al. |
| 2013/0150650 A1 | 6/2013 | Phillips et al. |
| 2013/0150651 A1 | 6/2013 | Phillips et al. |
| 2013/0150659 A1 | 6/2013 | Shaw et al. |
| 2013/0150702 A1 | 6/2013 | Hokari |
| 2013/0150921 A1 | 6/2013 | Singhal et al. |
| 2013/0151163 A1 | 6/2013 | Taylor et al. |
| 2013/0158883 A1 | 6/2013 | Hasegawa et al. |
| 2013/0159041 A1 | 6/2013 | Jayaraman et al. |
| 2013/0165766 A1 | 6/2013 | Nishikawa et al. |
| 2013/0165804 A1 | 6/2013 | Johnson et al. |
| 2013/0165812 A1 | 6/2013 | Aksenova et al. |
| 2013/0165846 A1 | 6/2013 | Peyman |
| 2013/0165996 A1 | 6/2013 | Meadows et al. |
| 2013/0167360 A1 | 7/2013 | Masmanidis et al. |
| 2013/0172663 A1 | 7/2013 | Leonard |
| 2013/0172686 A1 | 7/2013 | Addison et al. |
| 2013/0172691 A1 | 7/2013 | Tran |
| 2013/0172716 A1 | 7/2013 | Lozano et al. |
| 2013/0172763 A1 | 7/2013 | Wheeler |
| 2013/0172767 A1 | 7/2013 | Dripps et al. |
| 2013/0172772 A1 | 7/2013 | Alshaer et al. |
| 2013/0172774 A1 | 7/2013 | Crowder et al. |
| 2013/0178693 A1 | 7/2013 | Neuvonen et al. |
| 2013/0178718 A1 | 7/2013 | Tran et al. |
| 2013/0178733 A1 | 7/2013 | Langleben |
| 2013/0178913 A1 | 7/2013 | Lozano |
| 2013/0182860 A1 | 7/2013 | Adachi et al. |
| 2013/0184218 A1 | 7/2013 | Paul et al. |
| 2013/0184516 A1 | 7/2013 | Genereux et al. |
| 2013/0184552 A1 | 7/2013 | Westermann et al. |
| 2013/0184558 A1 | 7/2013 | Gallant et al. |
| 2013/0184597 A1 | 7/2013 | Hopenfeld |
| 2013/0184603 A1 | 7/2013 | Rothman |
| 2013/0184639 A1 | 7/2013 | Whitehurst et al. |
| 2013/0184728 A1 | 7/2013 | Mishelevich |
| 2013/0184781 A1 | 7/2013 | Eskandar et al. |
| 2013/0184786 A1 | 7/2013 | Goetz |
| 2013/0184792 A1 | 7/2013 | Simon et al. |
| 2013/0184997 A1 | 7/2013 | Mott |
| 2013/0185144 A1 | 7/2013 | Pradeep et al. |
| 2013/0185145 A1 | 7/2013 | Pradeep et al. |
| 2013/0188830 A1 | 7/2013 | Ernst et al. |
| 2013/0188854 A1 | 7/2013 | Bilgic et al. |
| 2013/0189663 A1 | 7/2013 | Tuchschmid et al. |
| 2013/0190577 A1 | 7/2013 | Brunner et al. |
| 2013/0190642 A1 | 7/2013 | Muesch et al. |
| 2013/0197321 A1 | 8/2013 | Wilson |
| 2013/0197322 A1 | 8/2013 | Tran |
| 2013/0197328 A1 | 8/2013 | Diab et al. |
| 2013/0197339 A1 | 8/2013 | Bardakjian et al. |
| 2013/0197401 A1 | 8/2013 | Sato et al. |
| 2013/0197944 A1 | 8/2013 | Drew et al. |
| 2013/0203019 A1 | 8/2013 | Nolen |
| 2013/0204085 A1 | 8/2013 | Alexander et al. |
| 2013/0204122 A1 | 8/2013 | Hendler et al. |
| 2013/0204144 A1 | 8/2013 | Colborn et al. |
| 2013/0204150 A1 | 8/2013 | Similowski et al. |
| 2013/0211183 A1 | 8/2013 | Schiffer |
| 2013/0211224 A1 | 8/2013 | Isenhart et al. |
| 2013/0211238 A1 | 8/2013 | DeCharms |
| 2013/0211276 A1 | 8/2013 | Luo et al. |
| 2013/0211291 A1 | 8/2013 | Tran |
| 2013/0211728 A1 | 8/2013 | Taylor et al. |
| 2013/0217982 A1 | 8/2013 | Behzadi |
| 2013/0218043 A1 | 8/2013 | Yoshida |
| 2013/0218053 A1 | 8/2013 | Kaiser et al. |
| 2013/0218232 A1 | 8/2013 | Giftakis et al. |
| 2013/0218233 A1 | 8/2013 | Warschewske et al. |
| 2013/0218819 A1 | 8/2013 | Lujan et al. |
| 2013/0221961 A1 | 8/2013 | Liu |
| 2013/0223709 A1 | 8/2013 | Wagner |
| 2013/0225940 A1 | 8/2013 | Fujita et al. |
| 2013/0225953 A1 | 8/2013 | Oliviero et al. |
| 2013/0225992 A1 | 8/2013 | Osorio |
| 2013/0226261 A1 | 8/2013 | Sparks et al. |
| 2013/0226408 A1 | 8/2013 | Fung et al. |
| 2013/0226464 A1 | 8/2013 | Marci et al. |
| 2013/0231574 A1 | 9/2013 | Tran |
| 2013/0231580 A1 | 9/2013 | Chen et al. |
| 2013/0231709 A1 | 9/2013 | Lozano |
| 2013/0231716 A1 | 9/2013 | Skelton et al. |
| 2013/0231721 A1 | 9/2013 | DeCharms |
| 2013/0231947 A1 | 9/2013 | Shusterman |
| 2013/0234823 A1 | 9/2013 | Kahn et al. |
| 2013/0235550 A1 | 9/2013 | Stevenson et al. |
| 2013/0237541 A1 | 9/2013 | Teegarden et al. |
| 2013/0237874 A1 | 9/2013 | Zoicas |
| 2013/0238049 A1 | 9/2013 | Simon et al. |
| 2013/0238050 A1 | 9/2013 | Simon et al. |
| 2013/0238053 A1 | 9/2013 | Ignagni et al. |
| 2013/0238063 A1 | 9/2013 | Nofzinger |
| 2013/0242262 A1 | 9/2013 | Lewis |
| 2013/0243287 A1 | 9/2013 | Thomson et al. |
| 2013/0244323 A1 | 9/2013 | Deisseroth et al. |
| 2013/0245416 A1 | 9/2013 | Yarmush et al. |
| 2013/0245422 A1 | 9/2013 | D'arcy et al. |
| 2013/0245424 A1 | 9/2013 | deCharms |
| 2013/0245464 A1 | 9/2013 | Colborn et al. |
| 2013/0245466 A1 | 9/2013 | Sachanandani et al. |
| 2013/0245485 A1 | 9/2013 | Mashour et al. |
| 2013/0245486 A1 | 9/2013 | Simon et al. |
| 2013/0245711 A1 | 9/2013 | Simon et al. |
| 2013/0245712 A1 | 9/2013 | Simon et al. |
| 2013/0245886 A1 | 9/2013 | Fung et al. |
| 2013/0251641 A1 | 9/2013 | Akhtari et al. |
| 2013/0253363 A1 | 9/2013 | Juffali et al. |
| 2013/0253612 A1 | 9/2013 | Chow |
| 2013/0255586 A1 | 10/2013 | Gerashchenko |
| 2013/0261490 A1 | 10/2013 | Truccolo et al. |
| 2013/0261506 A1 | 10/2013 | Mishelevich |
| 2013/0261703 A1 | 10/2013 | Chow et al. |
| 2013/0266163 A1 | 10/2013 | Morikawa et al. |
| 2013/0267760 A1 | 10/2013 | Jin |
| 2013/0267866 A1 | 10/2013 | Nakashima et al. |
| 2013/0267928 A1 | 10/2013 | Imran et al. |
| 2013/0274562 A1 | 10/2013 | Ghaffari et al. |
| 2013/0274580 A1 | 10/2013 | Madsen et al. |

(56) References Cited

U.S. PATENT DOCUMENTS

| | | |
|---|---|---|
| 2013/0274586 A1 | 10/2013 | Miyazaki et al. |
| 2013/0274625 A1 | 10/2013 | Sarma et al. |
| 2013/0275159 A1 | 10/2013 | Seely |
| 2013/0281758 A1 | 10/2013 | Solvason et al. |
| 2013/0281759 A1 | 10/2013 | Hagedorn et al. |
| 2013/0281811 A1 | 10/2013 | Imran |
| 2013/0281879 A1 | 10/2013 | Raniere |
| 2013/0281890 A1 | 10/2013 | Mishelevich |
| 2013/0282075 A1 | 10/2013 | De Ridder |
| 2013/0282339 A1 | 10/2013 | Ricci et al. |
| 2013/0289360 A1 | 10/2013 | Hyde et al. |
| 2013/0289364 A1 | 10/2013 | Colman et al. |
| 2013/0289385 A1 | 10/2013 | Lozano et al. |
| 2013/0289386 A1 | 10/2013 | Deisseroth et al. |
| 2013/0289401 A1 | 10/2013 | Colbaugh et al. |
| 2013/0289413 A1 | 10/2013 | Ochs et al. |
| 2013/0289417 A1 | 10/2013 | Grunwald et al. |
| 2013/0289424 A1 | 10/2013 | Brockway et al. |
| 2013/0289433 A1 | 10/2013 | Jin et al. |
| 2013/0289653 A1 | 10/2013 | Kilgard et al. |
| 2013/0289669 A1 | 10/2013 | Deisseroth et al. |
| 2013/0293844 A1 | 11/2013 | Gross et al. |
| 2013/0295016 A1 | 11/2013 | Gerber et al. |
| 2013/0296406 A1 | 11/2013 | Deisseroth et al. |
| 2013/0296637 A1 | 11/2013 | Kilgard et al. |
| 2013/0300573 A1 | 11/2013 | Brown et al. |
| 2013/0303828 A1 | 11/2013 | Hargrove |
| 2013/0303934 A1 | 11/2013 | Collura |
| 2013/0304153 A1 | 11/2013 | Hargrove et al. |
| 2013/0304159 A1 | 11/2013 | Simon et al. |
| 2013/0304472 A1 | 11/2013 | Pakhomov |
| 2013/0308099 A1 | 11/2013 | Stack |
| 2013/0309278 A1 | 11/2013 | Peyman |
| 2013/0310422 A1 | 11/2013 | Brown et al. |
| 2013/0310660 A1 | 11/2013 | Zuckerman-Stark et al. |
| 2013/0310909 A1 | 11/2013 | Simon et al. |
| 2013/0314243 A1 | 11/2013 | Le |
| 2013/0317380 A1 | 11/2013 | Liley et al. |
| 2013/0317382 A1 | 11/2013 | Le |
| 2013/0317384 A1 | 11/2013 | Le |
| 2013/0317474 A1 | 11/2013 | Rezai et al. |
| 2013/0317568 A1 | 11/2013 | Skelton |
| 2013/0317580 A1 | 11/2013 | Simon et al. |
| 2013/0318546 A1 | 11/2013 | Kothuri et al. |
| 2013/0324880 A1 | 12/2013 | Adachi et al. |
| 2013/0330428 A1 | 12/2013 | Geng |
| 2013/0338449 A1 | 12/2013 | Warwick et al. |
| 2013/0338450 A1 | 12/2013 | Osorio et al. |
| 2013/0338459 A1 | 12/2013 | Lynn et al. |
| 2013/0338518 A1 | 12/2013 | Zoica |
| 2013/0338526 A1 | 12/2013 | Howard |
| 2013/0338738 A1 | 12/2013 | Garcia Molina et al. |
| 2013/0338803 A1 | 12/2013 | Maoz et al. |
| 2013/0339043 A1 | 12/2013 | Bakar et al. |
| 2013/0344465 A1 | 12/2013 | Dickinson et al. |
| 2013/0345522 A1 | 12/2013 | Sun et al. |
| 2013/0345523 A1 | 12/2013 | Diab et al. |
| 2014/0000630 A1 | 1/2014 | Ford |
| 2014/0003696 A1 | 1/2014 | Taghva |
| 2014/0005518 A1 | 1/2014 | Ko et al. |
| 2014/0005743 A1 | 1/2014 | Giuffrida et al. |
| 2014/0005744 A1 | 1/2014 | Hershey et al. |
| 2014/0005988 A1 | 1/2014 | Brockway |
| 2014/0012061 A1 | 1/2014 | Song et al. |
| 2014/0012110 A1 | 1/2014 | Watson et al. |
| 2014/0012133 A1 | 1/2014 | Sverdlik et al. |
| 2014/0012153 A1 | 1/2014 | Greenwald |
| 2014/0015852 A1 | 1/2014 | Kantartzis et al. |
| 2014/0018649 A1 | 1/2014 | Jespersen et al. |
| 2014/0018792 A1 | 1/2014 | Gang et al. |
| 2014/0019165 A1 | 1/2014 | Horseman |
| 2014/0023999 A1 | 1/2014 | Greder |
| 2014/0025133 A1 | 1/2014 | Lozano |
| 2014/0025396 A1 | 1/2014 | Horseman |
| 2014/0025397 A1 | 1/2014 | Horseman |
| 2014/0029830 A1 | 1/2014 | Vija et al. |
| 2014/0031703 A1 | 1/2014 | Rayner et al. |
| 2014/0031889 A1 | 1/2014 | Mashiach |
| 2014/0031903 A1 | 1/2014 | Mashiach |
| 2014/0032512 A1 | 1/2014 | Drew et al. |
| 2014/0038147 A1 | 2/2014 | Morrow |
| 2014/0039279 A1 | 2/2014 | Jarvik et al. |
| 2014/0039290 A1 | 2/2014 | De Graff et al. |
| 2014/0039336 A1 | 2/2014 | Osorio et al. |
| 2014/0039571 A1 | 2/2014 | Wolpaw et al. |
| 2014/0039577 A1 | 2/2014 | Kothandaraman et al. |
| 2014/0039578 A1 | 2/2014 | Whitehurst et al. |
| 2014/0039975 A1 | 2/2014 | Hill |
| 2014/0046203 A1 | 2/2014 | Osorio et al. |
| 2014/0046208 A1 | 2/2014 | Sejdic et al. |
| 2014/0046407 A1 | 2/2014 | Ben-Ezra et al. |
| 2014/0051044 A1 | 2/2014 | Badower et al. |
| 2014/0051960 A1 | 2/2014 | Badower et al. |
| 2014/0051961 A1 | 2/2014 | Badower et al. |
| 2014/0052213 A1 | 2/2014 | Osorio |
| 2014/0055284 A1 | 2/2014 | Tran et al. |
| 2014/0056815 A1 | 2/2014 | Peyman |
| 2014/0057232 A1 | 2/2014 | Wetmore et al. |
| 2014/0058189 A1 | 2/2014 | Stubbeman |
| 2014/0058218 A1 | 2/2014 | Randlov et al. |
| 2014/0058219 A1 | 2/2014 | Kiraly |
| 2014/0058241 A1 | 2/2014 | Apparies et al. |
| 2014/0058289 A1 | 2/2014 | Panken et al. |
| 2014/0058292 A1 | 2/2014 | Alford et al. |
| 2014/0058528 A1 | 2/2014 | Contreras-Vidal et al. |
| 2014/0062472 A1 | 3/2014 | Nishikawa |
| 2014/0063054 A1 | 3/2014 | Osterhout et al. |
| 2014/0063055 A1 | 3/2014 | Osterhout et al. |
| 2014/0066739 A1 | 3/2014 | He et al. |
| 2014/0066763 A2 | 3/2014 | Rothberg et al. |
| 2014/0066796 A1 | 3/2014 | Davis et al. |
| 2014/0067740 A1 | 3/2014 | Solari |
| 2014/0070958 A1 | 3/2014 | Foo |
| 2014/0072127 A1 | 3/2014 | Adachi et al. |
| 2014/0072130 A1 | 3/2014 | Adachi et al. |
| 2014/0073863 A1 | 3/2014 | Engelbrecht et al. |
| 2014/0073864 A1 | 3/2014 | Engelbrecht et al. |
| 2014/0073866 A1 | 3/2014 | Engelbrecht et al. |
| 2014/0073870 A1 | 3/2014 | Engelbrecht et al. |
| 2014/0073875 A1 | 3/2014 | Engelbrecht et al. |
| 2014/0073876 A1 | 3/2014 | Rodriguez-Llorente et al. |
| 2014/0073877 A1 | 3/2014 | Wooder |
| 2014/0073878 A1 | 3/2014 | Engelbrecht et al. |
| 2014/0073898 A1 | 3/2014 | Engelbrecht et al. |
| 2014/0073948 A1 | 3/2014 | Engelbrecht et al. |
| 2014/0073949 A1 | 3/2014 | Engelbrecht et al. |
| 2014/0073951 A1 | 3/2014 | Engelbrecht et al. |
| 2014/0073953 A1 | 3/2014 | Engelbrecht et al. |
| 2014/0073954 A1 | 3/2014 | Engelbrecht et al. |
| 2014/0073955 A1 | 3/2014 | Engelbrecht et al. |
| 2014/0073956 A1 | 3/2014 | Engelbrecht et al. |
| 2014/0073960 A1 | 3/2014 | Rodriguez-Llorente et al. |
| 2014/0073961 A1 | 3/2014 | Rodriguez-Llorente et al. |
| 2014/0073963 A1 | 3/2014 | Engelbrecht et al. |
| 2014/0073965 A1 | 3/2014 | Engelbrecht et al. |
| 2014/0073966 A1 | 3/2014 | Engelbrecht et al. |
| 2014/0073967 A1 | 3/2014 | Engelbrecht et al. |
| 2014/0073968 A1 | 3/2014 | Engelbrecht et al. |
| 2014/0073974 A1 | 3/2014 | Engelbrecht |
| 2014/0073975 A1 | 3/2014 | Engelbrecht et al. |
| 2014/0074060 A1 | 3/2014 | Imran |
| 2014/0074179 A1 | 3/2014 | Heldman et al. |
| 2014/0074180 A1 | 3/2014 | Heldman et al. |
| 2014/0074188 A1 | 3/2014 | Armstrong et al. |
| 2014/0077612 A1 | 3/2014 | Onuma et al. |
| 2014/0077946 A1 | 3/2014 | Tran |
| 2014/0081071 A1 | 3/2014 | Simon et al. |
| 2014/0081114 A1 | 3/2014 | Shachar et al. |
| 2014/0081115 A1 | 3/2014 | Gu |
| 2014/0081347 A1 | 3/2014 | Nelson et al. |
| 2014/0081353 A1 | 3/2014 | Cook et al. |
| 2014/0088341 A1 | 3/2014 | Altman et al. |
| 2014/0088377 A1 | 3/2014 | Manzke et al. |
| 2014/0094710 A1 | 4/2014 | Sarma et al. |

(56) References Cited

U.S. PATENT DOCUMENTS

| | | | |
|---|---|---|---|
| 2014/0094719 A1 | 4/2014 | Mishelevich |
| 2014/0094720 A1 | 4/2014 | Tyler |
| 2014/0098981 A1 | 4/2014 | Lunner et al. |
| 2014/0100467 A1 | 4/2014 | Baker et al. |
| 2014/0100633 A1 | 4/2014 | Mann et al. |
| 2014/0101084 A1 | 4/2014 | Li et al. |
| 2014/0104059 A1 | 4/2014 | Tran |
| 2014/0105436 A1 | 4/2014 | Adachi et al. |
| 2014/0107397 A1 | 4/2014 | Simon et al. |
| 2014/0107398 A1 | 4/2014 | Simon et al. |
| 2014/0107401 A1 | 4/2014 | Anderson et al. |
| 2014/0107464 A1 | 4/2014 | Aksenova et al. |
| 2014/0107519 A1 | 4/2014 | Musha et al. |
| 2014/0107521 A1 | 4/2014 | Galan |
| 2014/0107525 A1 | 4/2014 | Tass |
| 2014/0107728 A1 | 4/2014 | Fried et al. |
| 2014/0107935 A1 | 4/2014 | Taylor |
| 2014/0111335 A1 | 4/2014 | Kleiss et al. |
| 2014/0113367 A1 | 4/2014 | Deisseroth et al. |
| 2014/0114165 A1 | 4/2014 | Walker et al. |
| 2014/0114205 A1 | 4/2014 | Braun et al. |
| 2014/0114207 A1 | 4/2014 | Patterson |
| 2014/0114242 A1 | 4/2014 | Eckle |
| 2014/0114889 A1 | 4/2014 | Dagum |
| 2014/0119621 A1 | 5/2014 | Uber |
| 2014/0121446 A1 | 5/2014 | Phillips et al. |
| 2014/0121476 A1 | 5/2014 | Tran et al. |
| 2014/0121554 A1 | 5/2014 | Sarma et al. |
| 2014/0121565 A1 | 5/2014 | Kim |
| 2014/0122379 A1 | 5/2014 | Moffitt et al. |
| 2014/0128762 A1 | 5/2014 | Han et al. |
| 2014/0128763 A1 | 5/2014 | Fadem |
| 2014/0128764 A1 | 5/2014 | Gandhi |
| 2014/0128938 A1 | 5/2014 | Craig |
| 2014/0133720 A1 | 5/2014 | Lee et al. |
| 2014/0133722 A1 | 5/2014 | Lee et al. |
| 2014/0135642 A1 | 5/2014 | Ekpar |
| 2014/0135680 A1 | 5/2014 | Peyman |
| 2014/0135873 A1 | 5/2014 | An et al. |
| 2014/0135879 A1 | 5/2014 | Flint |
| 2014/0135886 A1 | 5/2014 | Cook et al. |
| 2014/0136585 A1 | 5/2014 | Brockway |
| 2014/0140567 A1 | 5/2014 | LeBoeuf et al. |
| 2014/0142448 A1 | 5/2014 | Bae et al. |
| 2014/0142653 A1 | 5/2014 | Osorio |
| 2014/0142654 A1 | 5/2014 | Simon et al. |
| 2014/0142669 A1 | 5/2014 | Cook et al. |
| 2014/0143064 A1 | 5/2014 | Tran |
| 2014/0148479 A1 | 5/2014 | Chesworth et al. |
| 2014/0148657 A1 | 5/2014 | Hendler et al. |
| 2014/0148693 A1 | 5/2014 | Taylor |
| 2014/0148716 A1 | 5/2014 | Hopenfeld et al. |
| 2014/0148723 A1 | 5/2014 | Nierenberg et al. |
| 2014/0148726 A1 | 5/2014 | Wagner |
| 2014/0148872 A1 | 5/2014 | Goldwasser et al. |
| 2014/0151563 A1 | 6/2014 | Rousso et al. |
| 2014/0152673 A1 | 6/2014 | Lynn et al. |
| 2014/0154647 A1 | 6/2014 | Nolen |
| 2014/0154650 A1 | 6/2014 | Stack |
| 2014/0155430 A1 | 6/2014 | Chesworth et al. |
| 2014/0155706 A1 | 6/2014 | Kochs et al. |
| 2014/0155714 A1 | 6/2014 | Gavish |
| 2014/0155730 A1 | 6/2014 | Bansal et al. |
| 2014/0155740 A1 | 6/2014 | Semenov |
| 2014/0155770 A1 | 6/2014 | Taylor |
| 2014/0155772 A1 | 6/2014 | Frei et al. |
| 2014/0155952 A1 | 6/2014 | Lozano et al. |
| 2014/0156000 A1 | 6/2014 | Campin et al. |
| 2014/0159862 A1 | 6/2014 | Yang et al. |
| 2014/0161352 A1 | 6/2014 | Buyens et al. |
| 2014/0163328 A1 | 6/2014 | Geva et al. |
| 2014/0163330 A1 | 6/2014 | Horseman |
| 2014/0163331 A1 | 6/2014 | Horseman |
| 2014/0163332 A1 | 6/2014 | Horseman |
| 2014/0163333 A1 | 6/2014 | Horseman |
| 2014/0163335 A1 | 6/2014 | Horseman |
| 2014/0163336 A1 | 6/2014 | Horseman |
| 2014/0163337 A1 | 6/2014 | Horseman |
| 2014/0163368 A1 | 6/2014 | Rousso et al. |
| 2014/0163385 A1 | 6/2014 | Kelleher et al. |
| 2014/0163409 A1 | 6/2014 | Arndt |
| 2014/0163425 A1 | 6/2014 | Tran |
| 2014/0163627 A1 | 6/2014 | Starr et al. |
| 2014/0163643 A1 | 6/2014 | Craig |
| 2014/0163893 A1 | 6/2014 | Harumatsu et al. |
| 2014/0163897 A1 | 6/2014 | Lynn et al. |
| 2014/0171749 A1 | 6/2014 | Chin et al. |
| 2014/0171757 A1 | 6/2014 | Kawato et al. |
| 2014/0171819 A1 | 6/2014 | Patterson |
| 2014/0171820 A1 | 6/2014 | Causevic |
| 2014/0174277 A1 | 6/2014 | Mann |
| 2014/0175261 A1 | 6/2014 | Addison et al. |
| 2014/0176944 A1 | 6/2014 | Addison et al. |
| 2014/0179980 A1 | 6/2014 | Phillips et al. |
| 2014/0180088 A1 | 6/2014 | Rothberg et al. |
| 2014/0180092 A1 | 6/2014 | Rothberg et al. |
| 2014/0180093 A1 | 6/2014 | Rothberg et al. |
| 2014/0180094 A1 | 6/2014 | Rothberg et al. |
| 2014/0180095 A1 | 6/2014 | Rothberg et al. |
| 2014/0180096 A1 | 6/2014 | Rothberg et al. |
| 2014/0180097 A1 | 6/2014 | Rothberg et al. |
| 2014/0180099 A1 | 6/2014 | Rothberg et al. |
| 2014/0180100 A1 | 6/2014 | Rothberg et al. |
| 2014/0180112 A1 | 6/2014 | Rothberg et al. |
| 2014/0180113 A1 | 6/2014 | Rothberg et al. |
| 2014/0180145 A1 | 6/2014 | Kanai et al. |
| 2014/0180153 A1 | 6/2014 | Zia et al. |
| 2014/0180160 A1 | 6/2014 | Brown et al. |
| 2014/0180161 A1 | 6/2014 | Bolger et al. |
| 2014/0180176 A1 | 6/2014 | Rothberg et al. |
| 2014/0180177 A1 | 6/2014 | Rothberg et al. |
| 2014/0180194 A1 | 6/2014 | Lozano |
| 2014/0180358 A1 | 6/2014 | Giftakis et al. |
| 2014/0180597 A1 | 6/2014 | Brown et al. |
| 2014/0184550 A1 | 7/2014 | Hennessey et al. |
| 2014/0187901 A1 | 7/2014 | Cui et al. |
| 2014/0187994 A1 | 7/2014 | Thornton |
| 2014/0188006 A1 | 7/2014 | Alshaer et al. |
| 2014/0188770 A1 | 7/2014 | Agrafioti et al. |
| 2014/0193336 A1 | 7/2014 | Rousso et al. |
| 2014/0194702 A1 | 7/2014 | Tran |
| 2014/0194720 A1 | 7/2014 | Hua |
| 2014/0194726 A1 | 7/2014 | Mishelevich et al. |
| 2014/0194758 A1 | 7/2014 | Korenberg |
| 2014/0194759 A1 | 7/2014 | Weiland et al. |
| 2014/0194768 A1 | 7/2014 | Nierenberg et al. |
| 2014/0194769 A1 | 7/2014 | Nierenberg et al. |
| 2014/0194780 A1 | 7/2014 | Alshaer et al. |
| 2014/0194793 A1 | 7/2014 | Nakata et al. |
| 2014/0200414 A1 | 7/2014 | Osorio |
| 2014/0200432 A1 | 7/2014 | Banerji et al. |
| 2014/0200623 A1 | 7/2014 | Lindenthaler et al. |
| 2014/0203797 A1 | 7/2014 | Stivoric et al. |
| 2014/0206981 A1 | 7/2014 | Nagasaka |
| 2014/0207224 A1 | 7/2014 | Simon |
| 2014/0207432 A1 | 7/2014 | Taylor |
| 2014/0211593 A1 | 7/2014 | Tyler et al. |
| 2014/0213842 A1 | 7/2014 | Simon et al. |
| 2014/0213843 A1 | 7/2014 | Pilla et al. |
| 2014/0213844 A1 | 7/2014 | Pilla et al. |
| 2014/0213937 A1 | 7/2014 | Bianchi et al. |
| 2014/0213961 A1 | 7/2014 | Whitehurst et al. |
| 2014/0214135 A1 | 7/2014 | Ben-David et al. |
| 2014/0214330 A1 | 7/2014 | Iyer et al. |
| 2014/0214335 A1 | 7/2014 | Siefert |
| 2014/0221726 A1 | 8/2014 | Pilla et al. |
| 2014/0221866 A1 | 8/2014 | Quy |
| 2014/0222113 A1 | 8/2014 | Gliner et al. |
| 2014/0222406 A1 | 8/2014 | Taylor |
| 2014/0226131 A1 | 8/2014 | Lopez et al. |
| 2014/0226888 A1 | 8/2014 | Skidmore |
| 2014/0228620 A1 | 8/2014 | Vasishta |
| 2014/0228649 A1 | 8/2014 | Rayner et al. |
| 2014/0228651 A1 | 8/2014 | Causevic et al. |

(56)  References Cited

U.S. PATENT DOCUMENTS

| | | |
|---|---|---|
| 2014/0228653 A1 | 8/2014 | Kiraly |
| 2014/0228702 A1 | 8/2014 | Shahaf et al. |
| 2014/0232516 A1 | 8/2014 | Stivoric et al. |
| 2014/0235826 A1 | 8/2014 | Deisseroth et al. |
| 2014/0235965 A1 | 8/2014 | Tran |
| 2014/0236039 A1 | 8/2014 | Strokova Aksenova et al. |
| 2014/0236077 A1 | 8/2014 | Robertson et al. |
| 2014/0236272 A1 | 8/2014 | Simon et al. |
| 2014/0236492 A1 | 8/2014 | Taylor |
| 2014/0237073 A1 | 8/2014 | Schiff |
| 2014/0243608 A1 | 8/2014 | Hunt |
| 2014/0243613 A1 | 8/2014 | Osorio |
| 2014/0243614 A1 | 8/2014 | Rothberg et al. |
| 2014/0243621 A1 | 8/2014 | Weng et al. |
| 2014/0243628 A1 | 8/2014 | Ochs et al. |
| 2014/0243647 A1 | 8/2014 | Clark et al. |
| 2014/0243652 A1 | 8/2014 | Pashko |
| 2014/0243663 A1 | 8/2014 | Taylor |
| 2014/0243694 A1 | 8/2014 | Baker et al. |
| 2014/0243714 A1 | 8/2014 | Ward et al. |
| 2014/0243926 A1 | 8/2014 | Carcieri |
| 2014/0243934 A1 | 8/2014 | Vo-Dinh et al. |
| 2014/0245191 A1 | 8/2014 | Serena |
| 2014/0247970 A1 | 9/2014 | Taylor |
| 2014/0249360 A1 | 9/2014 | Jaeger et al. |
| 2014/0249396 A1 | 9/2014 | Shacham-Diamand et al. |
| 2014/0249429 A1 | 9/2014 | Tran |
| 2014/0249445 A1 | 9/2014 | Deadwyler et al. |
| 2014/0249447 A1 | 9/2014 | Sereno et al. |
| 2014/0249454 A1 | 9/2014 | Carpentier |
| 2014/0249608 A1 | 9/2014 | Rogers |
| 2014/0249791 A1 | 9/2014 | Taylor |
| 2014/0249792 A1 | 9/2014 | Taylor |
| 2014/0257047 A1 | 9/2014 | Sillay et al. |
| 2014/0257073 A1 | 9/2014 | Machon et al. |
| 2014/0257118 A1 | 9/2014 | DiLorenzo et al. |
| 2014/0257128 A1 | 9/2014 | Moxon et al. |
| 2014/0257132 A1 | 9/2014 | Kilgard et al. |
| 2014/0257147 A1 | 9/2014 | John et al. |
| 2014/0257430 A1 | 9/2014 | Kilgard et al. |
| 2014/0257437 A1 | 9/2014 | Simon et al. |
| 2014/0257438 A1 | 9/2014 | Simon et al. |
| 2014/0266696 A1 | 9/2014 | Addison et al. |
| 2014/0266787 A1 | 9/2014 | Tran |
| 2014/0270438 A1 | 9/2014 | Declerck et al. |
| 2014/0271483 A1 | 9/2014 | Satchi-Fainaro et al. |
| 2014/0275716 A1 | 9/2014 | Connor |
| 2014/0275741 A1 | 9/2014 | Vandenbelt et al. |
| 2014/0275807 A1 | 9/2014 | Redei |
| 2014/0275847 A1 | 9/2014 | Perryman et al. |
| 2014/0275851 A1 | 9/2014 | Amble et al. |
| 2014/0275886 A1 | 9/2014 | Teixeira |
| 2014/0275889 A1 | 9/2014 | Addison et al. |
| 2014/0275891 A1 | 9/2014 | Muehlemann et al. |
| 2014/0275944 A1 | 9/2014 | Semenov |
| 2014/0276012 A1 | 9/2014 | Semenov |
| 2014/0276013 A1 | 9/2014 | Muehlemann et al. |
| 2014/0276014 A1 | 9/2014 | Khanicheh et al. |
| 2014/0276090 A1 | 9/2014 | Breed |
| 2014/0276123 A1 | 9/2014 | Yang |
| 2014/0276130 A1 | 9/2014 | Mirelman et al. |
| 2014/0276181 A1 | 9/2014 | Sun et al. |
| 2014/0276183 A1 | 9/2014 | Badower |
| 2014/0276185 A1 | 9/2014 | Carlson et al. |
| 2014/0276187 A1 | 9/2014 | Iasemidis et al. |
| 2014/0276194 A1 | 9/2014 | Osorio |
| 2014/0276549 A1 | 9/2014 | Osorio |
| 2014/0276702 A1 | 9/2014 | McKay et al. |
| 2014/0276944 A1 | 9/2014 | Farritor et al. |
| 2014/0277255 A1 | 9/2014 | Sabesan |
| 2014/0277256 A1 | 9/2014 | Osorio |
| 2014/0277282 A1 | 9/2014 | Jaax |
| 2014/0277286 A1 | 9/2014 | Cinbis |
| 2014/0277582 A1 | 9/2014 | Leuthardt et al. |
| 2014/0279341 A1 | 9/2014 | Bhardwaj et al. |
| 2014/0279746 A1 | 9/2014 | De Bruin et al. |
| 2014/0288381 A1 | 9/2014 | Faarbaek et al. |
| 2014/0288614 A1 | 9/2014 | Hagedorn et al. |
| 2014/0288620 A1 | 9/2014 | DiLorenzo |
| 2014/0288953 A1 | 9/2014 | Lynn et al. |
| 2014/0289172 A1 | 9/2014 | Rothman et al. |
| 2014/0296646 A1 | 10/2014 | Wingeier et al. |
| 2014/0296655 A1 | 10/2014 | Akhbardeh et al. |
| 2014/0296724 A1 | 10/2014 | Guttag et al. |
| 2014/0296733 A1 | 10/2014 | Omurtag et al. |
| 2014/0296750 A1 | 10/2014 | Einav et al. |
| 2014/0297397 A1 | 10/2014 | Bakalash et al. |
| 2014/0300532 A1 | 10/2014 | Karkkainen et al. |
| 2014/0303424 A1 | 10/2014 | Glass |
| 2014/0303425 A1 | 10/2014 | Pilla et al. |
| 2014/0303452 A1 | 10/2014 | Ghaffari |
| 2014/0303453 A1 | 10/2014 | Seely et al. |
| 2014/0303454 A1 | 10/2014 | Clifton et al. |
| 2014/0303486 A1 | 10/2014 | Baumgartner et al. |
| 2014/0303508 A1 | 10/2014 | Plotnik-Peleg et al. |
| 2014/0303511 A1 | 10/2014 | Sajda et al. |
| 2014/0304773 A1 | 10/2014 | Woods et al. |
| 2014/0309484 A1 | 10/2014 | Chang |
| 2014/0309614 A1 | 10/2014 | Frei et al. |
| 2014/0309881 A1 | 10/2014 | Fung et al. |
| 2014/0309943 A1 | 10/2014 | Grundlehner et al. |
| 2014/0313303 A1 | 10/2014 | Davis et al. |
| 2014/0315169 A1 | 10/2014 | Bohbot |
| 2014/0316191 A1 | 10/2014 | de Zambotti et al. |
| 2014/0316192 A1 | 10/2014 | de Zambotti et al. |
| 2014/0316217 A1 | 10/2014 | Purdon et al. |
| 2014/0316221 A1 | 10/2014 | Rothman |
| 2014/0316230 A1 | 10/2014 | Denison et al. |
| 2014/0316235 A1 | 10/2014 | Davis et al. |
| 2014/0316243 A1 | 10/2014 | Niedermeyer |
| 2014/0316248 A1 | 10/2014 | deCharms |
| 2014/0316278 A1 | 10/2014 | Addison et al. |
| 2014/0323849 A1 | 10/2014 | Deisseroth et al. |
| 2014/0323899 A1 | 10/2014 | Silberstein |
| 2014/0323900 A1 | 10/2014 | Bibian et al. |
| 2014/0323924 A1 | 10/2014 | Mishelevich |
| 2014/0323946 A1 | 10/2014 | Bourke, Jr. et al. |
| 2014/0324118 A1 | 10/2014 | Simon et al. |
| 2014/0324138 A1 | 10/2014 | Wentz et al. |
| 2014/0328487 A1 | 11/2014 | Hiroe |
| 2014/0330093 A1 | 11/2014 | Pedro |
| 2014/0330102 A1 | 11/2014 | Zbrzeski et al. |
| 2014/0330157 A1 | 11/2014 | Snook |
| 2014/0330159 A1 | 11/2014 | Costa et al. |
| 2014/0330268 A1 | 11/2014 | Palti et al. |
| 2014/0330334 A1 | 11/2014 | Errico et al. |
| 2014/0330335 A1 | 11/2014 | Errico et al. |
| 2014/0330336 A1 | 11/2014 | Errico et al. |
| 2014/0330337 A1 | 11/2014 | Linke et al. |
| 2014/0330345 A1 | 11/2014 | John |
| 2014/0330357 A1 | 11/2014 | Stevenson et al. |
| 2014/0330394 A1 | 11/2014 | Leuthardt et al. |
| 2014/0330404 A1 | 11/2014 | Abdelghani et al. |
| 2014/0330580 A1 | 11/2014 | Grima et al. |
| 2014/0335489 A1 | 11/2014 | DeCharms |
| 2014/0336473 A1 | 11/2014 | Greco |
| 2014/0336489 A1 | 11/2014 | Angotzi et al. |
| 2014/0336514 A1 | 11/2014 | Peyman |
| 2014/0336547 A1 | 11/2014 | Tass et al. |
| 2014/0336730 A1 | 11/2014 | Simon et al. |
| 2014/0340084 A1 | 11/2014 | Alon |
| 2014/0343397 A1 | 11/2014 | Kim et al. |
| 2014/0343399 A1 | 11/2014 | Posse |
| 2014/0343408 A1 | 11/2014 | Tolkowsky |
| 2014/0343463 A1 | 11/2014 | Mishelevich |
| 2014/0343882 A1 | 11/2014 | Taulu et al. |
| 2014/0347265 A1 | 11/2014 | Aimone et al. |
| 2014/0347491 A1 | 11/2014 | Connor |
| 2014/0348183 A1 | 11/2014 | Kim et al. |
| 2014/0348412 A1 | 11/2014 | Taylor |
| 2014/0350353 A1 | 11/2014 | Connor |
| 2014/0350369 A1 | 11/2014 | Budiman et al. |
| 2014/0350380 A1 | 11/2014 | Eidelberg |
| 2014/0350431 A1 | 11/2014 | Hagedorn |

(56)     References Cited

U.S. PATENT DOCUMENTS

| | | |
|---|---|---|
| 2014/0350436 A1 | 11/2014 | Nathan et al. |
| 2014/0350634 A1 | 11/2014 | Grill et al. |
| 2014/0350636 A1 | 11/2014 | King et al. |
| 2014/0350864 A1 | 11/2014 | Fang et al. |
| 2014/0354278 A1 | 12/2014 | Subbarao |
| 2014/0355859 A1 | 12/2014 | Taylor et al. |
| 2014/0357507 A1 | 12/2014 | Umansky et al. |
| 2014/0357932 A1 | 12/2014 | Lozano |
| 2014/0357935 A1 | 12/2014 | Ilmoniemi et al. |
| 2014/0357936 A1 | 12/2014 | Simon et al. |
| 2014/0357962 A1 | 12/2014 | Harrington et al. |
| 2014/0358024 A1 | 12/2014 | Nelson et al. |
| 2014/0358025 A1 | 12/2014 | Parhi et al. |
| 2014/0358067 A1 | 12/2014 | Deisseroth et al. |
| 2014/0358193 A1 | 12/2014 | Lyons et al. |
| 2014/0358199 A1 | 12/2014 | Lim |
| 2014/0364721 A1 | 12/2014 | Lee et al. |
| 2014/0364746 A1 | 12/2014 | Addison et al. |
| 2014/0369537 A1 | 12/2014 | Pontoppidan et al. |
| 2014/0370479 A1 | 12/2014 | Gazzaley |
| 2014/0371515 A1 | 12/2014 | John |
| 2014/0371516 A1 | 12/2014 | Tsai et al. |
| 2014/0371544 A1 | 12/2014 | Wu et al. |
| 2014/0371573 A1 | 12/2014 | Komoto et al. |
| 2014/0371599 A1 | 12/2014 | Wu et al. |
| 2014/0371611 A1 | 12/2014 | Kim |
| 2014/0371984 A1 | 12/2014 | Fung et al. |
| 2014/0378809 A1 | 12/2014 | Weitnauer et al. |
| 2014/0378810 A1 | 12/2014 | Davis et al. |
| 2014/0378815 A1 | 12/2014 | Huang et al. |
| 2014/0378830 A1 | 12/2014 | Li |
| 2014/0378851 A1 | 12/2014 | Frei et al. |
| 2014/0378941 A1 | 12/2014 | Su et al. |
| 2014/0379620 A1 | 12/2014 | Sarrafzadeh et al. |
| 2015/0002815 A1 | 1/2015 | Gross et al. |
| 2015/0003698 A1 | 1/2015 | Davis et al. |
| 2015/0003699 A1 | 1/2015 | Davis et al. |
| 2015/0005592 A1 | 1/2015 | Osorio |
| 2015/0005594 A1 | 1/2015 | Chamoun et al. |
| 2015/0005640 A1 | 1/2015 | Davis et al. |
| 2015/0005644 A1 | 1/2015 | Rhoads |
| 2015/0005646 A1 | 1/2015 | Balakrishnan et al. |
| 2015/0005660 A1 | 1/2015 | Kraus et al. |
| 2015/0005680 A1 | 1/2015 | Lipani |
| 2015/0005839 A1 | 1/2015 | Sabesan et al. |
| 2015/0005840 A1 | 1/2015 | Pal et al. |
| 2015/0005841 A1 | 1/2015 | Pal et al. |
| 2015/0006186 A1 | 1/2015 | Davis et al. |
| 2015/0008916 A1 | 1/2015 | Le Prado et al. |
| 2015/0010223 A1 | 1/2015 | Sapiro et al. |
| 2015/0011866 A1 | 1/2015 | Baumgartner |
| 2015/0011877 A1 | 1/2015 | Baumgartner |
| 2015/0011907 A1 | 1/2015 | Purdon et al. |
| 2015/0012054 A1 | 1/2015 | Kilgard et al. |
| 2015/0012057 A1 | 1/2015 | Carlson et al. |
| 2015/0012111 A1 | 1/2015 | Contreras-Vidal et al. |
| 2015/0012466 A1 | 1/2015 | Sapiro et al. |
| 2015/0016618 A1 | 1/2015 | Adachi et al. |
| 2015/0017115 A1 | 1/2015 | Satchi-Fainaro et al. |
| 2015/0018665 A1 | 1/2015 | Jasanoff et al. |
| 2015/0018699 A1 | 1/2015 | Zeng et al. |
| 2015/0018702 A1 | 1/2015 | Galloway et al. |
| 2015/0018705 A1 | 1/2015 | Barlow et al. |
| 2015/0018706 A1 | 1/2015 | Segal |
| 2015/0018758 A1 | 1/2015 | John |
| 2015/0018893 A1 | 1/2015 | Kilgard et al. |
| 2015/0018905 A1 | 1/2015 | Nofzinger et al. |
| 2015/0019241 A1 | 1/2015 | Bennett et al. |
| 2015/0019266 A1 | 1/2015 | Stempora |
| 2015/0024356 A1 | 1/2015 | Hillyer et al. |
| 2015/0025351 A1 | 1/2015 | Govari |
| 2015/0025408 A1 | 1/2015 | Wingeier et al. |
| 2015/0025410 A1 | 1/2015 | Wolpaw et al. |
| 2015/0025421 A1 | 1/2015 | Wagner et al. |
| 2015/0025422 A1 | 1/2015 | Tyler |
| 2015/0025610 A1 | 1/2015 | Wingeier et al. |
| 2015/0025917 A1 | 1/2015 | Stempora |
| 2015/0026446 A1 | 1/2015 | Kim et al. |
| 2015/0029087 A1 | 1/2015 | Klappert et al. |
| 2015/0030220 A1 | 1/2015 | Cho et al. |
| 2015/0032017 A1 | 1/2015 | Babaeizadeh et al. |
| 2015/0032044 A9 | 1/2015 | Peyman |
| 2015/0032178 A1 | 1/2015 | Simon et al. |
| 2015/0033245 A1 | 1/2015 | Klappert et al. |
| 2015/0033258 A1 | 1/2015 | Klappert et al. |
| 2015/0033259 A1 | 1/2015 | Klappert et al. |
| 2015/0033262 A1 | 1/2015 | Klappert et al. |
| 2015/0033266 A1 | 1/2015 | Klappert et al. |
| 2015/0033363 A1 | 1/2015 | Pinsky et al. |
| 2015/0035959 A1 | 2/2015 | Amble et al. |
| 2015/0038804 A1 | 2/2015 | Younes |
| 2015/0038812 A1 | 2/2015 | Ayaz et al. |
| 2015/0038822 A1 | 2/2015 | Wingeier et al. |
| 2015/0038869 A1 | 2/2015 | Simon et al. |
| 2015/0039066 A1 | 2/2015 | Wingeier et al. |
| 2015/0039110 A1 | 2/2015 | Abeyratne et al. |
| 2015/0042477 A1 | 2/2015 | Kobetski et al. |
| 2015/0044138 A1 | 2/2015 | Lansbergen et al. |
| 2015/0045606 A1 | 2/2015 | Hagedorn et al. |
| 2015/0045607 A1 | 2/2015 | Hakansson |
| 2015/0045686 A1 | 2/2015 | Lynn |
| 2015/0051655 A1 | 2/2015 | Kilgard et al. |
| 2015/0051656 A1 | 2/2015 | Kilgard et al. |
| 2015/0051657 A1 | 2/2015 | Kilgard et al. |
| 2015/0051658 A1 | 2/2015 | Kilgard et al. |
| 2015/0051659 A1 | 2/2015 | Kilgard et al. |
| 2015/0051663 A1 | 2/2015 | Hagedorn |
| 2015/0051668 A1 | 2/2015 | Bahmer |
| 2015/0057512 A1 | 2/2015 | Kapoor |
| 2015/0057715 A1 | 2/2015 | Kilgard et al. |
| 2015/0065803 A1 | 3/2015 | Douglas et al. |
| 2015/0065831 A1 | 3/2015 | Popovic et al. |
| 2015/0065838 A1 | 3/2015 | Wingeier et al. |
| 2015/0065839 A1 | 3/2015 | Farah et al. |
| 2015/0065845 A1 | 3/2015 | Takiguchi |
| 2015/0066124 A1 | 3/2015 | Stevenson et al. |
| 2015/0068069 A1 | 3/2015 | Tran et al. |
| 2015/0069846 A1 | 3/2015 | Hokari |
| 2015/0071907 A1 | 3/2015 | Crombez et al. |
| 2015/0072394 A1 | 3/2015 | Deisseroth et al. |
| 2015/0073141 A1 | 3/2015 | Teegarden et al. |
| 2015/0073237 A1 | 3/2015 | Osorio |
| 2015/0073249 A1 | 3/2015 | Musha |
| 2015/0073294 A1 | 3/2015 | Zhang et al. |
| 2015/0073306 A1 | 3/2015 | Abeyratne et al. |
| 2015/0073505 A1 | 3/2015 | Errico et al. |
| 2015/0073722 A1 | 3/2015 | Taylor et al. |
| 2015/0080327 A1 | 3/2015 | Paul et al. |
| 2015/0080671 A1 | 3/2015 | Christensen et al. |
| 2015/0080674 A1 | 3/2015 | Drew et al. |
| 2015/0080695 A1 | 3/2015 | Rogers et al. |
| 2015/0080703 A1 | 3/2015 | Reiman |
| 2015/0080746 A1 | 3/2015 | Bleich et al. |
| 2015/0080753 A1 | 3/2015 | Miyazaki et al. |
| 2015/0080985 A1 | 3/2015 | Yun et al. |
| 2015/0081226 A1 | 3/2015 | Baki |
| 2015/0081299 A1 | 3/2015 | Jasinschi et al. |
| 2015/0087931 A1 | 3/2015 | Banerjee et al. |
| 2015/0088015 A1 | 3/2015 | Taylor |
| 2015/0088024 A1 | 3/2015 | Sackellares et al. |
| 2015/0088093 A1 | 3/2015 | Goetz |
| 2015/0088120 A1 | 3/2015 | Garcia et al. |
| 2015/0088224 A1 | 3/2015 | Goldwasser et al. |
| 2015/0088228 A1 | 3/2015 | Moffitt |
| 2015/0088478 A1 | 3/2015 | Taylor |
| 2015/0091730 A1 | 4/2015 | Kangas et al. |
| 2015/0091791 A1 | 4/2015 | Segal |
| 2015/0092949 A1 | 4/2015 | Adachi et al. |
| 2015/0093729 A1 | 4/2015 | Plans et al. |
| 2015/0094962 A1 | 4/2015 | Hoegh et al. |
| 2015/0096564 A1 | 4/2015 | Cosnek |
| 2015/0099941 A1 | 4/2015 | Tran |
| 2015/0099946 A1 | 4/2015 | Sahin |
| 2015/0099959 A1 | 4/2015 | Bonmassar et al. |

(56) References Cited

U.S. PATENT DOCUMENTS

| | | | |
|---|---|---|---|
| 2015/0099962 A1 | 4/2015 | Weiss et al. | |
| 2015/0103360 A1 | 4/2015 | Addison et al. | |
| 2015/0105631 A1 | 4/2015 | Tran et al. | |
| 2015/0105641 A1 | 4/2015 | Austin et al. | |
| 2015/0105701 A1 | 4/2015 | Mayer et al. | |
| 2015/0105837 A1* | 4/2015 | Aguilar Domingo . A61B 5/374 | |
| | | 607/45 | |
| 2015/0105844 A1 | 4/2015 | Tass et al. | |
| 2015/0112222 A1 | 4/2015 | Sun et al. | |
| 2015/0112403 A1 | 4/2015 | Ruffini et al. | |
| 2015/0112409 A1 | 4/2015 | Hagedorn | |
| 2015/0112899 A1 | 4/2015 | Dagum | |
| 2015/0119652 A1 | 4/2015 | Hyde et al. | |
| 2015/0119658 A1 | 4/2015 | Osorio | |
| 2015/0119689 A1 | 4/2015 | Pascual-Leone et al. | |
| 2015/0119698 A1 | 4/2015 | Eyal et al. | |
| 2015/0119743 A1 | 4/2015 | Maksym et al. | |
| 2015/0119745 A1 | 4/2015 | Similowski et al. | |
| 2015/0119746 A1 | 4/2015 | Conradsen | |
| 2015/0119794 A1 | 4/2015 | Peyman | |
| 2015/0119898 A1 | 4/2015 | Desalles et al. | |
| 2015/0119956 A1 | 4/2015 | Libbus et al. | |
| 2015/0120007 A1 | 4/2015 | Guez et al. | |
| 2015/0123653 A1 | 5/2015 | Nagasaka | |
| 2015/0124220 A1 | 5/2015 | Gross et al. | |
| 2015/0126821 A1 | 5/2015 | Kempfner et al. | |
| 2015/0126845 A1 | 5/2015 | Jin et al. | |
| 2015/0126848 A1 | 5/2015 | Baker et al. | |
| 2015/0126873 A1 | 5/2015 | Connor | |
| 2015/0133716 A1 | 5/2015 | Suhami et al. | |
| 2015/0133811 A1 | 5/2015 | Suzuki et al. | |
| 2015/0133812 A1 | 5/2015 | deCharms | |
| 2015/0133830 A1 | 5/2015 | Dirks et al. | |
| 2015/0134031 A1 | 5/2015 | Moffitt et al. | |
| 2015/0134264 A1 | 5/2015 | Tansey | |
| 2015/0137817 A1 | 5/2015 | Wilson et al. | |
| 2015/0137988 A1 | 5/2015 | Gravenstein et al. | |
| 2015/0140528 A1 | 5/2015 | Sikstrom et al. | |
| 2015/0141529 A1 | 5/2015 | Hargrove | |
| 2015/0141773 A1 | 5/2015 | Einav et al. | |
| 2015/0141789 A1 | 5/2015 | Knight et al. | |
| 2015/0141794 A1 | 5/2015 | Foo | |
| 2015/0142082 A1 | 5/2015 | Simon et al. | |
| 2015/0145519 A1 | 5/2015 | Lee et al. | |
| 2015/0145676 A1 | 5/2015 | Adhikari et al. | |
| 2015/0148617 A1 | 5/2015 | Friedman | |
| 2015/0148619 A1 | 5/2015 | Berg et al. | |
| 2015/0148700 A1 | 5/2015 | Mhuircheartaigh et al. | |
| 2015/0148878 A1 | 5/2015 | Yoo et al. | |
| 2015/0150122 A1 | 5/2015 | Son et al. | |
| 2015/0150473 A1 | 6/2015 | Knight et al. | |
| 2015/0150475 A1 | 6/2015 | Varcoe | |
| 2015/0150530 A1 | 6/2015 | Taylor et al. | |
| 2015/0150753 A1 | 6/2015 | Racette | |
| 2015/0151142 A1 | 6/2015 | Tyler et al. | |
| 2015/0153477 A1 | 6/2015 | Wikelski et al. | |
| 2015/0154721 A1 | 6/2015 | Thompson | |
| 2015/0154764 A1* | 6/2015 | Xie et al. | |
| 2015/0154889 A1 | 6/2015 | Tuchschmid et al. | |
| 2015/0157235 A1 | 6/2015 | Jelen et al. | |
| 2015/0157266 A1 | 6/2015 | Machon et al. | |
| 2015/0157271 A1 | 6/2015 | Zhang | |
| 2015/0157859 A1 | 6/2015 | Besio | |
| 2015/0161326 A1 | 6/2015 | Taylor et al. | |
| 2015/0161348 A1 | 6/2015 | Taylor et al. | |
| 2015/0161738 A1 | 6/2015 | Stempora | |
| 2015/0164349 A1 | 6/2015 | Gopalakrishnan et al. | |
| 2015/0164362 A1 | 6/2015 | Morrow | |
| 2015/0164375 A1 | 6/2015 | Schindhelm et al. | |
| 2015/0164404 A1 | 6/2015 | Euliano et al. | |
| 2015/0164431 A1 | 6/2015 | Terry et al. | |
| 2015/0165226 A1 | 6/2015 | Simon et al. | |
| 2015/0165239 A1 | 6/2015 | Mishelevich | |
| 2015/0167459 A1 | 6/2015 | Sen et al. | |
| 2015/0174362 A1 | 6/2015 | Panova et al. | |
| 2015/0174398 A1 | 6/2015 | Chow et al. | |
| 2015/0174403 A1 | 6/2015 | Pal et al. | |
| 2015/0174405 A1 | 6/2015 | Kilgard et al. | |
| 2015/0174406 A1 | 6/2015 | Lamensdorf et al. | |
| 2015/0174407 A1 | 6/2015 | Osorio | |
| 2015/0174418 A1 | 6/2015 | Tyler et al. | |
| 2015/0177413 A1 | 6/2015 | Wilt et al. | |
| 2015/0178631 A1 | 6/2015 | Thomas et al. | |
| 2015/0178978 A1 | 6/2015 | Durand et al. | |
| 2015/0181840 A1 | 7/2015 | Tupin, Jr. et al. | |
| 2015/0182417 A1 | 7/2015 | Nagatani | |
| 2015/0182753 A1 | 7/2015 | Harris et al. | |
| 2015/0182756 A1 | 7/2015 | Peyman | |
| 2015/0186923 A1 | 7/2015 | Gurumoorthy et al. | |
| 2015/0190062 A1 | 7/2015 | Han et al. | |
| 2015/0190070 A1 | 7/2015 | Bonmassar et al. | |
| 2015/0190077 A1 | 7/2015 | Kim et al. | |
| 2015/0190085 A1 | 7/2015 | Nathan et al. | |
| 2015/0190094 A1 | 7/2015 | Lee et al. | |
| 2015/0190636 A1 | 7/2015 | Simon et al. | |
| 2015/0190637 A1 | 7/2015 | Simon et al. | |
| 2015/0192532 A1 | 7/2015 | Clevenson et al. | |
| 2015/0192776 A1 | 7/2015 | Lee et al. | |
| 2015/0196213 A1 | 7/2015 | Pandia et al. | |
| 2015/0196246 A1 | 7/2015 | Osorio | |
| 2015/0196249 A1 | 7/2015 | Brown et al. | |
| 2015/0196800 A1 | 7/2015 | Macri et al. | |
| 2015/0199010 A1 | 7/2015 | Coleman et al. | |
| 2015/0199121 A1 | 7/2015 | Gulaka et al. | |
| 2015/0200046 A1 | 7/2015 | Park et al. | |
| 2015/0201849 A1 | 7/2015 | Taylor | |
| 2015/0201879 A1 | 7/2015 | Hargrove | |
| 2015/0202330 A1 | 7/2015 | Yang et al. | |
| 2015/0202428 A1 | 7/2015 | Miller | |
| 2015/0202447 A1 | 7/2015 | Afshar et al. | |
| 2015/0203822 A1 | 7/2015 | Tremolada et al. | |
| 2015/0206051 A1 | 7/2015 | McIntosh et al. | |
| 2015/0206174 A1 | 7/2015 | Barnett et al. | |
| 2015/0208940 A1 | 7/2015 | Addison et al. | |
| 2015/0208975 A1 | 7/2015 | Ghajar | |
| 2015/0208978 A1 | 7/2015 | Osorio et al. | |
| 2015/0208982 A1 | 7/2015 | Ho et al. | |
| 2015/0208994 A1 | 7/2015 | Rapoport | |
| 2015/0212168 A1 | 7/2015 | Shah et al. | |
| 2015/0213012 A1 | 7/2015 | Marvit et al. | |
| 2015/0213019 A1 | 7/2015 | Marvit et al. | |
| 2015/0213020 A1 | 7/2015 | Marvit et al. | |
| 2015/0213191 A1 | 7/2015 | Abdelghani et al. | |
| 2015/0215412 A1 | 7/2015 | Marvit et al. | |
| 2015/0216436 A1 | 8/2015 | Bosl et al. | |
| 2015/0216439 A1 | 8/2015 | Muraskin et al. | |
| 2015/0216468 A1 | 8/2015 | Vidal-Naquet et al. | |
| 2015/0216469 A1 | 8/2015 | DiLorenzo et al. | |
| 2015/0216762 A1 | 8/2015 | Oohashi et al. | |
| 2015/0217082 A1 | 8/2015 | Kang et al. | |
| 2015/0219729 A1 | 8/2015 | Takahashi | |
| 2015/0219732 A1 | 8/2015 | Diamond et al. | |
| 2015/0220486 A1 | 8/2015 | Karakonstantis et al. | |
| 2015/0220830 A1 | 8/2015 | Li et al. | |
| 2015/0223721 A1 | 8/2015 | De Ridder | |
| 2015/0223731 A1 | 8/2015 | Sahin | |
| 2015/0223743 A1 | 8/2015 | Pathangay et al. | |
| 2015/0223905 A1 | 8/2015 | Karmarkar et al. | |
| 2015/0226813 A1 | 8/2015 | Yu et al. | |
| 2015/0227702 A1 | 8/2015 | Krishna et al. | |
| 2015/0227793 A1 | 8/2015 | Ernst et al. | |
| 2015/0230719 A1 | 8/2015 | Berg et al. | |
| 2015/0230744 A1 | 8/2015 | Faubert et al. | |
| 2015/0230750 A1 | 8/2015 | McDarby et al. | |
| 2015/0231330 A1 | 8/2015 | Lozano et al. | |
| 2015/0231395 A1 | 8/2015 | Saab | |
| 2015/0231397 A1 | 8/2015 | Nudo, Jr. et al. | |
| 2015/0231405 A1 | 8/2015 | Okada | |
| 2015/0231408 A1 | 8/2015 | Williams et al. | |
| 2015/0234477 A1 | 8/2015 | Abovitz et al. | |
| 2015/0235088 A1 | 8/2015 | Abovitz et al. | |
| 2015/0235370 A1 | 8/2015 | Abovitz et al. | |
| 2015/0235441 A1 | 8/2015 | Abovitz et al. | |
| 2015/0235447 A1 | 8/2015 | Abovitz et al. | |

(56)  References Cited

U.S. PATENT DOCUMENTS

| | | |
|---|---|---|
| 2015/0238104 A1 | 8/2015 | Tass |
| 2015/0238106 A1 | 8/2015 | Lappalainen et al. |
| 2015/0238112 A1 | 8/2015 | Park et al. |
| 2015/0238137 A1 | 8/2015 | Eyal et al. |
| 2015/0238693 A1 | 8/2015 | Skelton et al. |
| 2015/0238761 A1 | 8/2015 | Sabesan |
| 2015/0238765 A1 | 8/2015 | Zhu |
| 2015/0241705 A1 | 8/2015 | Abovitz et al. |
| 2015/0241916 A1 | 8/2015 | Choi et al. |
| 2015/0241959 A1 | 8/2015 | Abovitz et al. |
| 2015/0242575 A1 | 8/2015 | Abovitz et al. |
| 2015/0242608 A1 | 8/2015 | Kim et al. |
| 2015/0242943 A1 | 8/2015 | Abovitz et al. |
| 2015/0243100 A1 | 8/2015 | Abovitz et al. |
| 2015/0243105 A1 | 8/2015 | Abovitz et al. |
| 2015/0243106 A1 | 8/2015 | Abovitz et al. |
| 2015/0245781 A1 | 9/2015 | Hua |
| 2015/0245800 A1 | 9/2015 | Sorensen et al. |
| 2015/0246238 A1 | 9/2015 | Moses et al. |
| 2015/0247723 A1 | 9/2015 | Abovitz et al. |
| 2015/0247921 A1 | 9/2015 | Rothberg et al. |
| 2015/0247975 A1 | 9/2015 | Abovitz et al. |
| 2015/0247976 A1 | 9/2015 | Abovitz et al. |
| 2015/0248167 A1 | 9/2015 | Turbell et al. |
| 2015/0248169 A1 | 9/2015 | Abovitz et al. |
| 2015/0248170 A1 | 9/2015 | Abovitz et al. |
| 2015/0248470 A1 | 9/2015 | Coleman et al. |
| 2015/0248615 A1 | 9/2015 | Parra et al. |
| 2015/0248764 A1 | 9/2015 | Keskin et al. |
| 2015/0248765 A1 | 9/2015 | Criminisi et al. |
| 2015/0248787 A1 | 9/2015 | Abovitz et al. |
| 2015/0248788 A1 | 9/2015 | Abovitz et al. |
| 2015/0248789 A1 | 9/2015 | Abovitz et al. |
| 2015/0248791 A1 | 9/2015 | Abovitz et al. |
| 2015/0248792 A1 | 9/2015 | Abovitz et al. |
| 2015/0248793 A1 | 9/2015 | Abovitz et al. |
| 2015/0250393 A1 | 9/2015 | Tran |
| 2015/0250401 A1 | 9/2015 | Tveit |
| 2015/0250415 A1 | 9/2015 | Leininger et al. |
| 2015/0251016 A1 | 9/2015 | Vo-Dinh et al. |
| 2015/0253391 A1 | 9/2015 | Toda et al. |
| 2015/0253410 A1 | 9/2015 | Warfield et al. |
| 2015/0254413 A1 | 9/2015 | Soederstroem |
| 2015/0257645 A1 | 9/2015 | Bae et al. |
| 2015/0257648 A1 | 9/2015 | Semenov |
| 2015/0257649 A1 | 9/2015 | Semenov |
| 2015/0257673 A1 | 9/2015 | Lawrence et al. |
| 2015/0257674 A1 | 9/2015 | Jordan et al. |
| 2015/0257700 A1 | 9/2015 | Fu |
| 2015/0257712 A1 | 9/2015 | Sarrafzadeh et al. |
| 2015/0262016 A1 | 9/2015 | Rothblatt |
| 2015/0264492 A1 | 9/2015 | Laudanski et al. |
| 2015/0265164 A1 | 9/2015 | Gopalakrishnan et al. |
| 2015/0265207 A1 | 9/2015 | Wu et al. |
| 2015/0265583 A1 | 9/2015 | Chesworth et al. |
| 2015/0265830 A1 | 9/2015 | Simon et al. |
| 2015/0265836 A1 | 9/2015 | Simon et al. |
| 2015/0269825 A1 | 9/2015 | Tran |
| 2015/0272448 A1 | 10/2015 | Fonte et al. |
| 2015/0272461 A1 | 10/2015 | Morimoto et al. |
| 2015/0272465 A1 | 10/2015 | Ishii |
| 2015/0272496 A1 | 10/2015 | Klappert et al. |
| 2015/0272510 A1 | 10/2015 | Chin |
| 2015/0272652 A1 | 10/2015 | Ghaffari et al. |
| 2015/0273211 A1 | 10/2015 | Ollivier |
| 2015/0273223 A1 | 10/2015 | John |
| 2015/0282705 A1 | 10/2015 | Avital |
| 2015/0282730 A1 | 10/2015 | Knight et al. |
| 2015/0282749 A1 | 10/2015 | Zand et al. |
| 2015/0282755 A1 | 10/2015 | Deriche et al. |
| 2015/0282760 A1 | 10/2015 | Badower et al. |
| 2015/0283019 A1 | 10/2015 | Feingold |
| 2015/0283265 A1 | 10/2015 | Peyman |
| 2015/0283379 A1 | 10/2015 | Venkatesan |
| 2015/0283393 A1 | 10/2015 | Schmidt |
| 2015/0287223 A1 | 10/2015 | Bresler et al. |
| 2015/0289217 A1 | 10/2015 | Ban et al. |
| 2015/0289779 A1 | 10/2015 | Fischl et al. |
| 2015/0289813 A1 | 10/2015 | Lipov |
| 2015/0289929 A1 | 10/2015 | Toth et al. |
| 2015/0290419 A1 | 10/2015 | Kare et al. |
| 2015/0290420 A1 | 10/2015 | Nofzinger |
| 2015/0290453 A1 | 10/2015 | Tyler et al. |
| 2015/0290454 A1 | 10/2015 | Tyler et al. |
| 2015/0293004 A1 | 10/2015 | Adolphi et al. |
| 2015/0294067 A1 | 10/2015 | Kare et al. |
| 2015/0294074 A1 | 10/2015 | Kawato et al. |
| 2015/0294085 A1 | 10/2015 | Kare et al. |
| 2015/0294086 A1 | 10/2015 | Kare et al. |
| 2015/0294445 A1 | 10/2015 | Sakaue |
| 2015/0296288 A1 | 10/2015 | Anastas |
| 2015/0297106 A1 | 10/2015 | Pasley et al. |
| 2015/0297108 A1 | 10/2015 | Chase et al. |
| 2015/0297109 A1 | 10/2015 | Garten et al. |
| 2015/0297139 A1 | 10/2015 | Toth |
| 2015/0297141 A1 | 10/2015 | Siegel et al. |
| 2015/0297444 A1 | 10/2015 | Tass |
| 2015/0297719 A1 | 10/2015 | Deisseroth et al. |
| 2015/0297889 A1 | 10/2015 | Simon et al. |
| 2015/0297893 A1 | 10/2015 | Kokones et al. |
| 2015/0301218 A1 | 10/2015 | Donderici |
| 2015/0304048 A1 | 10/2015 | Kim et al. |
| 2015/0304101 A1 | 10/2015 | Gupta et al. |
| 2015/0305685 A1 | 10/2015 | Shahaf et al. |
| 2015/0305686 A1 | 10/2015 | Coleman et al. |
| 2015/0305689 A1 | 10/2015 | Gourmelon et al. |
| 2015/0305799 A1 | 10/2015 | Trieu |
| 2015/0305800 A1 | 10/2015 | Trieu |
| 2015/0305801 A1 | 10/2015 | Trieu |
| 2015/0306057 A1 | 10/2015 | Goodenowe |
| 2015/0306340 A1 | 10/2015 | Giap et al. |
| 2015/0306390 A1 | 10/2015 | Zalay et al. |
| 2015/0306391 A1 | 10/2015 | Wu et al. |
| 2015/0306392 A1 | 10/2015 | Sabesan |
| 2015/0309563 A1 | 10/2015 | Connor |
| 2015/0309582 A1 | 10/2015 | Gupta |
| 2015/0310862 A1 | 10/2015 | Dauphin et al. |
| 2015/0313496 A1 | 11/2015 | Connor |
| 2015/0313498 A1 | 11/2015 | Coleman et al. |
| 2015/0313535 A1 | 11/2015 | Alshaer et al. |
| 2015/0313539 A1 | 11/2015 | Connor |
| 2015/0313540 A1 | 11/2015 | Deuchar et al. |
| 2015/0313949 A1 | 11/2015 | Cutillo |
| 2015/0313971 A1 | 11/2015 | Haslett et al. |
| 2015/0315554 A1 | 11/2015 | Shekdar et al. |
| 2015/0317447 A1 | 11/2015 | Helleputte et al. |
| 2015/0317796 A1 | 11/2015 | Schett et al. |
| 2015/0320591 A1 | 11/2015 | Smith et al. |
| 2015/0321000 A1 | 11/2015 | Rosenbluth et al. |
| 2015/0324544 A1 | 11/2015 | Maslowski et al. |
| 2015/0324545 A1 | 11/2015 | Fonte |
| 2015/0324692 A1 | 11/2015 | Ritchey et al. |
| 2015/0325151 A1 | 11/2015 | Tuchschmid et al. |
| 2015/0327813 A1 | 11/2015 | Fu |
| 2015/0327837 A1 | 11/2015 | Qi et al. |
| 2015/0328330 A1 | 11/2015 | Satchi-Fainaro et al. |
| 2015/0328455 A1 | 11/2015 | Meadows et al. |
| 2015/0331929 A1 | 11/2015 | El-Saban et al. |
| 2015/0332015 A1 | 11/2015 | Taylor |
| 2015/0335281 A1 | 11/2015 | Scroggins |
| 2015/0335288 A1 | 11/2015 | Toth et al. |
| 2015/0335292 A1 | 11/2015 | Mittal |
| 2015/0335294 A1 | 11/2015 | Witcher et al. |
| 2015/0335295 A1 | 11/2015 | Park et al. |
| 2015/0335303 A1 | 11/2015 | Chandelier et al. |
| 2015/0335876 A1 | 11/2015 | Jeffery et al. |
| 2015/0335877 A1 | 11/2015 | Jeffery et al. |
| 2015/0338915 A1 | 11/2015 | Publicover et al. |
| 2015/0339363 A1 | 11/2015 | Moldoveanu et al. |
| 2015/0339459 A1 | 11/2015 | Taylor |
| 2015/0342472 A1 | 12/2015 | Semenov |
| 2015/0342478 A1 | 12/2015 | Galen et al. |
| 2015/0342493 A1 | 12/2015 | Hardt |
| 2015/0343215 A1 | 12/2015 | De Ridder |

(56)     References Cited

U.S. PATENT DOCUMENTS

| 2015/0343222 A1 | 12/2015 | Kilgard et al. |
| 2015/0343242 A1 | 12/2015 | Tyler et al. |
| 2015/0351655 A1 | 12/2015 | Coleman |
| 2015/0351690 A1 | 12/2015 | Toth et al. |
| 2015/0351701 A1 | 12/2015 | Moxon et al. |
| 2015/0352362 A1 | 12/2015 | Craig |
| 2015/0352363 A1 | 12/2015 | McIntyre et al. |
| 2015/0359431 A1 | 12/2015 | Bakalash et al. |
| 2015/0359441 A1 | 12/2015 | Giovangrandi et al. |
| 2015/0359450 A1 | 12/2015 | Lee et al. |
| 2015/0359452 A1 | 12/2015 | Giovangrandi et al. |
| 2015/0359467 A1 | 12/2015 | Tran |
| 2015/0359486 A1 | 12/2015 | Kovacs et al. |
| 2015/0359492 A1 | 12/2015 | Giovangrandi et al. |
| 2015/0360026 A1 | 12/2015 | Wagner |
| 2015/0360030 A1 | 12/2015 | Cartledge et al. |
| 2015/0360039 A1 | 12/2015 | Lempka et al. |
| 2015/0363941 A1 | 12/2015 | Taylor |
| 2015/0366482 A1 | 12/2015 | Lee |
| 2015/0366497 A1 | 12/2015 | Cavuoto et al. |
| 2015/0366503 A1 | 12/2015 | Sjaaheim et al. |
| 2015/0366504 A1 | 12/2015 | Connor |
| 2015/0366516 A1 | 12/2015 | Dripps et al. |
| 2015/0366518 A1 | 12/2015 | Sampson |
| 2015/0366656 A1 | 12/2015 | Wortz et al. |
| 2015/0366659 A1 | 12/2015 | Wortz et al. |
| 2015/0369864 A1 | 12/2015 | Marlow et al. |
| 2015/0370320 A1 | 12/2015 | Connor |
| 2015/0370325 A1 | 12/2015 | Jarosiewicz et al. |
| 2015/0374250 A1 | 12/2015 | Hatano et al. |
| 2015/0374285 A1 | 12/2015 | Chang et al. |
| 2015/0374292 A1 | 12/2015 | Wyeth et al. |
| 2015/0374300 A1 | 12/2015 | Najarian et al. |
| 2015/0374973 A1 | 12/2015 | Morrell |
| 2015/0374983 A1 | 12/2015 | Simon et al. |
| 2015/0374986 A1 | 12/2015 | Bahmer |
| 2015/0374987 A1 | 12/2015 | Bahmer |
| 2015/0374993 A1 | 12/2015 | Morrell |
| 2015/0375006 A1 | 12/2015 | Denison et al. |
| 2015/0379230 A1 | 12/2015 | Taylor |
| 2015/0379370 A1 | 12/2015 | Clifton et al. |
| 2015/0379878 A1 | 12/2015 | Walter et al. |
| 2015/0380009 A1 | 12/2015 | Chang et al. |
| 2016/0000348 A1 | 1/2016 | Kitajo et al. |
| 2016/0000354 A1 | 1/2016 | Hagedorn et al. |
| 2016/0000383 A1 | 1/2016 | Lee et al. |
| 2016/0001065 A1 | 1/2016 | Wingeier et al. |
| 2016/0001096 A1 | 1/2016 | Mishelevich |
| 2016/0001098 A1 | 1/2016 | Wingeier et al. |
| 2016/0002523 A1 | 1/2016 | Huh et al. |
| 2016/0004298 A1 | 1/2016 | Mazed et al. |
| 2016/0004396 A1 | 1/2016 | Gulaka et al. |
| 2016/0004821 A1 | 1/2016 | Fueyo et al. |
| 2016/0004957 A1 | 1/2016 | Solari |
| 2016/0005235 A1 | 1/2016 | Fateh |
| 2016/0005320 A1 | 1/2016 | deCharms et al. |
| 2016/0007899 A1 | 1/2016 | Durkee et al. |
| 2016/0007904 A1 | 1/2016 | Vardy |
| 2016/0007915 A1 | 1/2016 | Berka et al. |
| 2016/0007918 A1 | 1/2016 | Badower et al. |
| 2016/0007945 A1 | 1/2016 | Taylor |
| 2016/0008489 A1 | 1/2016 | Korzus |
| 2016/0008568 A1 | 1/2016 | Attia et al. |
| 2016/0008598 A1 | 1/2016 | McLaughlin et al. |
| 2016/0008600 A1 | 1/2016 | Hershey et al. |
| 2016/0008620 A1 | 1/2016 | Stubbeman |
| 2016/0008632 A1 | 1/2016 | Wetmore et al. |
| 2016/0012011 A1 | 1/2016 | Llinas et al. |
| 2016/0012583 A1 | 1/2016 | Cales et al. |
| 2016/0012749 A1 | 1/2016 | Connor |
| 2016/0015281 A1 | 1/2016 | McKenna et al. |
| 2016/0015289 A1 | 1/2016 | Simon et al. |
| 2016/0015307 A1 | 1/2016 | Kothuri |
| 2016/0015673 A1 | 1/2016 | Goodenowe |
| 2016/0016014 A1 | 1/2016 | Wagner et al. |
| 2016/0019434 A1 | 1/2016 | Caldwell |
| 2016/0019693 A1 | 1/2016 | Silbersweig et al. |
| 2016/0022141 A1 | 1/2016 | Mittal et al. |
| 2016/0022156 A1 | 1/2016 | Kovacs et al. |
| 2016/0022164 A1 | 1/2016 | Brockway et al. |
| 2016/0022165 A1 | 1/2016 | Sackellares et al. |
| 2016/0022167 A1 | 1/2016 | Simon |
| 2016/0022168 A1 | 1/2016 | Luczak et al. |
| 2016/0022206 A1 | 1/2016 | Simon et al. |
| 2016/0022207 A1 | 1/2016 | Roberts et al. |
| 2016/0022981 A1 | 1/2016 | Wingeier et al. |
| 2016/0023016 A1 | 1/2016 | Bonmassar et al. |
| 2016/0026913 A1 | 1/2016 | Moon et al. |
| 2016/0027178 A1 | 1/2016 | Yu et al. |
| 2016/0027293 A1 | 1/2016 | Esteller et al. |
| 2016/0027342 A1 | 1/2016 | Ben-Haim |
| 2016/0027423 A1 | 1/2016 | Deuel et al. |
| 2016/0029896 A1 | 2/2016 | Lee et al. |
| 2016/0029917 A1 | 2/2016 | Baker et al. |
| 2016/0029918 A1 | 2/2016 | Baker et al. |
| 2016/0029946 A1 | 2/2016 | Simon et al. |
| 2016/0029950 A1 | 2/2016 | Chang et al. |
| 2016/0029958 A1 | 2/2016 | Le et al. |
| 2016/0029959 A1 | 2/2016 | Le et al. |
| 2016/0029965 A1 | 2/2016 | Simon |
| 2016/0029998 A1 | 2/2016 | Brister et al. |
| 2016/0030666 A1 | 2/2016 | Lozano et al. |
| 2016/0030702 A1 | 2/2016 | Yang |
| 2016/0030749 A1 | 2/2016 | Carcieri et al. |
| 2016/0030750 A1 | 2/2016 | Bokil et al. |
| 2016/0030834 A1 | 2/2016 | Brown et al. |
| 2016/0031479 A1 | 2/2016 | Fung et al. |
| 2016/0035093 A1 | 2/2016 | Kateb et al. |
| 2016/0038037 A1 | 2/2016 | Kovacs |
| 2016/0038038 A1 | 2/2016 | Kovacs |
| 2016/0038042 A1 | 2/2016 | Mulligan et al. |
| 2016/0038043 A1 | 2/2016 | Mulligan et al. |
| 2016/0038049 A1 | 2/2016 | Geva et al. |
| 2016/0038069 A1 | 2/2016 | Stack |
| 2016/0038091 A1 | 2/2016 | Krishnaswamy et al. |
| 2016/0038559 A1 | 2/2016 | Palmer et al. |
| 2016/0038770 A1 | 2/2016 | Tyler et al. |
| 2016/0040514 A1 | 2/2016 | Rahmani et al. |
| 2016/0044841 A1 | 2/2016 | Chamberlain |
| 2016/0045128 A1 | 2/2016 | Sitt et al. |
| 2016/0045150 A1 | 2/2016 | Leininger et al. |
| 2016/0045162 A1 | 2/2016 | De Graff et al. |
| 2016/0045731 A1 | 2/2016 | Simon et al. |
| 2016/0045756 A1 | 2/2016 | Phillips et al. |
| 2016/0048659 A1 | 2/2016 | Pereira et al. |
| 2016/0048948 A1 | 2/2016 | Bajic |
| 2016/0048965 A1 | 2/2016 | Stehle et al. |
| 2016/0051161 A1 | 2/2016 | Labyt et al. |
| 2016/0051162 A1 | 2/2016 | Durand et al. |
| 2016/0051187 A1 | 2/2016 | Damadian |
| 2016/0051195 A1 | 2/2016 | Pang et al. |
| 2016/0051793 A1 | 2/2016 | Gibson-Horn |
| 2016/0051812 A1 | 2/2016 | Montgomery, Jr. et al. |
| 2016/0051818 A1 | 2/2016 | Simon et al. |
| 2016/0055236 A1 | 2/2016 | Frank et al. |
| 2016/0055304 A1 | 2/2016 | Russell et al. |
| 2016/0055415 A1 | 2/2016 | Baxi |
| 2016/0055842 A1 | 2/2016 | DeFranks et al. |
| 2016/0058301 A1 | 3/2016 | Shusterman |
| 2016/0058304 A1 | 3/2016 | Emblem et al. |
| 2016/0058322 A1 | 3/2016 | Brister et al. |
| 2016/0058354 A1 | 3/2016 | Phan et al. |
| 2016/0058359 A1 | 3/2016 | Osorio |
| 2016/0058366 A1 | 3/2016 | Choi et al. |
| 2016/0058376 A1 | 3/2016 | Baek et al. |
| 2016/0058392 A1 | 3/2016 | Hasson et al. |
| 2016/0058673 A1 | 3/2016 | Francis |
| 2016/0060926 A1 | 3/2016 | Kim et al. |
| 2016/0062459 A1 | 3/2016 | Publicover et al. |
| 2016/0063207 A1 | 3/2016 | Schmidt |
| 2016/0063883 A1 | 3/2016 | Jeyanandarajan |
| 2016/0065724 A1 | 3/2016 | Lee et al. |
| 2016/0065840 A1 | 3/2016 | Kim et al. |
| 2016/0066788 A1 | 3/2016 | Tran et al. |

(56)　　　　　References Cited

U.S. PATENT DOCUMENTS

| | | |
|---|---|---|
| 2016/0066789 A1 | 3/2016 | Rogers et al. |
| 2016/0066828 A1 | 3/2016 | Phan et al. |
| 2016/0066838 A1 | 3/2016 | DeCharms |
| 2016/0067485 A1 | 3/2016 | Lindenthaler et al. |
| 2016/0067492 A1 | 3/2016 | Wolpaw et al. |
| 2016/0067494 A1 | 3/2016 | Lipani |
| 2016/0067496 A1 | 3/2016 | Gliner et al. |
| 2016/0067526 A1 | 3/2016 | Yang |
| 2016/0070436 A1 | 3/2016 | Thomas et al. |
| 2016/0073886 A1 | 3/2016 | Connor |
| 2016/0073916 A1 | 3/2016 | Aksenova et al. |
| 2016/0073947 A1 | 3/2016 | Anderson |
| 2016/0073991 A1 | 3/2016 | Taylor |
| 2016/0074657 A1 | 3/2016 | Kwan et al. |
| 2016/0074660 A1 | 3/2016 | Osorio et al. |
| 2016/0074661 A1 | 3/2016 | Lipani |
| 2016/0077547 A1 | 3/2016 | Aimone et al. |
| 2016/0078780 A1 | 3/2016 | Alexander et al. |
| 2016/0081577 A1 | 3/2016 | Sridhar et al. |
| 2016/0081610 A1 | 3/2016 | Osorio et al. |
| 2016/0081613 A1 | 3/2016 | Braun et al. |
| 2016/0081616 A1 | 3/2016 | Li |
| 2016/0081625 A1 | 3/2016 | Kim et al. |
| 2016/0081793 A1 | 3/2016 | Galstian et al. |
| 2016/0082180 A1 | 3/2016 | Toth et al. |
| 2016/0082319 A1 | 3/2016 | Macri et al. |
| 2016/0084925 A1 | 3/2016 | Le Prado et al. |
| 2016/0085302 A1 | 3/2016 | Publicover et al. |
| 2016/0086622 A1 | 3/2016 | Yamamoto |
| 2016/0087603 A1 | 3/2016 | Ricci et al. |
| 2016/0089031 A1 | 3/2016 | Hu |
| 2016/0091448 A1 | 3/2016 | Soleimani |
| 2016/0095546 A1 | 4/2016 | Sahasrabudhe et al. |
| 2016/0095838 A1 | 4/2016 | Satchi-Fainaro et al. |
| 2016/0096025 A1 | 4/2016 | Moffitt et al. |
| 2016/0097824 A1 | 4/2016 | Fujii et al. |
| 2016/0100769 A1 | 4/2016 | Kim et al. |
| 2016/0101260 A1 | 4/2016 | Austin et al. |
| 2016/0102500 A1 | 4/2016 | Donderici et al. |
| 2016/0103487 A1 | 4/2016 | Crawford et al. |
| 2016/0103963 A1 | 4/2016 | Mishra |
| 2016/0104006 A1 | 4/2016 | Son et al. |
| 2016/0106331 A1 | 4/2016 | Zorick et al. |
| 2016/0106344 A1 | 4/2016 | Nazari |
| 2016/0106513 A1 | 4/2016 | De Stavola et al. |
| 2016/0106950 A1 | 4/2016 | Vasapollo |
| 2016/0106997 A1 | 4/2016 | Arendash et al. |
| 2016/0107309 A1 | 4/2016 | Walsh et al. |
| 2016/0107653 A1 | 4/2016 | Fung et al. |
| 2016/0109851 A1 | 4/2016 | Tsang |
| 2016/0109959 A1 | 4/2016 | Heo |
| 2016/0110517 A1 | 4/2016 | Taylor |
| 2016/0110866 A1 | 4/2016 | Taylor |
| 2016/0110867 A1 | 4/2016 | Taylor |
| 2016/0112022 A1 | 4/2016 | Butts |
| 2016/0112684 A1 | 4/2016 | Connor |
| 2016/0113517 A1 | 4/2016 | Lee et al. |
| 2016/0113528 A1 | 4/2016 | Taylor |
| 2016/0113539 A1 | 4/2016 | Sinharay et al. |
| 2016/0113545 A1 | 4/2016 | Kim et al. |
| 2016/0113567 A1 | 4/2016 | Osvath et al. |
| 2016/0113569 A1 | 4/2016 | Zhao et al. |
| 2016/0113587 A1 | 4/2016 | Kothe et al. |
| 2016/0113726 A1 | 4/2016 | Taylor |
| 2016/0114165 A1 | 4/2016 | Levine et al. |
| 2016/0116472 A1 | 4/2016 | Ay |
| 2016/0116553 A1 | 4/2016 | Kim et al. |
| 2016/0117815 A1 | 4/2016 | Taylor |
| 2016/0117816 A1 | 4/2016 | Taylor |
| 2016/0117819 A1 | 4/2016 | Taylor |
| 2016/0119726 A1 | 4/2016 | Pontoppidan et al. |
| 2016/0120048 A1 | 4/2016 | Seo et al. |
| 2016/0120428 A1 | 5/2016 | Yoshida et al. |
| 2016/0120432 A1 | 5/2016 | Sridhar et al. |
| 2016/0120433 A1 | 5/2016 | Hughes et al. |
| 2016/0120434 A1 | 5/2016 | Park et al. |
| 2016/0120436 A1 | 5/2016 | Silberstein |
| 2016/0120437 A1 | 5/2016 | Graham et al. |
| 2016/0120457 A1 | 5/2016 | Wu et al. |
| 2016/0120464 A1 | 5/2016 | Lau et al. |
| 2016/0120480 A1 | 5/2016 | Turnbull et al. |
| 2016/0121074 A1 | 5/2016 | Ashby |
| 2016/0121114 A1 | 5/2016 | Simon et al. |
| 2016/0121116 A1 | 5/2016 | Simon et al. |
| 2016/0125228 A1 | 5/2016 | Son et al. |
| 2016/0125572 A1 | 5/2016 | Yoo et al. |
| 2016/0128589 A1 | 5/2016 | Tabib-Azar |
| 2016/0128596 A1 | 5/2016 | Morshed et al. |
| 2016/0128597 A1 | 5/2016 | Lin et al. |
| 2016/0128632 A1 | 5/2016 | Wiebe et al. |
| 2016/0128661 A1 | 5/2016 | Taylor |
| 2016/0128864 A1 | 5/2016 | Nofzinger et al. |
| 2016/0129249 A1 | 5/2016 | Yun et al. |
| 2016/0131723 A1 | 5/2016 | Nagasaka |
| 2016/0132654 A1 | 5/2016 | Rothman et al. |
| 2016/0133015 A1 | 5/2016 | Taylor |
| 2016/0135691 A1 | 5/2016 | Dripps et al. |
| 2016/0135727 A1 | 5/2016 | Osorio |
| 2016/0135748 A1 | 5/2016 | Lin et al. |
| 2016/0135754 A1 | 5/2016 | Marshall et al. |
| 2016/0136423 A1 | 5/2016 | Simon et al. |
| 2016/0136427 A1 | 5/2016 | De Ridder |
| 2016/0136429 A1 | 5/2016 | Massoumi et al. |
| 2016/0136430 A1 | 5/2016 | Moffitt et al. |
| 2016/0136443 A1 | 5/2016 | Grandhe et al. |
| 2016/0139215 A1 | 5/2016 | Fujii |
| 2016/0140306 A1 | 5/2016 | Hua et al. |
| 2016/0140313 A1 | 5/2016 | Taylor |
| 2016/0140707 A1 | 5/2016 | Abe et al. |
| 2016/0140834 A1 | 5/2016 | Tran |
| 2016/0140975 A1 | 5/2016 | Kamamoto et al. |
| 2016/0143540 A1 | 5/2016 | Gencer et al. |
| 2016/0143541 A1 | 5/2016 | He et al. |
| 2016/0143554 A1 | 5/2016 | Lim et al. |
| 2016/0143560 A1 | 5/2016 | Grunwald et al. |
| 2016/0143574 A1 | 5/2016 | Jones et al. |
| 2016/0143582 A1 | 5/2016 | Connor |
| 2016/0143594 A1 | 5/2016 | Moorman et al. |
| 2016/0144175 A1 | 5/2016 | Simon et al. |
| 2016/0144186 A1 | 5/2016 | Kaemmerer et al. |
| 2016/0147964 A1 | 5/2016 | Corey et al. |
| 2016/0148077 A1 | 5/2016 | Cox et al. |
| 2016/0148371 A1 | 5/2016 | Itu et al. |
| 2016/0148372 A1 | 5/2016 | Itu et al. |
| 2016/0148400 A1 | 5/2016 | Bajic |
| 2016/0148531 A1 | 5/2016 | Bleich et al. |
| 2016/0150988 A1 | 6/2016 | Prerau et al. |
| 2016/0151014 A1 | 6/2016 | Ujhazy et al. |
| 2016/0151018 A1 | 6/2016 | Machon et al. |
| 2016/0151628 A1 | 6/2016 | Simon et al. |
| 2016/0152233 A1 | 6/2016 | Fung et al. |
| 2016/0155005 A1 | 6/2016 | Varkuti et al. |
| 2016/0157742 A1 | 6/2016 | Huang et al. |
| 2016/0157773 A1 | 6/2016 | Baek et al. |
| 2016/0157777 A1 | 6/2016 | Attal et al. |
| 2016/0157828 A1 | 6/2016 | Sumi et al. |
| 2016/0158553 A1 | 6/2016 | Panken et al. |
| 2016/0158554 A1 | 6/2016 | Graig |
| 2016/0162652 A1 | 6/2016 | Siekmeier |
| 2016/0164813 A1 | 6/2016 | Anderson et al. |
| 2016/0165852 A1 | 6/2016 | Goldfain |
| 2016/0165853 A1 | 6/2016 | Goldfain |
| 2016/0166169 A1 | 6/2016 | Badower et al. |
| 2016/0166197 A1 | 6/2016 | Venkatraman et al. |
| 2016/0166199 A1 | 6/2016 | Sun et al. |
| 2016/0166205 A1 | 6/2016 | Ernst et al. |
| 2016/0166207 A1 | 6/2016 | Falconer |
| 2016/0166208 A1 | 6/2016 | Girouard et al. |
| 2016/0166219 A1 | 6/2016 | Majewski et al. |
| 2016/0167672 A1 | 6/2016 | Krueger |
| 2016/0168137 A1 | 6/2016 | Van Leyen et al. |
| 2016/0170996 A1 | 6/2016 | Frank et al. |
| 2016/0170998 A1 | 6/2016 | Frank et al. |
| 2016/0171514 A1 | 6/2016 | Frank et al. |

(56) References Cited

U.S. PATENT DOCUMENTS

| | | |
|---|---|---|
| 2016/0174099 A1 | 6/2016 | Goldfain |
| 2016/0174862 A1 | 6/2016 | Yu et al. |
| 2016/0174863 A1 | 6/2016 | Foerster et al. |
| 2016/0174867 A1 | 6/2016 | Hatano et al. |
| 2016/0174907 A1 | 6/2016 | Colman et al. |
| 2016/0175557 A1 | 6/2016 | Tass |
| 2016/0175607 A1 | 6/2016 | Deisseroth et al. |
| 2016/0176053 A1 | 6/2016 | Rognini et al. |
| 2016/0178392 A1 | 6/2016 | Goldfain |
| 2016/0180042 A1 | 6/2016 | Menon et al. |
| 2016/0180054 A1 | 6/2016 | Luo et al. |
| 2016/0180055 A1 | 6/2016 | Fonte |
| 2016/0183812 A1 | 6/2016 | Zhang et al. |
| 2016/0183828 A1 | 6/2016 | Ouyang et al. |
| 2016/0183861 A1 | 6/2016 | Hayes et al. |
| 2016/0183881 A1 | 6/2016 | Keenan et al. |
| 2016/0184029 A1 | 6/2016 | Peng et al. |
| 2016/0184596 A1 | 6/2016 | Fried et al. |
| 2016/0184599 A1 | 6/2016 | Segal |
| 2016/0187524 A1 | 6/2016 | Suhami |
| 2016/0191517 A1 | 6/2016 | Bae et al. |
| 2016/0192841 A1 | 7/2016 | Inagaki et al. |
| 2016/0192842 A1 | 7/2016 | Inagaki |
| 2016/0192847 A1 | 7/2016 | Inagaki |
| 2016/0192879 A1 | 7/2016 | Yamashita |
| 2016/0193499 A1 | 7/2016 | Kim et al. |
| 2016/0196185 A1 | 7/2016 | Gu et al. |
| 2016/0196393 A1 | 7/2016 | Avinash et al. |
| 2016/0196635 A1 | 7/2016 | Cho et al. |
| 2016/0196758 A1 | 7/2016 | Causevic et al. |
| 2016/0198950 A1 | 7/2016 | Gross et al. |
| 2016/0198963 A1 | 7/2016 | Addison et al. |
| 2016/0198966 A1 | 7/2016 | Uematsu et al. |
| 2016/0198968 A1 | 7/2016 | Plenz et al. |
| 2016/0198973 A1 | 7/2016 | Fukuda et al. |
| 2016/0199241 A1 | 7/2016 | Rapoport |
| 2016/0199577 A1 | 7/2016 | Hyde et al. |
| 2016/0199656 A1 | 7/2016 | Phillips |
| 2016/0199662 A1 | 7/2016 | Wundrich et al. |
| 2016/0202755 A1 | 7/2016 | Connor |
| 2016/0203597 A1 | 7/2016 | Chang et al. |
| 2016/0203726 A1 | 7/2016 | Hibbs et al. |
| 2016/0204937 A1 | 7/2016 | Edwards et al. |
| 2016/0205450 A1 | 7/2016 | Gartseev et al. |
| 2016/0205489 A1 | 7/2016 | Jabri |
| 2016/0206236 A1 | 7/2016 | Dilorenzo et al. |
| 2016/0206241 A1 | 7/2016 | Cho et al. |
| 2016/0206380 A1 | 7/2016 | Sparks et al. |
| 2016/0206581 A1 | 7/2016 | Wittkowski |
| 2016/0206671 A1 | 7/2016 | Geng |
| 2016/0206871 A1 | 7/2016 | Weisend |
| 2016/0206877 A1 | 7/2016 | Hargrove |
| 2016/0206880 A1 | 7/2016 | Koubeissi |
| 2016/0210872 A1 | 7/2016 | Roberts et al. |
| 2016/0213261 A1 | 7/2016 | Fleischer et al. |
| 2016/0213276 A1 | 7/2016 | Gadot et al. |
| 2016/0213314 A1 | 7/2016 | Zuckerman-Stark et al. |
| 2016/0213317 A1 | 7/2016 | Richardson et al. |
| 2016/0213947 A1 | 7/2016 | Han et al. |
| 2016/0216760 A1 | 7/2016 | Trutna et al. |
| 2016/0217586 A1 | 7/2016 | John et al. |
| 2016/0217595 A1 | 7/2016 | Han et al. |
| 2016/0219345 A1 | 7/2016 | Knight et al. |
| 2016/0220133 A1 | 8/2016 | Inagaki |
| 2016/0220134 A1 | 8/2016 | Inagaki |
| 2016/0220136 A1 | 8/2016 | Schultz |
| 2016/0220163 A1 | 8/2016 | Yamada et al. |
| 2016/0220166 A1 | 8/2016 | Thornton |
| 2016/0220439 A1 | 8/2016 | Wojciechowski et al. |
| 2016/0220821 A1 | 8/2016 | O'Connell et al. |
| 2016/0220836 A1 | 8/2016 | Parks |
| 2016/0220837 A1 | 8/2016 | Jin |
| 2016/0220850 A1 | 8/2016 | Tyler |
| 2016/0222073 A1 | 8/2016 | Deisseroth et al. |
| 2016/0223622 A1 | 8/2016 | Yu et al. |
| 2016/0223627 A1 | 8/2016 | Shah et al. |
| 2016/0223703 A1 | 8/2016 | Wu et al. |
| 2016/0224757 A1 | 8/2016 | Melkonyan |
| 2016/0224803 A1 | 8/2016 | Frank et al. |
| 2016/0228019 A1 | 8/2016 | Grunwald et al. |
| 2016/0228028 A1 | 8/2016 | Van Der Kooi et al. |
| 2016/0228029 A1 | 8/2016 | Ware |
| 2016/0228059 A1 | 8/2016 | Badower |
| 2016/0228064 A1 | 8/2016 | Jung et al. |
| 2016/0228204 A1 | 8/2016 | Quaid et al. |
| 2016/0228640 A1 | 8/2016 | Pindado et al. |
| 2016/0228702 A1 | 8/2016 | Kempe et al. |
| 2016/0228705 A1 | 8/2016 | Crowder et al. |
| 2016/0231401 A1 | 8/2016 | Wang et al. |
| 2016/0232330 A1 | 8/2016 | Dowson |
| 2016/0232625 A1 | 8/2016 | Akutagawa et al. |
| 2016/0232667 A1 | 8/2016 | Taylor |
| 2016/0232811 A9 | 8/2016 | Connor |
| 2016/0235323 A1 | 8/2016 | Tadi et al. |
| 2016/0235324 A1 | 8/2016 | Mershin et al. |
| 2016/0235341 A1 | 8/2016 | Choi et al. |
| 2016/0235351 A1 | 8/2016 | Intrator |
| 2016/0235352 A1 | 8/2016 | DiLorenzo |
| 2016/0235359 A1 | 8/2016 | Cho et al. |
| 2016/0235980 A1 | 8/2016 | Berman et al. |
| 2016/0235983 A1 | 8/2016 | Berman et al. |
| 2016/0238673 A1 | 8/2016 | Honkura |
| 2016/0239084 A1 | 8/2016 | Connor |
| 2016/0239966 A1 | 8/2016 | Parsey et al. |
| 2016/0239968 A1 | 8/2016 | Parsey et al. |
| 2016/0240212 A1 | 8/2016 | Wilson et al. |
| 2016/0240765 A1 | 8/2016 | Washington et al. |
| 2016/0242645 A1 | 8/2016 | Muller |
| 2016/0242659 A1 | 8/2016 | Yamashita et al. |
| 2016/0242665 A1 | 8/2016 | Galloway et al. |
| 2016/0242669 A1 | 8/2016 | Muraskin et al. |
| 2016/0242670 A1 | 8/2016 | Suzuki et al. |
| 2016/0242690 A1 | 8/2016 | Principe et al. |
| 2016/0242699 A1 | 8/2016 | Das et al. |
| 2016/0243362 A1 | 8/2016 | Hehrmann et al. |
| 2016/0243381 A1 | 8/2016 | Alford et al. |
| 2016/0245670 A1 | 8/2016 | Nelson et al. |
| 2016/0245766 A1 | 8/2016 | Nelson et al. |
| 2016/0245952 A1 | 8/2016 | Dupuis et al. |
| 2016/0246939 A1 | 8/2016 | Taylor |
| 2016/0247064 A1 | 8/2016 | Yoo et al. |
| 2016/0248434 A1 | 8/2016 | Govari |
| 2016/0248994 A1 | 8/2016 | Liu |
| 2016/0249826 A1 | 9/2016 | Derchak |
| 2016/0249841 A1 | 9/2016 | Gerber et al. |
| 2016/0249846 A1 | 9/2016 | Yoo et al. |
| 2016/0249857 A1 | 9/2016 | Choi et al. |
| 2016/0249864 A1 | 9/2016 | Kang et al. |
| 2016/0250355 A1 | 9/2016 | Macknik |
| 2016/0250465 A1 | 9/2016 | Simon et al. |
| 2016/0250473 A1 | 9/2016 | Alberts et al. |
| 2016/0256063 A1 | 9/2016 | Friedman et al. |
| 2016/0256086 A1 | 9/2016 | Byrd et al. |
| 2016/0256105 A1 | 9/2016 | Boyle et al. |
| 2016/0256108 A1 | 9/2016 | Yun et al. |
| 2016/0256109 A1 | 9/2016 | Semenov |
| 2016/0256112 A1 | 9/2016 | Brockway et al. |
| 2016/0256118 A1 | 9/2016 | Iyer et al. |
| 2016/0256130 A1 | 9/2016 | Hamilton et al. |
| 2016/0256690 A1 | 9/2016 | Cecchi et al. |
| 2016/0256691 A1 | 9/2016 | Cecchi et al. |
| 2016/0256693 A1 | 9/2016 | Parramon |
| 2016/0257957 A1 | 9/2016 | Greenberg et al. |
| 2016/0259085 A1 | 9/2016 | Wilson et al. |
| 2016/0259905 A1 | 9/2016 | Park et al. |
| 2016/0260216 A1 | 9/2016 | Wu et al. |
| 2016/0261962 A1 | 9/2016 | Petersen et al. |
| 2016/0262623 A1 | 9/2016 | Semenov |
| 2016/0262664 A1 | 9/2016 | Linderman |
| 2016/0262680 A1 | 9/2016 | Martucci et al. |
| 2016/0262685 A1 | 9/2016 | Wagner et al. |
| 2016/0262695 A1 | 9/2016 | Zhang et al. |
| 2016/0262703 A1 | 9/2016 | Maccallum |
| 2016/0263318 A1 | 9/2016 | Osorio |

(56)                  References Cited

U.S. PATENT DOCUMENTS

| | | |
|---|---|---|
| 2016/0263376 A1 | 9/2016 | Yoo et al. |
| 2016/0263380 A1 | 9/2016 | Starr et al. |
| 2016/0263393 A1 | 9/2016 | Vo-Dinh et al. |
| 2016/0267809 A1 | 9/2016 | deCharms et al. |
| 2016/0270656 A1 | 9/2016 | Samec et al. |
| 2016/0270723 A1 | 9/2016 | Deisseroth et al. |
| 2016/0274660 A1 | 9/2016 | Publicover et al. |
| 2016/0275536 A1 | 9/2016 | Anderson |
| 2016/0278651 A1 | 9/2016 | Lu et al. |
| 2016/0278653 A1 | 9/2016 | Clark et al. |
| 2016/0278662 A1 | 9/2016 | Brister et al. |
| 2016/0278672 A1 | 9/2016 | Cho et al. |
| 2016/0278687 A1 | 9/2016 | Xia |
| 2016/0278697 A1 | 9/2016 | John et al. |
| 2016/0278713 A1 | 9/2016 | Shoaran et al. |
| 2016/0278736 A1 | 9/2016 | Hamilton et al. |
| 2016/0278870 A1 | 9/2016 | Quaid et al. |
| 2016/0279021 A1 | 9/2016 | Hyde et al. |
| 2016/0279022 A1 | 9/2016 | Hyde et al. |
| 2016/0279023 A1 | 9/2016 | Hyde et al. |
| 2016/0279024 A1 | 9/2016 | Hyde et al. |
| 2016/0279025 A1 | 9/2016 | Hyde et al. |
| 2016/0279267 A1 | 9/2016 | Deisseroth et al. |
| 2016/0279410 A1 | 9/2016 | Simon et al. |
| 2016/0279417 A1 | 9/2016 | Kilgard et al. |
| 2016/0279435 A1 | 9/2016 | Hyde et al. |
| 2016/0282113 A1 | 9/2016 | Lee |
| 2016/0282941 A1 | 9/2016 | Aksenova et al. |
| 2016/0284082 A1 | 9/2016 | Varkuti |
| 2016/0287117 A1 | 10/2016 | Breakspear et al. |
| 2016/0287118 A1 | 10/2016 | Sarma et al. |
| 2016/0287120 A1 | 10/2016 | Sun et al. |
| 2016/0287142 A1 | 10/2016 | Han et al. |
| 2016/0287157 A1 | 10/2016 | Simpson |
| 2016/0287162 A1 | 10/2016 | Bardakjian et al. |
| 2016/0287166 A1 | 10/2016 | Tran |
| 2016/0287169 A1 | 10/2016 | Kortelainen et al. |
| 2016/0287308 A1 | 10/2016 | Grant et al. |
| 2016/0287334 A1 | 10/2016 | Grant et al. |
| 2016/0287436 A1 | 10/2016 | Wingeier et al. |
| 2016/0287869 A1 | 10/2016 | Errico et al. |
| 2016/0287871 A1 | 10/2016 | Bardakjian et al. |
| 2016/0287889 A1 | 10/2016 | Bokil et al. |
| 2016/0287895 A1 | 10/2016 | Deisseroth et al. |
| 2016/0296157 A1 | 10/2016 | Girouard |
| 2016/0296287 A1 | 10/2016 | Taylor |
| 2016/0296746 A1 | 10/2016 | Wingeier et al. |
| 2016/0298449 A1 | 10/2016 | Orban |
| 2016/0299568 A1 | 10/2016 | Segal |
| 2016/0300252 A1 | 10/2016 | Frank et al. |
| 2016/0300352 A1 | 10/2016 | Raj |
| 2016/0302683 A1 | 10/2016 | Lawrence et al. |
| 2016/0302704 A9 | 10/2016 | Lynn et al. |
| 2016/0302709 A1 | 10/2016 | Mossbridge |
| 2016/0302711 A1 | 10/2016 | Frank et al. |
| 2016/0302720 A1 | 10/2016 | John et al. |
| 2016/0302737 A1 | 10/2016 | Watson et al. |
| 2016/0303322 A1 | 10/2016 | John |
| 2016/0303396 A9 | 10/2016 | Deisseroth et al. |
| 2016/0303397 A1 | 10/2016 | Hirschman et al. |
| 2016/0303402 A1 | 10/2016 | Tyler |
| 2016/0306844 A1 | 10/2016 | Frank et al. |
| 2016/0306942 A1 | 10/2016 | Rapaka et al. |
| 2016/0310031 A1 | 10/2016 | Sarkar |
| 2016/0310070 A1 | 10/2016 | Sabesan |
| 2016/0310071 A1 | 10/2016 | Kim |
| 2016/0313408 A1 | 10/2016 | Hatano et al. |
| 2016/0313417 A1 | 10/2016 | Kawabata et al. |
| 2016/0313418 A1 | 10/2016 | Fujii et al. |
| 2016/0313798 A1 | 10/2016 | Connor |
| 2016/0317056 A1 | 11/2016 | Moon et al. |
| 2016/0317060 A1 | 11/2016 | Connor |
| 2016/0317077 A1 | 11/2016 | Sillay |
| 2016/0317383 A1 | 11/2016 | Stanfield et al. |
| 2016/0317824 A1 | 11/2016 | Moffitt et al. |
| 2016/0320210 A1 | 11/2016 | Nelson et al. |
| 2016/0321742 A1 | 11/2016 | Phillips et al. |
| 2016/0324445 A1 | 11/2016 | Kim et al. |
| 2016/0324457 A1 | 11/2016 | Dagum |
| 2016/0324465 A1 | 11/2016 | Osvath et al. |
| 2016/0324478 A1 | 11/2016 | Goldstein |
| 2016/0324580 A1 | 11/2016 | Esterberg |
| 2016/0324677 A1 | 11/2016 | Hyde et al. |
| 2016/0324942 A1 | 11/2016 | Lester et al. |
| 2016/0325111 A1 | 11/2016 | Bourke, Jr. et al. |
| 2016/0331264 A1 | 11/2016 | Helms-Tillery et al. |
| 2016/0331307 A1 | 11/2016 | Purdon et al. |
| 2016/0331952 A1 | 11/2016 | Faltys et al. |
| 2016/0331970 A1 | 11/2016 | Lozano |
| 2016/0331974 A1 | 11/2016 | Lyons et al. |
| 2016/0331982 A1 | 11/2016 | Chow et al. |
| 2016/0334475 A1 | 11/2016 | Ueno |
| 2016/0334534 A1 | 11/2016 | Mandviwala et al. |
| 2016/0334866 A9 | 11/2016 | Mazed et al. |
| 2016/0338608 A1 | 11/2016 | Nagasaka et al. |
| 2016/0338634 A1 | 11/2016 | Neu et al. |
| 2016/0338644 A1 | 11/2016 | Connor |
| 2016/0338798 A1 | 11/2016 | Vora et al. |
| 2016/0338825 A1 | 11/2016 | Wortz et al. |
| 2016/0339237 A1 | 11/2016 | Ahmed et al. |
| 2016/0339238 A1 | 11/2016 | Ahmed et al. |
| 2016/0339239 A1 | 11/2016 | Yoo et al. |
| 2016/0339242 A1 | 11/2016 | Cook et al. |
| 2016/0339243 A1 | 11/2016 | Wingeier et al. |
| 2016/0339300 A1 | 11/2016 | Todasco |
| 2016/0341684 A1 | 11/2016 | Choi |
| 2016/0342241 A1 | 11/2016 | Chung et al. |
| 2016/0342762 A1 | 11/2016 | Goetz |
| 2016/0345856 A1 | 12/2016 | Semenov |
| 2016/0345895 A1 | 12/2016 | Loetsch et al. |
| 2016/0345901 A1 | 12/2016 | Connor |
| 2016/0345911 A1 | 12/2016 | Leuthardt et al. |
| 2016/0346530 A1 | 12/2016 | Jeffery et al. |
| 2016/0346542 A1 | 12/2016 | Simon et al. |
| 2016/0351069 A1 | 12/2016 | Faubert et al. |
| 2016/0354003 A1 | 12/2016 | Baker et al. |
| 2016/0354027 A1 | 12/2016 | Benson et al. |
| 2016/0356911 A1 | 12/2016 | Wilson et al. |
| 2016/0357003 A1 | 12/2016 | Hauger et al. |
| 2016/0357256 A1 | 12/2016 | Siefert |
| 2016/0360100 A1 | 12/2016 | Kim et al. |
| 2016/0360965 A1 | 12/2016 | Tran |
| 2016/0360970 A1 | 12/2016 | Tzvieli et al. |
| 2016/0361021 A1 | 12/2016 | Salehizadeh et al. |
| 2016/0361027 A1 | 12/2016 | Jang et al. |
| 2016/0361041 A1 | 12/2016 | Barsimantov et al. |
| 2016/0361532 A1 | 12/2016 | Wingeier et al. |
| 2016/0361534 A9 | 12/2016 | Weisend |
| 2016/0361540 A9 | 12/2016 | Simon et al. |
| 2016/0361546 A1 | 12/2016 | Salam et al. |
| 2016/0363483 A1 | 12/2016 | Tzvieli et al. |
| 2016/0364859 A1 | 12/2016 | Taylor |
| 2016/0364860 A1 | 12/2016 | Taylor |
| 2016/0364861 A1 | 12/2016 | Taylor |
| 2016/0366462 A1 | 12/2016 | Klappert et al. |
| 2016/0367138 A1 | 12/2016 | Kim et al. |
| 2016/0367186 A1 | 12/2016 | Freeman et al. |
| 2016/0367195 A1 | 12/2016 | Park et al. |
| 2016/0367198 A1 | 12/2016 | Chon et al. |
| 2016/0367204 A1 | 12/2016 | Won et al. |
| 2016/0367209 A1 | 12/2016 | Odry et al. |
| 2016/0367808 A9 | 12/2016 | Simon et al. |
| 2016/0367812 A1 | 12/2016 | De Ridder |
| 2016/0371387 A1 | 12/2016 | Serena |
| 2016/0371455 A1 | 12/2016 | Taylor |
| 2016/0371721 A1 | 12/2016 | Bogdon et al. |
| 2016/0374581 A1 | 12/2016 | Jensen |
| 2016/0374616 A1 | 12/2016 | Mullins et al. |
| 2016/0374618 A1 | 12/2016 | Giovangrandi |
| 2016/0374990 A1 | 12/2016 | Teegarden et al. |
| 2016/0375245 A1 | 12/2016 | Frei et al. |
| 2016/0375259 A1 | 12/2016 | Davis et al. |
| 2016/0378608 A1 | 12/2016 | Kong et al. |
| 2016/0378965 A1 | 12/2016 | Choe et al. |

(56)  References Cited

U.S. PATENT DOCUMENTS

| | | | |
|---|---|---|---|
| 2017/0000324 A1 | 1/2017 | Samec et al. |
| 2017/0000325 A1 | 1/2017 | Samec et al. |
| 2017/0000326 A1 | 1/2017 | Samec et al. |
| 2017/0000329 A1 | 1/2017 | Samec et al. |
| 2017/0000330 A1 | 1/2017 | Samec et al. |
| 2017/0000331 A1 | 1/2017 | Samec et al. |
| 2017/0000332 A1 | 1/2017 | Samec et al. |
| 2017/0000333 A1 | 1/2017 | Samec et al. |
| 2017/0000334 A1 | 1/2017 | Samec et al. |
| 2017/0000335 A1 | 1/2017 | Samec et al. |
| 2017/0000337 A1 | 1/2017 | Samec et al. |
| 2017/0000340 A1 | 1/2017 | Samec et al. |
| 2017/0000341 A1 | 1/2017 | Samec et al. |
| 2017/0000342 A1 | 1/2017 | Samec et al. |
| 2017/0000343 A1 | 1/2017 | Samec et al. |
| 2017/0000345 A1 | 1/2017 | Samec et al. |
| 2017/0000404 A1 | 1/2017 | Leininger et al. |
| 2017/0000422 A1 | 1/2017 | Moturu et al. |
| 2017/0000454 A1 | 1/2017 | Samec et al. |
| 2017/0000683 A1 | 1/2017 | Samec et al. |
| 2017/0001016 A1 | 1/2017 | De Ridder |
| 2017/0001032 A1 | 1/2017 | Samec et al. |
| 2017/0006931 A1 | 1/2017 | Guez et al. |
| 2017/0007111 A1 | 1/2017 | Samec et al. |
| 2017/0007115 A1 | 1/2017 | Samec et al. |
| 2017/0007116 A1 | 1/2017 | Samec et al. |
| 2017/0007122 A1 | 1/2017 | Samec et al. |
| 2017/0007123 A1 | 1/2017 | Samec et al. |
| 2017/0007165 A1 | 1/2017 | Jain et al. |
| 2017/0007173 A1 | 1/2017 | Adamczyk et al. |
| 2017/0007182 A1 | 1/2017 | Samec et al. |
| 2017/0007450 A1 | 1/2017 | Samec et al. |
| 2017/0007799 A1 | 1/2017 | Samec et al. |
| 2017/0007820 A9 | 1/2017 | Simon et al. |
| 2017/0007828 A1 | 1/2017 | Monteiro |
| 2017/0007843 A1 | 1/2017 | Samec et al. |
| 2017/0010469 A1 | 1/2017 | Samec et al. |
| 2017/0010470 A1 | 1/2017 | Samec et al. |
| 2017/0013562 A1 | 1/2017 | Lim et al. |
| 2017/0014037 A1 | 1/2017 | Coppola et al. |
| 2017/0014080 A1 | 1/2017 | Barber et al. |
| 2017/0014083 A1 | 1/2017 | Diab et al. |
| 2017/0014625 A1 | 1/2017 | Rosenbluth et al. |
| 2017/0014630 A1 | 1/2017 | Fried et al. |
| 2017/0017083 A1 | 1/2017 | Samec et al. |
| 2017/0020434 A1 | 1/2017 | Walker et al. |
| 2017/0020447 A1 | 1/2017 | Grossman et al. |
| 2017/0020454 A1 | 1/2017 | Keteyian et al. |
| 2017/0020627 A1 | 1/2017 | Tesar et al. |
| 2017/0021158 A1 | 1/2017 | Wingeier et al. |
| 2017/0021161 A1 | 1/2017 | De Ridder |
| 2017/0024886 A1 | 1/2017 | Dickrell et al. |
| 2017/0027467 A1 | 2/2017 | Hagedorn |
| 2017/0027517 A9 | 2/2017 | Le et al. |
| 2017/0027521 A1 | 2/2017 | Geva et al. |
| 2017/0027539 A1 | 2/2017 | Uber |
| 2017/0027651 A1 | 2/2017 | Esterberg |
| 2017/0027812 A1 | 2/2017 | Hyde et al. |
| 2017/0028563 A1 | 2/2017 | Hemken |
| 2017/0031440 A1 | 2/2017 | Randolph |
| 2017/0031441 A1 | 2/2017 | Muller et al. |
| 2017/0032098 A1 | 2/2017 | Ghorbanian et al. |
| 2017/0032221 A1 | 2/2017 | Wu et al. |
| 2017/0032524 A1 | 2/2017 | Dickrell et al. |
| 2017/0032527 A1 | 2/2017 | Murthy et al. |
| 2017/0032544 A1 | 2/2017 | Dempsey et al. |
| 2017/0034638 A1 | 2/2017 | Anastas |
| 2017/0035309 A1 | 2/2017 | Kang et al. |
| 2017/0035317 A1 | 2/2017 | Jung et al. |
| 2017/0035344 A1 | 2/2017 | Tzvieli et al. |
| 2017/0035392 A1 | 2/2017 | Grunwald et al. |
| 2017/0036024 A1 | 2/2017 | Hershey et al. |
| 2017/0039591 A1 | 2/2017 | Knight et al. |
| 2017/0039706 A1 | 2/2017 | Mikhno et al. |
| 2017/0041699 A1 | 2/2017 | Mackellar et al. |
| 2017/0042430 A1 | 2/2017 | Kovacs |
| 2017/0042444 A1 | 2/2017 | Bardy et al. |
| 2017/0042469 A1 | 2/2017 | Prerau et al. |
| 2017/0042474 A1 | 2/2017 | Widge et al. |
| 2017/0042475 A1 | 2/2017 | Verghese et al. |
| 2017/0042476 A1 | 2/2017 | Reiman |
| 2017/0042485 A1 | 2/2017 | Chung et al. |
| 2017/0042713 A1 | 2/2017 | Nurmikko et al. |
| 2017/0042827 A1 | 2/2017 | Margel et al. |
| 2017/0043160 A1 | 2/2017 | Goodall et al. |
| 2017/0043166 A1 | 2/2017 | Choi et al. |
| 2017/0043167 A1 | 2/2017 | Widge et al. |
| 2017/0043178 A1 | 2/2017 | Vo-Dinh et al. |
| 2017/0045601 A1 | 2/2017 | Akhtari |
| 2017/0046052 A1 | 2/2017 | Lee et al. |
| 2017/0046971 A1 | 2/2017 | Moreno |
| 2017/0050046 A1 | 2/2017 | Walder et al. |
| 2017/0052170 A1 | 2/2017 | Shekdar et al. |
| 2017/0053082 A1 | 2/2017 | Pereira et al. |
| 2017/0053088 A1 | 2/2017 | Walker et al. |
| 2017/0053092 A1 | 2/2017 | Taylor |
| 2017/0053461 A1 | 2/2017 | Pal et al. |
| 2017/0053513 A1 | 2/2017 | Savolainen et al. |
| 2017/0053665 A1 | 2/2017 | Quatieri, Jr. et al. |
| 2017/0055839 A1 | 3/2017 | Levinson et al. |
| 2017/0055898 A1 | 3/2017 | Bandyopadhyay et al. |
| 2017/0055900 A1 | 3/2017 | Jain et al. |
| 2017/0055913 A1 | 3/2017 | Bandyopadhyay et al. |
| 2017/0056363 A1 | 3/2017 | Goodenowe |
| 2017/0056467 A1 | 3/2017 | Deisseroth et al. |
| 2017/0056642 A1 | 3/2017 | Moffitt et al. |
| 2017/0056655 A1 | 3/2017 | Lineaweaver |
| 2017/0056663 A1 | 3/2017 | Kaemmerer et al. |
| 2017/0060298 A1 | 3/2017 | Hwang et al. |
| 2017/0061034 A1 | 3/2017 | Ritchey et al. |
| 2017/0061589 A1 | 3/2017 | Kuo et al. |
| 2017/0061760 A1 | 3/2017 | Lee et al. |
| 2017/0065199 A1 | 3/2017 | Meisel |
| 2017/0065218 A1 | 3/2017 | Leininger et al. |
| 2017/0065229 A1 | 3/2017 | Howard |
| 2017/0065349 A1 | 3/2017 | Ourselin et al. |
| 2017/0065379 A1 | 3/2017 | Cowburn et al. |
| 2017/0065638 A1 | 3/2017 | Fraser |
| 2017/0065816 A1 | 3/2017 | Wingeier et al. |
| 2017/0066806 A1 | 3/2017 | Deisseroth et al. |
| 2017/0067323 A1 | 3/2017 | Katterbauer et al. |
| 2017/0069306 A1 | 3/2017 | Asaei et al. |
| 2017/0071495 A1 | 3/2017 | Denison et al. |
| 2017/0071521 A1 | 3/2017 | Mestha et al. |
| 2017/0071523 A1 | 3/2017 | Jain et al. |
| 2017/0071529 A1 | 3/2017 | Haugland et al. |
| 2017/0071532 A1 | 3/2017 | Greco |
| 2017/0071537 A1 | 3/2017 | Jain et al. |
| 2017/0071546 A1 | 3/2017 | Jain et al. |
| 2017/0071551 A1 | 3/2017 | Jain et al. |
| 2017/0071552 A1 | 3/2017 | Harpe et al. |
| 2017/0076452 A1 | 3/2017 | Yui et al. |
| 2017/0079538 A1 | 3/2017 | Liang et al. |
| 2017/0079543 A1 | 3/2017 | Sadeghian-Motahar |
| 2017/0079573 A1 | 3/2017 | Osorio |
| 2017/0079588 A1 | 3/2017 | Ghaffari et al. |
| 2017/0079589 A1 | 3/2017 | Ghaffari et al. |
| 2017/0079596 A1 | 3/2017 | Teixeira |
| 2017/0080050 A1 | 3/2017 | Deisseroth et al. |
| 2017/0080234 A1 | 3/2017 | Gillespie et al. |
| 2017/0080256 A1 | 3/2017 | Kim et al. |
| 2017/0080320 A1 | 3/2017 | Smith |
| 2017/0084175 A1 | 3/2017 | Sedlik et al. |
| 2017/0084187 A1 | 3/2017 | Mollicone et al. |
| 2017/0085547 A1 | 3/2017 | De Aguiar et al. |
| 2017/0085855 A1 | 3/2017 | Roberts et al. |
| 2017/0086672 A1 | 3/2017 | Tran |
| 2017/0086695 A1 | 3/2017 | Mullins et al. |
| 2017/0086727 A1 | 3/2017 | Dagum |
| 2017/0086729 A1 | 3/2017 | Bruno |
| 2017/0086763 A1 | 3/2017 | Verma et al. |
| 2017/0087302 A1 | 3/2017 | Osorio |
| 2017/0087330 A1 | 3/2017 | Kahn et al. |
| 2017/0087354 A1 | 3/2017 | Stevenson et al. |

(56)　　　　References Cited

U.S. PATENT DOCUMENTS

| | | |
|---|---|---|
| 2017/0087355 A1 | 3/2017 | Stevenson et al. |
| 2017/0087356 A1 | 3/2017 | Stevenson et al. |
| 2017/0087364 A1 | 3/2017 | Cartledge et al. |
| 2017/0087367 A1 | 3/2017 | Weisend |
| 2017/0090475 A1 | 3/2017 | Choi et al. |
| 2017/0091418 A1 | 3/2017 | Chen et al. |
| 2017/0091567 A1 | 3/2017 | Wang et al. |
| 2017/0094385 A1 | 3/2017 | Lee et al. |
| 2017/0095157 A1 | 4/2017 | Tzvieli et al. |
| 2017/0095174 A1 | 4/2017 | Fokas et al. |
| 2017/0095199 A1 | 4/2017 | Kranck |
| 2017/0095670 A1 | 4/2017 | Ghaffari et al. |
| 2017/0095676 A1 | 4/2017 | Caparso et al. |
| 2017/0095721 A1 | 4/2017 | Bleich et al. |
| 2017/0099479 A1 | 4/2017 | Browd et al. |
| 2017/0099713 A1 | 4/2017 | Perez et al. |
| 2017/0100051 A1 | 4/2017 | Honkura |
| 2017/0100540 A1 | 4/2017 | Hyde et al. |
| 2017/0100591 A1 | 4/2017 | Nudo et al. |
| 2017/0103440 A1 | 4/2017 | Xing et al. |
| 2017/0105647 A1 | 4/2017 | Duffy |
| 2017/0106193 A1 | 4/2017 | Carcieri |
| 2017/0107575 A1 | 4/2017 | Umansky et al. |
| 2017/0108926 A1 | 4/2017 | Moon et al. |
| 2017/0112379 A1 | 4/2017 | Swiston et al. |
| 2017/0112403 A1 | 4/2017 | Doidge et al. |
| 2017/0112427 A1 | 4/2017 | Simon et al. |
| 2017/0112446 A1 | 4/2017 | Dagum |
| 2017/0112577 A1 | 4/2017 | Bonutti et al. |
| 2017/0112671 A1 | 4/2017 | Goldstein |
| 2017/0112947 A1 | 4/2017 | Abebe |
| 2017/0113042 A1 | 4/2017 | Goodall et al. |
| 2017/0113046 A1 | 4/2017 | Fried et al. |
| 2017/0113056 A1 | 4/2017 | Stocco et al. |
| 2017/0113057 A1 | 4/2017 | Goodall et al. |
| 2017/0117866 A1 | 4/2017 | Stevenson et al. |
| 2017/0119270 A1 | 5/2017 | Juan et al. |
| 2017/0119271 A1 | 5/2017 | Leuthardt et al. |
| 2017/0119994 A1 | 5/2017 | Argaman |
| 2017/0120041 A1 | 5/2017 | Wenger et al. |
| 2017/0120043 A1 | 5/2017 | John |
| 2017/0120052 A9 | 5/2017 | Simon et al. |
| 2017/0120054 A1 | 5/2017 | Moffitt et al. |
| 2017/0120066 A1 | 5/2017 | Phillips et al. |
| 2017/0127727 A1 | 5/2017 | Davidson et al. |
| 2017/0127946 A1 | 5/2017 | Levinson et al. |
| 2017/0128006 A1 | 5/2017 | Seo et al. |
| 2017/0128015 A1 | 5/2017 | Rogers et al. |
| 2017/0128032 A1 | 5/2017 | Buchert et al. |
| 2017/0131293 A1 | 5/2017 | Haslett et al. |
| 2017/0132816 A1 | 5/2017 | Aston et al. |
| 2017/0133576 A1 | 5/2017 | Marcus et al. |
| 2017/0133577 A1 | 5/2017 | Cybart et al. |
| 2017/0135594 A1 | 5/2017 | Hartings et al. |
| 2017/0135597 A1 | 5/2017 | Mann |
| 2017/0135604 A1 | 5/2017 | Kent et al. |
| 2017/0135626 A1 | 5/2017 | Singer |
| 2017/0135629 A1 | 5/2017 | Kent et al. |
| 2017/0135631 A1 | 5/2017 | Zuckerman-Stark et al. |
| 2017/0135633 A1 | 5/2017 | Connor |
| 2017/0135640 A1 | 5/2017 | Gunasekar et al. |
| 2017/0136238 A1 | 5/2017 | Hartig et al. |
| 2017/0136240 A1 | 5/2017 | Mogul |
| 2017/0136264 A1 | 5/2017 | Hyde et al. |
| 2017/0136265 A1 | 5/2017 | Hyde et al. |
| 2017/0138132 A1 | 5/2017 | Wilson et al. |
| 2017/0140124 A1 | 5/2017 | Sehgal et al. |
| 2017/0143231 A1 | 5/2017 | Ostberg et al. |
| 2017/0143249 A1 | 5/2017 | Davis et al. |
| 2017/0143255 A1 | 5/2017 | Babaeizadeh et al. |
| 2017/0143257 A1 | 5/2017 | Kent et al. |
| 2017/0143259 A1 | 5/2017 | Kent et al. |
| 2017/0143266 A1 | 5/2017 | Kovacs et al. |
| 2017/0143267 A1 | 5/2017 | Kovacs et al. |
| 2017/0143268 A1 | 5/2017 | Kovacs et al. |
| 2017/0143273 A1 | 5/2017 | Osorio et al. |
| 2017/0143280 A1 | 5/2017 | Kent et al. |
| 2017/0143282 A1 | 5/2017 | Kovacs et al. |
| 2017/0143442 A1 | 5/2017 | Tesar et al. |
| 2017/0143550 A1 | 5/2017 | Kilgard et al. |
| 2017/0143960 A1 | 5/2017 | Kent et al. |
| 2017/0143963 A1 | 5/2017 | Osorio |
| 2017/0143966 A1 | 5/2017 | Reymers et al. |
| 2017/0143986 A1 | 5/2017 | Deisseroth et al. |
| 2017/0146386 A1 | 5/2017 | Wiard et al. |
| 2017/0146387 A1 | 5/2017 | Wiard et al. |
| 2017/0146390 A1 | 5/2017 | Kovacs |
| 2017/0146391 A1 | 5/2017 | Kovacs et al. |
| 2017/0146615 A1 | 5/2017 | Wolf et al. |
| 2017/0146801 A1 | 5/2017 | Stempora |
| 2017/0147578 A1 | 5/2017 | Hecht et al. |
| 2017/0147754 A1 | 5/2017 | Kovacs |
| 2017/0148213 A1 | 5/2017 | Thomas et al. |
| 2017/0148240 A1 | 5/2017 | Kovacs et al. |
| 2017/0148340 A1 | 5/2017 | Popa-Simil et al. |
| 2017/0148592 A1 | 5/2017 | Tabib-Azir |
| 2017/0149945 A1 | 5/2017 | Lee et al. |
| 2017/0150896 A9 | 6/2017 | Lu et al. |
| 2017/0150916 A1 | 6/2017 | Osorio |
| 2017/0150921 A1 | 6/2017 | Yun et al. |
| 2017/0150925 A1 | 6/2017 | Jung |
| 2017/0151433 A1 | 6/2017 | Simon et al. |
| 2017/0151435 A1 | 6/2017 | Deadwyler et al. |
| 2017/0151436 A1 | 6/2017 | Flaherty et al. |
| 2017/0154167 A1 | 6/2017 | Ovtchinnikov |
| 2017/0156593 A1 | 6/2017 | Ferber et al. |
| 2017/0156606 A1 | 6/2017 | Ferber et al. |
| 2017/0156622 A1 | 6/2017 | Mahoor et al. |
| 2017/0156655 A1 | 6/2017 | Austin et al. |
| 2017/0156662 A1 | 6/2017 | Goodall et al. |
| 2017/0156674 A1 | 6/2017 | Hochman |
| 2017/0157343 A1 | 6/2017 | Davidson et al. |
| 2017/0157402 A1 | 6/2017 | Osorio |
| 2017/0157410 A1 | 6/2017 | Moffitt et al. |
| 2017/0160360 A1 | 6/2017 | Deisseroth et al. |
| 2017/0162072 A1 | 6/2017 | Horseman et al. |
| 2017/0164861 A1 | 6/2017 | Cahan et al. |
| 2017/0164862 A1 | 6/2017 | Dolev et al. |
| 2017/0164876 A1 | 6/2017 | Hyde et al. |
| 2017/0164878 A1 | 6/2017 | Connor |
| 2017/0164893 A1 | 6/2017 | Narayan et al. |
| 2017/0164894 A1 | 6/2017 | Yoo et al. |
| 2017/0164895 A1 | 6/2017 | Howard |
| 2017/0164901 A1 | 6/2017 | Shusterman |
| 2017/0165020 A1 | 6/2017 | Martel |
| 2017/0165481 A1 | 6/2017 | Menon |
| 2017/0165496 A1 | 6/2017 | Pilla et al. |
| 2017/0168121 A1 | 6/2017 | Yu et al. |
| 2017/0168566 A1 | 6/2017 | Osterhout et al. |
| 2017/0168568 A1 | 6/2017 | Petrov |
| 2017/0169714 A1 | 6/2017 | Lin et al. |
| 2017/0171441 A1 | 6/2017 | Kearns et al. |
| 2017/0172414 A1 | 6/2017 | Nierenberg et al. |
| 2017/0172446 A1 | 6/2017 | Kuzum et al. |
| 2017/0172499 A1 | 6/2017 | Yoo |
| 2017/0172501 A1 | 6/2017 | Badower et al. |
| 2017/0172520 A1 | 6/2017 | Kannan et al. |
| 2017/0172527 A1 | 6/2017 | Uber |
| 2017/0173262 A1 | 6/2017 | Veltz |
| 2017/0173326 A1 | 6/2017 | Bloch et al. |
| 2017/0173391 A1 | 6/2017 | Wiebe et al. |
| 2017/0177023 A1 | 6/2017 | Simon et al. |
| 2017/0178001 A1 | 6/2017 | Anderson et al. |
| 2017/0178340 A1 | 6/2017 | Schadewaldt et al. |
| 2017/0180558 A1 | 6/2017 | Li et al. |
| 2017/0181252 A1 | 6/2017 | Wouhaybi et al. |
| 2017/0181693 A1 | 6/2017 | Kim et al. |
| 2017/0182176 A1 | 6/2017 | Satchi-Fainaro et al. |
| 2017/0182285 A1 | 6/2017 | Tyler et al. |
| 2017/0182312 A1 | 6/2017 | Durand et al. |
| 2017/0185149 A1 | 6/2017 | Oluwafemi et al. |
| 2017/0185714 A1 | 6/2017 | Halter et al. |
| 2017/0185741 A1 | 6/2017 | Moffitt et al. |
| 2017/0188862 A1 | 7/2017 | Kale et al. |

(56)             References Cited

U.S. PATENT DOCUMENTS

| | | | |
|---|---|---|---|
| 2017/0188865 | A1 | 7/2017 | Nierenberg et al. |
| 2017/0188866 | A1 | 7/2017 | Kale et al. |
| 2017/0188868 | A1 | 7/2017 | Kale et al. |
| 2017/0188869 | A1 | 7/2017 | Kale et al. |
| 2017/0188870 | A1 | 7/2017 | Hilty |
| 2017/0188872 | A1 | 7/2017 | Hughes et al. |
| 2017/0188876 | A1 | 7/2017 | Marci et al. |
| 2017/0188905 | A1 | 7/2017 | Lee et al. |
| 2017/0188916 | A1 | 7/2017 | Wang et al. |
| 2017/0188922 | A1 | 7/2017 | Lee et al. |
| 2017/0188932 | A1 | 7/2017 | Singer et al. |
| 2017/0188933 | A1 | 7/2017 | Huggins et al. |
| 2017/0188947 | A1 | 7/2017 | Connor |
| 2017/0188992 | A1 | 7/2017 | O'Brien et al. |
| 2017/0189685 | A1 | 7/2017 | Steinke et al. |
| 2017/0189686 | A1 | 7/2017 | Steinke et al. |
| 2017/0189687 | A1 | 7/2017 | Steinke et al. |
| 2017/0189688 | A1 | 7/2017 | Steinke et al. |
| 2017/0189689 | A1 | 7/2017 | Steinke et al. |
| 2017/0189691 | A1 | 7/2017 | De Ridder |
| 2017/0189700 | A1 | 7/2017 | Moffitt et al. |
| 2017/0189707 | A1 | 7/2017 | Zabara |
| 2017/0190765 | A1 | 7/2017 | El-Agnaf |
| 2017/0193161 | A1 | 7/2017 | Sapiro et al. |
| 2017/0193831 | A1 | 7/2017 | Walter et al. |
| 2017/0196497 | A1 | 7/2017 | Ray et al. |
| 2017/0196501 | A1 | 7/2017 | Watson et al. |
| 2017/0196503 | A1 | 7/2017 | Narayan et al. |
| 2017/0196519 | A1 | 7/2017 | Miller et al. |
| 2017/0197080 | A1 | 7/2017 | Wagner et al. |
| 2017/0197081 | A1 | 7/2017 | Charlesworth et al. |
| 2017/0197086 | A1 | 7/2017 | Howard et al. |
| 2017/0198017 | A1 | 7/2017 | Deisseroth et al. |
| 2017/0198349 | A1 | 7/2017 | Rice |
| 2017/0199251 | A1 | 7/2017 | Fujii et al. |
| 2017/0202474 | A1 | 7/2017 | Banerjee et al. |
| 2017/0202475 | A1 | 7/2017 | Leuthardt |
| 2017/0202476 | A1 | 7/2017 | Desain et al. |
| 2017/0202518 | A1 | 7/2017 | Furman et al. |
| 2017/0202621 | A1 | 7/2017 | Taylor |
| 2017/0202633 | A1 | 7/2017 | Liu |
| 2017/0203154 | A1 | 7/2017 | Solinsky |
| 2017/0205259 | A1 | 7/2017 | Jang et al. |
| 2017/0206654 | A1 | 7/2017 | Shiroishi et al. |
| 2017/0206691 | A1 | 7/2017 | Harrises et al. |
| 2017/0206913 | A1 | 7/2017 | Nahman et al. |
| 2017/0209043 | A1 | 7/2017 | Gross et al. |
| 2017/0209044 | A1 | 7/2017 | Ito et al. |
| 2017/0209053 | A1 | 7/2017 | Pantelopoulos et al. |
| 2017/0209062 | A1 | 7/2017 | Iwasaki et al. |
| 2017/0209083 | A1 | 7/2017 | Zarandi et al. |
| 2017/0209094 | A1 | 7/2017 | Derchak et al. |
| 2017/0209225 | A1 | 7/2017 | Wu |
| 2017/0209389 | A1 | 7/2017 | Toth et al. |
| 2017/0209737 | A1 | 7/2017 | Tadi et al. |
| 2017/0212188 | A1 | 7/2017 | Kikitsu et al. |
| 2017/0213339 | A1 | 7/2017 | Hibbard et al. |
| 2017/0214786 | A1 | 7/2017 | Lee et al. |
| 2017/0216595 | A1 | 8/2017 | Geva et al. |
| 2017/0221206 | A1 | 8/2017 | Han et al. |
| 2017/0224990 | A1 | 8/2017 | Goldwasser et al. |
| 2017/0224994 | A1 | 8/2017 | Kilgard et al. |
| 2017/0231560 | A1 | 8/2017 | Hyde et al. |
| 2017/0239486 | A1 | 8/2017 | Suryavanshi |
| 2017/0239489 | A1 | 8/2017 | Bourke, Jr. et al. |
| 2018/0169430 | A1* | 6/2018 | Kamei ..................... A61N 5/06 |
| 2018/0221620 | A1* | 8/2018 | Metzger .................. A61B 5/38 |

FOREIGN PATENT DOCUMENTS

| | | | |
|---|---|---|---|
| WO | WO2000025668 | A1 | 9/2003 |
| WO | WO2001087153 | A1 | 9/2003 |

* cited by examiner

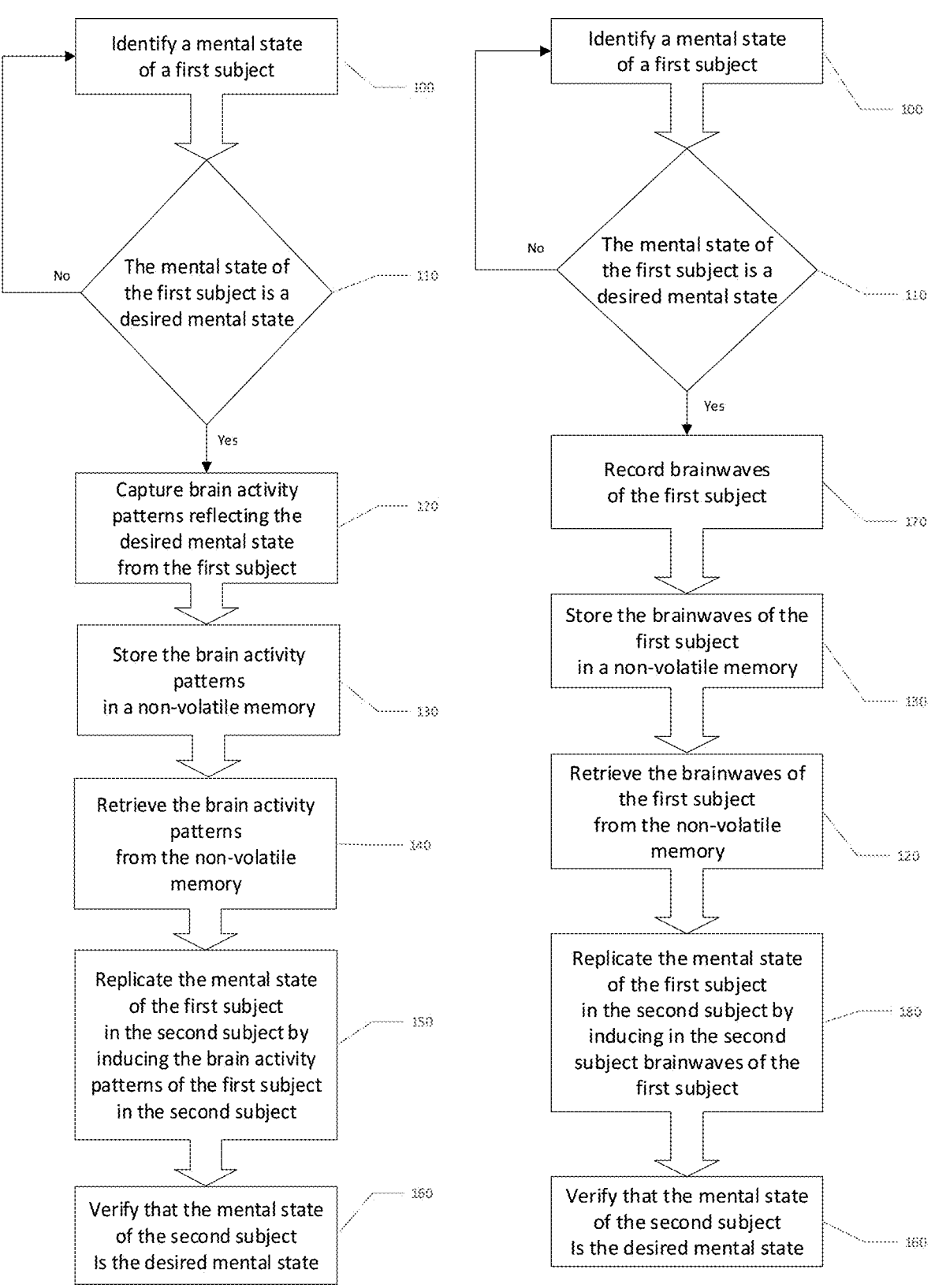
Fig. 1                                    Fig. 2

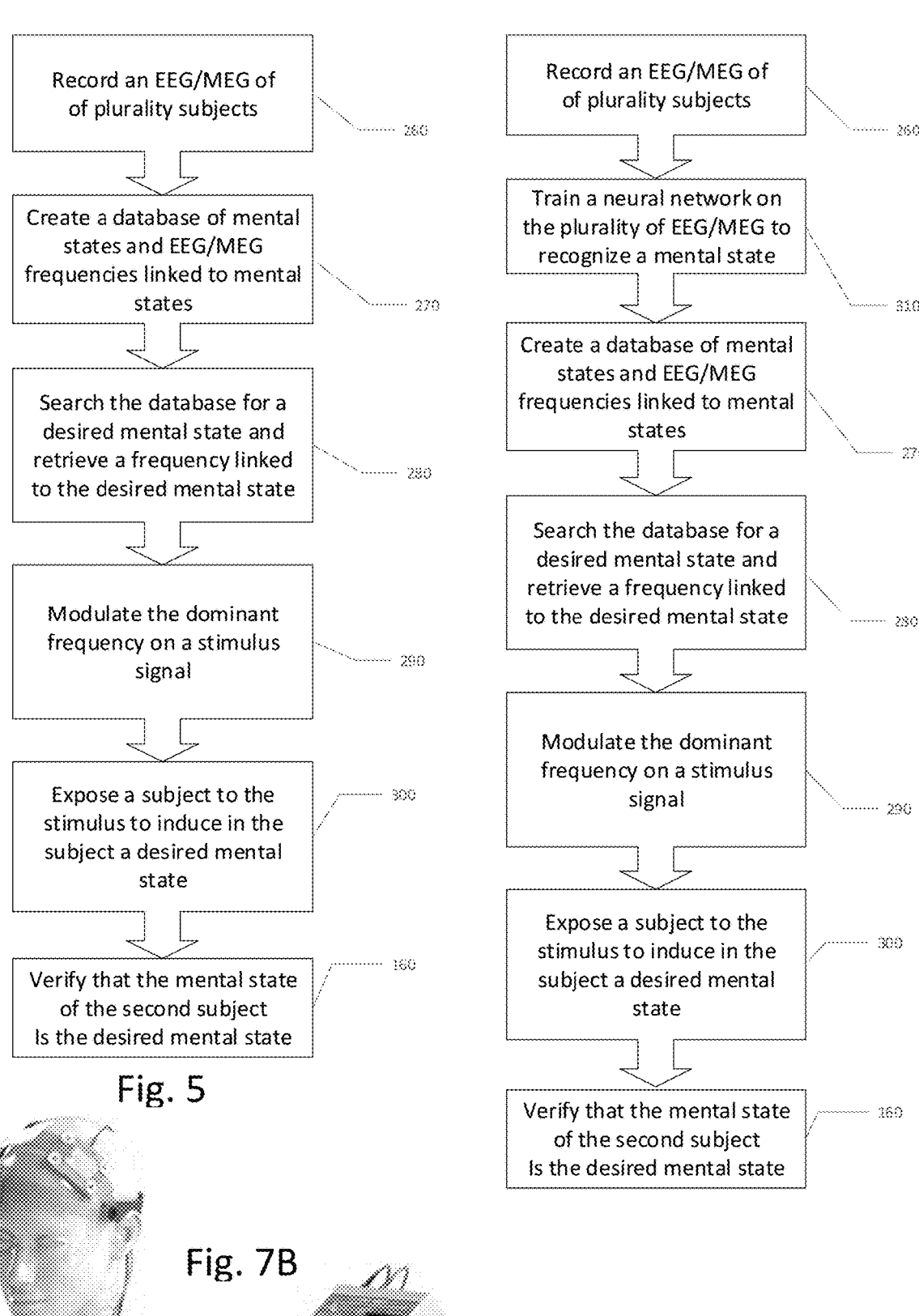

Record an EEG/MEG of
of plurality subjects
— 260

Create a database of mental
states and EEG/MEG
frequencies linked to mental
states
— 270

Search the database for a
desired mental state and
retrieve a frequency linked
to the desired mental state
— 280

Modulate the dominant
frequency on a stimulus
signal
— 290

Expose a subject to the
stimulus to induce in the
subject a desired mental
state
— 300

Verify that the mental state
of the second subject
Is the desired mental state
— 160

Fig. 5

Record an EEG/MEG of
of plurality subjects
— 260

Train a neural network on
the plurality of EEG/MEG to
recognize a mental state
— 310

Create a database of mental
states and EEG/MEG
frequencies linked to mental
states
— 270

Search the database for a
desired mental state and
retrieve a frequency linked
to the desired mental state
— 280

Modulate the dominant
frequency on a stimulus
signal
— 290

Expose a subject to the
stimulus to induce in the
subject a desired mental
state
— 300

Verify that the mental state
of the second subject
Is the desired mental state
— 160

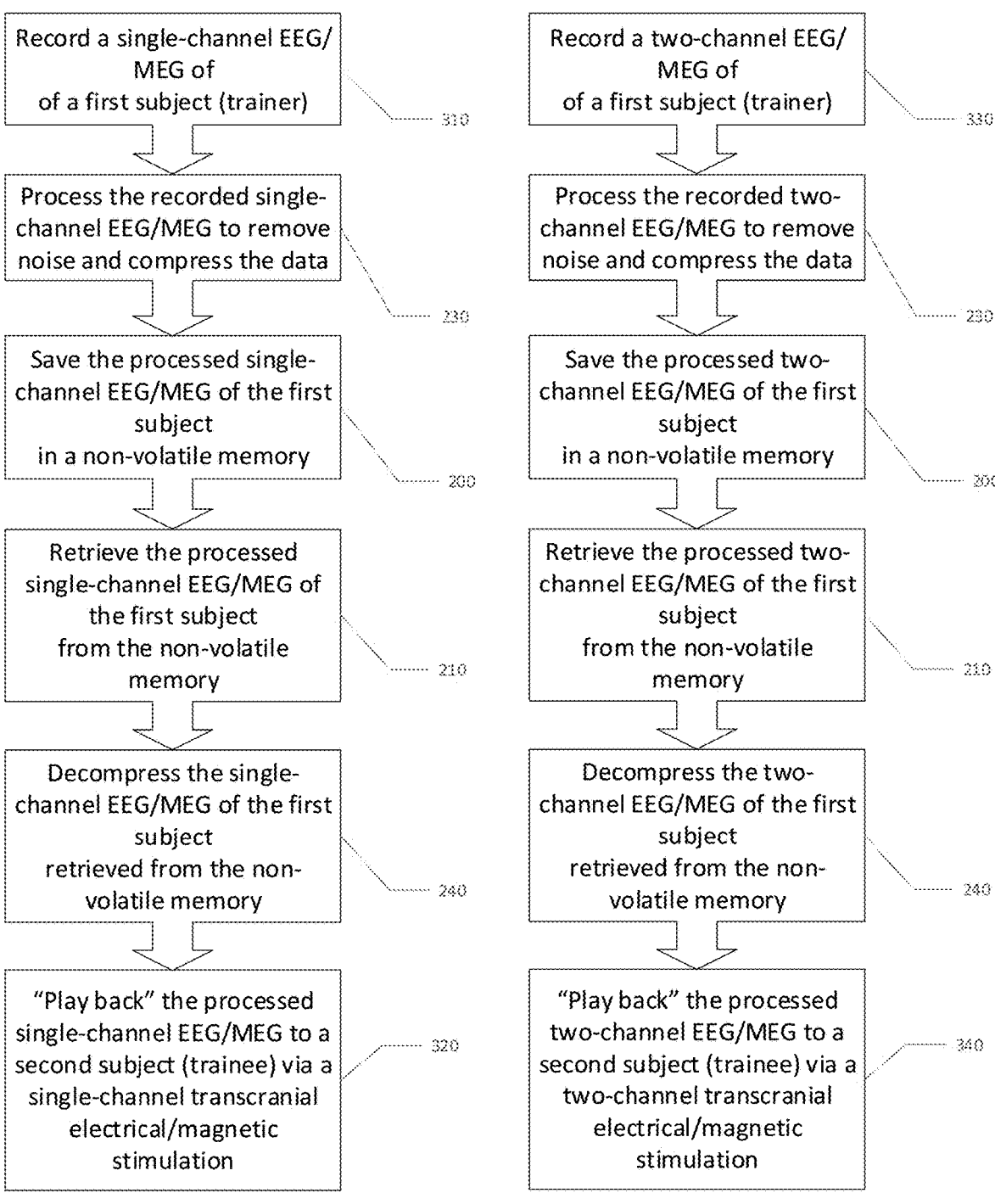
Fig. 7A                  Fig. 8

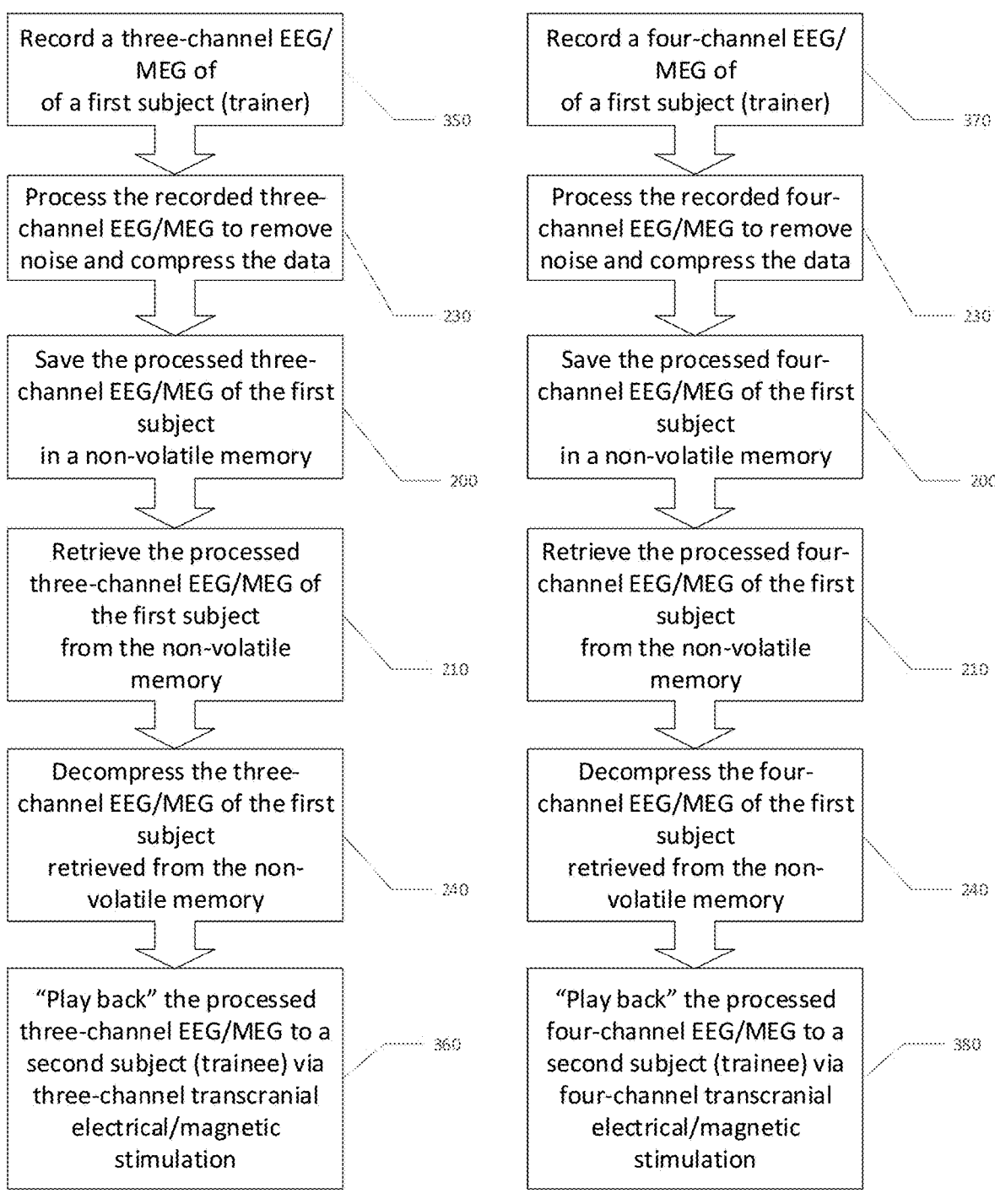

Record a three-channel EEG/MEG of
of a first subject (trainer) — 350

Process the recorded three-channel EEG/MEG to remove noise and compress the data — 230

Save the processed three-channel EEG/MEG of the first subject in a non-volatile memory — 200

Retrieve the processed three-channel EEG/MEG of the first subject from the non-volatile memory — 210

Decompress the three-channel EEG/MEG of the first subject retrieved from the non-volatile memory — 240

"Play back" the processed three-channel EEG/MEG to a second subject (trainee) via three-channel transcranial electrical/magnetic stimulation — 360

Record a four-channel EEG/MEG of
of a first subject (trainer) — 370

Process the recorded four-channel EEG/MEG to remove noise and compress the data — 230

Save the processed four-channel EEG/MEG of the first subject in a non-volatile memory — 200

Retrieve the processed four-channel EEG/MEG of the first subject from the non-volatile memory — 210

Decompress the four-channel EEG/MEG of the first subject retrieved from the non-volatile memory — 240

"Play back" the processed four-channel EEG/MEG to a second subject (trainee) via four-channel transcranial electrical/magnetic stimulation — 380

Fig. 9                    Fig. 10

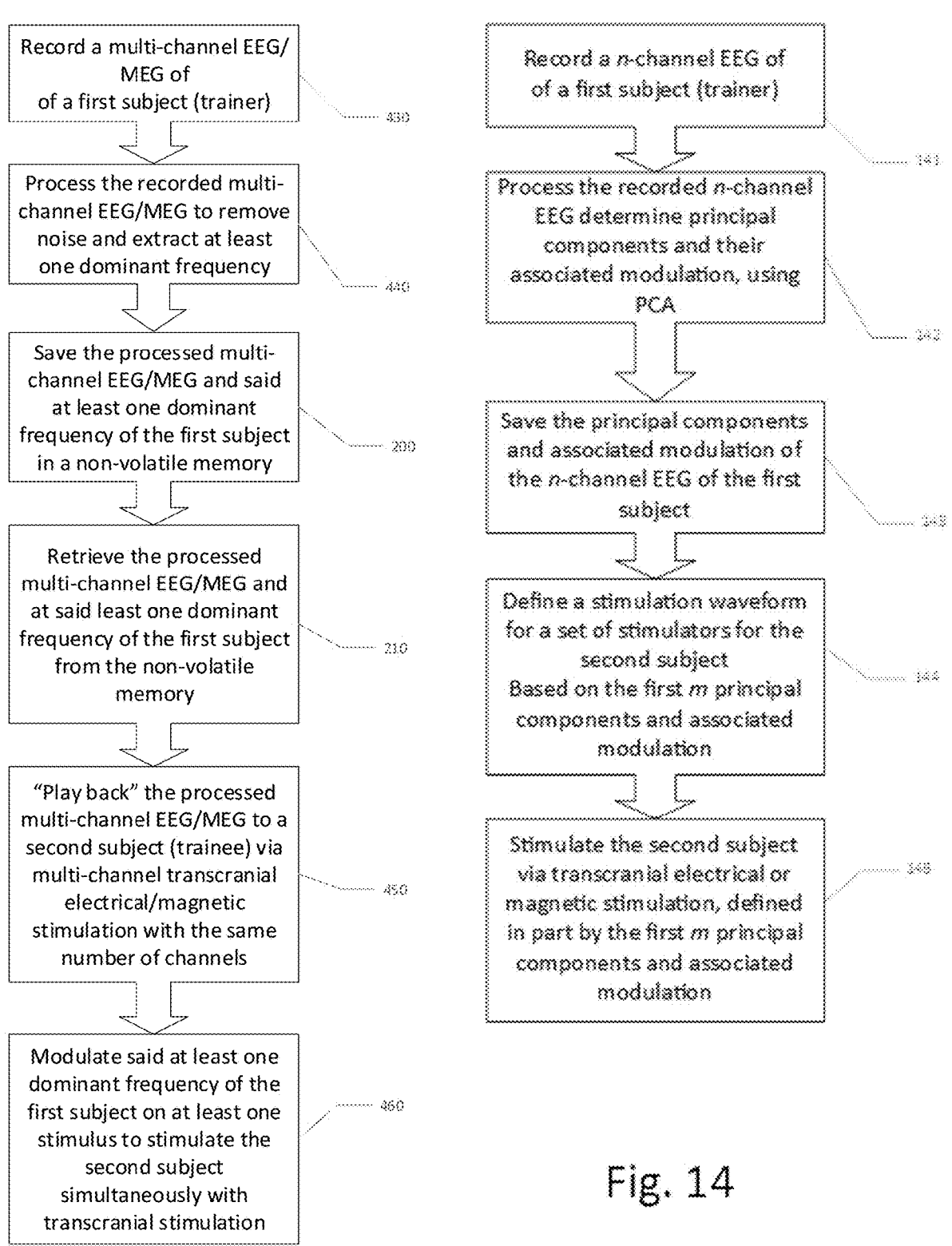

Record a multi-channel EEG/MEG of
of a first subject (trainer)                    430

Process the recorded multi-channel EEG/MEG to remove noise and extract at least one dominant frequency                    440

Save the processed multi-channel EEG/MEG and said at least one dominant frequency of the first subject in a non-volatile memory                    200

Retrieve the processed multi-channel EEG/MEG and at said least one dominant frequency of the first subject from the non-volatile memory                    210

"Play back" the processed multi-channel EEG/MEG to a second subject (trainee) via multi-channel transcranial electrical/magnetic stimulation with the same number of channels                    450

Modulate said at least one dominant frequency of the first subject on at least one stimulus to stimulate the second subject simultaneously with transcranial stimulation                    460

Fig. 13

Record a n-channel EEG of
of a first subject (trainer)                    141

Process the recorded n-channel EEG determine principal components and their associated modulation, using PCA                    142

Save the principal components and associated modulation of the n-channel EEG of the first subject                    143

Define a stimulation waveform for a set of stimulators for the second subject Based on the first m principal components and associated modulation                    144

Stimulate the second subject via transcranial electrical or magnetic stimulation, defined in part by the first m principal components and associated modulation                    146

Fig. 14

Recording EEG or MEG of a plurality of sleeping donors

Analyzing the EEG or MEG recordings using PCA or other tools to extract a temporal and/or spatial patterns representative a sleeping stage

Transforming temporal and/or Spatial Patterns representative a sleeping stage into a waveform

Modulating the waveform onto a light and/or sound stimuli

Stimulating a subject with the light and/or sound stimuli modulated with the waveform to liduce sleep

Monitoring the sleep of the subject

Fig. 17

SYSTEM AND METHOD FOR INDUCING SLEEP BY TRANSPLANTING MENTAL STATES

CROSS REFERENCE TO RELATED APPLICATIONS

This application is a Continuation of U.S. patent application Ser. No. 16/388,845, filed Apr. 19, 2019, now U.S. Pat. No. 11,364,361, issued Jun. 21, 2022, which is a non-provisional of, and claims benefit of priority from U.S. Provisional Patent Application No. 62/660,839, filed Apr. 20, 2018, which is expressly incorporated herein by reference in its entirety. This Application incorporates by reference the entirety of U.S. Provisional Patent Application No. 62/612,565, filed Dec. 31, 2017, and U.S. patent application Ser. Nos. 16/237,497, 16/237,471, and 16/237,483, filed Dec. 31, 2018.

FIELD OF THE INVENTION

The present invention generally relates to the field of neuromodulation, and more specifically to systems and methods for selectively replicating desired mental states in a human or an animal.

BACKGROUND

Mental State. A mental state is a state of mind that a subject is in. Some mental states are pure and unambiguous, while humans are capable of complex states that are a combination of mental representations, which may have in their pure state contradictory characteristics. There are several paradigmatic states of mind that a subject has: love, hate, pleasure, fear, and pain. Mental states can also include a waking state, a sleeping state, a flow (or being in the "zone"), and a mood (an emotional state). A mental state is a hypothetical state that corresponds to thinking and feeling, and consists of a conglomeration of mental representations. A mental state is related to an emotion, though it can also relate to cognitive processes. Because the mental state itself is complex and potentially possess inconsistent attributes, clear interpretation of mental state through external analysis (other than self-reporting) is difficult or impossible. However, a number of studies report that certain attributes of mental state or thought processes may in fact be determined through passive monitoring, such as EEG, with some degree of statistical reliability. In most studies, the characterization of mental state was an endpoint, and the raw signals, after statistical classification or semantic labelling, are superseded and the remaining signal energy treated as noise. Current technology does not permit an accurate or precise abstract encoding or characterization of the full range of mental states based on neural correlates of mental state.

Brain The brain is a key part of the central nervous system, enclosed in the skull. In humans, and mammals more generally, the brain controls both autonomic processes, as well as cognitive processes. The brain (and to a lesser extent, the spinal cord) controls all volitional functions of the body and interprets information from the outside world. Intelligence, memory, emotions, speech, thoughts, movements and creativity are controlled by the brain. The central nervous system also controls autonomic functions and many homeostatic and reflex actions, such as breathing, heart rate, etc.

The human brain consists of the cerebrum, cerebellum, and brainstem. The brainstem includes the midbrain, the pons, and the medulla oblongata. Sometimes the diencephalon, the caudal part of the forebrain, is included.

The brainstem provides the main motor and sensory innervation to the face and neck via the cranial nerves. Of the twelve pairs of cranial nerves, ten pairs come from the brainstem. This is an extremely important part of the brain, as the nerve connections of the motor and sensory systems from the main part of the brain to the rest of the body pass through the brainstem. This includes the corticospinal tract (motor), the posterior column-medial lemniscus pathway (fine touch, vibration sensation, and proprioception), and the spinothalamic tract (pain, temperature, itch, and crude touch). The brainstem also plays an important role in the regulation of cardiac and respiratory function. It also regulates the central nervous system and is pivotal in maintaining consciousness and regulating the sleep cycle. The brainstem has many basic functions including heart rate, breathing, sleeping, and eating.

The function of the skull is to protect delicate brain tissue from injury. The skull consists of eight fused bones: the frontal, 2 parietal, 2 temporal, sphenoid, occipital and ethmoid. The face is formed by 14 paired bones including the maxilla, zygoma, nasal, palatine, lacrimal, inferior nasal conchae, mandible, and vomer. The bony skull is separated from the brain by the dura, a membranous organ, which in turn contains cerebrospinal fluid. The cortical surface of the brain typically is not subject to localized pressure from the skull. The skull therefore imposes a barrier to electrical access to the brain functions, and in a healthy human, breaching the dura to access the brain is highly disfavored. The result is that electrical readings of brain activity are filtered by the dura, the cerebrospinal fluid, the skull, the scalp, skin appendages (e.g., hair), resulting in a loss of potential spatial resolution and amplitude of signals emanating from the brain. While magnetic fields resulting from brain electrical activity are accessible, the spatial resolution using feasible sensors is also limited.

The cerebrum is the largest part of the brain and is composed of right and left hemispheres. It performs higher functions, such as interpreting inputs from the senses, as well as speech, reasoning, emotions, learning, and fine control of movement. The surface of the cerebrum has a folded appearance called the cortex. The human cortex contains about 70% of the nerve cells (neurons) and gives an appearance of gray color (grey matter). Beneath the cortex are long connecting fibers between neurons, called axons, which make up the white matter.

The cerebellum is located behind the cerebrum and brainstem. It coordinates muscle movements, helps to maintain balance and posture. The cerebellum may also be involved in some cognitive functions such as attention and language, as well as in regulating fear and pleasure responses. There is considerable evidence that the cerebellum plays an essential role in some types of motor learning. The tasks where the cerebellum most clearly comes into play are those in which it is necessary to make fine adjustments to the way an action is performed. There is dispute about whether learning takes place within the cerebellum itself, or whether it merely serves to provide signals that promote learning in other brain structures.

The brain communicates with the body through the spinal cord and twelve pairs of cranial nerves. Ten of the twelve pairs of cranial nerves that control hearing, eye movement, facial sensations, taste, swallowing and movement of the face, neck, shoulder and tongue muscles originate in the brainstem. The cranial nerves for smell and vision originate in the cerebrum.

The right and left hemispheres of the brain are joined by a structure consisting of fibers called the corpus callosum. Each hemisphere controls the opposite side of the body. Not all functions of the hemispheres are shared.

The cerebral hemispheres have distinct structures, which divide the brain into lobes. Each hemisphere has four lobes: frontal, temporal, parietal, and occipital. There are very complex relationships between the lobes of the brain and between the right and left hemispheres: Frontal lobes control judgment, planning, problem-solving, behavior, emotions, personality, speech, self-awareness, concentration, intelligence, body movements; Temporal lobes control understanding of language, memory, organization and hearing; Parietal lobes control interpretation of language; input from vision, hearing, sensory, and motor; temperature, pain, tactile signals, memory, spatial and visual perception; and Occipital lobes interpret visual input (movement, light, color).

Neurons A neuron is a fundamental unit of the nervous system, which comprises the autonomic nervous system and the central nervous system.

Neurons are electrically excitable cells that receive, process, and transmit information, and based on that information sends a signal to other neurons, muscles, or glands through electrical and chemical signals. These signals between neurons occur via specialized connections called synapses. Neurons can connect to each other to form neural networks. The basic purpose of a neuron is to receive incoming information and, based upon that information send a signal to other neurons, muscles, or glands. Neurons are designed to rapidly send signals across physiologically long distances. They do this using electrical signals called nerve impulses or action potentials. When a nerve impulse reaches the end of a neuron, it triggers the release of a chemical, or neurotransmitter. The neurotransmitter travels rapidly across the short gap between cells (the synapse) and acts to signal the adjacent cell. See www.biologyreference.com/Mo-Nu/Neuron.html#ixzz5AVxCuM5a.

Neurons can receive thousands of inputs from other neurons through synapses. Synaptic integration is a mechanism whereby neurons integrate these inputs before the generation of a nerve impulse, or action potential. The ability of synaptic inputs to effect neuronal output is determined by a number of factors:

Size, shape and relative timing of electrical potentials generated by synaptic inputs;

the geometric structure of the target neuron;

the physical location of synaptic inputs within that structure; and the expression of voltage-gated channels in different regions of the neuronal membrane.

Neurons within a neural network receive information from, and send information to, many other cells, at specialized junctions called synapses. Synaptic integration is the computational process by which an individual neuron processes its synaptic inputs and converts them into an output signal. Synaptic potentials occur when neurotransmitter binds to and opens ligand-operated channels in the dendritic membrane, allowing ions to move into or out of the cell according to their electrochemical gradient. Synaptic potentials can be either excitatory or inhibitory depending on the direction and charge of ion movement. Action potentials occur if the summed synaptic inputs to a neuron reach a threshold level of depolarisation and trigger regenerative opening of voltage-gated ion channels. Synaptic potentials are often brief and of small amplitude, therefore summation of inputs in time (temporal summation) or from multiple synaptic inputs (spatial summation) is usually required to reach action potential firing threshold.

There are two types of synapses: electrical synapses and chemical synapses. Electrical synapses are a direct electrical coupling between two cells mediated by gap junctions, which are pores constructed of connexin proteins-essentially result in the passing of a gradient potential (may be depolarizing or hyperpolarizing) between two cells. Electrical synapses are very rapid (no synaptic delay). It is a passive process where signal can degrade with distance and may not produce a large enough depolarization to initiate an action potential in the postsynaptic cell. Electrical synapses are bidirectional, i.e., postsynaptic cell can actually send messages to the "presynaptic cell.

Chemical synapses are a coupling between two cells through neuro-transmitters, ligand or voltage gated channels, receptors. They are influenced by the concentration and types of ions on either side of the membrane. Among the neurotransmitters, Glutamate, sodium, potassium, and calcium are positively charged. GABA and chloride are negatively charged. Neurotransmitter junctions provide an opportunity for pharmacological intervention, and many different drugs, including illicit drugs, act at synapses.

An excitatory postsynaptic potential (EPSP) is a postsynaptic potential that makes the postsynaptic neuron more likely to fire an action potential. An electrical charge (hyperpolarization) in the membrane of a postsynaptic neuron is caused by the binding of an inhibitory neurotransmitter from a presynaptic cell to a postsynaptic receptor. It makes it more difficult for a postsynaptic neuron to generate an action potential. An electrical change (depolarization) in the membrane of a postsynaptic neuron caused by the binding of an excitatory neurotransmitter from a presynaptic cell to a postsynaptic receptor. It makes it more likely for a postsynaptic neuron to generate an action potential. In a neuronal synapse that uses glutamate as receptor, for example, receptors open ion channels that are non-selectively permeable to cations. When these glutamate receptors are activated, both Na+ and K+ flow across the postsynaptic membrane. The reversal potential (Erev) for the post-synaptic current is approximately 0 mV. The resting potential of neurons is approximately −60 mV. The resulting EPSP will depolarize the post synaptic membrane potential, bringing it toward 0 mV.

An inhibitory postsynaptic potential (IPSP) is a kind of synaptic potential that makes a postsynaptic neuron less likely to generate an action potential. An example of inhibitory post synaptic s action is a neuronal synapse that uses gamma-Aminobutyric acid (γ-Aminobutyric acid, or GABA) as its transmitter. At such synapses, the GABA receptors typically open channels that are selectively permeable to Cl−. When these channels open, negatively charged chloride ions can flow across the membrane. The postsynaptic neuron has a resting potential of −60 mV and an action potential threshold of −40 mV. Transmitter release at this synapse will inhibit the postsynaptic cell. Since He is more negative than the action potential threshold, e.g., −70 mV, it reduces the probability that the postsynaptic cell will fire an action potential.

Some types of neurotransmitters, such as glutamate, consistently result in EPSPs. Others, such as GABA, consistently result in IPSPs. The action potential lasts about one millisecond (1 msec). In contrast, the EPSPs and IPSPs can last as long as 5 to 10 msec. This allows the effect of one postsynaptic potential to build upon the next and so on.

Membrane leakage, and to a lesser extent, potentials per se, can be influenced by external electrical and magnetic fields. These fields may be generated focally, such as through implanted electrodes, or less specifically, such as through transcranial stimulation. Transcranial stimulation may be subthreshold or superthreshold. In the former case, the external stimulation acts to modulate resting membrane potential, making nerves more or less excitable. Such stimulation may be direct current or alternating current. In the latter case, this will tend to synchronize neuron depolarization with the signals. Superthreshold stimulation can be painful (at least because the stimulus directly excites pain neurons) and must be pulsed. Since this has correspondence to electroconvulsive therapy, superthresold transcranial stimulation is sparingly used.

Neural Correlates A neural correlate of a mental state is an electro-neuro-biological state or the state assumed by some biophysical subsystem of the brain, whose presence necessarily and regularly correlates with such specific mental state. All properties credited to the mind, including consciousness, emotion, and desires are thought to have direct neural correlates. For our purposes, neural correlates of a mental state can be defined as the minimal set of neuronal oscillations that correspond to the given mental state. Neuroscientists use empirical approaches to discover neural correlates of subjective mental states.

Brainwaves At the root of all our thoughts, emotions and behaviors is the communication between neurons within our brains, a rhythmic or repetitive neural activity in the central nervous system. The oscillation can be produced by a single neuron or by synchronized electrical pulses from ensembles of neurons communicating with each other. The interaction between neurons can give rise to oscillations at a different frequency than the firing frequency of individual neurons. The synchronized activity of large numbers of neurons produces macroscopic oscillations, which can be observed in an electroencephalogram. They are divided into bandwidths to describe their purported functions or functional relationships. Oscillatory activity in the brain is widely observed at different levels of organization and is thought to play a key role in processing neural information. Numerous experimental studies support a functional role of neural oscillations. A unified interpretation, however, is still not determined. Neural oscillations and synchronization have been linked to many cognitive functions such as information transfer, perception, motor control and memory. Electroencephalographic (EEG) signals are relatively easy and safe to acquire, have a long history of analysis, and can have high dimensionality, e.g., up to 128 or 256 separate recording electrodes. While the information represented in each electrode is not independent of the others, and the noise in the signals high, there is much information available through such signals that has not been fully characterized to date.

Brain waves have been widely studied in neural activity generated by large groups of neurons, mostly by EEG. In general, EEG signals reveal oscillatory activity in specific frequency bands: alpha (7.5-12.5 Hz) that can be detected from the occipital lobe during relaxed wakefulness and which increases when the eyes are closed; delta (1-4 Hz), theta (4-8 Hz), beta (13-30 Hz), low gamma (30-70 Hz), and high gamma (70-150) Hz) frequency bands, where faster rhythms such as gamma activity have been linked to cognitive processing. Neural oscillations of specific characteristics have been linked to cognitive states, such as awareness and consciousness and different sleep stages. It is a useful analogy to think of brainwaves as musical notes. Like in symphony, the higher and lower frequencies link and cohere with each other through harmonics. Oscillatory activity is observed throughout the central nervous system at all levels of organization. The dominant neuro oscillation frequency determines a mental state.

The functions of brain waves are wide-ranging and vary for different types of oscillatory activity. Neural oscillations also play an important role in many neurological disorders.

In standard ERG recording practice, 19 recording electrodes are placed uniformly on the scalp (the International 10-20 System). In addition, one or two reference electrodes (often placed on earlobes) and a ground electrode (often placed on the nose to provide amplifiers with reference voltages) are required. However, additional electrodes may add minimal useful information unless supplemented by computer algorithms to reduce raw EEG data to a manageable form. When large numbers of electrodes are employed, the potential at each location may be measured with respect to the average of all potentials (the common average reference), which often provides a good estimate of potential at infinity. The common average reference is not appropriate when electrode coverage is sparse (perhaps less than 64 electrodes. Dipole localization algorithms may be useful to determine spatial emission patterns in EEG.

Scalp potential may be expressed as a volume integral of dipole moment per unit volume over the entire brain provided P(r,t) is defined generally rather than in columnar terms. For the important case of dominant cortical sources, scalp potential may be approximated by the following integral over the cortical volume $\Theta$, $VS(r,t)=\iiint\Theta G(r,r')\cdot P(r',t)d\Theta(r')$. If the volume element $d\Theta(r')$ is defined in terms of cortical columns, the volume integral may be reduced to an integral over the folded cortical surface. The time-dependence of scalp potential is the weighted sum of all dipole time variations in the brain, although deep dipole volumes typically make negligible contributions. The vector Green's function $G(r\cdot r')$ contains all geometric and conductive information about the head volume conductor and weights the integral accordingly. Thus, each scalar component of the Green's function is essentially an inverse electrical distance between each source component and scalp location. For the idealized case of sources in an infinite medium of constant conductivity, the electrical distance equals the geometric distance. The Green's function accounts for the tissue's finite spatial extent and its inhomogeneity and anisotropy. The forward problem in ERG consists of choosing a head model to provide G(r,r') and carrying out the integral for some assumed source distribution. The inverse problem consists of using the recorded scalp potential distribution VS(r,t) plus some constraints (usual assumptions) on P(r,t) to find the best fit source distribution P(r,t). Since the inverse problem has no unique solution, any inverse solution depends critically on the chosen constraints, for example, only one or two isolated sources, distributed sources confined to the cortex, or spatial and temporal smoothness criteria. High-resolution EEG uses the experimental scalp potential VS(r,t) to predict the potential on the dura surface (the unfolded membrane surrounding the cerebral cortex) VD(r,t). This may be accomplished using a head model Green's function G(r,r') or by estimating the surface Laplacian with either spherical or 3D splines. These two approaches typically provide very similar dura potentials VD(r,t); the estimates of dura potential distribution are unique subject to head model, electrode density, and noise issues.

In an EEG recording system, each electrode is connected to one input of a differential amplifier (one amplifier per pair of electrodes); a common system reference electrode (or synthesized reference) is connected to the other input of each differential amplifier. These amplifiers amplify the voltage between the active electrode and the reference (typically 1,000-100,000 times, or 60-100 dB of voltage gain). The amplified signal is digitized via an analog-to-digital converter, after being passed through an anti-aliasing filter. Analog-to-digital sampling typically occurs at 256-512 Hz in clinical scalp EEG; sampling rates of up to 20 KHz are used in some research applications. The EEG signals can be captured with open source hardware such as OpenBCI, and the signal can be processed by freely available EEG software such as EEGLAB or the Neurophysiological Biomarker Toolbox. A typical adult human EEG signal is about 10 μV to 100 μV in amplitude when measured from the scalp and is about 10-20 mV when measured from subdural electrodes.

Delta is the frequency range up to 4 Hz. It tends to be the highest in amplitude and the slowest waves. It is normally seen in adults in slow-wave sleep. It is also seen normally in babies. It may occur focally with subcortical lesions and in general distribution with diffuse lesions, metabolic encephalopathy hydrocephalus or deep midline lesions. It is usually most prominent frontally in adults (e.g., FIRDA-frontal intermittent rhythmic delta) and posteriorly in children (e.g., OIRDA-occipital intermittent rhythmic delta).

Theta is the frequency range from 4 Hz to 7 Hz. Theta is normally seen in young children. It may be seen in drowsiness or arousal in older children and adults; it can also be seen in meditation. Excess theta for age represents abnormal activity. It can be seen as a focal disturbance in focal subcortical lesions; it can be seen in generalized distribution in diffuse disorder or metabolic encephalopathy or deep midline disorders or some instances of hydrocephalus. On the contrary, this range has been associated with reports of relaxed, meditative, and creative states.

Alpha is the frequency range from 7 Hz to 14 Hz. This was the "posterior basic rhythm" (also called the "posterior dominant rhythm" or the "posterior alpha rhythm"), seen in the posterior regions of the head on both sides, higher in amplitude on the dominant side. It emerges with the closing of the eyes and with relaxation and attenuates with eye opening or mental exertion. The posterior basic rhythm is actually slower than 8 Hz in young children (therefore technically in the theta range). In addition to the posterior basic rhythm, there are other normal alpha rhythms such as the sensorimotor, or mu rhythm (alpha activity in the contralateral sensory and motor cortical areas) that emerges when the hands and arms are idle; and the "third rhythm" (alpha activity in the temporal or frontal lobes). Alpha can be abnormal; for example, an EEG that has diffuse alpha occurring in coma and is not responsive to external stimuli is referred to as "alpha coma."

Beta is the frequency range from 15 Hz to about 30 Hz. It is usually seen on both sides in symmetrical distribution and is most evident frontally. Beta activity is closely linked to motor behavior and is generally attenuated during active movements. Low-amplitude beta with multiple and varying frequencies is often associated with active, busy or anxious thinking and active concentration. Rhythmic beta with a dominant set of frequencies is associated with various pathologies, such as Dup15q syndrome, and drug effects, especially benzodiazepines. It may be absent or reduced in areas of cortical damage. It is the dominant rhythm in patients who are alert or anxious or who have their eyes open.

Gamma is the frequency range approximately 30-100 Hz. Gamma rhythms are thought to represent binding of different populations of neurons together into a network to carry out a certain cognitive or motor function.

Mu range is 8-13 Hz and partly overlaps with other frequencies. It reflects the synchronous firing of motor neurons in a rest state. Mu suppression is thought to reflect motor mirror neuron systems, because when an action is observed, the pattern extinguishes, possibly because of the normal neuronal system and the mirror neuron system "go out of sync" and interfere with each other. (en.wikipedia.org/wiki/Electroencephalography)

TABLE 1

| | Freq. | | | |
|---|---|---|---|---|
| Band | (Hz) | Location | Normally | Pathologically |
| | | Comparison of EEG bands | | |
| Delta | <4 | frontally in adults, posteriorly in children; high-amplitude waves | adult slow-wave sleep in babies Has been found during some continuous-attention tasks | subcortical lesions diffuse lesions metabolic encephalopathy hydrocephalus deep midline lesions |
| Theta | 4-7 | Found in locations not related to task at hand | higher in young children drowsiness in adults and teens idling Associated with inhibition of elicited responses (has been found to spike in situations where a person is actively trying to repress a response or action). | focal subcortical lesions metabolic encephalopathy deep midline disorders some instances of hydrocephalus |
| Alpha | 8-15 | posterior regions of head, both sides, higher in amplitude on dominant side. Central sites (c3-c4) at rest | relaxed/reflecting closing the eyes Also associated with inhibition control, seemingly with the purpose of timing inhibitory activity in different locations across the brain. | Coma |
| Beta | 16-31 | both sides, symmetrical distribution, most evident frontally; low-amplitude waves | range span: active calm → intense → stressed → mild obsessive active thinking, focus, high alert, anxious | benzodiazepines Dup15q syndrome |

TABLE 1-continued

Comparison of EEG bands

| Band | Freq. (Hz) | Location | Normally | Pathologically |
|------|------------|----------|----------|----------------|
| Gamma | >32 | Somatosensory cortex | Displays during cross-modal sensory processing (perception that combines two different senses, such as sound and sight) Also is shown during short-term memory matching of recognized objects, sounds, or tactile sensations | A decrease in gamma-band activity may be associated with cognitive decline, especially when related to the theta band; however, this has not been proven for use as a clinical diagnostic measurement |
| Mu | 8-12 | Sensorimotor cortex | Shows rest-state motor neurons. | Mu suppression could indicate that motor mirror neurons are working. Deficits in Mu suppression, and thus in mirror neurons, might play a role in autism. |

Neurodynamics Neurodynamics is the mobilization of the nervous system as an approach to physical treatment. The method relies on influencing pain and other neural physiology via mechanical treatment of neural tissues and the non-neural structures surrounding the nervous system. The body presents the nervous system with a mechanical interface via the musculoskeletal system. With movement, the musculoskeletal system exerts non-uniform stresses and movement in neural tissues, depending on the local anatomical and mechanical characteristics and the pattern of body movement. This activates an array of mechanical and physiological responses in neural tissues. These responses include neural sliding, pressurization, elongation, tension and changes in intraneural microcirculation, axonal transport and impulse traffic.

EEG and qEEG EEG (electroencephalography) and MEG (magnetoencephalography) are available technologies to monitor brain electrical activity. Each generally has sufficient temporal resolution to follow dynamic changes in brain electrical activity. Electroencephalography (EEG) and quantitative electroencephalography (qEEG) are electrophysiological monitoring methods that analyze the electrical activity of the brain to measure and display patterns that correspond to cognitive states and/or diagnostic information. It is typically noninvasive, with the electrodes placed on the scalp, although invasive electrodes are also used in some cases. EEG signals may be captured and analyzed by a mobile device, often referred as "brain wearables". There are a variety of "brain wearables" readily available on the market today. EEGs can be obtained with a non-invasive method where the aggregate oscillations of brain electric potentials are recorded with numerous electrodes attached to the scalp of a person. Most EEG signals originate in the brain's outer layer (the cerebral cortex), believed largely responsible for our thoughts, emotions, and behavior. Cortical synaptic action generates electrical signals that change in the 10 to 100-millisecond range. Transcutaneous EEG signals are limited by the relatively insulating nature of the skull surrounding the brain, the conductivity of the cerebrospinal fluid and brain tissue, relatively low amplitude of individual cellular electrical activity, and distances between the cellular current flows and the electrodes. EEG is characterized by: (1) Voltage; (2) Frequency: (3) Spatial location; (4) Inter-hemispheric symmetries; (5) Reactivity (reaction to state change); (6) Character of waveform occurrence (random, serial, continuous); and (7) Morphology of transient events. EEGs can be separated into two main categories. Spontaneous EEG which detect brainwaves that occur in the absence of specific sensory stimuli and evoked potentials (EPs) which are associated with sensory stimuli like repeated light flashes, auditory tones, finger pressure or mild electric shocks. The latter is recorded for example by time averaging to remove effects of spontaneous EEG. Non-sensory triggered potentials are also known. EP's typically are time synchronized with the trigger, and thus have an organization principle. Event-related potentials (ERPs) provide evidence of a direct link between cognitive events and brain electrical activity in a wide range of cognitive paradigms. It has generally been held that an ERP is the result of a set of discrete stimulus-evoked brain events. Event-related potentials (ERPs) are recorded in the same way as EPs, but occur at longer latencies from the stimuli and are more associated with an endogenous brain state.

EEG-based studies of emotional specificity at the single-electrode level demonstrated that asymmetric activity at the frontal site, especially in the alpha (8-12 Hz) band, is associated with emotion. Voluntary facial expressions of smiles of enjoyment produce higher left frontal activation. Decreased left frontal activity is observed during the voluntary facial expressions of fear. In addition to alpha band activity, theta band power at the frontal midline (Fm) has also been found to relate to emotional states. Pleasant (as opposed to unpleasant) emotions are associated with an increase in frontal midline theta power. Many studies have sought to utilize pattern classification, such as neural networks, statistical classifiers, clustering algorithms, etc., to differentiate between various emotional states reflected in EEG.

Detecting different emotional states by EEG may be more appropriate using EEG-based functional connectivity. There are various ways to estimate EEG-based functional brain connectivity: correlation, coherence and phase synchronization indices between each pair of EEG electrodes had been used. The assumption is that a higher correlation map indicates a stronger relationship between two signals. Coherence gives information similar to correlation, but also includes the covariation between two signals as a function of frequency. The assumption is that higher correlation indicates a stronger relationship between two signals. Phase synchronization among the neuronal groups estimated based on the phase difference between two signals is another way to estimate the EEG-based functional connectivity among brain areas.

A number of groups have examined emotional specificity using EEG-based functional brain connectivity. When emotional states become more negative at high room temperatures, correlation coefficients between the channels in temporal and occipital sites increase. Coherence decreases in the alpha band during sadness, compared to happiness. EEG coherence between the prefrontal cortex and the posterior cortex increases while viewing highly emotionally arousing (i.e., threatening) images, compared to viewing neutral images. A synchronization index may be applied to detect interaction in different brain sites under different emotional states. Test results showed an overall increase in the synchronization index among frontal channels during emotional stimulation, particularly during negative emotion (i.e., sadness). Furthermore, phase synchronization patterns were found to differ between positive and negative emotions. Sadness was more synchronized than happiness at each frequency band and was associated with a wider synchronization both between the right and left frontal sites and within the left hemisphere. In contrast, happiness was associated with a wider synchronization between the frontal and occipital sites.

Different connectivity indices are sensitive to different characteristics of EEG signals. Correlation is sensitive to phase and polarity, but is independent of amplitudes. Changes in both amplitude and phase lead to a change in coherence. The phase synchronization index is only sensitive to a change in phase. A number of studies have tried to classify emotional states by means of recording and statistically analyzing EEG signals from the central nervous systems.

These emotional states are based on the dimensional theory of emotion, which asserts that there are neutral, positive, and negative emotional states, because numerous studies have suggested that the responses of the central nervous system correlate with emotional valence and arousal. EEG-based functional connectivity change is found to be significantly different among emotional states of neutral, positive, or negative. Furthermore, the connectivity pattern was detected by pattern classification analysis using Quadratic Discriminant Analysis.

To assess a user's state of mind, a computer may be used to analyze the EEG signals produced by the brain of the user. However, the emotional states of a brain are complex, and the brain waves associated with specific emotions seem to change over time. Machine learning may be used to reliably identify the emotional brain states. A set of patterns may be defined that clearly distinguish positive, negative, and neutral emotions.

MEG Magnetoencephalography (MEG) is a functional neuroimaging technique for mapping brain activity by recording magnetic fields produced by electrical currents occurring naturally in the brain, using very sensitive magnetometers. Arrays of SQUIDs (superconducting quantum interference devices) are currently the most common magnetometer, while the SERF (spin exchange relaxation-free) magnetometer is being investigated. MEGs seek to detect the magnetic dipole emission from an electrical discharge in cells, e.g., neural action potentials. Typical sensors for MEGs are superconducting quantum interference devices (SQUIDs). These currently require cooling to liquid nitrogen or liquid helium temperatures and, therefore, are currently suitable only for laboratory environments. However, the development of room temperature, or near room temperature superconductors, and miniature cryocoolers, may permit field deployments and portable or mobile detectors. Because MEGs are less influenced by medium conductivity and dielectric properties, and because they inherently detect the magnetic field vector, MEG technology permits volumetric mapping of brain activity and distinction of complementary activity that might suppress detectable EEG signals. MEG technology also supports vector mapping of fields, since magnetic emitters are inherently dipoles, and therefore a larger amount of information is inherently available.

Functional near infrared spectroscopy (fNIRS) fNIR is a non-invasive imaging method involving the quantification of chromophore concentration resolved from the measurement of near infrared (NIR) light attenuation or temporal or phasic changes. NIR spectrum light takes advantage of the optical window in which skin, tissue, and bone are mostly transparent to NIR light in the spectrum of 700-900 nm, while hemoglobin (Hb) and deoxygenated-hemoglobin (deoxy-Hb) are stronger absorbers of light. Differences in the absorption spectra of deoxy-Hb and oxy-Hb allow the measurement of relative changes in hemoglobin concentration through the use of light attenuation at multiple wavelengths. Two or more wavelengths are selected, with one wavelength above and one below the isosbestic point of 810 nm at which deoxy-Hb and oxy-Hb have identical absorption coefficients. Using the modified Beer-Lambert law (mBLL), relative concentration can be calculated as a function of total photon path length. Typically the light emitter and detector are placed ipsilaterally on the subjects skull so recorded measurements are due to back-scattered (reflected) light following elliptical pathways. The use of fNIR as a functional imaging method relies on the principle of neuro-vascular coupling also known as the haemodynamic response or blood-oxygen-level dependent (BOLD) response. This principle also forms the core of fMRI techniques. Through neuro-vascular coupling, neuronal activity is linked to related changes in localized cerebral blood flow. fNIR and fMRI are sensitive to similar physiologic changes and are often comparative methods. Studies relating fMRI and fNIR show highly correlated results in cognitive tasks. fNIR has several advantages in cost and portability over fMRI, but cannot be used to measure cortical activity more than 4 cm deep due to limitations in light emitter power and has more limited spatial resolution. fNIR includes the use of diffuse optical tomography (DOT/NIRDOT) for functional purposes. Multiplexing fNIRS channels can allow 2D topographic functional maps of brain activity (e.g., with Hitachi ETG-4000 or Artinis Oxymon) while using multiple emitter spacings may be used to build 3D tomographic maps.

Neuromodulation/neuroenhancement Neuromodulation is the alteration of nerve activity through targeted delivery of a stimulus, such as electrical stimulation or chemical agents, to specific neurological sites in the body. It is carried out to normalize- or modulate-nervous tissue function. Neuromodulation is an evolving therapy that can involve a range of electromagnetic stimuli such as a magnetic field (rTMS), an electric current, or a drug instilled directly in the subdural space (intrathecal drug delivery). Emerging applications involve targeted introduction of genes or gene regulators and light (optogenetics), and by 2014, these had been at minimum demonstrated in mammalian models, or first-in-human data had been acquired. The most clinical experience has been with electrical stimulation. Neuromodulation, whether electrical or magnetic, employs the body's natural biological response by stimulating nerve cell activity that can influence populations of nerves by releasing transmitters, such as dopamine, or other chemical messengers such as the peptide Substance P, that can modulate the excitability and firing patterns of neural circuits. There may also be more direct electrophysiological effects on neural membranes as the mechanism of action of electrical interaction with neural elements. The end effect is a "normalization" of a neural network function from its perturbed state. Presumed mechanisms of action for neurostimulation include depolarizing blockade, stochastic normalization of neural firing, axonal blockade, reduction of neural firing keratosis, and suppression of neural network oscillations. Although the exact mechanisms of neurostimulation are not known, the empirical effectiveness has led to considerable application clinically.

Neuroenhancement refers to the targeted enhancement and extension of cognitive and affective abilities based on an understanding of their underlying neurobiology in healthy persons who do not have any mental illness. As such, it can be thought of as an umbrella term that encompasses pharmacological and non-pharmacological methods of improving cognitive, affective, and motor functionality, as well as the overarching ethico-legal discourse that accompanies these aims. Critically, for any agent to qualify as a neuroenhancer, it must reliably engender substantial cognitive, affective, or motor benefits beyond normal functioning in healthy individuals, whilst causing few side effects: at most at the level of commonly used comparable legal substances or activities, such as caffeine, alcohol, and sleep-deprivation. Pharmacological neuroenhancement agents include the well-validated nootropics, such as racetam, vinpocetine, and phosphatidylserine, as well as other drugs used for treating patients suffering from neurological disorders. Non-pharmacological measures include non-invasive brain stimulation, which has been employed to improve various cognitive and affective functions, and brain-machine interfaces, which hold much potential to extend the repertoire of motor and cognitive actions available to humans.

Brain-to-Brain interface A brain-brain interface is a direct communication pathway between the brain of one animal and the brain of another animal. Brain to brain interfaces have been used to help rats collaborate with each other. When a second rat was unable to choose the correct lever, the first rat noticed (not getting a second reward), and produced a round of task-related neuron firing that made the second rat more likely to choose the correct lever. Human studies have also been conducted. In 2013, researcher from the University of Washington were able to use electrical brain recordings and a form of magnetic stimulation to send a brain signal to a recipient, which caused the recipient to hit the fire button on a computer game. In 2015, researchers linked up multiple brains, of both monkeys and rats, to form an "organic computer." It is hypothesized that by using brain-to-brain interfaces (BTBIs) a biological computer, or brain-net, could be constructed using animal brains as its computational units. Initial exploratory work demonstrated collaboration between rats in distant cages linked by signals from cortical microelectrode arrays implanted in their brains. The rats were rewarded when actions were performed by the "decoding rat" which conformed to incoming signals and when signals were transmitted by the "encoding rat" which resulted in the desired action. In the initial experiment the rewarded action was pushing a lever in the remote location corresponding to the position of a lever near a lighted LED at the home location. About a month was required for the rats to acclimate themselves to incoming "brainwaves."

Brain-to-Computer interface A brain-computer interface (BCI), sometimes called a neural-control interface (NCI), mind-machine interface (MMI), direct neural interface (DNI), or brain-machine interface (BMI), is a direct communication pathway between an enhanced or wired brain and an external device. BCI differs from neuromodulation in that it allows for bidirectional information flow. BCIs are often directed at researching, mapping, assisting, augmenting, or repairing human cognitive or sensory-motor functions.

Brain entrainment Brainwave entrainment, also referred to as brainwave synchronization and neural entrainment, refers to the capacity of the brain to naturally synchronize its brainwave frequencies with the rhythm of periodic external stimuli, most commonly auditory, visual, or tactile. It is hypothesized that listening to these beats of certain frequencies one can induce a desired state of consciousness that corresponds with specific neural activity. It is widely accepted that patterns of neural firing, measured in Hz, correspond with states of alertness such as focused attention, deep sleep, etc.

Neural oscillations are rhythmic or repetitive electrochemical activity in the brain and central nervous system. Such oscillations can be characterized by their frequency, amplitude and phase. Neural tissue can generate oscillatory activity driven by mechanisms within individual neurons, as well as by interactions between them. They may also adjust frequency to synchronize with the periodic vibration of external acoustic or visual stimuli. The functional role of neural oscillations is still not fully understood; however, they have been shown to correlate with emotional responses, motor control, and a number of cognitive functions including information transfer, perception, and memory. Specifically, neural oscillations, in particular theta activity, are extensively linked to memory function, and coupling between theta and gamma activity is considered to be vital for memory functions, including episodic memory. Electroencephalography (EEG) has been most widely used in the study of neural activity generated by large groups of neurons, known as neural ensembles, including investigations of the changes that occur in electroencephalographic profiles during cycles of sleep and wakefulness. EEG signals change dramatically during sleep and show a transition from faster frequencies to increasingly slower frequencies, indicating a relationship between the frequency of neural oscillations and cognitive states including awareness and consciousness.

The term 'entrainment' has been used to describe a shared tendency of many physical and biological systems to synchronize their periodicity and rhythm through interaction. This tendency has been identified as specifically pertinent to the study of sound and music generally, and acoustic rhythms specifically. The most ubiquitous and familiar examples of neuromotor entrainment to acoustic stimuli is observable in spontaneous foot or finger tapping to the rhythmic beat of a song. Exogenous rhythmic entrainment, which occurs outside the body, has been identified and documented for a variety of human activities, which include the way people adjust the rhythm of their speech patterns to those of the subject with whom they communicate, and the rhythmic unison of an audience clapping. Even among groups of strangers, the rate of breathing, locomotive and subtle expressive motor movements, and rhythmic speech patterns have been observed to synchronize and entrain, in response to an auditory stimulus, such as a piece of music with a consistent rhythm. Furthermore, motor synchronization to repetitive tactile stimuli occurs in animals, including cats and monkeys as well as humans, with accompanying shifts in electroencephalogram (EEG) readings. Examples of endogenous entrainment, which occurs within the body, include the synchronizing of human circadian sleep-wake cycles to the 24-hour cycle of light and dark. and the synchronization of a heartbeat to a cardiac pacemaker.

Brainwaves, or neural oscillations, share the fundamental constituents with acoustic and optical waves, including frequency, amplitude and periodicity. The synchronous electrical activity of cortical neural ensembles can synchronize in response to external acoustic or optical stimuli and also entrain or synchronize their frequency and phase to that of a specific stimulus. Brainwave entrainment is a colloquialism for such 'neural entrainment', which is a term used to denote the way in which the aggregate frequency of oscillations produced by the synchronous electrical activity in ensembles of cortical neurons can adjust to synchronize with the periodic vibration of an external stimuli, such as a sustained acoustic frequency perceived as pitch, a regularly repeating pattern of intermittent sounds, perceived as rhythm, or of a regularly rhythmically intermittent flashing light.

Changes in neural oscillations, demonstrable through electroencephalogram (EEG) measurements, are precipitated by listening to music, which can modulate autonomic arousal ergotropically and trophotropically, increasing and decreasing arousal respectively. Musical auditory stimulation has also been demonstrated to improve immune function, facilitate relaxation, improve mood, and contribute to the alleviation of stress.

The Frequency following response (FFR), also referred to as Frequency Following Potential (FFP), is a specific response to hearing sound and music, by which neural oscillations adjust their frequency to match the rhythm of auditory stimuli. The use of sound with intent to influence cortical brainwave frequency is called auditory driving, by which frequency of neural oscillation is 'driven' to entrain with that of the rhythm of a sound source.

Neurofeedback Neurofeedback (NFB), also called neurotherapy or neurobiofeedback, is a type of biofeedback that uses real-time displays of brain activity—most commonly electroencephalography (EEG), to teach self-regulation of brain function. Typically, sensors are placed on the scalp to measure activity, with measurements displayed using video displays or sound. The feedback may be in various other forms as well. Typically, the feedback is sought to be presented through primary sensory inputs, but this is not a limitation on the technique.

The applications of neurofeedback to enhance performance extend to the arts in fields such as music, dance, and acting. A study with conservatoire musicians found that alpha-theta training benefitted the three music domains of musicality, communication, and technique. Historically, alpha-theta training, a form of neurofeedback, was created to assist creativity by inducing hypnagogia, a "borderline waking state associated with creative insights", through facilitation of neural connectivity. Alpha-theta training has also been shown to improve novice singing in children. Alpha-theta neurofeedback, in conjunction with heart rate variability training, a form of biofeedback, has also produced benefits in dance by enhancing performance in competitive ballroom dancing and increasing cognitive creativity in contemporary dancers. Additionally, neurofeedback has also been shown to instill a superior flow state in actors, possibly due to greater immersion while performing.

Transcranial Stimulation Non-invasive brain stimulation (NIBS) bypasses the correlative approaches of other imaging techniques, making it possible to establish a causal relationship between cognitive processes and the functioning of specific brain areas. NIBS can provide information about where a particular process occurs. NIBS offers the opportunity to study brain mechanisms beyond process localization, providing information about when activity in a given brain region is involved in a cognitive process, and even how it is involved. When using NIBS to explore cognitive processes, it is important to understand not only how NIBS functions but also the functioning of the neural structures themselves. Non-invasive brain stimulation (NIBS) methods, which include transcranial magnetic stimulation (TMS) and transcranial electric stimulation (IES), are used in cognitive neuroscience to induce transient changes in brain activity and thereby alter the behavior of the subject. The application of NIBS aims at establishing the role of a given cortical area in an ongoing specific motor, perceptual or cognitive process. Physically, NIBS techniques affect neuronal states through different mechanisms. In TMS, a solenoid (coil) is used to deliver a strong and transient magnetic field, or "pulse," to induce a transitory electric current at the cortical surface beneath the coil. The pulse causes the rapid and above-threshold depolarisation of cell membranes affected by the current, followed by the transynaptic depolarisation or hyperpolarisation of interconnected neurons. Therefore, TMS induces a current that elicits action potentials in neurons. A complex set of coils can deliver a complex 3D excitation field. By contrast, in tES techniques, the stimulation involves the application of weak electrical currents directly to the scalp through a pair of electrodes. As a result, tES induces a subthreshold polarization of cortical neurons that is too weak to generate an action potential. However, by changing the intrinsic neuronal excitability, tES can induce changes in the resting membrane potential and the postsynaptic activity of cortical neurons. This, in turn, can alter the spontaneous firing rate of neurons and modulate their response to afferent signals, leading to changes in synaptic efficacy. The typical application of NIBS involves different types of protocols: TMS can be delivered as a single pulse (spTMS) at a precise time, as pairs of pulses separated by a variable interval, or as a series of stimuli in conventional or patterned protocols of repetitive TMS (rTMS). In tES, different protocols are established by the electrical current used and by its polarity, which can be direct (anodal or cathodal transcranial direct current stimulation: tDCS), alternating at a fixed frequency (transcranial alternating current stimulation: tACS) or at random frequencies (transcranial random noise stimulation: tRNS). In general, the final effects of NIBS on the central nervous system depend on a lengthy list of parameters (e.g., frequency, temporal characteristics, intensity, geometric configuration of the coil/electrode, current direction), when it is delivered before (off-line) or during (on-line) the task as part of the experimental procedure. In addition, these factors interact with several variables related to the anatomy (e.g., properties of the brain tissue and its location), as well as physiological (e.g., gender and age) and cognitive states of the stimulated area/subject. The entrainment hypothesis, suggests the possibility of inducing a particular oscillation frequency in the brain using an external oscillatory force (e.g., rTMS, but also tACS). The physiological basis of oscillatory cortical activity lies in the timing of the interacting neurons; when groups of neurons synchronize their firing activities, brain rhythms emerge, network oscillations are generated, and the basis for interactions between brain areas may develop. Because of the variety of experimental protocols for brain stimulation, limits on descriptions of the actual protocols employed, and limited controls, consistency of reported studies is lacking, and extrapolability is limited. Thus, while there is various consensus in various aspects of the effects of extra cranial brain stimulation, the results achieved have a degree of uncertainty dependent on details of implementation. On the other hand, within a specific experimental protocol, it is possible to obtain statistically significant and repeatable results. This implies that feedback control might be effective to control implementation of the stimulation for a given purpose; however, studies that employ feedback control are lacking.

Changes in the neuronal threshold result from changes in membrane permeability, which influence the response of the task-related network. The same mechanism of action may be responsible for both tES methods and TMS, i.e., the induction of noise in the system. However, the neural activity induced by tES will be highly influenced by the state of the system because it is a neuromodulatory method, and its effect will depend on the activity of the stimulated area. Therefore, the final result will depend strongly on the task characteristics, the system state and the way in which tES will interact with such a state. In TMS, the magnetic pulse causes the rapid and above-threshold depolarisation of cell membranes affected by the current, leading to the trans-synaptic depolarization or hyperpolarization of connected cortical neurons. Therefore, TMS activates a neural population that, depending on several factors, can be congruent (facilitate) or incongruent (inhibit) with task execution. tES induces a polarization of cortical neurons at a subthreshold level that is too weak to evoke an action potential. However, by inducing a polarity shift in the intrinsic neuronal excitability, tES can alter the spontaneous firing rate of neurons and modulate the response to afferent signals. In this sense, tES-induced effects are even more bound to the state of the stimulated area that is determined by the emotion conditions. In short, NIBS leads to a stimulation-induced modulation of mood that can be substantially defined as noise induction. Induced noise will not be just random activity, but will depend on the interaction of many parameters, from the characteristics of the stimulation to the emotion. The noise induced by NIBS will be influenced by the state of the neural population of the stimulated area. Although the types and number of neurons "triggered" by NIBS are theoretically random, the induced change in neuronal activity is likely to be correlated with ongoing emotion-relevant activity, yet even if we are referring to a non-deterministic process, the noise introduced will not be a totally random element. Because it will be partially determined by the experimental variables, the level of noise that will be introduced by the stimulation and by the emotion can be estimated, as well as the interaction between the two levels of noise (stimulation and emotion). Known transcranial stimulation does not permit stimulation with a focused and highly targeted signal to a clearly defined area of the brain to establish a unique brain-behavior relationship; therefore, the known introduced stimulus activity in the brain stimulation is 'noise.'

Transcranial Direct Current Stimulation (tDCS) tDCS. Cranial electrotherapy stimulation (CES) is a form of non-invasive brain stimulation that applies a small, pulsed electric current across a person's head to treat a variety of conditions such as anxiety, depression and insomnia. See, en.wikipedia.org/wiki/Cranial_electrotherapy_stimulation. Transcranial direct current stimulation (tDCS) is a form of neurostimulation that uses constant, low current delivered to the brain area of interest via electrodes on the scalp. It was originally developed to help patients with brain injuries or psychiatric conditions like major depressive disorder. tDCS appears to have some potential for treating depression. See, en.wikipedia.org/wiki/Transcranial_direct-current_stimulation.

tES (tDCS, tACS, and tRNS) is a noninvasive method of cortical stimulation, using weak direct currents to polarize target brain regions. The most used and best-known method is tDCS, as all considerations for the use of tDCS have been extended to the other tES methods. The hypotheses concerning the application of tDCS in cognition are very similar to those of TMS, with the exception that tDCS was never considered a virtual lesion method. tDCS can increase or decrease cortical excitability in the stimulated brain regions and facilitate or inhibit behavior accordingly. tES does not induce action potentials but instead modulates the neuronal response threshold so that it can be defined as subthreshold stimulation.

High-Definition-tDCS High-Definition transcranial Direct Current Stimulation (HD-tDCS) was invented at The City University of New York with the introduction of the 4×1 HD-IDCS montage. The 4×1 HD-tDCS montage allows precise targeting of cortical structures. The region of current flow is circumscribed by the area of the 4× ring, such that decreasing ring radius increases focality. 4×1 HD-tDCS allows for unifocal stimulation, meaning the polarity of the center 1× electrode will determine the direction of neuro-modulation under the ring. This is in contrast to conventional tDCS where the need for one anode and one cathode always produces bidirectional modulation (even when an extra-cephalic electrode is used). 4×1 HD-tDCS thus provides the ability not only to select a cortical brain region to target, but to modulate the excitability of that brain region with a designed polarity without having to consider return counter-electrode flow.

Transcranial Alternative Current Stimulation (tACS) Transcranial alternating current stimulation (tACS) is a noninvasive means by which alternating electrical current applied through the skin and skull entrains in a frequency-specific fashion the neural oscillations of the underlying brain. See, en.wikipedia.org/wiki/Transcranial_alternating_current_stimulation.

Transcranial Magnetic Stimulation (TMS) Transcranial magnetic stimulation (TMS) is a method in which a changing magnetic field is used to cause electric current to flow in a small region of the brain via electromagnetic induction. During a TMS procedure, a magnetic field generator, or "coil", is placed near the head of the person receiving the treatment. The coil is connected to a pulse generator, or stimulator, that delivers a changing electric current to the coil. TMS is used diagnostically to measure the connection between the central nervous system and skeletal muscle to evaluate damage in a wide variety of disease states, including stroke, multiple sclerosis, amyotrophic lateral sclerosis, movement disorders, and motor neuron diseases. Evidence is available suggesting that TMS is useful in treating neuropathic pain, major depressive disorder, and other conditions.

Low Energy Neurofeedback System (LENS) The LENS, or Low Energy Neurofeedback System, uses a very low power electromagnetic field, to carry feedback to the person receiving it. The feedback travels down the same wires carrying the brain waves to the amplifier and computer. Although the feedback signal is weak, it produces a measurable change in the brainwaves without conscious effort from the individual receiving the feedback. The system is software controlled, to receive input from EEG electrodes, to control the stimulation through the scalp. Neurofeedback uses a feedback frequency that is different from, but correlates with, the dominant brainwave frequency. When exposed to this feedback frequency, the EEG amplitude distribution changes in power. Most of the time the brain waves reduce in power; but at times they also increase in power. In either case the result is a changed brainwave state, and much greater ability for the brain to regulate itself.

Binaural beats Binaural beats are auditory brainstem responses which originate in the superior olivary nucleus of each hemisphere. They result from the interaction of two different auditory impulses, originating in opposite ears, below 1000 Hz and which differ in frequency between one and 30 Hz. For example, if a pure tone of 400 Hz is presented to the right ear and a pure tone of 410 Hz is presented simultaneously to the left ear, an amplitude modulated standing wave of 10 Hz, the difference between the two tones, is experienced as the two wave-forms mesh in and out of phase within the superior olivary nuclei. This binaural beat is not heard in the ordinary sense of the word (the human range of hearing is from 20-20,000 Hz). It is perceived as an auditory beat and theoretically can be used to entrain specific neural rhythms through the frequency-following response (FFR)—the tendency for cortical potentials to entrain to or resonate at the frequency of an external stimulus. Thus, it is theoretically possible to utilize a specific binaural-beat frequency as a consciousness management technique to entrain a specific cortical rhythm. The binaural-beat appears to be associated with an electroencephalographic (EEG) frequency-following response in the brain.

Uses of audio with embedded binaural beats that are mixed with music or various pink or background sound are diverse. They range from relaxation, meditation, stress reduction, pain management, improved sleep quality, decrease in sleep requirements, super learning, enhanced creativity and intuition, remote viewing, telepathy, and out-of-body experience and lucid dreaming. Audio embedded with binaural beats is often combined with various meditation techniques, as well as positive affirmations and visualization.

When signals of two different frequencies are presented, one to each ear, the brain detects phase differences between these signals. "Under natural circumstances a detected phase difference would provide directional information. The brain processes this anomalous information differently when these phase differences are heard with stereo headphones or speakers. A perceptual integration of the two signals takes place, producing the sensation of a third "beat" frequency. The difference between the signals waxes and wanes as the two different input frequencies mesh in and out of phase. As a result of these constantly increasing and decreasing differences, an amplitude-modulated standing wave—the binaural beat—is heard. The binaural beat is perceived as a fluctuating rhythm at the frequency of the difference between the two auditory inputs. Evidence suggests that the binaural beats are generated in the brainstem's superior olivary nucleus, the first site of contralateral integration in the auditory system. Studies also suggest that the frequency-following response originates from the inferior colliculus. This activity is conducted to the cortex where it can be recorded by scalp electrodes. Binaural beats can easily be heard at the low frequencies (<30) Hz) that are characteristic of the EEG spectrum.

Synchronized brain waves have long been associated with meditative and hypnogogic states, and audio with embedded binaural beats has the ability to induce and improve such states of consciousness. The reason for this is physiological. Each ear is "hardwired" (so to speak) to both hemispheres of the brain. Each hemisphere has its own olivary nucleus (sound-processing center) which receives signals from each ear. In keeping with this physiological structure, when a binaural beat is perceived there are actually two standing waves of equal amplitude and frequency present, one in each hemisphere. So, there are two separate standing waves entraining portions of each hemisphere to the same frequency. The binaural beats appear to contribute to the hemispheric synchronization evidenced in meditative and hypnogogic states of consciousness. Brain function is also enhanced through the increase of cross-collosal communication between the left and right hemispheres of the brain.

Isochronic Tones Isochronic tones are regular beats of a single tone that are used alongside monaural beats and binaural beats in the process called brainwave entrainment. At its simplest level, an isochronic tone is a tone that is being turned on and off rapidly. They create sharp, distinctive pulses of sound.

Light Stimulation The functional relevance of brain oscillations in the alpha frequency range (8-13 Hz) has been repeatedly investigated through the use of rhythmic visual stimulation. There are two hypotheses on the origin of steady-state visual evoked potential (SSVEP) measured in EEG during rhythmic stimulation: entrainment of brain oscillations and superposition of event-related responses (ERPs). The entrainment but not the superposition hypothesis justifies rhythmic visual stimulation as a means to manipulate brain oscillations, because superposition assumes a linear summation of single responses, independent from ongoing brain oscillations. Participants stimulated with rhythmic flickering light of different frequencies and intensities, and entrainment was measured by comparing the phase coupling of brain oscillations stimulated by rhythmic visual flicker with the oscillations induced by arrhythmic jittered stimulation, varying the time, stimulation frequency, and intensity conditions. Phase coupling was found to be more pronounced with increasing stimulation intensity as well as at stimulation frequencies closer to each participant's intrinsic frequency. Even in a single sequence of an SSVEP, non-linear features (intermittency of phase locking) were found that contradict the linear summation of single responses, as assumed by the superposition hypothesis. Thus, evidence suggests that visual rhythmic stimulation entrains brain oscillations, validating the approach of rhythmic stimulation as a manipulation of brain oscillations. See, Notbohm A, Kurths J, Herrmann C S, Modification of Brain Oscillations via Rhythmic Light Stimulation Provides Evidence for Entrainment but Not for Superposition of Event-Related Responses, Front Hum Neurosci. 2016 Feb. 3; 10:10. doi: 10.3389/fnhum.2016.00010. eCollection 2016.

It is also known that periodic visual stimulation can trigger epileptic seizures.

Principal Component Analysis Principal component analysis (PCA) is a statistical procedure that uses an orthogonal transformation to convert a set of observations of possibly correlated variables into a set of values of linearly uncorrelated variables called principal components. If there are n observations with p variables, then the number of distinct principal components is $\min(n-1,p)$. This transformation is defined in such a way that the first principal component has the largest possible variance (that is, accounts for as much of the variability in the data as possible), and each succeeding component in turn has the highest variance possible under the constraint that it is orthogonal to the preceding components. The resulting vectors are an uncorrelated orthogonal basis set. PCA is sensitive to the relative scaling of the original variables. PCA is the simplest of the true eigenvector-based multivariate analyses. Often, its operation can be thought of as revealing the internal structure of the data in a way that best explains the variance in the data. If a multivariate dataset is visualized as a set of coordinates in a high-dimensional data space (1 axis per variable), PCA can supply the user with a lower-dimensional picture, a projection of this object when viewed from its most informative viewpoint. This is done by using only the first few principal components so that the dimensionality of the transformed data is reduced. PCA is closely related to factor analysis. Factor analysis typically incorporates more domain specific assumptions about the underlying structure and solves eigenvectors of a slightly different matrix. PCA is also related to canonical correlation analysis (CCA). CCA defines coordinate systems that optimally describe the cross-covariance between two datasets while PCA defines a new orthogonal coordinate system that optimally describes variance in a single dataset. See, en.wikipedia.org/wiki/Principal_component_analysis A general model for confirmatory factor analysis is expressed as $x=\alpha+\Lambda\zeta+\varepsilon$. The covariance matrix is expressed as $E[(x-\mu)(x-\mu)']=\Lambda\Phi\Lambda'+\Theta$. If residual covariance matrix $\Theta=0$ and correlation matrix among latent factors $\Phi=I$, then factor analysis is equivalent to principal component analysis and the resulting covariance matrix is simplified to $\Sigma=\Lambda\Lambda'$. When there are p number of variables and all p components (or factors) are extracted, this covariance matrix can alternatively be expressed into $\Sigma=D\Lambda D'$, or $\Sigma=\lambda DAD'$, where $D=n\times p$ orthogonal matrix of eigenvectors, and $\Delta=\lambda A$, $p\times p$ matrix of eigenvalues, where $\lambda$ is a scalar and A is a diagonal matrix whose elements are proportional to the eigenvalues of $\Sigma$. The following three components determine the geometric features of the observed data: $\lambda$ parameterizes the volume of the observation, D indicates the orientation, and A represents the shape of the observation.

When population heterogeneity is explicitly hypothesized as in model-based cluster analysis, the observed covariance matrix is decomposed into the following general form $$\sum\nolimits_{k} = \lambda_k D_k A_k D_k^T,$$

where $\lambda_k$ parameterizes the volume of the $k^{th}$ cluster, $D_k$ indicates the orientation of that cluster, and $A_k$ represents the shape of that cluster. The subscript k indicates that each component (or cluster) can have different volume, shape, and orientation.

Assume a random vector X, taking values in R", has a mean and covariance matrix of $\mu_X$ and $\Sigma_X$ respectively. $\lambda_1 > \lambda_2 > \ldots > \lambda_m > 0$ are ordered eigenvalues of $\Sigma_X$, such that the 1-th eigenvalue of $\Sigma_X$ means the i-th largest of them. Similarly, a vector $\alpha_i$ is the i-th eigenvector of $\Sigma_X$ when it corresponds to the i-th eigenvalue of $\Sigma_X$. To derive the form of principal components (PCs), consider the optimization problem of maximizing $$\mathrm{var}\!\left[\alpha_1^T X\right] = \alpha_1^T \sum\nolimits_X \alpha_1,$$

subject to $$\alpha_1^T \alpha_1 = 1.$$

The Lagrange multiplier method is used to solve this question.

$$L(\alpha_1, \phi_1) = \alpha_1^T \sum\nolimits_X \alpha_1 + \phi_1\!\left(\alpha_1^T \alpha_1 - 1\right)$$

$$\frac{\partial L}{\partial \alpha_1} = 2\sum\nolimits_X \alpha_1 + 2\phi_1\alpha_1 = 0$$

$$\Rightarrow \sum\nolimits_X \alpha_1 = -\phi_1\alpha_1 \Rightarrow \mathrm{var}\!\left[\alpha_1^T X\right] = -\phi_1\alpha_1^T\alpha_1 = -\phi_1.$$

Because $+\phi_1$ is the eigenvalue of $\Sigma_X$, with $\alpha_1$ being the corresponding normalized eigenvector, $$\mathrm{var}[\alpha_1^T X]$$

is maximized by choosing $\alpha_1$ to be the first eigenvector of $\Sigma_X$. In this case, $$z_1 = \alpha_1^T X$$

is named the first PC of X, $\alpha_1$ is the vector of coefficients for $z_1$, and $\mathrm{var}(z_1)=\lambda_1$.

To find the second PC, $$z_2 = \alpha_2^T X,$$

we need to maximize $$\mathrm{var}[\alpha_2^T X] = \alpha_2^T \sum\nolimits_X \alpha_2$$

subject to $z_2$ being uncorrelated with $z_1$. Because $$\mathrm{cov}(\alpha_1^T X, \alpha_2^T X) = 0 \Rightarrow \alpha_1^T \sum\nolimits_X \alpha_2 = 0 \Rightarrow \alpha_1^T \alpha_2 = 0,$$

this problem is equivalently set as maximizing $$\alpha_2^T \sum\nolimits_X \alpha_2,$$

subject to $$\alpha_1^T \alpha_2 = 0, \text{ and } \alpha_2^T \alpha_2 = 1.$$

We still make use of the Lagrange multiplier method.

$$L(\alpha_2, \phi_1, \phi_2) = \alpha_2^T \sum\nolimits_X \alpha_2 + \phi_1\alpha_1^T\alpha_2 + \phi_2\!\left(\alpha_2^T\alpha_2 - 1\right) \quad \frac{\partial L}{\partial \alpha_2} = 2\sum\nolimits_X \alpha_2 + \phi_1\alpha_1 + 2\phi_2\alpha_2 = 0$$

$$\Rightarrow \alpha_1^T\!\left(2\sum\nolimits_X \alpha_2 + \phi_1\alpha_1 + 2\phi_2\alpha_2\right) = 0 \Rightarrow \phi_1 = 0 \Rightarrow \sum\nolimits_X \alpha_2 = -\phi_2\alpha_2 \Rightarrow \alpha_2^T \sum\nolimits_X \alpha_2 = -\phi_2.$$

Because $-\phi_2$ is the eigenvalue of $\Sigma_X$, with $\alpha_2$ being the corresponding normalized eigenvector, 23 24

$$\mathrm{var}\left[\alpha_2^T X\right]$$

is maximized by choosing $\alpha_2$ to be the second eigenvector of $\Sigma_X$. In this case, $$z_2 = \alpha_2^T X$$

is named the second PC of X, $\alpha_2$ is the vector of coefficients for $z_2$, and $\mathrm{var}(z_2)=z_2$. Continuing in this way, it can be shown that the i-th PC $$z_i = \alpha_i^T X$$

is constructed by selecting $\alpha_i$ to be the i-th eigenvector of $\Sigma_X$, and has variance of $\lambda_i$. The key result in regards to PCA is that the principal components are the only set of linear functions of original data that are uncorrelated and have orthogonal vectors of coefficients.

For any positive integer $p \le m$ let $B=[\beta_1, \beta_2, \ldots, \beta_p]$ be an real m×p matrix with orthonormal columns, i.e., $$\beta_i^T \beta_j = \delta_{ij},$$

and $Y=B^T X$. Then the trace of covariance matrix of Y is maximized by taking $B=[\alpha_1, \alpha_2 \ldots, \alpha_p]$ where $\alpha_i$ is the i-th eigenvector of $\Sigma_X$. Because $\Sigma_X$ is symmetric with all distinct eigenvalues, so $\{\alpha_1, \alpha_2 \ldots \alpha_m\}$ is an orthonormal basis with $\alpha_i$ being the i-th eigenvector of $\Sigma_X$, and we can represent the columns of B as $$\beta_i = \sum_{j=1}^m c_{ji}\alpha_j,$$

i=1, . . . , p. So we have B=PC, where $P=[\alpha_1, \ldots, \alpha_m]$, $C=\{c_{ij}\}$ is an m×p matrix. Then, $P^T\Sigma_X P=\Lambda$, with $\Lambda$ being a diagonal matrix whose k-th diagonal element is $\lambda_k$, and the covariance matrix of Y is, $$\sum_Y = B^T \sum_X B = C^T P^T \sum_X PC = C^T \Lambda C = \lambda_1 c_1 c_1^T + \ldots + \lambda_m c_m c_m^T,$$

where $$c_i^T$$

$$\begin{aligned}\mathrm{trace}\left(\sum_Y\right) &= \sum_{i=1}^m \lambda_i \mathrm{trace}\left(c_i c_i^T\right)\\ &= \sum_{i=1}^m \lambda_i \mathrm{trace}\left(c_i c_i^T\right)\\ &= \sum_{i=1}^m \lambda_i c_i^T c_i\\ &= \sum_{i=1}^m \left(\sum_{j=1}^p c_{ij}^2\right)\lambda_i\end{aligned}$$

Because $C^T C=B^T PP^T B=B^T B=I$, so $$\mathrm{trace}\left(C^T C\right) = \sum_{i=1}^m \sum_{j=1}^p c_{ij}^2 = p,$$

and the columns of C are orthonormal. By the Gram-Schmidt method, C can expand to D, such that D has its columns as an orthonormal basis of $R^m$ and contains C as its first P columns. D is square shape, thus being an orthogonal matrix and having its rows as another orthonormal basis of $R^m$. One row of C is a part of one row of D, so $$\sum_{j=1}^p c_{ij}^2 \le 1,$$

i=1, . . . ,m. Considering the constraints $$\sum_{j=1}^p c_{ij}^2 \le 1, \sum_{i=1}^m \sum_{j=1}^p c_{ij}^2 = p$$

and the objective $$\sum_{i=1}^m \left(\sum_{j=1}^p c_{ij}^2\right)\lambda_i.$$

We derive that trace $(\Sigma_Y)$ is maximized if $$\sum_{j=1}^p c_{ij}^2 = 1$$

for i=1, . . . , p, and $$\sum_{j=1}^p c_{ij}^2 = 0$$

for i=p+1, . . . , m. When $B=[\alpha_1, \alpha_2, \ldots, \alpha_p]$, straightforward calculation yields that C is an all-zero matrix except, $C_{ii}=1$ i=1, . . . , p. This fulfills the maximization condition. Actually, by taking $B=[\gamma_1, \gamma_2, \ldots, \gamma_p]$ where $\{\gamma_1, \gamma_2 \ldots, \gamma_p\}$ is any orthonormal basis of the subspace of span $\{\alpha_1, \alpha_2, \ldots, \alpha_p\}$, the maximization condition is also satisfied, thus yielding the same trace of covariance matrix of Y.

Suppose that we wish to approximate the random vector X by its projection onto a subspace spanned by columns of B, where $B=[\beta_1, \beta_2, \ldots, \beta_p]$ is a real m×p matrix with orthonormal columns, i.e., $$\beta_i^T \beta_j = \delta_{ij}.$$

If $$\sigma_i^2$$

is the residual variance for each component of X, then $$\sum_{i=1}^{m} \sigma_i^2$$

is minimized if $B=[\alpha_1, \alpha_2, \ldots, \alpha_p]$, where $\{\alpha_1, \alpha_2, \ldots, \alpha_p\}$ are the first p eigenvectors of $\Sigma_X$. In other words, the trace of covariance matrix of $X-BB^TX$ is minimized if $B=[\alpha_1, \alpha_2, \ldots, \alpha_p]$. When E(X)=0 which is a commonly applied preprocessing step in data analysis methods, this property is saying that $E\|X-BB^TX\|^2$ is minimized if $B=[\alpha_1, \alpha_2 \ldots, \alpha_p]$.

The projection of a random vector X onto a subspace spanned by columns of B is $\hat{X}=BB^TX$. Then the residual vector is $\varepsilon=X-BB^TX$, which has a covariance matrix $\Sigma_\varepsilon=(1-BB^T)\Sigma_X(1-BB^T)$. Then, $$\sum_{i=1}^{m} \sigma_i^2 = \text{trace}(\textstyle\sum_\varepsilon) = \text{trace}\Big(\textstyle\sum_X - \sum_X BB^T - BB^T \sum_X + BB^T \sum_X BB^T\Big).$$

Also, we know $$\text{trace}(\Sigma_X BB^T)=\text{trace}(BB^T\Sigma_X)=\text{trace}(B^T\Sigma_X B)$$

$$\text{trace}(BB^T\Sigma_X BB^T)=\text{trace}(B^T\Sigma_X BB^T B)=\text{trace}(B^T\Sigma_X B)$$

The last equation comes from the fact that B has orthonormal columns. So, $$\sum_{i=1}^{m} \sigma_i^2 = \text{trace}(\textstyle\sum_X) - \text{trace}\Big(B^T \textstyle\sum_X B\Big).$$

To minimize $$\sum_{i=1}^{m} \sigma_i^2,$$

it suffices to maximize $\text{trace}(B^T\Sigma_X B)$. This can be done by choosing $B=[\alpha_1, \alpha_2, \ldots, \alpha_p]$, where $\{\alpha_1, \alpha_2 \ldots \alpha_p\}$ are the first P eigenvectors of $\Sigma_X$, as above.

See, Pietro Amenta, Luigi D'Ambra, "Generalized Constrained Principal Component Analysis with External Information," (2000). We assume that data on K sets of explanatory variables and S criterion variables of n statistical units are collected in matrices $X_k$ (k=1, . . . , K) and $Y_s$ (s=1, . . . , S) of orders (n×$p_1$), . . . . , (n×$p_K$) and (n×$q_1$), . . . , (n×$q_s$), respectively. We suppose, without loss of generality, identity matrices for the metrics of the spaces of variables of $X_k$ and $Y_s$ with $D_n=\text{diag}(1/n)$ weight matrix of statistical units. We assume, moreover, that $X_k$'s and $Y_k$'s are centered as to the weights $D_n$.

Let $X=[X_1| \ldots |X_K]$ and $Y=[Y_1| \ldots |Y_S]$, respectively, be K and S matrices column linked of orders (n×$\Sigma_k p_k$) and (n×$\Sigma_s q_s$) Let be, also, $W_Y=YY'$ while we denote $v_k$ the coefficients vector ($p_k$,1) the linear combination for each $X_k$ such that $z_k=X_k v_k$. Let CR be the matrix of dimension $p_k$×m (m≤$p_k$), associated to the external information explanatory variables of set k.

Generalized CPCA (GCPCA) (Amenta, D'Ambra, 1999) with external information consists in seeking for K coefficients vectors $v_k$ (or, in same way, K linear combinations $z_k$) subject to the restriction $C_k' v_k=0$ simultaneously, such that:

$$\begin{cases} \max \sum_{i=1}^{K}\sum_{j=1}^{K} \langle Y'X_i v_i, Y'X_j v_j\rangle \\ \\ \text{with the constraints } \begin{aligned} &\sum_{k=1}^{K}\|X_k v_k\|^2 = 1 \\ &\sum_{k=1}^{K} C_k' v_k = 0 \end{aligned} \end{cases} \tag{1}$$

or, in equivalent way, $$\begin{cases} \max v'(A'A)v \\ \text{with the constraints } \begin{aligned} v'Bv &= 1 \\ C'v &= 0 \end{aligned} \end{cases} \text{or} \begin{cases} \max f'B^{-0.5}A'AB^{-0.5}f \\ \text{with the constraints } \begin{aligned} f'f &= 1 \\ C'v &= 0 \end{aligned} \end{cases}$$

where $A=Y'X$, $B=\text{diag}(X_1',X_1, \ldots, X_K'X_K)$, $C'=[C_1'| \ldots |C_K']$, $v'=(v_1'| \ldots |v_k')$ and $f=B^{0.5}v$ with $$A'A = \begin{bmatrix} X_1'YY'X_1 & \ldots & X_1'YY'X_K \\ \vdots & \ddots & \vdots \\ X_K'YY'X_1 & \ldots & X_K'YY'X_k \end{bmatrix}.$$

The constrained maximum problem (1) turns out to be an extension of criterion $$\sup_{\Sigma_k\|z_k\|^2=1} \sum_i \sum_k \langle \mathcal{Z}_i, \mathcal{Z}_k\rangle$$

(Sabatier, 1993) with more sets of criterion variables with external information. The solution of this constrained maximum problem leads to solve the eigen-equation $$(P_X - P_{XB^{-1}C})W_Y g = \lambda g \tag{2}$$

where g=Xv, $P_X - P_{XB^{-1}C} = \Sigma_{k=1}^{K}(P_{X_k} - P_{X_k(X_k'X_k)^{-1}C_k})$ is the oblique projector operator associated to, the direct sum decomposition of $R^n$ $$R^n = \text{Im}(P_X - P_{XB^{-1}C}) \oplus \text{Im}(P_C) \oplus \text{Ker}(P_X)$$

with $P_{X_k}=X_k(X_k'X_k)^{-1}X_k'$ and $P_C=C(C'B^{-1}C)^{-1}C'B^{-1}$, respectively, I and $B^{-1}$ orthogonal projector operators onto the subspaces spanned by the columns of matrices $X_k$ and C. Furthermore, $P_{XB^{-1}C}=XB^{-1}C(C'B^{-1}C)^{-1}C'B^{-1}X'$ is the orthogonal projector operator onto the subspace spanned the columns of the matrix $XB^{-1}C$. Starting from the relation $$P_{X_k} - P_{X_k(X_k'X_k)^{-1}C_k}) W_Y g = \lambda X_k v_k \tag{3}$$

(which is obtained from the expression $(I-P_C)$ $X'W_Yg=\lambda Bv$) the coefficients vectors $V_k$ and the linear combinations $z_k=X_kv_k$ maximizing (1) can be given by the relations $$v_k = \frac{1}{\lambda}(X_k'X_k)^{-1}(I - P_{C_k})X_k'W_YXv \text{ and } Z_k = \frac{1}{\lambda}\left(P_{X_k} - P_{X_k(X_k'X_k)^{-1}C_k}\right)W_YXv,$$

respectively.

The solution eigenvector g can be written, according to (2) and (3), as sum of the linear combinations $z_k$: $g=\Sigma_k X_k v_k$. Notice that the eigenvalues associated to the eigen-system (2) are, according to the Sturm theorem, lower or equal than those of GCPCA eigen-system: $\Sigma_{k=1}^{K}P_{X_k}W_Yg=\lambda g$.

Spatial Principal Component Analysis

We introduce the following notation. Let $J(t,i;\alpha,s)$ be the current density in voxel i, as estimated by LORETA, in condition $\alpha$ at t time-frames after stimulus onset for subject s. Let area: Voxel→fBA be a function, which assigns to each voxel i∈Voxel the corresponding fBA b∈fBA. In a first pre-processing step, we calculate for each subject s the value of the current density averaged over each Fba $$x(t, b; \alpha, s) = \frac{1}{N_b}\sum_{i\in b}J(t, i; \alpha, s) \qquad (1)$$

where $N_b$ is the number of voxels in the fBA b, in condition $\alpha$ for subject s.

In the second analysis stage, the mean current density $x(t,b;\alpha,s)$ from each fBA b, for every subject s and condition $\alpha$, was subjected to spatial PCA analysis of the correlation matrix and varimax rotation In the present study the spatial PCA uses the above-defined fBAs as variables sampled along the time epoch for which EEG has been sampled (0-1000 ms; 512 time-frames), and the inverse solution was estimated. Spatial matrices (each matrix was sized b×t=36×512 elements) for every subject and condition were collected, and subjected to PCA analyses, including the calculation of the covariance matrix; eigenvalue decomposition and varimax rotation, in order to maximize factor loadings. In other words, in the spatial PCA analysis we approximate the mean current density for each subject in each condition as $$x(t; \alpha, s) \approx x_0(\alpha, s) + \sum_k c_k(t)x_k(\alpha, s), \qquad (2)$$

where here $x(t;\alpha,s)\in R^{36}$ is a vector, which denotes the time-dependent activation of the fBAs, $x_0(\alpha,s)$ is their mean activation, and $x_k(\alpha,s)$ and $c_k$ are the principal components and their corresponding coefficients (factor loadings) as computed using the principal component analysis.

EEG analysis approaches have emerged, in which event-related changes in EEG dynamics in single event-related data records are analyzed. See Allen D. Malony et al., Computational Neuroinformatics for Integrated Electromagnetic Neuroimaging and Analysis, PAR-99-138. Pfurtscheller, reported a method for quantifying the average transient suppression of alpha band (circa 10-Hz) activity following stimulation. Event-related desynchronization (ERD, spectral amplitude decreases), and event-related synchronization (ERS, spectral amplitude increases) are observed in a variety of narrow frequency bands (4-40 Hz) which are systematically dependent on task and cognitive state variables as well as on stimulus parameters. Makeig (1993) reported event-related changes in the full EEG spectrum, yielding a 2-D time/frequency measure he called the event-related spectral perturbation (ERSP). This method avoided problems associated with analysis of a priori narrow frequency bands, since bands of interest for the analysis could be based on significant features of the complete time/frequency transform. Rappelsburger et al. introduced event-related coherence (ERCOH).

A wide variety of other signal processing measures have been tested for use on EEG and/or MEG data, including dimensionality measures based on chaos theory and the bispectrum. Use of neural networks has also been proposed for EEG pattern recognition applied to clinical and practical problems, though usually these methods have not been employed with an aim of explicitly modeling the neurodynamics involved.

The availability of and interest in larger and larger numbers of EEG (and MEG) channels led immediately to the question of how to combine data from different channels. Donchin advocated the use of linear factor analysis methods based on principal component analysis (PCA) for this purpose. Temporal PCA assumes that the time course of activation of each derived component is the same in all data conditions. Because this is unreasonable for many data sets, spatial PCA (usually followed by a component rotation procedure such as Varimax or Promax) is of potentially greater interest. To this end, several variants of PCA have been proposed for ERP decomposition.

Bell and Sejnowski published an iterative algorithm based on information theory for decomposing linearly mixed signals into temporally independent by minimizing their mutual information. First approaches to blind source separation minimized third and fourth-order correlations among the observed variables and achieved limited success in simulations. A generalized approach uses a simple neural network algorithm that used joint information maximization or 'infomax' as a training criterion. By using a compressive nonlinearity to transform the data and then following the entropy gradient of the resulting mixtures, ten recorded voice and music sound sources were unmixed. A similar approach was used for performing blind deconvolution, and the 'infomax' method was used for decomposition of visual scenes.

The first applications of blind decomposition to biomedical time series analysis applied the infomax independent component analysis (ICA) algorithm to decomposition of EEG and event-related potential (ERP) data and reported the use of ICA to monitor alertness. This separated artifacts, and EEG data into constituent components defined by spatial stability and temporal independence. ICA can also be used to remove artifacts from continuous or event-related (single-trial) EEG data prior to averaging. Vigario et al. (1997), using a different ICA algorithm, supported the use of ICA for identifying artifacts in MEG data. Meanwhile, widespread interest in ICA has led to multiple applications to biomedical data as well as to other fields (Jung et al., 2000b). Most relevant to EEG/MEG analysis, ICA is effective in separating functionally independent components of functional magnetic resonance imaging (fMRI) data Since the publication of the original infomax ICA algorithm, several extensions have been proposed. Incorporation of a 'natural gradient' term avoided matrix inversions, greatly speeding the convergence of the algorithm and making it practical for use with personal computers on large data EEG and fMRI data sets. An initial 'sphering' step further increased the reliability of convergence of the algorithm. The original algorithm assumed that sources have 'sparse' (super-Gaussian) distributions of activation values. This restriction has recently been relaxed in an 'extended-ICA' algorithm that allows both super-Gaussian and sub-Gaussian sources to be identified. A number of variant ICA algorithms have appeared in the signal processing literature. In general, these make more specific assumptions about the temporal or spatial structure of the components to be separated, and typically are more computationally intensive than the infomax algorithm.

Since individual electrodes (or magnetic sensors) each record a mixture of brain and non-brain sources, spectral measures are difficult to interpret and compare across scalp channels. For example, an increase in coherence between two electrode signals may reflect the activation of a strong brain source projecting to both electrodes, or the deactivation of a brain generator projecting mainly to one of the electrodes. If independent components of the EEG (or MEG) data can be considered to measure activity within functionally distinct brain networks, however, event-related coherence between independent components may reveal transient, event-related changes in their coupling and decoupling (at one or more EEG/MEG frequencies). ERCOH analysis has been applied to independent EEG components in a selective attention task.

Nonlinear Dimensionality Reduction High-dimensional data, meaning data that requires more than two or three dimensions to represent, can be difficult to interpret. One approach to simplification is to assume that the data of interest lie on an embedded non-linear manifold within the higher-dimensional space. If the manifold is of low enough dimension, the data can be visualized in the low-dimensional space. Non-linear methods can be broadly classified into two groups: those that provide a mapping (either from the high-dimensional space to the low-dimensional embedding or vice versa), and those that just give a visualization. In the context of machine learning, mapping methods may be viewed as a preliminary feature extraction step, after which pattern recognition algorithms are applied. Typically, those that just give a visualization are based on proximity data—that is, distance measurements. Related Linear Decomposition Methods include Independent component analysis (ICA), Principal component analysis (PCA) (also called Karhunen-Loève transform—KLT), Singular value decomposition (SVD)), and Factor analysis.

The self-organizing map (SOM, also called Kohonen map) and its probabilistic variant generative topographic mapping (GTM) use a point representation in the embedded space to form a latent variable model based on a non-linear mapping from the embedded space to the high-dimensional space. These techniques are related to work on density networks, which also are based around the same probabilistic model.

Principal curves and manifolds give the natural geometric framework for nonlinear dimensionality reduction and extend the geometric interpretation of PCA by explicitly constructing an embedded manifold, and by encoding using standard geometric projection onto the manifold. How to define the "simplicity" of the manifold is problem-dependent, however, it is commonly measured by the intrinsic dimensionality and/or the smoothness of the manifold. Usually, the principal manifold is defined as a solution to an optimization problem. The objective function includes a quality of data approximation and some penalty terms for the bending of the manifold. The popular initial approximations are generated by linear PCA, Kohonen's SOM or autoencoders. The elastic map method provides the expectation-maximization algorithm for principal manifold learning with minimization of quadratic energy functional at the "maximization" step.

An autoencoder is a feed-forward neural network which is trained to approximate the identity function. That is, it is trained to map from a vector of values to the same vector. When used for dimensionality reduction purposes, one of the hidden layers in the network is limited to contain only a small number of network units. Thus, the network must learn to encode the vector into a small number of dimensions and then decode it back into the original space. Thus, the first half of the network is a model which maps from high to low-dimensional space, and the second half maps from low to high-dimensional space. Although the idea of autoencoders is quite old, training of deep autoencoders has only recently become possible through the use of restricted Boltzmann machines and stacked denoising autoencoders. Related to autoencoders is the NeuroScale algorithm, which uses stress functions inspired by multidimensional scaling and Sammon mappings (see below) to learn a non-linear mapping from the high-dimensional to the embedded space. The mappings in NeuroScale are based on radial basis function networks.

Gaussian process latent variable models (GPLVM) are probabilistic dimensionality reduction methods that use Gaussian Processes (GPs) to find a lower dimensional non-linear embedding of high dimensional data. They are an extension of the Probabilistic formulation of PCA. The model is defined probabilistically and the latent variables are then marginalized and parameters are obtained by maximizing the likelihood. Like kernel PCA they use a kernel function to form a nonlinear mapping (in the form of a Gaussian process). However, in the GPLVM the mapping is from the embedded (latent) space to the data space (like density networks and GTM) whereas in kernel PCA it is in the opposite direction. It was originally proposed for visualization of high dimensional data but has been extended to construct a shared manifold model between two observation spaces. GPLVM and its many variants have been proposed specially for human motion modeling, e.g., back constrained GPLVM, GP dynamic model (GPDM), balanced GPDM (B-GPDM) and topologically constrained GPDM. To capture the coupling effect of the pose and gait manifolds in the gait analysis, a multi-layer joint gait-pose manifolds was proposed.

Curvilinear component analysis (CCA) looks for the configuration of points in the output space that preserves original distances as much as possible while focusing on small distances in the output space (conversely to Sammon's mapping which focus on small distances in original space). It should be noticed that CCA, as an iterative learning algorithm, actually starts with focus on large distances (like the Sammon algorithm), then gradually change focus to small distances. The small distance information will overwrite the large distance information, if compromises between the two have to be made. The stress function of CCA is related to a sum of right Bregman divergences. Curvilinear distance analysis (CDA) trains a self-organizing neural network to fit the manifold and seeks to preserve geodesic distances in its embedding. It is based on Curvilinear Component Analysis (which extended Sammon's mapping), but uses geodesic distances instead. Diffeomorphic Dimensionality Reduction or Diffeomap learns a smooth diffeomorphic mapping which transports the data onto a lower-dimensional linear subspace. The method solves for a smooth time indexed vector field such that flows along the field which start at the data points will end at a lower-dimensional linear subspace, thereby attempting to preserve pairwise differences under both the forward and inverse mapping.

Perhaps the most widely used algorithm for manifold learning is Kernel principal component analysis (kernel PCA). It is a combination of Principal component analysis and the kernel trick. PCA begins by computing the covariance matrix of the M×n Matrix X. It then projects the data onto the first k eigenvectors of that matrix. By comparison, KPCA begins by computing the covariance matrix of the data after being transformed into a higher-dimensional space. It then projects the transformed data onto the first k eigenvectors of that matrix, just like PCA. It uses the kernel trick to factor away much of the computation, such that the entire process can be performed without actually computing $\Phi(x)$. Of course $\Phi$ must be chosen such that it has a known corresponding kernel.

Laplacian Eigenmaps, LLE) are special cases of kernel PCA, performed by constructing a data-dependent kernel matrix. KPCA has an internal model, so it can be used to map points onto its embedding that were not available at training time. Laplacian Eigenmaps uses spectral techniques to perform dimensionality reduction. This technique relies on the basic assumption that the data lies in a low-dimensional manifold in a high-dimensional space. This algorithm cannot embed out of sample points, but techniques based on Reproducing kernel Hilbert space regularization exist for adding this capability. Such techniques can be applied to other nonlinear dimensionality reduction algorithms as well. Traditional techniques like principal component analysis do not consider the intrinsic geometry of the data. Laplacian eigenmaps builds a graph from neighborhood information of the data set. Each data point serves as a node on the graph and connectivity between nodes is governed by the proximity of neighboring points (using e.g., the k-nearest neighbor algorithm). The graph thus generated can be considered as a discrete approximation of the low-dimensional manifold in the high-dimensional space. Minimization of a cost function based on the graph ensures that points close to each other on the manifold are mapped close to each other in the low-dimensional space, preserving local distances. The eigenfunctions of the Laplace-Beltrami operator on the manifold serve as the embedding dimensions, since under mild conditions this operator has a countable spectrum that is a basis for square integrable functions on the manifold (compare to Fourier series on the unit circle manifold). Attempts to place Laplacian eigenmaps on solid theoretical ground have met with some success, as under certain non-restrictive assumptions, the graph Laplacian matrix has been shown to converge to the Laplace-Beltrami operator as the number of points goes to infinity. In classification applications, low dimension manifolds can be used to model data classes which can be defined from sets of observed instances. Each observed instance can be described by two independent factors termed 'content' and 'style', where 'content' is the invariant factor related to the essence of the class and 'style' expresses variations in that class between instances. Unfortunately, Laplacian Eigenmaps may fail to produce a coherent representation of a class of interest when training data consist of instances varying significantly in terms of style. In the case of classes which are represented by multivariate sequences, Structural Laplacian Eigenmaps has been proposed to overcome this issue by adding additional constraints within the Laplacian Eigenmaps neighborhood information graph to better reflect the intrinsic structure of the class. More specifically, the graph is used to encode both the sequential structure of the multivariate sequences and, to minimize stylistic variations, proximity between data points of different sequences or even within a sequence, if it contains repetitions. Using dynamic time warping, proximity is detected by finding correspondences between and within sections of the multivariate sequences that exhibit high similarity.

Like LLE, Hessian LLE is also based on sparse matrix techniques. It tends to yield results of a much higher quality than LLE. Unfortunately, it has a very costly computational complexity, so it is not well-suited for heavily sampled manifolds. It has no internal model. Modified LLE (MLLE) is another LLE variant which uses multiple weights in each neighborhood to address the local weight matrix conditioning problem which leads to distortions in LLE maps. MLLE produces robust projections similar to Hessian LLE, but without the significant additional computational cost.

Manifold alignment takes advantage of the assumption that disparate data sets produced by similar generating processes will share a similar underlying manifold representation. By learning projections from each original space to the shared manifold, correspondences are recovered and knowledge from one domain can be transferred to another. Most manifold alignment techniques consider only two data sets, but the concept extends to arbitrarily many initial data sets. Diffusion maps leverages the relationship between heat diffusion and a random walk (Markov Chain); an analogy is drawn between the diffusion operator on a manifold and a Markov transition matrix operating on functions defined on the graph whose nodes were sampled from the manifold. Relational perspective map is a multidimensional scaling algorithm. The algorithm finds a configuration of data points on a manifold by simulating a multi-particle dynamic system on a closed manifold, where data points are mapped to particles and distances (or dissimilarity) between data points represent a repulsive force. As the manifold gradually grows in size the multi-particle system cools down gradually and converges to a configuration that reflects the distance information of the data points. Local tangent space alignment (LTSA) is based on the intuition that when a manifold is correctly unfolded, all of the tangent hyperplanes to the manifold will become aligned. It begins by computing the k-nearest neighbors of every point. It computes the tangent space at every point by computing the d-first principal components in each local neighborhood. It then optimizes to find an embedding that aligns the tangent spaces. Local Multidimensional Scaling performs multidimensional scaling in local regions, and then uses convex optimization to fit all the pieces together.

Maximum Variance Unfolding was formerly known as Semidefinite Embedding. The intuition for this algorithm is that when a manifold is properly unfolded, the variance over the points is maximized. This algorithm also begins by finding the k-nearest neighbors of every point. It then seeks to solve the problem of maximizing the distance between all non-neighboring points, constrained such that the distances between neighboring points are preserved. Nonlinear PCA (NLPCA) uses backpropagation to train a multi-layer perceptron (MLP) to fit to a manifold. Unlike typical MLP training, which only updates the weights, NLPCA updates both the weights and the inputs. That is, both the weights and inputs are treated as latent values. After training, the latent inputs are a low-dimensional representation of the observed vectors, and the MLP maps from that low-dimensional representation to the high-dimensional observation space. Manifold Sculpting uses graduated optimization to find an embedding. Like other algorithms, it computes the k-nearest neighbors and tries to seek an embedding that preserves relationships in local neighborhoods. It slowly scales variance out of higher dimensions, while simultaneously adjusting points in lower dimensions to preserve those relationships.

Ruffini (2015) discusses Multichannel transcranial current stimulation (tCS) systems that offer the possibility of EEG-guided optimized, non-invasive brain stimulation. A tCS electric field realistic brain model is used to create a forward "lead-field" matrix and, from that, an EEG inverter is employed for cortical mapping. Starting from EEG, 2D) cortical surface dipole fields are defined that could produce the observed EEG electrode voltages.

Schestatsky et al. (2017) discuss tanscranial direct current stimulation (tDCS), which stimulates through the scalp with a constant electric current that induces shifts in neuronal membrane excitability, resulting in secondary changes in cortical activity. Although tDCS has most of its neuromodulatory effects on the underlying cortex, tDCS effects can also be observed in distant neural networks. Concomitant EEG monitoring of the effects of tDCS can provide valuable information on the mechanisms of tDCS. EEG findings can be an important surrogate marker for the effects of tDCS and thus can be used to optimize its parameters. This combined EEG-tDCS system can also be used for preventive treatment of neurological conditions characterized by abnormal peaks of cortical excitability, such as seizures. Such a system would be the basis of a non-invasive closed-loop device. tDCS and EEG can be used concurrently.

SUMMARY OF THE INVENTION

The present technology provides a method of replicating a mental state of a first subject in a second subject. (In some embodiments, a first and a second subject may be the same subject at different points in time.) The mental state typically is not a state of consciousness or an idea, but rather a subconscious (in a technical sense) state, representing an emotion, readiness, receptivity, or other state, often independent of particular thoughts or ideas. In essence, a mental state of the first subject (a "trainer" or "donor" who is in a desired mental state) is captured by recording neural correlates of the mental state, e.g., as expressed by brain activity patterns, such as EEG or MEG signals. The neural correlates of the first subject, either as direct or recorded representations, may then be used to control a stimulation of the second subject (a "trainee" or "recipient"), seeking to induce the same brain activity patterns in the second subject (recipient/trainee) as were present in the first subject (donor/trainer) to assist the second subject (recipient/trainee) to attain the desired mental state that had been attained by the donor/trainer. In an alternative embodiment, the signals from the first subject (donor/trainer) being in the first mental state are employed to prevent the second subject (recipient/trainee) from achieving a second mental state, wherein the second mental state is an undesirable one.

In some embodiments, the acquiring of the mental state information is preceded by or followed by identifying the mental state, by direct annotation by the first subject or an observer, or by automated analysis of the brain activity patterns, or both.

In other embodiments, the processing of the brain activity patterns does not seek to classify or characterize it, but rather to filter and transform the information to a form suitable for control of the stimulation of the second subject. In particular, according to this embodiment, the subtleties that are not yet reliably classified in traditional brain activity pattern analysis are respected. For example, it is understood that all brain activity is reflected in synaptic currents and other neural modulation, and therefore to a large extent, conscious and subconscious information is in theory accessible through brain activity pattern analysis. Since the available processing technology generally fails to distinguish a large number of different brain activity patterns, that available processing technology, is necessarily deficient. However, just because a computational algorithm is unavailable to extract the information, does not mean that the information is absent. Therefore, this embodiment employs relatively raw brain activity pattern data, such as filtered EEGs, to control the stimulation of the second subject, without a full comprehension or understanding of exactly what information of significance is present. Typically, the stimulation is a relatively low dimensionality stimulus, such as stereooptic, binaural, tactile, or other sensory stimulation, operating bilaterally, and with control over frequency and phase and/or waveform.

Likewise, a lack of present understanding of the essential characteristics of the signal components in the brain activity patterns does not prevent their acquisition, storage, communication, and processing (to some extent). The stimulation may be direct, i.e., a visual or auditory stimulus corresponding to the brain activity pattern, or a derivative or feedback control based on the second subject's brain activity pattern.

According to one embodiment, the stimulation of the second subject is associated with a feedback process, to verify that the second subject has appropriately responded to the stimulation, e.g., has a predefined similarity to the mental state as the first subject, has a mental state with a predefined difference from the first subject, or has a desire change from a baseline mental state. Advantageously, the stimulation may be adaptive to the feedback. In some cases, the feedback may be functional, i.e., not based on brain activity per se, or neural correlates of mental state, but rather physical, psychological, or behavioral effects that may be reported or observed.

The feedback typically is provided to a model-based controller for the stimulator, which alters stimulation parameters to optimize the stimulation.

For example, it is believed that brainwaves represent a form of resonance, where ensembles of neurons interact in a coordinated fashion. The frequency of the wave is related to neural responsivity to neurotransmitters, distances along neural pathways, diffusion limitations, etc. That is, the same mental state may be represented by different frequencies in two different individuals, based on differences in the size of their brains, neuromodulators present, physiological differences, etc. These differences may be measured in microseconds or less, resulting in fractional changes in frequency. However, if the stimulus is different from the natural or resonant frequency of the target process, the result may be different from that expected. Therefore, the model-based controller can determine the parameters of neural transmission and ensemble characteristics, vis-à-vis stimulation, and resynthesize the stimulus wave to match the correct waveform, with the optimization of the waveform adaptively determined. This may not be as simple as speeding up or slowing down playback of the signal, as different elements of the various waveforms representing neural correlates of mental state may have different relative differences between subjects.

Thus, a hybrid approach is provided, with use of source-derived waveforms, on one hand, which may be extracted from the brain activity readings of the first subject, processed by principal component analysis, or spatial principal component analysis, autocorrelation, or other statistical processing technique which separates components of brain activity, which can then be modified or modulated based on high-level parameters, e.g., abstractions. However, in the general case, the present technology maintains use of components or subcomponents of the source subject brain activity readings, e.g., EEG or MEG, and does not seek to characterize or abstract them to a semantic level Of course, in some cases, one or more components of the stimulation of the target subject may be represented as abstract or semantically defined signals, and more generally the processing of the signals to define the stimulation will involve high level modulation or transformation between the source signal received from the first subject, to define the target signal for stimulation of the second subject.

Preferably, each component represents a subset of the neural correlates reflecting brain activity that have a high autocorrelation in space and time, or in a hybrid representation such as wavelet. For example, one signal may represent a modulated 10.2 Hz signal, while another signal represents a superposed modulated 15.7 Hz signal, with respectively different spatial origins. These may be separated by optimal filtering (e.g., spatial PCA), once the characteristics of the signal are known, and bearing in mind that the signal is accompanied by a modulation pattern, and that the two components themselves may have some weak coupling and interaction.

In some cases, the base frequency, modulation, coupling, noise, phase jitter, or other characteristic of the signal may be substituted. For example, if the first subject is listening to music, there will be significant components of the neural correlates that are synchronized with the particular music. On the other hand, the music per se may not be part of the desired stimulation of the target subject. Therefore, through signal analysis and decomposition, the components of the signal from the first subject, which have a high temporal correlation with the music, may be extracted or suppressed from the resulting signal. Further, the target subject may be in a different acoustic environment, and it may be appropriate to modify the residual signal dependent on the acoustic environment of the target subject, so that the stimulation is appropriate for achieving the desired effect, and does not represent phantoms, distractions, or irrelevant or inappropriate content. In order to perform signal processing, it is convenient to store the signals or a partially processed representation, though a complete real-time signal processing chain may be implemented. Such a real-time signal processing chain is generally characterized in that the average size of a buffer remains constant, i.e., the lag between output and input is relatively constant, bearing in mind that there may be periodicity to the processing.

According to another embodiment, the mental state of the first subject (trainer or donor) is identified, and the neural correlates of brain activity are captured, and the second subject (trainee or recipient) is subject to stimulation based on the captured neural correlates and the identified mental state. The mental state is typically represented as a semantic variable, within a limited classification space. The mental state identification need not be through analysis of the neural correlates signal, and may be a volitional self-identification by the first subject, or a manual classification by third parties using, for example, fMRI or psychological assessment. The identified mental state is useful, for example, because it represents a target toward (or, in some cases, against) which the second subject (trainee or recipient) can be steered.

The stimulation may be one or more stimulus applied to the second subject (trainee or recipient), which may be an electrical or magnetic transcranial stimulation, sensory stimulation (e.g., visual, auditory or tactile), mechanical stimulation, ultrasonic stimulation, etc., and controlled with respect to waveform, intensity/amplitude, duration, or controlled via feedback, self-reported effect by the second subject, manual classification by third parties, automated analysis of brain activity, behavior, physiological parameters, etc. of the second subject.

Typically, the goal of the process is to induce in the second subject (trainee or recipient) neural correlates of the mental state of the first subject (trainer or donor) corresponding to the mental state of the first subject, through the use of stimulation parameters comprising a waveform over a period of time derived from the neural correlates of the mental state of the first subject.

Typically, the first and the second subjects are spatially remote from each other and may be temporally remote as well. In some cases, the first and second subject are the same subject (human or animal), temporally displaced. In other cases, the first and the second subject are spatially proximate to each other. These different embodiments differ principally in the transfer of the signal from the first subject to the second subject. However, when the first and the second subjects share a common environment, the signal processing of the neural correlates and, especially of real-time feedback of neural correlates from the second subject, may involve interactive algorithms with the neural correlates of the first subject.

According to another embodiment, the first and second subjects are each subject to stimulation. In one particularly interesting embodiment, the first subject and the second subject communicate with each other in real-time, with the first subject receiving stimulation based on the second subject, and the second subject receiving feedback based on the first subject. This can lead to synchronization of neural correlates (e.g., neuronal oscillations, or brainwaves) and, consequently, of mental state between the two subjects. However, the first subject need not receive stimulation based on real-time signals from the second subject, as the stimulation may derive from a third subject, or the first or second subjects at different points in time.

The neural correlates may be neuronal oscillations resulting in brainwaves that are detectable as, for example, EEG, qEEG, or MEG signals. Traditionally, these signals are found to have dominant frequencies, which may be determined by various analyses, such as spectral analysis, wavelet analysis, or principal part analysis (PCA), for example. One embodiment provides that the modulation pattern of a brainwave of the first subject is determined independent of the dominant frequency of the brainwave (though, typically, within the same class of brainwaves), and this modulation imposed on a brainwave corresponding to the dominant frequency of the second subject. That is, once the second subject achieves that same brainwave pattern as the first subject (which may be achieved by means other than electromagnetic, mechanical, or sensory stimulation), the modulation pattern of the first subject is imposed as a way of guiding the mental state of the second subject.

According to another embodiment, the second subject is stimulated with a stimulation signal which faithfully represents the frequency composition of a defined component of the neural correlates of the first subject. The defined component may be determined based on a principal component analysis or related technique.

The stimulation may be performed, for example, by using a tDCS device, a high-definition tDCS device, a tACS device, a TMS device, a deep TMS device, a light source, or a sound source configured to modulate the dominant frequency on the light signal or the sound signal. The stimulus may be a light signal, a sound signal, an electric signal, a magnetic field, olfactory or a tactile stimulation. The electric signal may be a direct current signal or an alternating current signal. The stimulus may be applied via a transcranial electric stimulation, a transcranial magnetic stimulation, a deep magnetic stimulation, a light stimulation, or a sound stimulation. A visual stimulus may be ambient light or a direct light. An auditory stimulus may be binaural beats or isochronic tones.

The technology also provides a processor configured to process the neural correlates of mental state from the first subject (trainer or donor), and to produce or define a stimulation pattern for the second subject (trainee or recipient) selectively dependent on a waveform pattern of the neural correlates from the first subject. Typically, the processor performs signal analysis and calculates at least a dominant frequency of the brainwaves of the first subject, and preferably also spatial and phase patterns within the brain of the first subject. The processor may also perform a PCA, a spatial PCA, an independent component analysis (ICA), eigenvalue decomposition, eigenvector-based multivariate analyses, factor analysis, an autoencoder neural network with a linear hidden layer, linear discriminant analysis, network component analysis, nonlinear dimensionality reduction (NLDR), or another statistical method of data analysis.

A signal is presented to a second apparatus, configured to stimulate the second subject (trainee or recipient), which may be an open loop stimulation dependent on a non-feedback controlled algorithm, or a closed loop feedback dependent algorithm. In other cases, analog processing is employed in part or in whole, wherein the algorithm comprises an analog signal processing chain. The second apparatus receives information from the processor (first apparatus), typically comprising a representation of a portion of a waveform represented in the neural correlates. The second apparatus produces a stimulation intended to induce in the second subject the desired mental state, e.g., representing the same mental state as was present in the first subject.

A typically process performed on the neural correlates is a filtering to remove noise. For example, noise filters may be provided at 50 Hz, 60 Hz, 100 Hz, 120 Hz, and additional overtones (e.g., secondary harmonics). Other environmental signals may also be filtered in a frequency-selective or waveform-selective (temporal) manner. Higher level filtering may also be employed, as is known in the art. The neural correlates, after noise filtering, may be encoded, compressed (lossy or losslessly), encrypted, or otherwise processed or transformed. The stimulator associated with the second subject (trainee or recipient) would typically perform decoding, decompression, decryption, inverse transformation, etc.

Information security and copy protection technology, similar to that employed for audio signals, may be employed to protect the neural correlate signals from copying or content analysis before use. In some cases, it is possible to use the stored encrypted signal in its encrypted for, without decryption. For example, with an asymmetric encryption scheme, which supports distance determination.

In practice, the feedback signal from the second subject may be correspondingly encoded as per the source signal, and the error between the two minimized. In such an algorithm, the signal sought to be authenticated is typically brought within an error tolerance of the encrypted signal before usable feedback is available. One way to accomplish this is to provide a predetermined range of acceptable authenticatable signals which are then encoded, such that an authentication occurs when the putative signal matches any of the predetermined range. In the case of the neural correlates, a large set of digital hash patterns may be provided representing different signals as hash patterns. The net result is relatively weakened encryption, but the cryptographic strength may still be sufficiently high to abate the risks.

According to one embodiment, the processor may perform a noise reduction distinct from a frequency-band filtering. According to one embodiment, the neural correlates is transformed into a sparse matrix, and in the transform domain, components representing high probability noise are masked, while components representing high probability signal are preserved. The distinction may be optimized or adaptive. That is, in some cases, the components which represent modulation that are important may not be known a priori. However, dependent on their effect in inducing the desired response in the second subject, the "important" components may be identified, and the remainder filtered or suppressed. The transformed signal may then be inverse-transformed, and used as a basis for a stimulation signal.

According to another embodiment, a method of mental state modification, e.g., brain entrainment, is provided, comprising: ascertaining a mental state in a plurality of first subjects; acquiring brain waves of the plurality of first subjects (trainer or donors), e.g., using one of EEG and MEG, to create a dataset containing brain waves corresponding to different mental states. The database may be encoded with a classification of mental states, activities, environment, or stimulus patterns, applied to the plurality of first subjects, and the database may include acquired brain waves across a large number of mental states, activities, environment, or stimulus patterns, for example. In many cases, the database records will reflect a characteristic or dominate frequency of the respective brain waves.

The database may be accessed according to its indexing, e.g., mental states, activities, environment, or stimulus patterns, for example, and a stimulation pattern for a second subject (trainee or recipient) defined based on the database records of one or more subjects.

The record(s) thus retrieved are used to define a stimulation pattern for the second subject (trainee or recipient). The selection of records, and their use, may be dependent on the second subject and/or feedback from the second subject. As a relatively trivial example, a female second subject could be stimulated principally dependent on records from female first subjects. Of course, a more nuanced approach is to process the entirety of the database and stimulate the second subject based on a global brain wave-stimulus model, though this is not required, and also, the underlying basis for the model may prove unreliable or inaccurate. In fact, it may be preferred to derive a stimulus waveform from only a single first subject, in order to preserve micro-modulation aspects of the signal, which as discussed above have not been fully characterized. However, the selection of the first subject(s) need not be static, and can change frequently. The selection of first subject records may be based on population statistics of other users of the records, i.e., whether or not the record had the expected effect, collaborative filtering, i.e., filtering the first subjects whose response pattern correlates highest with a given subject, etc. The selection of first subject records may also be based on feedback patterns from the second subject.

The process of stimulation typically seeks to target a desired mental state in the second subject (trainee or recipient), which is automatically or semi-automatically determined or manually entered. That target then represents a part of the query against the database to select the desired record(s). The selection of records may be a dynamic process, and reselection of records may be feedback dependent.

In one embodiment, the records are used to define a modulation waveform of a synthesized carrier or set of carriers, and the process may include a frequency domain multiplexed multi-subcarrier signal (which is not necessarily orthogonal). A plurality of stimuli may be applied concurrently, through the suffered subchannels and/or though different stimulator electrodes, magnetic field generators, mechanical stimulators, sensory stimulators, etc. The stimuli for the different subchannels or modalities need not be derived from the same records.

The stimulus may be applied to achieve brain entrainment (i.e., synchronization) of the second subject (trainee or recipient) with one or more first subjects (trainer or donor). Brain entrainment is not the only possible outcome of this process. If the plurality of first subjects are mutually entrained, then each will have a corresponding brain wave pattern dependent on the basis of brainwave entrainment. This link between first subject may be helpful in determining compatibility between a respective first subject and the second subject. For example, characteristic patterns in the entrained brainwaves may be determined, even for different target mental states, and the characteristic patterns correlated to find relatively close matches and to exclude relatively poor matches.

This technology may also provide a basis for a social network, dating site, employment or vocational testing, or other interpersonal environments, wherein people may be matched with each other based on entrainment characteristics. For example, people who efficiently entrain with each other may have better social relationships than those who do not.

As discussed above, the plurality of first subjects (trainers or donors) may have their respective brain wave patterns stored in association with separate database records. However, they may also be combined into a more global model. One such model is a neural network or deep neural network. Typically, such a network would have recurrent features. Data from a plurality of first subjects (trainers or donors) is used to train the neural network, which is then accessed by inputting the target state and/or feedback information, and which outputs a stimulation pattern or parameters for controlling a stimulator. When multiple first subjects form the basis for the stimulation pattern, it is preferred that the neural network output parameters of the stimulation, derived from and comprising features of the brain wave patterns or other neural correlates of mental state from the plurality of first subjects, which are then used to control a stimulator which, for example, generates its own carrier wave(s) which are then modulated based on the output of the neural network. The neural network need not periodically retrieve records, and therefore may operate in a more time-continuous manner, rather than the more segmented scheme of record-based control.

In any of the feedback dependent methods, the brainwave patterns or other neural correlates of mental states may be processed by a neural network, to produce an output that guides or controls the stimulation. The stimulation, is, for example, at least one of a light signal, a sound signal, an electric signal, a magnetic field, and a vibration or mechanical stimulus. The fields may be static or dynamically varying.

The process may employ a relational database of mental states and brainwave patterns, e.g., frequencies/neural correlate waveform patterns associated with the respective mental states. The relational database may comprise a first table, the first table further comprising a plurality of data records of brainwave patterns, and a second table, the second table comprising a plurality of mental states, each of the mental states being linked to at least one brainwave pattern. Data related to mental states and brainwave patterns associated with the mental states are stored in the relational database and maintained. The relational database is accessed by receiving queries for selected mental states, and data records are returned representing the associated brainwave pattern. The brainwave pattern retrieved from the relational database may then be used for modulating a stimulator seeking to produce an effect selectively dependent on the mental state at issue.

A further aspect of the technology provides a computer apparatus for creating and maintaining a relational database of mental states and frequencies associated with the mental state. The computer apparatus may comprise a non-volatile memory for storing a relational database of mental states and neural correlates of brain activity associated with the mental states, the database comprising a first table comprising a plurality of data records of neural correlates of brain activity associated with the mental states, and a second table comprising a plurality of mental states, each of the mental states being linked to one or more records in the first table; a processor coupled with the non-volatile memory, and being configured to process relational database queries, which are then used for searching the database; RAM coupled with the processor and the non-volatile memory for temporary holding database queries and data records retrieved from the relational database; and an IO interface configured to receive database queries and deliver data records retrieved from the relational database. A SQL or noSQL database may also be used to store and retrieve records. A relational database described above maintained and operated by a general purpose computer, improves the operations of the general purpose computer by making searches of specific mental states and brainwaves associated therewith more efficient.

A further aspect of the technology provides a method of brain entrainment comprising: ascertaining a mental state in a first subject; recording brain waves of the plurality of subjects using at least one channel one of EEG and MEG; storing the recorded brain waves in a physical memory device; retrieving the brain waves from the memory device; applying a stimulus signal comprising a brainwave pattern derived from at least one-channel one of the EEG and MEG to a second subject via transcranial stimulation, whereby the mental state desired by the second subject is achieved. The stimulation may be of the same order (number of channels) as the EEG or MEG, or a different number of channels, typically reduced. For example, the EEG or MEG may comprise 128 or 256 channels, while the transcranial stimulator may have 8 or fewer channels. Sensory stimulation of various modalities and patterns may accompany the transcranial stimulation.

It is therefore an object to provide a method of inducing sleep in a mammal, comprising: retrieving a stored modulation sequence for at least one of an audio signal and a visual signal derived from captured neural correlates of at least one sleep cycle, which is adapted, when used to stimulate the mammal, to induce at least one sleep cycle in the mammal; and presenting the at least one of the audio signal and the visual signal having the modulation sequence to the mammal, to induce the mammal to enter a respective sleep cycle.

It is a further object to provide a system for inducing sleep in a subject shown in FIG. 18, comprising: a memory 1801 configured to store a waveform, derived from neural correlates of at least one sleep stage 1803, processed by an automated processor 1905 to derive at least one of a temporal and a spatial pattern transformed into the waveform 1907 for modulating at least one of a visual stimulus and an auditory stimulus; and at least one of a visual stimulator and an auditory stimulator, configured to retrieve the waveform and modulate the waveform on at least one of a visual stimulus and an auditory stimulus 1811, for use in stimulating a subject to induce a sleep.

It is another object to provide a computer readable medium, storing non-transitory instructions for controlling a programmable processor for presenting at least one of a visual stimulus and an auditory stimulus to a subject to induce sleep, comprising: instructions to define a waveform pattern derived from neural correlates of at least one sleep stage, processed to derive at least one of a temporal and a spatial pattern transformed into the waveform; instructions to modulate the waveform on at least one of a visual stimulus and an auditory stimulus for presentation to the subject; and instructions for controlling the modulation of the waveform according to a sleep cycle.

It is also an object to provide a method of inducing a sleep cycle in a subject, comprising modulating a waveform on at least one of a visual stimulus and an auditory stimulus for use in visual or auditory stimulation of the subject, to induce the sleep cycle in the subject, wherein the waveform is generated by recording neural correlates of at least one sleep cycle of a donor, processing the recorded neural correlates of the at least one sleep cycle to decode at least one of a temporal and a spatial pattern; and transforming the at least one of the temporal and the spatial pattern into the waveform.

The recording of the neural correlates of at least one sleep stage of a donor may be done by recording at least one of an electroencephalogram (EEG), a magnetoencephalogram (MMG), and a functional magnetic resonance (fMRI). The recorded neural correlates of at the sleep stage may be processed using a statistical analysis technique. The statistical analysis technique may be one of a Principal Component Analysis (PCA), a Spatial Principal Component Analysis (Spatial PCA), a Kernel Principal Component Analysis (Kernel PCA), a Nonlinear Principal Component Analysis (NLPCA), an Independent Component Analysis (ICA), Singular Value Decomposition (SVD), Factor Analysis, a Gaussian Process Latent Variable Model (GPLVM), a Curvilinear Component Analysis (CCA), a Diffeomorphic Dimensionality Reduction (Diffeomap), a Gelfand transform, a Fourier transform, a Fourier-Pontryagin transform, a Laplace transform, a short-time Fourier transform (STFT), a fractional Fourier transform (FRFT), Laplacian Eigenmaps, a spectral analysis, a wavelet analysis, an eigenvector-based multivariable analysis, a factor analysis, canonical correlation analysis (CCA), and a nonlinear dimensionality reduction (NLDR).

The transforming of the at least one of the temporal and a spatial pattern into the waveform may comprise performing an inversion transform on the at least one of the temporal and the spatial pattern of the donor into the waveform, adapted to expose the at least one of the temporal and the spatial pattern to the subject.

The subject and the donor may be a single human at different times.

The at least one of a light stimulus and a sound stimulus may be frequency modulated, amplitude modulated, pulse rate modulate, pulse frequency modulated, and/or phase modulated corresponding to the waveform.

The at least one of the light stimulus and the sound stimulus may be modulated to provide at least one of a binaural stimulation and an isochronic tones stimulation. The sound stimulus may comprise at least one of an audible sound frequency, an ultrasonic sound frequency, and an infrasonic sound frequency. The light stimulus may be at least one of amplitude modulated and pulse modulated. The sound stimulus may comprise at least one of a random noise, music, a sound of rainfall, a sound of ocean waves, and a sound of a human voice.

The sleep cycle may comprise a plurality of sleep stages, comprising a REM sleep stage, and/or a non-REM sleep stage. The sleep cycle may comprise a natural sequence of sleep stages comprising at least one full sleep cycle, e.g., at least two recorded sleep cycles. The method may comprise monitoring the sleep stage of the subject, distinct from recording the neural correlates, and adapting the waveform selectively dependent on the monitored sleep stage.

The subject may be stimulated with at least one of a visual stimulus and an auditory stimulus modulated according to a first portion of the waveform, correlating the stimulation of the subject with a respective sleep stage of the subject during stimulation, and selecting a second portion of the waveform representative of the at least one sleep stage of the donor that corresponds to the respective sleep stage of the subject. The method may further comprise stimulating the subject with the at least one of the visual stimulus and the auditory stimulus, and modifying the stimulation after determining that the subject is not in the sleep stage sought to be induced corresponding to the at least one sleep stage of the donor.

The method may further comprise adjusting an ambient temperature surrounding the subject for a specific sleep stage corresponding to the at least one sleep stage of the donor.

The method may further comprise superimposing on said at least one of the light stimulus and the sound stimulus a signal having a rhythm having a frequency less than approximately 100 Hz. The frequency may be approximately 40 Hz. In this case, the approximation means, for example, within 13%, or a signal having a corresponding physiological effect in the subject as a signal of that frequency in a mean normal male Caucasian adult, to the extent that the physiological effect varies across gender, race, size, condition, of other characteristics. The at least one channel may be less than six channels and the placement of electrodes used for transcranial stimulation may be approximately the same as the placement of electrodes used in recording of said one of EEG and MEG.

The present technology may be responsive to chronobiology, and in particular to the subjective sense of time. For a subject, this may be determined volitionally subjectively, but also automatically, for example by judging attention span, using e.g., eye movements, and analyzing persistence of brainwave patterns after a discrete stimulus. Further, time constants of the brain, reflected by delays and phase may also be analyzed. Further, the contingent negative variation (CNV) preceding a volitional act may be used, both to sense conscious action timing, and also the time relationships between thought and action more generally.

Typically, brainwave activity is measured with a large number of EEG electrodes, which each receive signals from a small area on the scalp, or in the case of an MEG, by a number of sensitive magnetic field detectors which are responsive to local field differences. Typically, the brainwave capture is performed in a relatively high number of spatial dimensions, e.g., corresponding to the number of sensors. Typically, it is infeasible to process the brainwave signals to create a source model, given that the brainwaves are created by billions of neurons, connected through axons which have long distances. Further, the neurons are generally no-linear, and interconnected. However, a source model is not required.

Various types of artificial intelligence may be exploited to analyze the neural correlates of mental state represented in the brain activity data, of both the first subject (source) and the second subject (target). The algorithm or implementation need to be the same, though in some cases, it is useful to conform the approach of the source processing and feedback processing so that the feedback does not achieve or seek a suboptimal target mental state. However, given the possible differences in conditions, resources, equipment, and purpose, there is no necessary coordination of these processes. The artificial intelligence may take the form of neural networks or deep neural networks, though rule/expert based systems, hybrids, and more classical statistical analysis may be used. In a typical case, an artificial intelligence process will have at least one aspect which is non-linear in its output response to an input signal, and thus at least the principle of linear superposition is violated. Such systems tend to permit discrimination, since a decision, and the process of decision-making, is ultimately non-linear. An artificially intelligent system requires a base of experience or information upon which to train. This can be a supervised (external labels applied to data), unsupervised (self-discrimination of classes), or semisupervised (a portion of the data is externally labelled). A self-learning or genetic algorithm may be used to tune the system, including both or either the signal processing at the trainer system and the target system. In a genetic algorithm feedback-dependent self-learning system, the responsivity of a subject, e.g., the target, to various kinds of stimuli may be determined over a stimulus space. This stimulation may be in the context of use, with a specific target mental state provided, or unconstrained. The stimulator may operate using a library of stimulus patterns, or seek to generate synthetic patterns or modifications of patterns. Over a period of time, the system will learn to map a desired mental state to optimal context-dependent parameters of the stimulus pattern.

The technology may be used for both the creation of mental states in the target, elimination of existing mental states in the target. In the latter case, a decision of what end state is to be achieved is less constrained, and therefore the optimization is distinct. For example, in the former case, it may be hard to achieve a particular mental state that is desired, requiring a set of transitions to cause the brain of the target to be enabled/prepared to enter the target state. In the case of a system seeking to eliminate an undesired mental state, the issue is principally what path to take to most efficiently leave the current state, bearing in mind the various costs, such as the comfort/discomfort of the stimulation, the time value cost, etc. Therefore, the series of states may differ in the implementation of these distinct goals, even if the endpoints are identical, i.e., the optimal algorithm to achieve state B from state A, may be different from the optimal algorithm to exit state A, and end up at state B.

The technology may be used to address mental states classified as emotions. Typically, an emotional state at a lower level operates in different brain regions, than cognitive processes. As such, the biology of these mental state is different. Often, the emotional states have a biochemical or hormonal component, and perhaps a physiological component, that may be attenuated or absent from cognitive states. Therefore, while the general brainwave or other neural correlates acquisition may be similar or identical, the stimulus used on the second subject may be distinct, in modality, spatial location, intensity/waveform, other stimulation parameters, and the types and application of feedback employed. In e medical treatment implementation, in some cases it may be appropriate to administer a drug or pharmacological agent that assists in achieving the target mental state, and for emotional states, this may include certain psychotropic drugs, such as epinephrine, norepinephrine reuptake inhibitors, serotonin reuptake inhibitors, peptide endocrine hormones, such as oxytocin, ACTH fragments, insulin, etc.

BRIEF DESCRIPTION OF THE DRAWINGS

The detailed description is described with reference to the accompanying figures. In the figures, the left-most digit(s) of a reference number identifies the figure in which the reference number first appears. The use of the same reference number in different figures indicates similar or identical items.

FIG. 1 shows a flowchart according to one embodiment of the invention illustrating a process of replicating a desired mental person from one subject to another subject.

FIG. 2 shows a flowchart according to one embodiment of the invention illustrating a process of replicating a mental state from one subject to another subject by recording and replicating brainwaves associated with the desired mental state, according to one embodiment of the invention.

FIG. 5 shows a block diagram according to one embodiment of the invention illustrating creation of a database of mental states and their associated frequencies for later brain entrainment.

FIG. 6 shows a block diagram according to one embodiment of the invention illustrating using a neural network in the creation of a database of mental states and their associated frequencies for later brain entrainment.

FIG. 7A shows a block diagram according to one embodiment of the invention illustrating using a single channel EEG/MEG of a trainer and a stimulation of a trainee using a single stimulus signal.

FIG. 7B shows a set-up according to one embodiment of the invention illustrating using a single-channel 1×1 transcranial Direct Current Stimulation (tDCS) made by Soterix Medical.

FIG. 8 shows a block diagram according to one embodiment of the invention illustrating using two-channel EEG/MEG of a trainer and a stimulation of a trainee using two-stimulus signal.

FIG. 9 shows a block diagram according to one embodiment of the invention illustrating using three-channel EEG/MEG of a trainer and a stimulation of a trainee using three-stimulus signal.

FIG. 10 shows a block diagram according to one embodiment of the invention illustrating using four-channel EEG/MEG of a trainer and a stimulation of a trainee using four-stimulus signal.

FIG. 13 shows a block diagram according to one embodiment of the invention illustrating using n-channel EEG EEG/MEG of a trainer and a dominant frequency, and a stimulation of a trainee using n-stimulus signal transcranial stimulation simultaneously with a single stimulus on which the dominant frequency is modulated.

FIG. 14 shows a block diagram according to one embodiment of the invention illustrating using n-channel EEG EEG/MEG of a first subject, processed using principal component analysis, with the second subject being stimulated based on the principal components of the brainwave pattern of the first subject.

FIG. 17 shows a flowchart of an embodiment of the invention to record EEG or MEG from a plurality of sleeping donors, analyzing the data, to extract patterns, transforming the patterns into a waveform, modulating the waveform onto a light or sound stimulus, stimulating the subject with the light or sound stimulus modulated with the waveform to induce sleep.

FIG. further shows that the method further monitors the sleep of the subject.

Figure 18:
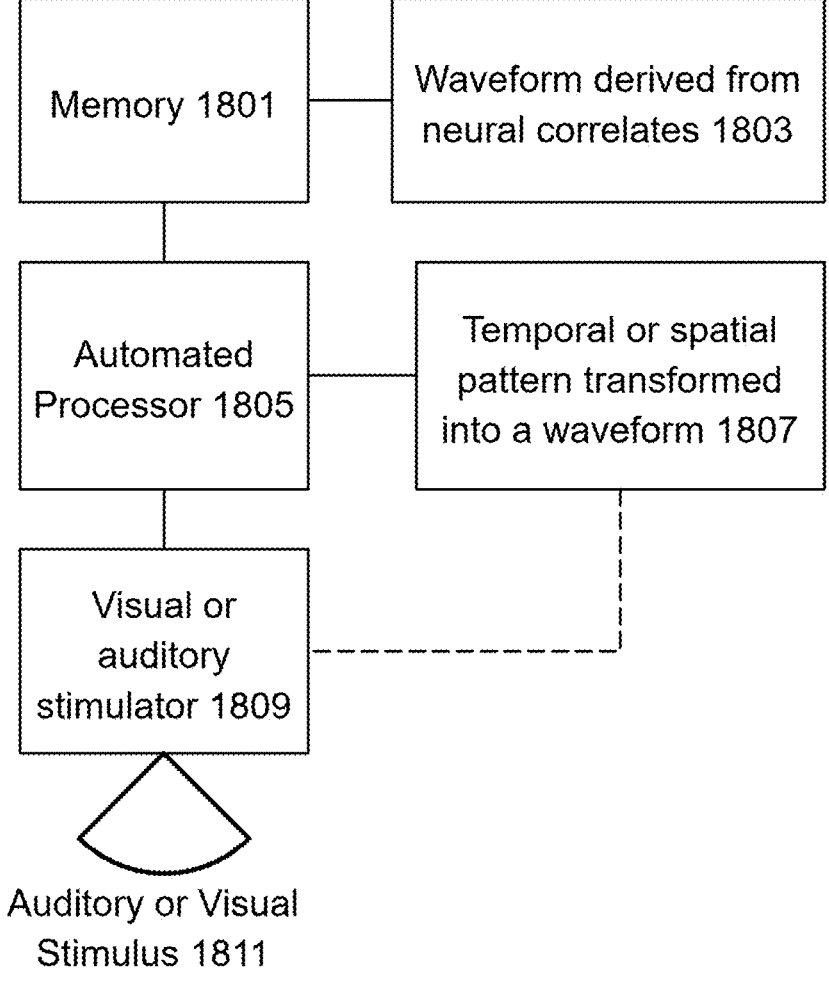

FIG. 18 shows a system with a memory which stores a waveform derived from neural correlates of at least one sleep stage, a processor to derive at a temporal or a spatial pattern to be transformed into a waveform for modulating at a visual or auditory stimulus, and a visual or auditory stimulator which retrieves the waveform and modulates the waveform on the visual or auditory stimulus.

DETAILED DESCRIPTION OF THE PREFERRED EMBODIMENTS

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "unit" or "module" includes a unit implemented by hardware or software and a unit implemented by both of them. One unit may be implemented by two or more pieces of hardware, and two or more units may be implemented by one piece of hardware.

FIG. 1 shows a flowchart illustrating the process of replicating a mental state from one subject to another subject according to one embodiment of the invention. As illustrated in FIG. 1, a mental state of the first subject may be initially identified in step 100. The mental state may be, for example, a state of high alertness or relaxation, a state of deep non-rem sleep or a state of REM sleep, a state of emotional arousal or a state of calm, a happy state, a focused state, etc. Any conceivable mental state that is desirable by the second subject may be sought in the first subject for replication. The first subject, a donor, may be an expert in particular field that allows him to achieve a desirable mental state at will. Alternatively, the donor may be required to perform certain actions or exercises, or meditate to achieve the desirable state. If the mental state of the first subject is a desirable mental state, as may be ascertained in step 110, the desired mental state of the first subject is captured in step 120 by recording the brain activity patterns. The mental state may be ascertained by any number of known methods including, but not limited to, EEG, MEG, fMRI, functional near infrared spectroscopy (fNIRS), facial image recognition, self-reporting by the first subject, a test or a questionnaire administered to the first subject, a psychological evaluation, etc. The mental state may be captured by any number of known methods including, but not limited to, EEG, MEG, fMRI, etc. The brain activity patterns associated with the desired mental state may be saved in a non-volatile memory 130 for further retrieval 140. The desired mental state of the first subject (donor) is then replicated in a second subject (recipient) 150 by inducing the brain activity patterns associated with the desired mental state in the second subject. Inducing the brain activity patterns associated with the desired mental state may be done by modulating the brain activity patterns on a stimulus or stimuli such as light, sound (binaural beats, or isochronic tones), transcranial direct current stimulation (tDCS), high-definition-tDCS, transcranial alternating current stimulation (tACS), transcranial magnetic stimulation (TMS), Deep Transcranial Magnetic Stimulation (Deep TMS), etc. Finally, the mental state of the second subject may be ascertained to confirm that it is the desired mental state 160.

FIG. 2 shows a flowchart according to one embodiment of the invention illustrating a process of replicating a mental state from one subject to another subject by recording and replicating brainwaves associated with the desired mental state according to one embodiment of the invention. As illustrated in FIG. 2, a mental state of the first subject may be initially identified in step 100. If the mental state of the first subject is a desirable mental state, as may be ascertained in step 110, brainwaves of the first subject are recorded in step 170. Brainwaves may be recorded by any number of known techniques including but not limited to EEG, qEEG and MEG. The brainwaves of the first subject may be stored in non-volatile memory 130 for later retrieval 140. The desired mental state of the first subject is then replicated in the second subject in step 180 by inducing in the second subject the brainwaves of the first subject. Finally, the mental state of the second subject may be ascertained to confirm that it is the desired mental state 160.

Figures 3, 4:
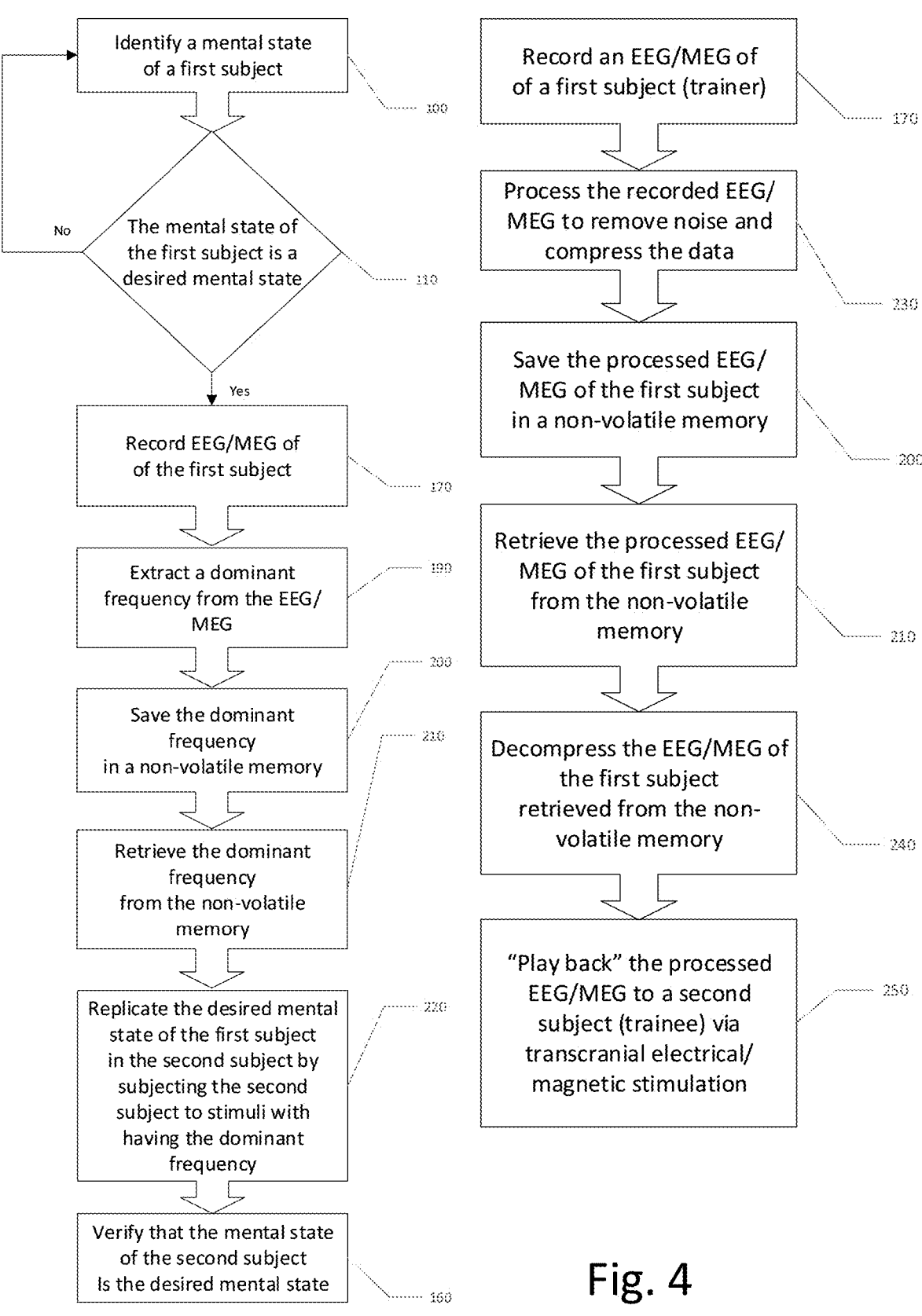
FIG. 3 shows a flowchart according to one embodiment of the invention illustrating a process of replicating a mental state from one subject to another subject by recording electroencephalogram (EEG) of a first subject, extracting a dominant frequency from the EEG and replicating the mental state of the first subject in a second subject by stimulating the second subject with stimuli having the dominant frequency associated with the desired mental state, according to one embodiment of the invention.
FIG. 4 shows a block diagram according to one embodiment of the invention illustrating recording EEG or MEG of one subject (trainer) and "playing it back" to another subject (trainee) via transcranial stimulation.

FIG. 3 shows a flowchart according to one embodiment of the invention illustrating a process of replicating a mental state from one subject to another subject by extracting a dominant frequency from the EEG of a first subject in a desired mental state and replicating the desired mental state in a second subject according to one embodiment of the invention. As illustrated in FIG. 2, a mental state of the first subject may be initially identified in step 100. If the mental state of the first subject is a desirable mental state, as may be ascertained in step 110, EEG (or MEG) of the first subject are recorded in step 170. At least one dominant frequency is extracted from the EEG/MEG in step 190 and may be saved in a non-volatile memory in step 200 for later retrieval 210. The dominant frequency is then modulated on at least one stimulus or stimuli to stimulate a second subject. The desired mental state of the first subject is replicated in the second subject (recipient) in step 220 by subjecting the second subject to a stimulus or stimuli having at least one dominant frequency. A person of ordinary skill in the art will appreciate that the dominant frequency may be modulated on any number of signals including but not limited to a light signal, a sound signal, an electrical signal (having a direct or alternating current) or magnetic field. The light signal may be applied to the second subject as an ambient light or a direct light. Two different (or identical) light signals may be applied separately into each eye of the recipient. An audio signal may be used to generate binaural beats or isochronic tones directed into each ear of the recipient. An electric signal may be used in transcranial electric stimulation via tDCS, high-definition of tDCS, or tACS. An electric signal may be used to stimulate the recipient via TMS or deep magnetic stimulation. Finally, the mental state of the second subject may be ascertained to confirm that it is the desired mental state 160.

FIG. 4 shows a block diagram illustrating the process of recording an EEG or MEG of a first subject (trainer) and "playing it" back to another subject (trainee) after some digital processing. EEG (or MEG) of the first subject (trainer) are recorded in step 170. The EEG or MEG may be digitally processed to remove noise and compress the recording (similar to MPEG compression) in step 230. The processed and/or compressed EEG or MEG may be stored in a non-volatile memory in step 200 for later retrieval 210. The data retrieved from the non-volatile memory is decompressed in step 240 and played back to a second subject (trainee) via transcranial stimulation in step 250 for brain entrainment.

FIG. 5 shows a block diagram according to one embodiment of the invention illustrating the creation of a database of mental states and their associated frequencies for later use in brain entrainment. A plurality of subjects are tested to determine their respective mental state, and their brainwaves are recorded using EEG or MEG in step 260. A database is created where mental states and their associated frequencies of EEG/MEG are saved in step 270. When a particular mental state is desired, the data base is searched for this mental state and the associated frequency (or frequencies) is (are) retrieved in step 280. The frequency associated with the desired mental state is modulated on a stimulus signal in step 290. A subject is stimulated with the stimulus signal in step 300 to achieve the desired mental state. The mental state of the subject may be ascertained in step 160.

FIG. 6 shows a block diagram according to one embodiment of the invention illustrating the use of neural network in creation of a database of mental states and their associated frequencies for later brain entrainment. A plurality of subjects are tested to determine their respective mental state, and their brainwaves are recorded using EEG or MEG in step 260. A neural network is trained on the set of EEG or MEG recordings to recognize a mental state in step 310. A database is created were mental states and their associated frequencies of EEG/MEG are saved in step 270. When a particular mental state is desired, the data base is searched for this mental state and the associated frequency (or frequencies) is (are) retrieved in step 280. The frequency associated with the desired mental state is modulated on a stimulus signal in step 290. A subject is stimulated with the stimulus signal in step 300 to achieve the desired mental state. The mental state of the subject may be ascertained in step 160 using, for example, the neural network trained to recognize mental states, to confirm that the subject is in the desired mental state.

FIG. 7A shows a block diagram illustrating the process of recording a single-channel EEG or MEG of a first subject (trainer) and "playing it" back to another subject (trainee) after some digital processing. The single-channel EEG (or MEG) of the first subject (trainer) are recorded in step 310. In a single-channel EEG, a single electrode may be placed on a forehead or another desirable location of the scalp of the first subject (trainer). A ground electrode for EEG recordings is often placed on the forehead, but could be placed anywhere else on the body (the location of the ground on the subject is generally irrelevant). In the present embodiment, a ground electrode may be placed behind the ear, or another place. The single-channel EEG or MEG may be digitally processed to remove noise and/or compress the recording in step 230. The processed and/or compressed single-channel EEG or MEG may be stored in a non-volatile memory in step 200 for later retrieval 210. The data retrieved from the non-volatile memory may be decompressed in step 240 and played back to a second subject (trainee) via a single-channel transcranial stimulation (tDCS, tACS or TMS) in step 320 for brain entrainment. In a single-channel transcranial electric stimulation (TES), a single electrode may be placed on a forehead or another desirable location of the scalp of the second subject (trainee). Another electrode (ground) may be place, for example, behind the ear.

FIG. 7B shows a photograph of a set-up according to one embodiment of the invention illustrating using a single-channel 1×1 transcranial Direct Current Stimulation (tDCS) made by Soterix Medical. The set-up shows two electrodes-cathode and anode-attached to the scalp of a subject. It is important to place the tDCS electrodes in the same places as the EEG electrodes.

FIG. 8 shows a block diagram illustrating the process of recording a two-channel EEG or MEG of a first subject (trainer) and "playing it" back to another subject (trainee) after some digital processing. The two-channel EEG (or MEG) of the first subject (trainer) are recorded in step 330. In a two-channel EEG, a pair of electrodes may be placed on a forehead, on the temples, or other desirable locations of the scalp of the first subject (trainer). A ground electrode for EEG recordings is often placed on the forehead, but could be placed anywhere else on the body. In the present embodiment, a ground electrode may be placed behind the ear, or another place. The two-channel EEG or MEG may be digitally processed to remove noise and/or compress the recording in step 230. The processed and/or compressed two-channel EEG or MEG may be stored in a non-volatile memory in step 200 for later retrieval 210. The data retrieved from the non-volatile memory may be decompressed in step 240 and played back to a second subject (trainee) via two-channel transcranial stimulation (tDCS, tACS or TMS) in step 340 for brain entrainment. In two-channel transcranial electric stimulation (TES), a pair of electrodes should be preferably placed at the same locations on the scalp of the second subject (trainee) as the EEG electrodes in step 330. An additional electrode (ground) may be placed elsewhere, for example, behind the ear.

FIG. 9 shows a block diagram illustrating the process of recording a three-channel EEG or MEG of a first subject (trainer) and "playing it" back to another subject (trainee) after some digital processing. The three-channel EEG (or MEG) of the first subject (trainer) are recorded in step 350. In a three-channel EEG, three electrodes are placed on scalp of the first subject. In one embodiment, one electrode may be placed on a forehead, and two electrodes may be placed on the temples, behind the ears, on the neck at the base of the skull, or other desirable locations of the scalp of the first subject (trainer). A ground electrode for EEG recordings can be placed anywhere on the body. The three-channel EEG or MEG may be digitally processed to remove noise and/or compress the recording in step 230. The processed and/or compressed three-channel EEG or MEG may be stored in a non-volatile memory in step 200 for later retrieval 210. The data retrieved from the non-volatile memory may be decompressed in step 240 and played back to a second subject (trainee) via three-channel transcranial stimulation (tDCS, tACS or TMS) in step 360 for brain entrainment. In three-channel transcranial electric stimulation (TES), three electrodes should be preferably placed at the same location on the scalp of the second subject (trainee) as the EEG electrodes in step 350. An additional electrode (ground) may be placed elsewhere on the scalp or the body of the second subject.

FIG. 10 shows a block diagram illustrating the process of recording a four-channel EEG or MEG of a first subject (trainer) and "playing it" back to another subject (trainee) after some digital processing. The four-channel EEG (or MEG) of the first subject (trainer) are recorded in step 370. In a four-channel EEG, four electrodes are placed on scalp of the first subject. In one embodiment, one pair of electrodes may be placed on a forehead, and another pair of electrodes may be placed on the temples, behind the ears, on the neck at the base of the skull, or other desirable locations of the scalp of the first subject (trainer). A ground electrode for ERG recordings can be placed on the forehead or anywhere else on the body. The four-channel EEG or MEG may be digitally processed to remove noise and/or compress the recording in step 230. The processed and/or compressed four-channel EEG or MEG may be stored in a non-volatile memory in step 200 for later retrieval 210. The data retrieved from the non-volatile memory may be decompressed in step 240 and played back to a second subject (trainee) via four-channel transcranial stimulation (tDCS, tACS or TMS) in step 380 for brain entrainment. In four-channel transcranial electric stimulation (TES), four electrodes should be preferably placed at the same locations on the scalp of the second subject (trainee) as the EEG electrodes in step 370. An additional electrode (ground) may be placed on the forehead or elsewhere on the scalp or the body of the second subject.

Figures 11, 12:
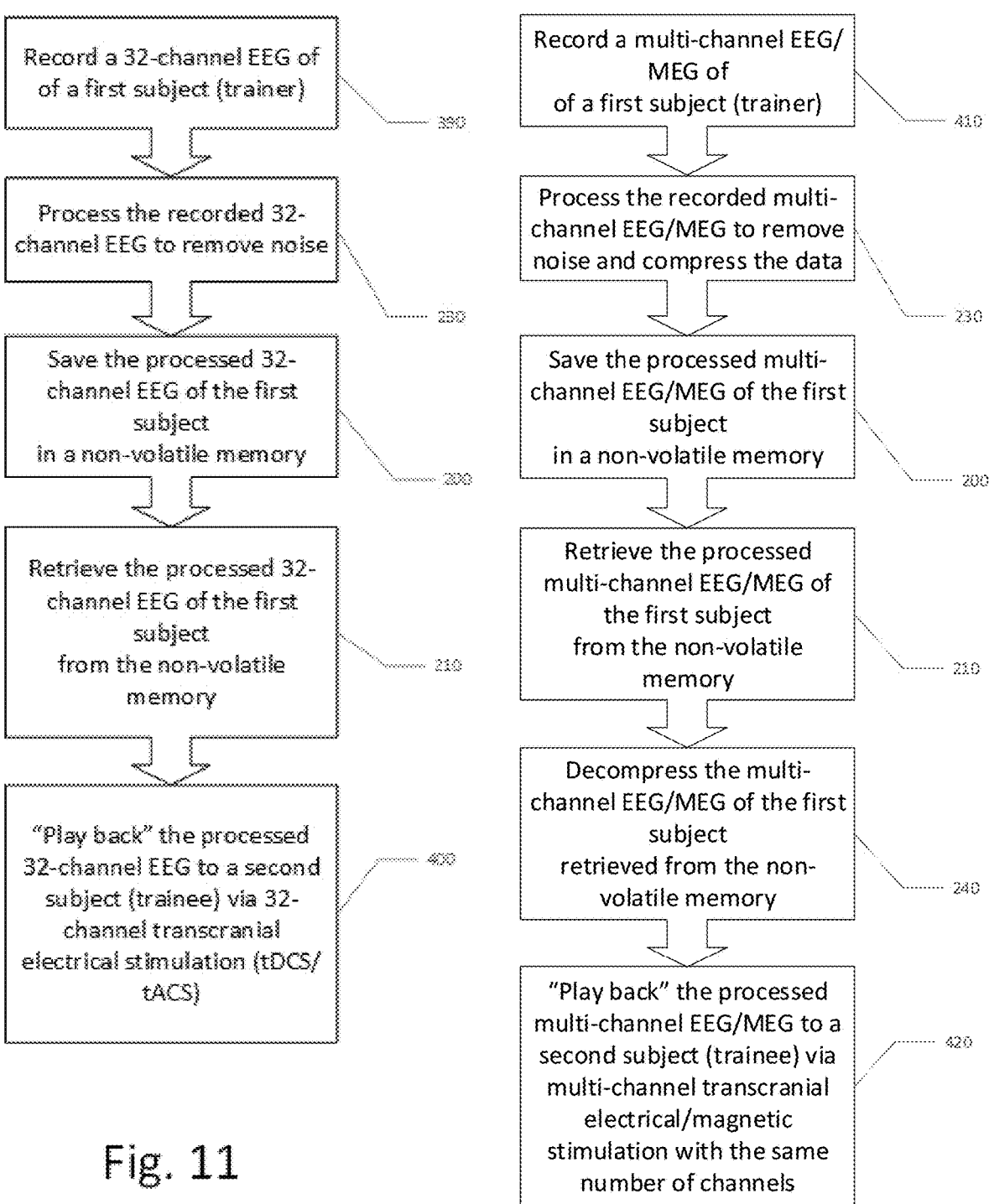
FIG. 11 shows a block diagram according to one embodiment of the invention illustrating using thirty-two-channel EEG/MEG of a trainer and a stimulation of a trainee using thirty-two-stimulus signal.
FIG. 12 shows a block diagram according to one embodiment of the invention illustrating using multi-channel EEG EEG/MEG of a trainer arranged along a circular band and a stimulation of a trainee using multi-stimulus signal arranged along a circular band.

FIG. 11 shows a block diagram illustrating the process of recording a thirty-two-channel EEG or MEG of a first subject (trainer) and "playing it" back to another subject (trainee) after some digital processing. The thirty-two-channel EEG (or MEG) of the first subject (trainer) are recorded in step 390. In a thirty-two-channel EEG, thirty-two electrodes are placed on scalp of the first subject. In one embodiment, one electrode is placed on a forehead, first pair of electrodes may be placed on the temples, and the second pair of electrodes may be placed behind the ears, on the neck at the base of the skull, or other desirable locations of the scalp of the first subject (trainer). A ground electrode for EEG recordings can be placed on the forehead or anywhere else on the body. The thirty-two-channel EEG or MEG may be digitally processed to remove noise and/or compress the recording in step 230. The processed and/or compressed thirty-two-channel EEG or MEG may be stored in a non-volatile memory in step 200 for later retrieval 210. The data retrieved from the non-volatile memory may be decompressed in step 240 and played back to a second subject (trainee) via thirty-two-channel transcranial stimulation (tDCS, tACS or TMS) in step 400 for brain entrainment. In thirty-two-channel transcranial electric stimulation (TES), four electrodes should be preferably placed at the same locations on the scalp of the second subject (trainee) as the EEG electrodes in step 390. An additional electrode (ground) may be placed on the forehead or elsewhere on the scalp or the body of the second subject.

FIG. 12 shows a block diagram illustrating the process of recording a multi-channel EEG or MEG of a first subject (trainer) and "playing it" back to another subject (trainee) after some digital processing. The multi-channel EEG (or MEG) of the first subject (trainer) are recorded in step 410. In a multi-channel EEG, a plurality of n electrodes are used on the first subject. In one embodiment, electrodes are arranged on a circular or semi-circular band that is placed on the scalp of the first subject (trainer). A ground electrode for EEG recordings can be placed on the forehead or anywhere else on the body. The multi-channel EEG or MEG may be digitally processed to remove noise and/or compress the recording in step 230. The processed and/or compressed multi-channel EEG or MEG may be stored in a non-volatile memory in step 200 for later retrieval 210. The data retrieved from the non-volatile memory may be decompressed in step 240 and played back to a second subject (trainee) via multi-channel transcranial stimulation (tDCS, tACS or TMS) in step 400 for brain entrainment. In multi-channel transcranial electric stimulation (TES), the same number (n) of electrodes should be arranged on a circular or semi-circular band and preferably placed at the same locations on the scalp of the second subject (trainee) as in step 410. An additional electrode (ground) may be placed on the forehead or elsewhere on the scalp or the body of the second subject.

FIG. 13 shows a block diagram illustrating the process of recording a multi-channel EEG or MEG of a first subject (trainer) and "playing it" back to another subject (trainee) after some digital processing along with additional simultaneous stimulation by a stimulus, on which the dominant frequency of the brainwaves of the first subject is modulated. The multi-channel EEG (or MEG) of the first subject (trainer) are recorded in step 410. In a multi-channel EEG, a plurality of n electrodes are used on the first subject. An additional ground electrode for EEG recordings can be placed on the scalp or anywhere else on the body. The multi-channel EEG or MEG may be digitally processed to remove noise and to extract at least one dominant frequency 230. The processed multi-channel EEG or MEG and said at least one dominant frequency may be stored in a non-volatile memory in step 200 for later retrieval 210. The data retrieved from the non-volatile memory is played back to a second subject (trainee) via multi-channel transcranial stimulation (tDCS, tACS or TMS) in step 450. In multi-channel transcranial electric stimulation (TES), the same number (n) of electrodes should be used and placed at the same locations on the scalp of the second subject (trainee) as in step 410. An additional electrode (ground) may be placed on the forehead or elsewhere on the scalp or the body of the second subject. In step 460, said at least one dominant frequency is modulated on at least one stimulus and applied to the second subject (trainee) simultaneously with the transcranial stimulation of step 450. The dominant frequency may be modulated on a light signal, on binaural beats, on isochronic tones, or any number of other physical stimuli as will be understood by a person with ordinary skills in the art.

FIG. 14 shows a block diagram illustrating the process of recording a multi-channel EEG and/or MEG of a first subject and using the data derived from the recording to generate a stimulus for a second subject. The data from the first subject, from an n-channel EEG 141 is entered into a data matrix, representing the respective location and recorded signals from each sensor. There may be, for example, 128 sensors recording data concurrently. Each of the sensors may acquire data representing hundreds of potential sources. An automated digital processor then processes the data matrix according to a statistical variance analysis, such as principal component analysis 142 or a non-linear dimensionality reduction, to produce a set of principal components, and as a result reduce the complexity of the data matrix by excluding components that have low contribution to information content of the matrix. For example, the number of independent modulated oscillators modelled by the matrix may be 32 or fewer. This reduction in complexity or dimensionality may be accompanied be a reduction in spatial degrees of freedom. For example, a stimulator may have 32 or fewer stimulus electrodes. The principal components, and their associated modulation components, are then stored e.g., in a non-volatile memory 143. A second process determines the optimal stimulation pattern for the second subject 144. While the composite model of the source represented in the processed matrix may encompass 32 discrete sources, the stimulation will typically include a subset of these sources, for example one to three, which are then used to control the stimulator, which for example has 4-32 electrodes, the higher end representing high definition transcranial electrical stimulation. In addition, the second subject has simultaneous EEG recordings, which are also processed, optionally subject to principal component analysis, another dimensionality reduction algorithm, or neural network processing, which may further modulate the stimulation 145. In some cases, brainwave patterns in the second subject begin to emerge which are distinct from the target state. The stimulator may, in this case, be controlled to suppress those emergent states, and in some cases, control of the stimulation according to the brainwave pattern of the first subject is interrupted while the brainwave pattern of the second subject is steered to readiness for achieving the desired mental state. In other cases, the signal derived from the first subject is maintained, while the parameters of the stimulation are modified according to the EEG feedback, and optionally, other stimulation components independent of the first subject may also be produced.

Figures 15, 16:
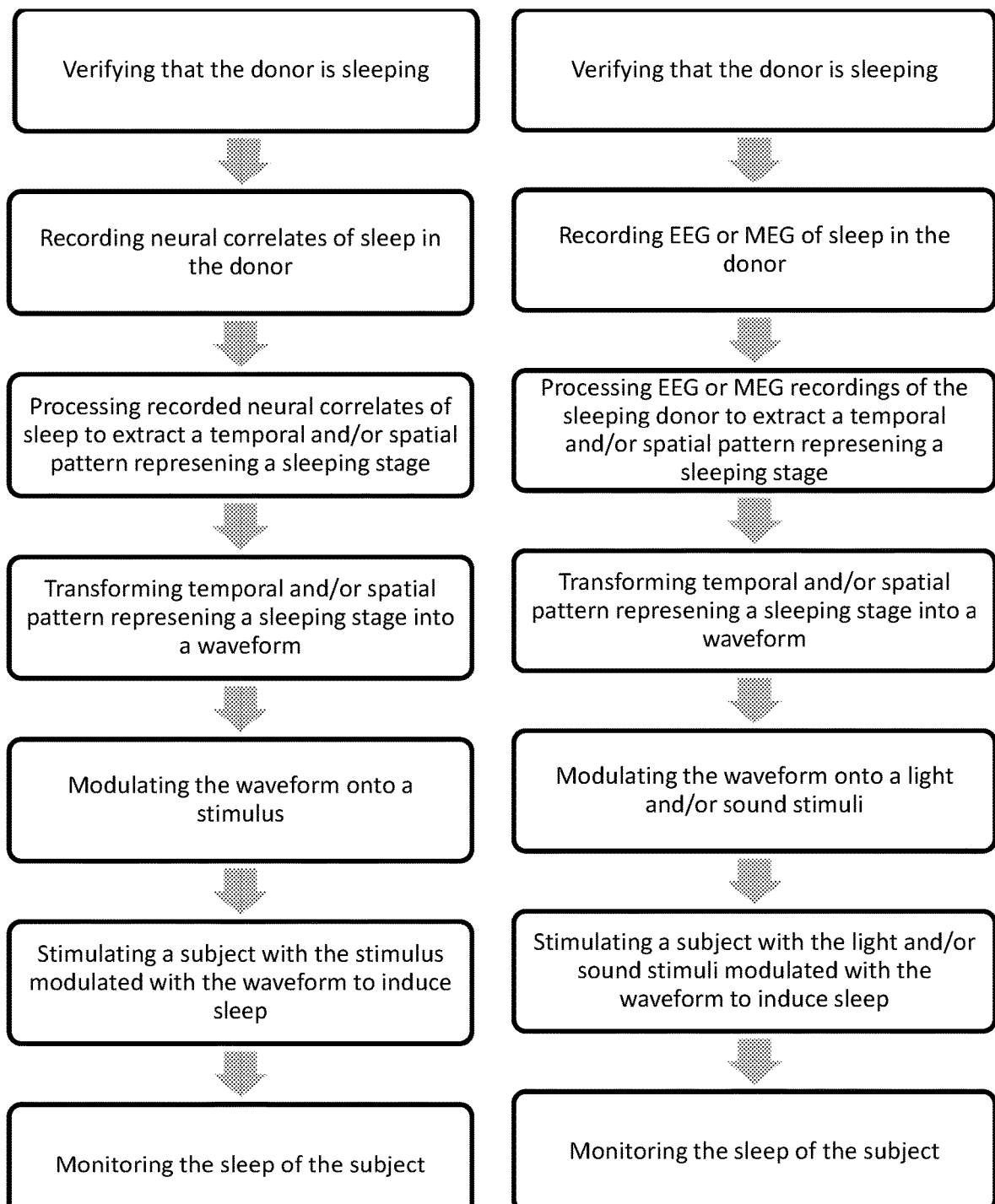
FIG. 15 shows a flowchart of an embodiment of the invention to record neural correlates to stimulate a subject into a sleeping state.
FIG. 16 shows a flowchart of an embodiment of the invention to record EEG or MEG to stimulate a subject into a sleeping state.

FIG. 15 shows a flowchart of a method for inducing sleep in a subject, by verifying that the donor is sleeping; recording neural correlates of sleep in the donor; processing recorded neural correlates of sleep to extract a temporal and/or spatial pattern representing a sleeping stage; transforming temporal and/or spatial pattern representing a sleeping stage into a waveform; modulating the waveform onto a stimulus; stimulating a subject with the stimulus modulated with the waveform to induce sleep; and monitoring the sleep of the subject. FIG. 16 shows a flowchart of a method of inducing sleep in a subject, by verifying that the donor is sleeping; recording EEG or MEG of sleep in the donor; processing EEG or MEG recordings of the sleeping donor to extract a temporal and/or spatial pattern representing a sleeping stage; transforming temporal and/or spatial pattern representing a sleeping stage into a waveform; modulating the waveform onto a light and/or sound stimulus; stimulating a subject with the light and/or sound stimuli modulated with the waveform to induce sleep; and monitoring the sleep of the subject.

FIG. 17 shows a flowchart of a method for inducing sleep in a subject, by recording EEG or MEG of a plurality of sleeping donors; analyzing the EEG or MEG recordings using PCA or other tools to extract a temporal and/or spatial patterns representative a sleeping stage; transforming temporal and/or spatial patterns representative a sleeping stage into a waveform; modulating the waveform onto a light and/or sound stimuli; and stimulating a subject with the light and/or sound stimuli modulated with the waveform to induce sleep.

The method further includes monitoring the sleep of the subject.

Each of the following references is expressly incorporated herein by reference in its entirety.

U.S. Pat. Nos. 2,858,388; 3,951,134; 4,172,014; 4,296,756; 4,367,527; 4,407,299; 4,408,616; 4,421,122; 4,437,064; 4,493,327; 4,550,736; 4,557,270; 4,562,540; 4,579,125; 4,583,190; 4,585,011; 4,591,787; 4,594,662; 4,610,259; 4,613,817; 4,649,482; 4,689,559; 4,693,000; 4,700,135; 4,705,049; 4,733,180; 4,736,307; 4,736,751; 4,744,029; 4,749,946; 4,753,246; 4,761,611; 4,776,345; 4,792,145; 4,794,533; 4,801,882; 4,846,190; 4,862,359; 4,883,067; 4,907,597; 4,913,152; 4,924,875; 4,937,525; 4,940,058; 4,947,480; 4,949,725; 4,951,674; 4,974,602; 4,977,505; 4,982,157; 4,983,912; 4,996,479; 5,008,622; 5,010,891; 5,012,190; 5,020,538; 5,020,540; 5,027,817; 5,029,082; 5,059,814; 5,061,680; 5,069,218; 5,070,399; 5,083,571; 5,088,497; 5,092,341; 5,092,835; 5,095,270; 5,105,354; 5,109,862; 5,118,606; 5,126,315; 5,136,687; 5,158,932; 5,159,703; 5,159,928; 5,166,614; 5,187,327; 5,198,977; 5,213,338; 5,215,086; 5,218,530; 5,224,203; 5,230,344; 5,230,346; 5,231,988; 5,233,517; 5,241,967; 5,243,281; 5,243,517; 5,263,488; 5,265,611; 5,269,315; 5,269,325; 5,273,038; 5,280,791; 5,282,474; 5,283,523; 5,287,859; 5,291,888; 5,293,187; 5,299,569; 5,303,705; 5,306,228; 5,307,807; 5,309,095; 5,309,917; 5,309,923; 5,311,129; 5,320,109; 5,323,777; 5,325,862; 5,326,745; 5,331,970; 5,335,657; 5,339,811; 5,339,826; 5,343,871; 5,359,363; 5,377,100; 5,384,588; 5,406,956; 5,406,957; 5,409,445; 5,417,211; 5,418,512; 5,422,689; 5,442,289; 5,443,073; 5,447,154; 5,447,166; 5,458,117; 5,458,142; 5,459,536; 5,461,699; 5,469,057; 5,474,082; 5,476,438; 5,491,492; 5,496,798; 5,503,149; 5,513,649; 5,515,301; 5,522,863;

5,546,943; 5,552,375; 5,555,889; 5,568,816; 5,571,150;
5,579,241; 5,594,849; 5,600,243; 5,601,081; 5,611,350;
5,617,856; 5,619,995; 5,622,168; 5,626,145; 5,632,272;
5,640,493; 5,643,325; 5,649,061; 5,650,726; 5,656,937;
5,662,109; 5,671,740; 5,678,561; 5,682,889; 5,685,313;
5,692,517; 5,694,939; 5,699,808; 5,701,909; 5,706,402;
5,706,811; 5,711,305; 5,715,821; 5,719,561; 5,720,619;
5,722,418; 5,724,987; 5,729,046; 5,730,146; 5,736,543;
5,737,485; 5,740,812; 5,742,748; 5,743,854; 5,743,860;
5,747,492; 5,752,514; 5,752,521; 5,752,911; 5,755,227;
5,755,739; 5,761,332; 5,762,611; 5,767,043; 5,771,261;
5,771,893; 5,771,894; 5,771,897; 5,791,342; 5,794,623;
5,795,304; 5,797,840; 5,797,853; 5,810,737; 5,813,993;
5,815,413; 5,816,247; 5,825,830; 5,827,195; 5,840,040;
5,842,986; 5,845,639; 5,846,189; 5,846,208; 5,853,005;
5,857,978; 5,859,533; 5,871,517; 5,877,801; 5,884,626;
5,885,976; 5,891,131; 5,899,867; 5,911,581; 5,916,171;
5,921,245; 5,928,272; 5,938,598; 5,938,688; 5,954,662;
5,970,499; 5,971,923; 5,983,129; 5,995,868; 5,999,856;
6,002,254; 6,002,952; 6,011,990; 6,011,991; 6,016,444;
6,021,345; 6,023,161; 6,026,173; 6,032,072; 6,042,548;
6,044,292; 6,050,940; 6,050,962; 6,052,619; 6,053,739;
6,057,846; 6,066,084; 6,067,462; 6,067,467; 6,069,369;
6,070,098; 6,071,246; 6,080,164; 6,081,735; 6,088,611;
6,092,058; 6,097,980; 6,097,981; 6,099,319; 6,104,956;
6,115,631; 6,117,075; 6,129,681; 6,132,724; 6,144,872;
6,149,586; 6,154,026; 6,155,966; 6,155,993; 6,157,850;
6,157,857; 6,161,031; 6,167,298; 6,167,311; 6,171,239;
6,171,258; 6,182,013; 6,188,924; 6,195,576; 6,196,972;
6,205,359; 6,208,902; 6,224,549; 6,226,418; 6,230,037;
6,236,872; 6,239,145; 6,240,308; 6,241,686; 6,248,126;
6,259,399; 6,263,189; 6,266,453; 6,269,270; 6,272,370;
6,280,393; 6,287,328; 6,290,638; 6,292,688; 6,293,904;
6,294,917; 6,298,259; 6,305,943; 6,306,077; 6,309,342;
6,309,361; 6,315,736; 6,317,627; 6,319,205; 6,322,515;
6,325,475; 6,325,761; 6,331,164; 6,332,087; 6,338,713;
6,339,725; 6,341,236; 6,343,229; 6,354,087; 6,354,299;
6,356,079; 6,356,781; 6,356,788; 6,358,201; 6,364,845;
6,366,813; 6,366,814; 6,370,414; 6,370,423; 6,374,131;
6,375,614; 6,377,833; 6,385,479; 6,385,486; 6,390,979;
6,393,363; 6,394,963; 6,402,520; 6,402,689; 6,408,107;
6,418,344; 6,419,629; 6,427,086; 6,428,490; 6,430,443;
6,435,878; 6,442,421; 6,442,948; 6,466,816; 6,470,220;
6,475,163; 6,482,165; 6,487,441; 6,488,617; 6,490,472;
6,493,577; 6,496,724; 6,497,658; 6,497,699; 6,503,085;
6,507,754; 6,510,340; 6,511,424; 6,516,246; 6,520,905;
6,520,921; 6,522,906; 6,524,249; 6,526,297; 6,526,415;
6,527,715; 6,527,730; 6,529,759; 6,529,773; 6,530,884;
6,534,986; 6,538,436; 6,539,245; 6,539,263; 6,544,170;
6,546,378; 6,547,736; 6,547,746; 6,549,804; 6,551,243;
6,553,252; 6,556,695; 6,556,861; 6,556,868; 6,557,558;
6,560,486; 6,565,518; 6,574,573; 6,587,727; 6,587,729;
6,591,132; 6,591,137; 6,594,524; 6,597,954; 6,602,202;
6,603,502; 6,609,030; 6,611,698; 6,615,158; 6,616,611;
6,622,036; 6,622,047; 6,625,485; 6,626,676; 6,633,686;
6,644,976; 6,648,822; 6,648,880; 6,650,917; 6,652,458;
6,652,470; 6,654,632; 6,654,729; 6,656,137; 6,658,287;
6,663,571; 6,665,552; 6,665,553; 6,665,562; 6,671,555;
6,671,556; 6,678,548; 6,684,098; 6,684,105; 6,687,525;
6,695,761; 6,697,660; 6,699,194; 6,701,173; 6,703,838;
6,708,051; 6,708,064; 6,708,184; 6,709,399; 6,725,080;
6,726,624; 6,728,424; 6,728,564; 6,731,975; 6,735,460;
6,735,467; 6,735,475; 6,740,032; 6,743,167; 6,743,182;
6,745,060; 6,745,156; 6,746,409; 6,751,499; 6,758,813;
6,768,920; 6,773,400; 6,774,929; 6,775,405; 6,782,292;
6,785,409; 6,788,975; 6,791,331; 6,795,724; 6,798,898;
6,801,648; 6,801,803; 6,804,558; 6,804,661; 6,815,949;

6,816,744; 6,819,956; 6,826,426; 6,843,774; 6,853,186;
6,856,830; 6,863,127; 6,865,494; 6,873,872; 6,875,174;
6,876,196; 6,879,859; 6,882,881; 6,885,192; 6,885,886;
6,886,964; 6,893,407; 6,896,655; 6,907,280; 6,915,241;
6,920,357; 6,926,921; 6,928,354; 6,931,274; 6,931,275;
6,936,012; 6,947,790; 6,950,697; 6,950,698; 6,959,215;
6,961,618; 6,963,770; 6,963,771; 6,978,179; 6,980,863;
6,981,947; 6,983,184; 6,983,264; 6,985,769; 6,988,056;
6,990,377; 6,993,380; 6,996,261; 6,996,549; 7,003,352;
7,006,872; 7,010,340; 7,010,351; 7,011,410; 7,011,814;
7,014,613; 7,016,722; 7,022,083; 7,023,206; 7,024,247;
7,030,617; 7,035,686; 7,037,260; 7,038,450; 7,039,266;
7,039,547; 7,043,293; 7,053,610; 7,054,454; 7,062,391;
7,063,535; 7,070,571; 7,079,977; 7,089,927; 7,092,748;
7,099,714; 7,104,947; 7,104,963; 7,105,824; 7,107,090;
7,116,102; 7,117,026; 7,119,553; 7,120,486; 7,123,955;
7,127,100; 7,128,713; 7,130,673; 7,130,675; 7,130,691;
7,145,333; 7,146,211; 7,146,217; 7,146,218; 7,149,572;
7,149,773; 7,150,710; 7,150,715; 7,150,717; 7,150,718;
7,151,961; 7,155,279; 7,163,512; 7,164,941; 7,167,751;
7,170,294; 7,171,252; 7,171,339; 7,174,206; 7,176,680;
7,177,675; 7,177,678; 7,181,505; 7,183,381; 7,184,837;
7,186,209; 7,187,169; 7,190,826; 7,190,995; 7,193,413;
7,196,514; 7,197,352; 7,199,708; 7,203,548; 7,207,948;
7,209,787; 7,209,788; 7,212,851; 7,215,986; 7,215,994;
7,218,104; 7,221,981; 7,222,964; 7,224,282; 7,225,013;
7,228,167; 7,228,169; 7,228,171; 7,228,178; 7,231,245;
7,231,254; 7,236,830; 7,236,831; 7,239,731; 7,239,926;
7,242,983; 7,242,984; 7,252,090; 7,254,433; 7,254,439;
7,254,500; 7,257,439; 7,258,659; 7,260,430; 7,267,644;
7,267,652; 7,269,455; 7,269,456; 7,269,516; 7,276,916;
7,277,758; 7,278,966; 7,280,861; 7,280,867; 7,280,870;
7,282,030; 7,283,861; 7,286,871; 7,288,066; 7,292,890;
7,295,019; 7,297,110; 7,299,088; 7,299,096; 7,302,298;
7,305,268; 7,309,315; 7,313,442; 7,321,837; 7,324,845;
7,324,851; 7,328,053; 7,330,032; 7,333,619; 7,333,851;
7,334,892; 7,338,171; 7,338,455; 7,340,125; 7,340,289;
7,343,198; 7,346,382; 7,346,395; 7,353,064; 7,353,065;
7,355,597; 7,359,837; 7,363,164; 7,366,571; 7,367,807;
7,367,949; 7,369,896; 7,371,365; 7,373,198; 7,376,453;
7,376,459; 7,378,056; 7,381,185; 7,383,070; 7,383,237;
7,386,347; 7,389,144; 7,392,079; 7,394,246; 7,395,292;
7,396,333; 7,399,282; 7,400,984; 7,403,809; 7,403,814;
7,403,815; 7,403,820; 7,407,485; 7,409,321; 7,418,290;
7,420,033; 7,422,555; 7,429,247; 7,437,196; 7,440,789;
7,440,806; 7,444,184; 7,450,986; 7,453,263; 7,454,240;
7,454,243; 7,454,245; 7,454,387; 7,457,653; 7,457,665;
7,461,045; 7,462,151; 7,462,155; 7,463,024; 7,463,142;
7,463,927; 7,466,132; 7,468,040; 7,468,350; 7,469,697;
7,471,971; 7,471,978; 7,478,108; 7,482,298; 7,483,747;
7,486,986; 7,488,294; 7,489,958; 7,489,964; 7,490,085;
7,491,173; 7,493,171; 7,493,172; 7,496,393; 7,497,828;
7,499,741; 7,499,745; 7,499,752; 7,499,894; 7,502,720;
7,509,154; 7,509,161; 7,509,163; 7,510,531; 7,510,699;
7,515,054; 7,530,955; 7,537,568; 7,539,528; 7,539,532;
7,539,533; 7,539,543; 7,547,284; 7,553,810; 7,558,622;
7,559,903; 7,561,918; 7,565,193; 7,565,199; 7,565,200;
7,565,809; 7,567,693; 7,570,054; 7,570,991; 7,572,225;
7,573,264; 7,573,268; 7,574,007; 7,574,254; 7,577,472;
7,577,481; 7,580,798; 7,582,062; 7,583,857; 7,593,767;
7,594,122; 7,594,889; 7,596,535; 7,597,665; 7,603,168;
7,603,174; 7,604,603; 7,606,405; 7,608,579; 7,610,083;
7,610,094; 7,610,096; 7,610,100; 7,613,502; 7,613,519;
7,613,520; 7,617,002; 7,618,381; 7,620,455; 7,620,456;
7,623,912; 7,623,927; 7,623,928; 7,624,293; 7,625,340;
7,627,370; 7,629,889; 7,630,757; 7,634,317; 7,640,055;
7,643,655; 7,643,881; 7,647,097; 7,647,098; 7,648,498;

7,649,351; 7,653,433; 7,654,948; 7,657,316; 7,668,579;
7,668,591; 7,670,838; 7,672,707; 7,672,717; 7,672,730;
7,676,263; 7,678,047; 7,678,061; 7,678,767; 7,680,526;
7,680,540; 7,684,856; 7,684,858; 7,684,866; 7,684,867;
7,697,979; 7,702,387; 7,702,502; 7,706,871; 7,706,992;
7,711,417; 7,711,432; 7,714,936; 7,715,894; 7,715,910;
7,715,919; 7,720,519; 7,720,530; 7,725,174; 7,725,192;
7,727,161; 7,729,740; 7,729,753; 7,729,755; 7,729,773;
7,733,224; 7,733,973; 7,734,334; 7,734,340; 7,734,355;
7,736,382; 7,737,687; 7,738,683; 7,740,592; 7,742,820;
7,746,979; 7,747,318; 7,747,325; 7,747,326; 7,747,551;
7,749,155; 7,751,877; 7,751,878; 7,753,836; 7,754,190;
7,756,564; 7,756,568; 7,756,584; 7,757,690; 7,758,503;
7,763,588; 7,764,987; 7,765,088; 7,766,827; 7,769,424;
7,769,431; 7,769,461; 7,769,464; 7,771,341; 7,771,364;
7,774,052; 7,774,064; 7,775,993; 7,778,490; 7,778,692;
7,778,693; 7,783,362; 7,787,937; 7,787,946; 7,792,575;
7,794,403; 7,794,406; 7,797,040; 7,800,493; 7,801,591;
7,801,592; 7,801,593; 7,801,601; 7,801,686; 7,803,118;
7,803,119; 7,804,441; 7,805,203; 7,809,433; 7,809,434;
7,811,279; 7,819,794; 7,819,812; 7,822,481; 7,829,562;
7,831,302; 7,831,305; 7,834,627; 7,835,787; 7,840,039;
7,840,248; 7,840,250; 7,840,257; 7,840,280; 7,841,986;
7,844,324; 7,848,803; 7,852,087; 7,853,321; 7,853,322;
7,853,323; 7,853,329; 7,856,264; 7,860,548; 7,860,552;
7,860,561; 7,860,570; 7,863,272; 7,865,234; 7,865,235;
7,865,244; 7,869,867; 7,869,884; 7,869,885; 7,872,235;
7,873,411; 7,876,938; 7,878,965; 7,879,043; 7,881,760;
7,881,770; 7,881,780; 7,882,135; 7,884,101; 7,887,493;
7,890,155; 7,890,176; 7,890,185; 7,891,814; 7,892,764;
7,894,890; 7,894,903; 7,895,033; 7,896,807; 7,899,524;
7,899,525; 7,899,539; 7,899,545; 7,901,211; 7,904,134;
7,904,139; 7,904,144; 7,904,151; 7,904,175; 7,904,507;
7,907,994; 7,907,998; 7,908,008; 7,908,009; 7,909,771;
7,912,530; 7,917,199; 7,917,206; 7,917,221; 7,917,225;
7,918,779; 7,920,914; 7,920,915; 7,920,916; 7,925,353;
7,929,693; 7,930,035; 7,932,225; 7,933,645; 7,933,646;
7,933,727; 7,937,138; 7,937,152; 7,937,222; 7,938,782;
7,938,785; 7,941,209; 7,942,824; 7,944,551; 7,945,304;
7,945,316; 7,945,330; 7,957,796; 7,957,797; 7,957,806;
7,957,809; 7,961,922; 7,962,204; 7,962,214; 7,962,219;
7,962,220; 7,970,734; 7,972,278; 7,974,688; 7,974,693;
7,974,696; 7,974,697; 7,974,701; 7,974,787; 7,976,465;
7,983,740; 7,983,741; 7,983,757; 7,983,762; 7,986,991;
7,988,613; 7,988,969; 7,991,461; 7,991,477; 7,993,279;
7,996,075; 7,996,079; 8,000,767; 8,000,773; 8,000,788;
8,000,793; 8,000,794; 8,000,795; 8,001,179; 8,002,553;
8,005,534; 8,005,624; 8,005,894; 8,010,178; 8,010,347;
8,012,107; 8,014,847; 8,014,870; 8,016,597; 8,019,400;
8,019,410; 8,024,029; 8,024,032; 8,025,404; 8,027,730;
8,029,553; 8,031,076; 8,032,209; 8,032,229; 8,032,486;
8,033,996; 8,036,434; 8,036,728; 8,036,736; 8,036,745;
8,041,136; 8,041,418; 8,041,419; 8,046,041; 8,046,042;
8,046,076; 8,050,768; 8,055,348; 8,055,591; 8,059,879;
8,060,181; 8,060,194; 8,064,994; 8,065,011; 8,065,012;
8,065,017; 8,065,240; 8,065,360; 8,066,637; 8,066,647;
8,068,904; 8,068,911; 8,069,125; 8,073,534; 8,073,546;
8,073,631; 8,075,499; 8,079,953; 8,082,031; 8,082,033;
8,082,215; 8,083,786; 8,086,294; 8,086,296; 8,086,563;
8,088,057; 8,089,283; 8,090,164; 8,092,549; 8,095,209;
8,095,210; 8,097,926; 8,099,299; 8,103,333; 8,108,033;
8,108,036; 8,108,038; 8,108,039; 8,108,042; 8,112,148;
8,112,153; 8,114,021; 8,116,874; 8,116,877; 8,116,883;
8,121,361; 8,121,673; 8,121,694; 8,121,695; 8,126,228;
8,126,243; 8,126,528; 8,126,542; 8,126,567; 8,126,568;
8,128,572; 8,131,354; 8,131,526; 8,133,172; 8,135,472;
8,135,957; 8,137,269; 8,137,270; 8,140,152; 8,145,295;

8,145,310; 8,148,417; 8,148,418; 8,150,508; 8,150,523;
8,150,524; 8,150,796; 8,152,732; 8,155,726; 8,155,736;
8,160,273; 8,160,317; 8,160,680; 8,160,689; 8,160,696;
8,165,687; 8,167,784; 8,167,826; 8,170,315; 8,170,347;
8,172,759; 8,172,766; 8,174,430; 8,175,359; 8,175,360;
8,175,686; 8,175,696; 8,175,700; 8,177,724; 8,177,726;
8,177,727; 8,180,125; 8,180,148; 8,180,420; 8,180,436;
8,180,601; 8,185,186; 8,185,207; 8,185,382; 8,187,181;
8,187,201; 8,188,749; 8,190,227; 8,190,248; 8,190,249;
8,190,251; 8,190,264; 8,195,295; 8,195,298; 8,195,300;
8,195,593; 8,197,395; 8,197,437; 8,199,982; 8,199,985;
8,200,319; 8,200,340; 8,204,583; 8,204,603; 8,209,009;
8,209,018; 8,209,019; 8,209,224; 8,211,035; 8,212,556;
8,213,670; 8,214,007; 8,214,035; 8,219,188; 8,221,330;
8,222,378; 8,223,023; 8,224,431; 8,224,433; 8,224,444;
8,224,451; 8,229,540; 8,229,559; 8,233,682; 8,233,689;
8,233,965; 8,233,990; 8,235,907; 8,236,005; 8,236,038;
8,239,014; 8,239,028; 8,239,029; 8,239,030; 8,241,213;
8,244,340; 8,244,341; 8,244,347; 8,244,475; 8,244,552;
8,244,553; 8,248,069; 8,249,316; 8,249,698; 8,249,718;
8,249,815; 8,260,426; 8,262,714; 8,263,574; 8,267,851;
8,270,814; 8,271,077; 8,280,502; 8,280,503; 8,280,505;
8,280,514; 8,280,517; 8,285,351; 8,285,368; 8,290,575;
8,290,596; 8,295,914; 8,295,934; 8,295,935; 8,296,108;
8,298,078; 8,298,140; 8,301,222; 8,301,232; 8,301,233;
8,301,257; 8,303,636; 8,304,246; 8,305,078; 8,306,607;
8,306,610; 8,306,627; 8,308,646; 8,308,661; 8,311,622;
8,311,747; 8,311,748; 8,311,750; 8,313,441; 8,314,707;
8,315,703; 8,315,704; 8,315,710; 8,315,812; 8,315,813;
8,315,814; 8,315,962; 8,315,970; 8,320,649; 8,321,150;
8,323,188; 8,323,189; 8,323,204; 8,326,418; 8,326,420;
8,326,433; 8,328,718; 8,332,017; 8,332,024; 8,332,038;
8,332,041; 8,332,191; 8,334,690; 8,335,561; 8,335,664;
8,335,715; 8,335,716; 8,337,404; 8,340,752; 8,340,753;
8,340,771; 8,343,026; 8,343,027; 8,343,066; 8,346,331;
8,346,342; 8,346,349; 8,346,354; 8,346,365; 8,350,804;
8,352,023; 8,352,031; 8,353,837; 8,354,438; 8,354,881;
8,355,768; 8,356,004; 8,356,594; 8,358,818; 8,359,080;
8,362,780; 8,364,226; 8,364,254; 8,364,255; 8,364,271;
8,364,272; 8,369,940; 8,374,411; 8,374,412; 8,374,690;
8,374,696; 8,374,701; 8,374,703; 8,376,965; 8,379,947;
8,379,952; 8,380,289; 8,380,290; 8,380,296; 8,380,314;
8,380,316; 8,380,658; 8,382,667; 8,386,188; 8,386,244;
8,386,312; 8,386,313; 8,388,529; 8,388,530; 8,388,555;
8,391,942; 8,391,956; 8,391,966; 8,392,250; 8,392,251;
8,392,253; 8,392,254; 8,392,255; 8,396,542; 8,396,545;
8,396,546; 8,396,557; 8,396,565; 8,396,744; 8,398,692;
8,401,624; 8,401,626; 8,401,634; 8,401,654; 8,401,655;
8,401,666; 8,403,848; 8,406,838; 8,406,841; 8,406,848;
8,406,862; 8,406,890; 8,412,334; 8,412,335; 8,412,337;
8,412,338; 8,412,655; 8,415,123; 8,417,344; 8,423,118;
8,423,125; 8,423,144; 8,423,155; 8,423,297; 8,425,415;
8,425,583; 8,428,696; 8,428,703; 8,428,704; 8,428,726;
8,429,225; 8,430,805; 8,430,816; 8,431,537; 8,433,388;
8,433,410; 8,433,414; 8,433,418; 8,435,166; 8,437,843;
8,437,844; 8,437,861; 8,439,845; 8,442,626; 8,444,571;
8,445,021; 8,445,851; 8,447,392; 8,447,407; 8,447,411;
8,449,471; 8,452,387; 8,452,544; 8,454,555; 8,456,164;
8,456,166; 8,456,309; 8,457,730; 8,457,746; 8,457,747;
8,461,988; 8,463,006; 8,463,007; 8,463,349; 8,463,370;
8,463,374; 8,463,378; 8,463,386; 8,463,387; 8,464,288;
8,465,408; 8,467,877; 8,467,878; 8,473,024; 8,473,044;
8,473,306; 8,473,345; 8,475,354; 8,475,368; 8,475,371;
8,475,387; 8,475,506; 8,478,389; 8,478,394; 8,478,402;
8,478,417; 8,478,428; 8,480,554; 8,483,795; 8,483,815;
8,483,816; 8,484,081; 8,484,270; 8,485,979; 8,487,760;
8,489,185; 8,492,336; 8,494,610; 8,494,829; 8,494,857;

8,494,905; 8,496,594; 8,498,697; 8,498,699; 8,498,708;
8,500,282; 8,500,636; 8,504,150; 8,506,469; 8,509,879;
8,509,881; 8,509,885; 8,509,904; 8,512,219; 8,512,221;
8,512,240; 8,515,535; 8,515,538; 8,515,541; 8,515,549;
8,515,550; 8,517,909; 8,517,912; 8,519,705; 8,519,853;
8,520,974; 8,521,284; 8,523,779; 8,525,673; 8,525,687;
8,527,029; 8,527,035; 8,527,435; 8,529,463; 8,531,291;
8,532,756; 8,532,757; 8,533,042; 8,536,667; 8,538,108;
8,538,512; 8,538,513; 8,538,514; 8,538,523; 8,538,536;
8,538,543; 8,538,700; 8,538,705; 8,542,900; 8,542,916;
8,543,189; 8,543,199; 8,543,214; 8,543,219; 8,545,378;
8,545,416; 8,545,420; 8,545,436; 8,548,583; 8,548,594;
8,548,604; 8,548,786; 8,548,852; 8,553,956; 8,554,311;
8,554,325; 8,559,645; 8,560,034; 8,560,041; 8,560,073;
8,562,525; 8,562,526; 8,562,527; 8,562,536; 8,562,540;
8,562,548; 8,562,660; 8,562,951; 8,565,606; 8,565,864;
8,565,867; 8,565,883; 8,565,886; 8,568,231; 8,568,329;
8,571,293; 8,571,629; 8,571,642; 8,571,643; 8,571,653;
8,574,164; 8,574,279; 8,577,103; 8,577,464; 8,577,465;
8,577,466; 8,577,467; 8,577,468; 8,577,472; 8,577,478;
8,579,786; 8,579,793; 8,579,795; 8,579,834; 8,583,238;
8,583,252; 8,585,568; 8,586,019; 8,586,932; 8,587,304;
8,588,486; 8,588,552; 8,588,899; 8,588,929; 8,588,933;
8,588,941; 8,589,316; 8,591,419; 8,591,498; 8,593,141;
8,593,154; 8,594,798; 8,594,800; 8,594,950; 8,597,171;
8,597,193; 8,600,493; 8,600,502; 8,600,513; 8,600,521;
8,600,696; 8,603,790; 8,606,349; 8,606,351; 8,606,356;
8,606,360; 8,606,361; 8,606,530; 8,606,592; 8,612,005;
8,613,695; 8,613,905; 8,614,254; 8,614,873; 8,615,293;
8,615,309; 8,615,479; 8,615,664; 8,618,799; 8,620,206;
8,620,419; 8,626,264; 8,626,301; 8,628,328; 8,628,480;
8,630,699; 8,630,705; 8,630,812; 8,632,465; 8,632,750;
8,634,616; 8,634,922; 8,635,105; 8,636,640; 8,638,950;
8,641,632; 8,641,646; 8,644,754; 8,644,910; 8,644,914;
8,644,921; 8,644,945; 8,644,946; 8,644,954; 8,644,957;
8,647,278; 8,648,017; 8,649,845; 8,649,866; 8,649,871;
8,652,038; 8,652,187; 8,652,189; 8,655,428; 8,655,437;
8,655,817; 8,657,732; 8,657,756; 8,658,149; 8,660,642;
8,660,649; 8,660,666; 8,660,799; 8,664,258; 8,666,099;
8,666,467; 8,666,478; 8,666,501; 8,668,496; 8,670,603;
8,672,852; 8,675,936; 8,675,945; 8,675,983; 8,676,324;
8,676,325; 8,676,330; 8,679,009; 8,680,119; 8,680,991;
8,682,422; 8,682,441; 8,682,449; 8,682,687; 8,684,742;
8,684,900; 8,684,921; 8,684,922; 8,684,926; 8,688,209;
8,690,748; 8,693,756; 8,693,765; 8,694,087; 8,694,089;
8,694,092; 8,694,107; 8,694,118; 8,694,157; 8,696,722;
8,696,724; 8,698,639; 8,700,137; 8,700,141; 8,700,142;
8,700,163; 8,700,167; 8,700,174; 8,700,183; 8,703,114;
8,706,183; 8,706,205; 8,706,206; 8,706,207; 8,706,237;
8,706,241; 8,706,518; 8,708,903; 8,708,934; 8,711,655;
8,712,507; 8,712,512; 8,712,513; 8,712,547; 8,716,447;
8,717,430; 8,718,747; 8,718,776; 8,718,777; 8,718,779;
8,721,695; 8,724,871; 8,725,238; 8,725,243; 8,725,311;
8,725,668; 8,725,669; 8,725,796; 8,727,978; 8,728,001;
8,729,040; 8,731,650; 8,731,656; 8,731,987; 8,733,290;
8,734,356; 8,734,357; 8,734,498; 8,738,121; 8,738,126;
8,738,136; 8,738,140; 8,738,395; 8,744,562; 8,744,563;
8,747,313; 8,747,336; 8,747,382; 8,750,971; 8,750,974;
8,750,992; 8,751,008; 8,751,011; 8,753,296; 8,754,238;
8,755,854; 8,755,856; 8,755,868; 8,755,869; 8,755,871;
8,755,877; 8,755,901; 8,756,017; 8,758,274; 8,761,438;
8,761,866; 8,761,868; 8,761,869; 8,761,889; 8,762,065;
8,762,202; 8,764,651; 8,764,652; 8,764,653; 8,764,673;
8,768,022; 8,768,427; 8,768,431; 8,768,446; 8,768,447;
8,768,449; 8,768,471; 8,768,477; 8,768,718; 8,771,194;
8,774,923; 8,775,340; 8,781,193; 8,781,197; 8,781,557;
8,781,563; 8,781,595; 8,781,597; 8,781,796; 8,784,109;

8,784,322; 8,785,441; 8,786,624; 8,787,637; 8,788,030;
8,788,033; 8,788,044; 8,788,055; 8,788,057; 8,790,255;
8,790,272; 8,790,297; 8,792,972; 8,792,974; 8,792,991;
8,795,175; 8,798,717; 8,798,728; 8,798,735; 8,798,736;
8,798,773; 8,801,620; 8,805,516; 8,805,518; 8,812,126;
8,812,237; 8,812,245; 8,812,246; 8,814,923; 8,815,582;
8,821,376; 8,821,408; 8,821,559; 8,825,149; 8,825,166;
8,825,167; 8,825,428; 8,827,912; 8,827,917; 8,829,908;
8,831,705; 8,831,731; 8,831,732; 8,834,392; 8,834,546;
8,838,201; 8,838,225; 8,838,226; 8,838,227; 8,838,247;
8,843,199; 8,843,201; 8,843,210; 8,845,545; 8,849,390;
8,849,392; 8,849,407; 8,849,409; 8,849,632; 8,849,681;
8,852,073; 8,852,100; 8,852,103; 8,855,758; 8,855,773;
8,855,775; 8,858,440; 8,858,449; 8,861,819; 8,862,196;
8,862,210; 8,862,236; 8,862,581; 8,864,310; 8,864,806;
8,868,148; 8,868,163; 8,868,172; 8,868,173; 8,868,174;
8,868,175; 8,868,177; 8,868,189; 8,868,201; 8,870,737;
8,871,797; 8,872,640; 8,874,205; 8,874,218; 8,874,227;
8,874,439; 8,880,207; 8,880,576; 8,886,299; 8,886,302;
8,888,672; 8,888,673; 8,888,702; 8,888,708; 8,888,723;
8,892,207; 8,893,120; 8,898,037; 8,900,284; 8,902,070;
8,903,479; 8,903,483; 8,903,486; 8,903,494; 8,906,360;
8,907,668; 8,909,345; 8,910,638; 8,913,810; 8,914,100;
8,914,115; 8,914,119; 8,914,122; 8,915,741; 8,915,871;
8,918,162; 8,918,176; 8,918,178; 8,918,183; 8,921,320;
8,922,376; 8,922,788; 8,923,958; 8,924,235; 8,926,959;
8,929,991; 8,929,999; 8,932,218; 8,932,227; 8,932,562;
8,933,696; 8,934,685; 8,934,965; 8,934,967; 8,934,979;
8,934,986; 8,936,629; 8,936,630; 8,938,102; 8,938,289;
8,938,290; 8,938,301; 8,939,903; 8,942,777; 8,942,813;
8,942,817; 8,945,006; 8,948,834; 8,948,849; 8,948,855;
8,948,860; 8,951,189; 8,951,190; 8,951,192; 8,951,203;
8,954,139; 8,954,146; 8,954,293; 8,955,010; 8,955,974;
8,956,277; 8,956,363; 8,958,868; 8,958,870; 8,958,882;
8,961,187; 8,961,385; 8,961,386; 8,962,042; 8,962,589;
8,964,298; 8,965,492; 8,965,513; 8,965,514; 8,968,172;
8,968,176; 8,968,195; 8,968,376; 8,971,936; 8,972,004;
8,972,013; 8,974,365; 8,977,024; 8,977,110; 8,977,362;
8,980,891; 8,983,155; 8,983,591; 8,983,620; 8,983,628;
8,983,629; 8,985,119; 8,986,207; 8,989,835; 8,989,836;
8,989,863; 8,989,867; 8,989,868; 8,989,871; 8,992,230;
8,993,623; 8,996,112; 8,996,120; 8,998,828; 9,002,458;
9,002,471; 9,002,477; 9,004,687; 9,005,102; 9,005,126;
9,005,649; 9,008,367; 9,008,754; 9,008,771; 9,008,780;
9,008,970; 9,011,329; 9,014,216; 9,014,453; 9,014,804;
9,014,811; 9,014,819; 9,014,823; 9,015,057; 9,015,087;
9,020,576; 9,020,582; 9,020,585; 9,020,586; 9,020,598;
9,020,612; 9,020,789; 9,022,930; 9,022,936; 9,025,845;
9,026,194; 9,026,202; 9,026,217; 9,026,218; 9,026,372;
9,028,405; 9,028,412; 9,031,644; 9,031,653; 9,031,655;
9,031,658; 9,033,884; 9,034,055; 9,034,911; 9,034,923;
9,035,657; 9,036,844; 9,037,224; 9,037,225; 9,037,254;
9,037,256; 9,037,530; 9,042,074; 9,042,201; 9,042,952;
9,042,958; 9,042,988; 9,043,001; 9,044,188; 9,044,612;
9,050,469; 9,050,470; 9,050,471; 9,053,516; 9,053,534;
9,055,871; 9,055,974; 9,056,195; 9,058,473; 9,060,671;
9,060,683; 9,060,695; 9,060,722; 9,060,746; 9,061,132;
9,061,133; 9,061,151; 9,061,153; 9,063,183; 9,063,643;
9,064,036; 9,067,052; 9,067,054; 9,067,070; 9,069,031;
9,069,097; 9,070,492; 9,072,449; 9,072,482; 9,072,832;
9,072,870; 9,072,905; 9,074,976; 9,076,212; 9,078,564;
9,078,577; 9,078,584; 9,079,039; 9,079,940; 9,081,488;
9,081,882; 9,081,890; 9,082,169; 9,084,584; 9,084,885;
9,084,896; 9,084,900; 9,087,147; 9,089,310; 9,089,400;
9,089,683; 9,089,707; 9,089,713; 9,089,719; 9,091,785;
9,092,556; 9,092,895; 9,095,266; 9,095,268; 9,095,295;
9,095,303; 9,095,314; 9,095,618; 9,095,713; 9,100,758;

9,101,263; 9,101,276; 9,101,279; 9,101,690; 9,101,759; 9,101,766; 9,102,717; 9,107,586; 9,107,595; 9,108,041; 9,113,777; 9,113,801; 9,113,803; 9,113,830; 9,116,201; 9,116,835; 9,118,775; 9,119,533; 9,119,551; 9,119,583; 9,119,597; 9,119,598; 9,121,964; 9,125,574; 9,125,581; 9,125,788; 9,126,050; 9,131,864; 9,133,024; 9,133,709; 9,135,221; 9,135,400; 9,138,156; 9,138,175; 9,138,183; 9,138,579; 9,138,580; 9,142,145; 9,142,185; 9,144,392; 9,149,195; 9,149,197; 9,149,210; 9,149,214; 9,149,226; 9,149,255; 9,149,577; 9,149,599; 9,149,719; 9,152,757; 9,155,373; 9,155,484; 9,155,487; 9,155,521; 9,161,715; 9,162,051; 9,162,052; 9,165,472; 9,167,970; 9,167,974; 9,167,976; 9,167,977; 9,167,978; 9,167,979; 9,171,353; 9,171,366; 9,173,582; 9,173,609; 9,173,610; 9,174,045; 9,174,055; 9,174,066; 9,175,095; 9,177,379; 9,177,416; 9,179,850; 9,179,854; 9,179,855; 9,179,858; 9,179,875; 9,179,876; 9,183,351; 9,186,060; 9,186,106; 9,186,503; 9,186,510; 9,187,745; 9,192,300; 9,192,309; 9,198,563; 9,198,612; 9,198,621; 9,198,624; 9,198,637; 9,198,707; 9,198,733; 9,204,796; 9,204,835; 9,204,838; 9,204,998; 9,208,430; 9,208,557; 9,208,558; 9,211,076; 9,211,077; 9,211,212; 9,211,411; 9,211,417; 9,213,074; 9,213,076; 9,215,298; 9,215,978; 9,220,910; 9,220,917; 9,221,755; 9,226,672; 9,227,056; 9,229,080; 9,230,065; 9,230,539; 9,232,910; 9,232,984; 9,233,244; 9,233,245; 9,233,246; 9,233,258; 9,235,679; 9,235,685; 9,238,142; 9,238,150; 9,241,647; 9,241,665; 9,242,067; 9,242,092; 9,247,890; 9,247,911; 9,247,924; 9,248,003; 9,248,280; 9,248,286; 9,248,288; 9,248,290; 9,248,291; 9,248,296; 9,249,200; 9,249,234; 9,251,566; 9,254,097; 9,254,099; 9,254,383; 9,254,387; 9,256,982; 9,259,177; 9,259,482; 9,259,591; 9,261,573; 9,265,458; 9,265,660; 9,265,661; 9,265,662; 9,265,663; 9,265,931; 9,265,943; 9,265,946; 9,265,965; 9,265,974; 9,268,014; 9,268,015; 9,268,902; 9,271,651; 9,271,657; 9,271,660; 9,271,674; 9,271,679; 9,272,091; 9,272,139; 9,272,145; 9,272,153; 9,273,035; 9,275,191; 9,275,451; 9,277,871; 9,277,873; 9,278,159; 9,278,231; 9,280,784; 9,282,927; 9,282,930; 9,282,934; 9,283,279; 9,283,394; 9,284,353; 9,285,249; 9,289,143; 9,289,595; 9,289,599; 9,289,603; 9,289,609; 9,292,471; 9,292,858; 9,292,920; 9,295,838; 9,296,382; 9,302,069; 9,302,093; 9,302,103; 9,302,109; 9,302,110; 9,302,114; 9,302,116; 9,305,376; 9,307,925; 9,307,944; 9,308,372; 9,308,392; 9,309,296; 9,310,985; 9,311,335; 9,314,190; 9,314,613; 9,314,633; 9,314,635; 9,320,449; 9,320,450; 9,320,451; 9,320,900; 9,320,913; 9,320,914; 9,322,895; 9,326,705; 9,326,720; 9,326,742; 9,327,069; 9,327,070; 9,328,107; 9,329,758; 9,330,206; 9,330,523; 9,331,841; 9,332,939; 9,333,334; 9,333,347; 9,333,350; 9,336,302; 9,336,535; 9,336,611; 9,339,200; 9,339,227; 9,339,641; 9,339,654; 9,340,589; 9,345,412; 9,345,609; 9,345,886; 9,345,901; 9,348,974; 9,349,178; 9,351,640; 9,351,651; 9,352,145; 9,352,152; 9,352,156; 9,357,240; 9,357,298; 9,357,941; 9,357,949; 9,357,970; 9,358,361; 9,358,381; 9,358,392; 9,358,393; 9,358,398; 9,359,449; 9,360,472; 9,364,462; 9,364,665; 9,364,674; 9,364,679; 9,365,628; 9,367,131; 9,367,738; 9,368,018; 9,368,265; 9,370,309; 9,370,667; 9,375,145; 9,375,151; 9,375,171; 9,375,564; 9,375,571; 9,375,573; 9,377,348; 9,377,515; 9,380,976; 9,381,346; 9,381,352; 9,383,208; 9,387,320; 9,387,338; 9,390,233; 9,392,955; 9,393,406; 9,393,418; 9,394,347; 9,395,425; 9,396,533; 9,396,669; 9,398,873; 9,399,126; 9,399,133; 9,399,134; 9,399,144; 9,401,021; 9,401,033; 9,402,558; 9,402,994; 9,403,000; 9,403,001; 9,403,009; 9,403,010; 9,403,038; 9,405,366; 9,408,530; 9,409,013; 9,409,022; 9,409,028; 9,410,885; 9,411,033; 9,411,935; 9,412,076; 9,412,233; 9,414,029; 9,414,749; 9,414,763; 9,414,764;

9,414,776; 9,414,780; 9,414,907; 9,415,215; 9,415,216; 9,415,219; 9,415,222; 9,415,233; 9,418,368; 9,420,970; 9,421,258; 9,421,372; 9,421,373; 9,421,379; 9,424,761; 9,427,474; 9,427,581; 9,427,585; 9,427,598; 9,430,615; 9,432,777; 9,433,797; 9,434,692; 9,436,989; 9,438,650; 9,439,150; 9,440,063; 9,440,064; 9,440,070; 9,440,084; 9,440,089; 9,440,646; 9,442,088; 9,442,525; 9,443,141; 9,444,998; 9,445,713; 9,445,730; 9,445,739; 9,445,763; 9,446,238; 9,448,289; 9,449,147; 9,451,303; 9,451,734; 9,451,883; 9,451,886; 9,451,899; 9,452,287; 9,453,215; 9,454,646; 9,458,208; 9,459,597; 9,460,400; 9,462,733; 9,462,956; 9,462,975; 9,462,977; 9,463,327; 9,468,541; 9,468,761; 9,470,728; 9,471,978; 9,472,000; 9,474,481; 9,474,852; 9,474,903; 9,475,502; 9,480,402; 9,480,425; 9,480,812; 9,480,841; 9,480,845; 9,480,854; 9,483,117; 9,483,613; 9,486,168; 9,486,381; 9,486,389; 9,486,618; 9,486,632; 9,489,854; 9,492,084; 9,492,114; 9,492,120; 9,492,313; 9,492,656; 9,492,678; 9,495,684; 9,497,017; 9,498,134; 9,498,628; 9,498,634; 9,500,722; 9,501,829; 9,504,390; 9,504,410; 9,504,420; 9,504,788; 9,505,402; 9,505,817; 9,510,790; 9,513,398; 9,517,020; 9,517,031; 9,517,222; 9,519,981; 9,521,958; 9,522,085; 9,522,278; 9,522,282; 9,522,288; 9,526,419; 9,526,902; 9,526,906; 9,526,913; 9,526,914; 9,533,113; 9,533,144; 9,533,147; 9,533,148; 9,533,150; 9,533,151; 9,534,044; 9,538,635; 9,538,948; 9,538,951; 9,539,118; 9,541,383; 9,545,221; 9,545,222; 9,545,225; 9,545,226; 9,545,285; 9,545,510; 9,545,515; 9,549,691; 9,550,064; 9,556,149; 9,556,487; 9,557,439; 9,558,558; 9,560,458; 9,560,967; 9,560,984; 9,560,986; 9,561,380; 9,562,988; 9,563,273; 9,563,740; 9,563,950; 9,566,426; 9,567,327; 9,568,564; 9,568,635; 9,572,996; 9,577,992; 9,578,425; 9,579,035; 9,579,048; 9,579,247; 9,579,457; 9,579,506; 9,582,072; 9,582,152; 9,582,925; 9,584,928; 9,585,581; 9,585,723; 9,586,047; 9,586,053; 9,588,203; 9,588,490; 9,590,986; 9,592,003; 9,592,004; 9,592,384; 9,592,387; 9,592,389; 9,592,409; 9,596,224; 9,597,493; 9,597,494; 9,597,501; 9,597,504; 9,600,138; 9,600,778; 9,604,056; 9,604,067; 9,604,073; 9,607,023; 9,607,377; 9,609,453; 9,610,442; 9,610,456; 9,610,459; 9,612,295; 9,613,184; 9,613,186; 9,615,746; 9,615,749; 9,615,789; 9,616,166; 9,616,227; 9,618,591; 9,622,660; 9,622,672; 9,622,675; 9,622,676; 9,622,700; 9,622,702; 9,622,703; 9,623,240; 9,623,241; 9,626,756; 9,629,548; 9,629,568; 9,629,976; 9,630,004; 9,630,008; 9,630,011; 9,630,029; 9,636,019; 9,636,185; 9,640,167; 9,641,665; 9,642,552; 9,642,553; 9,642,554; 9,642,699; 9,643,015; 9,643,017; 9,643,019; 9,646,248; 9,649,030; 9,649,036; 9,649,439; 9,649,493; 9,649,494; 9,649,501; 9,651,368; 9,651,706; 9,652,626; 9,652,871; 9,655,573; 9,655,669; 9,656,069; 9,656,075; 9,656,078; 9,656,096; 9,659,186; 9,659,229; 9,662,049; 9,662,069; 9,662,083; 9,662,490; 9,662,492; 9,662,502; 9,664,856; 9,665,824; 9,665,987; 9,668,694; 9,669,185; 9,669,239; 9,672,302; 9,672,617; 9,674,621; 9,675,254; 9,675,255; 9,675,292; 9,675,794; 9,675,809; 9,681,814; 9,681,820; 9,682,232; 9,682,241; 9,684,051; 9,684,335; 9,685,600; 9,687,187; 9,687,562; 9,693,684; 9,693,724; 9,693,725; 9,693,734; 9,694,155; 9,694,178; 9,694,197; 9,697,330; 9,697,336; 9,700,256; 9,700,716; 9,700,723; 9,704,205; 9,706,910; 9,706,925; 9,706,957; 9,706,963; 9,707,372; 9,707,390; 9,707,391; 9,707,396; 9,710,788; 9,712,736; 9,713,428; 9,713,433; 9,713,444; 9,713,712; 9,715,032; 9,717,461; 9,717,904; 9,717,920; 9,724,517; 9,729,252; 9,732,039; 9,734,589; 9,734,601; 9,734,632; 9,737,230; 9,740,710; 9,740,946; 9,741,114; 9,743,197; 9,743,835; 9,744,358; 9,763,592; 9,991,026; D627476; RE34015; RE38476; RE38749; RE44097; RE44408; RE45336; RE45337;

RE45766; RE46189; RE46209; 20010003799; 20040138517; 20040138518; 20040138536;
20010009975; 20010014818; 20010020127; 20040138580; 20040138581; 20040138647;
20010021800; 20010029391; 20010049480; 20040138711; 20040138721; 20040140811;
20010051774; 20010051787; 20020000808; 20040143170; 20040144925; 20040145370;
20020005784; 20020006875; 20020013612; 20040151368; 20040152958; 20040152995;
20020013613; 20020016552; 20020017905; 20040153129; 20040158119; 20040158298;
20020017994; 20020024450; 20020032375; 20040158300; 20040166536; 20040167418;
20020033454; 20020035317; 20020035338; 20040172089; 20040172091; 20040172094;
20020037095; 20020042563; 20020052539; 20040181162; 20040184024; 20040186542;
20020055675; 20020058867; 20020059159; 20040193037; 20040193068; 20040193220;
20020072776; 20020072782; 20020077536; 20040195512; 20040199482; 20040204636;
20020082513; 20020082665; 20020085174; 20040204637; 20040204656; 20040204659;
20020087201; 20020091319; 20020091335; 20040210127; 20040210146; 20040210156;
20020091419; 20020095099; 20020097332; 20040215082; 20040220494; 20040220782;
20020099273; 20020099295; 20020099306; 20040225179; 20040230105; 20040243017;
20020099412; 20020099417; 20020099418; 20040243182; 20040254493; 20040260169;
20020103428; 20020103429; 20020103512; 20040260356; 20040263162; 20040267152;
20020107454; 20020112732; 20020117176; 20050004489; 20050007091; 20050010091;
20020128540; 20020128544; 20020128638; 20050010116; 20050015205; 20050018858;
20020138013; 20020151771; 20020151939; 20050019734; 20050020483; 20050020918;
20020158631; 20020173714; 20020177882; 20050021105; 20050025704; 20050027284;
20020182574; 20020183607; 20020183644; 20050032827; 20050033122; 20050033154;
20020188330; 20020193670; 20030001098; 20050033174; 20050033379; 20050038354;
20030004429; 20030009078; 20030009096; 20050043774; 20050049651; 20050059689;
20030013981; 20030018277; 20030018278; 20050059874; 20050060001; 20050060007;
20030023183; 20030023282; 20030028081; 20050060008; 20050060009; 20050060010;
20030028121; 20030028348; 20030031357; 20050065412; 20050065427; 20050075568;
20030032870; 20030032888; 20030032889; 20050079474; 20050079636; 20050080124;
20030035301; 20030036689; 20030040660; 20050080349; 20050080828; 20050085744;
20030045914; 20030046018; 20030055355; 20050096311; 20050096517; 20050106713;
20030068605; 20030070685; 20030074032; 20050107654; 20050113713; 20050118286;
20030081818; 20030083596; 20030083716; 20050119547; 20050119586; 20050124848;
20030088274; 20030093004; 20030093005; 20050124851; 20050124863; 20050131311;
20030093129; 20030097159; 20030097161; 20050135102; 20050136002; 20050137494;
20030100844; 20030105408; 20030114886; 20050137645; 20050144042; 20050148828;
20030120140; 20030120172; 20030125786; 20050148893; 20050148894; 20050148895;
20030128801; 20030130706; 20030130709; 20050149123; 20050149157; 20050153268;
20030135128; 20030139681; 20030144601; 20050154290; 20050154419; 20050154425;
20030149351; 20030149678; 20030153818; 20050154426; 20050156602; 20050159670;
20030158466; 20030158495; 20030158496; 20050159671; 20050165458; 20050167588;
20030158497; 20030158587; 20030160622; 20050171410; 20050182287; 20050182288;
20030163027; 20030163028; 20030167019; 20050182389; 20050182450; 20050182453;
20030171658; 20030171685; 20030171689; 20050182456; 20050182467; 20050182468;
20030176804; 20030181791; 20030181821; 20050182469; 20050187600; 20050192514;
20030181954; 20030181955; 20030185408; 20050192644; 20050192647; 20050197590;
20030187359; 20030195429; 20030195574; 20050197675; 20050197678; 20050209512;
20030199749; 20030204135; 20030216654; 20050209517; 20050209654; 20050209664;
20030225335; 20030225340; 20030229291; 20050209665; 20050209666; 20050215889;
20030233039; 20030233250; 20030234781; 20050216070; 20050216071; 20050222522;
20030236458; 20030236557; 20030236558; 20050222639; 20050228451; 20050228785;
20040002635; 20040006265; 20040006376; 20050240087; 20050240229; 20050240253;
20040010203; 20040015204; 20040015205; 20050244045; 20050245796; 20050251055;
20040019257; 20040019370; 20040024287; 20050251220; 20050256378; 20050256385;
20040030585; 20040034299; 20040039268; 20050256418; 20050267011; 20050267343;
20040049124; 20040049484; 20040059203; 20050267344; 20050267362; 20050267542;
20040059241; 20040064020; 20040064066; 20050273017; 20050277813; 20050277912;
20040068164; 20040068172; 20040068199; 20050283053; 20050283090; 20060004298;
20040072133; 20040073098; 20040073129; 20060004422; 20060009704; 20060009815;
20040073273; 20040077960; 20040077967; 20060014753; 20060015034; 20060015153;
20040078056; 20040079372; 20040082862; 20060018525; 20060020184; 20060036152;
20040082876; 20040088732; 20040092809; 20060036153; 20060041201; 20060047187;
20040096395; 20040097802; 20040101146; 20060047216; 20060047324; 20060047325;
20040116784; 20040116791; 20040116798; 20060051814; 20060052386; 20060052657;
20040116825; 20040117098; 20040122787; 20060052706; 20060058590; 20060058683;
20040122790; 20040127803; 20040131998; 20060058856; 20060061544; 20060064138;
20040133118; 20040133119; 20040133120; 20060064139; 20060064140; 20060069059;
20040133248; 20040133390; 20040138516; 20060069415; 20060074290; 20060074298;

20060074334;    20060074822;    20060078183;
20060079936;    20060082727;    20060084858;
20060084877;    20060087746;    20060089541;
20060089549;    20060094968;    20060094970;
20060094971;    20060094972;    20060095091;
20060095092;    20060100526;    20060100530;
20060100671;    20060102171;    20060106274;
20060106326;    20060106430;    20060106434;
20060111644;    20060116556;    20060122481;
20060129022;    20060129202;    20060129277;
20060129324;    20060135879;    20060135880;
20060136135;    20060142802;    20060149144;
20060149160;    20060149337;    20060152227;
20060153396;    20060155206;    20060155207;
20060155348;    20060155495;    20060161071;
20060161075;    20060161217;    20060161218;
20060161384;    20060167370;    20060167497;
20060167564;    20060167722;    20060170424;
20060173259;    20060173364;    20060173493;
20060173494;    20060173495;    20060173510;
20060176062;    20060178709;    20060184058;
20060184059;    20060188134;    20060189866;
20060189880;    20060189882;    20060189899;
20060191543;    20060195039;    20060195154;
20060195155;    20060200013;    20060200016;
20060200034;    20060200035;    20060200206;
20060204532;    20060206033;    20060206108;
20060206155;    20060206165;    20060206174;
20060212090;    20060212091;    20060217609;
20060217781;    20060217816;    20060224216;
20060224421;    20060225437;    20060229164;
20060233390;    20060235315;    20060235324;
20060235484;    20060235489;    20060239482;
20060241373;    20060241382;    20060241562;
20060241718;    20060247728;    20060251303;
20060252978;    20060252979;    20060258896;
20060258950;    20060259077;    20060265022;
20060276695;    20060281543;    20060281980;
20060282123;    20060287691;    20060293578;
20060293721;    20060293723;    20070000372;
20070005115;    20070005391;    20070007454;
20070008172;    20070014454;    20070015985;
20070016095;    20070016264;    20070019846;
20070021673;    20070021675;    20070021800;
20070025608;    20070027486;    20070027498;
20070027499;    20070027500;    20070027501;
20070031798;    20070032733;    20070032737;
20070032834;    20070036355;    20070036402;
20070038067;    20070038264;    20070038382;
20070043392;    20070043401;    20070049844;
20070049988;    20070050715;    20070055145;
20070060830;    20070060831;    20070060954;
20070060974;    20070060984;    20070066403;
20070066914;    20070066915;    20070066997;
20070067003;    20070067004;    20070072857;
20070078134;    20070081712;    20070083128;
20070093721;    20070093870;    20070100246;
20070100251;    20070100278;    20070100377;
20070100378;    20070100389;    20070100392;
20070100398;    20070100666;    20070112404;
20070118197;    20070127793;    20070129647;
20070129769;    20070129774;    20070135724;
20070135728;    20070138886;    20070142862;
20070142873;    20070142874;    20070149860;
20070150024;    20070150025;    20070150026;
20070150029;    20070156180;    20070156457;
20070159185;    20070161919;    20070162085;

20070162086;    20070165915;    20070167694;
20070167723;    20070167853;    20070167858;
20070167991;    20070173733;    20070173902;
20070179395;    20070179396;    20070179534;
20070179558;    20070179734;    20070184507;
20070191688;    20070191691;    20070191697;
20070191704;    20070191727;    20070197930;
20070198063;    20070203401;    20070203448;
20070208212;    20070208269;    20070209669;
20070213785;    20070213786;    20070225581;
20070225674;    20070225774;    20070225932;
20070233192;    20070233193;    20070238934;
20070239059;    20070244387;    20070244407;
20070249918;    20070249949;    20070249952;
20070250119;    20070250138;    20070255122;
20070255135;    20070255155;    20070255320;
20070255379;    20070255531;    20070259323;
20070260151;    20070265508;    20070265533;
20070273504;    20070273611;    20070276270;
20070276278;    20070276279;    20070276441;
20070276609;    20070280508;    20070282228;
20070287896;    20070291832;    20070293760;
20070299370;    20070299371;    20080001600;
20080001735;    20080004514;    20080004550;
20080004904;    20080009685;    20080009772;
20080013747;    20080015458;    20080015459;
20080021332;    20080021336;    20080021340;
20080021341;    20080021342;    20080021345;
20080027347;    20080027348;    20080027515;
20080033266;    20080033291;    20080033297;
20080033502;    20080033503;    20080033508;
20080033513;    20080036752;    20080039677;
20080039698;    20080039737;    20080039904;
20080042067;    20080045775;    20080045823;
20080045844;    20080046012;    20080046035;
20080049376;    20080051669;    20080051858;
20080058664;    20080058668;    20080058773;
20080064934;    20080065183;    20080069446;
20080071150;    20080071326;    20080074307;
20080077010;    20080077015;    20080077191;
20080081963;    20080082018;    20080086182;
20080091118;    20080091240;    20080097197;
20080097235;    20080097553;    20080097785;
20080103547;    20080103548;    20080109050;
20080119716;    20080119747;    20080119763;
20080119900;    20080123927;    20080125669;
20080125829;    20080125830;    20080125831;
20080128626;    20080132383;    20080139953;
20080140141;    20080140149;    20080140403;
20080147137;    20080154111;    20080154126;
20080154148;    20080154331;    20080154332;
20080157980;    20080161700;    20080161879;
20080161880;    20080161881;    20080161886;
20080161894;    20080162182;    20080167535;
20080167540;    20080167569;    20080167571;
20080177195;    20080177196;    20080177197;
20080183072;    20080183097;    20080188765;
20080194981;    20080195166;    20080200831;
20080208072;    20080208073;    20080208280;
20080208285;    20080214902;    20080215112;
20080219917;    20080221400;    20080221401;
20080221441;    20080221472;    20080221969;
20080228077;    20080228100;    20080228239;
20080229408;    20080230702;    20080230705;
20080234113;    20080234601;    20080235469;
20080241804;    20080242521;    20080242976;
20080243005;    20080243014;    20080243017;

20080243021; 20080247618; 20080249430; 20090264956; 20090264957; 20090264958;
20080249589; 20080255469; 20080255816; 20090264967; 20090267758; 20090270687;
20080255949; 20080257349; 20080260212; 20090270688; 20090270692; 20090270693;
20080262327; 20080262367; 20080262371; 20090270694; 20090270754; 20090270758;
20080269542; 20080269812; 20080269833; 20090270786; 20090270944; 20090271011;
20080269834; 20080269840; 20080269843; 20090271120; 20090271122; 20090271347;
20080275327; 20080275340; 20080275526; 20090275853; 20090276011; 20090276012;
20080279436; 20080281238; 20080281381; 20090280153; 20090281400; 20090281448;
20080281667; 20080286453; 20080287774; 20090281594; 20090287035; 20090287107;
20080287821; 20080288018; 20080294019; 20090287108; 20090287271; 20090287272;
20080294063; 20080298653; 20080298659; 20090287273; 20090287274; 20090287467;
20080304691; 20080304731; 20080306365; 20090290767; 20090290772; 20090292180;
20080310697; 20080311549; 20080317317; 20090292478; 20090292551; 20090292713;
20080319326; 20080319505; 20090005654; 20090292724; 20090297000; 20090299126;
20090005667; 20090005675; 20090006001; 20090299169; 20090299435; 20090304582;
20090009284; 20090012387; 20090018407; 20090306491; 20090306531; 20090306532;
20090018419; 20090018429; 20090018431; 20090306534; 20090306741; 20090311655;
20090018432; 20090018462; 20090022825; 20090312595; 20090312624; 20090312646;
20090024007; 20090024050; 20090030476; 20090312663; 20090312664; 20090312668;
20090030930; 20090033333; 20090036781; 20090312808; 20090312817; 20090312998;
20090036791; 20090036950; 20090039889; 20090316925; 20090316968; 20090316969;
20090043221; 20090048507; 20090048530; 20090318773; 20090318779; 20090318794;
20090054788; 20090054800; 20090054801; 20090319000; 20090319001; 20090319002;
20090054946; 20090054958; 20090058660; 20090319004; 20090322331; 20090323049;
20090062660; 20090062670; 20090062676; 20090326353; 20090326604; 20090326605;
20090062679; 20090062680; 20090062696; 20090327068; 20100003656; 20100004500;
20090062698; 20090069707; 20090074279; 20100004705; 20100004717; 20100004762;
20090076339; 20090076399; 20090076400; 20100004977; 20100010289; 20100010316;
20090076406; 20090076407; 20090076567; 20100010363; 20100010364; 20100010365;
20090078875; 20090082688; 20090082689; 20100010366; 20100010383; 20100010388;
20090082690; 20090082829; 20090083071; 20100010391; 20100010392; 20100010571;
20090088658; 20090088680; 20090093403; 20100010572; 20100010573; 20100010574;
20090093862; 20090094305; 20090099474; 20100010575; 20100010576; 20100010577;
20090099627; 20090099783; 20090105785; 20100010578; 20100010579; 20100010580;
20090112117; 20090112273; 20090112277; 20100010584; 20100010585; 20100010587;
20090112278; 20090112279; 20090112280; 20100010588; 20100010589; 20100010590;
20090112281; 20090112523; 20090118593; 20100010844; 20100014730; 20100014732;
20090118610; 20090118622; 20090118636; 20100015583; 20100016783; 20100017001;
20090118780; 20090118786; 20090118787; 20100021378; 20100022820; 20100023089;
20090119154; 20090124869; 20090124921; 20100028841; 20100030073; 20100030089;
20090124922; 20090124923; 20090131995; 20100030097; 20100030287; 20100036211;
20090132275; 20090137915; 20090137923; 20100036233; 20100036276; 20100036453;
20090143654; 20090148019; 20090149148; 20100041949; 20100041958; 20100041962;
20090149736; 20090156907; 20090156954; 20100041964; 20100042011; 20100042578;
20090156955; 20090156956; 20090157323; 20100043795; 20100045467; 20100049069;
20090157481; 20090157482; 20090157625; 20100049075; 20100049276; 20100049482;
20090157660; 20090157662; 20090157751; 20100056276; 20100056854; 20100056939;
20090157813; 20090163777; 20090163980; 20100057159; 20100057160; 20100057655;
20090163981; 20090163982; 20090164131; 20100063368; 20100063563; 20100068751;
20090164132; 20090164302; 20090164401; 20100069724; 20100069739; 20100069762;
20090164403; 20090164458; 20090164503; 20100069775; 20100069777; 20100069780;
20090164549; 20090171164; 20090171232; 20100070001; 20100076249; 20100076253;
20090171240; 20090171405; 20090172540; 20100076274; 20100076333; 20100076334;
20090177050; 20090177090; 20090177108; 20100076338; 20100076525; 20100079292;
20090177144; 20090179642; 20090182211; 20100080432; 20100081860; 20100081861;
20090187230; 20090191131; 20090192394; 20100082506; 20100087719; 20100087900;
20090192556; 20090198144; 20090198145; 20100090835; 20100092934; 20100094103;
20090204015; 20090209831; 20090209835; 20100094152; 20100094154; 20100094155;
20090209845; 20090210018; 20090216091; 20100098289; 20100099954; 20100099975;
20090216146; 20090216288; 20090220425; 20100100036; 20100100164; 20100106041;
20090220429; 20090221904; 20090221928; 20100106043; 20100106044; 20100106217;
20090221930; 20090227876; 20090227877; 20100113959; 20100114190; 20100114192;
20090227882; 20090227889; 20090234419; 20100114193; 20100114237; 20100114272;
20090240119; 20090243756; 20090246138; 20100114813; 20100121415; 20100125219;
20090247893; 20090247894; 20090259277; 20100125304; 20100125561; 20100130811;
20090261832; 20090264785; 20090264789; 20100130812; 20100130869; 20100130878;
20090264952; 20090264954; 20090264955; 20100131030; 20100131034; 20100132448;

| | | | | | |
|---|---|---|---|---|---|
| 20100134113; | 20100135556; | 20100137728; | 20110112426; | 20110112427; | 20110112590; |
| 20100137937; | 20100142774; | 20100143256; | 20110115624; | 20110118536; | 20110118618; |
| 20100145215; | 20100145219; | 20100145427; | 20110118619; | 20110119212; | 20110125046; |
| 20100145428; | 20100152621; | 20100160737; | 20110125048; | 20110125077; | 20110125078; |
| 20100163027; | 20100163028; | 20100163035; | 20110125203; | 20110125238; | 20110129129; |
| 20100165593; | 20100168053; | 20100168525; | 20110130615; | 20110130643; | 20110130675; |
| 20100168529; | 20100168602; | 20100172567; | 20110137371; | 20110137381; | 20110144520; |
| 20100174161; | 20100174533; | 20100179415; | 20110144521; | 20110150253; | 20110152284; |
| 20100179447; | 20100185113; | 20100189318; | 20110152710; | 20110152729; | 20110152967; |
| 20100191095; | 20100191124; | 20100191139; | 20110152988; | 20110160543; | 20110160607; |
| 20100191304; | 20100191305; | 20100195770; | 20110160608; | 20110160795; | 20110160796; |
| 20100197610; | 20100197993; | 20100198090; | 20110161011; | 20110162645; | 20110166430; |
| 20100198098; | 20100198101; | 20100198282; | 20110166471; | 20110166546; | 20110172500; |
| 20100198296; | 20100198519; | 20100204604; | 20110172509; | 20110172553; | 20110172554; |
| 20100204614; | 20100204748; | 20100204749; | 20110172562; | 20110172564; | 20110172567; |
| 20100204750; | 20100217100; | 20100217146; | 20110172725; | 20110172732; | 20110172738; |
| 20100217341; | 20100217348; | 20100219820; | 20110172739; | 20110172743; | 20110172927; |
| 20100222640; | 20100222694; | 20100222845; | 20110178359; | 20110178441; | 20110178442; |
| 20100224188; | 20100231221; | 20100231327; | 20110178581; | 20110181422; | 20110182501; |
| 20100234705; | 20100234752; | 20100234753; | 20110184305; | 20110184487; | 20110184650; |
| 20100238763; | 20100241020; | 20100241195; | 20110190569; | 20110190600; | 20110190846; |
| 20100241449; | 20100245093; | 20100248275; | 20110191275; | 20110191350; | 20110196693; |
| 20100249573; | 20100249627; | 20100249635; | 20110201944; | 20110207988; | 20110208012; |
| 20100249638; | 20100256592; | 20100258126; | 20110208094; | 20110208264; | 20110208539; |
| 20100260402; | 20100261977; | 20100261993; | 20110213200; | 20110213222; | 20110217240; |
| 20100262377; | 20100268055; | 20100268057; | 20110218405; | 20110218453; | 20110218456; |
| 20100268108; | 20100268288; | 20100274106; | 20110218950; | 20110224569; | 20110224570; |
| 20100274141; | 20100274147; | 20100274303; | 20110224571; | 20110224602; | 20110224749; |
| 20100274305; | 20100274308; | 20100274577; | 20110229005; | 20110230701; | 20110230738; |
| 20100274578; | 20100280332; | 20100280334; | 20110230755; | 20110230938; | 20110238130; |
| 20100280335; | 20100280372; | 20100280403; | 20110238136; | 20110245709; | 20110245734; |
| 20100280500; | 20100280571; | 20100280574; | 20110251583; | 20110251985; | 20110256520; |
| 20100280579; | 20100286549; | 20100286747; | 20110257501; | 20110257517; | 20110257519; |
| 20100292602; | 20100292752; | 20100293002; | 20110263962; | 20110263968; | 20110263995; |
| 20100293115; | 20100298624; | 20100298735; | 20110264182; | 20110270074; | 20110270095; |
| 20100303101; | 20100305962; | 20100305963; | 20110270096; | 20110270117; | 20110270346; |
| 20100312188; | 20100312579; | 20100318025; | 20110270347; | 20110270348; | 20110270579; |
| 20100318160; | 20100322488; | 20100322497; | 20110270914; | 20110275927; | 20110276107; |
| 20100324441; | 20100331649; | 20100331715; | 20110276112; | 20110282225; | 20110282230; |
| 20100331976; | 20110004115; | 20110004270; | 20110282234; | 20110288119; | 20110288400; |
| 20110004283; | 20110004412; | 20110007129; | 20110288424; | 20110288431; | 20110293193; |
| 20110009715; | 20110009729; | 20110009752; | 20110295142; | 20110295143; | 20110295166; |
| 20110009777; | 20110009920; | 20110009928; | 20110295338; | 20110295344; | 20110295345; |
| 20110015209; | 20110015469; | 20110015501; | 20110295346; | 20110295347; | 20110298706; |
| 20110015515; | 20110015536; | 20110015539; | 20110301436; | 20110301439; | 20110301441; |
| 20110021899; | 20110021970; | 20110022981; | 20110301448; | 20110301486; | 20110301487; |
| 20110028798; | 20110028799; | 20110028802; | 20110301488; | 20110301529; | 20110306845; |
| 20110028825; | 20110028827; | 20110028859; | 20110306846; | 20110307029; | 20110307030; |
| 20110029038; | 20110029044; | 20110034812; | 20110307079; | 20110308789; | 20110311021; |
| 20110034821; | 20110034822; | 20110034912; | 20110311489; | 20110313268; | 20110313274; |
| 20110035231; | 20110038515; | 20110038850; | 20110313308; | 20110313487; | 20110313760; |
| 20110040202; | 20110040356; | 20110040546; | 20110319482; | 20110319724; | 20110319726; |
| 20110040547; | 20110040713; | 20110043759; | 20110319975; | 20120003615; | 20120004518; |
| 20110046451; | 20110046473; | 20110046491; | 20120004561; | 20120004564; | 20120004579; |
| 20110050232; | 20110054272; | 20110054279; | 20120004749; | 20120010493; | 20120010536; |
| 20110054345; | 20110054562; | 20110054569; | 20120011927; | 20120016218; | 20120016252; |
| 20110060382; | 20110066005; | 20110066041; | 20120016336; | 20120016430; | 20120016432; |
| 20110066042; | 20110066053; | 20110074396; | 20120016435; | 20120021394; | 20120022336; |
| 20110077503; | 20110077538; | 20110077548; | 20120022340; | 20120022343; | 20120022350; |
| 20110077721; | 20110082154; | 20110082360; | 20120022351; | 20120022365; | 20120022384; |
| 20110082381; | 20110082522; | 20110087125; | 20120022392; | 20120022611; | 20120022844; |
| 20110087127; | 20110092800; | 20110092834; | 20120022884; | 20120029320; | 20120029378; |
| 20110092839; | 20110092882; | 20110093033; | 20120029379; | 20120029591; | 20120029601; |
| 20110098583; | 20110098778; | 20110105859; | 20120035428; | 20120035431; | 20120035433; |
| 20110105915; | 20110105938; | 20110105998; | 20120035698; | 20120035765; | 20120036004; |
| 20110106206; | 20110106750; | 20110110868; | 20120041279; | 20120041318; | 20120041319; |
| 20110112379; | 20110112381; | 20110112394; | 20120041320; | 20120041321; | 20120041322; |

20120041323;
20120041324;
20120041330;
20120041498;
20120041735;
20120041739;
20120046531;
20120046535;
20120046711;
20120046715;
20120046971;
20120052469;
20120052905;
20120053394;
20120053433;
20120053449;
20120053473;
20120053476;
20120053478;
20120053479;
20120053483;
20120053491;
20120053508;
20120053919;
20120053921;
20120059246;
20120059273;
20120059431;
20120060851;
20120065536;
20120070044;
20120071771;
20120078115;
20120078323;
20120078327;
20120080305;
20120083668;
20120083690;
20120083700;
20120083701;
20120083708;
20120088987;
20120088992;
20120089004;
20120089205;
20120092156;
20120092157;
20120095352;
20120095357;
20120100514;
20120101326;
20120101387;
20120101401;
20120101402;
20120101430;
20120101544;
20120108909;
20120108918;
20120108995;
20120108997;
20120108998;
20120108999;
20120109020;
20120116149;
20120116179;
20120116235;
20120116244;
20120116475;
20120116741;
20120123232;
20120123290;
20120125337;
20120128683;
20120130204;
20120130228;
20120130229;
20120130300;
20120130641;
20120136242;
20120136274;
20120136605;
20120143038;
20120143074;
20120143075;
20120143104;
20120143285;
20120145152;
20120149042;
20120149997;
20120150255;
20120150257;
20120150262;
20120150516;
20120150545;
20120157804;
20120157963;
20120158092;
20120159656;
20120162002;
20120163689;
20120164613;
20120165624;
20120165631;
20120165696;
20120165898;
20120165899;
20120165904;
20120172682;
20120172689;
20120172743;
20120177716;
20120179071;
20120179228;
20120184801;
20120184826;
20120185020;
20120191000;
20120191158;
20120191542;
20120195860;
20120197092;
20120197153;
20120197163;
20120197322;
20120203079;
20120203087;
20120203130;
20120203131;
20120203133;
20120203725;
20120207362;
20120209126;
20120209136;
20120209139;
20120209346;
20120212353;
20120215114;
20120215448;
20120219195;
20120219507;
20120220843;
20120220889;
20120221310;
20120226091;
20120226130;
20120226185;
20120226334;
20120232327;
20120232376;
20120232433;
20120238890;
20120242501;
20120245464;
20120245474;
20120245481;
20120245493;
20120245655;
20120249274;
20120253101;
20120253141;
20120253168;
20120253219;
20120253249;
20120253261;
20120253421;
20120253429;
20120253434;
20120253442;
20120259249;
20120262250;
20120262558;
20120263393;
20120265080;
20120265262;
20120265267;
20120265270;
20120265271;
20120268272;
20120269385;
20120271148;
20120271151;
20120271183;
20120271189;
20120271190;
20120271374;
20120271375;
20120271376;
20120271377;
20120271380;
20120277545;
20120277548;
20120277816;
20120277833;
20120283502;
20120283604;
20120288143;
20120289854;
20120289869;
20120290058;
20120296182;
20120296241;

20120296253;
20120296569;
20120302842;
20120302845;
20120302856;
20120302867;
20120302894;
20120302912;
20120303080;
20120303087;
20120310050;
20120310100;
20120310105;
20120310106;
20120310107;
20120310298;
20120316622;
20120316630;
20120316793;
20120321152;
20120321160;
20120321759;
20120323108;
20120323132;
20120330109;
20120330369;
20130006124;
20130006332;
20130009783;
20130011819;
20130012786;
20130012787;
20130012788;
20130012789;
20130012790;
20130012802;
20130012804;
20130012830;
20130013327;
20130013339;
20130013667;
20130018435;
20130018438;
20130018439;
20130018440;
20130018592;
20130018596;
20130019325;
20130023783;
20130028496;
20130030241;
20130030257;
20130031038;
20130034837;
20130035579;
20130039498;
20130041235;
20130041281;
20130046151;
20130046193;
20130046358;
20130046715;
20130053656;
20130054214;
20130054215;
20130058548;
20130060110;
20130060125;
20130060158;
20130063434;
20130063550;
20130064438;
20130066350;
20130066391;
20130066392;
20130066394;
20130066395;
20130066618;
20130069780;
20130070929;
20130072292;
20130072775;
20130072780;
20130072807;
20130072996;
20130073022;
20130076885;
20130079606;
20130079621;
20130079647;
20130079656;
20130079657;
20130080127;
20130080489;
20130085678;
20130089503;
20130090454;
20130090706;
20130091941;
20130095459;
20130096391;
20130096393;
20130096394;
20130096408;
20130096441;
20130096453;
20130096454;
20130096839;
20130096840;
20130102833;
20130102877;
20130102897;
20130102907;
20130102919;
20130104066;
20130109995;
20130109996;
20130110616;
20130113816;
20130116520;
20130116540;
20130116561;
20130116578;
20130116588;
20130116748;
20130118494;
20130120246;
20130121984;
20130123568;
20130123584;
20130123607;
20130123684;
20130127708;
20130127980;
20130130799;
20130131438;
20130131461;
20130131537;
20130131746;
20130131753;
20130131755;
20130132029;
20130137717;
20130137936;
20130137938;
20130138002;
20130138176;
20130138177;
20130141103;
20130144106;
20130144107;
20130144108;
20130144183;
20130144192;
20130144353;
20130144537;
20130150650;
20130150651;
20130150659;
20130150702;
20130150921;
20130151163;
20130158883;
20130159041;
20130165766;
20130165804;
20130165812;
20130165846;
20130165996;
20130167360;
20130172663;
20130172686;
20130172691;
20130172716;
20130172763;
20130172767;
20130172772;
20130172774;
20130178693;
20130178718;
20130178733;
20130178913;
20130182860;
20130184218;
20130184516;
20130184552;
20130184558;
20130184597;
20130184603;
20130184639;
20130184728;
20130184781;
20130184786;
20130184792;
20130184997;
20130185144;
20130185145;
20130188830;
20130188854;
20130189663;
20130190577;

20130190642;
20130197321;
20130197322;
20140073955;
20140073956;
20140073960;
20130197328;
20130197339;
20130197401;
20140073961;
20140073963;
20140073965;
20130197944;
20130203019;
20130204085;
20140073966;
20140073967;
20140073968;
20130204122;
20130204144;
20130204150;
20140073974;
20140073975;
20140074060;
20130211183;
20130211224;
20130211238;
20140074179;
20140074180;
20140074188;
20130211276;
20130211291;
20130211728;
20140077612;
20140077946;
20140081071;
20130217982;
20130218043;
20130218053;
20140081114;
20140081115;
20140081347;
20130218232;
20130218233;
20130218819;
20140081353;
20140088341;
20140088377;
20130221961;
20130223709;
20130225940;
20140094710;
20140094719;
20140094720;
20130225953;
20130225992;
20130226261;
20140098981;
20140100467;
20140100633;
20130226408;
20130226464;
20130231574;
20140101084;
20140104059;
20140105436;
20130231580;
20130231709;
20130231716;
20140107397;
20140107398;
20140107401;
20130231721;
20130231947;
20130234823;
20140107464;
20140107519;
20140107521;
20130235550;
20130237541;
20130237874;
20140107525;
20140107728;
20140107935;
20130238049;
20130238050;
20130238053;
20140111335;
20140113367;
20140114165;
20130238063;
20130242262;
20130243287;
20140114205;
20140114207;
20140114242;
20130244323;
20130245416;
20130245422;
20140114889;
20140119621;
20140121446;
20130245424;
20130245464;
20130245466;
20140121476;
20140121554;
20140121565;
20130245485;
20130245486;
20130245711;
20140122379;
20140128762;
20140128763;
20130245712;
20130245886;
20130251641;
20140128764;
20140128938;
20140133720;
20130253363;
20130253612;
20130255586;
20140133722;
20140135642;
20140135680;
20130261490;
20130261506;
20130261703;
20140135873;
20140135879;
20140135886;
20130266163;
20130267760;
20130267866;
20140136585;
20140140567;
20140142448;
20130267928;
20130274562;
20130274580;
20140142653;
20140142654;
20140142669;
20130274586;
20130274625;
20130275159;
20140143064;
20140148479;
20140148657;
20130281758;
20130281759;
20130281811;
20140148693;
20140148716;
20140148723;
20130281879;
20130281890;
20130282075;
20140148726;
20140148872;
20140151563;
20130282339;
20130289360;
20130289364;
20140152673;
20140154647;
20140154650;
20130289385;
20130289386;
20130289401;
20140155430;
20140155706;
20140155714;
20130289413;
20130289417;
20130289424;
20140155730;
20140155740;
20140155770;
20130289433;
20130289653;
20130289669;
20140155772;
20140155952;
20140156000;
20130293844;
20130295016;
20130296406;
20140159862;
20140161352;
20140163328;
20130296637;
20130300573;
20130303828;
20140163330;
20140163331;
20140163332;
20130303934;
20130304153;
20130304159;
20140163333;
20140163335;
20140163336;
20130304472;
20130308099;
20130309278;
20140163337;
20140163368;
20140163385;
20130310422;
20130310660;
20130310909;
20140163409;
20140163425;
20140163627;
20130314243;
20130317380;
20130317382;
20140163643;
20140163893;
20140163897;
20130317384;
20130317474;
20130317568;
20140171749;
20140171757;
20140171819;
20130317580;
20130318546;
20130324880;
20140171820;
20140174277;
20140175261;
20130330428;
20130338449;
20130338450;
20140176944;
20140179980;
20140180088;
20130338459;
20130338518;
20130338526;
20140180092;
20140180093;
20140180094;
20130338738;
20130338803;
20130339043;
20140180095;
20140180096;
20140180097;
20130344465;
20130345522;
20130345523;
20140180099;
20140180100;
20140180112;
20140000630;
20140003696;
20140005518;
20140180113;
20140180145;
20140180153;
20140005743;
20140005744;
20140005988;
20140180160;
20140180161;
20140180176;
20140012061;
20140012110;
20140012133;
20140180177;
20140180194;
20140180358;
20140012153;
20140015852;
20140018649;
20140180597;
20140184550;
20140187901;
20140018792;
20140019165;
20140023999;
20140187994;
20140188006;
20140188770;
20140025133;
20140025396;
20140025397;
20140193336;
20140194702;
20140194720;
20140029830;
20140031703;
20140031889;
20140194726;
20140194758;
20140194759;
20140031903;
20140032512;
20140038147;
20140194768;
20140194769;
20140194780;
20140039279;
20140039290;
20140039336;
20140194793;
20140200414;
20140200432;
20140039571;
20140039577;
20140039578;
20140200623;
20140203797;
20140206981;
20140039975;
20140046203;
20140046208;
20140207224;
20140207432;
20140211593;
20140046407;
20140051044;
20140051960;
20140213842;
20140213843;
20140213844;
20140051961;
20140052213;
20140055284;
20140213937;
20140213961;
20140214135;
20140056815;
20140057232;
20140058189;
20140214330;
20140214335;
20140221726;
20140058218;
20140058219;
20140058241;
20140221866;
20140222113;
20140222406;
20140058289;
20140058292;
20140058528;
20140226131;
20140226888;
20140228620;
20140062472;
20140063054;
20140063055;
20140228649;
20140228651;
20140228653;
20140066739;
20140066763;
20140066796;
20140228702;
20140232516;
20140235826;
20140067740;
20140070958;
20140072127;
20140235965;
20140236039;
20140236077;
20140072130;
20140073863;
20140073864;
20140236272;
20140236492;
20140237073;
20140073866;
20140073870;
20140073875;
20140243608;
20140243613;
20140243614;
20140073876;
20140073877;
20140073878;
20140243621;
20140243628;
20140243647;
20140073898;
20140073948;
20140073949;
20140243652;
20140243663;
20140243694;
20140073951;
20140073953;
20140073954;
20140243714;
20140243926;
20140243934;

| | | | | | |
|---|---|---|---|---|---|
| 20140245191; | 20140247970; | 20140249360; | 20150024356; | 20150025351; | 20150025408; |
| 20140249396; | 20140249429; | 20140249445; | 20150025410; | 20150025421; | 20150025422; |
| 20140249447; | 20140249454; | 20140249608; | 20150025610; | 20150025917; | 20150026446; |
| 20140249791; | 20140249792; | 20140257047; | 20150029087; | 20150030220; | 20150032017; |
| 20140257073; | 20140257118; | 20140257128; | 20150032044; | 20150032178; | 20150033245; |
| 20140257132; | 20140257147; | 20140257430; | 20150033258; | 20150033259; | 20150033262; |
| 20140257437; | 20140257438; | 20140266696; | 20150033266; | 20150033363; | 20150035959; |
| 20140266787; | 20140270438; | 20140271483; | 20150038804; | 20150038812; | 20150038822; |
| 20140275716; | 20140275741; | 20140275807; | 20150038869; | 20150039066; | 20150039110; |
| 20140275847; | 20140275851; | 20140275886; | 20150042477; | 20150044138; | 20150045606; |
| 20140275889; | 20140275891; | 20140275944; | 20150045607; | 20150045686; | 20150051655; |
| 20140276012; | 20140276013; | 20140276014; | 20150051656; | 20150051657; | 20150051658; |
| 20140276090; | 20140276123; | 20140276130; | 20150051659; | 20150051663; | 20150051668; |
| 20140276181; | 20140276183; | 20140276185; | 20150057512; | 20150057715; | 20150065803; |
| 20140276187; | 20140276194; | 20140276549; | 20150065831; | 20150065838; | 20150065839; |
| 20140276702; | 20140276944; | 20140277255; | 20150065845; | 20150066124; | 20150068069; |
| 20140277256; | 20140277282; | 20140277286; | 20150069846; | 20150071907; | 20150072394; |
| 20140277582; | 20140279341; | 20140279746; | 20150073141; | 20150073237; | 20150073249; |
| 20140288381; | 20140288614; | 20140288620; | 20150073294; | 20150073306; | 20150073505; |
| 20140288953; | 20140289172; | 20140296646; | 20150073722; | 20150080327; | 20150080671; |
| 20140296655; | 20140296724; | 20140296733; | 20150080674; | 20150080695; | 20150080703; |
| 20140296750; | 20140297397; | 20140300532; | 20150080746; | 20150080753; | 20150080985; |
| 20140303424; | 20140303425; | 20140303452; | 20150081226; | 20150081299; | 20150087931; |
| 20140303453; | 20140303454; | 20140303486; | 20150088015; | 20150088024; | 20150088093; |
| 20140303508; | 20140303511; | 20140304773; | 20150088120; | 20150088224; | 20150088228; |
| 20140309484; | 20140309614; | 20140309881; | 20150088478; | 20150091730; | 20150091791; |
| 20140309943; | 20140313303; | 20140315169; | 20150092949; | 20150093729; | 20150094962; |
| 20140316191; | 20140316192; | 20140316217; | 20150096564; | 20150099941; | 20150099946; |
| 20140316221; | 20140316230; | 20140316235; | 20150099959; | 20150099962; | 20150103360; |
| 20140316243; | 20140316248; | 20140316278; | 20150105631; | 20150105641; | 20150105701; |
| 20140323849; | 20140323899; | 20140323900; | 20150105837; | 20150105844; | 20150112222; |
| 20140323924; | 20140323946; | 20140324118; | 20150112403; | 20150112409; | 20150112899; |
| 20140324138; | 20140328487; | 20140330093; | 20150119652; | 20150119658; | 20150119689; |
| 20140330102; | 20140330157; | 20140330159; | 20150119698; | 20150119743; | 20150119745; |
| 20140330268; | 20140330334; | 20140330335; | 20150119746; | 20150119794; | 20150119898; |
| 20140330336; | 20140330337; | 20140330345; | 20150119956; | 20150120007; | 20150123653; |
| 20140330357; | 20140330394; | 20140330404; | 20150124220; | 20150126821; | 20150126845; |
| 20140330580; | 20140335489; | 20140336473; | 20150126848; | 20150126873; | 20150133716; |
| 20140336489; | 20140336514; | 20140336547; | 20150133811; | 20150133812; | 20150133830; |
| 20140336730; | 20140340084; | 20140343397; | 20150134031; | 20150134264; | 20150137817; |
| 20140343399; | 20140343408; | 20140343463; | 20150137988; | 20150140528; | 20150141529; |
| 20140343882; | 20140347265; | 20140347491; | 20150141773; | 20150141789; | 20150141794; |
| 20140348183; | 20140348412; | 20140350353; | 20150142082; | 20150145519; | 20150145676; |
| 20140350369; | 20140350380; | 20140350431; | 20150148617; | 20150148619; | 20150148700; |
| 20140350436; | 20140350634; | 20140350636; | 20150148878; | 20150150122; | 20150150473; |
| 20140350864; | 20140354278; | 20140355859; | 20150150475; | 20150150530; | 20150150753; |
| 20140357507; | 20140357932; | 20140357935; | 20150151142; | 20150153477; | 20150154721; |
| 20140357936; | 20140357962; | 20140358024; | 20150154764; | 20150154889; | 20150157235; |
| 20140358025; | 20140358067; | 20140358193; | 20150157266; | 20150157271; | 20150157859; |
| 20140358199; | 20140364721; | 20140364746; | 20150161326; | 20150161348; | 20150161738; |
| 20140369537; | 20140370479; | 20140371515; | 20150164349; | 20150164362; | 20150164375; |
| 20140371516; | 20140371544; | 20140371573; | 20150164404; | 20150164431; | 20150165226; |
| 20140371599; | 20140371611; | 20140371984; | 20150165239; | 20150167459; | 20150174362; |
| 20140378809; | 20140378810; | 20140378815; | 20150174398; | 20150174403; | 20150174405; |
| 20140378830; | 20140378851; | 20140378941; | 20150174406; | 20150174407; | 20150174418; |
| 20140379620; | 20150002815; | 20150003698; | 20150177413; | 20150178631; | 20150178978; |
| 20150003699; | 20150005592; | 20150005594; | 20150181840; | 20150182417; | 20150182753; |
| 20150005640; | 20150005644; | 20150005646; | 20150182756; | 20150186923; | 20150190062; |
| 20150005660; | 20150005680; | 20150005839; | 20150190070; | 20150190077; | 20150190085; |
| 20150005840; | 20150005841; | 20150006186; | 20150190094; | 20150190636; | 20150190637; |
| 20150008916; | 20150010223; | 20150011866; | 20150192532; | 20150192776; | 20150196213; |
| 20150011877; | 20150011907; | 20150012054; | 20150196246; | 20150196249; | 20150196800; |
| 20150012057; | 20150012111; | 20150012466; | 20150199010; | 20150199121; | 20150200046; |
| 20150016618; | 20150017115; | 20150018665; | 20150201849; | 20150201879; | 20150202330; |
| 20150018699; | 20150018702; | 20150018705; | 20150202428; | 20150202447; | 20150203822; |
| 20150018706; | 20150018758; | 20150018893; | 20150206051; | 20150206174; | 20150208940; |
| 20150018905; | 20150019241; | 20150019266; | 20150208975; | 20150208978; | 20150208982; |

20150208994;     20150212168;     20150213012;       20150359452;     20150359467;     20150359486;
20150213019;     20150213020;     20150213191;       20150359492;     20150360026;     20150360030;
20150215412;     20150216436;     20150216439;       20150360039;     20150363941;     20150366482;
20150216468;     20150216469;     20150216762;       20150366497;     20150366503;     20150366504;
20150217082;     20150219729;     20150219732;   5   20150366516;     20150366518;     20150366656;
20150220486;     20150220830;     20150223721;       20150366659;     20150369864;     20150370320;
20150223731;     20150223743;     20150223905;       20150370325;     20150374250;     20150374285;
20150226813;     20150227702;     20150227793;       20150374292;     20150374300;     20150374973;
20150230719;     20150230744;     20150230750;       20150374983;     20150374986;     20150374987;
20150231330;     20150231395;     20150231397;  10   20150374993;     20150375006;     20150379230;
20150231405;     20150231408;     20150234477;       20150379370;     20150379878;     20150380009;
20150235088;     20150235370;     20150235441;       20160000348;     20160000354;     20160000383;
20150235447;     20150238104;     20150238106;       20160001065;     20160001096;     20160001098;
20150238112;     20150238137;     20150238693;       20160002523;     20160004298;     20160004396;
20150238761;     20150238765;     20150241705;  15   20160004821;     20160004957;     20160005235;
20150241916;     20150241959;     20150242575;       20160005320;     20160007899;     20160007904;
20150242608;     20150242943;     20150243100;       20160007915;     20160007918;     20160007945;
20150243105;     20150243106;     20150245781;       20160008489;     20160008568;     20160008598;
20150245800;     20150246238;     20150247723;       20160008600;     20160008620;     20160008632;
20150247921;     20150247975;     20150247976;  20   20160012011;     20160012583;     20160012749;
20150248167;     20150248169;     20150248170;       20160015281;     20160015289;     20160015307;
20150248470;     20150248615;     20150248764;       20160015673;     20160016014;     20160019434;
20150248765;     20150248787;     20150248788;       20160019693;     20160022141;     20160022156;
20150248789;     20150248791;     20150248792;       20160022164;     20160022165;     20160022167;
20150248793;     20150250393;     20150250401;  25   20160022168;     20160022206;     20160022207;
20150250415;     20150251016;     20150253391;       20160022981;     20160023016;     20160026913;
20150253410;     20150254413;     20150257645;       20160027178;     20160027293;     20160027342;
20150257648;     20150257649;     20150257673;       20160027423;     20160029896;     20160029917;
20150257674;     20150257700;     20150257712;       20160029918;     20160029946;     20160029950;
20150262016;     20150264492;     20150265164;  30   20160029958;     20160029959;     20160029965;
20150265207;     20150265583;     20150265830;       20160029998;     20160030666;     20160030702;
20150265836;     20150269825;     20150272448;       20160030749;     20160030750;     20160030834;
20150272461;     20150272465;     20150272496;       20160031479;     20160035093;     20160038037;
20150272510;     20150272652;     20150273211;       20160038038;     20160038042;     20160038043;
20150273223;     20150282705;     20150282730;  35   20160038049;     20160038069;     20160038091;
20150282749;     20150282755;     20150282760;       20160038559;     20160038770;     20160040514;
20150283019;     20150283265;     20150283379;       20160044841;     20160045128;     20160045150;
20150283393;     20150287223;     20150289217;       20160045162;     20160045731;     20160045756;
20150289779;     20150289813;     20150289929;       20160048659;     20160048948;     20160048965;
20150290419;     20150290420;     20150290453;  40   20160051161;     20160051162;     20160051187;
20150290454;     20150293004;     20150294067;       20160051195;     20160051793;     20160051812;
20150294074;     20150294085;     20150294086;       20160051818;     20160055236;     20160055304;
20150294445;     20150296288;     20150297106;       20160055415;     20160055842;     20160058301;
20150297108;     20150297109;     20150297139;       20160058304;     20160058322;     20160058354;
20150297141;     20150297444;     20150297719;  45   20160058359;     20160058366;     20160058376;
20150297889;     20150297893;     20150301218;       20160058392;     20160058673;     20160060926;
20150304048;     20150304101;     20150305685;       20160062459;     20160063207;     20160063883;
20150305686;     20150305689;     20150305799;       20160065724;     20160065840;     20160066788;
20150305800;     20150305801;     20150306057;       20160066789;     20160066828;     20160066838;
20150306340;     20150306390;     20150306391;  50   20160067485;     20160067492;     20160067494;
20150306392;     20150309563;     20150309582;       20160067496;     20160067526;     20160070436;
20150310862;     20150313496;     20150313498;       20160073886;     20160073916;     20160073947;
20150313535;     20150313539;     20150313540;       20160073991;     20160074657;     20160074660;
20150313949;     20150313971;     20150315554;       20160074661;     20160077547;     20160078780;
20150317447;     20150317796;     20150320591;  55   20160081577;     20160081610;     20160081613;
20150321000;     20150324544;     20150324545;       20160081616;     20160081625;     20160081793;
20150324692;     20150325151;     20150327813;       20160082180;     20160082319;     20160084925;
20150327837;     20150328330;     20150328455;       20160085302;     20160086622;     20160087603;
20150331929;     20150332015;     20150335281;       20160089031;     20160091448;     20160095546;
20150335288;     20150335292;     20150335294;  60   20160095838;     20160096025;     20160097824;
20150335295;     20150335303;     20150335876;       20160100769;     20160101260;     20160102500;
20150335877;     20150338915;     20150339363;       20160103487;     20160103963;     20160104006;
20150339459;     20150342472;     20150342478;       20160106331;     20160106344;     20160106513;
20150342493;     20150343215;     20150343222;       20160106950;     20160106997;     20160107309;
20150343242;     20150351655;     20150351690;  65   20160107653;     20160109851;     20160109959;
20150351701;     20150352362;     20150352363;       20160110517;     20160110866;     20160110867;
20150359431;     20150359441;     20150359450;       20160112022;     20160112684;     20160113517;

20160113528; 20160113539; 20160113545; 20160239968; 20160240212; 20160240765;
20160113567; 20160113569; 20160113587; 20160242645; 20160242659; 20160242665;
20160113726; 20160114165; 20160116472; 20160242669; 20160242670; 20160242690;
20160116553; 20160117815; 20160117816; 20160242699; 20160243362; 20160243381;
20160117819; 20160119726; 20160120048; 20160245670; 20160245766; 20160245952;
20160120428; 20160120432; 20160120433; 20160246939; 20160247064; 20160248434;
20160120434; 20160120436; 20160120437; 20160248994; 20160249826; 20160249841;
20160120457; 20160120464; 20160120480; 20160249846; 20160249857; 20160249864;
20160121074; 20160121114; 20160121116; 20160250355; 20160250465; 20160250473;
20160125228; 20160125572; 20160128589; 20160256063; 20160256086; 20160256105;
20160128596; 20160128597; 20160128632; 20160256108; 20160256109; 20160256112;
20160128661; 20160128864; 20160129249; 20160256118; 20160256130; 20160256690;
20160131723; 20160132654; 20160133015; 20160256691; 20160256693; 20160257957;
20160135691; 20160135727; 20160135748; 20160259085; 20160259905; 20160260216;
20160135754; 20160136423; 20160136427; 20160261962; 20160262623; 20160262664;
20160136429; 20160136430; 20160136443; 20160262680; 20160262685; 20160262695;
20160139215; 20160140306; 20160140313; 20160262703; 20160263318; 20160263376;
20160140707; 20160140834; 20160140975; 20160263380; 20160263393; 20160267809;
20160143540; 20160143541; 20160143554; 20160270656; 20160270723; 20160274660;
20160143560; 20160143574; 20160143582; 20160275536; 20160278651; 20160278653;
20160143594; 20160144175; 20160144186; 20160278662; 20160278672; 20160278687;
20160147964; 20160148077; 20160148371; 20160278697; 20160278713; 20160278736;
20160148372; 20160148400; 20160148531; 20160278870; 20160279021; 20160279022;
20160150988; 20160151014; 20160151018; 20160279023; 20160279024; 20160279025;
20160151628; 20160152233; 20160155005; 20160279267; 20160279410; 20160279417;
20160157742; 20160157773; 20160157777; 20160279435; 20160282113; 20160282941;
20160157828; 20160158553; 20160158554; 20160284082; 20160287117; 20160287118;
20160162652; 20160164813; 20160165852; 20160287120; 20160287142; 20160287157;
20160165853; 20160166169; 20160166197; 20160287162; 20160287166; 20160287169;
20160166199; 20160166205; 20160166207; 20160287308; 20160287334; 20160287436;
20160166208; 20160166219; 20160167672; 20160287869; 20160287871; 20160287889;
20160168137; 20160170996; 20160170998; 20160287895; 20160296157; 20160296287;
20160171514; 20160174099; 20160174862; 20160296746; 20160298449; 20160299568;
20160174863; 20160174867; 20160174907; 20160300252; 20160300352; 20160302683;
20160175557; 20160175607; 20160176053; 20160302704; 20160302709; 20160302711;
20160178392; 20160180042; 20160180054; 20160302720; 20160302737; 20160303322;
20160180055; 20160183812; 20160183828; 20160303396; 20160303397; 20160303402;
20160183861; 20160183881; 20160184029; 20160306844; 20160306942; 20160310031;
20160184596; 20160184599; 20160187524; 20160310070; 20160310071; 20160313408;
20160191517; 20160192841; 20160192842; 20160313417; 20160313418; 20160313798;
20160192847; 20160192879; 20160193499; 20160317056; 20160317060; 20160317077;
20160196185; 20160196393; 20160196635; 20160317383; 20160317824; 20160320210;
20160196758; 20160198950; 20160198963; 20160321742; 20160324445; 20160324457;
20160198966; 20160198968; 20160198973; 20160324465; 20160324478; 20160324580;
20160199241; 20160199577; 20160199656; 20160324677; 20160324942; 20160325111;
20160199662; 20160202755; 20160203597; 20160331264; 20160331307; 20160331952;
20160203726; 20160204937; 20160205450; 20160331970; 20160331974; 20160331982;
20160205489; 20160206236; 20160206241; 20160334475; 20160334534; 20160334866;
20160206380; 20160206581; 20160206671; 20160338608; 20160338634; 20160338644;
20160206871; 20160206877; 20160206880; 20160338798; 20160338825; 20160339237;
20160210872; 20160213261; 20160213276; 20160339238; 20160339239; 20160339242;
20160213314; 20160213317; 20160213947; 20160339243; 20160339300; 20160341684;
20160216760; 20160217586; 20160217595; 20160342241; 20160342762; 20160345856;
20160219345; 20160220133; 20160220134; 20160345895; 20160345901; 20160345911;
20160220136; 20160220163; 20160220166; 20160346530; 20160346542; 20160351069;
20160220439; 20160220821; 20160220836; 20160354003; 20160354027; 20160356911;
20160220837; 20160220850; 20160222073; 20160357003; 20160357256; 20160360100;
20160223622; 20160223627; 20160223703; 20160360965; 20160360970; 20160361021;
20160224757; 20160224803; 20160228019; 20160361027; 20160361041; 20160361532;
20160228028; 20160228029; 20160228059; 20160361534; 20160361540; 20160361546;
20160228064; 20160228204; 20160228640; 20160363483; 20160364859; 20160364860;
20160228702; 20160228705; 20160231401; 20160364861; 20160366462; 20160367138;
20160232330; 20160232625; 20160232667; 20160367186; 20160367195; 20160367198;
20160232811; 20160235323; 20160235324; 20160367204; 20160367209; 20160367808;
20160235341; 20160235351; 20160235352; 20160367812; 20160371387; 20160371455;
20160235359; 20160235980; 20160235983; 20160371721; 20160374581; 20160374616;
20160238673; 20160239084; 20160239966; 20160374618; 20160374990; 20160375245;

20160375259; 20160378608; 20160378965;
20170000324; 20170000325; 20170000326;
20170000329; 20170000330; 20170000331;
20170000332; 20170000333; 20170000334;
20170000335; 20170000337; 20170000340;
20170000341; 20170000342; 20170000343;
20170000345; 20170000404; 20170000422;
20170000454; 20170000683; 20170001016;
20170001032; 20170006931; 20170007111;
20170007115; 20170007116; 20170007122;
20170007123; 20170007165; 20170007173;
20170007182; 20170007450; 20170007799;
20170007820; 20170007828; 20170007843;
20170010469; 20170010470; 20170013562;
20170014037; 20170014080; 20170014083;
20170014625; 20170014630; 20170017083;
20170020434; 20170020447; 20170020454;
20170020627; 20170021158; 20170021161;
20170024886; 20170027467; 20170027517;
20170027521; 20170027539; 20170027651;
20170027812; 20170028563; 20170031440;
20170031441; 20170032098; 20170032221;
20170032524; 20170032527; 20170032544;
20170034638; 20170035309; 20170035317;
20170035344; 20170035392; 20170036024;
20170039591; 20170039706; 20170041699;
20170042430; 20170042444; 20170042469;
20170042474; 20170042475; 20170042476;
20170042485; 20170042713; 20170042827;
20170043160; 20170043166; 20170043167;
20170043178; 20170045601; 20170046052;
20170046971; 20170050046; 20170052170;
20170053082; 20170053088; 20170053092;
20170053461; 20170053513; 20170053665;
20170055839; 20170055898; 20170055900;
20170055913; 20170056363; 20170056467;
20170056642; 20170056655; 20170056663;
20170060298; 20170061034; 20170061589;
20170061760; 20170065199; 20170065218;
20170065229; 20170065349; 20170065379;
20170065638; 20170065816; 20170066806;
20170067323; 20170069306; 20170071495;
20170071521; 20170071523; 20170071529;
20170071532; 20170071537; 20170071546;
20170071551; 20170071552; 20170076452;
20170079538; 20170079543; 20170079573;
20170079588; 20170079589; 20170079596;
20170080050; 20170080234; 20170080256;
20170080320; 20170084175; 20170084187;
20170085547; 20170085855; 20170086672;
20170086695; 20170086727; 20170086729;
20170086763; 20170087302; 20170087330;
20170087354; 20170087355; 20170087356;
20170087364; 20170087367; 20170090475;
20170091418; 20170091567; 20170094385;
20170095157; 20170095174; 20170095199;
20170095670; 20170095676; 20170095721;
20170099479; 20170099713; 20170100051;
20170100540; 20170100591; 20170103440;
20170105647; 20170106193; 20170107575;
20170108926; 20170112379; 20170112403;
20170112427; 20170112446; 20170112577;
20170112671; 20170112947; 20170113042;
20170113046; 20170113056; 20170113057;
20170117866; 20170119270; 20170119271;
20170119994; 20170120041; 20170120043;
20170120052; 20170120054; 20170120066;

20170127727; 20170127946; 20170128006;
20170128015; 20170128032; 20170131293;
20170132816; 20170133576; 20170133577;
20170135594; 20170135597; 20170135604;
20170135626; 20170135629; 20170135631;
20170135633; 20170135640; 20170136238;
20170136240; 20170136264; 20170136265;
20170138132; 20170140124; 20170143231;
20170143249; 20170143255; 20170143257;
20170143259; 20170143266; 20170143267;
20170143268; 20170143273; 20170143280;
20170143282; 20170143442; 20170143550;
20170143960; 20170143963; 20170143966;
20170143986; 20170146386; 20170146387;
20170146390; 20170146391; 20170146615;
20170146801; 20170147578; 20170147754;
20170148213; 20170148240; 20170148340;
20170148592; 20170149945; 20170150896;
20170150916; 20170150921; 20170150925;
20170151433; 20170151435; 20170151436;
20170154167; 20170156593; 20170156606;
20170156622; 20170156655; 20170156662;
20170156674; 20170157343; 20170157402;
20170157410; 20170160360; 20170162072;
20170164861; 20170164862; 20170164876;
20170164878; 20170164893; 20170164894;
20170164895; 20170164901; 20170165020;
20170165481; 20170165496; 20170168121;
20170168566; 20170168568; 20170169714;
20170171441; 20170172414; 20170172446;
20170172499; 20170172501; 20170172520;
20170172527; 20170173262; 20170173326;
20170173391; 20170177023; 20170178001;
20170178340; 20170180558; 20170181252;
20170181693; 20170182176; 20170182285;
20170182312; 20170185149; 20170185714;
20170185741; 20170188862; 20170188865;
20170188866; 20170188868; 20170188869;
20170188870; 20170188872; 20170188876;
20170188905; 20170188916; 20170188922;
20170188932; 20170188933; 20170188947;
20170188992; 20170189685; 20170189686;
20170189687; 20170189688; 20170189689;
20170189691; 20170189700; 20170189707;
20170190765; 20170193161; 20170193831;
20170196497; 20170196501; 20170196503;
20170196519; 20170197080; 20170197081;
20170197086; 20170198017; 20170198349;
20170199251; 20170202474; 20170202475;
20170202476; 20170202518; 20170202621;
20170202633; 20170203154; 20170205259;
20170206654; 20170206691; 20170206913;
20170209043; 20170209044; 20170209053;
20170209062; 20170209083; 20170209094;
20170209225; 20170209389; 20170209737;
20170212188; 20170213339; 20170214786;
20170216595; 20170221206; 20170224990;
20170224994; 20170231560; 20170239486;
20170239489; EP1304073A2; EP1304073A3;
WO2000025668A1; and WO2001087153A1;
"Stimulating the Brain with Light and Sound," Transparent
Corporation, Neuroprogrammer™ 3, www.transparent-
corp.com/products/np/entrainment.php.
A new method for detecting state changes in the EEG:
exploratory application to sleep data. J. Sleep Res. 7
suppl. 1:48-56, 1998b.

Abeles M, Local Cortical Circuits (1982) New York: Springer-Verlag.

Abeln, Vera, et al. "Brainwave entrainment for better sleep and post-sleep state of young elite soccer players-A pilot study." European J. Sport science 14.5 (2014): 393-402;

Abraham, W. C., 2008. Metaplasticity: tuning synapses and networks for plasticity. Nature Reviews Neuroscience 9, 387.

Abrahamyan, A., Clifford, C. W., Arabzadeh, E., Harris, J. A., 2011. Improving visual sensitivity with subthreshold transcranial magnetic stimulation. J. Neuroscience 31, 3290-3294.

Acton, George. "Methods for independent entrainment of visual field zones." U.S. Pat. No. 9,629,976. 25 Apr. 2017.

Adee, Sally, "Zap your brain into the zone: Fast track to pure focus" New Scientist, No. 2850 Feb. 1, 2012, www.newscientist.com/article/mg21328501-600-zap-your-brain-into-the-zone-fast-track-to-pure-focus/).

adegenet.r-forge.r-project.org/files/tutorial-spca.pdf,

Adler G, Brassen S, Jajcevic A (2003) EEG coherence in Alzheimer's dementia. J Neural Transm 110:1051-1058;

Adrian Rodriguez Aguiñaga, Miguel Angel Lopez Ramirez, Lecture Notes in Computer Science, vol. 9456, pp. 177, 2015, ISSN 0302-9743, ISBN 978-3-319-26507-0).

Adrian, E. D., 1928. The Basis of Sensation. W.W. Norton, New York.

Ahonen, A. I., M. S. Hämäläinen, M. J. Kajola, J. E. T. Knuutila, P. P. Laine, O. V. Lounasmaa, L. T. Parkkonen, J. T. Simola, and C. D. Tesche Physica Scripta, Volume 1993, T49A).

Alam M, Truong D Q, Khadka N, Bikson M. Spatial and polarity precision of concentric high-definition transcranial direct current stimulation (HD-tDCS). Phys Med Biol. 2016 Jun. 21; 61 (12): 4506-21. doi: 10.1088/0031-9155/61/12/4506.

Albouy, Philippe, et al. "Selective entrainment of theta oscillations in the dorsal stream causally enhances auditory working memory performance." Neuron 94.1 (2017): 193-206.

Alexander W H & Brown J W (2011) Medial prefrontal cortex as an action-outcome predictor. Nature Neuroscience 14 (10): 1338-1344.

Alexander W H & Brown J W (2015) Hierarchical error representation: A computational model of anterior cingulate and dorsolateral prefrontal cortex. Neural Computation 27:2354-2410.

Alicia Heraz, Claude Frasson, Lecture Notes in Computer Science, vol. 5535, pp. 367, 2009, ISSN 0302-9743, ISBN 978-3-642-02246-3.

Alicia Heraz, Ryad Razaki; Claude Frasson, "Using machine learning to predict learner mental state from brainwaves" Advanced Learning Technologies, 2007. ICALT 2007. Seventh IEEE International Conference on Advanced Learning Technologies (ICALT 2007)) See also:

Allen, Philip B., et al. High-temperature superconductivity. Springer Science & Business Media, 2012;

Alonzo A, Aaronson S, Bikson M, Husain M, Lisanby S, Martin D, Mcclintock S M, McDonald W M, O'Reardon J, Esmailpoor 7, Loo C. Study design and methodology for a multicentre, randomised controlled trial of transcranial direct current stimulation as a treatment for unipolar and bipolar depression. Contemp Clin Trials. 2016 November; 51:65-71. doi: 10.1016/j.cct.2016.10.002.

Amari S., Cichocki, A. & Yang, H. H., A new learning algorithm for blind signal separation. In: Advances in Neural Information Processing Systems 8, MIT Press, 1996.

Amari, S., Natural gradient works efficiently in learning, Neural Computation 10:251-276, 1998.

Amassian, V. E., Cracco, R. Q., Maccabee, P. J., Cracco, J. B., Rudell, A., Eberle, L., 1989. Suppression of visual perception by magnetic coil stimulation of human occipital cortex. Electroencephalography and Clin. Neurophysiology 74, 458-462.

Amassian, V. E., Eberle, L., Maccabee, P. J., Cracco, R. Q., 1992. Modelling magnetic coil excitation of human cerebral cortex with a peripheral nerve immersed in a brain-shaped volume conductor: the significance of fiber bending in excitation. Electroencephalography and Clin. Neurophysiology 85, 291-301.

Amengual, J., et al. "P018 Local entrainment and distribution across cerebral networks of natural oscillations elicited in implanted epilepsy patients by intracranial stimulation: Paving the way to develop causal connectomics of the healthy human brain." Clin. Neurophysiology 128.3 (2017): e18;

Amenta P., D'Ambra L. (1999) Generalized Constrained Principal Component Analysis. Atti Riunione Scientifica del Gruppo di Classificazione dell'IFCS su "Classificazione e Analisi dei Dati", Roma.

Amenta P., D'Ambra L. (1994) Analisi non Simmetrica delle Corrispondenze Multiple con Vincoli Lineari. Atti S. I. S. XXXVII Sanremo, Aprile 1994.

Amenta P., D'Ambra L. (1996) L'Analisi in Componenti Principali in rapporto ad un sottospazio di riferimento con informazioni esterne, Quaderni del D. M. Q. T. E., Università di Pescara, n. 18.

An J H, Radman T, Su Y, Bikson M. Effects of glucose and glutamine concentration in the formulation of the artificial cerebrospinal fluid (ACSF). Brain Research. 2008; 1218: 1586-93

Anguera J A, et al. (2013) Video game training enhances cognitive control in older adults. Nature 501:97-101.

Antal A, Alekseichuk I, Bikson M, Brockmöller J, Brunoni A R, Chen R, Cohen L G, Dowthwaite G, Ellrich J, Flöel A, Fregni F, George M S, Hamilton R, Haueisen J, Herrmann C S, Hummel F C, Lefaucheur J P, Liebetanz D, Loo C K, McCaig C D, Miniussi C, Miranda P C, Moliadze V, Nitsche M A, Nowak R, Padberg F, Pascual-Leone A, Poppendieck W, Priori A, Rossi S, Rossini P M, Rothwell J, Rueger M A, Ruffini G, Schellhorn K, Siebner H R, Ugawa Y, Wexler A, Ziemann U, Hallett M, Paulus W. Low intensity transcranial electric stimulation: Safety, ethical, legal regulatory and application guidelines. Clin Neurophysiol. 2017 Jun. 19. doi: 10.1016/j.clinph.2017.06.001.

Antal A, Bikson M, Datta A, Lafon B, Dechent P, Parra L C, Paulus W. Imaging artifacts induced by electrical stimulation during conventional fMRI of the brain. Neuroimage 2014; 85:1040-1047 (Cover).

Antal, A., Boros, K., Poreisz, C., Chaieb, L., Terney, D., Paulus, W., 2008. Comparatively weak after-effects of transcranial alternating current stimulation (tACS) on cortical excitability in humans. Brain Stimulation 1, 97-105.

Antal, A., Nitsche, M. A., Kruse, W., Kincses, T. Z., Hoffmann, K. P., Paulus, W., 2004. Direct current stimulation over V5 enhances visuomotor coordination by improving motion perception in humans. J. Cognitive Neuroscience 16, 521-527.

Argento, Emanuele, et al. "Augmented Cognition via Brain-wave Entrainment in Virtual Reality: An Open, Integrated Brain Augmentation in a Neuroscience System Approach." Augmented Human Research 2.1 (2017): 3.

Arlotti M, Rahman A, Minhas P, Bikson M. Axon terminal polarization induced by weak uniform D C electric fields: a modeling study. Conf Proc IEEE Eng Med Biol Soc. 2012; 4575-8. doi: 10.1109/EMBC.2012.6346985

Aron A R, Fletcher P C, Bullmore E T, Sahakian B J, Robbins T W (2003) Stop-signal inhibition disrupted by damage to right inferior frontal gyrus in humans. Nat Neurosci 6:115-116.

Arzouan Y, Goldstein A, Faust M. Brainwaves are stetho-scopes: ERP correlates of novel metaphor comprehen-sion. Brain Res 2007; 1160:69-81.

Arzouan Y, Goldstein A, Faust M. Dynamics of hemispheric activity during metaphor comprehension: electrophysi-ological measures. NeuroImage 2007; 36:222-231.

Ashbridge, E., Walsh, V., Cowey, A., 1997. Temporal aspects of visual search studied by transcranial magnetic stimulation. Neuropsychologia 35, 1121-1131.

Atwater, F. H. (2001). Binaural beats and the regulation of arousal levels. Proceedings of the TANS, 11;

Au J, et al. (2015) Improving fluid intelligence with training on working memory: a meta-analysis. Psychonomic Bul-letin & Review 22:366-377.

Azcarraga, Judith, John Francis Ibanez Jr., Ianne Robert Lim, Nestor Lumanas Jr., "Use of Personality Profile in Predicting Academic Emotion Based on Brainwaves Sig-nals and Mouse Behavior", Knowledge and Systems Engineering (KSE) 2011 Third International Conference on, pp. 239-244, 2011.

Azcarraga, Judith, Merlin Teodosia Suarez, "Recognizing Student Emotions using Brainwaves and Mouse Behavior Data", International Journal of Distance Education Tech-nologies, vol. 11, pp. 1, 2013, ISSN 1539-3100.

B. Bah, "Diffusion Maps: Applications and Analysis", Mas-ters Thesis, University of Oxford B. Schölkopf, A. Smola, K.-R. Müller, Nonlinear Compo-nent Analysis as a Kernel Eigenvalue Problem. Neural Computation 10 (5): 1299-1319, 1998, MIT PressCam-bridge, M A, USA, doi: 10.1162/089976698300017467

Bai S, Gálvez V, Dokos S, Martin D, Bikson M, Loo C. Computational models of Bitemporal, Bifrontal and Right Unilateral ECT predict differential stimulation of brain regions associated with efficacy and cognitive side effects. Eur Psychiatry. 2017 March; 41:21-29. doi: 10.1016/j.eurpsy.2016.09.005.

Bailey, D. L.; D. W. Townsend; P. E. Valk; M. N. Maisey (2005). Positron Emission Tomography: Basic Sciences. Secaucus, N J: Springer-Verlag. ISBN 1-85233-798-2.

Bandettini P A, Wong E C, Hinks R S, Tikofsky R S, Hyde J S, Time course EPI of human brain function during task activation. Magn Reson Med 25:390-7, 1992.

Barker, A. T., Freeston, I. L., Jalinous, R., Jarratt, J. A., 1987. Magnetic stimulation of the human brain and peripheral nervous system: an introduction and the results of an initial clinical evaluation. Neurosurgery 20, 100-109.

Barker, A. T., Jalinous, R., Freeston, I. L., 1985. Non-invasive magnetic stimulation of human motor cortex. Lancet 1, 1106-1107.

Begich, Nick, Controlling the Human Mind, Earth Pulse Press Anchorage-isbn=1-890693-54-5

Bell A. J. & Sejnowski T. J. An information-maximization approach to blind separation and blind deconvolution. Neural Comput 7:1129-59, 1995.

Bell, A. J. & Sejnowski, T. J., Learning the higher-order structure of a natural sound, Network: Computation in Neural Systems 7, 1996b.

Bellman R, Kalaba R (1959) A mathematical theory of adaptive control processes. Proc Natl Acad Sci USA 45:1288-1290.

Bello, Nicholas P. "Altering Cognitive and Brain States Through Cortical Entrainment." (2014); Costa-Faidella, Jordi, Elyse S. Sussman, and Carles Escera. "Selective entrainment of brain oscillations drives auditory percep-tual organization." NeuroImage (2017).

Bench C J, Frith C D, Grasby P M, Friston K J, Paulesu E, Frackowiak R S, Dolan R J, Investigations of the func-tional anatomy of attention using the Stroop test. Neuro-psychologia 31:907-22, 1993.

Bengio et al. "Out-of-Sample Extensions for LLE, Isomap, MDS, Eigenmaps, and Spectral Clustering" in Advances in Neural Information Processing Systems (2004)

Berker A O, Bikson M, Bestmann S. Predicting the behav-ioural impact of transcranial direct current stimulation: issues and limitations Frontiers of Human Neuroscience 2013; doi 10.3389/fnhum.2013.00613 Journal Link Berkman E, Wong D K, Guimaraes M P, Uy E T, Gross J J, et al. (2004) Brain wave recognition of emotions in EEG. Psychophysiology 41: S71-S71.

Bernard Balleine, Proceedings of the National Academy of Sciences, DOI: 10.1073/pnas. 1113158108.

Bi, G., Poo, M., 2001. Synaptic modification by correlated activity: Hebb's postulate revisited. Annual Review of Neuroscience 24, 139-166.

Bialek, W., Rieke, F., 1992. Reliability and information transmission in spiking neurons. Trends in Neurosciences 15, 428-434.

Bibbig A, Traub R D, Whittington M A (2002) Long-range synchronization of gamma and beta oscillations and the plasticity of excitatory and inhibitory synapses: A network model. J Neurophysiol 88:1634-1654.

Bienenstock, E. L., Cooper, L. N., Munro, P. W., 1982. Theory for the development of neuron selectivity: orien-tation specificity and binocular interaction in visual cor-tex. J. Neuroscience 2, 32-48.

Biever, Celeste, 'Mind-reading' software could record your dreams" By Celeste Biever. New Scientist, 12 Dec. 2008, www.newscientist.com/article/dn16267-mind-reading-software-could-record-your-dreams/

Bikson M, Aboseria M, Uchida R R, Cordeiro Q. Targeting negative symptoms in schizophrenia: results from a proof-of-concept trial assessing prefrontal anodic tDCS proto-col. Schizophr Res. 2015 August; 166 (1-3): 362-3. doi: 10.1016/j.schres.2015.05.029.

Bikson M, Baraban S C, Durand D M. Conditions sufficient for non-synaptic epileptogenesis in the CA1 region of rat hippocampal slices. Journal of Neurophysiology 2001; 87:62-71

Bikson M, Bestmann S, Edwards D. Transcranial Devices are not playthings. Nature 2013; correspondence 501: 7466

Bikson M, Brunoni A R, Charvet L E, Clark V P, Cohen L G, Deng Z, Dmochowski J, Edwards D J, Frohlich F, Kappenman E S, Lim K O, Loo C, Mantovani A, McMul-len D P, Parra L C, Pearson M, Richardson J D, Rumsey J M, Sehatpour P, Sommers D, Unal G, Wassermann E M, Woods A J, Lisanby S H. Rigor and reproducibility in research with transcranial electrical stimulation: An NIMH-sponsored workshop. Brain Stimul. 2017 Dec. 29. doi.org/10.1016/j.brs.2017.12.008 (Article in Press)

Bikson M, Bulow P, Stiller J W, Datta A, Battaglia F, Karnup S V, Postolache T T. Transcranial direct current stimulation for major depression: a general system for quantifying transcranial electrotherapy dosage. Current Treatment Options in Neurology. 2008; 10:377-85.

Bikson M, Datta A, Elwassif M, Bansal V, Peterchev A V. Introduction to Electrotherapy Technology. in Brain Stimulation in the Treatment of Pain. ed. Helena Knotkova, Ricardo Crucianim, and Joav Merrick. Nova Science, New York 2011 ISBN 978-1-60876-690-1

Bikson M, Datta A, Elwassif M. Bio-heat transfer model of transcranial D C stimulation: Comparison of conventional pad versus ring electrode IEEE EMBS. 2009

Bikson M, Datta A. Guidlines for precise and accurate models of tDCS. Brain Stimulation 2012; 5:430-4

Bikson M, Dmochowski J, Rahman A. The "Quasi-Uniform" Assumption in Animal and Computational Models of Non-Invasive Electrical Stimulation. Brain Stimulation Letter to the Editor 2013; 6:704-705

Bikson M, Edwards D), Kappenman E. The outlook for non-invasive brain stimulation. Brain Stimulation 2014, 7 (6): 771-2. doi: 10.1016/j.brs.2014.10.005 Journal Link Bikson M, Fox J E, Jefferys J G R. Neuronal aggregate formation underlies spatio-temporal dynamics of non-synaptic seizure initiation. Journal of Neurophysiology. 2003; 89:2330-2331

Bikson M, Ghai R, Baraban S C, Durand D M. Modulation of burst frequency, duration, and amplitude in the zero-Ca+2 model of epileptiform activity. Journal of Neurophysiology 1999; 82:2262-70

Bikson M, Grossman P, Zannou A L, Kronberg G, Truong D, Boggio P, Brunoni A R, Charvet L, Fregni F, Fritsch B, Gillick B, Hamilton R H, Hampstead B M, Kirton A, Knotkova H, Liebetanz D, Liu A, Loo C, Nitsche M A, Reis J, Richardson J D, Rotenberg A, Turkeltaub P E, Woods A J. Response to letter to the editor: Safety of transcranial direct current stimulation: Evidence based update 2016. Brain Stimul. 2017 September-October; 10 (5): 986-987. doi: doi.org/10.1016/j.brs.2017.06.007.

Bikson M, Hahn P J, Fox J E, Jefferys J G R. Depolarization block of neurons during maintenance of electrographic seizures. Journal of Neurophysiology. 2003; 90:2402-2408

Bikson M, Id Bihi R, Vreugdenhil M, Kohling R, Fox J E, Jefferys J G R. Quinine suppresses extracellular potassium transients and ictal epileptiform activity without decreasing neuronal excitability in vitro. Neuroscience 2002; 115:253-263

Bikson M, Inoue M, Akiyama H, Deans J K, Fox J E, Miyakawa H, Jefferys J G R. "Effects of uniform extracellular D C electric fields on excitability in rat hippocampal slices in vitro." The Journal of physiology 557, no. 1 (2004): 175-190.

Bikson M, Lian J, Hahn P J, Stacey W C, Sciortino C, Durand D M. Suppression of epileptiform activity by high frequency sinusoidal fields in rat hippocampal slices. Journal of Physiology 2001:531:181-191

Bikson M, Paneri B, Mourdoukoutas A, Esmaeilpour Z, Badran B W, Azzam R, Adair D, Datta A, Fang X H, Wingeiner B, Chao D, Alonso-Alonso M, Lee K, Knotkova H, Woods A J, Hagedorn D, Jeffery D), Giordane J, Tyler W J. Limited output transcranial electrical stimulation (LOTES-2017): Engineering principles, regulatory statutes and industry standards for wellness, over-the-counter, or prescription devices with low risk. Brain Stimul. 2017 Oct. 15. 11:134-157 doi: 10.1016/j.brs.2017.10.012

Bikson M, Rahman A, Datta A, Fregni F, Merabet L. High-Resolution Modeling Assisted Design of Customized and Individualized Transcranial Direct Current Stimulation Protocols. Neuromodulation: Technology at the Neural Interface. 2012; 15:306-315

Bikson M, Rahman A, Datta A. Computational Models of Transcranial Direct Current Stimulation. Clinical EEG and Neuroscience. 2012; 43 (3) 176-183

Bikson M, Reato D), Rahman A. Cellular effects of electric and magnetic fields: insights animal models and in slice. In Transcranial Brain Stimulation (Frontiers in Neuroscience) 2012 ed. Carolo Miniussi, Walter Paulus, Paolo M. Rossini. CRC Press. ISBN 978-1439875704 p 55-92

Bikson M, Ruiz-Nuño A, Miranda D, Kronberg G, Jiruska P, Fox J E, Jefferys J G R. Synaptic transmission modulates while non-synaptic processes govern the transition from pre-ictal to seizure activity in vitro. bioRxiv 280321. 2018 Mar. 11 doi: doi.org/10.1101/280321

Bikson M, Truong D Q, Mourdoukoutas A P, Aboseria M, Khadka N, Adair D, Rahman A. Modeling sequence and quasi-uniform assumption in computational neurostimulation. Prog Brain Res. 2015; 222:1-23 doi: 10.1016/bs.pbr.2015.08.005

Bikson M, Unal G, Brunoni A, Loo C. Special Reports: What psychiatrists need to know about Transcranial Direct Current Stimulation. Psychiatric Times. 2017 Oct. 24. Online Link Bikson M, Paneri B, Giordano J. The off-label use, utility and potential value of tDCS in the clinical care of particular neuropsychiatric conditions. Journal of Law and the Biosciences. 2016 September; 1-5 doi: 10.1093/jlb/lsw044

Bikson M. . . . Woods A et al. Safety of Transcranial Direct Current Stimulation: Evidence Based Update. Brain Stimul. 2016 September-October; 9 (5): 641-61. doi: 10.1016/j.brs.2016.06.004.

Bindman, L. J., Lippold, O. C., Milne, A. R., 1979. Prolonged changes in excitability of pyramidal tract neurones in the cat: a post-synaptic mechanism. J. Physiology 286, 457-477.

Bindman, L. J., Lippold, O. C., Redfearn, J. W., 1962. Long-lasting changes in the level of the electrical activity of the cerebral cortex produced by polarizing currents. Nature 196, 584-585.

Bindman, L. J., Lippold, O. C., Redfearn, J. W., 1964. The action of brief polarizing currents on the cerebral cortex of the rat (1) during current flow and (2) in the production of long-lasting after-effects. J. Physiology 172, 369-382.

Boateng Jr. A, Paneri B, Dufau A, Borges H, Bikson M. Conference proceedings: The effect of cooling electrodes on tDCS tolerability. Brain Stimul. July-August 2017; 10 (4): e82-e83. doi: doi.org/10.1016/j.brs.2017.04.119.

Borchardt J J, Bikson M, Frohman H, Reeves S T, Datta A, Bansal V, Madan A, Barth K, George M S. A Pilot Study of the Tolerability and Effects of High-Definition Transcranial Direct Current Stimulation (HD)-(DCS) on Pain Perception. Journal of Pain. 2012; 13 (2): 112-120

Borgers, Christoph. "Entrainment by Excitatory Input Pulses." An Introduction to Modeling Neuronal Dynamics. Springer International Publishing, 2017. 183-192.

Botvinick M M (2012) Hierarchical reinforcement learning and decision making. Current Opinion in Neurobiology 22 (6): 956-962.

Botvinick M M, Braver T S, Barch D M, Carter C S, & Cohen J D (2001) Conflict monitoring and cognitive control. Psychological Review 108 (3): 624-652.

Boynton G M, Engel S A, Glover G H, Heeger D J, Linear systems analysis of functional magnetic resonance imaging in human V1. J Neurosci 16:4207-21, 1996.

Brainworks, "QEEG Brain Mapping", www.brainworksneurotherapy.com/qeeg-brain-mapping Braitenberg V and Schuz A (1991) Anatomy of the Cortex. Statistics and Geometry. New York: Springer-Verlag.

Brazier M A, Casby J U (1952) Cross-correlation and autocorrelation studies of electroencephalographic potentials. Electroen clin neuro 4:201-211.

Brian J. Roach and Daniel H. Mathalon, "Event-related EEG time-frequency analysis: an overview of measures and analysis of early gamma band phase locking in schizophrenia. Schizophrenia Bull. USA. 2008; 34:5:907-926.

Brignani, D., Ruzzoli, M., Mauri, P., Miniussi, C., 2013. Is transcranial alternating current stimulation effective in modulating brain oscillations? PLOS ONE 8, e56589. Buzsaki, G., 2006. Rhythms of the Brain. Oxford University Press, Oxford.

Bringer, Julien, Hervé Chabanne, and Bruno Kindarji. "Error-tolerant searchable encryption." In Communications, 2009. ICC'09. IEEE International Conference on, pp. 1-6. IEEE, 2009.

Brunoni A R, Nitsche M A, Bolognini N, Bikson M et al. Clinical research with transcranial direct current stimulation (tDCS): Challenges and Future Directions. Brain Stimulation 2012; 5 (3): 175-95

Brunoni A R, Shiozawa P, Truong D, Javitt D C, Elkis, H, Fregni F, Bikson M. Understanding tDCS effects in schizophrenia: a systematic review of clinical data and an integrated computation modeling analysis. Expert Reviews of Medical Devices 2014; epub Bruoni A R. Bikson M et al. The Escitalopram versus Electric Current Therapy to treat Depression Clinical Study (ELECT-TDCS): rationale and study design of a non-inferiority, triple-arm, placebo-controlled clinical trial. São Paulo Med J. 2015 May-June; 133 (3): 252-63. doi: 10.1590/1516-3180.2014.00351712.

Bryck R L & Fisher P A (2012) Training the brain: practical applications of neural plasticity from the intersection of cognitive neuroscience, developmental psychology, and prevention science. American Psychologist 67:87-100.

Buck R (1999) The biological affects: A typology. Psychological Review 106:301-336; Izard C E (2007) Basic Emotions, Natural Kinds, Emotion Schemas, and a New Paradigm. Perspect Psychol Sci 2:260-280;

Buckner, R. L., Bandettini, P. A., O'Craven, K M, Savoy, R. L., Petersen, S. E., Raichle, M. E. & Rosen, B. R., Proc Natl Acad Sci USA 93, 14878-83, 1996.

Calderone, Daniel J., et al. "Entrainment of neural oscillations as a modifiable substrate of attention." Trends in cognitive sciences 18.6 (2014): 300-309;

Cancelli A, Cottone C, Parazzini M, Fiocchi S, Truong D Q, Bikson M, Tecchio D. Transcranial Direct Current Stimulation: Personalizing the Neuromodulation. Conf Proc IEEE Eng Med Biol Soc. 2015; 234-7. doi: 10.1109/EMBC.2015.7318343.

Cancelli A, Cottone C, Tecchio F, Truong D, Dmochowski J, Bikson M. A simple method for EEG guided transcranial Electrical Stimulation without models. J Neural Eng. 2016 June; 13 (3): 036022. doi: 10.1088/1741-2560/13/3/036022.

Cancelli, A., C. Cottone, F. Tecchio, D. Truong, J. Dmochowski, D. Adair, M. Bikson. P094 Method for EEG guided transcranial Electrical Stimulation without models. Clinical Neurophysiology 2017 March; 128 (3): e54-e56. doi: 10.1016/j.clinph.2016.10.219.

Cano T, Morales-Quezada J L, Bikson M, Fregni F. Methods to focalize noninvasive electrical brain stimulation: principles and future clinical development for the treatment of pain. Expert Reviews Neurotherapy 2013; 13 (5): 465-7 Proof Canolty R T, Edwards E, Dalal S S, et al. High gamma power is phase-locked to theta oscillations in human neocortex. Science. 2006; 313:1626-1628.

Canolty, R. T., Knight, R. T., 2010. The functional role of cross-frequency coupling. Trends in Cognitive Sciences 14, 506-515.

Cantero J L, Atienza M, Salas R M, Gomez C M (1999) Alpha EEG coherence in different brain states: an electrophysiological index of the arousal level in human subjects. Neurosci lett 271:167-70.

Caparelli-Daquer E, Zimmermann T J, Mooshagian E, Parra L, Rice J, Datta A, Bikson M, Wassermann E A. Pilot Study on Effects of 4×1 High-Definition tDCS on Motor Cortex Excitability. Conf Proc IEEE Eng Med Biol Soc. 2012; 735-8. doi: 10.1109/EMBC.2012.6346036.

Cappiello M, Xie W, David A, Bikson M. Zhang W. Transcranial Direct Current Stimulation Modulates Pattern Separation. NeuroReport. 2016 Aug. 3; 27 (11): 826-32. doi: 10.1097/WNR.0000000000000621.

Carandini, M., Ferster, D., 1997. A tonic hyperpolarization underlying contrast adaptation in cat visual cortex. Science 276, 949-952.

Cardoso, J-F. & Laheld, B., Equivalent Equivariant adaptive source separation, IEEE Trans. Signal Proc., 44 (12), 3017-3030 (1996) in press.

Carmon, A., Mor, J., & Goldberg, J. (1976). Evoked cerebral responses to noxious thermal stimuli in humans. Experimental Brain Research, 25 (1), 103-107.

Carter, J., and H. Russell. "A pilot investigation of auditory and visual entrainment of brain wave activity in learning disabled boys." Texas Researcher 4.1 (1993): 65-75;

Casciaro, Francesco, et al. "Alpha-rhythm stimulation using brain entrainment enhances heart rate variability in subjects with reduced HRV." World J. Neuroscience 3.04 (2013): 213;

Castillo-Saavedra L, Gebodh N, Bikson M, Diaz-Cruz C, Brandao R, Coutinho L, Truong D, Datta A, Shani-Hershkovich R, Weiss M, Laufer I, Reches A, Peremen Z, Geva A, Parra L C, Fregni F. Clinically Effective Treatment of Fibromyalgia Pain With High-Definition Transcranial Direct Current Stimulation: Phase II Open-Label Dose Optimization. J Pain. 2016 January; 17 (1): 14-26. doi: 10.1016/j.jpain.2015.09.009.

Cattaneo, L., Sandrini, M., Schwarzbach, J., 2010. State-dependent TMS reveals a hierarchical representation of observed acts in the temporal, parietal, and premotor cortices. Cerebral Cortex 20, 2252-2258.

Cattaneo, Z., Rota, F., Vecchi, T., Silvanto, J., 2008. Using state-dependency of trans-cranial magnetic stimulation (TMS) to investigate letter selectivity in the left posterior parietal cortex: a comparison of TMS-priming and TMS-adaptation paradigms. Eur. J. Neuroscience 28, 1924-1929.

Cavanagh J F, Cohen M X, & Allen J J (2009) Prelude to and resolution of an error: EEG phase synchrony reveals cognitive control dynamics during action monitoring. Journal of Neuroscience 29 (1): 98-105.

Cavanagh J F, Frank M J (2014) Frontal theta as a mechanism for cognitive control. Trends Cogn Sci 18:414-421.

cbcg.org/gjcs1.htm%7C God's Judgment Cometh Soon

Chakraborty D, Truong D Q, Bikson M, Kaphzan H. Neuromodulation of axon terminals. Cereb Cortex.

2017 Jun. 24; 1-9. doi: 10.1093/cercor/bhx158.

Chambers, C. D., Payne, J. M., Stokes, M. G., Mattingley, J. B., 2004. Fast and slow parietal pathways mediate spatial attention. Nature Neuroscience 7, 217-218.

Chanel G, Kronegg J, Grandjean D, Pun T (2006) Emotion assessment: Arousal evaluation using EEG's and peripheral physiological signals. Multimedia Content Representation, Classification and Security 4105:530-537.

Chang, Daniel Wonchul. "Method and system for brain entertainment." U.S. Pat. No. 8,636,640. 28 Jan. 2014;

Chapman R M, Mccrary J W. EP component identification and measurement by principal components analysis. Brain and cognition 1995; 27:288-310.

Chapman, R. M. & McCrary, J. W., EP component identification and measurement by principal components analysis. Brain Lang. 27, 288-301, 1995.

Charvet L, Kasschau M, Datta A, Knotkova H, Stevens M C, Alonzo A, Loo C, Krull K R, Bikson M. Remotely-Supervised Transcranial Direct Current Stimulation (tDCS) for Clinical Trials: Guidelines for Technology and Protocols. Front Syst Neurosci. 2015 Mar. 17; 9:26. doi: 10.3389/fnsys.2015.00026. Free Online Charvet L, Shaw M, Dobbs B, Frontario A, Sherman K, Bikson M, Datta A, Krupp L, Zeinapour E, Kasschau M. Remotely-Supervised Transcranial Direct Current Stimulation (RS-tDCS) Increases the Benefit of At-Home Cognitive Training in Multiple Sclerosis. Neuromodulation: Technology at the Neural Interface. Neuromodulation. 2017 Feb. 22. doi: 10.1111/ner.12583

Charvet L E, Dobbs B, Shaw M T, Bikson M, Datta A, Krupp L B. Remotely supervised transcranial direct current stimulation for the treatment of fatigue in multiple sclerosis: Results from a randomized, sham-controlled trial. Mult. Scler. J. 2017 Sep. 22; 00 (0)): 1-10. doi: doi.org/10.1177/1352458517732842.

Chen C, Bikson M, Chou L, Shan C, Khadka N, Chen W, Fregn F. Higher-order power harmonics of pulsed electrical stimulation modulates corticospinal contribution of peripheral nerve stimulation. Sci Rep. 2017 Mar. 3; 7:43619. doi: 10.1038/srep43619.

Chhatbar P Y, Kautz S A, Takacs I, Rowland N C, Revuelta G J, George M S, Bikson M, Feng W. Evidence of transcranial direct current stimulation-generated electric fields at subthalamic level in human brain in vivo. Brain Stimul. 2018, doi: 10.1016/j.brs.2018.03.006

Christian Walder and Bernhard Schölkopf, Diffeomorphic Dimensionality Reduction, Advances in Neural Information Processing Systems 22, 2009, pp. 1713-1720, MIT Press Christie G J, Tata M S (2009) Right frontal cortex generates reward-related theta-band oscillatory activity. Neuroimage 48:415-422.

Chrysikou E G, Berryhill M, Bikson M and Coslett H B. Editorial: Revisiting the Effectiveness of Transcranial Direct Current Brain Stimulation for Cognition: Evidence, Challenges, and Open Questions. Front. Hum. Neurosci. 2017 August doi: 10.3389/fnhum.2017.00448. Online Link (article in production)

Chrysikou E G, Berryhill M E, Bikson M, Coslett H B. Editorial: Revisiting the Effectiveness of Transcranial Direct Current Brain Stimulation for Cognition: Evidence, Challenges, and Open Questions. Front Hum Neurosci. 2017 Sep. 8; 11:448. doi: 10.3389/fnhum.2017.00448.

Chrysikou E G, Hamilton R H, Coslett H B, Datta A, Bikson N, Thompson-Schill S L. Non-invasive transcranial direct current stimulation over the left prefrontal cortex facilitates cognitive flexibility in tool use. Cognitive Neuroscience 2013; 4 (2) 81-89

Cichocki A., Unbehauen R., & Rummert E., Robust learning algorithm for blind separation of signals, Electronics Letters 30, 1386-1387, 1994.

cnslab.ss.uci.edu/muri/research.html, #Dewan, #Farwell-Donchin, #ImaginedSpeechProduction, #Overview, MURI: Synthetic Telepathy Coghlan, Andy, "Our brains record and remember things in exactly the same way"

Cohen M X, Wilmes K, Vijver Iv (2011) Cortical electrophysiological network dynamics of feedback learning. Trends Cogn Sci 15:558-566.

Colzato, L. S., Barone, H., Sellaro, R., & Hommel, B. (2017). More attentional focusing through binaural beats: evidence from the global-local task. Psychological research, 81 (1), 271-277;

Colzato, Lorenza S., Amengual, Julià L., et al. "Local entrainment of oscillatory activity induced by direct brain stimulation in humans." Scientific Reports 7 (2017);

Combes J M, Grossmann A, Tchamitchian P. Wavelets: Time-Frequency Methods and Phase Space-Proceedings of the International Conference; Dec. 14-18, 1987; Marseille, France Comon P, Independent component analysis, A new concept? Signal Processing 36:11-20, 1994.

Conte, Elio, et al. "A Fast Fourier Transform analysis of time series data of heart rate variability during alfa-rhythm stimulation in brain entrainment." NeuroQuantology 11.3 (2013);

Corazzol, Martina et al., "Restoring consciousness with vagus nerve stimulation", Current Biology, Volume 27, Issue 18, R994-R996

Corbett A, et al. (2015) The effect of an online cognitive training package in healthy older adults: An online randomized controlled trial. J Am Med Dir Assoc 16:990-997.

Corthout, E., Uttl, B., Walsh, V., Hallett, M., Cowey, A., 1999. Timing of activity in early visual cortex as revealed by transcranial magnetic stimulation. Neuroreport 10, 2631-2634.

Costa T, Rognoni E, Galati D (2006) EEG phase synchronization during emotional response to positive and negative film stimuli. Neurosci Lett 406:159-164.

Cover, T. M. & Thomas, J. A., Elements of Information Theory John Wiley, 1991.

Cox, R. W. & Hyde J. S. Software tools for analysis and visualization of fMRI data, NMR in Biomedicine, in press.

Cox, R. W., AFNI: software for analysis and visualization of functional magnetic resonance neuroimages. Comput Biomed Res 29:162-73, 1996.

Creutzfeldt, O. D., Fromm, G. H., Kapp, H., 1962. Influence of transcortical d-c currents on cortical neuronal activity. Experimental Neurology 5, 436-452.

D. Donoho and C. Grimes, "Hessian eigenmaps: Locally linear embedding techniques for high-dimensional data" Proc Natl Acad Sci USA. 2003 May 13; 100 (10): 5591-5596

D'Ambra L., Lauro N. C. (1982) Analisi in componenti principali in rapporto ad un sottospazio di riferimento, Rivista di Statistica Applicata, n.1, vol. 15.

D'Ambra L., Sabatier R., Amenta P. (1998) Analisi fattoriale delle matrici a tre vie: sintesi e nuovi approcci, (invited lecture) Atti XXXIX Riunione SIS.

Dale A M & Sereno M I (1993) Improved localization of cortical activity by combining EEG and MEG with MRI cortical surface reconstruction: A linear approach. Journal of Cognitive Neuroscience 5:162-176.

Dale, A. M. & Sereno, M. I., Improved localization of cortical activity by combining EEG and MEG with MRI cortical surface reconstruction—a linear approach. J. Cogn. Neurosci. 5:162-176, 1993.

Dalley J W, Robbins T W (2017) Fractionating impulsivity: Neuropsychiatric implications. Nat Rev Neurosci 18:158-171.

Dan N, Xiao-Wei W, Li-Chen S, Bao-Liang L. EEG-based emotion recognition during watching movies; 2011 Apr. 27, 2011-May 1, 2011:667-670.

daprocess.com/01.welcome.html DaProcess of A Federal Investigation

Dasilva A F, Mendonca M E, Zaghi S, Lopes M, Dossantos M F, Spierings E L, Bajwa Z, Datta A, Bikson M, Fregni F. tDCS-Induced Analgesia and Electrical Fields in Pain-Related Neural Networks in Chronic Migraine. Headache. 2012; 52 (8) 1283-95

DaSilva A F, Truong D Q, DosSantos M F, Toback R L, Datta A, Bikson M. State-of-art neuroanatomical target analysis of high-definition and conventional tDCS montages used for migraine and pain control. Front Neuroanat. 2015 Jul. 15; 9:89. doi: 10.3389/fnana.2015.00089. Free Online Dasilva A F, Volz M S, Bikson M, Fregni F. Electrode positioning and montage in transcranial direct current stimulation. JOVE. 2011; (51) video Datta A, Baker J, Bikson M, Fridriksson F. Individualized model predicts brain current flow during transcranial direct-current stimulation treatment in responsive stroke patient. Brain Stimulation2011; 4:169-74 Pub Med HTML Datta A, Bansal V, Diaz J, Patel J, Reato D, Bikson M. Gyri-precise head model of transcranial D C stimulation: Improved spatial focality using a ring electrode versus conventional rectangular pad. Brain Stimulation. 2009; 2 (4): 201-207.

Datta A, Bikson M, Fregni F. Transcranial direct current stimulation in patients with skull defects and skull plates: High-resolution computational FEM study of factors altering cortical current flow. Neuroimage. 2010; 52 (4): 1268-78

Datta A, Dmochowski J, Guleyupoglu B, Bikson N, Fregni F. Cranial Electrotherapy Stimulation and transcranial Pulsed Current Stimulation: A computer based high-resolution modeling studyNeuroimage 2012; 65:280-287.

Datta A, Elwassif M, Battaglia F, Bikson M. Transcranial current stimulation focality using disc and ring electrode configurations: FEM analysis. Journal of Neural Engineering. 2008; 5:163-174.

Datta A, Elwassif M. Bikson M. Establishing safety limits for transcranial direct current stimulationClinical Neurophysiology. 2009; 120:1033-1034

Datta A, Rahman A, Scaturro J, Bikson M. Electrode montages for tDCS and weak transcranial electrical stimulation Role of "return" electrode's position and size. Clinical Neurophysiology. 2010; 121:1976-1978

Datta A, Troung D, Minhas P, Parra L C, Bikson M. Inter-individual variation during transcranial Direct Current Stimulation and normalization of dose using MRI-derived computational models. Frontiers in Neuropsychiatric Imaging and Stimulation. 2012; 3:91. doi: 10.3389/fpsyt.2012.00091 Open Access Datta A, Zhou X, Su Y, Parra L C, Bikson M. Validation of finite element model of transcranial electrical stimulation using scalp potentials: implications for clinical dose. J Neural Engineering2013; 10 (3): 036018. doi: 10.1088/1741-2560/10/3/036018

Daubechies I. Ten Lectures on Wavelets. Philadelphia, Pa: Society for Industrial and Applied Mathematics; 1992: 357. 21.

Davidson R J (1993) Cerebral Asymmetry and Emotion-Conceptual and Methodological Conundrums. Cognition Emotion 7:115-138.

De Paolis A, Bikson M, Nelson J T, de Ru J A, Packer M, Cardoso L. Analytical and numerical modeling of the hearing system: advances towards the assessment of hearing damage. Hear Res. 2017 June; 349:111-128. doi: 10.1016/j.heares.2017.01.015.

De Paolis A, Watanabe H, Nelson J T, Bikson M, Packer M, Cardoso L. Human Cochlear Hydrodynamics: A High-Resolution μCT Images-Based Finite Element Study. J Biomech. 2017 Jan. 4; 50:209-216. doi: 10.1016/j.jbiomech.2016.11.020.

Deans, J. K., Powell, A. D., Jefferys, J. G., 2007. Sensitivity of coherent oscillations in rat hippocampus to A C electric fields. J. Physiology 583, 555-565.

Deeny S P, Hillman C H, Janelle C M, Hatfield B I) (2003) Cortico-cortical communication and superior performance in skilled marksmen: An EEG coherence analysis. J Sport Exercise Psy 25:188-204.)

deepthought.newsvine.com/_news/2012/01/01/9865851-nsa-disinformation-watch-the-watchers-with-me deepthought.newsvine.com/_news/2012/01/09/10074589-nsa-disinformation-watch-the-watchers-with-me-part-2 deepthought.newsvine.com/_news/2012/01/16/10169491-the-nsa-behind-the-curtain

Delorme A & Makeig S (2004) EEGLAB: An open source toolbox for analysis of singel-trial EEG dynamics including independent component analysis. Journal of Neuroscience Methods 134 (1): 9-21.

Demartines, P., and J. Herault, Curvilinear Component Analysis: A Self-Organizing Neural Network for Nonlinear Mapping of Data Sets, IEEE Transactions on Neural Networks, Vol. 8 (1), 1997, pp. 148-154

Dewan, E. M., "Occipital Alpha Rhythm Eye Position and Lens Accommodation." Nature 214, 975-977 (0) 3 Jun. 1967)

Dhawan, V. I. J. A. Y., A. Poltorak, J. R. Moeller, J. O. Jarden, S. C. Strother, H. Thaler, and D. A. Rottenberg. "Positron emission tomographic measurement of blood-to-brain and blood-to-tumour transport of 82Rb. I: Error analysis and computer simulations." Physics in medicine and biology 34, no. 12 (1989): 1773.

Diamond A & Lee K (2011) Interventions and programs demonstrated to aid executive function development in children 4-12 years of age. Science 333:959964.

Dias D R, Trevizol A P, Miorin L A, Bikson M, Aboseria M, Shiozawa P, Cordeiro Q. Effect of Transcranial Direct Current Stimulation Protocol for Treating Depression Among Hemodialysis Patients: A Proof-of-Concept Trial. JECT. 2016 June; 32 (2): e3-4. doi: 10.1097/YCT.0000000000000273. Online Link Dien J, Frishkoff G A, Cerbone A, Tucker D M. Parametric analysis of event-related potentials in semantic comprehension: evidence for parallel brain mechanisms. Brain research 2003; 15:137-153.

Dien J, Frishkoff G A. Principal components analysis of event-related potential datasets. In: Handy T (ed). Event-Related Potentials: A Methods Handbook. Cambridge, Mass MIT Press; 2004.

93

Diffusion Maps and Geometric Harmonics, Stephane Lafon, PhD) Thesis, Yale University, May 2004 Diffusion Maps, Ronald R. Coifman and Stephane Lafon, Science, 19 Jun. 2006

Dikker, Suzanne, et al. "Brain-to-brain synchrony tracks real-world dynamic group interactions in the classroom." Current Biology 27.9 (2017): 1375-1380.

Ding, M., G. Fan, Multilayer Joint Gait-Pose Manifolds for Human Gait Motion Modeling, IEEE Transactions on Cybernetics, Volume: 45, Issue: 11, November 2015.

Ding, Nai, and Jonathan 7 . . . . Simon. "Cortical entrainment to continuous speech: functional roles and interpretations." Frontiers in human neuroscience 8 (2014);

Dmochowski J, Bikson M, Datta A, Richardson J, Fridriksson J, Parra L. On the Role of Electric Field Orientation in Optimal Design of Transcranial Electrical Stimulation Conf Proc IEEE Eng Med Biol Soc. 2012; 6426-9. doi: 10.1109/EMBC.2012.6347465.

Dmochowski J, Datta A, Huang Y, Richardson J C, Bikson M, Fridriksson J, Parra K C. Targeted Transcranial Direct Current Stimulation for Rehabilitation after Stroke. J Neuroimage 2013; 75:12-19

Dmochowski J P, Bikson M, Parra L C. The point spread function of the human head and its implications for transcranial current stimulation. Phys Med Biol. 2012; 57 (20) 6459-77

Dmochowski J P, Bikson M. Noninvasive Neuromodulation Goes Deep. Cell 169, Jun. 1, 2017, Elsevier Inc. doi: dx.doi.org/10.1016/j.cell.2017.05.017.

Dmochowski J P, Datta A, Bikson M, Su Y, Parra L C. Optimized multi-electrode stimulation increases focality and intensity at target. Journal of Neural Engineering. 2011; 8 (4)

Dmochowski J P, Koessler L, Norcia A M, Bikson M, Parra L C. Optimal use of EEG recordings to target active brain areas with transcranial electrical stimulation. Neuroimage. 2017 May 31:157:69-80. doi: 10.1016/j.neuroimage.2017.05.059.

Dobbs B, Shaw M, Frontario A, Sherman K, Bikson M, Datta A, Kasschau M, Charvet L. Conference proceedings: Remotely-Supervised Transcranial Direct Current Stimulation (RS-tDCS) Improves Fatigue in Multiple Sclerosis. Brain Stimul. July-August 2017; 10 (4): e57-e58. doi: doi.org/10.1016/j.brs.2017.04.103.

Dockery, C. A., Hueckel-Weng, R., Birbaumer, N., Plewnia, C., 2009. Enhancement of planning ability by transcranial direct current stimulation. J. Neuroscience 29, 7271-7277.

Doherty, Cormac. "A comparison of alpha brainwave entrainment, with and without musical accompaniment." (2014);

Donnell A, Nascimento T, Lawrence M, Gupta V, Zieba T, Truong D Q, Bikson M, Datta A, Bellile E, DaSilva A F. High-Definition and Non-Invasive Brain Modulation of Pain and Motor Dysfunction in Chronic TMD. Brain Stimul. 2015 November-December; 8 (6): 1085-92. doi: 10.1016/j.brs.2015.06.008.

dos Santos M D, Cavenaghi V B, Mac-Kay APMG, Serafim V, Venturi A, Truong D Q, Huang Y, Boggio P S, Fregni F, Simis M, Bikson M, Gagliardi R J. Non-invasive brain stimulation and computational models in post-stroke aphasic patients: single session of transcranial magnetic stimulation and transcranial direct current stimulation. A randomized clinical trial. Sao Paulo Med J. 2017 Nov. 6. doi: 10.1590/1516-3180.2016.0194060617

DosSantos M F, Martikainen L K, Nascimento T D, Love T M, DeBoer M D, Schambra H M, Bikson M, Zubieta J, DaSilva A F. Building up Analgesia in Humans via the Endogenous μ-Opioid System by Combining Placebo and Active DCS: A Preliminary Report. PLOS ONE 2014; 9(7) e 102350 DOI: 10.1371/journal.pone.0102350 Free Online Drummond, Katie, Soldier-Telepathy", Pentagon Preps Soldier Telepathy Push, www.wired.com/2009/05/pentagon-preps-soldier-telepathy-push/

Durand D M, Bikson M. Control of neuronal activity by electric fields: in-vitro models of epilepsy. In. Deep Brain Stimulation and Epilepsy. 2003; Hans Luders ed. Martin Dunitz Ltd. ISBN 978-1841842592

Durand D M, Bikson M. Suppression and control of epileptiform activity by electrical stimulation: a review. Proceedings of the IEEE 2001; 89:1065-1082 earthpulse.net/tpcs-transcranial-pulsed-current-stimulation/; help.foc.us/article/16-tpcs-transcranial-pulsed-current-stimulation.

Ebersole J S (1997) Defining epileptogenic foci: past, present, future. J. Clin. Neurophysiology 14:470-483.

Edelman G M and Tononi G (2000) A Universe of Consciousness, New York: Basic Books.

Edemann-Callesen H, Habelt B, Wieske F, Jackson M, Khadka N, Mattei D, Bernhardt N, Heinz A, Liebetanz D, Bikson M, Padberg F, Hadar R, Nitsche M A, Winter C. Non-invasive modulation reduces repetitive behavior in a rat model through the sensorimotor cortico-striatal circuit. Trans Psy. 2018. doi: 10.1038/s41398-017-0059-5.

Edwards D, Cortes M, Datta A, Minhas P, Wassermann E M, Bikson M. Physiological and modeling evidence for focal transcranial electrical brain stimulation in humans: a basis for high-definition tDCS NeuroImage 2013; 74:266-275

Edwards D, Cortes M, Wortman-Jutt S, Putrino D, Bikson M, Thickbroom G, Pascual-Leone A. Transcranial Direct Current Stimulation and Sports Performance. Front Hum Neurosci. 2017 May 10; 11:243. doi: 10.3389/fnhum.2017.00243. Free online Effects of uniform extracellular D C electric fields on excitability in rat hippocampal Ella T. Mampusti, Jose S. Ng, Jarren James I. Quinto, Grizelda L. Teng, Merlin Teodosia C. Suarez, Rhia S. Trogo, "Measuring Academic Affective States of Students via Brainwave Signals", Knowledge and Systems Engineering (KSE) 2011 Third International Conference on, pp. 226-231, 2011

Elwassif M M, Datta A, Rahman A, Bikson M. Temperature control at DBS electrodes using a heat sink: experimentally validated FEM model of DBS lead architecture. Journal of Neural Engineering. 2012; 8 (4)

Elwassif M M, Kong Q, Vazquez M, Bikson M. Bio-heat transfer model of deep brain stimulation-induced temperature changes. Journal of Neural Engineering. 2006; 3:306-15.

en.wikipedia.org/wiki/Beat_(acoustics)#Binaural_beats.
en.wikipedia.org/wiki/Brainwave_entrainment;
en.wikipedia.org/wiki/Cluster_analysis.
en.wikipedia.org/wiki/Cochlear_implant;
en.wikipedia.org/wiki/Cranial_electrotherapy_stimulation.
en.wikipedia.org/wiki/Deep_brain_stimulation.
en.wikipedia.org/wiki/Electrical_brain_stimulation.
en.wikipedia.org/wiki/Electroencephalography.
en.wikipedia.org/wiki/Nonlinear_dimensionality_reduction.
en.wikipedia.org/wiki/Principal_component_analysis.
en.wikipedia.org/wiki/Pulsed_electromagnetic_field_therapy.
en.wikipedia.org/wiki/Transcranial_alternating_current_stimulation.

en.wikipedia.org/wiki/Transcranial_direct-current_stimulation.

en.wikipedia.org/wiki/Transcranial_magnetic_stimulation.

en.wikipedia.org/wiki/Transcranial_pulsed_ultrasound.

en.wikipedia.org/wiki/Transcranial_random_noise_stimulation.

en.wikipedia.org/wiki/Vagus_nerve_stimulation.

Engel A K, Fries P, Singer W (2001) Dynamic predictions: Oscillations and synchrony in top-down processing. Nat Rev Neurosci 2:704-716.

Epstein, C. M., Rothwell, J. C., 2003. Therapeutic uses of rTMS. Cambridge University Press, Cambridge, pp. 246-263.

Ermentrout, G. B., Galan, R. F., Urban, N. N., 2008. Reliability, synchrony and noise. Trends in Neurosciences 31, 428-434.

Esmaeilpour Z, Marangolo P, Hampstead B M, Bestmann S, Galletta E, Knotkova H, Bikson M. Incomplete evidence that increasing current intensity of tDCS boosts outcomes. Brain Stimul. March-April 2017; 11 (2): 310-321 doi: 10.1016/j.brs.2017.12.002

Esmaeilpour Z, Milosevic M, Azevedo K, Khadka N, Navarro J, Brunoni A, Popovic M R, Bikson M, Fonoff E T. Conference proceedings: Intracranial Voltage Recording During Transcranial Direct Current Stimulation (tDCS) in Human Subjects With Validation of a Standard Model. Brain Stimul. July-August 2017; 10 (4): e72-e75. doi: doi.org/10.1016/j.brs.2017.04.114.

Esmaeilpour Z, Schestatsky P, Bikson M, Brunoni A R, Pellegrinelli A, Piovesan F X, Santos M M, Menezes R B, Fregni F. Notes on Human Trials of Transcranial Direct Current Stimulation between 1960 and 1998. Front Hum Neurosci. 2017 Feb. 23; 11:71. doi: 10.3389/fnhum.2017.00071. Free online Experimental Brain Research, vol 213, p 9

Ezquerro F, Moffa A H, Bikson M, Khadka N, Aparicio L V, Sampaio-Junior B, Fregni F, Bensenor I M, Lotufo P A, Pereira A C, Brunoni A R. The Influence of Skin Redness on Blinding in Transcranial Direct Current Stimulation Studies: A Crossover Trial. Neuromodulation. 2017 April; 20 (3): 248-255. doi: 10.1111/ner.12527.

Fairclough S H & Houston K (2004) A metabolic measure of mental effort. Biological Psychology 66:177-190.

Faisal, A. A., Selen, L. P., Wolpert, D. M., 2008. Noise in the nervous system. Nature Reviews Neuroscience 9, 292-303.

Falk, Simone, Cosima Lanzilotti, and Daniele Schön. "Tuning neural phase entrainment to speech." J. Cognitive Neuroscience (2017);

Farwell, L. A., & Donchin, E. (1988). Talking off the top of your head: toward a mental prosthesis utilizing event-related brain potentials. Electroencephalography and Clinical Neurophysiology, 70 (6), 510-523

Fausti, Daniele, et al. "Light-induced superconductivity in a stripe-ordered cuprate." Science 331.6014 (2011): 189-191;

Fell J, Axmacher N (2011) The role of phase synchronization in memory processes. Nat Rev Neurosci 12:105-118.

Ferbert, A., Caramia, D., Priori, A., Bertolasi, L., Rothwell, J. C., 1992. Cortical projection to erector spinae muscles in man as assessed by focal transcranial magnetic stimulation. Electroencephalography and Clin. Neurophysiology 85, 382-387.

Fertonani, A., Pirulli, C., Miniussi, C., 2011. Random noise stimulation improves neuroplasticity in perceptual learning. J. Neuroscience 31, 15416-15423. Feurra, M., Galli, G., Rossi, S., 2012. Transcranial alternating current stimulation affects decision making. Frontiers in Systems Neuroscience 6, 39.

Fitzgerald K D, et al. (2005) Error-related hyperactivity of the anterior cingulate cortex in obsessive-compulsive disorder. Biol Psychiatry 57:287-294.

Foerster B R, Nascimento T, DeBoer M, Bender M, Rice I, Truong D, Bikson M, Clauw D, Zubieta J, Harris R, DaSilva A. Excitatory and Inhibitory Brain Metabolites as Targets and Predictors of Effective Motor Cortex tDCS Therapy in Fibromyalgia. Arthritis Rheumatol. 2015 February; 67 (2): 576-81. doi: 10.1002/art.38945.

Foster, D. S. (1990). EEG and subjective correlates of alpha frequency binaural beats stimulation combined with alpha biofeedback (Doctoral dissertation, Memphis State University);

Foti D, Weinberg A, Dien J, Hajcak G (2011) Event-related potential activity in the basal ganglia differentiates rewards from nonrewards: Temporospatial principal components analysis and source localization of the feedback negativity. Hum Brain Mapp 32:2207-2216.

Fox J E, Bikson M, Jefferys J G. The effect of neuronal population size on the development of epileptiform discharges in the low calcium model of epilepsy. Neuroscience Letters. 2007; 411:158-61.

Fox J E, Bikson M, Jefferys J G R. Tissue resistance changes and the profile of synchronized neuronal activity during ictal events in the low calcium model of epilepsy. Journal of Neurophysiology. 2004; 92:181-188

Franaszczuk P J, Bergey G K (1999) An autoregressive method for the measurement of synchronization of inter-ictal and ictal EEG signals. Biol Cybern 81:3-9.

Freeman W J (1975) Mass Action in the Nervous System, New York: Academic Press.

Fregni F, Nitsche M A, Loo C K, Brunoni A R, Marangolo P, Leite J, Carvalho S, Bolognini N, Caumo W, Paik N J, Simis M, Ueda K, Ekhtiari H, Luu P, Tucker D M, Tyler W J, Brunelin J, Datta A, Juan C H, Venkatasubramanian G, Boggio P M, Bikson M. Regulatory Considerations for the Clinical and Research Use of Transcranial Direct Current Stimulation (tDCS): review and recommendations from an expert panel. Clin Res Regul Aff. 2015 Mar. 1; 32 (1): 22-35. doi: 10.3109/10601333.2015.980944.

Friston K. J., Commentary and opinion: II. Statistical parametric mapping: ontology and current issues. J Cereb Blood Flow Metab 15:361-70, 1995.

Friston K. J., Modes or models: A critique on independent component analysis for fMRI. Trends in Cognitive Sciences2 (10), 373-375 (1998), in press.

Friston K. J., Statistical Parametric Mapping and Other Analyses of Functional Imaging Data. In: A. W. Toga, J. C. Mazziotta eds., Brain Mapping, The Methods. San Diego: Academic Press, 1996:363-396, 1995.

Friston K J, Frith C D, Liddle P F, Frackowiak R S, Functional connectivity: the principal-component analysis of large (PET) data sets. J Cereb Blood Flow Metab 13:5-14, 1993.

Friston K J, Holmes A P, Worsley K J, Poline J P, Frith C D, and Frackowiak R. S. J., Statistical Parametric Maps in Functional Imaging: A General Linear Approach, Human Brain Mapping 2:189-210, 1995.

Friston K J, Williams S, Howard R, Frackowiak R S and Turner R, Movement-related effects in fMRI time-series. Magn Reson Med 35:346-55, 1996.

Fuchs M, Drenckhahn R, Wischmann H A, & Wagner M (1998) An improved boundary element method for realistic volume-conductor modeling. IEEE Trans Biomed Eng 45 (8): 980-997.

Gabor D. Theory of Communication. J. Inst. Electr. Engrs. 1946; 93:429-457.

Gailliot M T & Baumeister R F (2007) The physiology of willpower: linking blood glucose to self-control. Personality and Social Psychology Review 11 (4): 303-327.

Galambos, R. and S. Makeig, "Dynamic changes in steady-state potentials," in: Dynamics of Sensory and Cognitive Processing of the Brain, ed. E. Basar Springer, pp. 178-199, 1987.

Galambos, R., S. Makeig, and P. Talmachoff, A 40 Hz auditory potential recorded from the human scalp, Proc Natl Acad Sci USA 78 (4): 2643-2647, 1981.

Galbraith, Gary C., Darlene M. Olfman, and Todd M. Huffman. "Selective attention affects human brain stem frequency-following response." Neuroreport 14, no. 5 (2003): 735-738, journals.lww.com/neuroreport/Abstract/2003/04150/Selective_attention_affects_human_brain_stem. 15.aspx.

Galil, Zvi, Stuart Haber, and Moti Yung. "Cryptographic computation: Secure fault-tolerant protocols and the public-key model." In Conference on the Theory and Application of Cryptographic Techniques, pp. 135-155. Springer, Berlin, Heidelberg, 1987.

Galletta E E, Cancelli A, Cottone C, Simonelli I, Tecchio F, Bikson M, Marangolo P. Use of computational modeling to inform tDCS electrode montages for the promotion of language recovery in post-stroke aphasia. Brain Stimul. 2015 November-December; 8 (6): 1108-15. doi: 10.1016/j.brs.2015.06.018.

Gandiga P, Hummel F, & Cohen L (2006) Transcranial D C stimulation (tDCS): A tool for double-blind sham-controlled clinical studies in brain stimulation. Clinical Neurophysiology 117 (4): 845-850.

Gao, Junling, et al. "Entrainment of chaotic activities in brain and heart during MBSR mindfulness training." Neuroscience letters 616 (2016): 218-223.

Gao, X., Cao, H., Ming, D., Qi, H., Wang, X., Wang, X., & Zhou, P. (2014). Analysis of EEG activity in response to binaural beats with different frequencies. International Journal of Psychophysiology, 94 (3), 399-406;

Gashler, M. and Martinez, T., Temporal Nonlinear Dimensionality Reduction, In Proceedings of the International Joint Conference on Neural Networks IJCNN'11, pp. 1959-1966, 2011

Gashler, M. and Ventura, D. and Martinez, T., Iterative Non-linear Dimensionality Reduction with Manifold Sculpting, In Platt, J. C. and Koller, D. and Singer, Y. and Roweis, S., editor, Advances in Neural Information Processing Systems 20, pp. 513-520, MIT Press, Cambridge, M A, 2008

Gebodh N, Adair D, Chelette K, Esmaeilpour Z, Bikson M, Dmochowski J, Parra L C, Woods A J, Kappenman E. Modulation of physiologic artifacts during concurrent tDCS and EEG. Brain Stimul. 2017 Mar. 1; 10 (2): 429-430. doi: dx.doi.org/10.1016/j.brs.2017.01.278.

Gebodh N, Adair D, Chelette K, Esmaeilpour Z, Bikson M, Dmochowski J, Woods A, Kappenman E. Physiologic Artifacts When Combining EEG and tDCS. Brain Stimul. 2017 Jul. 1; 10 (4): e33-e33.

genamason.wordpress.com/2009/10/18/more-on-synthetic-telepathy/

George J S, Aine C J, Mosher J C, Schmidt D M, Ranken D M, Schlitt H A, Wood C C, Lewine J D, Sanders J A, Belliveau J W. Mapping function in the human brain with magnetoencephalography, anatomical magnetic resonance imaging, and functional magnetic resonance imaging. J Clin Neurophysiol 12:406-31, 1995.

Gevins A S and Cutillo B A (1995) Neuroelectric measures of mind. In: P L Nunez (Au), Neocortical Dynamics and Human EEG Rhythms. N Y: Oxford U. Press, pp. 304-338.

Gevins A S, Le J, Martin N, Brickett P, Desmond J, and Reutter B (1994) High resolution EEG: 124-channel recording, spatial enhancement, and MRI integration methods. Electroencephalography and Clin. Neurophysiology 90:337-358.

Gevins A S, Smith M E, McEvoy L. and Yu I) (1997) High-resolution mapping of cortical activation related to working memory: effects of task difficulty, type of processing, and practice. Cerebral Cortex 7:374-385.

Ghai R, Bikson M, Durand D M. Effects of applied electric fields on low calcium epileptiform activity in the CAI region of rat hippocampal slices. Journal of Neurophysiology 2000; 84:274-280

Gillick B T, Kirton A, Carmel J, Minhas P, Bikson M. Pediatric Stroke and transcranial Direct Current Stimulation: Methods for Rational Individualized Dose Optimization Front. Hum. Neurosci. 2014; doi: 10.3389/fnhum.2014.00739 Free Online Giordano J, Bikson M, Kappenman E S, Clark V P, Coslett B, Hamblin M R, Hamilton R, Jankord R, Kozumbo W J, Mckinley A, Nitsche M A, Reilly J P, Richardson J, Wurzman R, Calabrese E. Mechanisms and Effects of Transcranial Direct Current Stimulation. Dose Response. 2017 Feb. 9; 15 (1). doi: 10.1177/1559325816685467.

Gooding-Williams, Gerard, Hongfang Wang, and Klaus Kessler. "THETA-Rhythm Makes the World Go Round: Dissociative Effects of TMS Theta Versus Alpha Entrainment of Right pTPJ on Embodied Perspective Transformations." Brain Topography (2017): 1-4;

Gorban, A. N., A. Zinovyev, Principal manifolds and graphs in practice: from molecular biology to dynamical systems, International Journal of Neural Systems, Vol. 20, No. 3 (2010) 219-232.

Gorban, A. N., B. Kégl, D. C. Wunsch, A. Zinovyev (Eds.), Principal Manifolds for Data Visualisation and Dimension Reduction, Lecture Notes in Computer Science and Engineering (LNCSE), Vol. 58, Springer, Berlin-Heidelberg-New York, 2007. ISBN 978-3-540-73749-0

Grecco L H, Li S, Michel S, Castillo-Saavedra L, Mourdoukoutas A, Bikson M, Fregni F. Transcutaneous Spinal Stimulation as a therapeutic strategy for spinal cord injury: State of the art. Journal of Neurorestoratology 2015 Mar. 23; 3:73-82. doi: doi.org/10.2147/JN. S77813.

Gregoriou G G, Gotts S J, Zhou H, Desimone R (2009) High-frequency, long-range coupling between prefrontal and visual cortex during attention. Science 324:1207-1210.

Grossman N, Bono D, Dedic N, Kodandaramaiah S B, Rudenko A, Suk H J, Cassara A M, Neufeld E, Kuster N, Tsai L H, Pascual-Leone A, Boyden E S, "Noninvasive Deep Brain Stimulation via Temporally Interfering Electric Fields", Cell. 2017 Jun. 1; 169 (6): 1029-1041.e16. doi: 10.1016/j.cell.2017.05.024.

Guarienti F, Caumo W, Shiozawa P, Cordeiro Q, Boggio P S, Benseñor I M, Lotufo P A, Bikson M, Brunoni A R. Reducing transcranial direct current stimulation (tDCS)-induced erythema with skin pretreatment: considerations for sham-controlled tDCS clinical trials. Neuromodulation: Technology at the Neural Interface 2014; DOI: 10.1111/ner.12230)

Guevara M A, Corsi-Cabrera M (1996) EEG coherence or EEG correlation? Int J Psychophysiology 23:145-153;

Guleyupoglu B, Febles N, Minhas P, Hahn C, Bikson M. Reduced discomfort during High-Definition transcutaneous stimulation using 6% benzocaine. Frontiers of Human Neuroscience 2014; doi: 10.3389/fneng.2014.00028 Free Online Guleyupoglu B, Schestatsky P, Edwards D, Fregni F, Bikson M. Classification of methods in transcranial Electrical Stimulation (tES) and evolving strategy from historical approaches to contemporary innovations. Journal of Neuroscience Methods 2013; 219:291-311 Journal Link Guleyupoglu B, Schestatsky P, Fregni F, Bikson M. Methods and technologies for low-intensity transcranial electrical stimulation: waveforms, terminology, and historical notes. Chapter in Textbook of Neuromodulation. (Helena Knotkova and Dirk Rasche ed.) Springer. ISBN: 978-1-4939-1407-4, 2015. Page 7-16.

Guyonneau, R., Vanrullen, R., Thorpe, S. J., 2004. Temporal codes and sparse representations: a key to understanding rapid processing in the visual system. J. Physiology, Paris 98, 487-497.

Hagiwara KIaM (2003) A Feeling Estimation System Using a Simple Electroencephalograph. IEEE International Conference on Systems, Man and Cybernetics. 4204-4209.

Hahn C, Rice J, Macuff S, Minhas P, Rahman A, Bikson M. Methods for extra-low voltage transcranial Direct Current Stimulation: Current and time dependent impedance decreases. Clinical Neurophysiology 2013; 124 (3) 551-556

Haken H (1983) Synergetics: An Introduction, 3rd Edition, Springer-Verlag.

Haken H (1999) What can synergetics contribute to the understanding of brain functioning? In: Analysis of Neurophysiological Brain Functioning, (Uhl (Ed), Berlin: Springer-Verlag, pp 7-40.

Halko M, Datta A, Plow E, Scaturro J, Bikson M, Merabet L. Neuroplastic changes following rehabilitative training correlate with regional electrical field induced with tDCS. NeuroImage. 2011; 57:885-891

Hallett, M., 2000. Transcranial magnetic stimulation and the human brain. Nature 406, 147-150.

Hamilton, Roy, Samuel Messing, and Anjan Chatterjee, "Rethinking the thinking cap-Ethics of neural enhancement using noninvasive brain stimulation." Neurology, Jan. 11, 2011, vol. 76 no. 2 187-193. (www.neurology.org/content/76/2/187.)

Hämmerer D, Bonaiuto J, Klein-Flügge M, Bikson M, Bestmann S. Selective alteration of human value decisions with medial frontal tDCS is predicted by changes in attractor dynamics. Sci Rep. 2016 May 5; 6:25160. doi: 10.1038/srep25160.

Hampstead B M, Briceño E M, Mascaro N, Mourdoukoutas A, Bikson M. Current Status of Transcranial Direct Current Stimulation in Posttraumatic Stress and Other Anxiety Disorders. Curr Behav Neurosci Rep. 2016 June; 3 (2): 95-101. doi: 10.1007/s40473-016-0070-9.

Hampstead B M, Sathian K, Bikson M, Stringer A Y. Combined mnemonic strategy training and high-definition transcranial direct current stimulation for memory deficits in mild cognitive impairment. Alzheimers Dement (N Y). 2017 May 15; 3:459-470. doi: 10.1016/j.trci.2017.04.008

Hamwira Yaacob, Wahab Abdul, Norhaslinda Kamaruddin, "Classification of EEG signals using MLP based on categorical and dimensional perceptions of emotions", Information and Communication Technology for the Muslim World (ICT4M) 2013 5th International Conference on, pp. 1-6, 2013.

Handbook of Transcranial Stimulation. Oxford University Press, Oxford, U K.

Hanslmayr, Simon, Jonas Matuschek, and Marie-Christin Fellner. "Entrainment of prefrontal beta oscillations induces an endogenous echo and impairs memory formation." Current Biology 24.8 (2014): 904-909;

Harris, I. M., Miniussi, C., 2003. Parietal lobe contribution to mental rotation demonstrated with rTMS. J. Cognitive Neuroscience 15, 315-323.

Harris, J. A., Clifford, C. W., Miniussi, C., 2008. The functional effect of transcranial magnetic stimulation: signal suppression or neural noise generation. J. Cognitive Neuroscience 20, 734-740.

Hebb, D. O., 1949. The Organization of Behavior; A Neuropsychological Theory. Wiley, New York.

Hee Lee W, Kennedy N I, Bikson M, Frangou S. A computational assessment of target engagement in the treatment of auditory hallucinations with transcranial direct current stimulation. Front. Psychol. 9:48. 2018 Feb. 22. doi: 10.3389/fpsyt.2018.00048

Heideman, Simone G., Erik S. te Woerd, and Peter Praamstra. "Rhythmic entrainment of slow brain activity preceding leg movements." Clin. Neurophysiology 126.2 (2015): 348-355;

Helfrich, Randolph F., et al. "Entrainment of brain oscillations by transcranial alternating current stimulation." Current Biology 24.3 (2014): 333-339;

Henry, Molly J., et al. "Aging affects the balance of neural entrainment and top-down neural modulation in the listening brain." Nature Communications 8 (2017): ncomms15801;

Hillman C H, Erickson K I, & Kramer A F (2008) Be smart, exercise your heart: exercise effects on brain and cognition. Nature Reviews Neuroscience 9 (1): 5865.

Hink, R. F., Kodera, K., Yamada, O., Kaga, K., & Suzuki, J. (1980). Binaural interaction of a beating frequency-following response. Audiology, 19 (1), 36-43.

Hinrichs H, Machleidt W (1992) Basic emotions reflected in EEG-coherences. Int J Psychophysiol 13:225-232.

Hogeveen J, Grafman J, Aboseria M, David A, Bikson M, Hauner K K. Effects of high-definition and conventional tDCS on response inhibition. Brain Stimul. 2016: S1935-861X (16) 30091-2. doi: 10.1016/j.brs.2016.04.015.

Holroyd C B & Yeung N (2012) Motivation of extended behaviors by anterior cingulate cortex. Trends in Cognitive Sciences 16:122-128.

Hoogenboom N, Schoffelen J M, Oostenveld R, Parkes L M, Fries P. Localizing human visual gamma-band activity in frequency, time and space. Neuroimage. 2006; 29:764-773;

Horr, Ninja K., Maria Wimber, and Massimiliano Di Luca. "Perceived time and temporal structure: Neural entrainment to isochronous stimulation increases duration estimates." Neuroimage 132 (2016): 148-156;

Hosseini, Mersedeh Bahr, Jessey Hou, Marom Bikson, Marco Iacoboni, and Jeffrey L. Saver. "Abstract TP72: Transcranial Direct Current Stimulation (tDCS) for Neuroprotection in Acute Cerebral Ischemia: Meta-analysis of Preclinical Studies and Implications for Human Clinical Trials." (2018): ATP72-ATP72.

How One Intelligent Machine Learned to Recognize Human
Emotions, MIT Technology Review, Jan. 23, 2016.

Howard D, Slezak D, editors. Convergence and Hybrid
Information Technology. Springer Berlin Heidelberg,
488-500.

Huang Y, Liu A A, Lafon B, Friedman D, Dayan M, Wang
X, Bikson M, Doyle W K, Devinsky O, Parra L C
Measurements and models of electric fields in the 'in
vivo' human brain during transcranial electric stimulation.
Elife. 2017 Feb. 7; 6. doi: dx.doi.org/10.7554/eLife.
18834 Journal Link Huang, Tina L., and Christine Charyton. "A comprehensive
review of the psychological effects of brainwave entrain-
ment." Alternative therapies in health and medicine 14.5
(2008): 38.

Huettel, Song & McCarthy, "Magnetic Resonance, a critical
peer-reviewed introduction; functional MRI". European
Magnetic Resonance Forum. (2009)).

Huon de Kermadec F., Durand J. F., Sabatier R. (1996)
Comparaison de méthodes de régression pour l'étude des
liens entre données hédoniques, in Third Sensometrics
Meeting, E.N.T.I.A.A., Nantes.

Huon de Kermadec F., Durand J. F., Sabatier R. (1997)
Comparison between linear and nonlinear PLS methods to
explain overall liking from sensory characteristics, Food
Quality and Preference, 8, n. 5/6.

Hutcheon, B., Yarom, Y., 2000. Resonance, oscillation and
the intrinsic frequency preferences of neurons. Trends in
Neurosciences 23, 216-222.

Ingber L. (1995) Statistical mechanics of multiple scales of
neocortical interactions. In: P L Nunez (Au), Neocortical
Dynamics and Human EEG Rhythms. N Y: Oxford U.
Press, 628-681.

Inoue, Mitsuteru, et al. "Investigating the use of magnonic
crystals as extremely sensitive magnetic field sensors at
room temperature." Applied Physics Letters 98.13 (2011):
132511.

Inzlicht M, Schmeichel B J, & Macrae C N (2014) Why
self-control seems (but may not be) limited. Trends in
Cognitive Sciences 18 (3): 127-133.

Irwin, Rosie. "Entraining Brain Oscillations to Influence
Facial Perception." (2015);

Ives, J. R., Warach S, Schmitt F, Edelman R R and Schomer
D L. Monitoring the patient's EEG during echo planar
MRI, Electroencephalogr Clin Neurophysiol, 87:417-420,
1993.

Izhikevich E M (1999) Weakly connected quasi-periodic
oscillators, F M interactions, and multiplexing in the
brain, SIAM J. Applied Mathematics 59:2193-2223.

Jackson M P, Bikson M, Liebetanz D, Nitsche M. How to
consider animal data in tDCS safety standards. Brain
Stimul. P. 1141, 2017 Aug. 18. pii: S1935-861X (17)
30883-5. doi: 10.1016/j.brs.2017.08.004. Online Link (ar-
ticle in production)

Jackson M P, Rahman A, Lafon B, Kronberg G, Ling D,
Parra L C, Bikson M. Animal Models of transcranial
Direct Current Stimulation: Methods and Mechanisms.
Clin Neurophysiol. 2016 November; 127 (11): 3425-
3454. doi: 10.1016/j.clinph.2016.08.016.

Jackson M P, Truong D, Brownlow M L., Wagner J A,
Mckinley R A, Bikson M, Jankord R. Safety parameter
considerations of anodal transcranial Direct Current
Stimulation in rats. Brain Behav Immun. 2017 August;
64:152-161. doi: 10.1016/j.bbi.2017.04.008.

Jackson, J. E., A User's Guide to Principal Components.
New York: John Wiley & Sons, Inc., 1991.

Jacobson, L., Koslowsky, M., Lavidor, M., 2011. DCS
polarity effects in motor and cognitive domains: a meta-
analytical review. Experimental Brain Research 216,
1-10.

James W (1884.) What is an emotion? Mind 9:188-205;
Lacey J I, Bateman D E, Vanlehn R (1953) Autonomic
response specificity; an experimental study. Psychosom
Med 15:8-21;

James X. Li, Visualizing high-dimensional data with rela-
tional perspective map, Information Visualization (2004)
3, 49-59

Jarden, Jens O., Vijay Dhawan, Alexander Poltorak, Jerome
B. Posner, and David A. Rottenberg. "Positron emission
tomographic measurement of blood-to-brain and blood-
to-tumor transport of 82Rb: The effect of dexamethasone
and whole-brain radiation therapy." Annals of neurology
18, no. 6 (1985): 636-646.

Jefferys J G R, Deans J, Bikson M, Fox J. Effects of weak
electric fields on the activity of neurons and neuronal
network. Radiation Protection Dosimetry. 2003; 106:321-
323

Jennings J R & Wood C C (1976) The e-adjustment proce-
dure for repeated measures analyses of variance. Psycho-
physiology 13:277-278.

Jigang Sun, Malcolm Crowe, and Colin Fyfe, Curvilinear
component analysis and Bregman divergences, In Euro-
pean Symposium on Artificial Neural Networks (Esann),
pages 81-86. d-side publications, 2010

Jihun Ham, Daniel D. Lee, Sebastian Mika, Bernhard
Schölkopf. A kernel view of the dimensionality reduction
of manifolds. Proceedings of the 21st International Con-
ference on Machine Learning, Banff, Canada, 2004. doi:
10.1145/1015330.1015417

Jirsa V K and Haken H (1997) A derivation of a macroscopic
field theory of the brain from the quasi-microscopic
neural dynamics. Physica D 99:503-526.

Jirsa V K and Kelso J A S (2000) Spatiotemporal pattern
formation in continuous systems with heterogeneous con-
nection topologies. Physical Review E 62:8462-8465.

Jog M V, Smith R X, Jann K, Dunn W, Lafon B, Truong D,
Wu A, Parra L., Bikson M, Wang D J. In-vivo Imaging of
Magnetic Fields Induced by Transcranial Direct Current
Stimulation (tDCS) in Human Brain using MRI. Sci Rep.
2016 Oct. 4; 6:34385. doi: 10.1038/srep34385. Online John A. Lee, Michel Verleysen, Nonlinear Dimensionality
Reduction, Springer, 2007.

Jokeit, H. and Makeig, S., Different event-related patterns of
gamma-band power in brain waves of fast- and slow-
reacting subjects, Proc. Nat. Acad. Sci USA 91:6339-
6343, 1994.

Jones K T, Stephens J A, Alam M, Bikson M, Berryhill M
E. Longitudinal Neurostimulation in Older Adults
Improves Working Memory. PLOS One. 2015 Apr. 7; 10
(4): e0121904. doi: 10.1371/journal.pone.0121904. Free
Online Jones N A, Fox N A (1992) Electroencephalogram asym-
metry during emotionally evocative films and its relation
to positive and negative affectivity. Brain Cogn 20:280-
299 [PubMed].

Joundi, R. A., Jenkinson, N., Brittain, J. S., Aziz, T. Z.,
Brown, P., 2012. Driving oscillatory activity in the human
cortex enhances motor performance. Current Biology 22,
403-407.

Joyce, Michael, and Dave Siever. "Audio-visual entrainment
program as a treatment for behavior disorders in a school
setting." J. Neurotherapy 4.2 (2000): 9-25;

Juels, Ari, and Madhu Sudan. "A fuzzy vault scheme." Designs, Codes and Cryptography 38, no. 2 (2006): 237-257.

Jueptner, M., K. M. Stephan, C. D. Frith, D. J. Brooks, R. S J. Frackowiak & R. E. Passingham, Anatomy of Motor Learning. I. Frontal Cortex and Attention. J. Neurophysiology 77:1313-1324, 1977.

Jung, T-P., Humphries, C., Lee, T-W., Makeig, S., Mckeown, M., Iragui, V. and Sejnowski, T. J., "Extended ICA removes artifacts from electroencephalographic recordings," In: Advances in Neural Information Processing Systems p. 894-900, 199810, MIT Press, Cambridge, M A, in press.

Jung, T-P., Humphries, C., Lee, T-W., Mckeown, M. J., Iragui, V., Makeig, S. & Sejnowski, T. J., Removing electroencephalographic artifacts by blind source separation, submitted-a.

Jung, T-P., Makeig, S., Westerfield, M., Townsend, J., Courchesne, E. and Sejnowski, T. J., Analysis and visualization of single-trial event-related potentials, submitted-b.

Jung, T-P., S. Makeig, M. Stensmo & T. Sejnowski, Estimating Alertness from the EEG Power Spectrum, IEEE Transactions on Trans. Biomedical Eng. Engineering, 44 (1), 60-69, 1997.

Junior, L. R. S., Cesar, F. H. G., Rocha, F. T., and Thomaz, C. E. EEG and Eye Movement Maps of Chess Players. Proceedings of the Sixth International Conference on Pattern Recognition Applications and Methods. (ICPRAM 2017) pp. 343-441. (fei.edu.br/~cet/icpram 17_LaercioJunior.pdf).

Jutten, C. & Herault, J., Blind separation of sources, part I: an adaptive algorithm based on neuromimetic architecture. Signal Processing 24, 1-10, 1991.

Kahn, I., Pascual-Leone, A., Theoret, H., Fregni, F., Clark, D., Wagner, A. D., 2005. Transient disruption of ventrolateral prefrontal cortex during verbal encoding affects subsequent memory performance. J. Neurophysiology 94, 688-698.

Kaiser, Stefan, et al. "Optically induced coherent transport far above T c in underdoped YBa 2 Cu 3 O 6+8." Physical Review B 89.18 (2014): 184516;

Kalyan, Ritu, and Bipan Kaushal. "Binaural Entrainment and Its Effects on Memory." (2016);

Kamitani, Yukiyasu et al., Neuron (DOI: 10.1016/j.neuron.2008.11.004).

Kanai R, Chaieb L, Antal A, Walsh V, & Paulus W (2008) Frequency-dependent electrical stimulation of the visual cortex. Current Biology 18 (23): 1839-1843.

Kanai, R., Chaieb, L., Antal, A., Walsh, V., Paulus, W., 2008. Frequency-dependent electrical stimulation of the visual cortex. Current Biology 18, 1839-1843.

Karhumen, J., Oja, E., Wang, L., Vigario, R. & Joutsenalo, J., A class of neural networks for independent component analysis, IEEE Trans. Neural Networks, in press.

Kasprzak, C. (2011). Influence of binaural beats on EEG signal. Acta Physica Polonica A, 119 (6A), 986-990;

Kasschau M, Reisner J, Sherman K, Bikson M, Datta A, Charvet L E. Transcranial Direct Current Stimulation Is Feasible for Remotely Supervised Home Delivery in Multiple Sclerosis. Neuromodulation. 2016 December; 19 (8): 824-831. doi: 10.1111/ner.12430.

Kasschau M, Sherman K, Haider L, Frontario A, Shaw M, Datta A, Bikson M, Charvet L. A Protocol for the Use of Remotely-Supervised Transcranial Direct Current Stimulation (tDCS) in Multiple Sclerosis (MS). J Vis Exp. 2015 Dec. 26; (106): e53542. doi: 10.3791/53542. Video Katznelson R D (1981) Normal modes of the brain: Neuroanatomical basis and a physiological theoretical model. In P L Nunez (Au), Electric Fields of the Brain: The Neurophysics of EEG, 1st Edition, N Y: Oxford U. Press, pp 401-442.

Kayser J & Tenke C E (2006) Principal components analysis of Laplacian waveforms as a generic method for identifying estimates: II. Adequacy of low density estimates. Clinical Neurophysiology 117:369-380.

Keitel, Anne, et al. "Auditory cortical delta-entrainment interacts with oscillatory power in multiple fronto-parietal networks." NeuroImage 147 (2017): 32-42;

Keitel, Christian, Cliodhna Quigley, and Philipp Ruhnau. "Stimulus-driven brain oscillations in the alpha range: entrainment of intrinsic rhythms or frequency-following response?" J. Neuroscience 34.31 (2014): 10137-10140;

Kessler S K, Woods A J, Minhas O, Rosen A R, Gorman C, Bikson M. Dosage considerations for transcranial direct current stimulation in children: a computational modeling study. PLOSE ONE In Press 2013, 8 (9): e76112. doi: 10.1371/journal.pone.0076112. Free Online Khadka N, Rahman A, Sarantos C, Truong D, Bikson M. Methods for Specific Electrode Resistance Measurement during Transcranial Direct Current Stimulation Brain Stimulation 2014 8 (1): 150-9. doi: 10.1016/j.brs.2014.10.004.

Khadka N, Truong D Q, Bikson M. Principles of Within Electrode Current Steering (WECS). J Med Device 2015 Apr. 13-16; 9, 020947-1. doi: 10.1115/1.4030126.

Khadka N, Zannou A L, Zunura F, Truong D Q, Dmochowski J, Bikson M. Minimal heating at the Skin surface during transcranial direct current stimulation (tDCS). Neuromodulation. 2017 Jan. 22. doi: 10.1111/ner.12554.

Kiers H. A. L. (1991) Hierarchical relations among three way methods Psychometrika, 56.

Kitajo, K., Doesburg, S. M., Yamanaka, K., Nozaki, D., Ward, L. M., Yamamoto, Y., 2007. Noise-induced large-scale phase synchronization of human-brain activity associated with behavioral stochastic resonance. EPL—Europhysics Letters, 80.

Kitajo, K., Nozaki, D., Ward, L. M., Yamamoto, Y., 2003. Behavioral stochastic resonance within the human brain. Physical Review Letters 90, 218103.

Klimesch W (1996) Memory processes, brain oscillations and EEG synchronization. International J. Psychophysiology 24:61-100.

Knotkova H, Woods A J, Bikson M, Nitche M A. Transcranial Direct Current Stimulation (tDCS): What Pain Practitioners Need to Know. Practical Pain Management. 2015; 15 (3) link.

Koelsch, Stefan. "Music-evoked emotions: principles, brain correlates, and implications for therapy." Annals N Y Acad Sci of the New York Academy of Sciences 1337.1 (2015): 193-201;

Kösem, Anne, et al. "Neural entrainment reflects temporal predictions guiding speech comprehension." the Eighth Annual Meeting of the Society for the Neurobiology of Language (SNL 2016). 2016;

Kramer A F & Erickson K I (2007) Capitalizing on cortical plasticity: influence of physical activity on cognition and brain function. Trends in Cognitive Sci Sciences 11:342-348.

Kronberg G, Bikson M. Electrode assembly design for transcranial Direct Current Stimulation: A FEM modeling study. Conf Proc IEEE Eng Med Biol Soc. 2012; 891-5. doi: 10.1109/EMBC.2012.6346075.

Kronberg G, Bridi M, Abel T, Bikson M, Parra L C. Direct Current Stimulation Modulates LTP and LTD: Activity Dependence and Dendritic Effects. Brain Stimul. 2017 January-February; 10 (1): 51-58. doi: 10.1016/j.brs.2016.10.001.

Kuo H I, Datta A, Bikson M, Minhas P. Paulus W, Kuo M F, Nitsche M A. Comparing cortical plasticity induced by conventional and high-definition 4×1 ring tDCS: a neurophysiological study Brain Stimulation 2013; 6 (4): 644-8 Journal Link.

Kurland J, Baldwin K, Tauer ((2010) Treatment-induced neuroplasticity following intensive naming therapy in a case of chronic wernicke's aphasia. Aphasiology 24:737-751.

Kvalheim O. M. (1988) A partial least squares approach to interpretative analysis of multivariate analysis, Chemometrics and Intelligent Laboratory System, 3.

Kwong K. K., Belliveau J W, Chesler D A, Goldberg I E, Weisskoff R M, Poncelet B P, Kennedy D N, Hoppel B E, Cohen M S, Turner R, et al., Dynamic magnetic resonance imaging of human brain activity during primary sensory stimulation. Proc Natl Acad Sci USA 89:5675-9, 1992.

Kwong K. K., Functional magnetic resonance imaging with echo planar imaging. Magn Reson Q 11:1-20, 1995.

Kwong, Kenneth K., John W. Belliveau, David A. Chesler, Inna E. Goldberg, Robert M. Weisskoff, Brigitte P. Poncelet, David N. Kennedy, Bernice E. Hoppel, Mark S. Cohen, and Robert Turner. "Dynamic magnetic resonance imaging of human brain activity during primary sensory stimulation." Proceedings of the National Academy of Sciences 89, no. 12 (1992): 5675-5679.

Lachaux J P, Rodriguez E, Martinerie J, & Varela F J (1999) Measuring phase synchrony in brain signals. Human Brain Mapping 8:194-208.

Lachaux J P, Rodriguez E, Martinerie J, Varela F J (1999) Measuring phase synchrony in brain signals. Hum Brain Mapp 8:194-208.

Lafon B, Rahman A, Bikson M, Parra L C. Direct Current Stimulation Alters Neuronal Input/Output Function. Brain Stimul. 2017 January-February; 10 (1): 36-45. doi: 10.1016/j.brs.2016.08.014.

Lakatos, Peter, et al. "Entrainment of neuronal oscillations as a mechanism of attentional selection." science 320.5872 (2008): 110-113;

Landi, D., Rossini, P. M., 2010. Cerebral restorative plasticity from normal aging to brain diseases: a never-ending story. Restorative Neurology and Neuroscience 28, 349-366.

Lane, J. D., Kasian, S. J., Owens, J. E., & Marsh, G. R. (1998). Binaural auditory beats affect vigilance performance and mood. Physiology & behavior, 63 (2), 249-252;

Lang, N., Rothkegel, H., Reiber, H., Hasan, A., Sueske, E., Tergau, F., Ehrenreich, H., Wuttke, W., Paulus, W., 2011. Circadian modulation of GABA-mediated cortical inhibition. Cerebral Cortex 21, 2299-2306.

Law S K, Nunez P L and Wijesinghe R S (1993) High resolution EEG using spline generated surface Laplacians on spherical and ellipsoidal surfaces. IEEE Transactions on Biomedical Engineering 40:145-153.

Lawrence, N., Probabilistic Non-linear Principal Component Analysis with Gaussian Process Latent Variable Models, Journal of Machine Learning Research 6 (November): 1783-1816, 2005.

Lawrence, Neil D) (2012). "A unifying probabilistic perspective for spectral dimensionality reduction: insights and new models". Journal of Machine Learning Research. 13 (May): 1609-1638.

Laycock, R., Crewther, D. P., Fitzgerald, P. B., Crewther, S. G., 2007. Evidence for fast signals and later processing in human V1/V2 and V5/MT+. A TMS study of motion perception. J. Neurophysiology 98, 1253-1262.

Le Van Quyen M, Foucher J, Lachaux J, et al. Comparison of Hilbert transform and wavelet methods for the analysis of neuronal synchrony. J Neurosci Methods. 2001; 111: 83-98, Lee Y-Y, Hsieh S (2014) Classifying Different Mental states by Means of EEG-Based Functional Connectivity Patterns. PLOS ONE 9 (4): e95415. doi.org/10.1371/journal.pone.0095415.

Lee, Daniel Keewoong, Dongyeup Daniel Synn, and Daniel Chesong Lee. "Intelligent earplug system." U.S. patent application Ser. No. 15/106,989;

Lee, T.-W., Girolami, M., and Sejnowski, T. J., Independent component analysis using an extended infomax algorithm for mixed Sub-gaussian and Super-gaussian sources, Neural Computation, 11 (2): 417-441 (1999) submitted for publication.

Lee, You-Yun, Shulan Hsieh. Classifying Different Mental states by Means of EEG-Based Functional Connectivity Patterns. Apr. 17, 2014. (doi.org/10.1371/journal.pone.0095415.

Lefournour, Joseph, Ramaswamy Palaniappan, and Ian V. McLoughlin. "Inter-hemispheric and spectral power analyses of binaural beat effects on the brain." Matters 2.9 (2016): e201607000001;

Leite J, Goncalves O F, Pereira P, Khadka N, Bikson M, Fregni F, Carvalho S. The differential effects of unihemispheric and bihemispheric tDCS over the inferior frontal gyrus on proactive control. Neurosci Res. 130, 39-46 2017. doi.org/10.1016/j.neures.2017.08.005. (Article in Press)

Lennie P(2003) The cost of cortical computation. Current Biology 13:493-497.

Lespinats S., Fertil B., Villemain P. and Herault J., Rankvisu: Mapping from the neighbourhood network, Neurocomputing, vol. 72 (13-15), pp. 2964-2978, 2009.

Lespinats, S., M. Verleysen, A. Giron, B. Fertil, D D-HDS: a tool for visualization and exploration of high-dimensional data, IEEE Transactions on Neural Networks 18 (5) (2007) 1265-1279.

Levenson R W, Heider K, Ekman P, Friesen W V (1992) Emotion and Autonomic Nervous-System Activity in the Minangkabau of West Sumatra. J Pers Soc Psychol 62:972-988.

Lewandowski, M., D. Makris, S. A. Velastin and J.-C. Nebel, Structural Laplacian Eigenmaps for Modeling Sets of Multivariate Sequences, IEEE Transactions on Cybernetics, 44 (6): 936-949, 2014.

Lewandowski, M., J. Martinez-del Rincon, D. Makris, and J.-C. Nebel, Temporal extension of laplacian eigenmaps for unsupervised dimensionality reduction of time series, Proceedings of the International Conference on Pattern Recognition (ICPR), 2010.

Lewicki, Michael S., and Sejnowski, Terence J., Learning nonlinear overcomplete representations for efficient coding, Eds. M. Kearns, M. Jordan, and S. Solla, Advances in Neural Information Processing Systems pp. 556-562 (1998) 10, in press.

Lian J, Bikson M, Sciortino C, Stacey W C, Durand D M. Local suppression of epileptiform activity by Electrical Stimulation in Rat Hippocampus In Vitro. Journal of Physiology. 2003; 547:427-434.

Lian J, Bikson M, Shuai J, Durand D M. Propagation of non-synaptic epileptiform activity across lesion in rat hippocampal slices. Journal of J. Physiology 2001; 537; 191-199.

Liebetanz, D., Nitsche, M. A., Tergau, F., Paulus, W., 2002. Pharmacological approach to the mechanisms of transcranial D C-stimulation-induced after-effects of human motor cortex excitability. Brain 125, 2238-2247.

Liley D T J, Cadusch P J and Dafilis M P(2002) A spatially continuous mean field theory of electrocortical activity network. Computation in Neural Systems 13:67-113.

Lin Y P, Wang C H, Jung T P, Wu T L, Jeng S K, et al. (2010) EEG-Based Emotion Recognition in Music Listening. Ieee T Bio Med Eng 57:1798-1806;

Linsker, R., Local synaptic learning rules suffice to maximise mutual information in a linear network. Neural Computation 4, 691-702, 1992.

Lisman J, Buzsaki G. A neural coding scheme formed by the combined function of gamma and theta oscillations. Schizophr Bull. Jun. 16, 2008; doi: 10.1093/schbul/sbn060.

Liu A K, Belliveau J W, Dale A M. Spatiotemporal imaging of human brain activity using functional MRI-constrained magnetoencephalography data: Monte Carlo simulations. Proc Natl Acad Sci USA 95:8945-50, 1998.

Longtin, A., 1997. Autonomous stochastic resonance in bursting neurons. Physical Review E 55, 868-876.

looxidlabs.com/device-2/.

Lopez-Quitero S V, Datta A, Amaya R, Elwassif M, Bikson M, Tarbell J M. DBS-relevant electric fields increase hydraulic conductivity of in vitro endothelial monolayers. Journal of Neural Engineering. 2010; 7 (1).

Luft C D B, Nolte G, & Bhattacharya J (2013) High-learners present larger midfrontal theta power and connectivity in response to incorrect performance feedback. Journal of Neuroscience 33 (5): 2029-2038.

Lyons R G. Understanding Digital Signal Processing. 2nd ed. Upper Saddle River, N J: Prentice Hall PTR; 2004: 688.

MacFie H. J. H, Thomson D. M. H. (1988) Preference mapping and multidimensional scaling methods, in: Sensory Analysis of Foods. Elsevier Applied Science, London.

Mai, Guangting, James W. Minett, and William S-Y. Wang. "Delta, theta, beta, and gamma brain oscillations index levels of auditory sentence processing." Neuroimage 133 (2016): 516-528.

Makeig, S. and Galambos, R., The CERP: Event-related perturbations in steady-state responses, in: Brain Dynamics Progress and Perspectives, (pp. 375-400), ed. E. Basar and T. H. Bullock, 1989.

Makeig, S. and Inlow, M., Lapses in alertness: coherence of fluctuations in performance and the EEG spectrum, Electroencephalogr clin Neurophysiol, 86:23-35, 1993.

Makeig, S. and Jung, T-P., Changes in alertness are a principal component of variance in the EEG spectrum, NeuroReport 7:213-216, 1995.

Makeig, S. and T-P. Jung, Tonic, phasic, and transient EEG correlates of auditory awareness during drowsiness, Cognitive Brain Research 4:15-25, 1996.

Makeig, S. Auditory event-related dynamics of the EEG spectrum and effects of exposure to tones, Electroencephalogr clin Neurophysiol, 86:283-293, 1993.

Makeig, S. Toolbox for independent component analysis of psychophysiological data, www.cnl.salk.edu/~scott/ica.html, 1997.

Makeig, S., Bell, A. J., Jung, T-P. and Sejnowski, T. J., "Independent component analysis of electroencephalographic data," In: D. Touretzky, M. Mozer and M. Hasselmo (Eds). Advances in Neural Information Processing Systems 8:145-151 MIT Press, Cambridge, M A, 1996.

Makeig, S., Jung, T-P, and Sejnowski, T. J., "Using feedforward neural networks to monitor alertness from changes in EEG correlation and coherence," In: D. Touretzky, M. Mozer & M. Hasselmo (Eds). Advances in Neural Information Processing Systems 8:931-937 MIT Press, Cambridge, M A, 1996.

Makeig, S., T-P. Jung, D. Ghahremani, A. J. Bell & T. J. Sejnowski, Blind separation of auditory event-related brain responses into independent components. Proc. Natl. Acad. Sci. USA, 94:10979-10984, 1997.

Makeig, S., Westerfield, M., Jung, T-P., Covington, J., Townsend, J., Sejnowski, T. J. and Courchesne, E., Independent components of the late positive event-related potential in a visual spatial attention task, Soc. Neurosci. Abst 24 (1998): 507submitted.

Malik, M. A., and B. A. Malik. "High Temperature Superconductivity: Materials, Mechanism and Applications." Bulgarian J. Physics 41.4 (2014).

Mallat S, Zhang 7. Matching pursuits with time-frequency dictionaries. IEEE Trans. Signal Proc. 1993; 41 (12): 3397-3415).

Mallat S G. A theory for multiresolution signal decomposition: the wavelet representation. IEEE Trans Pattern Anal Mach Intell. 1989; 11:674-693.

Malmuvino J and Plonsey R (1995) Bioelectromagetism. N Y: Oxford U. Press.

Manenti, R., Cappa, S. F., Rossini, P. M., Miniussi, C., 2008. The role of the prefrontal cortex in sentence comprehension: an rTMS study. Cortex 44, 337-344.

Mankowsky, Roman, et al. "Nonlinear lattice dynamics as a basis for enhanced superconductivity in YBa2Cu3O6. 5." arXiv preprint arXiv: 1405.2266 (2014);

Manoach D S, Schlaug G, Siewert B, Darby D G, Bly B M, Benfield A, Edelman R R, Warach S, Prefrontal cortex fMRI signal changes are correlated with working memory load. Neuroreport 8:545-9, 1997.

Manuel A L, David A W, Bikson M, Schnider A. Frontal tDCS modulates orbitofrontal reality filtering. Neuroscience 2014; 264:21-27 Journal Link.

Marconi, Pier Luigi, et al. "The phase amplitude coupling to assess brain network system integration." Medical Measurements and Applications (MeMeA), 2016 IEEE International Symposium on. IEEE, 2016;

Marco-Pallares J, et al. (2008) Human oscillatory activity associated to reward processing in a gambling task. Neuropsychologia 46:241-248.

Marcora S M, Staiano W, & Manning V (2009) Mental fatigue impairs physical performance in humans. Journal of Applied Physiology 106:857-864.

Martinez-del-Rincon, J., M. Lewandowski, J.-C. Nebel and D. Makris, Generalized Laplacian Eigenmaps for Modeling and Tracking Human Motions, IEEE Transactions on Cybernetics, 44 (9), pp 1646-1660, 2014.

Marzi, C. A., Miniussi, C., Maravita, A., Bertolasi, L., Zanette, G., Rothwell, J. C., Sanes, J. N., 1998. Transcranial magnetic stimulation selectively impairs interhemispheric transfer of visuo-motor information in humans. Experimental Brain Research 118, 435-438.

Masquelier, T., Thorpe, S. J., 2007. Unsupervised learning of visual features through spike timing dependent plasticity. PLOS Computational Biology 3, e31.

Matlab Wavelet Toolbox, www.mathworks.com/products/wavelet.html.

McCarthy, G., Luby, M., Gore, J. and Goldman-Rakic, P., Infrequent events transiently activate human prefrontal and parietal cortex as measured by functional MRI. J. Neurophysiology 77:1630-1634, 1997.

Mcfetridge, Grant. "Room temperature superconductor." U. S. Pub. application No. 20020006875.

Mckeown, M. J., Tzyy-Ping Jung, Scott Makeig, Greg Brown, Sandra S. Kindermann, Te-Won Lee and Terrence J. Sejnowski, Spatially independent activity patterns in functional magnetic resonance imaging data during the Stroop color-naming task, Proc. Natl. Acad. Sci USA, 95:803-810, 1998c.

Mckeown, M., Makeig, S., Brown, G., Jung, T-P., Kindermann, S., Bell, Iragui, V. and Sejnowski, T. J., Blind separation of functional magnetic resonance imaging (fMRI) data, Human Brain Mapping, 6:160,18, 1998a.

Mckeown, M. J. and Sejnowski, T. J., Independent component analysis of fMRI data: examining the assumptions. Human Brain Mapping 6:368-372, 1998d.

Mckeown, M. J., Humphries, C., Achermann, P., Borbely, A. A. and Sejnowski, T. J., A new method for detecting state changes in the EEG: exploratory application to sleep data. J. Sleep Res. 7 suppl. 1:48-56, 1998b.

Mclaren, Elgin-Skye, and Alissa N. Antle. "Exploring and Evaluating Sound for Helping Children Self-Regulate with a Brain-Computer Application." Proceedings of the 2017 Conference on Interaction Design and Children. ACM, 2017;

Medina J, Beauvais J, Datta A, Bikson M, Coslett H B, Hamilton R H. Transcranial direct current stimulation accelerates allocentric target detection. Brain Stimulation. 2012; 6 (3) 433-9 Journal Link.

Mehmetali Gülpınar, Berrak (Yeğen, "The Physiology of Learning and Memory: Role of Peptides and Stress", Current Protein and Peptide Science, 2004 (5).

Meiron O, Gale R, Namestnic J, Bennet-Back O, Davia J, Gebodh N, Adair D, Esmaeilpour Z, Bikson M. High-Definition transcranial direct current stimulation in early onset epileptic encephalopathy: a case study. Brain Inj. 2017 Nov. 20. doi: 10.1080/02699052.2017.1390254.

Mendonca M E, Santana M B, Baptista A F, Datta A, Bikson M, Fregni D, Araujo C P. Transcranial D C Stimulation in Fibromyalgia: Optimized cortical target supported by high-resolution computational models. Journal of Pain. 2011; 12 (5): 610-617 (Cover).

Merrill D, Bikson M, Jefferys J G R. Electrical stimulation of excitable tissue: design of efficacious and safe protocols. Journal of J. Neuroscience Methods. 2005; 141:171-198.

Michael A. Nitsche, and Armin Kibele. "Noninvasive brain stimulation and neural entrainment enhance athletic performance—a review." J. Cognitive Enhancement 1.1 (2017): 73-79.

Mikhail Belkin and Partha Niyogi, Laplacian Eigenmaps and Spectral Techniques for Embedding and Clustering, Advances in Neural Information Processing Systems 14, 2001, p. 586-691, MIT Press.

Mikhail Belkin Problems of Learning on Manifolds, PHD Thesis, Department of Mathematics, The University Of Chicago, August 2003

Mikhail Belkin Problems of Learning on Manifolds, PHD Thesis, Department of Mathematics, The University Of Chicago, August 2003

Miltner W H R, Braun C H, & Coles M G H (1997) Event-related brain potentials following incorrect feedback in a time-estimation task: evidence for a "generic" neural system for error detection. Journal of Cognitive Neuroscience 9:788-798.

MindMaze, scottamyx.com/2017/10/13/looxid-labs-vr-brain-waves-human-emotions/.

Minhas P, Bikson M, Woods A, Rosen A, Kessler S. Transcranial Direct Current Stimulation in Pediatric Brain: A computational modeling study. 859-62. doi: 10.1109/EMBC.2012.6346067. Conf Proc IEEE Eng Med Biol Soc. 2012; Free PMIC Minhas P, Datta A, Bikson M. Cutaneous perception during tDCS: Role of electrode shape and sponge salinity. Clinical Neurophysiology. 2011; 122:637-638.

Minhas P, Patel J, Bansal V, Ho J, Datta A, Bikson M. Electrodes for high-definition transcutaneous DC stimulation for applications in drug-delivery and electrotherapy, including tDCS. Journal of Neuroscience Methods. 2010; 190 (2): 188-97.

Miniussi, C., Brignani, D., Pellicciari, M. C., 2012a. Combining transcranial electrical stimulation with electroencephalography: a multimodal approach. Clin. EEG and Neuroscience 43, 184-191.

Miniussi, C., Paulus, W., Rossini, P. M., 2012b. Transcranial Brain Stimulation. CRC Press, Boca Raton, FL.

Miniussi, C., Ruzzoli, M., Walsh, V., 2010. The mechanism of transcranial magnetic stimulation in cognition. Cortex 46, 128-130.

Miskovic V, Schmidt L A (2010) Cross-regional cortical synchronization during affective image viewing. Brain Res 1362:102-111.

Mitra P P, Ogawa S, Hu X, Ugurbil K, The nature of spatiotemporal changes in cerebral hemodynamics as manifested in functional magnetic resonance imaging. Magn Reson Med. 37:511-8, 1997.

Mitrano, Matteo, et al. "Possible light-induced superconductivity in K3C60 at high temperature." Nature 530.7591 (2016): 461-464;

Moisa, Marius, et al. "Brain network mechanisms underlying motor enhancement by transcranial entrainment of gamma oscillations." J. Neuroscience 36.47 (2016): 12053-12065.

Moliadze, V., Zhao, Y., Eysel, U., Funke, K., 2003. Effect of transcranial magnetic stimulation on single-unit activity in the cat primary visual cortex. J. Physiology 553, 665-679.

Molinaro, Nicola, et al. "Out-of-synchrony speech entrainment in developmental dyslexia." Human brain mapping 37.8 (2016): 2767-2783;

Moreno-Duarte I, Gebodh N, Schestatsky P, Guleyupoglu B, Reato D, Bikson M, Fregni F. Transcranial Electrical Stimulation: transcranial Direct Current Stimulation (tDCS), transcranial Alternating Current Stimulation (tACS), transcranial Pulsed Current Stimulation (tPCS), and Transcranial Random Noise Stimulation (tRNS). The Stimulated Brain 2014; (ed. R Cohen Kadosh). Elsevier ISBN 9780124047044, Chapter 2, p. 35-60.

Moreno-Duarte I, Morse L, Alam M, Bikson M, Zafonte R, Fregni F. Targeted therapies using electric and magnetic neural stimulation for the treatment of chronic pain in spinal cord injury. Neuroimage2013; 85 (3) 1003-1013.

Mori, Toshio, and Shoichi Kai. "Noise-induced entrainment and stochastic resonance in human brain waves." Physical review letters 88.21 (2002): 218101;

Mortazavi, S. M. J., Zahraei-Moghadam, S. M., Masoumi, S., Rafati, A., Haghani, M., Mortazavi, S. A. R., & Zehtabian, M. (2017). Short Term Exposure to Binaural Beats Adversely Affects Learning and Memory in Rats. Journal of Biomedical Physics and Engineering.

Moseley, Ralph. "Immersive brain entrainment in virtual worlds: actualizing meditative states." Emerging Trends and Advanced Technologies for Computational Intelligence. Springer International Publishing, 2016. 315-346;

Moss, F., Ward, L. M., Sannita, W. G., 2004. Stochastic resonance and sensory information processing: a tutorial and review of application. Clin. Neurophysiology 115, 267-281.

Mottaghy, F. M., Gangitano, M., Krause, B. J., Pascual-Leone, A., 2003. Chronometry of parietal and prefrontal activations in verbal working memory revealed by transcranial magnetic stimulation. Neuroimage 18, 565-575.

Mourachkine, Andrei. Room-temperature superconductivity. Cambridge Int Science Publishing, 2004;

Mourdoukoutas A P, Truong D Q, Adair D K, Simon B, Bikson M. High-Resolution Multi-Scale Computational Model for Non-Invasive Cervical Vagus Nerve Stimulation. Neuromodulation 2017. doi: 10.1111/ner/12706.

Murugappan M, Nagarajan R, Yaacob S (2010) Classification of human emotion from EEG using discrete wavelet transform. J Biomed Sci Eng 3:390-396;

Murugappan M, Nagarajan R, Yaacob S (2011) Combining Spatial Filtering and Wavelet Transform for Classifying Human Emotions Using EEG Signals. J Med. Bio. Eng. 31:45-51.

Nachmias, J., Sansbury, R. V., 1974. Grating contrast: discrimination may be better than detection. Vision Research 14, 1039-1042.

Narlikar, Anant V., ed. High Temperature Superconductivity 2. Springer Science & Business Media, 2013;

Nature Neuroscience, DOI: 10.1038/nn.4450.

Neuling, Toralf, et al. "Friends, not foes: magnetoencephalography as a tool to uncover brain dynamics during transcranial alternating current stimulation." Neuroimage 118 (2015): 406-413;

New Scientist, Dec. 5, 2016 (www.newscientist.com/article/2115093-our-brains-record-and-remember-things-in-exactly-the-same-way/).

Niedermeyer E and Lopes da Silva F H (Eds) (2005) Electroencephalography. Basic Principals, Clin. Applications, and Related Fields. Fifth Edition. 5th Ed London: Williams and Wilkins.

Nitsche M, Bikson M, Bestmann S. On the use of meta-analysis in neuromodulatory non-invasive brain stimulation. Brain Stimul. 2015 May-June; 8 (3): 666-7. doi: 10.1016/j.brs.2015.03.008.

Nitsche M. Bikson M. Extending the parameter range for tDCS: Safety and tolerability of 4 mA stimulation. Brain Stimul. May-June 2017; 10 (3): 541-542. doi: 10.1016/j.brs.2017.03.002.

Nitsche, M. A., Cohen, L. G., Wassermann, E. M., Priori, A., Lang, N., Antal, A., Paulus, W., Hummel, F., Boggio, P. S., Fregni, F., Pascual-Leone, A., 2008. Transcranial direct current stimulation: state of the art 2008. Brain Stimulation 1, 206-223.

Nitsche, M. A., Liebetanz, D., Lang, N., Antal, A., Tergau, F., Paulus, W., 2003a. Safety criteria for transcranial direct current stimulation (tDCS) in humans. Clin. Neurophysiology 114, 2220-2222, author reply 2222-2223.

Nitsche, M. A., Niehaus, L., Hoffmann, K. T., Hengst, S., Liebetanz, D., Paulus, W., Meyer, B. U., 2004. MRI study of human brain exposed to weak direct current stimulation of the frontal cortex. Clin. Neurophysiology 115, 2419-2423.

Nitsche, M. A., Nitsche, M. S., Klein, C. C., Tergau, F., Rothwell, J. C., Paulus, W., 2003b. Level of action of cathodal D C polarisation induced inhibition of the human motor cortex. Clin. Neurophysiology 114, 600-604.

Nitsche, M. A., Paulus, W., 2000. Excitability changes induced in the human motor cortex by weak transcranial direct current stimulation. J. Physiology 527 (Pt 3), 633-639.

Nitsche, M. A., Paulus, W., 2011. Transcranial direct current stimulation-update 2011. Restorative Neurology and Neuroscience 29, 463-492.

Nitsche, M. A., Seeber, A., Frommann, K., Klein, C. C., Rochford, C., Nitsche, M. S., Fricke, K., Liebetanz, D., Lang, N., Antal, A., Paulus, W., Tergau, F., 2005. Modulating parameters of excitability during and after transcranial direct current stimulation of the human motor cortex. J. Physiology 568, 291-303.

Nobre A C, Sebestyen G N, Gitelman D R, Mesulam M M, Frackowiak R S, Frith C D, Functional localization of the system for visuospatial attention using positron emission tomography. Brain 120:515-33, 1997.

Notbohm, Annika, Jürgen Kurths, and Christoph S. Herrmann. "Modification of brain oscillations via rhythmic light stimulation provides evidence for entrainment but not for superposition of event-related responses." Frontiers in human neuroscience 10 (2016);

Noury N, Hipp J F, Siegel M (2016) Physiological processes non-linearly affect electrophysiological recordings during transcranial electric stimulation. Neuroimage 140:99-109.

Nowogrodzki, Anna, "Mind-reading tech helps beginners quickly learn to play Bach." New Scientist, 9 Feb. 2016 available online at www.newscientist.com/article/2076899-mind-reading-tech-helps-beginners-quickly-learn-to-play-bach/.

Nozaradan, S., et al. "P943: Neural entrainment to musical rhythms in the human auditory cortex, as revealed by intracerebral recordings." Clin. Neurophysiology 125 (2014): S299;

Nunez P L (1989) Generation of human EEG by a combination of long and short range neocortical interactions. Brain Topography 1:199-215.

Nunez P L (1995) Neocortical Dynamics and Human EEG Rhythms. N Y: Oxford U. Press.

Nunez P L (2000) Neocortical dynamic theory should be as simple as possible, but not simpler (Response to 18 commentaries on target article), Behavioral and Brain Sciences 23:415-437.

Nunez P L (2000) Toward a large-scale quantitative description of neocortical dynamic function and EEG (Target article), Behavioral and Brain Sciences 23:371-398.

Nunez P L (2002) EEG. In V S Ramachandran (Ed) Encyclopedia of the Human Brain, La Jolla: Academic Press, 169-179.

Nunez P L and Silberstein R B (2001) On the relationship of synaptic activity to macroscopic measurements: Does co-registration of EEG with fMRI make sense? Brain Topog. 13:79-96.

Nunez P L and Srinivasan R (2006) A theoretical basis for standing and traveling brain waves measured with human EEG with implications for an integrated consciousness. Clin. Neurophysiology 117:2424-2435.

Nunez P L and Srinivasan R (2006) Electric Fields of the Brain: The Neurophysics of EEG, 2nd Edition, N Y: Oxford U. Press.

Nunez P L, Srinivasan R, Westdorp A F, Wijesinghe R S, Tucker D M, Silberstein R B, and Cadusch P J (1997) EEG coherency I: Statistics, reference electrode, volume conduction, Laplacians, cortical imaging, and interpretation at multiple scales. Electroencephalography and Clin. Neurophysiology 103:516-527.

Nunez P L. Wingeier B M and Silberstein R B (2001) Spatial-temporal structures of human alpha rhythms: theory, micro-current sources, multiscale measurements, and global binding of local networks, Human Brain Mapping 13:125-164.

Nunez, P. L., Electric Fields of the Brain. New York: Oxford, 1981.

Nunez, Paul L., and Ramesh Srinivasan (2007) Electroencephalogram. Scholarpedia, 2 (2): 1348, scholarpedia.org/article/Electroencephalogram.

Nuwer M (1997) Assessment of digital EEG, quantitative EEG, and EEG brain mapping: report of the American Academy of Neurology and the American Clin. Neurophysiology Society. Neurology 49:277-292.

Ogawa S, Tank D W, Menon R, Ellermann J M, Kim S G, Merkle H, Ugurbil K, Intrinsic signal changes accompanying sensory stimulation: functional brain mapping with magnetic resonance imaging. Proc Natl Acad Sci USA 89:5951-5, 1992.

Okano A H, Fontes E B, Montenegro R A, Farinatti P V, Cyrino E S, Min L L, Bikson M, Noakes T D. Brain stimulation modulates the autonomic nervous system, rating of perceived exertion and performance during maximal exercise. British Journal of Sports Medicine 2013; epub.

Oostenveld R, Fries P, Maris E, & Schoffelen J M (2011) FieldTrip: Open source software for advanced analysis of MEG, EEG, and invasive electrophysiological data. Computational Intelligence and Neuroscience 2011:1-9.

Oster, G (October 1973). "Auditory beats in the brain". Scientific American. 229 (4): 94-102. See:

Owen A M, et al. (2010) Putting brain training to the test. Nature 465:775-778.

Padmanabhan, R., A. J. Hildreth, and D. Laws. "A prospective, randomised, controlled study examining binaural beat audio and pre-operative anxiety in patients undergoing general anaesthesia for day case surgery." Anaesthesia 60.9 (2005): 874-877;

Palaniappan, Ramaswamy, et al. "Improving the feature stability and classification performance of bimodal brain and heart biometrics." Advances in Signal Processing and Intelligent Recognition Systems. Springer, Cham, 2016. 175-186;

Palaniappan, Ramaswamy, Somnuk Phon-Amnuaisuk, and Chikkannan Eswaran. "On the binaural brain entrainment indicating lower heart rate variability." Int. J. Cardiol 190 (2015): 262-263;

Paneri B, Adair D, Thomas C, Khadka N, Patel V, Tyler W J, Parra L, Bikson M. Tolerability of Repeated Application of Transcranial Electrical Stimulation with Limited Outputs to Healthy Subjects. Brain Stimul. 2016 September-October; 9 (5): 740-54. doi: 10.1016/j.brs.2016.05.008.

Panksepp J (2007) Neurologizing the Psychology of Affects How Appraisal-Based Constructivism and Basic Emotion Theory Can Coexist. Perspect Psychol Sci 2:281-296.

Papagiannakis, G., et al. A virtual reality brainwave entrainment method for human augmentation applications. Technical Report, FORTH-ICS/TR-458, 2015;

Park, Hyojin, et al. "Frontal top-down signals increase coupling of auditory low-frequency oscillations to continuous speech in human listeners." Current Biology 25.12 (2015): 1649-1653;

Pascual-Leone, A., Walsh, V., Rothwell, J., 2000. Transcranial magnetic stimulation in cognitive neuroscience-virtual lesion, chronometry, and functional connectivity. Current Opinion in Neurobiology 10, 232-237.

Pascual-Marqui R I) (2002) Standardized low-resolution brain electromagnetic tomography (sLORETA): technical details. Methods & Findings in Experimental & Clinical Pharmacology 24:5-12.

Pasley, B. N., Allen, E. A., Freeman, R. D., 2009. State-dependent variability of neuronal responses to transcranial magnetic stimulation of the visual cortex. Neuron 62, 291-303.

Pasley, Brian, Frontiers in Neuroengineering, doi.org/whb.

Pau W, Shaw M, Dobbs B, Kasschau M, Frontario A, Bikson M, Datta A, Charvet L. Conference proceedings: Mood Improvement with Transcranial Direct Current Stimulation (tDCS) is Specific to Positive vs. Negative Affect in Multiple Sclerosis. Brain Stimul. July-August 2017; 10 (4): e58-e59. doi: doi.org/10.1016/j.brs.2017.04.104.

Paulus W (2010) On the difficulties of separating retinal from cortical origins of phosphenes when using transcranial alternating current stimulation (tACS). Clinical Neurophysiology 121:987-991.

Paulus, W., 2011. Transcranial electrical stimulation (tES-tDCS; tRNS, tACS) methods. Neuropsychological Rehabilitation 21, 602-617.

Pawel Stepien, Wlodzimierz Klonowski and Nikolay Suvorov (Nonlinear analysis of EEG in chess players, EPJ Nonlinear Biomedical Physics 20153:1.

Pawlak N, Agarwal S, Biagioni M, Bikson M, Datta A, Charvet L E. Conference proceedings: Remotely-supervised Transcranial Direct Current Stimulation (RS-tDCS) for Parkinson's Disease (PD) Clinical Trials: Guidelines and Feasibility. Brain Stimul. July-August 2017; 10 (4): e59-e60. doi: doi.org/10.1016/j.brs.2017.04.105.

Pearlmutter, B. and Parra, L. C., Maximum likelihood blind source separation: a context-sensitive generalization of ICA. In: M. C. Mozer, M. I. Jordan and T. Petsche (Eds.), Advances in Neural Information Processing Systems 9:613-619 MIT Press, Cambridge, M A, 1996.

Penfield W and Jasper H D (1954) Epilepsy and the Functional Anatomy of the Human Brain. London: Little, Brown and Co.

Pérez, Alejandro, Manuel Carreiras, and Jon Andoni Duñabeitia. "Brain-to-brain entrainment: EEG interbrain synchronization while speaking and listening." Scientific Reports 7 (2017);

Peterchev A V, Wagner T M, Miranda P C, Nitsche M A, Paulus W, Lisanby S G, Pascual-Leone A, Bikson M. Fundamentals of transcranial electric and magnetic stimulation dose: definition, selection, and reporting practices. Brain Stimulation 2012; 5:435-53.

Pickett, Warren E. "Design for a room-temperature superconductor." J. superconductivity and novel magnetism 19.3 (2006): 291-297;

Pikovsky A S, Kurths J (1997) Coherence resonance in a noise-driven excitable system. Physical Review Letters 78:775-778.

pinktentacle.com/2008/12/scientists-extract-images-directly-from-brain/Scientists extract images directly from brain.

Plewnia, C., Rilk, A. J., Soekadar, S. R., Arfeller, C., Huber, H. S., Sauseng, P., Hummel, F., Gerloff, C., 2008. Enhancement of long-range EEG coherence by synchronous bifocal transcranial magnetic stimulation. European J. Neuroscience 27, 1577-1583.

Pogosyan, A., Gaynor, L. D., Eusebio, A., Brown, P., 2009. Boosting cortical activity at Beta-band frequencies slows movement in humans. Current Biology 19, 1637-1641.

Poreisz C, Boros K, Antal A, & Paulus W (2007) Safety aspects of transcranial direct current stimulation concerning healthy subjects and patients. Brain Research Bulletin 72 (4-6): 208-214.

Potts G F, Dien J, Hartry-Speiser A L, McDougal L. M, Tucker D M. Dense sensor array topography of the event-related potential to task-relevant auditory stimuli. Electroencephalography and clinical neurophysiology 1998; 106:444-456.

Pratt, H., Starr, A., Michalewski, H. J., Dimitrijevic, A., Bleich, N., & Mittelman, N. (2009). Cortical evoked potentials to an auditory illusion: binaural beats. Clinical Neurophysiology, 120 (8), 1514-1524;

Pratt, H., Starr, A., Michalewski, H. J., Dimitrijevic, A., Bleich, N., & Mittelman, N. (2010). A comparison of auditory evoked potentials to acoustic beats and to binaural beats. Hearing research, 262 (1), 34-44;

Priori, A., Berardelli, A., Rona, S., Accornero, N., Manfredi, M., 1998. Polarization of the human motor cortex through the scalp. Neuroreport 9, 2257-2260.

Rabau S, Shekhawat G S, Aboseria M, Griepp D, Rompaey V V, Bikson M, de Heyning P V. Comparison of the long-term effect of positioning the cathode in tDC'S in tinnitus patients. Front. Aging Neurosci. 2107 Jul. 28; 9 (217). doi: 10.3389/fnagi.2017.00217.

Radman T, Ramos R L, Brumberg J C, Bikson M. Role of cortical cell type and morphology in sub- and suprathreshold uniform electric field stimulation. Brain Stimulation. 2009; 2 (4): 215-228.

Radman T, Su Y, An J H, Parra L., Bikson M. Spike timing amplifies the effect of electric fields on neurons: Implications for endogenous field effects Journal of Neuroscience. 2007; 27:3030-3036.

Radman, T., Datta, A., Peterchev, A. V., 2007. In vitro modulation of endogenous rhythms by AC electric fields: syncing with clinical brain stimulation. J. Physiology 584, 369-370.

Rahman A, Bikson M. Origins of specificity during tDC'S: anatomical, activity-selective, and input-bias mechanisms Frontiers of Human Neuroscience 2013; doi 10.3389/fnhum.2013.00688 Journal Link.

Rahman A, Lafon B, Bikson M. Multilevel computational models for predicting the cellular effects of noninvasive brain stimulation. Prog Brain Res. 2015; 222:25-40. doi: 10.1016/bs.pbr.2015.09.003.

Rahman A, Lafon B, Parra L C, Bikson M. Direct current stimulation boosts synaptic gain and cooperativity in vitro. J Physiol. 2017 Feb. 13; 595 (11): 3535-3547. doi: 10.1113/JP273005.

Rahman A, Reato D, Arlotti M, Gasca F, Datta A, Parra L C, Bikson M. Cellular Effects of Acute Direct Current Stimulation: Somatic and Synaptic Terminal Effects. Journal of Physiology 2013; 591.10: 2563-2578.

Rahman A, Toshev P L, Bikson M. Polarizing cerebellar neurons with transcranial Direct Current Stimulation Clinical Neurophysiology 2014; 125:435-438

Rahnev, D. A., Maniscalco, B., Luber, B., Lau, H., Lisanby, S. H., 2012. Direct injection of noise to the visual cortex decreases accuracy but increases decision confidence. J. Neurophysiology 107, 1556-1563.

Raichle M E & Mintun M A (2006) Brain work and brain imaging. Annual Review of Neuroscience 29:449-476.

Rawji V, Ciocca M, Zacharia A, Soares D, Truong D, Bikson M, Rothwell J, Bestmann S. tDCS changes in motor excitability are specific to orientation of current flow. Brain Stimul 2017 Nov. 2. doi: 10.1016/j.brs.2017.11.001.

Reato D, Bikson M. Parra L. Lasting modulation of in-vitro oscillatory activity with weak direct current stimulation. J Neurophysiol. 2015 Mar. 1; 113 (5): 1334-41. doi: 10.1152/jn.00208.2014. Journal Link Reato D, Gasca F, Datta, A, Bikson M, Marshall L., Parra L. C. Transcranial electrical stimulation accelerates human sleep homeostasis. PLOS Computational Biology 2013; 9 (2): e1002898. doi: 10.1371/journal.pcbi.1002898 LINK.

Reato D, Rahman A, Bikson M, Parra L C. Effects of weak transcranial Alternating Current Stimulation on brain activity—a review of known mechanisms from animal studies. Frontiers of Human Neuroscience 2013; doi 10.3389/fnhum.2013.00687. Journal Link Reato, D., Rahman, A., Bikson, M., Parra, L. C., 2010. Low-intensity electrical stimulation affects network dynamics by modulating population rate and spike timing. J. Neuroscience 30, 15067-15079.

Reedijk, S. A., Bolders, A., & Hommel, B. (2013). The impact of binaural beats on creativity. Frontiers in human neuroscience, 7, 187

Reinhart R M G & Woodman G F (2014) Causal control of medial-frontal cortex governs electrophysiological and behavioral indices of performance monitoring and learning. Journal of Neuroscience 34 (12): 4214-4227.

Reinhart R M G & Woodman G F (2015) Enhancing long-term memory with stimulation tunes visual attention in one trial. Proceedings of the National Academy of Sciences of the USA 112 (2): 625-630.

Reinhart R M G, Cosman J D, Fukuda K, & Woodman G F (2017) Using transcranial direct-current stimulation (DCS) to understand cognitive processing. Attention, Perception & Psychophysics 79 (1): 3-23.

Reinhart R M G, Woodman G F (2014) Oscillatory coupling reveals the dynamic reorganization of large-scale neural networks as cognitive demands change. J Cogn Neurosci 26:175-188.

Reinhart R M G, Xiao W, McClenahan L, & Woodman G F (2016) Electrical stimulation of visual cortex can immediately improve spatial vision. Current Biology 25 (14): 1867-1872.

Reinhart R M G, Zhu J, Park S, & Woodman G F (2015) Medial-frontal stimulation enhances learning in schizophrenia by restoring prediction-error signaling. Journal of Neuroscience 35 (35): 12232-12240.

Reinhart R M G, Zhu J, Park S, & Woodman G F (2015) Synchronizing theta oscillations with direct-current stimulation strengthens adaptive control in the human brain. Proceedings of the National Academy of Sciences of the USA 112 (30): 9448-9453.

Reinhart, Robert M G. "Disruption and rescue of interareal theta phase coupling and adaptive behavior." Proceedings of the National Academy of Sciences 14 (43), 11542-11547 (2017).

Richardson J D, Fillmore P, Datta A, Truong D, Bikson M, Fridriksson J. Toward Development of Sham Protocols for High-Definition Transcranial Direct Current Stimulation (HD-tDCS). NeuroRegulation2014; 1 (1) p. 62-72 doi: 10.15540/nr.2014.1.1.62.

Ridderinkhof K R, Ullsperger M, Crone E A, & Nieuwenhuis S (2004) The role of the medial frontal cortex in cognitive control. Science 306:443-447.

Ridding, M. C., Ziemann, U., 2010. Determinants of the induction of cortical plasticity by non-invasive brain stimulation in healthy subjects. J. Physiology 588, 2291-2304.

Riecke, Lars, Alexander T. Sack, and Charles E. Schroeder. "Endogenous delta/theta sound-brain phase entrainment accelerates the buildup of auditory streaming." Current Biology 25.24 (2015): 3196-3201;

Robinson C, Armenta M, Combs A, Lamphere M, Garza G, Neary J, Wolfe J, Molina E, Semey D, McKee C, Gallegos S, Jones A, Trumbo M C, Al-Azzawi H, Hunter M, lieberman G, Coffman B A, Aboseria M, Bikson M, Clark V P, Witkiewitz K. Modulating affective experience and emotional intelligence with loving kindness meditation and transcranial direct current stimulation: A pilot study. Soc Neurosci. 2017. doi: 10.1080/17470919.2017.1397054.

Robinson P A, Rennie C J, Rowe D L and O'Conner S C (2004) Estimation of multiscale neurophysiologic parameters by electroencephalographic means. Human Brain Mapping 23:53-72.

Rodriguez E, George N, Lachaux J P, Martinerie J, Renault B, Varela F J. Perception's shadow: long-distance synchronization of human brain activity. Nature. 1999; 397: 430-433, Rosanova, M., Casali, A., Bellina, V., Resta, F., Mariotti, M., Massimini, M., 2009. Natural frequencies of human corticothalamic circuits. J. Neuroscience 29, 7679-7685.

Rosler F, Manzey D. Principal components and varimax-rotated components in event-related potential research: some remarks on their interpretation. Biological psychology 1981; 13:3-26.

Rosman G., Bronstein M. M., Bronstein A. M. and Kimmel R., Nonlinear Dimensionality Reduction by Topologically Constrained Isometric Embedding, International Journal of Computer Vision, Volume 89, Number 1, 56-68, 2010.

Rossi, S., Hallett, M., Rossini, P. M., Pascual-Leone, A., Safety of TMS Consensus Group, 2009. Safety, ethical considerations, and application guidelines for the use of transcranial magnetic stimulation in clinical practice and research. Clin. Neurophysiology 120, 2008-2039.

Roth, B. J., 1994. Mechanisms for electrical stimulation of excitable tissue. Critical Reviews in Biomedical Engineering 22, 253-305.

Rothwell, J. C., Day, B. L., Thompson, P. D., Dick, J. P., Marsden, C. D., 1987. Some experiences of techniques for stimulation of the human cerebral motor cortex through the scalp. Neurosurgery 20, 156-163.

Roweis, S. T., L. K. Saul, Nonlinear Dimensionality Reduction by Locally Linear Embedding, Science Vol 290, 22 Dec. 2000, 2323-2326.

Ruchkin D S, McCalley M G, Glaser E M. Event related potentials and time estimation. Psychophysiology 1977; 14:451-455.

Ruffini, Giulio. "Application of the reciprocity theorem to EEG inversion and optimization of EEG-driven transcranial current stimulation (tCS, including tDCS, tACS, tRNS)." arXiv preprint arXiv: 1506.04835 (2015).

Ruohonen, J., 2003. Background physics for magnetic stimulation. Supplements to Clin. Neurophysiology 56, 3-12.

Ruzzoli, M., Abrahamyan, A., Clifford, C. W., Marzi, C. A., Miniussi, C., Harris, J. A., 2011. The effect of TMS on visual motion sensitivity: an increase in neural noise or a decrease in signal strength. J. Neurophysiology 106, 138-143.

Ruzzoli, M., Marzi, C. A., Miniussi, C., 2010. The neural mechanisms of the effects of transcranial magnetic stimulation on perception. J. Neurophysiology 103, 2982-2989.

Sabatier R. (1993) Critères et contraintes pour l'ordination simultanée de K tableaux, Biométrie et Environement, Masson, 332.

Sack, A. T., Linden, D. E., 2003. Combining transcranial magnetic stimulation and functional imaging in cognitive brain research: possibilities and limitations. Brain Research: Brain Research Reviews 43, 41-56.

Sahai, Amit, and Brent Waters. "Fuzzy identity-based encryption." In Annual International Conference on the Theory and Applications of Cryptographic Techniques, pp. 457-473. Springer, Berlin, Heidelberg, 2005.

Sakai K, Hikosaka O, Miyauchi S, Takino R, Sasaki Y, Putz B. Transition of brain activation from frontal to parietal areas in visuomotor sequence learning. J Neurosci 18:1827-40, 1998.

Salinas E, Sejnowski T J (2001) Correlated neuronal activity and the flow of neural information. Nat Rev Neurosci 2:539-550.

Sandrini, M., Umilta, C., Rusconi, E., 2011. The use of transcranial magnetic stimulation in cognitive neuroscience: a new synthesis of methodological issues. Neuroscience and Biobehavioral Reviews 35, 516-536.

Santos-Pontelli T E, Rimoli B P, Favoretto D B, Mazin S C, Truong D Q, Leite J P, Pontes-Neto O M, Babyar S R, Reding M, Bikson M, Edwards D J. Polarity-Dependent Misperception of Subjective Visual Vertical during and after Transcranial Direct Current Stimulation (tDCS). PLOS One. 2016 Mar. 31; 11 (3): e0152331. doi: 10.1371/journal.pone.0152331.

Schalles, Matt D., and Jaime A. Pineda. "Musical sequence learning and EEG correlates of audiomotor processing." Behavioural neurology 2015 (2015). www.hindawi.com/journals/bn/2015/638202/.

Schambra H M, Bikson M, Wager T D, DosSantos M F, DaSilva A F. It's all in your head: reinforcing the placebo response with tDCS. Brain Stimulation 2014; 7 (4): 623-4 Letter-to-Editor.

Scheldrup M, Greenwood P M, McKendrick R, Strohl J, Bikson M, Alam A, Mckinley R A, Parasuraman R. Transcranial direct current stimulation facilitates cognitive multi-task performance differentially depending on anode location and subtask Front. Hum. Neurosci. 2014; DOI: 10.3389/fnhum.2014.00665 Free Online.

Scherg, M. & Von Cramon, D., Evoked dipole source potentials of the human auditory cortex. Electroencephalogr. Clin. Neurophysiol. 65:344-601, 1986.

Schestatsky, Pedro, Leon Morales-Quezada, and Felipe Fregni. "Simultaneous EEG monitoring during transcranial direct current stimulation." Journal of visualized experiments: JOVE 76 (2013).

Schlich P. (1995) Preference mapping: relating consumer preferences to sensory or instrumental measurements, in: Bioflavour, INRA, Dijon.

Schmidt L A, Trainor I. J (2001) Frontal brain electrical activity (EEG) distinguishes valence and intensity of musical emotions. Cognition Emotion 15:487-500;

Schnitzler A, Gross J (2005) Normal and pathological oscillatory communication in the brain. Nat Rev Neurosci 6:285-296.

Scholz, M. Kaplan, F. Guy, C. L. Kopka, J. Selbig, J., Non-linear PCA: a missing data approach, In Bioinformatics, Vol. 21, Number 20, pp. 3887-3895, Oxford University Press, 2005.

Schutter D J & Hortensius R (2010) Retinal origin of phosphenes to transcranial alternating current stimulation. Clinical Neurophysiology 121 (7): 1080-1084.

Schwarzkopf, D. S., Silvanto, J., Rees, G., 2011. Stochastic resonance effects reveal the neural mechanisms of transcranial magnetic stimulation. J. Neuro-science 31, 3143-3147.

Schwiedrzik, C. M., 2009. Retina or visual cortex? The site of phosphene induction by transcranial alternating current stimulation. Frontiers in Integrative Neuro-science 3, 6.

Sclar, G., Lennie, P., DePriest, D. D., 1989. Contrast adaptation in striate cortex of macaque. Vision Research 29, 747-755.

Scott A C (1995) Stairway to the Mind. New York: Springer-Verlag.

Sebastian R, Saxena S, Tsapkini K, Faria A V, Long C, Wright A, Davis C, Tippett D C, Mourdoukoutas A P, Bikson M, Celnik P, Hillis A. Cerebellar tDCS: A novel approach to augment language treatment post stroke. Front Hum Neurosci. 2017 Jan. 12; 10:695. doi: 10.3389/fnhum.2016.00695. Free online Seibt O, Brunoni A R, Huang Y, Bikson M. The Pursuit of DLPFC: Non-neuronavigated Methods to Target the Left Dorsolateral Pre-frontal Cortex With Symmetric Bicephalic Transcranial Direct Current Stimulation (tDCS). Brain Stimul. 2015 May-June; 8 (3): 590-602. doi: 10.1016/j.brs.2015.01.401.

Senco N M, Huang Y, D'Urso G, Parra L C, Bikson M, Mantovani A, Shavitt E G, Hoexter M Q, Miguel E C, Brunoni A. Transcranial direct current stimulation in obsessive-compulsive disorder: emerging clinical evidence and considerations for optimal montage of electrodes. Expert Rev Med Devices. 2015 July; 12 (4): 381-91. doi: 10.1586/17434440.2015.1037832.

Servais E L, Rizk N P, McGwyver L O, Rusch V W, Bikson M, Adusumilli P S. Real-time intraoperative detection of tissue hypoxia in gastrointestinal surgery by Wireless Pulse Oximetry (WiPOX). Surgical Endoscopy. 2010; 25 (5): 1383-9.

Seyal, M., Masuoka, L. K., Browne, J. K., 1992. Suppression of cutaneous perception by magnetic pulse stimulation of the human brain. Electroencephalography and Clin. Neurophysiology 85, 397-401.

Shachtman, Noah, Pentagon's PCs Bend to Your Brain www.wired.com/dangerroom/2007/03/the_us_military.

Shahid S S, Bikson M, Wen P, Ahfock T. The value and cost of complexity in predictive modelling: role of tissue anisotropic conductivity and fibre tracts in neuromodulation Journal of Neural Engineering 2014; 11 (3): 036002. doi: 10.1088/1741-2560/11/3/036002.

Shallice T, Gazzaniga M S (2004) The fractionation of supervisory control. The Cognitive Neuroscience (MIT Press, Cambridge, MA), pp 943-956.

Shapour Jaberzadeh, Andisheh Bastani, Maryam Zoghi, "Anodal transcranial pulsed current stimulation: A novel technique to enhance corticospinal excitability," Clin. Neurophysiology, Volume 125, Issue 2, February 2014, Pages 344-351, doi.org/10.1016/j.clinph.2013.08.025;

Shaw M, Dobbs B, Pawlak N, Pau W, Sherman K, Bikson M, Datta A, Kasschau M, Frontario A, Charvet L. Conference proceedings: Updated Safety and Tolerability of Remotely-Supervised Transcranial Direct Current Stimulation (RS-tDCS). Brain Stimul. July-August 2017; 10 (4): e60-e61. doi: doi.org/10.1016/j.brs.2017.04.106.

Shaw M T, Kasschau M, Dobbs B, Pawlak N, Pau W, Sherman K, Bikson M, Datta A, Charvet L E. Remotely Supervised Transcranial Direct Current Stimulation: An Update on Safety and Tolerability. J. Vis. Exp. 2017 Oct. 7. (128), e56211, doi: 10.3791/56211. Free Online Shekhawat G S, Sundram F, Bikson M, Truong D, Ridder D D, Kirk I, Stinear C M, Welch D, Searchfield G D. Intensity, Duration, and Location of High-Definition Transcranial Direct Current Stimulation for Tinnitus Relief. Neurorehabil Neural Repair. 2016 May; 30 (4): 349-59. doi: 10.1177/1545968315595286.

Shenhav A, Botvinick M M, & Cohen J D (2013) The expected value of control: An integrative theory of anterior cingulate cortex function. Neuron 79:217-240.

Shenhav A, Cohen J D, & Botvinick M M (2016) Dorsal anterior cingulate cortex and the value of control. Nature Neuroscience 19:1286-1291.

Shin J-H, Park D-H. (2011) Analysis for Characteristics of Electroencephalogram (EEG) and Influence of Environmental Factors According to Emotional Changes. In Lee G, Howard D, Ślęzak D, editors. Convergence and Hybrid Information Technology. Springer Berlin Heidelberg, 488-500.

Shuai J, Bikson M, Lian J, Hahn P J, Durand D M. Ionic mechanisms underlying spontaneous CA1 neuronal firing in Ca2+-Free Solution. Biophysical Journal 2003; 84:2099-111.

Siebner, H. R., Lang, N., Rizzo, V., Nitsche, M. A., Paulus, W., Lemon, R. N., Rothwell, J. C., 2004. Preconditioning of low-frequency repetitive transcranial magnetic stimulation with transcranial direct current stimulation: evidence for homeostatic plasticity in the human motor cortex. The J. Neuroscience 24, 3379-3385.

Siegel M, Donner T H, Engel A K (2012) Spectral fingerprints of large-scale neuronal interactions. Nat Rev Neurosci 13:121-134.

Silberstein R B, Danieli F and Nunez P L (2003) Fronto-parietal evoked potential synchronization is increased during mental rotation, NeuroReport 14:67-71.

Silberstein R B, Song J, Nunez P L and Park W (2004) Dynamic sculpting of brain functional connectivity is correlated with performance, Brain Topography 16:240-254.

Silvanto, J., Muggleton, N., Walsh, V., 2008. State-dependency in brain stimulation studies of perception and cognition. Trends in Cognitive Sciences 12, 447-454.

Silvanto, J., Muggleton, N. G., Cowey, A., Walsh, V., 2007. Neural adaptation reveals state-dependent effects of transcranial magnetic stimulation. Eur. J. Neuroscience 25, 1874-1881.

Sleight, Arthur W. "Room temperature superconductors." Accounts of chemical research 28.3 (1995): 103-108.

slices in vitro. Journal of Physiology. 2004; 557:175-190

Solomon, J. A., 2009. The history of dipper functions. Attention, Perception, and Psychophysics 71, 435-443.

Song W, Truong D, Bikson M, Martin J H. Trans-spinal direct current stimulation immediately modifies motor cortex sensorimotor maps. J Neurophysiol. 2015 Apr. 1; 113 (7): 2801-11. doi: 10.1152/jn.00784.2014.

Spaak, Eelke, Floris P. de Lange, and Ole Jensen. "Local entrainment of alpha oscillations by visual stimuli causes cyclic modulation of perception." J. Neuroscience 34.10 (2014): 3536-3544;

Spencer K M, Dien J, Donchin E. Spatiotemporal analysis of the late ERP responses to deviant stimuli. Psychophysiology 2001; 38:343-358.

Spencer K M, Nestor P G, Perlmutter R, et al. Neural synchrony indexes disordered perception and cognition in schizophrenia. Proc Natl Acad Sci USA. 2004; 101: 17288-17293;

Squires K C, Squires N K, Hillyard S A. Decision-related cortical potentials during an auditory signal detection task with cued observation intervals. Journal of experimental psychology 1975; 1:268-279.

Srinivasan R and Petrovic S (2006) MEG phase follows conscious perception during binocular rivalry induced by visual stream segregation. Cerebral Cortex, 16:597-608.

Srinivasan R, Nunez P L and Silberstein R B (1998) Spatial filtering and neocortical dynamics: estimates of EEG coherence. IEEE Trans. on Biomedical EngineeringBiomed. Eng., 45:814-825.

Srinivasan R, Russell D P, Edelman G M, and Tononi G (1999) Frequency tagging competing stimuli in binocular rivalry reveals increased synchronization of neuromagnetic responses during conscious perception. J. Neuroscience 19:5435-5448.

Srinivasan R, Winter W R, Ding J, & Nunez P L (2007) EEG and MEG coherence: measures of functional connectivity at distinct spatial scales of neocortical dynamics. Journal of Neuroscience Methods 166 (1): 41-52.

Stein, R. B., Gossen, E. R., Jones, K. E., 2005. Neuronal variability: noise or part of the signal? Nature Reviews Neuroscience 6, 389-397.

Stevenson, Daniel, "Intro to Transcranial Direct Current Stimulation (tDCS)" (Mar. 26, 2017) www.slideshare.net/DanielStevenson27/intro-to-transcranial-direct-current-stimulation-tdcs.

Su Y, Radman T, Vaynshteyn J, Parra L C, Bikson M. Effects of high-frequency stimulation on epileptiform activity in vitro: ON/OFF control paradigm. Epilepsia. 2008; 49:1586-93.

Sunderam S, Gluckman B, Reato D, Bikson M. Toward rational design of electrical stimulation strategies for epilepsy control. Epilepsy & Behavior. 2010; 17:6-22.

Sung, H. C., Lee, W. L., Li, H. M., Lin, C. Y., Wu, Y. Z., Wang, J. J., & Li, T. L. (2017). Familiar Music Listening with Binaural Beats for Older People with Depressive Symptoms in Retirement Homes. Neuropsychiatry, 7 (4);

Synthetic telepathy geeldon.wordpress.com/2010/09/06/synthetic-telepathy-also-known-as-techlepathy-or-psychotronics/.

T. Hastie, Principal Curves and Surfaces, Ph.D Dissertation, Stanford Linear Accelerator Center, Stanford University, Stanford, California, US, November 1984.

Tallon-Baudry, C., Bertrand, O., Delpuech, C., & Pernier, J., Stimulus Specificity of Phase-Locked and Non-Phase-Locked 40 Hz Visual Responses in Human. J. Neurosci. 16:4240-4249, 1996.

Tang Y, et al. (2010) Short term mental training induces white-matter changes in the anterior cingulate. Proceedings of the National Academy of Sciences Proc. Nat Acad. Sci 107:16649-16652.

Tang Y Y, et al. (2009) Central and autonomic nervous system interaction is altered by short term meditation. Proceedings of the National Academy of Sciences Proc Nat Acad Sci 106:8865-8870.

Taylor, D., Klimm, F., Harrington, H. A., Kramar, M., Mischaikow, K., Porter, M. A., & Mucha, P. J. (2015).

Topological data analysis of contagion maps for examining spreading processes on networks. Nature Communications, 6, 7723.

Teichmann M, Lesoil C, Godard J, Vernet M, Bertrand A, Levy R, Dubois B, Lemoine L, Truong D Q, Bikson M, Kas A, Valero-Cabré A. Direct current stimulation over the anterior temporal areas boosts primary aphasia. Ann Neurol. 2016 November; 80 (5): 693-707. doi: 10.1002/ana.24766.

Tenenbaum, J. and W. Freeman, Separating style and content with bilinear models, Neural Computation, vol. 12, 2000.

Tenenbaum, J. B., V. de Silva, J. C. Langford, A Global Geometric Framework for Nonlinear Dimensionality Reduction, Science 290, (2000), 2319-2323.

Terney, D., Chaieb, L., Moliadze, V., Antal, A., Paulus, W., 2008. Increasing human brain excitability by transcranial high-frequency random noise stimulation. J. Neuroscience 28, 14147-14155.

Thaker, Darshan D., Diana Franklin, John Oliver, Susmit Biswas, Derek Lockhart, Tzvetan Metodi, and Frederic T. Chong. "Characterization of error-tolerant applications when protecting control data." In Workload Characterization, 2006 IEEE International Symposium on, pp. 142-149. IEEE, 2006.

Thaut, Michael H. "The discovery of human auditory-motor entrainment and its role in the development of neurologic music therapy." Progress in brain research 217 (2015): 253-266;

Thaut, Michael H., David A. Peterson, and Gerald C. McIntosh. "Temporal entrainment of cognitive functions." Annals of the New York Academy of Sciences 1060.1 (2005): 243-254.

Thaut, Michael H., Gerald C. McIntosh, and Volker Hoemberg. "Neurobiological foundations of neurologic music therapy: rhythmic entrainment and the motor system." Frontiers in psychology 5 (2014);

The illustration is prepared using free software: E. M. Mirkes, Principal Component Analysis and Self-Organizing Maps: applet. University of Leicester, 2011

The International J. Sport and Society, vol 1, p 87

Thomson, Helen, "Hearing our inner voice", New Scientist, Oct. 29, 2014 (available online at www.newscientist.com/article/mg22429934-000-brain-decoder-can-eavesdrop-on-your-inner-voice/).

Thong Tri Vo, Nam Phuong Nguyen, Toi Vo Van, IFMBE Proceedings, vol. 63, pp. 621, 2018, ISSN 1680-0737, ISBN 978-981-10-4360-4.

Thrane G, Friborg O, Anke A, Indredavik B (2014) A meta-analysis of constraint-induced movement therapy after stroke. J Rehabil Med 46:833-842.

Thut, G. "T030 Guiding TMS by EEG/MEG to interact with oscillatory brain activity and associated functions." Clin. Neurophysiology 128.3 (2017): e9.

Thut, G., Miniussi, C., 2009. New insights into rhythmic brain activity from TMS-EEG studies. Trends in Cognitive Sciences 13, 182-189.

Thut, G., Miniussi, C., Gross, J., 2012. The functional importance of rhythmic activity in the brain. Current Biology 22, R658-R663.

Thut, G., Schyns, P. G., Gross, J., 2011a. Entrainment of perceptually relevant brain oscillations by non-invasive rhythmic stimulation of the human brain. Front. Psychology 2, 170.

Thut, G., Veniero, D., Romei, V., Miniussi, C., Schyns, P., Gross, J., 2011b. Rhythmic TMS causes local entrainment of natural oscillatory signatures. Current Biology 21, 1176-1185.

Thut, Gregor, Philippe G. Schyns, and Joachim Gross. "Entrainment of perceptually relevant brain oscillations by non-invasive rhythmic stimulation of the human brain." Frontiers in Psychology 2 (2011).

timesofindia.indiatimes.com/HealthSci/US_army_developing_synthetic_telepathy/.

Tomarken A J, Davidson R J, Henriques J B (1990) Resting frontal brain asymmetry predicts affective responses to films. J Pers Soc Psychol 59:791-801.) As suggested by Mauss and Robins (2009).

Toshev P, Guleyupoglu B, Bikson M. Informing dose design by modeling transcutaneous spinal direct current stimulation Clinical Neurophysiology 2014; S1388-2457 (14) 00174-6. doi: 10.1016/j.clinph.2014.03.022;

Towers, G. W. E. N. Category Archives: Targeted Individuals, io9.com/5065304/tips-and-tricks-for-mind-control-from-the-us-military.

Towers, G. W. E. N. Category Archives: Targeted Individuals, newdawnmagazine.com.au/Article/Brain_Zapping_Part_One.html.

Treviño, Guadalupe Villarreal, et al. "The Effect of Audio Visual Entrainment on Pre-Attentive Dysfunctional Processing to Stressful Events in Anxious Individuals." Open J. Medical Psychology 3.05 (2014): 364;

Tri Thong Vo, Phuong Nam Nguyen, Van Toi Vo, IFMBE Proceedings, vol. 61, pp. 67, 2017, ISSN 1680-0737, ISBN 978-981-10-4219-5.

Trost, Wiebke, et al. "Getting the beat: entrainment of brain activity by musical rhythm and pleasantness." NeuroImage 103 (2014): 55-64;

Truong D, Minhas P, Mokrejs A, Bikson M. A Role of Computational Modeling in Customization of Transcranial Direct Current Stimulation for Susceptible. Chapter in Textbook of Neuromodulation. (Helena Knotkova and Dirk Rasche ed.) Springer. ISBN: 978-1-4939-1407-4, 2015. Page 113-126.

Truong D, Minhas P, Nair A, Bikson M. Computational modeling assisted design of optimized and individualized transcranial Direct Current Stimulation protocols. The Stimulated Brain 2014; (ed. R Cohen Kadosh). Elsevier ISBN 9780124047044 Chapter 4, p. 85-116.

Truong D Q, Datta A, Xu J, Fregni F, Bikson M. Optimization of Prefrontal Cortex transcranial Direct Current Stimulation via a Combined High Definition and Conventional Electrode Montage: A FEM modeling studying. Conf Proc IEEE Eng Med Biol Soc. 2012; Slides:

Truong D Q, Huber M, Xie X, Datta A, Rahman A, Parra L C, Dmochowski J, Bikson M. Clinician accessible tools for GUI computational models of transcranial electrical stimulation: BONSAI and SPHERES. Brain Stimulation 2014; 7 (4): 521-4. doi: 10.1016/j.brs.2014.03.009.

Truong D Q, Magerowski G, Blackburn G L, Bikson M, Alonso-Alonso M. Computational modeling of transcranial direct current stimulation (tDCS) in obesity: impact of head fat and dose guidelines. Neuroimage Clinical 2013; 2:759-766.

Truong D Q, Magerowski G, Pascual-Leone A, Alonso-Alonso M, Bikson M. Finite Element Study of Skin and Fat Delineation in an Obese Subject for Transcranial Direct Current Stimulation. Conf Proc IEEE Eng Med Biol Soc. 2012; 6587-90. doi: 10.1109/ EMBC.2012.6347504.

Tsai, Shu-Hui, and Yue-Der Lin. "Autonomie feedback with brain entrainment." Awareness Science and Technology and Ubi-Media Computing (iCAST-UMEDIA), 2013 International Joint Conference on. IEEE, 2013;

Tulving E, Markowitsch H J, Craik F E, Habib R, Houle S, Novelty and familiarity activations in PET studies of memory encoding and retrieval. Cereb Cortex 6:71-9, 1996.

Turkeltaub P E, Benson J, Hamilton R H, Datta A, Bikson M, Coslett H B. Left lateralizing transcranial direct current improves reading efficiency. Brain Stimulation 2011; 5:201-7.

Uhl C (Ed) (1999) Analysis of Neurophysiological Brain Functioning. Berlin: Springer-Verlag.

Uhlhaas P J, Singer W (2006) Neural synchrony in brain disorders: Relevance for cognitive dysfunctions and pathophysiology. Neuron 52:155-168.

Uhlhaas P J, Singer W (2010) Abnormal neural oscillations and synchrony in schizophrenia. Nat Rev Neurosci 11:100-113.

Vallar, G., Bolognini, N., 2011. Behavioural facilitation following brain stimula-tion: implications for neurorehabilitation. Neuropsychological Rehabilitation 21, 618-649.

van Boxtel A, Boelhouwer A J, Bos A R. Optimal EMG signal bandwidth and interelectrode distance for the recording of acoustic, electrocutaneous, and photic blink reflexes. Psychophysiology 1998; 35:690-697.

van de Vijver I, Ridderinkhof K R, & Cohen M X (2011) Frontal oscillatory dynamics predict feedback learning and action adjustment. Journal of Cognitive Neuroscience 23:4106-4121.

van der Maaten, L. J. P.; Hinton, G. E. (November 2008). "Visualizing High-Dimensional Data Using t-SNE" (PDF). Journal of Machine Learning Research 9:2579-2605.

van Driel J, Ridderinkhof K R, & Cohen M X (2012) Not all errors are alike: Theta and alpha EEG dynamics relate to differences in error-processing dynamics. Journal of Neuroscience 32 (47): 16795-16806.

van Meel C S, Heslenfeld D J, Oosterlaan J, Sergeant J A (2007) Adaptive control deficits in attention-deficit/hyperactivity disorder (ADHD)): The role of error processing. Psychiatry Res 151:211-220.

Varela, F., Lachaux, J. P., Rodriguez, E., Martinerie, J., 2001. The brainweb: phase synchronization and large-scale integration. Nature Reviews Neuroscience 2, 229-239 (2001).

Velligan D I, Ritch J I., Sui D, DiCocco M, Huntzinger C D) (2002) Frontal systems behavior scale in schizophrenia: Relationships with psychiatric symptomatology, cognition and adaptive function. Psychiatry Res 113:227-236.

Veniero, D., Brignani, D., Thut, G., Miniussi, C., 2011. Alpha-generation as basic response-signature to transcranial magnetic stimulation (TMS) targeting the human resting motor cortex: a TMS/EEG co-registration study. Psychophysiology 48, 1381-1389.

Venna J, and S Kaski, Local multidimensional scaling, Neural Networks, 2006.

Vicente R, Gollo L L, Mirasso C R, Fischer I, Pipa G (2008) Dynamical relaying can yield zero time lag neuronal synchrony despite long conduction delays. Proc Natl Acad Sci USA 105:17157-17162.

Villamar M F, Volz M S, Datta A, Bikson N, DaSilva A F, Fregni F. Technique and Considerations in the Use of 4×1 Ring High-definition Transcranial Direct Current Stimulation (HD-tDCS). JOVE 2013; (77) doi: 10.3791/50309. WATCH Villamar M F, Wivatvongvana P, Patumanond J, Bikson M, Truong D Q, Datta A, Fregi F. Focal modulation of primary motor cortex in Fibromyalgia using 4×1-Ring High-Definition Transcranial Direct Current Stimulation (HD-tDCS): Immediate and delayed analgesic effects of cathodal and anodal stimulation. J Pain 2013; 14 (4): 371-83.

Vossen, Alexandra, Joachim Gross, and Gregor Thut. "Alpha power increase after transcranial alternating current stimulation at alpha frequency (α-tACS) reflects plastic changes rather than entrainment." Brain Stimulation 8.3 (2015): 499-508;

Wagner M, Fuchs M, & Kastner J (2007) SWARM: sLORETA-weighted accurate minimum norm inverse solutions. International Congress Series 1300:185-188.

Wall, Judy, "Military Use of Mind Control Weapons", NEXUS, 5/06, October-November 1998.

Walsh, V., Cowey, A., 2000. Transcranial magnetic stimulation and cognitive neuroscience. Nature Reviews Neuroscience 1, 73-79.

Walsh, V., Ellison, A., Battelli, L., Cowey, A., 1998. Task-specific impairments and enhancements induced by magnetic stimulation of human visual area V5. Proceedings: Biological Sciences 265, 537-543.

Walsh, V., Pascual-Leone, A., 2003. Transcranial Magnetic Stimulation: A Neurochronometrics of Mind. MIT Press, Cambridge, M A.

Walsh, V., Rushworth, M., 1999. A primer of magnetic stimulation as a tool for neuropsychology. Neuropsychologia 37, 125-135.

Wang X J (2010) Neurophysiological and computational principles of cortical rhythms in cognition. Physiol Rev 90:1195-1268.

Wang, Chang; Mahadevan, Sridhar (July 2008). Manifold Alignment using Procrustes Analysis (PDF). The 25th International Conference Int. Conf. on Machine Learning. pp. 1120-1127.

Wang, Wen-Ting, and Hsin-Cheng Huang. "Regularized principal component analysis for spatial data." Journal of Computational and Graphical Statistics 26, no. 1 (2017): 14-25. arxiv.org/pdf/1501.03221v3.pdf, Warach, S., J. R. Ives, G. Schaug, M. R. Patel, D. G. Darby, V. Thangaraj, R. R. Edelman and D. L. Schomer, EEG-triggered echo-planar functional MRI in epilepsy, Neurology 47:89-93, 1996.

Ward, L. M., Doesburg, S. M., Kitajo, K., MacLean, S. E., Roggeveen, A. B., 2006. Neural synchrony in stochastic resonance, attention, and consciousness. Canadian J. Experimental Psychology 60, 319-326.

Wassermann, E. M., Epstein, C., Ziemann, U., Walsh, V., Paus, T., Lisanby, S., 2008.

Waterston, M. L., Pack, C. C., 2010. Improved discrimination of visual stimuli following repetitive transcranial magnetic stimulation. PLOS ONE 5, e10354.

Wei-Long Zheng, Jia-Yi Zhu, Bao-Liang Lu, Identifying Stable Patterns over Time for Emotion Recognition from EEG, arxiv.org/abs/1601.02197.

Weiss S A, Bikson M. Open questions on the mechanisms of neuromodulation with applied and endogenous electric fields. Frontiers of Human Neuroscience 2014; doi: 10.3389/fnhum.2014.00227 Free Online Opening editorial to special issue co-edited by M. Bikson and S. H Weiss.

Weiss S A, McKhann G, Goodman R, Emerson R G, Trevelyan A, Bikson M, Schevon C A. Field effects and ictal synchonization: insights from in homine observations Frontiers of Human Neuroscience2013; 7:828 Free Journal Link.

Will, Udo, and Eric Berg. "Brain wave synchronization and entrainment to periodic acoustic stimuli." Neuroscience letters 424.1 (2007): 55-60; and.

Wingeier B M, Nunez P L and Silberstein R B (2001) Spherical harmonic decomposition applied to spatial-temporal analysis of human high-density electroencephalogram. Physical Review E 64:051916-1 to 9.

Witkowski, Matthias, et al. "Mapping entrained brain oscillations during transcranial alternating current stimulation (tACS)." Neuroimage 140 (2016): 89-98;

Wold S., Geladi P., Esbensen K., Ohman J. (1987) Multi-way principal components and PLS-analysis, Journal of Chemometrics, vol. 1.

Wolpert D M, Diedrichsen J, & Flanagan J R (2011) Principles of sensorimotor learning. Nature Reviews Neuroscience 12:739-751.

Woods A J, Antal A, Bikson M, Boggio P S, Brunoni A R, Celnik P, Cohen L G, Fregni F, Herrmann C S, Kappenman E S, Knotkova H, Liebetanz D, Miniussi C, Miranda P C, Paulus W, Priori A, Reato D, Stagg C, Wenderoth N, Nitsche M A. A technical guide to tDCS, and related non-invasive brain stimulation tools. Clin Neurophysiol. 2016 February; 127 (2): 1031-48. doi: 10.1016/j.clinph.2015.11.012.

Woods A J, Hamilton R, Kranjec A, Minhaus P, Bikson M, Yu J, Chatterjee A. Exploring structure-function relationships using parallel fMRI and tDCS. Brain Stimul. 2014 March-April; 7 (2): e9. doi: dx.doi.org/10.1016/j.brs.2014.01.033.

Woods A J, Hamilton R H, Kranjec A, Minhas P, Bikson M, Yu J, Chatterjee A. Space, Time, and Causality in the Human Brain. Neuroimage 2014; 92:285-297.

Wu, S., Amari, S., Nakahara, H., 2002. Population coding and decoding in a neural field: a computational study. Neural Computation 14, 999-1026.

www.bibliotecapleyades.net/ciencia/ciencia_nonlethalweapons02.htm Eleanor White-New Devices That 'Talk' To The Human Mind Need Debate, Controls.

www.cbsnews.com/stories/2008/12/31/60 minutes/main4694713.shtml 60) Minutes: Incredible Research Lets Scientists Get A Glimpse At Your Thoughts.

www.cbsnews.com/video/watch/?id=5119805n& tag=related;photovideo 60) Minutes: Video—Mind Reading.

www.charlesrehn.com/charlesrehn/books/aconversation-withamerica/essays/myessays/The % 20NSA.doc.

www.govtrack.us/congress/billtext.xpd?bill=h107-2977 Space Preservation Act of 2001.

www.informaworld.com/smpp/content~db=all~content=a785359968 Partial Amnesia for a Narrative Following Application of Theta Frequency Electromagnetic Fields.

www.msnbc.msn.com/id/27162401/.

www.ncbi.nlm.nih.gov/pubmed/1510870).

www.psychology.nottingham.ac.uk/staff/lpxdts/TMS % 20info.html Transcranial Magnetic Stimulation.

www.raven1.net/silsoun2.htm PSY-OPS WEAPONRY USED IN THE PERSIAN GULF WAR.

www.researchgate.net/publication/8147320_The_Physiology_of_Learning_and_Memory_Role_of_Peptides_and-_Stress. Deep brain stimulation is described in NIH Research Matters, "A noninvasive deep brain stimulation technique", (2017), www.scribd.com/doc/24531011/Operation-Mind-Control.

www.scribd.com/doc/6508206/SYNTHETIC-TELEPA-THY-AND-THE-EARLY-MIND-WARS.

www.slavery.org.uk/Bioeffects_of_Selected_Non-Lethal_Weapons.pdf-Bioeffects of selected non-lethal weapons.

www.sst.ws/tempstandards.php?pab=1_1 TEMPEST mea-
surement standards.

www.uwe.ac.uk/hlss/research/cpss/Journal_Psycho-Social-
_Studies/v2-2/SmithC.shtml Journal of Psycho-Social
Studies-Vol 2 (2) 2003-On the Need for New Criteria of
Diagnosis of Psychosis in the Light of Mind Invasive
Technology by Dr. Carole Smith.

www.wired.com/wired/archive/7.11/persinger.html This Is
Your Brain on God.

Xu J, Healy S M, Truong D Q, Datta A, Bikson M, Potenza
M N. A Feasibility Study of Bilateral Anodal Stimulation
of the Prefrontal Cortex Using High-Definition Electrodes
in Healthy Participants. Yale J Biol Med. 2015 Sep. 3; 88
(3): 219-25.

Xue S, Tang Y Y, Tang R, & Posner M I (2014) Short-term
meditation induces changes in brain resting EEG theta
networks. Brain & Cognition 87:1-6.

Yi-Hung Liu, Chien-Te Wu, Yung-Hwa Kao, Ya-Ting Chen,
"Single-trial EEG-based emotion recognition using kernel
Eigen-emotion pattern and adaptive support vector
machine", Engineering in Medicine and Biology Society
(EMBC) 2013 35th Annual International Conference of
the IEEE, pp. 4306-4309, 2013, ISSN 1557-170X.

Yi-Hung Liu, Wei-Teng Cheng, Yu-Tsung Hsiao, Chien-Te
Wu, Mu-Der Jeng, "EEG-based emotion recognition
based on kernel Fisher's discriminant analysis and spec-
tral powers", Systems Man and Cybernetics (SMC) 2014
IEEE International Conference on, pp. 2221-2225, 2014.

Yin, Hujun; Learning Nonlinear Principal Manifolds by
Self-Organising Maps, in A. N. Gorban, B. Kégl, D. C.
Wunsch, and A. Zinovyev (Eds.), Principal Manifolds for
Data Visualization and Dimension Reduction, Lecture
Notes in Computer Science and Engineering (LNCSE),
vol. 58, Berlin, Germany: Springer, 2007, Ch. 3, pp.
68-95. ISBN 978-3-540-73749-0).

Yuan-Pin Lin, Chi-Hong Wang, Tzyy-Ping Jung, Tien-Lin
Wu, Shyh-Kang Jeng, Jeng-Ren Duann, Jyh-Horng Chen,
"EEG-Based Emotion Recognition in Music Listening",
Biomedical Engineering IEEE Transactions on, vol. 57,
pp. 1798-1806, 2010, ISSN 0018-9294.

Yuksel, Beste F., Kurt B. Oleson, Lane Harrison, Evan M.
Peck, Daniel Afergan, Remco Chang, and Robert J K
Jacob. "Learn plano with BACh: An adaptive learning
interface that adjusts task difficulty based on brain state."
In Proceedings of the 2016 chi conference on human
factors in computing systems, pp. 5372-5384. ACM CHI,
2016, DOI: 10.1145/2858036.2858388.

Zaehle, T., Rach, S., Herrmann, C. S., 2010. Transcranial
alternating current stimulation enhances individual alpha
activity in human EEG. PLOS ONE 5, e13766.

Zareen N, Shinozaki M, Ryan D, Alexander H, Amer A,
Truong D Q, Khadka N, Sarkar A, Naeem S, Bikson M,
Martin J H. Motor cortex and spinal cord neuromodula-
tion promote corticospinal tract axonal outgrowth and
motor recovery after cervical contusion spinal cord injury.
Exp Neurol. 2017 November; 297:179-189. doi: 10.1016/
j.expneurol.2017.08.004. Online Link (article in produc-
tion)

Zatorre R J, Fields R D, & Johansen-Berg H (2012) Plas-
ticity in gray and white: neuroimaging changes in brain
structure during learning. Nature Neuroscience 15 (4):
528-536.

Zhang, Z., J. Wang, "MLLE: Modified Locally Linear
Embedding Using Multiple Weights" citeseerx.ist.ps-
u.edu/viewdoc/summary?doi=10.1.1.70.382.

Zhang, Zhenyue; Hongyuan Zha (2005). "Principal Mani-
folds and Nonlinear Dimension Reduction via Local

128

Tangent Space Alignment". SIAM Journal on Scientific
Computing. 26 (1): 313-338. doi: 10.1137/
s1064827502419154.

Zhuang, Tianbao, Hong Zhao, and Zheng Tang. "A study of
brainwave entrainment based on EEG brain dynamics."
Computer and information science Comp. & Inf. Sci. 2.2
(2009): 80.

Zinovyev, A, ViDaExpert overview, IHES (Institut des
Hautes Études Scientifiques), Bures-Sur-Yvette, Île-de-
France.

Zinovyev, A., ViDaExpert-Multidimensional Data Visual-
ization Tool (free for non-commercial use). Institut Curie,
Paris.

Zlotnik, Anatoly, Raphael Nagao, and István Z. Kiss Jr-Shin
Li. "Phase-selective entrainment of nonlinear oscillator
ensembles." Nature Communications 7 (2016).

Zukerman, Wendy, "Habits form when brainwaves slow
down", New Scientist, Sep. 26, 2011 (www.newscientist-
.com/article/dn20964-habits-form-when-brainwaves-
slow-down/).

What is claimed is:

1. A system for inducing a selected mental state from at
least one mental state of a donor comprising the selected
mental state in a subject using brainwave patterns from the
donor, comprising:

an electroencephalographic input port configured to
receive captured brainwave patterns from a donor, the
brainwave patterns comprising neural correlates of the
at least one mental state of the donor during capture of
the brainwave patterns;

at least one automated processor communicatively
coupled to the input port, and being configured to:
determine the selected mental state;
process the captured brainwave patterns from the
donor, to automatically selectively extract the neural
correlates of the at least one mental state of the donor
comprising the selected mental state, comprising a
set of time-varying superposed signal components
from the captured brainwave patterns together cor-
responding to the at least one mental state of the
donor;

extract a subset of the set of time-varying superposed
signal components together corresponding to the
selected mental state; and define a sensory stimulus pattern for presentation to the
subject, the sensory stimulus pattern being selec-
tively dependent on the selected mental state and the
extracted subset of components of the set of time-
varying superposed signal components, and being
configured to entrain the brainwaves of the subject
with the defined sensory stimulus pattern in a manner
that the neural correlates of the subject having
entrained brainwaves correspond to the neural cor-
relates of the donor for the selected metal state; and a sensory stimulator, configured to generate a sensory
stimulus selected from the group consisting of at
least one of audio, visual, and tactile, configured to
stimulate the subject according to the defined sen-
sory stimulus pattern and entrain the brainwaves of
the subject with the selected sensory stimulus pat-
tern, inducing the selected mental state in the subject.

2. The system according to claim 1, wherein the subset of
the set of time-varying superposed signal components com-
prise at least one of a set of principal components and a set
of independent components, and the sensory stimulator
concurrently presents at least two concurrent sensory stimuli
to the subject.

3. The system according to claim 1, wherein the subset of the set of time-varying superposed signal components is a set of spatial principal components, and the at least one automated processor is further configured to perform a signal component rotation on the set of spatial principal components.

4. The system according to claim 1, wherein the subset of the set of time-varying superposed signal components comprises an orthogonal basis set.

5. The system according to claim 1, wherein the sensory stimulator comprises at least one of a visual stimulator and an auditory stimulator configured to present to the subject at least one of a visual stimulus and an auditory stimulus modulated based on the subset of the set of time-varying superposed signal components.

6. The system according to claim 1, wherein the donor is a different person than the subject.

7. The system according to claim 1, wherein the at least one processor is further configured to perform a blind decomposition of the captured brainwave patterns from the donor.

8. The system according to claim 1, wherein the at least one automated processor is further configured to automatically extract the subset of the set of time-varying superposed signal components using nonlinear dimensionality reduction.

9. The system according to claim 1, wherein the at least one automated processor is further configured to determine the sensory stimulus pattern with an autoencoder.

10. The system according to claim 1, wherein the sensory stimulator comprises an audio stimulator configured to entrain the brain of the subject with an isochronic tone or binaural beats audio pattern comprising a frequency in a range between 7.5-150 Hz.

11. The system according to claim 1, wherein the selected mental state is sleep, wherein the sensory stimulator is configured to stimulate the subject, according to the sensory stimulus pattern, to achieve sleep in the subject.

12. A system for inducing a selected mental state in a subject from at least one mental state of a donor comprising the selected mental state, comprising:

an electroencephalographic input port configured to receive captured brainwave patterns from at least one donor comprising a set of time-varying signal components, the brainwave patterns comprising neural correlates of the at least one mental state of the at least one donor during capture of the brainwave patterns;

at least one automated processor, configured to:

select the mental state;

process the captured brainwaves from the at least one donor, to automatically:

reduce a dimensionality of the brainwave patterns from the at least one donor to define a subset of the set of time-varying signal components of the brainwave patterns by extraction of the subset of the set of time-varying signal components that together selectively correspond to the neural correlates of the at least one mental state of the at least one donor comprising the selected mental state; and determine a subject-dependent sensory stimulus pattern for presentation to the subject, comprising the subset of the set of time-varying signal components that together selectively correspond to the at least one mental state of the at least one donor; and a sensory stimulator, configured to present the subject-dependent sensory stimulus pattern to the subject, and entrain the subject with the subject-dependent sensory stimulus pattern to induce the subject to achieve the selected mental state.

13. The system according to claim 12, wherein the at least one automated processor is further configured to determine at least one dominant frequency of the brainwave patterns, and the sensory stimulus pattern comprises a sensory stimulus modulated with the at least one dominant frequency of the brainwave pattern.

14. The system according to claim 12, further comprising:

a memory, configured to store a plurality of the subsets of the set of time-varying signal components, each respective subset of the set of time-varying signal components representing a respectively different mental state of the at least one donor; and the at least one automated processor is further configured to:

define a sequence of the different mental states of the at least one donor;

determine a brainwave characteristic of the subject;

retrieve the respective subsets of the set of time-varying signal components corresponding to the sequence of different mental states of the at least one donor from the memory; and determine, for the sequence of the different mental states of the at least one donor, the subject-dependent sensory stimulus pattern dependent on the brainwave characteristic of the subject, configured to induce the sequence of respective different mental states of the at least one donor in the subject.

15. A system for inducing a mental state of a donor in a subject, comprising:

an electroencephalographic input port configured to receive captured signals representing a brainwave pattern from the donor, the brainwave pattern comprising neural correlates of the mental state of the donor during capture of the brainwave pattern;

at least one automated processor, configured to:

process the captured brainwave pattern from the donor, to determine the neural correlates of the mental state of the donor, comprising a set of time-varying superposed signal components from the captured brainwave pattern;

extracting a subset of the set of time-varying superposed signal components together corresponding to the mental state of the donor; and define a sensory stimulus pattern selectively dependent on the extracted subset of the set of time-varying superposed signal components together corresponding to the mental state of the donor, and being configured to entrain the brainwaves of the subject with the defined sensory stimulus pattern; and a sensory stimulator, configured to generate a sensory stimulus selected from the group consisting of at least one of audio, visual, and tactile, to stimulate the subject with the defined sensory stimulus pattern.

16. The system according to claim 15, wherein the subset of the set of time-varying superposed signal components comprise at least one of a set of principal components and a set of independent components, and the sensory stimulator is configured to concurrently present at least two concurrent sensory stimuli of different modality.

17. The system according to claim 15, wherein the subset of the set of time-varying superposed signal components are extracted by the at least one automated processor using factor analysis.

18. The system according to claim 15, wherein the subset of the set of time-varying superposed signal components comprises an orthogonal basis set.

19. The system according to claim 15, wherein the sensory stimulator comprises a visual stimulator and an auditory stimulator configured to concurrently output a visual stimulus and an auditory stimulus to the subject.

20. The system according to claim 15, wherein the sensory stimulator comprises an audio stimulator configured to entrain the brain of the subject with an isochronic tone or binaural beats audio pattern.

* * * * *